US011408005B2

(12) United States Patent
Jensen et al.

(10) Patent No.: US 11,408,005 B2
(45) Date of Patent: Aug. 9, 2022

(54) CHIMERIC TRANSCRIPTION FACTOR VARIANTS WITH AUGMENTED SENSITIVITY TO DRUG LIGAND INDUCTION OF TRANSGENE EXPRESSION IN MAMMALIAN CELLS

(71) Applicant: Seattle Children's Hospital, Seattle, WA (US)

(72) Inventors: Michael C. Jensen, Bainbridge Island, WA (US); Tracy Ooi, Seattle, WA (US); Jia Wei, Redmond, WA (US)

(73) Assignee: Seattle Children's Hospital, Seattle, WA (US)

( * ) Notice: Subject to any disclaimer, the term of this patent is extended or adjusted under 35 U.S.C. 154(b) by 249 days.

(21) Appl. No.: 16/467,015

(22) PCT Filed: Dec. 11, 2017

(86) PCT No.: PCT/US2017/065597
§ 371 (c)(1),
(2) Date: Jun. 5, 2019

(87) PCT Pub. No.: WO2018/111763
PCT Pub. Date: Jun. 21, 2018

(65) Prior Publication Data

US 2020/0181624 A1 Jun. 11, 2020

Related U.S. Application Data

(60) Provisional application No. 62/433,183, filed on Dec. 12, 2016.

(51) Int. Cl.
*C12N 15/62* (2006.01)
*C07K 16/30* (2006.01)
*C12N 15/113* (2010.01)

(52) U.S. Cl.
CPC ............ *C12N 15/625* (2013.01); *C07K 16/30* (2013.01); *C12N 15/113* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,783,186 | A | 7/1998 | Arakawa et al. |
| 6,040,177 | A | 3/2000 | Riddell et al. |
| 7,070,995 | B2 | 7/2006 | Jensen |
| 7,709,253 | B2 | 5/2010 | Gambhir et al. |
| 7,910,101 | B2 | 3/2011 | Cunningham et al. |
| 8,822,647 | B2 | 9/2014 | Jensen |
| 10,172,885 | B2 | 1/2019 | Pule |
| 10,266,592 | B2 | 4/2019 | Jensen |
| 10,611,837 | B2 | 4/2020 | Jensen et al. |
| 10,780,118 | B2 | 9/2020 | Jensen |
| 11,123,369 | B2 | 9/2021 | Jensen et al. |
| 2002/0111474 | A1 | 8/2002 | Capon et al. |
| 2003/0148982 | A1 | 8/2003 | Brenner et al. |
| 2005/0060762 | A1 | 3/2005 | Bieck |
| 2005/0129671 | A1 | 6/2005 | Cooper et al. |
| 2006/0160090 | A1 | 7/2006 | Anzures et al. |
| 2006/0246548 | A1 | 11/2006 | Jensen |
| 2007/0087346 | A1 | 4/2007 | Ciliberto et al. |
| 2007/0166318 | A1 | 7/2007 | Macina et al. |

(Continued)

FOREIGN PATENT DOCUMENTS

| | | |
|---|---|---|
| CN | 102227503 A | 10/2011 |
| DE | 10 2011118018 | 4/2013 |

(Continued)

OTHER PUBLICATIONS

Aalberse et al., "IgG4 breaking the rules," Immunology (2002) 105:9-19.

(Continued)

*Primary Examiner* — Kagnew H Gebreyesus
(74) *Attorney, Agent, or Firm* — Knobbe, Martens, Olson & Bear LLP

(57) ABSTRACT

Provided herein is a system for inducible expression of a chimeric antigen receptor in cells, such as mammalian cells. The system comprises: a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and any other selected molecule expressed on a target cell population, wherein the ligand elicits recognition, modulation, inhibition, and/or elimination by a lymphocyte, a second polynucleotide, which encodes a spacer or an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor, or the system has an enhanced transcriptional expression at a given concentration of the drug compared to a wild type HEA3. Methods of making such cells and methods of treatment using these cells are also provided.

20 Claims, 22 Drawing Sheets

Specification includes a Sequence Listing.

(56) References Cited

U.S. PATENT DOCUMENTS

| | | | |
|---|---|---|---|
| 2008/0044413 A1 | 2/2008 | Hammond | |
| 2009/0098142 A1 | 4/2009 | Kasaian et al. | |
| 2009/0098604 A1 | 4/2009 | Gallo et al. | |
| 2010/0226901 A1 | 9/2010 | Smolke | |
| 2011/0287020 A1 | 11/2011 | Gruber et al. | |
| 2012/0046645 A1 | 2/2012 | Cal | |
| 2012/0297493 A1 | 11/2012 | Cooper et al. | |
| 2012/0301447 A1 | 11/2012 | Jensen | |
| 2013/0011394 A1 | 1/2013 | Knoetgen | |
| 2013/0143559 A1 | 6/2013 | Nishida et al. | |
| 2013/0280220 A1 | 10/2013 | Ahmed et al. | |
| 2013/0287748 A1 | 10/2013 | June et al. | |
| 2014/0056868 A1 | 2/2014 | Zechiedrich et al. | |
| 2014/0112956 A1 | 4/2014 | Karlsson-Parra et al. | |
| 2014/0271635 A1 | 9/2014 | Brogdon et al. | |
| 2014/0314795 A1 | 10/2014 | Riddell et al. | |
| 2015/0038684 A1 | 2/2015 | Jensen | |
| 2015/0038694 A1 | 2/2015 | Nicotra | |
| 2015/0120622 A1 | 4/2015 | Kobatake | |
| 2015/0299656 A1 | 10/2015 | Gattinoni et al. | |
| 2015/0329640 A1 | 11/2015 | Finer | |
| 2016/0017048 A1 | 1/2016 | Dotti et al. | |
| 2017/0015746 A1 | 1/2017 | Jensen | |
| 2017/0029774 A1 | 2/2017 | Jensen et al. | |
| 2017/0209543 A9 | 7/2017 | Jensen | |
| 2017/0224733 A1 | 8/2017 | Badie et al. | |
| 2018/0009891 A1 | 1/2018 | Jensen | |
| 2018/0028567 A1 | 2/2018 | Li et al. | |
| 2019/0248891 A1 | 8/2019 | Jensen et al. | |
| 2020/0181624 A1 | 6/2020 | Jensen et al. | |
| 2020/0215108 A1 | 7/2020 | Jensen et al. | |
| 2021/0002364 A1 | 1/2021 | Jensen et al. | |
| 2021/0139583 A1 | 5/2021 | Jensen et al. | |
| 2021/0371517 A1 | 12/2021 | Jensen | |

FOREIGN PATENT DOCUMENTS

| | | |
|---|---|---|
| RU | 2003 129 528 A | 4/2005 |
| WO | WO 92/08796 | 5/1992 |
| WO | WO 94/00143 | 1/1994 |
| WO | WO 00/23573 | 4/2000 |
| WO | WO 01/098506 | 12/2001 |
| WO | WO 02/072605 | 9/2002 |
| WO | WO 02/097099 | 12/2002 |
| WO | WO 03/087338 | 10/2003 |
| WO | WO 05/017102 | 2/2005 |
| WO | WO 05/040212 | 5/2005 |
| WO | WO 07/073499 | 6/2007 |
| WO | WO 08/012237 | 1/2008 |
| WO | WO 09/091826 | 7/2009 |
| WO | WO 10/036986 | 4/2010 |
| WO | WO 10/141543 | 12/2010 |
| WO | WO 11/056894 | 5/2011 |
| WO | WO 12/079000 | 6/2012 |
| WO | WO 12/099973 | 7/2012 |
| WO | WO 12/129514 | 9/2012 |
| WO | WO 12/140130 | 10/2012 |
| WO | WO 13/126733 | 8/2013 |
| WO | WO 13/154760 | 10/2013 |
| WO | WO 13/177533 | 11/2013 |
| WO | WO 13/178635 | 12/2013 |
| WO | WO 14/031687 | 2/2014 |
| WO | WO 14/039044 | 3/2014 |
| WO | WO 14/055668 | 4/2014 |
| WO | WO 14/153270 | 9/2014 |
| WO | WO 15/092024 | 6/2015 |
| WO | WO 15/105522 | 7/2015 |
| WO | WO 15/142675 | 9/2015 |
| WO | WO 15/157399 | 10/2015 |
| WO | WO 15/157432 | 10/2015 |
| WO | WO 2015/157432 A1 | 10/2015 |

OTHER PUBLICATIONS

Aertgeerts et al., "Structural analysis of the mechanism of inhibition and allosteric activation of the kinase domain of HER2 protein," Journal of Biological Chemistry (2011) vol. 286, No. 21, p. 18756-18765, Весь ТеКСТ, с. 18759-18765.

Ahmed et al., "Regression of experimental medulloblastoma following transfer of HER2-specific T cells," Cancer Res. (Jun. 15, 2007) 67(12):5957-64.

Ahmed, Nabil, "CMV-specific Cytotoxic T Lymphocytes Expressing CAR Targeting HER2 in Patients With GBM (HERT-GBM)," ClinicalTrials.gov Identifier: NCT01109095 (Apr. 22, 2010) pp. 1-8.

Ahmed, Nabil, "Her2 Chimeric Antigen Receptor Expressing T Cells in Advanced Sarcoma," ClinicalTrials.gov Identifier: NCT00902044 (May 14, 2009) pp. 1-11.

Altschul et al., "Local Alignment Statistics, [27] Multiple Alignment and Phylogenetic Trees," Methods in Enzymology (1996) 266:460-480.

Bejcek et al. "Development and Characterization of Three Recombinant Single Chain Antibody Fragments (scFvs) Directed against the CD19 Antigen," Cancer Res (1995) 55:2346-2351.

Berglund et al., "The epitope space of the human proteome," Protein Science (2008) 17:606-613.

Brentjens et al: "CD19-targeted T cells rapidly induce molecular remissions in adults with chemotherapy-refractory acute lymphoblastic leukemia", Science Translational Medicine, 5(177), Mar. 20, 2013.

Budde et al., "Combining a CD20 Chimeric Antigen Receptor and an Inducible Caspase 9 Suicide Switch to Improve the Efficacy and Safety of T Cell Adoptive Immunotherapy for Lymphoma", PLOS One (2013) 8(12): e82742. https://doi.org/10.1371/journal.pone.0082742.

Cartellieri et al., "A Novel Ex Vivo Isolation and Expansion Procedure for Chimeric Antigen Receptor Engrafted Human T Cells," PLOS One (Apr. 3, 2014) vol. 9, No. 4, e93745, pp. 1-12.

Cha et al., "IL-7 + IL-15 are superior to IL-2 for the ex vivo expansion of 4T1 mammary carcinoma-specific T cells with greater efficacy against tumors in vivo," Breast Cancer Research and Treatment, Springer, NY, US (Oct. 14, 2009) vol. 122, No. 2, pp. 359-369.

Chen et al., "Ex vivo expansion of dendritic-cell-activated antigen-specific CD4+ T cells with anti-CD3/CD28, interleukin 7, and interleukin-15: Potential for adoptive T-cell immunotherapy," Clinical Immunology (2006) vol. 119, pp. 21-31.

Chen et al., "Minicircle DNA vectors devoid of bacterial DNA result in persistent and high-level transgene expression in vivo", Mol Ther. (2003) 8(3), 495-500.

Chen et al., Sep. 15, 2005, NF-κ-B ReIA phosphorylation regulates ReIA acetylation, Molecular and Cellular Biology, 25(18):7966-7975.

Chen et al: "Fusion Protein Linkers: Property, Design and Functionality", Adv Drug Deliv Rev., Oct. 15, 2013; 65(10), pp. 1357-1369.

Cho et al., "Structure of the extracellular region of HER2 alone and in complex with the Herceptin Fab", Nature (Feb. 13, 2003) 421(6924):756-760.

Circosta et al., "T Cell Receptor (TCR) Gene Transfer with Lentiviral Vectors Allows Efficient Redirection of Tumor Specificity ikn Naive and Memory T Cells Without Prior Stimulation of Endogenous TCR," Human Gene Therapy (Nov. 18, 2009) vol. 20, No. 12, pp. 1576-1588.

Converse et al: "Counterselection and Co-Delivery of Transposon and Transposase Functions for Sleeping Beauty-Mediated Transposition in Cultured Mammalian Cells", Bioscience Reports, Kluwer Academic Publishers-Plenum Publishers, NE (Dec. 1, 2004) vol. 24, No. 6, pp. 577-594.

Crewe et al., "Metabolism of Tamoxifen by recombinant human cytochrome P-450 enzymes: Formation of the 4-hydroxy, 4-hydroxy and N-desmethyl metabolites and isomerization of trans-4-hydroxytamoxifen,"Drug Metab Dispos (2002) 30(8): 869-874.

Database Geneseq [Online] May 5, 2005 (May 5, 2005), "Human splice variant protein expressed in ovary cells DEX0487 002.orf. 4.", XP002771301, retrieved from EBI accession No. GSP:ADY30515. Database accession No. ADY30515 ; & WO 2005/017102 A2

(56) References Cited

OTHER PUBLICATIONS (Diadexus Inc [US]; Macina Roberto A [US]; Turner Leah R [US]; Sun Yong) Feb. 24, 2005 (Feb. 24, 2005).
Database UniProt [Online] Oct. 3, 2012 (Oct. 3, 2012), "SubName: Full=Receptor tyrosine-protein kinase erbB-2 {ECO: 00003131 Ensembl:ENSP00000464252}; Flags: Fragment;", XP002771300, retrieved from EBI accession No. UNIPORT:J3QRJ7 Database accession No. J3QRJ7.
Dotti, Gianpietro, et al. "Design and development of therapies using chimeric antigen receptor-expressing T cells." Immunological reviews 257.1 (2014): 107-126.
Ercikan-Abali et al., "Active Site-Directed Double Mutants of Dihydrofolate Reductase," Cancer Res., (1996) vol. 56, No. 18, pp. 4142-4145.
Frankel et al., "Characterization of diphtheria fusion proteins targeted to the human interleukin-3 receptor," Protein engineering (2000) vol. 13, No. 8, p. 575-581.
Gagnon et al., "IL-6, in Synergy with IL-7 or IL-15, Stimulates TCR-Independent Proliferation and Functional Differentiation of CD8+ T Lymphocytes," The Journal of Immunology (2008) 180:7958-7968.
Gallinari et al., "A Functionally Orthogonal Estrogen Receptor-Based Transcription Switch Specifically Induced by a Nonsteroid Synthetic Ligand," Chemistry and Biology (Aug. 1, 2005) vol. 12, No. 8, pp. 883-893.
Gargett et al., "Different cytokine and stimulation conditions influence the expansion and immune phenotype of third-generation chimeric antigen receptor T cells specific for tumor antigen GD2," Cytotherapy (2015) 17.4: 487-495.
Garrett et al., "Novel engineered trastuzumab conformational epitopes demonstrate in vitro and in vivo antitumor properties against HER-2/neu," The Journal of Immunology (Jun. 1, 2007) 178:7120-7131.
Ghatar et al., "Epitope Mapping of Human HER2 Specific Mouse Monoclonal Antibodies Using Recombinant Extracellular Subdomains," Asian Pacific Journal of Cancer Prevention (2017) 18(11):3103-3110.
Gianpietro Dotti et al.: "Design and development of therapies using chimeric antigen receptor-expressing T cells", Immunological Reviews, vol. 257, No. 1, Dec. 13, 2013 (Dec. 13, 2013), pp. 107-126.
Giry-Laterriere et al. "Polyswitch lentivectors: 'all-in-one' lentiviral vectors for drug-inducible gene expression, live selection, and recombination cloning", *Human Gene Therapy*, Oct. 2011, 22:1255-1267.
Godiska et al., "Linear plasmid vector for cloning of repectitive or unstable sequences in *Excherichia coli*," (Dec. 29, 2009) Nuc Acids Res, vol. 38, No. 6, e88, pp. 1-9.
Gottschalk, Stephen, "Her2 and TGFBeta CTLs in Treatment of Her2 Positive Malignancy (HERCREEM)", ClinicalTrials.gov Identifier: NCT00889954 (Apr. 29, 2009) pp. 1-9.
Grada et al., "TanCAR: A Novel Bispecific Chimeric Antigen Receptor for Cancer Immunotherapy", Mol Ther Nucleic Acids, (Jul. 9, 2013) 2:e105. doi: 10.1038/mtna.2013.32.
Han Weidong, "Treatment of Chemotherapy Refractory Human Epidermalgrowth Factor Receptor-2(HER-2) Positive Advanced Solid Tumors (CART-HER-2)", (Sep. 5, 2013) ClinicalTrials.gov Identifier: NCT01935843, pp. 1-7.
Holtkamp et al., "Modification of antigen-encoding RNA increases stability, tgranslational efficacy, and T-cell stimulatory capacity of dendritic cells," Blood (Oct. 28, 2014), 2006/108:509-4017.
Hong et al., "Diverse solid tumors expressing a restricted eptitope of L1-CAM can be targeted by chimeric antigen receptor redirected T lymphocytes," J Immunotherapy (2014) vol. 37, No. 2, pp. 93-104.
Hudecek et al. Receptor affinity and extracellular domain modifications affect tumor recognition by ROR1-specific chimeric antigen receptor T-cells. Clin Cancer Res. Jun. 15, 2013; 19(12): 3153-3164.
Hudecek et al., Nov. 16, 2012, The Non-Signaling Extracellular Spacer Domain of CD19-Specific Chimeric Antigen Receptors Is Decisive for in Vivo Anti-Tumor Activity, Blood, 120(21):951, 3 pp.
Hudecek et al., Sep. 11, 2014, "The Nonsignaling Extracellular Spacer Domain of Chimeric Antigen Receptors Is Decisive for In Vivo Antitumor Activity", Cancer Immunology Research. 3(2):125-135.
Huls et al., "First Clinical Trials Employing Sleeping Beauty Gene Transfer System and Artificial Antigen Presenting Cells to Generate and Infuse T Cells Expressing CD19-Specific Chimeric Antigen Receptor," Blood (2013) 122:166-166.
Jensen et al., "Designing chimeric antigen receptors to effectively and safely target tumors," Curr Opin Immunol. (Apr. 2015) 33:9-15.
Jensen et al: "Design and implementation of adoptive therapy with chimeric antigen receptor-modified T cells", Immunological Reviews., Special Issue, Dec. 13, 2013 vol. 257, No. 1; 127-144.
Johansen et al., "Evaluation of Tet-on system to avoid transgene down-regulation in ex vivo gene transfer to the CNS," Gene Therapy (2002) 9:1291-1301.
Johnston et al. "Regulated expression of erythropoietin from an AAV vector safely improves the anemia of beta-thalassemia in a mouse model," Mol Ther. Apr. 1, 2003, 7(4):493-497.
Kacherovsky et al., "Combination of Sleeping Beauty transposition and chemically induced dimerization selection for robust production of engineered cells," Nucleic Acids Research (2012) 49(11):e85.
Kay et al., "A robust system for production of minicircle DNA vectors". Nature Biotechnology, vol. 28, No. 12, Nov. 21, 2010, pp. 1287-1289.
Klebanoff et al., "IL-15 enhances the in vivo antitumor activity of tumor-reactive CD8+ T Cells," PNAS (Feb. 17, 2004) vol. 101, No. 7, pp. 1969-1974.
Kowolik et al., "CD28 costimulation provided through a CD19-specific chimeric antigen receptor enhances in vivo persistence and antitumor efficacy of adoptively transferred T cells," Cancer Res. (2006) 66(22):10995-11004.
Kunkele et al., "Functional Tuning of CARs Reveals Signaling Threshold above which CD8+ CTL Antitumor Potency is Attenuated Due to Cell Fas-FasL-Dependent AICD," Cancer Immunol Res. (Jan. 9, 2015) vol. 3, No. 4, pp. 368-379.
Lemaigre et al., "Transcriptional control of genes that regulate glycolysis and gluconeogenesis in adult liver," Biochem. J. (1994) 303:1-14.
Leung et al., "Luminescent detection of DNA-binding proteins," Nuc Acids Res (2012) 40(3): 941-955.
Likar et al., "Using a mutated variant human deoxycytidine-kinase as a reporter gene for assessing adoptive T-cell therapy," Questions hematology, oncology and immunopathology in pediatrics (2012) vol. 11, No. 2, pp. 23-31. (Russian Language).
Littlewood et al., "A modified oestrogen receptor ligand-binding domain as an improved switch for the regulation of heterologous proteins," Nucleic Acids Res (May 25, 1995) 23(10):1686-1690.
Litvinova et al., "The influence of immunoregulatory cytokines IL-2, IL-7, and IL-15 upon activation, proliferation, and apoptosis of immune memory T-cells in vitro." Cell and Tissue Biology (Dec. 11, 2013) vol. 7, No. 6, pp. 539-544.
Liu et al., "IL-21 synergizes with IL-7 to augment expansion and anti-tumor function of cytotoxic T cells," International Immunology (2007) vol. 19, No. 10, pp. 1213-1221.
Loeken, Mary R., "Effects of mutation of the CREB binding site of the somatostatin promoter on cyclic AMP responsiveness in CV-1 cells", *Gene Expr.* (1993) 3(3):253-264.
Lupton et al., "Dominant positive and negative selection using a hygromycin phosphotransferase-thymidine kinase fusion gene," Mol Cell Biol. (Jun. 1991) 11(6):3374-3378.
Maher, "Immunotherpay of Malignant Disease Using Chimeric Antigen Receptor Engrafted T Cells", *ISRN Oncology*, vol. 2012, pp. 1-23, Nov. 14, 2012.
Mátés et al., "Molecular evolution of a novelhyperactive Sleeping Beauty transposase enables robust stable gene transfer in vertebrates," Nature Genetics (Jun. 2009) vol. 41, No. 6, pp. 753-761.
McGehee et al., "Differentiation-specific element: a cis-acting developmental switch required for the sustained transcriptional expression of the angiotensinogen gene during hormonal-induced differentiation of 3T3-L1 fibroblasts to adipocytes," Mol. Endocrinol. (Apr. 1993) 7(4):551-560.

(56) References Cited

OTHER PUBLICATIONS

McKinlay et al., "Blood monocytes, myeloid dendritic cells and the cytokines interleukin (IL)-7 and IL-15 maintain human CD4+ T memory cellls with mixed helper/regulatory function," Immunology (2006) vol. 120, pp. 392-403.
Morgan et al., "Case report of a serious adverse event following the administration of T cells transduced with a chimeric antigen receptor recognizing ERBB2," Mol Ther. (Apr. 2010) 18(4):843-51. doi: 10.1038/mt.2010.24. Epub Feb. 23, 2010.
Muftuoglu et al., "CD161 Expression Identifies a Distinct Subset of Drug-Effluxing Viral-Specific Memory CD4+ T Cells That Preferentially Survive Cytotoxic Chemotherapy," Blood (2012) 122(21):2024.
O'Reilly et al., "Identification of an activating transcription factor (ATF) binding site in the human transforming growth factor-beta 2 promoter," J. Biol. Chem. (Oct. 5, 1992) 267:19938-19943.
Pakula et al., "Genetic analysis of protein stability and function," Annual review of genetics (1989) vol. 23, No. 1, p. 289-310, c.305-306.
Papapetrou et al. "Harnessing endogenous miR-181a to segregate transgenic antigen receptor expression in developing versus post-thymic T cells in murine hematopoietic chimeras", The Journal of clinical investigation. Jan. 5, 2009; 119(1):157-68.
Park et al., "Adoptive Transfer of Chimeric Antigen Receptor Re-Directed Cytolytic T Lmphocyte Clones in Patients with Neuroblastoma," Mol. Ther. (Apr. 2007) vol. 15, No. 4; pp. 825-833.
Pezutto et al., May 1, 1987, CD19 monoclonal antibody HD37 inhibits anti-immunoglobulin-induced B cell activation and proliferation, The Journal of Immunology, 138(9):2793-2799.
Pollock et al. "Delivery of a stringent dimerizer-regulated gene expression system in a single retroviral vector," Proc Natl Acad Sci. USA Nov. 21, 2000, 97(24):13221-1326.
Riddell et al. "Adoptive therapy with chimeric antigen receptor modified T cells of defined subset composition." Cancer journal (Sudbury, Mass.) 20.2 (2014): 141-144.
Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington," Human Gene Therapy (1992) 3(3):319-338.
Robinsons et al., Jan. 1991, Metabolites, pharmacodynamics, and pharmacokinetics of tamoxifen in rats and mice compared to the breast cancer patient, Drug Metab Dispos, 19(1):36-43.
Roscilli et al., "Long-term and tight control of gene expression in mouse skeletal muscle by a new hybrid human transcription factor," Molecular Therapy (Nov. 2002) 1;6(5):653-63.
Sadelain et al., "The basic principles of chimeric antigen receptor (CAR) design," Cancer discovery (2013) 3 (4): 388-98. DOI: 10.1158/2159-8290.CD-12-0548.
Sengupta et al., "Interleukin-13 Receptor Alpha 2-Targeted Glioblastoma Immunotherapy," BioMed Research International, (Aug. 27, 2014) vol. 2014, Article ID: 952128, pp. 1-8.
Terakura et al., "Generation of CD19-chimeric antigen receptor modified CD8+ T cells derived from virus-specific central memory T cells," Gene Therapy (Oct. 26, 2011) 119(1), pp. 72-82.
Treisman, R. "The SRE: a growth factor responsive transcriptional regulator. (PMID:2133110)", *Seminars in Cancer Biology*, Feb. 1, 1990, 1(1):47-58.
Vigna et al., "Robust and Efficient Regulation of Transgene Expression in Vivo by Improved Tetracycline-Dependent Lentiviral Vectors," Mol. Therapy (2002) 5(3):252-261.
Vogt et al., "Doxycycline-regulated gene expression in the opportunistic fungal pathogen Aspergillus fumigatus," BMC Microbiol. (2005) 5(1): 11 pages.
Wang et al., "Phenotypic and Functional Attributes of Lentivirus Modified CD19-specific Human CD8+ Central Memory Tcells Manufactured at Clinical Scale," J Immunotherapy (2012) vol. 35, pages 689-701
Wang et. al., "A transgene-encoded cell surface polypeptide for selection, in vivo tracking, and ablation of engineered cells", Blood, vol. 118, No. 5, Aug. 4, 2011 (Aug. 4, 2011), pp. 1255-1263.
Weill et al., "Translational control by changes in poly(A) tail length: recycling mRNAs," Nature Structural & Molecular Biology (Jun. 2012) vol. 19, No. 6, p. 577-585.
Xu et al., "Closely related T-memory stem cells correlate with in vivo expansion of CAR.CD19-T cells and are preserved by IL-7 and IL-15," Blood (Jun. 12, 2014) vol. 123, No. 24, p. 3750-3759.
Yang et al., Feb. 16, 2010, Functional interplay between acetylation and methylation of the RelA subunit of NF-κ-B, Molecular and Cellular Biology, 30(9):2170-2180.
Ye et al., "Characterization of a silencer regulatory element in the human interferon-gamma promoter," J. Biol. Chem., (Oct. 14, 1994) 269:25728-25734.
Zambon et al., "Increased Expression of the Pro-Apoptotic Protein BIM: A Mechanism for cAMP/PKA-Induced Apoptosis of Immature T Cells," J. Biol. Chem. (2011) 286(38):33260-33267.
Zheng, Changyu et al., "All Human EF1" Promoters Are Not Equal: Markedly Affect Gene Expression in Constructs from Different Sources." International Journal of Medical Sciences (2014) 11(5):404-408.
International Search Report for PCT/US2017/065597 dated Mar. 6, 2018.
Edwards et al., 2003, The remarkable flexibility of the human antibody repertoire; isolation of over one thousand different antibodies to a single protein, BLyS, J. Mol. Biol., 334:103-118.
Kanamori et al., A human-tissue type whose host is a human cell expression of plasminogen activator, Tissue Culture Research, 8(2):31-39, 1990.
Kochenderfer et al., Accession No. ADM64594.1, FMC63-28Z receptor protein, Jun. 11, 2012, Genbank.
Lin et al., 2009, Optimization and validation of a robust human T-cell culture method for monitoring phenotypic and polyfunctional antigen-specific CD4 and CD8 T-cell responses, Cytotherapy, 11(7):912-922.
Lloyd et al., 2009, Modelling the human immune response: performance of a $10^{11}$ human antibody repertoire against a broad panel of therapeutically relevant antigens, Protein Engineering, Design & Selection 22(3):159-168.
Sadelain et al., 2009, The promise and potential pitfalls of chimeric antigen receptors, Current Opinion in Immunology, 21:215-223.

CHIMERIC TRANSCRIPTION FACTOR VARIANTS WITH AUGMENTED SENSITIVITY TO DRUG LIGAND INDUCTION OF TRANSGENE EXPRESSION IN MAMMALIAN CELLS

INCORPORATION BY REFERENCE TO A PRIORITY APPLICATION

This application is a U.S. National Phase Application of PCT International Application Number PCT/US2017/065597, filed on Dec. 11, 2017, designating the United States of America and published in the English language, which is an International Application of and claims the benefit of priority to U.S. Provisional Application No. 62/433,183, filed on Dec. 12, 2016. The disclosures of the above-referenced applications are hereby expressly incorporated by reference in their entireties.

REFERENCE TO SEQUENCE LISTING, TABLE, OR COMPUTER PROGRAM LISTING

The present application is being filed along with a Sequence Listing in electronic format. The Sequence Listing is provided as a file entitled SeqList-SCRI-118NP.txt, created Jun. 4, 2019, which is 294 kb in size. The information provided is the electronic format of the Sequence Listing and is hereby expressly incorporated by reference in its entirety.

FIELD OF THE INVENTION

Disclosed herein are embodiments relating to genetic systems that facilitate drug-regulated transgene expression in cells, for instance mammalian cells. The present disclosure also concerns the identification of variants of the wild-type HEA3 and wild-type HEA4 chimeric transcription factors, which are useful for the regulation of transgene expression in genetically modified cells including mammalian cells.

BACKGROUND

Human T lymphocytes can be engineered by gene transfer to express chimeric antigen receptors (CARs), which are specific for surface molecules expressed on tumor cells. Methods of gene transfer useful for this purpose include several types of viral transduction using viral vectors encoding the chimeric antigen receptors. Cells expressing the chimeric antigen receptors can then be adoptively transferred to patients to treat cancer and infectious diseases. Chimeric antigen receptors are synthetic receptors. These synthetic receptors, can include an extracellular ligand binding domain, for example, a single chain variable fragment of a monoclonal antibody (scFv) linked to intracellular signaling components, such as CD3ζ alone or combined with one or more costimulatory domains. Research in the design of chimeric receptors has focused on defining scFvs and other ligand binding elements that target malignant cells without causing severe toxicity to normal tissues, and on defining the optimal composition of intracellular signaling modules to activate T cell effector functions. Additional genetic systems that facilitate expression of chimeric antigen receptors are needed.

SUMMARY OF THE INVENTION

Aspects of the present invention concern genetic systems that facilitate drug-regulated transgene expression in cells.

In one alternative, regulated transgene expression is targeted to cells, such as lymphocytes, preferably human lymphocytes, which are designed for use in adoptive immunotherapy. This system provides rigorous safety attributes to chimeric antigen receptor (CAR) redirected adoptive therapeutic strategies without sacrificing curative intent that permits real-time clinician control of CAR expression in vivo. By engineering vectors that enable drug responsive transcriptional control of CAR expression, the activity of CARs and other cell mediators can be turned "ON" and "OFF" in vivo, based on a clinician prescribed pharmaceutical drug input that exhibits clinically permissive pharmacokinetics, tissue distribution, and partitioning between the extracellular space and cytosol of lymphocytes. In addition to adenovirus and lentivirus genes, the vector platform can also include genes encoding minicircles or piggy bac transposons. The genetic systems described herein provide for drug regulated transgene expression to enforce a functional "OFF" state in the absence of the drug and a functional "ON" state transgene expression in the presence of the drug.

One alternative of such an approach utilizes the drug tamoxifen. Tamoxifen is an estrogen antagonist/partial agonist that is an FDA-approved and commercially available drug. It is taken orally and can be administered daily and over an extended period. Tamoxifen has a proven safety record, favorable pharmacokinetic profile, excellent tissue distribution and a low partition coefficient between the extracellular space and cytosol. Other drugs useful in the approaches described herein can be selected based on safety record, favorable pharmacokinetic profile, and excellent tissue distribution, a low partition coefficient between the extracellular space and cytosol, and/or low toxicities.

Tamoxifen can have several side effects, however, such as cataracts, changes in menstrual period, constipation, diarrhea, edema (swelling), fatigue, fluid retention, flushing, headache, hot flashes, high blood pressure, muscle pain, nausea, shortness of breath, vomiting and weight loss, for example. As such, it is necessary to turn on a gene for expressing the chimeric antigen receptor at a low plasma concentration of tamoxifen for some patients.

One aspect of the disclosure relates to changes that can be made to transcriptional activators so as to modulate the properties of the transcription factors including, without limitation, altering one or more amino acids in the estrogen receptor ligand binding domain so as to increase the affinity of the factor for estrogen analogs and altering one or more amino acids in the p65 transactivating domain and/or the RelA (p65) transactivation domain, in which altering the amino acids in the p65 transactivating domain (RelA) can enhance the transcriptional activity in response to a drug. The RelA mutations enhance transcriptional activity in response to the drug, however, they do not affect drug-to-receptor binding. Only the mutations in the ER-LBD affect drug-to-receptor binding. In some alternatives, the system employs a synthetic transcriptional regulator, which, in the presence of tamoxifen, binds a synthetic promoter upstream of a transgene to induce expression. The tamoxifen regulated transcription factors ("TamR-tf", also can refer to HEA3/HEA4 transcription factors) is a chimeric transcription factor composed of human subunits including the N-terminal DNA binding domain of Hepatocyte Nuclear Factor 1-alpha (HNF-1α) fused in frame to the mutant tamoxifen-specific ligand binding domain of the estrogen receptor ligand binding domain (ER-LBD), that is in turn fused to the p65 activation domain of NF-κB (p65). HEA4 is a chimeric transcription factor composed of human subunits including the N-terminal DNA binding domain of Hepatocyte Nuclear Factor 1-alpha (HNF-1α) fused in frame to the mutant tamoxifen-specific ligand binding domain of the estrogen receptor ligand binding domain (ER-LBD) containing three point mutations (G400V, M543A, L544A) that abolish estradiol binding but permit binding to tamoxifen metabolites and other estrogen analogues, that is in turn fused to the p65 activation domain of NF-κB (p65). An exemplary amino acid sequence is set forth in SEQ ID NO: 1 (MVSKLSQLQTELLAALLESGLSKEALIQALGEPGPYLLAGEGPLDKGESCGGGRGEL AELPNGLGETRGSEDETDDDGEDFTPPILKELENLSPEEAAHQKAVVETLLQE DPWR VAKMVKSYLQQHNIPQREVVDTTGLNQSHLSQHLNKGTPMKT QKRAALYTWYVR KQREVAQQFTHAGQGGLIEEPTGDELPTKKGRRNRFKWGPASQQILFQAYERQKNP SKEERETLVEECNRAECIQRGVSPSQAQGLGSNLVTEVRVYNWFANRRKEEAFRHK LSAGDMRAANLWPSPLMIKRSKKNSLALSLTADQMVSALLDAEPPILYSEYDPTRPF SEASMMGLLTNLADRELVHMINWAKRVPGFVDLTLHDQVHLLECAWLEILMIGLV WRSMEHPGKLLFAPNLLLDRNQGKCVEGMVEIFDMLLATSSRFRMMNLQGEEFVC LKSIILLNSGVYTFLSSTLKSLEEKDHIHRVLDKITDTLIHLMAKAGLTLQQQHQRLA QLLLILSHIRHMSNKRMEHLYSMKCKNVVPLYDLLLEMLDAHRLHAPTSRGGASVE ETDQSHLATAGSTSSHSLQKYYITGEAEGFPATVEFQYLPDTDDRHRIEEKRKRTYET FKSIMKKSPFSGPTDPRPPPRRIAVPSRSSASVPKPAPQPYPFTSSLSTINYDEFPTMVFP SGQISQASALAPAPPQVLPQAPAPAPAPAMVSALAQAPAPVPVLAPGPPQAVAPPAP KPTQAGEGTLSEALLQLQFDDEDLGALLGNSTDPAVFTDLASVDNSEFQQLLNQGIP VAPHTTEPMLMEYPEAITRLVTGAQRPPDPAPAPLGAPGLPNGLLSGDEDFSSIADM DFSALLSQISS). SEQ ID NO: 1 comprises one point mutation in the ER-LBD that ablates binding to endogenous estrogen, but confers nanomolar specificity to tamoxifen metabolite 4-OHT fulvestrant and other estrogen analogs. The mutant tamoxifen-specific ligand binding domain of the estrogen receptor ligand binding domain (ER-LBD) is found at amino acids 282-595 of the TamR-tf and has a mutation at position 521 (G521R), and affects drug-to-receptor binding. The p65 activation domain of NF-κB (p65) is found at amino acids 596-862 of SEQ ID NO: 1 (MVSKLSQLQTELLAALLESGLSKEALIQALGEPGPYLLAGEGPLDKGESCGGGRGEL AELPNGLGETRGSEDETDDDGEDFTPPILKELENLSPEEAAHQKAVVETLLQEDPWR VAKMVKSYLQQHNIPQREVVDTTGLNQSHLSQHLNKGTPMKT QKRAALYTWYVR KQREVAQQFTHAGQGGLIEEPTGDELPTKKGRRNRFKWGPASQQILFQAYERQKNP SKEERETLVEECNRAECIQRGVSPSQAQGLGSNLVTEVRVYNWFANRRKEEAFRHK LSAGDMRAANLWPSPLMIKRSKKNSLALSLTADQMVSALLDAEPPILYSEYDPTRPF SEASMMGLLTNLADRELVHMINWAKRVPGFVDLTLHDQVHLLECAWLEILMIGLV WRSMEHPGKLLFAPNLLLDRNQGKCVEGMVEIFDMLLATSSRFRMMNLQGEEFVC LKSIILLNSGVYTFLSSTLKSLEEKDHIHRVLDKITDTLIHLMAKAGLTLQQQHQRLA QLLLILSHIRHMSNKRMEHLYSMKCKNVVPLYDLLLEMLDAHRLHAPTSRGGASVE ETDQSHLATAGSTSSHSLQKYYITGEAEGFPATVEFQYLPDTDDRHRIEEKRKRTYET FKSIMKKSPFSGPTDPRPPPRRIAVPSRSSASVPKPAPQPYPFTSSLSTINYDEFPTMVFP SGQISQASALAPAPPQVLPQAPAPAPAPAMVSALAQAPAPVPVLAPGPPQAVAPPAP KPTQAGEGTLSEALLQLQFDDEDLGALLGNSTDPAVFTDLASVDNSEFQQLLNQGIP VAPHTTEPMLMEYPEAITRLVTGAQRPPDPAPAPLGAPGLPNGLLSGDEDFSSIADM DFSALLSQISS).

In the absence of tamoxifen, TamR-tf is excluded from the nucleus by binding of cytosolic heat-shock protein 90 (HSP90) to the tamoxifen binding active site and transgene expression is in the "OFF" state. Nanomolar concentrations of cytosolic tamoxifen actively out compete HSP90 for ER-LBD binding, resulting in TamR-tf translocation to the nucleus. Upon nuclear translocation, TamR-tf is readily available to bind its restricted synthetic promoter (e.g. 7×HBD/mE1B as set forth in the nucleic acid sequence of SEQ ID NO: 23 (tagttaataatctacaatagttaataatctacaatagttaataatctacaatagttaataatctacaatagttaataatctacaatagttaataatctacaatagttaataatctacaagagctcagggtatataatg). In the presence of tamoxifen, binding of TamR-tf to 7×HBD/mE1B promoter induces the "ON" state of transgene expression. In some alternatives, this transcriptional regulator can be modified to provide for a varying level of control of transgene expression. Amino acid substitutions in the LBD of TamR-tf permit selective responsiveness to tamoxifen and its metabolites, which affect the drug-to-receptor binding, where 4-hydroxy tamoxifen (4-OHT) is the most pharmacologically active metabolite, with respect to TamR-tf activity, while lacking interaction with endogenous estrogen.

In some alternatives, variants of wild-type HEA3 and wild-type HEA4 are identified with augmented sensitivity to a drug by virtue of substitutions of the human estrogen receptor ligand binding domain. Mutations in the RelA (p65) transactivation domain augment transcriptional activity in response to drug or drug ligand. In some alternatives, these high affinity forms are generated by amino acid substitutions within the human estrogen receptor that confer selective binding to 4-OHT and other estrogen analogs such as fulvestrant. These changes cooperatively enhance transgene expression in response to drug activators when combined with amino acid substitutions in the HEA3 and HEA4 RelA domain that function as phosphomimetics and acetyl-mimetics, for example. Also described herein is a preferred version of the variant housing all three modifications that does not adversely affect the stringency of the "OFF" state in the absence of ligand, but dramatically improves the sensitivity and magnitude of transgene expression to activating estrogen analogue drug inputs. In another aspect, HEA3 is rendered responsive to the drug CMP8 due to mutations in the ER-LBD (L384M, M421G, G521R), not RelA mutations. The RelA mutations may not affect specificity to drug. The RelA mutations may enhance transcriptional activity. These enhanced HEA3 and HEA4 chimeric transcription factors make this regulatory system responsive to input drug levels that can easily be reached with low dose non-toxic dosing of tamoxifen, fulvestrant, or CMP8.

In a first aspect, a system for inducible expression of a chimeric antigen receptor in cells, such as mammalian cells, is provided. The system comprises: a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and any other selected molecule expressed on a target cell population, wherein the ligand elicits recognition, modulation, inhibition, and/or elimination by a lymphocyte; a second polynucleotide, which encodes a polypeptide spacer, preferably an optimized spacer; a third polynucleotide, which encodes a transmembrane domain; and a fourth polynucleotide, which encodes an intracellular signaling domain; and b) a second nucleic acid comprising a second promoter that is operably linked to a nucleic acid encoding a transcriptional activator for the first promoter, which is inducible by a drug, wherein the system is inducible by an amount of the drug that is less than a comparable system utilizing a wild type HEA3 chimeric transcription factor, or the system has an enhanced transcriptional expression at a given concentration of the drug as compared to a wild type HEA3 chimeric transcription factor. In some alternatives, the transcriptional activator for the first promoter inducible by a drug, is HEA3 or HEA4. In some alternatives, HEA3 is a variant of a wild type HEA3 transcription factor. In some alternatives, HEA4 is a variant of a wild type HEA4 transcription factor. In some alternatives, HEA3 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives, the at least one mutation affects the drug-to-receptor binding. In some alternatives, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives, HEA4 comprises an estrogen receptor ligand binding domain (ER-LBD) and a RelA (p65) transactivation domain, wherein the RelA (p65) transactivation domain comprises at least one mutation that augments transcriptional expression at a given concentration compared to a system using a wild type HEA3. In some alternatives, the variant of the HEA3 or HEA4 chimeric transcription factor comprises p65 phosphomimetic and/or acetylmimetic amino acid substitutions that enhance transcriptional activity in response to the drug ligand. In some alternatives, the variant of the wild type HEA3 transcription factor comprises at least one or more amino acid sequence set forth in SEQ ID Nos: 1-3, 8-11 and 121. In some alternatives, the variant of the wild type HEA3 transcription factor is encoded by at least one or more nucleic acid sequences set forth in SEQ ID NO: 12, 13, 14, 19, 20, 21, 22 or 122. In some alternatives, the variant of a wild type HEA4 transcription factor comprises at least one or more amino acid sequences set forth in SEQ ID Nos: 4-7. In some alternatives, the variant of the wild type HEA4 transcription factor is encoded by at least one or more nucleic acid sequences set forth in SEQ ID NO: 15, 16, 17 or 18. In some alternatives, the drug is tamoxifen and/or its metabolites, 4-hydroxytamoxifen, fulvestrant or other estrogen analogs, or CMP8. In some alternatives, the first promoter comprises a nucleic acid sequence set forth in SEQ ID NO: 23. In some alternatives, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or at a concentration that is within a range defined by any two of the aforementioned values, as compared to a wild type HEA3 or a wild type HEA4 chimeric transcription factor. In some alternatives, the drug induces expression of the chimeric antigen receptor at a non-toxic dosing of drug at less than 10 nM drug but not zero. In some alternatives, the non-toxic dosing of drug decreases, eliminates or prevents drug side effects in comparison to a dosage amount for inducing expression with a wild type HEA3 chimeric transcription factor. In some alternatives, the side effects are cataracts, constipation, diarrhea, edema, fatigue, fluid retention, flushing, headache, hot flashes, high blood pressure, muscle pain, nausea, shortness of breath, vomiting or weight loss. In some alternatives, the signaling domain comprises a CD28, 4-1BB and/or CD3ζ domain. In some alternatives, the second promoter is an inducible promoter. In some alternatives, the second promoter is a constitutive promoter. In some alternatives, the second promoter is the EF1αp. In some alternatives, the transcriptional activator comprises at least one or more amino acid sequences set forth in SEQ ID NO: 1-11 or 121. In some alternatives, the transcriptional activator is encoded by at least one or more nucleic acid sequences set forth in SEQ ID NO: 12-22 or 122. In some alternatives, the first nucleic acid further comprises a first vector and the second nucleic acid further comprises a second vector. In some alternatives, both vectors are packaged in a viral vector. In some alternatives, the viral vector is an adeno-associated virus or a lentivirus. In some alternatives, the first nucleic acid further comprises a fifth polynucleotide that encodes a selectable marker. In some alternatives, the second nucleic acid further comprises a sixth polynucleotide that encodes a selectable marker. In some alternatives, the selectable marker is EGFRt and/or HER2t. In some alternatives, the selectable marker confers drug resistance. In some alternatives, the first nucleic acid further comprises a seventh polynucleotide that encodes a self-cleaving peptide. In some alternatives, the self-cleaving peptide comprises a P2A, T2A, E2A or F2A peptide. In some alternatives, the spacer is optimized for increased T cell proliferation and/or cytokine production in response to the ligand, as compared to a reference chimeric receptor. In some alternatives, the transcriptional regulator is a variant of a HEA3 chimeric transcription factor, wherein the variant comprises amino acid substitutions that allow selective binding to the drug. In some alternatives, the drug is tamoxifen and/or its metabolites, 4-hydroxytamoxifen, fulvestrant or other estrogen analogs, or CMP8. In some alternatives, the drug induces a level of expression of the chimeric antigen receptor that is greater than a wild type HEA3 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives, the drug induces expression of the chimeric antigen receptor at a non-toxic dosing of drug at less than 10 nM drug but not zero. In some alternatives, the non-toxic dosing of drug decreases, eliminates or prevents drug side effects in comparison to a dosage for inducing expression with a wild type HEA3 or wild type HEA4 chimeric transcription factor. In some alternatives, the side effects are cataracts, constipation, diarrhea, edema, fatigue, fluid retention, flushing, headache, hot flashes, high blood pressure, muscle pain, nausea, shortness of breath, vomiting or weight loss. In some alternatives, the second nucleic acid further comprises a polynucleotide encoding a chimeric antigen receptor comprising a ligand binding domain, which is a tumor specific molecule, viral specific molecule, or any other selected molecule expressed on a target cell population, wherein the ligand elicits recognition, modulation, inhibition, and/or elimination by a lymphocyte; a polynucleotide coding for a polypeptide spacer, wherein the spacer is preferably optimized, a polynucleotide coding for a transmembrane domain and a polynucleotide encoding an intracellular signaling domain. In some alternatives, the first promoter is in opposite orientation to the second promoter. In some alternatives, the ligand binding domain is an antibody fragment, such as a binding fragment. In some alternatives, the ligand binding domain is a single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combinations thereof. In some alternatives, the viral specific molecule is an HIV envelope protein or HIV envelope protein complex, Hepatitis C virus NS3 protein, HbcAg protein, HIV-1 GP120 protein, and/or Epstein-Barr virus early antigen protein. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives, the first nucleic acid further comprises a DNA spacer, wherein the spacer is operably linked to the first promoter and operably linked to the first polynucleotide that encodes the chimeric antigen receptor. In some alternatives, the DNA spacer is between the first promoter and the first polynucleotide that encodes the chimeric antigen receptor. In some alternatives, the DNA spacer comprises a sequence set forth in SEQ ID NO: 120. In some alternatives, the DNA spacer comprises a sequence that has 95%, 90%, 85% or 80% sequence identity to SEQ ID NO: 120 or any percent sequence identity in between a range defined by any two aforementioned values. In some alternatives, the DNA spacer enhances gene expression of the chimeric antigen receptor.

In a second aspect, a system for inducible expression of a gene that regulates a T cell function is provided. The system comprises: a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity, and b) a second nucleic acid comprising a second promoter, wherein the second nucleic acid is operably linked to a third nucleic acid that encodes a transcriptional activator for the first promoter, which is inducible by a drug and, wherein the system is configured to respond to an amount of the drug that is less than a comparable system utilizing a wild type HEA3 chimeric transcription factor, or the system has an enhanced transcriptional expression at a given concentration of the drug compared to a wild type HEA3. In some alternatives, the transcriptional activator is HEA3 or HEA4. In some alternatives, HEA3 is a variant of a wild type HEA3 transcription factor. In some alternatives, HEA4 is a variant of a wild type HEA4 transcription factor. In some alternatives, HEA3 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives, HEA3 or HEA4 chimeric transcription factor comprises p65 phosphomimetic and/or acetylmimetic amino acid substitutions that enhance transcriptional activity in response to the drug ligand. In some alternatives, the variant of a wild type HEA3 transcription factor comprises at least one or more amino acid sequences set forth in SEQ ID Nos: 1-3 and/or 8-11 and/or 121. In some alternatives, the variant of the wild type HEA3 transcription factor is encoded by at least one or more nucleic acid sequences set forth in SEQ ID NO: 12, 13, 14, 19, 20, 21, 22 and/or 122. In some alternatives, the variant of a wild type HEA4 transcription factor comprises at least one or more amino acid sequences set forth in SEQ ID Nos: 4-7. In some alternatives, the variant of the wild type HEA4 transcription factor is encoded by at least one or more nucleic acid sequences set forth in SEQ ID NO: 15, 16, 17 or 18. In some alternatives, the transcriptional regulator is a variant of a HEA3 chimeric transcription factor, wherein the variant comprises amino acid substitutions that allow selective binding to the drug. In some alternatives, the drug is tamoxifen and/or its metabolites, 4-hydroxytamoxifen, fulvestrant or other estrogen analogs, or CMP8. In some alternatives, the drug induces a level of expression of the chimeric antigen receptor that is greater than a wild type HEA3 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives, the drug induces expression of the chimeric antigen receptor at a non-toxic dosing of drug at less than 10 nM drug but not zero. In some alternatives, the non-toxic dosing of drug decreases, eliminates or prevents drug side effects in comparison to a dosage for inducing expression with a wild type HEA3 or wild type HEA4 chimeric transcription factor. In some alternatives, the side effects are cataracts, constipation, diarrhea, edema, fatigue, fluid retention, flushing, headache, hot flashes, high blood pressure, muscle pain, nausea, shortness of breath, vomiting or weight loss. In some alternatives, the second nucleic acid further comprises a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte, a polynucleotide coding for a polypeptide spacer, wherein the spacer is preferably optimized, a polynucleotide coding for a transmembrane domain; and a polynucleotide encoding an intracellular signaling domain. In some alternatives, the first promoter is in opposite orientation to the second promoter. In some alternatives, the ligand binding domain is an antibody fragment, such as a binding fragment. In some alternatives, the ligand binding domain is a single chain variable fragment. In some alternatives, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combinations thereof. In some alternatives, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives, the first nucleic acid further comprises a DNA spacer, wherein the spacer is operably linked to the first promoter and operably linked to the first polynucleotide that encodes the chimeric antigen receptor. In some alternatives, the DNA spacer is between the first promoter and the first polynucleotide that encodes the chimeric antigen receptor. In some alternatives, the DNA spacer comprises a sequence set forth in SEQ ID NO: 120. In some alternatives, the DNA spacer comprises a sequence that has 95%, 90%, 85% or 80% sequence identity to SEQ ID NO: 120 or any percent sequence identity in between a range defined by any two aforementioned values. In some alternatives, the DNA spacer enhances gene expression of the chimeric antigen receptor. In some alternatives, the first nucleic acid further comprises a first vector and the second nucleic acid further comprises a second vector. In some alternatives, both vectors are packaged in a viral vector. In some alternatives, the viral vector is an adeno-associated virus or a lentivirus. In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123.

In a third aspect, a chimeric receptor polypeptide coded for by the first second and/or second nucleic acid of the system of any one of the alternative systems described herein. In some alternatives, the system is for inducible expression of a chimeric antigen receptor in cells, such as mammalian cells. In some alternatives of the system for inducible expression of a chimeric antigen receptor in cells, such as mammalian cells, the system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral molecule, or other molecule expressed on a target cell population, wherein the ligand elicits recognition, modulation, inhibition, and/or elimination by a lymphocyte, a second polynucleotide, which encodes a polypeptide spacer, preferably an optimized spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system for inducible expression of a chimeric antigen receptor in cells, the transcriptional activator is HEA3 or HEA4. In some alternatives of the system for inducible expression of a chimeric antigen receptor in cells, HEA3 is a variant of a wild type HEA3 transcription factor. In some alternatives of the system for inducible expression of a chimeric antigen receptor in cells, HEA4 is a variant of a wild type HEA4 transcription factor. In some alternatives of the system for inducible expression of a chimeric antigen receptor in cells, HEA3 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a chimeric antigen receptor in cells, the variant of the wild type HEA3 transcription factor comprises at least one or more amino acid sequences set forth in SEQ ID Nos: 1-3, 8-11 and/or 121. In some alternatives of the system for inducible expression of a chimeric antigen receptor in cells, the variant of the wild type HEA3 transcription factor is encoded by at least one or more nucleic acid sequences set forth in SEQ ID NO: 12, 13, 14, 19, 20, 21, 22 and/or. 122 In some alternatives of the system for inducible expression of a chimeric antigen receptor in cells, the variant of a wild type HEA4 transcription factor comprises at least one or more amino acid sequences set forth in SEQ ID Nos: 4-7. In some alternatives of the system for inducible expression of a chimeric antigen receptor in cells, the variant of the wild type HEA4 transcription factor is encoded by at least one or more nucleic acid sequences set forth in SEQ ID NO: 15, 16, 17 and/or 18. In some alternatives of the system for inducible expression of a chimeric antigen receptor in cells, the drug is tamoxifen and/or its metabolites, 4-hydroxytamoxifen, fulvestrant or other estrogen analogs, or CMP8. In some alternatives of the system for inducible expression of a chimeric antigen receptor in cells, the first promoter comprises a nucleic acid sequence set forth in SEQ ID NO: 23. In some alternatives of the system for inducible expression of a chimeric antigen receptor in cells, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system for inducible expression of a chimeric antigen receptor in cells, the drug induces expression of the chimeric antigen receptor at a non-toxic dosing of drug at less than 10 nM drug but not zero. In some alternatives of the system for inducible expression of a chimeric antigen receptor in cells, the non-toxic dosing of drug decreases, eliminates or prevents drug side effects in comparison to a dosage amount for inducing expression with a wild type HEA3 or wild type HEA4 chimeric transcription factor. In some alternatives of the system for inducible expression of a chimeric antigen receptor in cells, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system for inducible expression of a chimeric antigen receptor in cells, the signaling domain comprises a CD28, 4-1BB and/or CD3ζ domain. In some alternatives of the system for inducible expression of a chimeric antigen receptor in cells, the second promoter is an inducible promoter. In some alternatives of the system for inducible expression of a chimeric antigen receptor in cells, the second promoter is a constitutive promoter. In some alternatives of the system for inducible expression of a chimeric antigen receptor in cells, the second promoter is the EF1αp. In some alternatives of the system for inducible expression of a chimeric antigen receptor in cells, the transcriptional activator comprises at least one or more amino acid sequences set forth in SEQ ID NO: 1-11 or 121. In some alternatives of the system for inducible expression of a chimeric antigen receptor in cells, the transcriptional activator is encoded by at least one or more nucleic acid sequences set forth in SEQ ID NO: 12-22 or 122. In some alternatives of the system for inducible expression of a chimeric antigen receptor in cells, the first nucleic acid further comprises a first vector and the second nucleic acid further comprises a second vector. In some alternatives of the system for inducible expression of a chimeric antigen receptor in cells, both vectors are packaged in a viral vector. In some alternatives of the system for inducible expression of a chimeric antigen receptor in cells, the viral vector is an adeno-associated virus or a lentivirus. In some alternatives of the system for inducible expression of a chimeric antigen receptor in cells, the first nucleic acid further comprises a fifth polynucleotide that encodes a selectable marker. In some alternatives of the system for inducible expression of a chimeric antigen receptor in cells, the second nucleic acid further comprises a sixth polynucleotide that encodes a selectable marker. In some alternatives of the system for inducible expression of a chimeric antigen receptor in cells, the selectable marker is EGFRt and/or HER2t. In some alternatives of the system for inducible expression of a chimeric antigen receptor in cells, the selectable marker confers drug resistance. In some alternatives of the system for inducible expression of a chimeric antigen receptor in cells, the first nucleic acid further comprises a seventh polynucleotide that encodes a self-cleaving peptide. In some alternatives of the system for inducible expression of a chimeric antigen receptor in cells, the self-cleaving peptide comprises a P2A, T2A, E2A or F2A peptide. In some alternatives of the system for inducible expression of a chimeric antigen receptor in cells, the spacer is optimized for increased T cell proliferation and/or cytokine production in response to the ligand as compared to a reference chimeric receptor. In some alternatives, the system is a system for inducible expression of a gene that regulates a T cell function. In some alternatives, the system for inducible expression of a gene that regulates a T cell function comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity and b) a second nucleic acid comprising a second promoter, wherein the second nucleic acid is operably linked to a third nucleic acid that encodes a transcriptional activator for the first promoter inducible by drug and wherein the system is configured to respond to an amount of the drug that is less than a comparable system utilizing a wild type HEA3 chimeric transcription factor or a wild type HEA4 chimeric transcription factor. In some alternatives of the system for inducible expression of a gene that regulates a T cell function, the transcriptional activator is HEA3 or HEA4. In some alternatives of the system for inducible expression of a gene that regulates a T cell function, HEA3 is a variant of a wild type HEA3 transcription factor. In some alternatives of the system for inducible expression of a gene that regulates a T cell function, HEA4 is a variant of a wild type HEA4 transcription factor. In some alternatives of the system for inducible expression of a gene that regulates a T cell function, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a gene that regulates a T cell function, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a gene that regulates a T cell function, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a gene that regulates a T cell function, the variant of a wild type HEA3 transcription factor comprises at least one or more amino acid sequences set forth in SEQ ID Nos: 1-3, 8-11 and/or 121. In some alternatives of the system for inducible expression of a gene that regulates a T cell function, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a gene that regulates a T cell function, the variant of a wild type HEA4 transcription factor comprises at least one or more amino acid sequences set forth in SEQ ID Nos: 4-7. In some alternatives of the system for inducible expression of a gene that regulates a T cell function, the variant of the wild type HEA4 transcription factor is encoded by at least one or more nucleic acid sequences set forth in SEQ ID NO: 15, 16, 17 or 18. In some alternatives of the systems described herein, the transcriptional regulator is a variant of a HEA3 chimeric transcription factor, and wherein the variant comprises amino acid substitutions that allow selective binding to the drug. In some alternatives of the systems described herein, the drug is tamoxifen and/or its metabolites, 4-hydroxytamoxifen, fulvestrant or other estrogen analogs, or CMP8. In some alternatives of the systems described herein, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the systems described herein, the drug induces expression of the chimeric antigen receptor at a non-toxic dosing of drug at less than 10 nM drug but not zero. In some alternatives of the systems described herein, the non-toxic dosing of drug decreases, eliminates or prevents drug side effects in comparison to a dosage for inducing expression with a wild type HEA3 or wild type HEA4 chimeric transcription factor. In some alternatives of the systems described herein, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the systems described herein, the second nucleic acid further comprises a polynucleotide encoding a chimeric antigen receptor comprising a ligand binding domain, which is a tumor specific molecule, viral specific molecule, or any other selected molecule expressed on a target cell population, wherein the ligand elicits recognition, modulation, inhibition, and/or elimination by a lymphocyte, a polynucleotide coding for a polypeptide spacer, wherein the spacer is preferably optimized, a polynucleotide coding for a transmembrane domain, and a polynucleotide encoding an intracellular signaling domain. In some alternatives of the systems described herein, the first promoter is in opposite orientation to the second promoter. In some alternatives of the systems described herein, the ligand binding domain is an antibody fragment. In some alternatives of the systems described herein, the ligand binding domain is a single chain variable fragment. In some alternatives of the systems described herein, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or combinations thereof. In some alternatives of the systems described herein, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives of the systems described herein, the first nucleic acid further comprises a DNA spacer, wherein the spacer is operably linked to the first promoter and operably linked to the first polynucleotide that encodes the chimeric antigen receptor. In some alternatives of the systems described herein, the DNA spacer is between the first promoter and the first polynucleotide that encodes the chimeric antigen receptor. In some alternatives of the systems described herein, the DNA spacer comprises a sequence set forth in SEQ ID NO: 120. In some alternatives of the systems described herein, the DNA spacer comprises a sequence that has 95%, 90%, 85% or 80% sequence identity to SEQ ID NO: 120 or any percent sequence identity in between a range defined by any two aforementioned values. In some alternatives of the systems described herein, the DNA spacer enhances gene expression of the chimeric antigen receptor. In some alternatives, the first nucleic acid further comprises a first vector and the second nucleic acid further comprises a second vector. In some alternatives of the systems described herein, both vectors are packaged in a viral vector. In some alternatives of the systems described herein, the viral vector is an adeno-associated virus or a lentivirus. In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123.

In a fourth aspect, a host cell comprising a system of any one of the alternative systems described herein is provided. In some alternatives, the system is for inducible expression of a chimeric antigen receptor in cells, such as mammalian cells. In some alternatives of the system for inducible expression of a chimeric antigen receptor in cells, such as mammalian cells the system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral molecule, or other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system for inducible expression of a chimeric antigen receptor in cells, the transcriptional activator is HEA3 or HEA4. In some alternatives of the system for inducible expression of a chimeric antigen receptor in cells, HEA3 is a variant of a wild type HEA3 transcription factor. In some alternatives of the system for inducible expression of a chimeric antigen receptor in cells, HEA4 is a variant of a wild type HEA4 transcription factor. In some alternatives of the system for inducible expression of a chimeric antigen receptor in cells, HEA3 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a chimeric antigen receptor in cells, the variant of the wild type HEA3 transcription factor comprises at least one or more amino acid sequences set forth in SEQ ID Nos: 1-3 8-11 and/or. 121 In some alternatives of the system for inducible expression of a chimeric antigen receptor in cells, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a chimeric antigen receptor in cells, the variant of a wild type HEA4 transcription factor comprises at least one or more amino acid sequences set forth in SEQ ID Nos: 4-7. In some alternatives of the system for inducible expression of a chimeric antigen receptor in cells, the variant of the wild type HEA4 transcription factor is encoded by at least one or more nucleic acid sequences set forth in SEQ ID NO: 15, 16, 17 or 18. In some alternatives of the system for inducible expression of a chimeric antigen receptor in cells, the drug is tamoxifen and/or its metabolites, 4-hydroxytamoxifen, fulvestrant or other estrogen analogs, or CMP8. In some alternatives of the system for inducible expression of a chimeric antigen receptor in cells, the first promoter comprises a nucleic acid sequence set forth in SEQ ID NO: 23. In some alternatives of the system for inducible expression of a chimeric antigen receptor in cells, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system for inducible expression of a chimeric antigen receptor in cells, the drug induces expression of the chimeric antigen receptor at a non-toxic dosing of drug at less than 10 nM drug but not zero. In some alternatives of the system for inducible expression of a chimeric antigen receptor in cells, the non-toxic dosing of drug decreases, eliminates or prevents drug side effects in comparison to a dosage amount for inducing expression with a wild type HEA3 or wild type HEA4 chimeric transcription factor. In some alternatives of the system for inducible expression of a chimeric antigen receptor in cells, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system for inducible expression of a chimeric antigen receptor in cells, the signaling domain comprises a CD28, 4-1BB and/or CD3ζ domain. In some alternatives of the system for inducible expression of a chimeric antigen receptor in cells, the second promoter is an inducible promoter. In some alternatives of the system for inducible expression of a chimeric antigen receptor in cells, the second promoter is a constitutive promoter. In some alternatives of the system for inducible expression of a chimeric antigen receptor in cells, the second promoter is the EF1αp. In some alternatives of the system for inducible expression of a chimeric antigen receptor in cells, the transcriptional activator comprises at least one or more amino acid sequences set forth in SEQ ID NO: 1-11 or 121. In some alternatives of the system for inducible expression of a chimeric antigen receptor in cells, the transcriptional activator is encoded by at least one or more nucleic acid sequences set forth in SEQ ID NO: 12-22 or 122. In some alternatives of the system for inducible expression of a chimeric antigen receptor in cells, the first nucleic acid further comprises a first vector and the second nucleic acid further comprises a second vector. In some alternatives of the system for inducible expression of a chimeric antigen receptor in cells, both vectors are packaged in a viral vector. In some alternatives of the system for inducible expression of a chimeric antigen receptor in cells, the viral vector is an adeno-associated virus or a lentivirus. In some alternatives of the system for inducible expression of a chimeric antigen receptor in cells, the first nucleic acid further comprises a fifth polynucleotide that encodes a selectable marker. In some alternatives of the system for inducible expression of a chimeric antigen receptor in cells, the second nucleic acid further comprises a sixth polynucleotide that encodes a selectable marker. In some alternatives of the system for inducible expression of a chimeric antigen receptor in cells, the selectable marker is EGFRt and/or HER2t. In some alternatives of the system for inducible expression of a chimeric antigen receptor in cells, the selectable marker confers drug resistance. In some alternatives of the system for inducible expression of a chimeric antigen receptor in cells, the first nucleic acid further comprises a seventh polynucleotide that encodes a self-cleaving peptide. In some alternatives of the system for inducible expression of a chimeric antigen receptor in cells, the self-cleaving peptide comprises a P2A, T2A, E2A or F2A peptide. In some alternatives of the system for inducible expression of a chimeric antigen receptor in cells, the spacer is optimized for increased T cell proliferation and/or cytokine production in response to the ligand as compared to a reference chimeric receptor. In some alternatives, the system is for inducible expression of a gene that regulates a T cell function. In some alternatives, the system for inducible expression of a gene that regulates a T cell function comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity and b) a second nucleic acid comprising a second promoter, wherein the second nucleic acid is operably linked to a third nucleic acid that encodes a transcriptional activator for the first promoter inducible by drug and wherein the system is configured to respond to an amount of the drug that is less than a comparable system utilizing a wild type HEA3 chimeric transcription factor or a wild type HEA4 chimeric transcription factor. In some alternatives of the system for inducible expression of a gene that regulates a T cell function, the transcriptional activator is HEA3 or HEA4. In some alternatives of the system for inducible expression of a gene that regulates a T cell function, HEA3 is a variant of a wild type HEA3 transcription factor. In some alternatives of the system for inducible expression of a gene that regulates a T cell function, HEA4 is a variant of a wild type HEA4 transcription factor. In some alternatives of the system for inducible expression of a gene that regulates a T cell function, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a gene that regulates a T cell function, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a gene that regulates a T cell function, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a gene that regulates a T cell function, the variant of a wild type HEA3 transcription factor comprises at least one or more amino acid sequences set forth in SEQ ID Nos: 1-3, 8-11 and 121. In some alternatives of the system for inducible expression of a gene that regulates a T cell function, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a gene that regulates a T cell function, the variant of a wild type HEA4 transcription factor comprises at least one or more amino acid sequences set forth in SEQ ID Nos: 4-7. In some alternatives of the system for inducible expression of a gene that regulates a T cell function, the variant of the wild type HEA4 transcription factor is encoded by at least one or more nucleic acid sequences set forth in SEQ ID NO: 15, 16, 17 and/or 18. In some alternatives of the systems described herein, the transcriptional regulator is a variant of a HEA3 chimeric transcription factor, and wherein the variant comprises amino acid substitutions that allow selective binding to the drug. In some alternatives of the systems described herein, the drug is tamoxifen and/or its metabolites, 4-hydroxytamoxifen, fulvestrant or other estrogen analogs, or CMP8. In some alternatives of the systems described herein, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the systems described herein, the drug induces expression of the chimeric antigen receptor at a non-toxic dosing of drug at less than 10 nM drug but not zero. In some alternatives of the systems described herein, the non-toxic dosing of drug decreases, eliminates or prevents drug side effects in comparison to a dosage for inducing expression with a wild type HEA3 or wild type HEA4 chimeric transcription factor. In some alternatives of the systems described herein, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the systems described herein, the second nucleic acid further comprises a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte, a polynucleotide coding for a polypeptide spacer, wherein the spacer is optimized, a polynucleotide coding for a transmembrane domain, and a polynucleotide encoding an intracellular signaling domain. In some alternatives of the systems described herein, the first promoter is in opposite orientation to the second promoter. In some alternatives of the systems described herein, the ligand binding domain is an antibody fragment. In some alternatives of the systems described herein, the ligand binding domain is a single chain variable fragment. In some alternatives of the systems described herein, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and/or combinations thereof. In some alternatives of the systems described herein, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the systems described herein, the first nucleic acid further comprises a DNA spacer, wherein the spacer is operably linked to the first promoter and operably linked to the first polynucleotide that encodes the chimeric antigen receptor. In some alternatives of the systems described herein, the DNA spacer is between the first promoter and the first polynucleotide that encodes the chimeric antigen receptor. In some alternatives of the systems described herein, the DNA spacer comprises a sequence set forth in SEQ ID NO: 120. In some alternatives of the systems described herein, the DNA spacer comprises a sequence that has 95%, 90%, 85% or 80% sequence identity to SEQ ID NO: 120 or any percent sequence identity in between a range defined by any two aforementioned values. In some alternatives of the systems described herein, the DNA spacer enhances gene expression of the chimeric antigen receptor. In some alternatives, the first nucleic acid further comprises a first vector and the second nucleic acid further comprises a second vector. In some alternatives of the systems described herein, both vectors are packaged in a viral vector. In some alternatives of the systems described herein, the viral vector is an adeno-associated virus or a lentivirus. In some alternatives of the host cell, the host cell is a mammalian cell, such as a precursor T cell. In some alternatives of the host cell, the precursor T cell is a hematopoietic stem cell. In some alternatives of the host cell, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives of the host cell, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123.

In a fifth aspect, a composition comprising a host cell of any one or more of alternative host cells, such as mammalian cells, provided herein, in a pharmaceutically acceptable excipient, is provided. The host cell, such as a mammalian cell, comprises a system of any one of the alternative systems described herein is provided. In some alternatives, the system is for inducible expression of a chimeric antigen receptor in cells, such as mammalian cells. In some alternatives of the system for inducible expression of a chimeric antigen receptor in cells, such as mammalian cells, the system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral molecule, or other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system for inducible expression of a chimeric antigen receptor in cells, the transcriptional activator is HEA3 or HEA4. In some alternatives of the system for inducible expression of a chimeric antigen receptor in cells, HEA3 is a variant of a wild type HEA3 transcription factor. In some alternatives of the system for inducible expression of a chimeric antigen receptor in cells, HEA4 is a variant of a wild type HEA4 transcription factor. In some alternatives of the system for inducible expression of a chimeric antigen receptor in cells, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a chimeric antigen receptor in cells, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a chimeric antigen receptor in cells, the variant of the wild type HEA3 transcription factor comprises at least one or more amino acid sequences set forth in SEQ ID Nos: 1-3, 8-11 and/or 121. In some alternatives of the system for inducible expression of a chimeric antigen receptor in cells, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a chimeric antigen receptor in cells, the variant of a wild type HEA4 transcription factor comprises at least one or more amino acid sequences set forth in SEQ ID Nos: 4-7. In some alternatives of the system for inducible expression of a chimeric antigen receptor in cells, the variant of the wild type HEA4 transcription factor is encoded by at least one or more nucleic acid sequences set forth in SEQ ID NO: 15, 16, 17 or 18. In some alternatives of the system for inducible expression of a chimeric antigen receptor in cells, the drug is tamoxifen and/or its metabolites, 4-hydroxytamoxifen, fulvestrant or other estrogen analogs, or CMP8. In some alternatives of the system for inducible expression of a chimeric antigen receptor in cells, the first promoter comprises a nucleic acid sequence set forth in SEQ ID NO: 23. In some alternatives of the system for inducible expression of a chimeric antigen receptor in cells, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system for inducible expression of a chimeric antigen receptor in cells, the drug induces expression of the chimeric antigen receptor at a non-toxic dosing of drug at less than 10 nM drug but not zero. In some alternatives of the system for inducible expression of a chimeric antigen receptor in cells, the non-toxic dosing of drug decreases, eliminates or prevents drug side effects in comparison to a dosage amount for inducing expression with a wild type HEA3 or wild type HEA4 chimeric transcription factor. In some alternatives of the system for inducible expression of a chimeric antigen receptor in cells, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system for inducible expression of a chimeric antigen receptor in cells, the signaling domain comprises a CD28, 4-1BB and/or CD3ζ domain. In some alternatives of the system for inducible expression of a chimeric antigen receptor in cells, the second promoter is an inducible promoter. In some alternatives of the system for inducible expression of a chimeric antigen receptor in cells, the second promoter is a constitutive promoter. In some alternatives of the system for inducible expression of a chimeric antigen receptor in cells, the second promoter is the EF1αp. In some alternatives of the system for inducible expression of a chimeric antigen receptor in cells, the transcriptional activator comprises at least one or more amino acid sequences set forth in SEQ ID NO: 1-11 or 121. In some alternatives of the system for inducible expression of a chimeric antigen receptor in cells, the transcriptional activator is encoded by at least one or more nucleic acid sequences set forth in SEQ ID NO: 12-22 or 122. In some alternatives of the system for inducible expression of a chimeric antigen receptor in cells, the first nucleic acid further comprises a first vector and the second nucleic acid further comprises a second vector. In some alternatives of the system for inducible expression of a chimeric antigen receptor in cells, both vectors are packaged in a viral vector. In some alternatives of the system for inducible expression of a chimeric antigen receptor in cells, the viral vector is an adeno-associated virus or a lentivirus. In some alternatives of the system for inducible expression of a chimeric antigen receptor in cells, the first nucleic acid further comprises a fifth polynucleotide that encodes a selectable marker. In some alternatives of the system for inducible expression of a chimeric antigen receptor in cells, the second nucleic acid further comprises a sixth polynucleotide that encodes a selectable marker. In some alternatives of the system for inducible expression of a chimeric antigen receptor in cells, the selectable marker is EGFRt and/or HER2t. In some alternatives of the system for inducible expression of a chimeric antigen receptor in cells, the selectable marker confers drug resistance. In some alternatives of the system for inducible expression of a chimeric antigen receptor in cells, the first nucleic acid further comprises a seventh polynucleotide that encodes a self-cleaving peptide. In some alternatives of the system for inducible expression of a chimeric antigen receptor in cells, the self-cleaving peptide comprises a P2A, T2A, E2A or F2A peptide. In some alternatives of the system for inducible expression of a chimeric antigen receptor in cells, the spacer is optimized for increased T cell proliferation and/or cytokine production in response to the ligand as compared to a reference chimeric receptor. In some alternatives, the system is for inducible expression of a gene that regulates a T cell function. In some alternatives, the system is for inducible expression of a gene that regulates a T cell function comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity and b) a second nucleic acid comprising a second promoter, wherein the second nucleic acid is operably linked to a third nucleic acid that encodes a transcriptional activator for the first promoter inducible by drug and wherein the system is configured to respond to an amount of the drug that is less than a comparable system utilizing a wild type HEA3 chimeric transcription factor or a wild type HEA4 chimeric transcription factor. In some alternatives of the system for inducible expression of a gene that regulates a T cell function, the transcriptional activator is HEA3 or HEA4. In some alternatives of the system for inducible expression of a gene that regulates a T cell function, HEA3 is a variant of a wild type HEA3 transcription factor. In some alternatives of the system for inducible expression of a gene that regulates a T cell function, HEA4 is a variant of a wild type HEA4 transcription factor. In some alternatives of the system for inducible expression of a gene that regulates a T cell function, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a gene that regulates a T cell function, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a gene that regulates a T cell function, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a gene that regulates a T cell function, the variant of a wild type HEA3 transcription factor comprises at least one or more amino acid sequences set forth in SEQ ID Nos: 1-3, 8-11 and/or 121. In some alternatives of the system for inducible expression of a gene that regulates a T cell function, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a gene that regulates a T cell function, the variant of a wild type HEA4 transcription factor comprises at least one or more amino acid sequences set forth in SEQ ID Nos: 4-7. In some alternatives of the system for inducible expression of a gene that regulates a T cell function, the variant of the wild type HEA4 transcription factor is encoded by at least one or more nucleic acid sequences set forth in SEQ ID NO: 15, 16, 17 or 18. In some alternatives of the systems described herein, the transcriptional regulator is a variant of a HEA3 chimeric transcription factor, and wherein the variant comprises amino acid substitutions that allow selective binding to the drug. In some alternatives of the systems described herein, the drug is tamoxifen and/or its metabolites, 4-hydroxytamoxifen, fulvestrant or other estrogen analogs, or CMP8. In some alternatives of the systems described herein, the drug induces a level of expression of the chimeric antigen receptor that is greater than a wild type HEA3 or a wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the systems described herein, the drug induces expression of the chimeric antigen receptor at a non-toxic dosing of drug at less than 10 nM drug but not zero. In some alternatives of the systems described herein, the non-toxic dosing of drug decreases, eliminates or prevents drug side effects in comparison to a dosage for inducing expression with a wild type HEA3 or a wild type HEA4 chimeric transcription factor. In some alternatives of the systems described herein, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the systems described herein, the second nucleic acid further comprises a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte, a polynucleotide coding for a polypeptide spacer, wherein the spacer is optimized, a polynucleotide coding for a transmembrane domain, and a polynucleotide encoding an intracellular signaling domain. In some alternatives of the systems described herein, the first promoter is in opposite orientation to the second promoter. In some alternatives of the systems described herein, the ligand binding domain is an antibody fragment. In some alternatives of the systems described herein, the ligand binding domain is a single chain variable fragment. In some alternatives of the systems described herein, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and/or any combinations thereof. In some alternatives of the systems described herein, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the host cell, the host cell is a precursor T cell. In some alternatives of the systems described herein, the first nucleic acid further comprises a DNA spacer, wherein the spacer is operably linked to the first promoter and operably linked to the first polynucleotide that encodes the chimeric antigen receptor. In some alternatives of the systems described herein, the DNA spacer is between the first promoter and the first polynucleotide that encodes the chimeric antigen receptor. In some alternatives of the systems described herein, the DNA spacer comprises a sequence set forth in SEQ ID NO: 120. In some alternatives of the systems described herein, the DNA spacer comprises a sequence that has 95%, 90%, 85% or 80% sequence identity to SEQ ID NO: 120 or any percent sequence identity in between a range defined by any two aforementioned values. In some alternatives of the systems described herein, the DNA spacer enhances gene expression of the chimeric antigen receptor. In some alternatives, the first nucleic acid further comprises a first vector and the second nucleic acid further comprises a second vector. In some alternatives of the systems described herein, both vectors are packaged in a viral vector. In some alternatives of the systems described herein, the viral vector is an adeno-associated virus or a lentivirus. In some alternatives of the host cell, such as a mammalian cell, the cell is a precursor T cell, which can be a hematopoietic stem cell. In some alternatives of the host cell, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives of the host cell, the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and a host cell, wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or wherein the host cell is a CD4+T helper lymphocyte cell that is selected from the group consisting of naïve CD4+ T cells, central memory CD4+ T cells, effector memory CD4+ T cells, and bulk CD4+ T cells and a host cell wherein the host cell is a precursor T cell or a hematopoietic stem cell. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123.

In a sixth aspect, an in vitro method for preparing a host cell of any one of the alternative host cells, such as mammalian cells, described herein is provided. The host cell, such as a mammalian cell, comprises a system of any one of the alternative systems described herein. In some alternatives, the system is for inducible expression of a chimeric antigen receptor in cells, such as mammalian cells. In some alternatives of the system for inducible expression of a chimeric antigen receptor in cells, such as mammalian cells, the system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral specific molecule, or any other selected molecule expressed on a target cell population, wherein the ligand elicits recognition, modulation, inhibition, and/or elimination by a lymphocyte, a second polynucleotide, which encodes an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system for inducible expression of a chimeric antigen receptor in cells, the transcriptional activator is HEA3 or HEA4. In some alternatives of the system for inducible expression of a chimeric antigen receptor in cells, HEA3 is a variant of a wild type HEA3 transcription factor. In some alternatives of the system for inducible expression of a chimeric antigen receptor in cells, HEA4 is a variant of a wild type HEA4 transcription factor. In some alternatives of the system for inducible expression of a chimeric antigen receptor in cells, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a chimeric antigen receptor in cells, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a chimeric antigen receptor in cells, the variant of the wild type HEA3 transcription factor comprises at least one or more amino acid sequences set forth in SEQ ID Nos: 1-3, 8-11 and/or 121. In some alternatives of the system for inducible expression of a chimeric antigen receptor in cells, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a chimeric antigen receptor in cells, the variant of a wild type HEA4 transcription factor comprises at least one or more amino acid sequences set forth in SEQ ID Nos: 4-7. In some alternatives of the system for inducible expression of a chimeric antigen receptor in cells, the variant of the wild type HEA4 transcription factor is encoded by at least one or more nucleic acid sequences set forth in SEQ ID NO: 15, 16, 17 or 18. In some alternatives of the system for inducible expression of a chimeric antigen receptor in cells, the drug is tamoxifen and/or its metabolites, 4-hydroxytamoxifen, fulvestrant or other estrogen analogs, or CMP8. In some alternatives of the system for inducible expression of a chimeric antigen receptor in cells, the first promoter comprises a nucleic acid sequence set forth in SEQ ID NO: 23. In some alternatives of the system for inducible expression of a chimeric antigen receptor in cells, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system for inducible expression of a chimeric antigen receptor in cells, the drug induces expression of the chimeric antigen receptor at a non-toxic dosing of drug at less than 10 nM drug but not zero. In some alternatives of the system for inducible expression of a chimeric antigen receptor in cells, the non-toxic dosing of drug decreases, eliminates or prevents drug side effects in comparison to a dosage amount for inducing expression with a wild type HEA3 or wild type HEA4 chimeric transcription factor. In some alternatives of the system for inducible expression of a chimeric antigen receptor in cells, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system for inducible expression of a chimeric antigen receptor in cells, the signaling domain comprises a CD28, 4-1BB and/or CD3ζ domain. In some alternatives of the system for inducible expression of a chimeric antigen receptor in cells, the second promoter is an inducible promoter. In some alternatives of the system for inducible expression of a chimeric antigen receptor in cells, the second promoter is a constitutive promoter. In some alternatives of the system for inducible expression of a chimeric antigen receptor in cells, the second promoter is the EF1αp. In some alternatives of the system for inducible expression of a chimeric antigen receptor in cells, the transcriptional activator comprises at least one or more amino acid sequences set forth in SEQ ID NO: 1-11 or 121. In some alternatives of the system for inducible expression of a chimeric antigen receptor in cells, the transcriptional activator is encoded by at least one or more nucleic acid sequences set forth in SEQ ID NO: 12-22 or 122. In some alternatives of the system for inducible expression of a chimeric antigen receptor in cells, the first nucleic acid further comprises a first vector and the second nucleic acid further comprises a second vector. In some alternatives of the system for inducible expression of a chimeric antigen receptor in cells, both vectors are packaged in a viral vector. In some alternatives of the system for inducible expression of a chimeric antigen receptor in cells, the viral vector is an adeno-associated virus or a lentivirus. In some alternatives of the system for inducible expression of a chimeric antigen receptor in cells, the first nucleic acid further comprises a fifth polynucleotide that encodes a selectable marker. In some alternatives of the system for inducible expression of a chimeric antigen receptor in cells, the second nucleic acid further comprises a sixth polynucleotide that encodes a selectable marker. In some alternatives of the system for inducible expression of a chimeric antigen receptor in cells, the selectable marker is EGFRt and/or HER2t. In some alternatives of the system for inducible expression of a chimeric antigen receptor in cells, the selectable marker confers drug resistance. In some alternatives of the system for inducible expression of a chimeric antigen receptor in cells, the first nucleic acid further comprises a seventh polynucleotide that encodes a self-cleaving peptide. In some alternatives of the system for inducible expression of a chimeric antigen receptor in cells, the self-cleaving peptide comprises a P2A, T2A, E2A or F2A peptide. In some alternatives of the system for inducible expression of a chimeric antigen receptor in cells, the spacer is optimized for increased T cell proliferation and/or cytokine production in response to the ligand as compared to a reference chimeric receptor. In some alternatives, the system is for inducible expression of a gene that regulates a T cell function. In some alternatives, the system is for inducible expression of a gene that regulates a T cell function comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity and b) a second nucleic acid comprising a second promoter, wherein the second nucleic acid is operably linked to a third nucleic acid that encodes a transcriptional activator for the first promoter inducible by drug and wherein the system is configured to respond to an amount of the drug that is less than a comparable system utilizing a wild type HEA3 chimeric transcription factor or a wild type HEA4 chimeric transcription factor. In some alternatives of the system for inducible expression of a gene that regulates a T cell function, the transcriptional activator is HEA3 or HEA4. In some alternatives of the system for inducible expression of a gene that regulates a T cell function, HEA3 is a variant of a wild type HEA3 transcription factor. In some alternatives of the system for inducible expression of a gene that regulates a T cell function, HEA4 is a variant of a wild type HEA4 transcription factor. In some alternatives of the system for inducible expression of a gene that regulates a T cell function, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a gene that regulates a T cell function, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a gene that regulates a T cell function, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a gene that regulates a T cell function, the variant of a wild type HEA3 transcription factor comprises at least one or more amino acid sequences set forth in SEQ ID Nos: 1-3, 8-11 and/or 121. In some alternatives of the system for inducible expression of a gene that regulates a T cell function, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a gene that regulates a T cell function, the variant of a wild type HEA4 transcription factor comprises at least one or more amino acid sequences set forth in SEQ ID Nos: 4-7. In some alternatives of the system for inducible expression of a gene that regulates a T cell function, the variant of the wild type HEA4 transcription factor is encoded by at least one or more nucleic acid sequences set forth in SEQ ID NO: 15, 16, 17 or 18. In some alternatives of the systems described herein, the transcriptional regulator is a variant of a HEA3 chimeric transcription factor, and wherein the variant comprises amino acid substitutions that allow selective binding to the drug. In some alternatives of the systems described herein, the drug is tamoxifen and/or its metabolites, 4-hydroxytamoxifen, fulvestrant or other estrogen analogs, or CMP8. In some alternatives of the systems described herein, the drug induces a level of expression of the chimeric antigen receptor that is greater than a wild type HEA3 or a wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the systems described herein, the drug induces expression of the chimeric antigen receptor at a non-toxic dosing of drug at less than 10 nM drug but not zero. In some alternatives of the systems described herein, the non-toxic dosing of drug decreases, eliminates or prevents drug side effects in comparison to a dosage for inducing expression with a wild type HEA3 or a wild type HEA4 chimeric transcription factor. In some alternatives of the systems described herein, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the systems described herein, the second nucleic acid further comprises a polynucleotide encoding a chimeric antigen receptor comprising a ligand binding domain, which is a tumor specific molecule, viral specific molecule, or any other selected molecule expressed on a target cell population, wherein the ligand elicits recognition, modulation, inhibition, and/or elimination by a lymphocyte, a polynucleotide coding for a polypeptide spacer, wherein the spacer is preferably optimized, a polynucleotide coding for a transmembrane domain, and a polynucleotide encoding an intracellular signaling domain. In some alternatives of the systems described herein, the first promoter is in opposite orientation to the second promoter. In some alternatives of the systems described herein, the ligand binding domain is an antibody fragment, such as a binding fragment. In some alternatives of the systems described herein, the ligand binding domain is a single chain variable fragment. In some alternatives of the systems described herein, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and/or any combinations thereof. In some alternatives of the systems described herein, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the host cell, the host cell is a mammalian cell, such as a precursor T cell. In some alternatives of the systems described herein, the first nucleic acid further comprises a DNA spacer, wherein the spacer is operably linked to the first promoter and operably linked to the first polynucleotide that encodes the chimeric antigen receptor. In some alternatives of the systems described herein, the DNA spacer is between the first promoter and the first polynucleotide that encodes the chimeric antigen receptor. In some alternatives of the systems described herein, the DNA spacer comprises a sequence set forth in SEQ ID NO: 120. In some alternatives of the systems described herein, the DNA spacer comprises a sequence that has 95%, 90%, 85% or 80% sequence identity to SEQ ID NO: 120 or any percent sequence identity in between a range defined by any two aforementioned values. In some alternatives of the systems described herein, the DNA spacer enhances gene expression of the chimeric antigen receptor. In some alternatives, the first nucleic acid further comprises a first vector and the second nucleic acid further comprises a second vector. In some alternatives of the systems described herein, both vectors are packaged in a viral vector. In some alternatives of the systems described herein, the viral vector is an adeno-associated virus or a lentivirus. In some alternatives of the host cell, the precursor T cell is a hematopoietic stem cell. In some alternatives of the host cell, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives of the host cell, the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and a host cell, wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or wherein the host cell is a CD4+T helper lymphocyte cell that is selected from the group consisting of naïve CD4+ T cells, central memory CD4+ T cells, effector memory CD4+ T cells, and bulk CD4+ T cells and a host cell wherein the host cell is a precursor T cell or a hematopoietic stem cell. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives, the in vitro method for preparing a host cell of any one of the alternative host cells comprises a) providing a system of any one of the alternative systems provided herein and b) introducing the system into an isolated T lymphocyte population and expanding each T lymphocyte population in vitro. In some alternatives of the method, the T lymphocytes are expanded, and wherein the method further comprises culturing the cells in the presence of anti-CD3 and/or anti CD28, and at least one homeostatic cytokine until the cells expand sufficiently for use as a cell infusion. In some alternatives of the method, the isolated T lymphocyte population comprises precursor T cells. In some alternatives of the method, the precursor T cells are hematopoietic stem cells. In some alternatives of the method, the lymphocyte is CD8+ or CD4+. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123.

In a seventh aspect, a method of treating, inhibiting, or ameliorating a disease in a subject in need thereof is provided. The method comprises administering to the subject the host cell of any one of the alternative host cells, such as mammalian cells, provided herein, or at least one composition or product combination of any one or more of the alternatives provided herein. The composition comprises a host cell of any one or more of alternative host cells, such as a mammalian cell, provided herein, in a pharmaceutically acceptable excipient. The host cell, such as a mammalian cell comprises a system of any one of the alternative systems described herein. In some alternatives, the system is for inducible expression of a chimeric antigen receptor in cells, such as mammalian cells. In some alternatives of the system for inducible expression of a chimeric antigen receptor in cells, such as mammalian cells, the system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral specific molecule, or other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system for inducible expression of a chimeric antigen receptor in cells, the transcriptional activator is HEA3 or HEA4. In some alternatives of the system for inducible expression of a chimeric antigen receptor in cells, HEA3 is a variant of a wild type HEA3 transcription factor. In some alternatives of the system for inducible expression of a chimeric antigen receptor in cells, HEA4 is a variant of a wild type HEA4 transcription factor. In some alternatives of the system for inducible expression of a chimeric antigen receptor in cells, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a chimeric antigen receptor in cells, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a chimeric antigen receptor in cells, the variant of the wild type HEA3 transcription factor comprises at least one or more amino acid sequences set forth in SEQ ID Nos: 1-3, 8-11 and/or 121. In some alternatives of the system for inducible expression of a chimeric antigen receptor in cells, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a chimeric antigen receptor in cells, the variant of a wild type HEA4 transcription factor comprises at least one or more amino acid sequences set forth in SEQ ID Nos: 4-7. In some alternatives of the system for inducible expression of a chimeric antigen receptor in cells, the variant of the wild type HEA4 transcription factor is encoded by at least one or more nucleic acid sequences set forth in SEQ ID NO: 15, 16, 17 or 18. In some alternatives of the system for inducible expression of a chimeric antigen receptor in cells, the drug is tamoxifen and/or its metabolites, 4-hydroxytamoxifen, fulvestrant or other estrogen analogs, or CMP8. In some alternatives of the system for inducible expression of a chimeric antigen receptor in cells, the first promoter comprises a nucleic acid sequence set forth in SEQ ID NO: 23. In some alternatives of the system for inducible expression of a chimeric antigen receptor in cells, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system for inducible expression of a chimeric antigen receptor in cells, the drug induces expression of the chimeric antigen receptor at a non-toxic dosing of drug at less than 10 nM drug but not zero. In some alternatives of the system for inducible expression of a chimeric antigen receptor in cells, the non-toxic dosing of drug decreases, eliminates or prevents drug side effects in comparison to a dosage amount for inducing expression with a wild type HEA3 or a wild type HEA4 chimeric transcription factor. In some alternatives of the system for inducible expression of a chimeric antigen receptor in cells, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system for inducible expression of a chimeric antigen receptor in cells, the signaling domain comprises a CD28, 4-1BB and/or CD3ζ domain. In some alternatives of the system for inducible expression of a chimeric antigen receptor in cells, the second promoter is an inducible promoter. In some alternatives of the system for inducible expression of a chimeric antigen receptor in cells, the second promoter is a constitutive promoter. In some alternatives of the system for inducible expression of a chimeric antigen receptor in cells, the second promoter is the EF1αp. In some alternatives of the system for inducible expression of a chimeric antigen receptor in cells, the transcriptional activator comprises at least one or more amino acid sequences set forth in SEQ ID NO: 1-11 or 121. In some alternatives of the system for inducible expression of a chimeric antigen receptor in cells, the transcriptional activator is encoded by at least one or more nucleic acid sequences set forth in SEQ ID NO: 12-22 or 122. In some alternatives of the system for inducible expression of a chimeric antigen receptor in cells, the first nucleic acid further comprises a first vector and the second nucleic acid further comprises a second vector. In some alternatives of the system for inducible expression of a chimeric antigen receptor in cells, both vectors are packaged in a viral vector. In some alternatives of the system for inducible expression of a chimeric antigen receptor in cells, the viral vector is an adeno-associated virus or a lentivirus. In some alternatives of the system for inducible expression of a chimeric antigen receptor in cells, the first nucleic acid further comprises a fifth polynucleotide that encodes a selectable marker. In some alternatives of the system for inducible expression of a chimeric antigen receptor in cells, the second nucleic acid further comprises a sixth polynucleotide that encodes a selectable marker. In some alternatives of the system for inducible expression of a chimeric antigen receptor in cells, the selectable marker is EGFRt and/or HER2t. In some alternatives of the system for inducible expression of a chimeric antigen receptor in cells, the selectable marker confers drug resistance. In some alternatives of the system for inducible expression of a chimeric antigen receptor in cells, the first nucleic acid further comprises a seventh polynucleotide that encodes a self-cleaving peptide. In some alternatives of the system for inducible expression of a chimeric antigen receptor in cells, the self-cleaving peptide comprises a P2A, T2A, E2A or F2A peptide. In some alternatives of the system for inducible expression of a chimeric antigen receptor in cells, the spacer is optimized for increased T cell proliferation and/or cytokine production in response to the ligand, as compared to a reference chimeric receptor. In some alternatives, the system is for inducible expression of a gene that regulates a T cell function. In some alternatives, the system is for inducible expression of a gene that regulates a T cell function comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity and b) a second nucleic acid comprising a second promoter, wherein the second nucleic acid is operably linked to a third nucleic acid that encodes a transcriptional activator for the first promoter inducible by drug and wherein the system is configured to respond to an amount of the drug that is less than a comparable system utilizing a wild type HEA3 chimeric transcription factor or a wild type HEA4 chimeric transcription factor. In some alternatives of the system for inducible expression of a gene that regulates a T cell function, the transcriptional activator is HEA3 or HEA4. In some alternatives of the system for inducible expression of a gene that regulates a T cell function, HEA3 is a variant of a wild type HEA3 transcription factor. In some alternatives of the system for inducible expression of a gene that regulates a T cell function, HEA4 is a variant of a wild type HEA4 transcription factor. In some alternatives of the system for inducible expression of a gene that regulates a T cell function, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a gene that regulates a T cell function, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a gene that regulates a T cell function, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a gene that regulates a T cell function, the variant of a wild type HEA3 transcription factor comprises at least one or more amino acid sequences set forth in SEQ ID Nos: 1-3, 8-11 and/or 121. In some alternatives of the system for inducible expression of a gene that regulates a T cell function, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a gene that regulates a T cell function, the variant of a wild type HEA4 transcription factor comprises at least one or more amino acid sequences set forth in SEQ ID Nos: 4-7. In some alternatives of the system for inducible expression of a gene that regulates a T cell function, the variant of the wild type HEA4 transcription factor is encoded by at least one or more nucleic acid sequences set forth in SEQ ID NO: 15, 16, 17 or 18. In some alternatives of the systems described herein, the transcriptional regulator is a variant of a HEA3 chimeric transcription factor, and wherein the variant comprises amino acid substitutions that allow selective binding to the drug. In some alternatives of the systems described herein, the drug is tamoxifen and/or its metabolites, 4-hydroxytamoxifen, fulvestrant or other estrogen analogs, or CMP8. In some alternatives of the systems described herein, the drug induces a level of expression of the chimeric antigen receptor that is greater than a wild type HEA3 or a wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the systems described herein, the drug induces expression of the chimeric antigen receptor at a non-toxic dosing of drug at less than 10 nM drug but not zero. In some alternatives of the systems described herein, the non-toxic dosing of drug decreases, eliminates or prevents drug side effects in comparison to a dosage for inducing expression with a wild type HEA3 or a wild type HEA4 chimeric transcription factor. In some alternatives of the systems described herein, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the systems described herein, the second nucleic acid further comprises a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte, a polynucleotide coding for a polypeptide spacer, wherein the spacer is optimized, a polynucleotide coding for a transmembrane domain, and a polynucleotide encoding an intracellular signaling domain. In some alternatives of the systems described herein, the first promoter is in opposite orientation to the second promoter. In some alternatives of the systems described herein, the ligand binding domain is an antibody fragment, such as a binding fragment. In some alternatives of the systems described herein, the ligand binding domain is a single chain variable fragment. In some alternatives of the systems described herein, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and/or any combinations thereof. In some alternatives of the systems described herein, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the systems described herein, the first nucleic acid further comprises a DNA spacer, wherein the spacer is operably linked to the first promoter and operably linked to the first polynucleotide that encodes the chimeric antigen receptor. In some alternatives of the systems described herein, the DNA spacer is between the first promoter and the first polynucleotide that encodes the chimeric antigen receptor. In some alternatives of the systems described herein, the DNA spacer comprises a sequence set forth in SEQ ID NO: 120. In some alternatives of the systems described herein, the DNA spacer comprises a sequence that has 95%, 90%, 85% or 80% sequence identity to SEQ ID NO: 120 or any percent sequence identity in between a range defined by any two aforementioned values. In some alternatives of the systems described herein, the DNA spacer enhances gene expression of the chimeric antigen receptor. In some alternatives of the host cell, such as a mammalian cell, the host cell is a precursor T cell. In some alternatives of the host cell, the precursor T cell is a hematopoietic stem cell. In some alternatives of the host cell, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives of the host cell, the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and a host cell, wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell, wherein the host cell is a CD8+T cytotoxic lymphocyte cell selected from the group consisting of naïve CD8+ T cells, central memory CD8+ T cells, effector memory CD8+ T cells and bulk CD8+ T cells or wherein the host cell is a CD4+T helper lymphocyte cell that is selected from the group consisting of naïve CD4+ T cells, central memory CD4+ T cells, effector memory CD4+ T cells, and bulk CD4+ T cells and a host cell wherein the host cell is a precursor T cell or a hematopoietic stem cell. In some alternatives of the method, the disease is cancer or a viral disease. In some alternatives of the method, the subject is identified or selected to receive an anti-cancer therapy. In some alternatives of the method, the subject is identified or selected to receive an anti-viral therapy. In some alternatives of the method, the method further comprises measuring or evaluating an inhibition of the disease. In some alternatives of the method, the method further comprises providing said subject an additional anti-cancer therapy or anti-viral therapy before, during, or after administration of the cells of any one or more of any one of the alternatives provided herein or at least one composition or product combination of any one or more of the alternatives provided herein. In some alternatives of the method, the cells described above or at least one composition or product combination described above are administered to said subject by adoptive cell transfer. In some alternatives of the method, the host cells described above or at least one composition or product combination described above are administered to said subject after said subject has received another form of anti-cancer therapy or anti-viral therapy. In some alternatives of the method, the method further comprises administering a drug that induces expression of a transgene in the host cell or composition for the treatment of cancer or a viral infection. In some alternatives of the method, the drug is tamoxifen and/or its metabolites, fulvestrant and/or other estrogen analogs or CMP8. In some alternatives of the method, tamoxifen is administered at a dose range of 10, 11, 12, 13, 14, 15, 16, 17, 18, 19 or 20 mg/dose or within a range defined by any two of the aforementioned values. In some alternatives of the method, fulvestrant is administered at a dose range of 250, 300, 350, 400, 450 or 500 mg/dose mg/dose or within a range defined by any two of the aforementioned values. In some alternatives of the method, the CMP8 is administered at a dose range to provide 30, 40 or 50 nM of drug levels in serum, or within a range defined by any two of the aforementioned values. In some alternatives of the method, the cancer is a solid tumor or hematologic malignancy. In some alternatives of the method, the solid tumor is selected from the group consisting of a breast cancer, brain cancer, lung cancer, colon cancer, renal cancer, pancreatic cancer, prostate cancer, and ovarian cancer. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123.

In an eighth aspect, a method of treating, inhibiting, or ameliorating a disease in a subject in need thereof, is provided. The method comprises administering to the subject the host cell, such as a mammalian cell, of any one of the alternatives provided herein or at least one composition or product combination of any one or more of the alternative compositions provided herein. In some alternatives, the composition comprises a host cell of any one or more of alternative host cells, such as mammalian cells, provided herein, in a pharmaceutically acceptable excipient. In some alternatives, the host cell, such as mammalian cells, comprises a system of any one of the alternative systems described herein. In some alternatives, the system is for inducible expression of a chimeric antigen receptor in cells, such as mammalian cells. In some alternatives of the system for inducible expression of a chimeric antigen receptor in cells, such as mammalian cells, the system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral specific molecule, or other molecule expressed on a target cell population, wherein the ligand elicits recognition, modulation, inhibition, and/or elimination by a lymphocyte, a second polynucleotide, which encodes an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system for inducible expression of a chimeric antigen receptor in cells, the transcriptional activator is HEA3 or HEA4. In some alternatives of the system for inducible expression of a chimeric antigen receptor in cells, HEA3 is a variant of a wild type HEA3 transcription factor. In some alternatives of the system for inducible expression of a chimeric antigen receptor in cells, HEA4 is a variant of a wild type HEA4 transcription factor. In some alternatives of the system for inducible expression of a chimeric antigen receptor in cells, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a chimeric antigen receptor in cells, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a chimeric antigen receptor in cells, the variant of the wild type HEA3 transcription factor comprises at least one or more amino acid sequences set forth in SEQ ID Nos: 1-3, 8-11 and/or 121. In some alternatives of the system for inducible expression of a chimeric antigen receptor in cells, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a chimeric antigen receptor in cells, the variant of a wild type HEA4 transcription factor comprises at least one or more amino acid sequences set forth in SEQ ID Nos: 4-7. In some alternatives of the system for inducible expression of a chimeric antigen receptor in cells, the variant of the wild type HEA4 transcription factor is encoded by at least one or more nucleic acid sequences set forth in SEQ ID NO: 15, 16, 17 or 18. In some alternatives of the system for inducible expression of a chimeric antigen receptor in cells, the drug is tamoxifen and/or its metabolites, 4-hydroxytamoxifen, fulvestrant or other estrogen analogs, or CMP8. In some alternatives of the system for inducible expression of a chimeric antigen receptor in cells, the first promoter comprises a nucleic acid sequence set forth in SEQ ID NO: 23. In some alternatives of the system for inducible expression of a chimeric antigen receptor in cells, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system for inducible expression of a chimeric antigen receptor in cells, the drug induces expression of the chimeric antigen receptor at a non-toxic dosing of drug at less than 10 nM drug but not zero. In some alternatives of the system for inducible expression of a chimeric antigen receptor in cells, the non-toxic dosing of drug decreases, eliminates or prevents drug side effects in comparison to a dosage amount for inducing expression with a wild type HEA3 or a wild type HEA4 chimeric transcription factor. In some alternatives of the system for inducible expression of a chimeric antigen receptor in cells, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system for inducible expression of a chimeric antigen receptor in cells, the signaling domain comprises a CD28, 4-1BB and/or CD3ζ domain. In some alternatives of the system for inducible expression of a chimeric antigen receptor in cells, the second promoter is an inducible promoter. In some alternatives of the system for inducible expression of a chimeric antigen receptor in cells, the second promoter is a constitutive promoter. In some alternatives of the system for inducible expression of a chimeric antigen receptor in cells, the second promoter is the EF1αp. In some alternatives of the system for inducible expression of a chimeric antigen receptor in cells, the transcriptional activator comprises at least one or more amino acid sequences set forth in SEQ ID NO: 1-11 or 121. In some alternatives of the system for inducible expression of a chimeric antigen receptor in cells, the transcriptional activator is encoded by at least one or more nucleic acid sequences set forth in SEQ ID NO: 12-22 or 122. In some alternatives of the system for inducible expression of a chimeric antigen receptor in cells, the first nucleic acid further comprises a first vector and the second nucleic acid further comprises a second vector. In some alternatives of the system for inducible expression of a chimeric antigen receptor in cells, both vectors are packaged in a viral vector. In some alternatives of the system for inducible expression of a chimeric antigen receptor in cells, the viral vector is an adeno-associated virus or a lentivirus. In some alternatives of the system for inducible expression of a chimeric antigen receptor in cells, the first nucleic acid further comprises a fifth polynucleotide that encodes a selectable marker. In some alternatives of the system for inducible expression of a chimeric antigen receptor in cells, the second nucleic acid further comprises a sixth polynucleotide that encodes a selectable marker. In some alternatives of the system for inducible expression of a chimeric antigen receptor in cells, the selectable marker is EGFRt and/or HER2t. In some alternatives of the system for inducible expression of a chimeric antigen receptor in cells, the selectable marker confers drug resistance. In some alternatives of the system for inducible expression of a chimeric antigen receptor in cells, the first nucleic acid further comprises a seventh polynucleotide that encodes a self-cleaving peptide. In some alternatives of the system for inducible expression of a chimeric antigen receptor in cells, the self-cleaving peptide comprises a P2A, T2A, E2A or F2A peptide. In some alternatives of the system for inducible expression of a chimeric antigen receptor in cells, the spacer is optimized for increased T cell proliferation and/or cytokine production in response to the ligand as compared to a reference chimeric receptor. In some alternatives, the system is for inducible expression of a gene that regulates a T cell function. In some alternatives, the system is for inducible expression of a gene that regulates a T cell function comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity and b) a second nucleic acid comprising a second promoter, wherein the second nucleic acid is operably linked to a third nucleic acid that encodes a transcriptional activator for the first promoter inducible by drug and wherein the system is configured to respond to an amount of the drug that is less than a comparable system utilizing a wild type HEA3 chimeric transcription factor or a wild type HEA4 chimeric transcription factor. In some alternatives of the system for inducible expression of a gene that regulates a T cell function, the transcriptional activator is HEA3 or HEA4. In some alternatives of the system for inducible expression of a gene that regulates a T cell function, HEA3 is a variant of a wild type HEA3 transcription factor. In some alternatives of the system for inducible expression of a gene that regulates a T cell function, HEA4 is a variant of a wild type HEA4 transcription factor. In some alternatives of the system for inducible expression of a gene that regulates a T cell function, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a gene that regulates a T cell function, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a gene that regulates a T cell function, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a gene that regulates a T cell function, the variant of a wild type HEA3 transcription factor comprises at least one or more amino acid sequences in SEQ ID Nos: 1-3, 8-11 and/or 121. In some alternatives of the system for inducible expression of a gene that regulates a T cell function, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a gene that regulates a T cell function, the variant of a wild type HEA4 transcription factor comprises at least one or more amino acid sequences set forth in SEQ ID Nos: 4-7. In some alternatives of the system for inducible expression of a gene that regulates a T cell function, the variant of the wild type HEA4 transcription factor is encoded by at least one or more nucleic acid sequences set forth in SEQ ID NO: 15, 16, 17 or 18. In some alternatives of the systems described herein, the transcriptional regulator is a variant of a HEA3 chimeric transcription factor, and wherein the variant comprises amino acid substitutions that allow selective binding to the drug. In some alternatives of the systems described herein, the drug is tamoxifen and/or its metabolites, 4-hydroxytamoxifen, fulvestrant or other estrogen analogs, or CMP8. In some alternatives of the systems described herein, the drug induces a level of expression of the chimeric antigen receptor that is greater than a wild type HEA3 or a wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the systems described herein, the drug induces expression of the chimeric antigen receptor at a non-toxic dosing of drug at less than 10 nM drug but not zero. In some alternatives of the systems described herein, the non-toxic dosing of drug decreases, eliminates or prevents drug side effects in comparison to a dosage for inducing expression with a wild type HEA3 or a wild type HEA4 chimeric transcription factor. In some alternatives of the systems described herein, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the systems described herein, the second nucleic acid further comprises a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte, a polynucleotide coding for a polypeptide spacer, wherein the spacer is optimized, a polynucleotide coding for a transmembrane domain, and a polynucleotide encoding an intracellular signaling domain. In some alternatives of the systems described herein, the first promoter is in opposite orientation to the second promoter. In some alternatives of the systems described herein, the ligand binding domain is an antibody fragment. In some alternatives of the systems described herein, the ligand binding domain is a single chain variable fragment. In some alternatives of the systems described herein, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and/or any combinations thereof. In some alternatives of the systems described herein, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the systems described herein, the first nucleic acid further comprises a DNA spacer, wherein the spacer is operably linked to the first promoter and operably linked to the first polynucleotide that encodes the chimeric antigen receptor. In some alternatives of the systems described herein, the DNA spacer is between the first promoter and the first polynucleotide that encodes the chimeric antigen receptor. In some alternatives of the systems described herein, the DNA spacer comprises a sequence set forth in SEQ ID NO: 120. In some alternatives of the systems described herein, the DNA spacer comprises a sequence that has 95%, 90%, 85% or 80% sequence identity to SEQ ID NO: 120 or any percent sequence identity in between a range defined by any two aforementioned values. In some alternatives of the systems described herein, the DNA spacer enhances gene expression of the chimeric antigen receptor. In some alternatives of the host cell, the host cell is a precursor T cell. In some alternatives of the host cell, such as a mammalian cell, the cell is a precursor T cell, which is a hematopoietic stem cell. In some alternatives of the host cell, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives of the host cell, the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and a host cell, wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or wherein the host cell is a CD4+T helper lymphocyte cell that is selected from the group consisting of naïve CD4+ T cells, central memory CD4+ T cells, effector memory CD4+ T cells, and bulk CD4+ T cells and a host cell wherein the host cell is a precursor T cell or a hematopoietic stem cell. In some alternatives of the method, the disease is cancer or a viral disease. In some alternatives of the method, the subject is identified or selected to receive an anti-cancer therapy. In some alternatives of the method, the subject is identified or selected to receive an anti-viral therapy. In some alternatives of the method, the method further comprises measuring or evaluating an inhibition of the disease. In some alternatives of the method, the method further comprises providing said subject an additional anti-cancer therapy or anti-viral therapy before, during, or after administration of the cells of any one or more of the alternative cells described herein or at least one composition or product combination of any one or more of alternatives described herein. In some alternatives of the method, the cells of any one or more of the alternatives described herein or at least one composition or product combination of any one or more of the alternatives described herein are administered to said subject by adoptive cell transfer. In some alternatives of the method, the host cells of any one or more of the alternatives described herein or at least one composition or product combination of any one or more of the alternatives described herein are administered to said subject after said subject has received another form of anti-cancer therapy or anti-viral therapy. In some alternatives of the method, the method further comprises administering a drug that induces expression of a transgene in the host cell or composition for the treatment of cancer or a viral infection. In some alternatives of the method, the drug is tamoxifen and/or its metabolites, fulvestrant and/or other estrogen analogs or CMP8. In some alternatives of the method, tamoxifen is administered at a dose range of 10, 11, 12, 13, 14, 15, 16, 17, 18, 19 or 20 mg/dose or within a range defined by any two of the aforementioned values. In some alternatives of the method, the fulvestrant is administered at a dose range of 250, 300, 350, 400, 450 or 500 mg/dose mg/dose or within a range defined by any two of the aforementioned values. In some alternatives of the method, the CMP8 is administered at a dose range to provide 30, 40 or 50 nM of drug levels in serum, or within a range defined by any two of the aforementioned values. In some alternatives of the method, the cancer is a solid tumor or hematologic malignancy. In some alternatives of the method, the solid tumor is selected from the group consisting of a breast cancer, brain cancer, lung cancer, colon cancer, renal cancer, pancreatic cancer, prostate cancer, and ovarian cancer. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123.

In a ninth aspect, a use of the host cell, such as a mammalian cell, of any one of or more of the alternatives described herein or at least one composition or product combination of any one or more of the alternatives described herein in combination with a drug that induces expression of a transgene in the host cell or composition for the treatment of cancer or a viral infection is provided. In some alternatives, the composition comprises a host cell, such as a mammalian cell, of any one or more of alternative host cells provided herein, in a pharmaceutically acceptable excipient. In some alternatives, the host cell, such as mammalian cell, comprises a system of any one of the alternative systems described herein. In some alternatives, the system is for inducible expression of a chimeric antigen receptor in cells, such as mammalian cells. In some alternatives of the system for inducible expression of a chimeric antigen receptor in cells, the system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral specific molecule, or any other selected molecule expressed on a target cell population, wherein the ligand elicits recognition, modulation, inhibition, and/or elimination by a lymphocyte, a second polynucleotide, which encodes an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system for inducible expression of a chimeric antigen receptor in cells, the transcriptional activator is HEA3 or HEA4. In some alternatives of the system for inducible expression of a chimeric antigen receptor in cells, HEA3 is a variant of a wild type HEA3 transcription factor. In some alternatives of the system for inducible expression of a chimeric antigen receptor in cells, HEA4 is a variant of a wild type HEA4 transcription factor. In some alternatives of the system for inducible expression of a chimeric antigen receptor in cells, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a chimeric antigen receptor in cells, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a chimeric antigen receptor in cells, the variant of the wild type HEA3 transcription factor comprises at least one or more amino acid sequences set forth in SEQ ID Nos: 1-3, 8-11 and/or 121. In some alternatives of the system for inducible expression of a chimeric antigen receptor in cells, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a chimeric antigen receptor in cells, the variant of a wild type HEA4 transcription factor comprises at least one or more amino acid sequences set forth in SEQ ID Nos: 4-7. In some alternatives of the system for inducible expression of a chimeric antigen receptor in cells, the variant of the wild type HEA4 transcription factor is encoded by at least one or more nucleic acid sequences set forth in SEQ ID NO: 15, 16, 17 or 18. In some alternatives of the system for inducible expression of a chimeric antigen receptor in cells, the drug is tamoxifen and/or its metabolites, 4-hydroxytamoxifen, fulvestrant or other estrogen analogs, or CMP8. In some alternatives of the system for inducible expression of a chimeric antigen receptor in cells, the first promoter comprises a nucleic acid sequence set forth in SEQ ID NO: 23. In some alternatives of the system for inducible expression of a chimeric antigen receptor in cells, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system for inducible expression of a chimeric antigen receptor in cells, the drug induces expression of the chimeric antigen receptor at a non-toxic dosing of drug at less than 10 nM drug but not zero. In some alternatives of the system for inducible expression of a chimeric antigen receptor in cells, the non-toxic dosing of drug decreases, eliminates or prevents drug side effects in comparison to a dosage amount for inducing expression with a wild type HEA3 or a wild type HEA4 chimeric transcription factor. In some alternatives of the system for inducible expression of a chimeric antigen receptor in cells, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system for inducible expression of a chimeric antigen receptor in cells, the signaling domain comprises a CD28, 4-1BB and/or CD3ζ domain. In some alternatives of the system for inducible expression of a chimeric antigen receptor in cells, the second promoter is an inducible promoter. In some alternatives of the system for inducible expression of a chimeric antigen receptor in cells, the second promoter is a constitutive promoter. In some alternatives of the system for inducible expression of a chimeric antigen receptor in cells, the second promoter is the EF1αp. In some alternatives of the system for inducible expression of a chimeric antigen receptor in cells, the transcriptional activator comprises at least one or more amino acid sequences set forth in SEQ ID NO: 1-11 or 121. In some alternatives of the system for inducible expression of a chimeric antigen receptor in cells, the transcriptional activator is encoded by at least one or more nucleic acid sequences set forth in SEQ ID NO: 12-22 or 122. In some alternatives of the system for inducible expression of a chimeric antigen receptor in cells, the first nucleic acid further comprises a first vector and the second nucleic acid further comprises a second vector. In some alternatives of the system for inducible expression of a chimeric antigen receptor in cells, both vectors are packaged in a viral vector. In some alternatives of the system for inducible expression of a chimeric antigen receptor in cells, the viral vector is an adeno-associated virus or a lentivirus. In some alternatives of the system for inducible expression of a chimeric antigen receptor in cells, the first nucleic acid further comprises a fifth polynucleotide that encodes a selectable marker. In some alternatives of the system for inducible expression of a chimeric antigen receptor in cells, the second nucleic acid further comprises a sixth polynucleotide that encodes a selectable marker. In some alternatives of the system for inducible expression of a chimeric antigen receptor in cells, the selectable marker is EGFRt and/or HER2t. In some alternatives of the system for inducible expression of a chimeric antigen receptor in cells, the selectable marker confers drug resistance. In some alternatives of the system for inducible expression of a chimeric antigen receptor in cells, the first nucleic acid further comprises a seventh polynucleotide that encodes a self-cleaving peptide. In some alternatives of the system for inducible expression of a chimeric antigen receptor in cells, the self-cleaving peptide comprises a P2A, T2A, E2A or F2A peptide. In some alternatives of the system for inducible expression of a chimeric antigen receptor in cells, the spacer is optimized for increased T cell proliferation and/or cytokine production in response to the ligand as compared to a reference chimeric receptor. In some alternatives, the system is for inducible expression of a gene that regulates a T cell function. In some alternatives, the system is for inducible expression of a gene that regulates a T cell function comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity and b) a second nucleic acid comprising a second promoter, wherein the second nucleic acid is operably linked to a third nucleic acid that encodes a transcriptional activator for the first promoter inducible by drug and wherein the system is configured to respond to an amount of the drug that is less than a comparable system utilizing a wild type HEA3 chimeric transcription factor or a wild type HEA4 chimeric transcription factor. In some alternatives of the system for inducible expression of a gene that regulates a T cell function, the transcriptional activator is HEA3 or HEA4. In some alternatives of the system for inducible expression of a gene that regulates a T cell function, HEA3 is a variant of a wild type HEA3 transcription factor. In some alternatives of the system for inducible expression of a gene that regulates a T cell function, HEA4 is a variant of a wild type HEA4 transcription factor. In some alternatives of the system for inducible expression of a gene that regulates a T cell function, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a gene that regulates a T cell function, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a gene that regulates a T cell function, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a gene that regulates a T cell function, the variant of a wild type HEA3 transcription factor comprises at least one or more amino acid sequences set forth in SEQ ID Nos: 1-3, 8-11 and/or 121. In some alternatives of the system for inducible expression of a gene that regulates a T cell function, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a gene that regulates a T cell function, the variant of a wild type HEA4 transcription factor comprises at least one or more amino acid sequences set forth in SEQ ID Nos: 4-7. In some alternatives of the system for inducible expression of a gene that regulates a T cell function, the variant of the wild type HEA4 transcription factor is encoded by at least one or more nucleic acid sequences set forth in SEQ ID NO: 15, 16, 17 or 18. In some alternatives of the systems described herein, the transcriptional regulator is a variant of a HEA3 chimeric transcription factor, and wherein the variant comprises amino acid substitutions that allow selective binding to the drug. In some alternatives of the systems described herein, the drug is tamoxifen and/or its metabolites, 4-hydroxytamoxifen, fulvestrant or other estrogen analogs, or CMP8. In some alternatives of the systems described herein, the drug induces a level of expression of the chimeric antigen receptor that is greater than a wild type HEA3 or a wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the systems described herein, the drug induces expression of the chimeric antigen receptor at a non-toxic dosing of drug at less than 10 nM drug but not zero. In some alternatives of the systems described herein, the non-toxic dosing of drug decreases, eliminates or prevents drug side effects in comparison to a dosage for inducing expression with a wild type HEA3 or a wild type HEA4 chimeric transcription factor. In some alternatives of the systems described herein, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the systems described herein, the second nucleic acid further comprises a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte, a polynucleotide coding for a polypeptide spacer, wherein the spacer is optimized, a polynucleotide coding for a transmembrane domain, and a polynucleotide encoding an intracellular signaling domain. In some alternatives of the systems described herein, the first promoter is in opposite orientation to the second promoter. In some alternatives of the systems described herein, the ligand binding domain is an antibody fragment. In some alternatives of the systems described herein, the ligand binding domain is a single chain variable fragment. In some alternatives of the systems described herein, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and/or any combinations thereof. In some alternatives of the systems described herein, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the systems described herein, the first nucleic acid further comprises a DNA spacer, wherein the spacer is operably linked to the first promoter and operably linked to the first polynucleotide that encodes the chimeric antigen receptor. In some alternatives of the systems described herein, the DNA spacer is between the first promoter and the first polynucleotide that encodes the chimeric antigen receptor. In some alternatives of the systems described herein, the DNA spacer comprises a sequence set forth in SEQ ID NO: 120. In some alternatives of the systems described herein, the DNA spacer comprises a sequence that has 95%, 90%, 85% or 80% sequence identity to SEQ ID NO: 120 or any percent sequence identity in between a range defined by any two aforementioned values. In some alternatives of the systems described herein, the DNA spacer enhances gene expression of the chimeric antigen receptor. In some alternatives of the host cell, the host cell, such as a mammalian cell, is a precursor T cell. In some alternatives of the host cell, the precursor T cell is a hematopoietic stem cell. In some alternatives of the host cell, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives of the host cell, the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and a host cell, wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or wherein the host cell is a CD4+T helper lymphocyte cell that is selected from the group consisting of naïve CD4+ T cells, central memory CD4+ T cells, effector memory CD4+ T cells, and bulk CD4+ T cells and a host cell wherein the host cell is a precursor T cell or a hematopoietic stem cell. In some alternatives of the use, the drug is tamoxifen and/or its metabolites, fulvestrant and/or other estrogen analogs or CMP8. In some alternatives of the use, tamoxifen is administered at a dose range of 10, 11, 12, 13, 14, 15, 16, 17, 18, 19 or 20 mg/dose or within a range defined by any two of the aforementioned values. In some alternatives of the use, the fulvestrant is administered at a dose range of 250, 300, 350, 400, 450 or 500 mg/dose or within a range defined by any two of the aforementioned values. In some alternatives of the use, the CMP8 is administered at a dose range to provide 30, 40 or 50 nM of drug levels in serum, or within a range defined by any two of the aforementioned values. In some alternatives of the use, the cancer is a solid tumor or hematologic malignancy. In some alternatives of the use, the solid tumor is selected from the group consisting of a breast cancer, brain cancer, lung cancer, colon cancer, renal cancer, pancreatic cancer, prostate cancer, and ovarian cancer. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123.

In a tenth aspect, a method of performing cellular immunotherapy in a subject having cancer or a viral infection is provided. The method comprises administering the host cells, such as mammalian cells, of any one or more of alternatives provided herein or at least one composition or product combination of any one or more of the alternatives provided herein to the subject and administering a drug that induces expression of a transgene in the composition or the host cells. The composition comprises a host cell of any one or more of alternative host cells, such as mammalian cells, provided herein, in a pharmaceutically acceptable excipient. In some alternatives, the host cell, such as a mammalian cell, comprises a system of any one of the alternative systems described herein. In some alternatives, the system is for inducible expression of a chimeric antigen receptor in cells, such as mammalian cells. In some alternatives of the system for inducible expression of a chimeric antigen receptor in cells, such as mammalian cells, the system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral molecule, or other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system for inducible expression of a chimeric antigen receptor in cells, the transcriptional activator is HEA3 or HEA4. In some alternatives of the system for inducible expression of a chimeric antigen receptor in cells, HEA3 is a variant of a wild type HEA3 transcription factor. In some alternatives of the system for inducible expression of a chimeric antigen receptor in cells, HEA4 is a variant of a wild type HEA4 transcription factor. In some alternatives of the system for inducible expression of a chimeric antigen receptor in cells, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a chimeric antigen receptor in cells, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a chimeric antigen receptor in cells, the variant of the wild type HEA3 transcription factor comprises at least one or more amino acid sequences set forth in SEQ ID Nos: 1-3, 8-11 and/or 121. In some alternatives of the system for inducible expression of a chimeric antigen receptor in cells, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a chimeric antigen receptor in cells, the variant of a wild type HEA4 transcription factor comprises at least one or more amino acid sequences set forth in SEQ ID Nos: 4-7. In some alternatives of the system for inducible expression of a chimeric antigen receptor in cells, the variant of the wild type HEA4 transcription factor is encoded by at least one or more nucleic acid sequences set forth in SEQ ID NO: 15, 16, 17 or 18. In some alternatives of the system for inducible expression of a chimeric antigen receptor in cells, the drug is tamoxifen and/or its metabolites, 4-hydroxytamoxifen, fulvestrant or other estrogen analogs, or CMP8. In some alternatives of the system for inducible expression of a chimeric antigen receptor in cells, the first promoter comprises a nucleic acid sequence set forth in SEQ ID NO: 23. In some alternatives of the system for inducible expression of a chimeric antigen receptor in cells, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system for inducible expression of a chimeric antigen receptor in cells, the drug induces expression of the chimeric antigen receptor at a non-toxic dosing of drug at less than 10 nM drug but not zero. In some alternatives of the system for inducible expression of a chimeric antigen receptor in cells, the non-toxic dosing of drug decreases, eliminates or prevents drug side effects in comparison to a dosage amount for inducing expression with a wild type HEA3 or a wild type HEA4 chimeric transcription factor. In some alternatives of the system for inducible expression of a chimeric antigen receptor in cells, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system for inducible expression of a chimeric antigen receptor in cells, the signaling domain comprises a CD28, 4-1BB and/or CD3ζ domain. In some alternatives of the system for inducible expression of a chimeric antigen receptor in cells, the second promoter is an inducible promoter. In some alternatives of the system for inducible expression of a chimeric antigen receptor in cells, the second promoter is a constitutive promoter. In some alternatives of the system for inducible expression of a chimeric antigen receptor in cells, the second promoter is the EF1αp. In some alternatives of the system for inducible expression of a chimeric antigen receptor in cells, the transcriptional activator comprises at least one or more amino acid sequences set forth in SEQ ID NO: 1-11 or 121. In some alternatives of the system for inducible expression of a chimeric antigen receptor in cells, the transcriptional activator is encoded by at least one or more nucleic acid sequences set forth in SEQ ID NO: 12-22 or 122. In some alternatives of the system for inducible expression of a chimeric antigen receptor in cells, the first nucleic acid further comprises a first vector and the second nucleic acid further comprises a second vector. In some alternatives of the system for inducible expression of a chimeric antigen receptor in cells, both vectors are packaged in a viral vector. In some alternatives of the system for inducible expression of a chimeric antigen receptor in cells, the viral vector is an adeno-associated virus or a lentivirus. In some alternatives of the system for inducible expression of a chimeric antigen receptor in cells, the first nucleic acid further comprises a fifth polynucleotide that encodes a selectable marker. In some alternatives of the system for inducible expression of a chimeric antigen receptor in cells, the second nucleic acid further comprises a sixth polynucleotide that encodes a selectable marker. In some alternatives of the system for inducible expression of a chimeric antigen receptor in cells, the selectable marker is EGFRt and/or HER2t. In some alternatives of the system for inducible expression of a chimeric antigen receptor in cells, the selectable marker confers drug resistance. In some alternatives of the system for inducible expression of a chimeric antigen receptor in cells, the first nucleic acid further comprises a seventh polynucleotide that encodes a self-cleaving peptide. In some alternatives of the system for inducible expression of a chimeric antigen receptor in cells, the self-cleaving peptide comprises a P2A, T2A, E2A or F2A peptide. In some alternatives of the system for inducible expression of a chimeric antigen receptor in cells, the spacer is optimized for increased T cell proliferation and/or cytokine production in response to the ligand as compared to a reference chimeric receptor. In some alternatives, the system is for inducible expression of a gene that regulates a T cell function. In some alternatives, the system is for inducible expression of a gene that regulates a T cell function comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity and b) a second nucleic acid comprising a second promoter, wherein the second nucleic acid is operably linked to a third nucleic acid that encodes a transcriptional activator for the first promoter inducible by drug and wherein the system is configured to respond to an amount of the drug that is less than a comparable system utilizing a wild type HEA3 chimeric transcription factor or a wild type HEA4 chimeric transcription factor. In some alternatives of the system for inducible expression of a gene that regulates a T cell function, the transcriptional activator is HEA3 or HEA4. In some alternatives of the system for inducible expression of a gene that regulates a T cell function, HEA3 is a variant of a wild type HEA3 transcription factor. In some alternatives of the system for inducible expression of a gene that regulates a T cell function, HEA4 is a variant of a wild type HEA4 transcription factor. In some alternatives of the system for inducible expression of a gene that regulates a T cell function, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a gene that regulates a T cell function, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a gene that regulates a T cell function, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a gene that regulates a T cell function, the variant of a wild type HEA3 transcription factor comprises at least one or more amino acid sequences set forth in SEQ ID Nos: 1-3, 8-11 and/or 121. In some alternatives of the system for inducible expression of a gene that regulates a T cell function, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a gene that regulates a T cell function, the variant of a wild type HEA4 transcription factor comprises at least one or more amino acid sequences set forth in SEQ ID Nos: 4-7. In some alternatives of the system for inducible expression of a gene that regulates a T cell function, the variant of the wild type HEA4 transcription factor is encoded by at least one or more nucleic acid sequences set forth in SEQ ID NO: 15, 16, 17 or 18. In some alternatives of the systems described herein, the transcriptional regulator is a variant of a HEA3 chimeric transcription factor, and wherein the variant comprises amino acid substitutions that allow selective binding to the drug. In some alternatives of the systems described herein, the drug is tamoxifen and/or its metabolites, 4-hydroxytamoxifen, fulvestrant or other estrogen analogs, or CMP8. In some alternatives of the systems described herein, the drug induces a level of expression of the chimeric antigen receptor that is greater than a wild type HEA3 or a wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the systems described herein, the drug induces expression of the chimeric antigen receptor at a non-toxic dosing of drug at less than 10 nM drug but not zero. In some alternatives of the systems described herein, the non-toxic dosing of drug decreases, eliminates or prevents drug side effects in comparison to a dosage for inducing expression with a wild type HEA3 or a wild type HEA4 chimeric transcription factor. In some alternatives of the systems described herein, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the systems described herein, the second nucleic acid further comprises a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte, a polynucleotide coding for a polypeptide spacer, wherein the spacer is optimized, a polynucleotide coding for a transmembrane domain, and a polynucleotide encoding an intracellular signaling domain. In some alternatives of the systems described herein, the first promoter is in opposite orientation to the second promoter. In some alternatives of the systems described herein, the ligand binding domain is an antibody fragment. In some alternatives of the systems described herein, the ligand binding domain is a single chain variable fragment. In some alternatives of the systems described herein, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and/or any combinations thereof. In some alternatives of the systems described herein, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the host cell, such as a mammalian cell, the host cell is a precursor T cell. In some alternatives of the systems described herein, the first nucleic acid further comprises a DNA spacer, wherein the spacer is operably linked to the first promoter and operably linked to the first polynucleotide that encodes the chimeric antigen receptor. In some alternatives of the systems described herein, the DNA spacer is between the first promoter and the first polynucleotide that encodes the chimeric antigen receptor. In some alternatives of the systems described herein, the DNA spacer comprises a sequence set forth in SEQ ID NO: 120. In some alternatives of the systems described herein, the DNA spacer comprises a sequence that has 95%, 90%, 85% or 80% sequence identity to SEQ ID NO: 120 or any percent sequence identity in between a range defined by any two aforementioned values. In some alternatives of the systems described herein, the DNA spacer enhances gene expression of the chimeric antigen receptor. In some alternatives of the host cell, such as a mammalian cell, the cell is a precursor T cell, which is a hematopoietic stem cell. In some alternatives of the host cell, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives of the host cell, the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and a host cell, wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or wherein the host cell is a CD4+T helper lymphocyte cell that is selected from the group consisting of naïve CD4+ T cells, central memory CD4+ T cells, effector memory CD4+ T cells, and bulk CD4+ T cells and a host cell wherein the host cell is a precursor T cell or a hematopoietic stem cell. In some alternatives of the method, the cancer is selected from a solid tumor or hematologic malignancy. In some alternatives of the method, the solid tumor is selected from the group consisting of a breast cancer, brain cancer, lung cancer, colon cancer, renal cancer, pancreatic cancer, prostate cancer, and ovarian cancer. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives, the spacer comprises IgG4, IgG4-CH2 (L235D, N297Q) or IgG4-CH3. In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123.

In an eleventh aspect, a use of the host cell of any one of or more of the alternatives described herein or at least one composition or product combination of any one or more of the alternatives described herein as a medicament, is provided. The composition comprises a host cell of any one or more of alternative host cells, such as mammalian cells, provided herein, in a pharmaceutically acceptable excipient. In some alternatives, the host cell, such as a mammalian cell, comprises a system of any one of the alternative systems described herein. In some alternatives, the system is for inducible expression of a chimeric antigen receptor in cells, such as mammalian cells. In some alternatives of the system for inducible expression of a chimeric antigen receptor in cells, such as mammalian cells, the system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral molecule, or other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system for inducible expression of a chimeric antigen receptor in cells, the transcriptional activator is HEA3 or HEA4. In some alternatives of the system for inducible expression of a chimeric antigen receptor in cells, HEA3 is a variant of a wild type HEA3 transcription factor. In some alternatives of the system for inducible expression of a chimeric antigen receptor in cells, HEA4 is a variant of a wild type HEA4 transcription factor. In some alternatives of the system for inducible expression of a chimeric antigen receptor in cells, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a chimeric antigen receptor in cells, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a chimeric antigen receptor in cells, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a chimeric antigen receptor in cells, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a chimeric antigen receptor in cells, the variant of the wild type HEA3 transcription factor comprises at least one or more amino acid sequences set forth in SEQ ID Nos: 1-3, 8-11 and/or 121. In some alternatives of the system for inducible expression of a chimeric antigen receptor in cells, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a chimeric antigen receptor in cells, the variant of a wild type HEA4 transcription factor comprises at least one or more amino acid sequences set forth in SEQ ID Nos: 4-7. In some alternatives of the system for inducible expression of a chimeric antigen receptor in cells, the variant of the wild type HEA4 transcription factor is encoded by at least one or more nucleic acid sequences set forth in SEQ ID NO: 15, 16, 17 or 18. In some alternatives of the system for inducible expression of a chimeric antigen receptor in cells, the drug is tamoxifen and/or its metabolites, 4-hydroxytamoxifen, fulvestrant or other estrogen analogs, or CMP8. In some alternatives of the system for inducible expression of a chimeric antigen receptor in cells, the first promoter comprises a nucleic acid sequence set forth in SEQ ID NO: 23. In some alternatives of the system for inducible expression of a chimeric antigen receptor in cells, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system for inducible expression of a chimeric antigen receptor in cells, the drug induces expression of the chimeric antigen receptor at a non-toxic dosing of drug at less than 10 nM drug but not zero. In some alternatives of the system for inducible expression of a chimeric antigen receptor in cells, the non-toxic dosing of drug decreases, eliminates or prevents drug side effects in comparison to a dosage amount for inducing expression with a wild type HEA3 or a wild type HEA4 chimeric transcription factor. In some alternatives of the system for inducible expression of a chimeric antigen receptor in cells, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system for inducible expression of a chimeric antigen receptor in cells, the signaling domain comprises a CD28, 4-1BB and/or CD3ζ domain. In some alternatives of the system for inducible expression of a chimeric antigen receptor in cells, the second promoter is an inducible promoter. In some alternatives of the system for inducible expression of a chimeric antigen receptor in cells, the second promoter is a constitutive promoter. In some alternatives of the system for inducible expression of a chimeric antigen receptor in cells, the second promoter is the EF1αp. In some alternatives of the system for inducible expression of a chimeric antigen receptor in cells, the transcriptional activator comprises at least one or more amino acid sequences set forth in SEQ ID NO: 1-11 or 121. In some alternatives of the system for inducible expression of a chimeric antigen receptor in cells, the transcriptional activator is encoded by at least one or more nucleic acid sequences set forth in SEQ ID NO: 12-22 or 122. In some alternatives of the system for inducible expression of a chimeric antigen receptor in cells, the first nucleic acid further comprises a first vector and the second nucleic acid further comprises a second vector. In some alternatives of the system for inducible expression of a chimeric antigen receptor in cells, both vectors are packaged in a viral vector. In some alternatives of the system for inducible expression of a chimeric antigen receptor in cells, the viral vector is an adeno-associated virus or a lentivirus. In some alternatives of the system for inducible expression of a chimeric antigen receptor in cells, the first nucleic acid further comprises a fifth polynucleotide that encodes a selectable marker. In some alternatives of the system for inducible expression of a chimeric antigen receptor in cells, the second nucleic acid further comprises a sixth polynucleotide that encodes a selectable marker. In some alternatives of the system for inducible expression of a chimeric antigen receptor in cells, the selectable marker is EGFRt and/or HER2t. In some alternatives of the system for inducible expression of a chimeric antigen receptor in cells, the selectable marker confers drug resistance. In some alternatives of the system for inducible expression of a chimeric antigen receptor in cells, the first nucleic acid further comprises a seventh polynucleotide that encodes a self-cleaving peptide. In some alternatives of the system for inducible expression of a chimeric antigen receptor in cells, the self-cleaving peptide comprises a P2A, T2A, E2A or F2A peptide. In some alternatives of the system for inducible expression of a chimeric antigen receptor in cells, the spacer is optimized for increased T cell proliferation and/or cytokine production in response to the ligand as compared to a reference chimeric receptor. In some alternatives, the system is for inducible expression of a gene that regulates a T cell function. In some alternatives, the system is for inducible expression of a gene that regulates a T cell function comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extra-cellular environment, a polypeptide that modulates check-point signaling, a microRNA product that regulates growth, a microRNA product that regulates survival, or a microRNA product that regulates cytolytic capacity and b) a second nucleic acid comprising a second promoter, wherein the second nucleic acid is operably linked to a third nucleic acid that encodes a transcriptional activator for the first promoter inducible by drug and wherein the system is configured to respond to an amount of the drug that is less than a comparable system utilizing a wild type HEA3 chimeric transcription factor or a wild type HEA4 chimeric transcription factor. In some alternatives of the system for inducible expression of a gene that regulates a T cell function, the transcriptional activator is HEA3 or HEA4. In some alternatives of the system for inducible expression of a gene that regulates a T cell function, HEA3 is a variant of a wild type HEA3 transcription factor. In some alternatives of the system for inducible expression of a gene that regulates a T cell function, HEA4 is a variant of a wild type HEA4 transcription factor. In some alternatives of the system for inducible expression of a gene that regulates a T cell function, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system for inducible expression of a gene that regulates a T cell function, HEA3 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system for inducible expression of a gene that regulates a T cell function, HEA4 comprises an estrogen receptor ligand binding domain (ER-LBD) and a RelA (p65) transactivation domain, wherein the RelA (p65) transactivation domain comprises at least one mutation that augments transcriptional activity in response to a drug. In some alternatives of the system for inducible expression of a gene that regulates a T cell function, the variant of the HEA3 or HEA4 chimeric transcription factor comprises p65 phosphomimetic and/or acetylmimetic amino acid substitutions that enhance transcriptional activity in response to the drug ligand. In some alternatives of the system for inducible expression of a gene that regulates a T cell function, the variant of a wild type HEA3 transcription factor comprises at least one or more amino acid sequences set forth in SEQ ID Nos: 1-3, 8-11 and/or 121. In some alternatives of the system for inducible expression of a gene that regulates a T cell function, the variant of the wild type HEA3 transcription factor is encoded by at least one or more nucleic acid sequences set forth in SEQ ID NO: 12, 13, 14, 19, 20, 21, 22 or 122. In some alternatives of the system for inducible expression of a gene that regulates a T cell function, the variant of a wild type HEA4 transcription factor comprises at least one or more amino acid sequences set forth in SEQ ID Nos: 4-7. In some alternatives of the system for inducible expression of a gene that regulates a T cell function, the variant of the wild type HEA4 transcription factor is encoded by at least one or more nucleic acid sequences set forth in SEQ ID NO: 15, 16, 17 or 18. In some alternatives of the systems described herein, the transcriptional regulator is a variant of a HEA3 chimeric transcription factor, and wherein the variant comprises amino acid substitutions that allow selective binding to the drug. In some alternatives of the systems described herein, the drug is tamoxifen and/or its metabolites, 4-hydroxytamoxifen, fulvestrant or other estrogen analogs, or CMP8. In some alternatives of the systems described herein, the drug induces a level of expression of the chimeric antigen receptor that is greater than a wild type HEA3 or a wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the systems described herein, the drug induces expression of the chimeric antigen receptor at a non-toxic dosing of drug at less than 10 nM drug but not zero. In some alternatives of the systems described herein, the non-toxic dosing of drug decreases, eliminates or prevents drug side effects in comparison to a dosage for inducing expression with a wild type HEA3 chimeric transcription factor. In some alternatives of the systems described herein, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the systems described herein, the second nucleic acid further comprises a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte, a polynucleotide coding for a polypeptide spacer, wherein the spacer is optimized, a polynucleotide coding for a transmembrane domain, and a polynucleotide encoding an intracellular signaling domain. In some alternatives of the systems described herein, the first promoter is in opposite orientation to the second promoter. In some alternatives of the systems described herein, the ligand binding domain is an antibody fragment. In some alternatives of the systems described herein, the ligand binding domain is a single chain variable fragment. In some alternatives of the systems described herein, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and/or any combinations thereof. In some alternatives of the systems described herein, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the systems described herein, the first nucleic acid further comprises a DNA spacer, wherein the spacer is operably linked to the first promoter and operably linked to the first polynucleotide that encodes the chimeric antigen receptor. In some alternatives of the systems described herein, the DNA spacer is between the first promoter and the first polynucleotide that encodes the chimeric antigen receptor. In some alternatives of the systems described herein, the DNA spacer comprises a sequence set forth in SEQ ID NO: 120. In some alternatives of the systems described herein, the DNA spacer comprises a sequence that has 95%, 90%, 85% or 80% sequence identity to SEQ ID NO: 120 or any percent sequence identity in between a range defined by any two aforementioned values. In some alternatives of the systems described herein, the DNA spacer enhances gene expression of the chimeric antigen receptor. In some alternatives of the host cell, such as a mammalian cell, the host cell is a precursor T cell. In some alternatives of the host cell, the precursor T cell is a hematopoietic stem cell. In some alternatives of the host cell, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives of the host cell, the host cell is a CD4+T helper lymphocyte cell that is selected from the group consisting of naïve CD4+ T cells, central memory CD4+ T cells, effector memory CD4+ T cells, and bulk CD4+T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells and a host cell, wherein the host cell is a CD4+T helper lymphocyte cell that is selected from the group consisting of naïve CD4+ T cells, central memory CD4+ T cells, effector memory CD4+ T cells, and bulk CD4+ T cells. In some alternatives of the composition, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or wherein the host cell is a CD4+T helper lymphocyte cell that is selected from the group consisting of naïve CD4+ T cells, central memory CD4+ T cells, effector memory CD4+ T cells, and bulk CD4+ T cells and a host cell wherein the host cell is a precursor T cell or a hematopoietic stem cell. In some alternatives, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC or VAR2CSA. In some alternatives, the spacer comprises IgG4, IgG4-CH2 (L235D, N297Q) or IgG4-CH3. In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123.

BRIEF DESCRIPTION OF THE DRAWINGS

(FIG. 3C) EGFRt expression was confirmed in sorted cells by flow cytometry, and leakiness of eGFP expression in the absence of inducing ligand was determined.

(FIG. 4A) CD4 and CD8 T cells were transduced with dual-packaged lentiviral constructs encoding drug-regulated transcription factor (HEA4(p65/S536E/K310Q)) and inducible fluorescent reporter eGFP:ffluc. Following purification and expansion of transduced CD4 and CD8 T cells, (FIG. 4B) T cells were incubated with 0 nM, 30 nM, or 500 nM of 4-OHT in the presence or absence of aCD3/aCD28 microbeads (2:1 bead:cell ratio) or PMA (2 uM)/Ionomycin (20 ng/mL) for 24 hours. eGFP expression was subsequently quantified by flow cytometry.

(FIG. 5A) CD4 and CD8 T cells were transduced with dual-packaged lentiviral constructs encoding drug-regulated transcription factor (HEA4(p65/S536E/K310Q)) and inducible fluorescent reporter eGFP:ffluc. Following purification and expansion of transduced CD4 and CD8 T cells, T cells were incubated with increasing concentrations of 4-OHT in the presence or absence of aCD3/aCD28 microbeads (2:1 bead:cell ratio) or PMA (2 uM)/Ionomycin (20 ng/mL) for 24 hours. eGFP expression was quantified by flow cytometry. (FIG. 5B) % EGFRt+eGFP+ CD4 and (FIG. 5C) CD8 T cells and (FIG. 5D) MFI of eGFP expression in (FIG. 5D) CD4 and (FIG. 5E) CD8 T cells following 24 hours of treatment with 4-OHT.

FIGS. 6A to 6D shows results of cells transduced with lentiviral constructs. Jurkat cells were transduced with dual-packaged lentiviral constructs encoding drug-regulated transcription factor (HEA4(p65/S536E/K310Q)) and inducible (FIG. 6A) chimeric cytokine receptor (CCR(CD122)) or (FIG. 6B) Survivin linked to Her2tG via a cleavable 2A linker. Expression of (FIG. 6C) CCR(CD122) and (FIG. 6D) Survivin following 24 hours of treatment with 500 nM 4-OHT was determined by Her2tG upregulation.

DETAILED DESCRIPTION

Figure 1A:
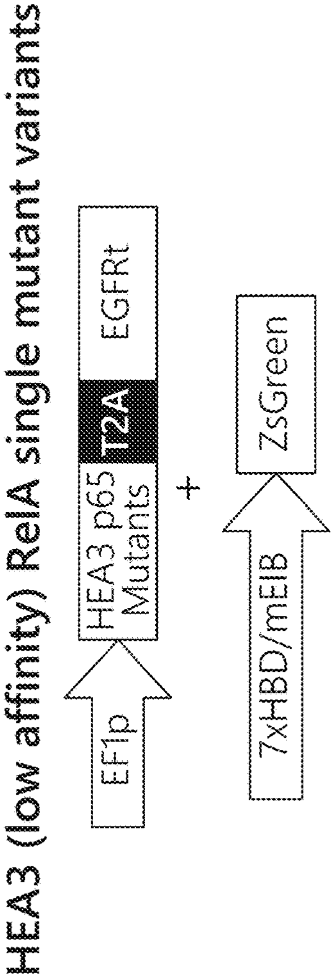
FIGS. 1A to 1F show HEA3 (low affinity) RelA single mutant variants and HEA4 (high affinity) RelA single mutant variants and their response when dosed with 4-OHT, when they are transduced into cells. Shown in the figures is a schematic of dual-packaged lentiviral constructs housing the constitutively expressed drug-inducible transcription factors, (FIG. 1A) HEA3 or (FIG. 1B) HEA4 single mutant RelA variants (S536E or K310Q positions in the RelA protein domain, which correspond to position S846E and K621Q in HEA3 and HEA4, respectively), and a ZsGreen fluorescent reporter. ZsGreen reporter expression in Jurkat cells expressing (FIG. 1C) HEA3 or (FIG. 1D) HEA4 RelA variants following 24 hours of culture with 500 nM 4-OHT. 4-OHT dose response: Percentage of EGFRt+ZsGreen+ cells and ZsGreen median fluorescent intensity of (FIG. 1E) HEA3 or (FIG. 1F) HEA4 RelA variant expressing Jurkat cells.
Figure 1B:
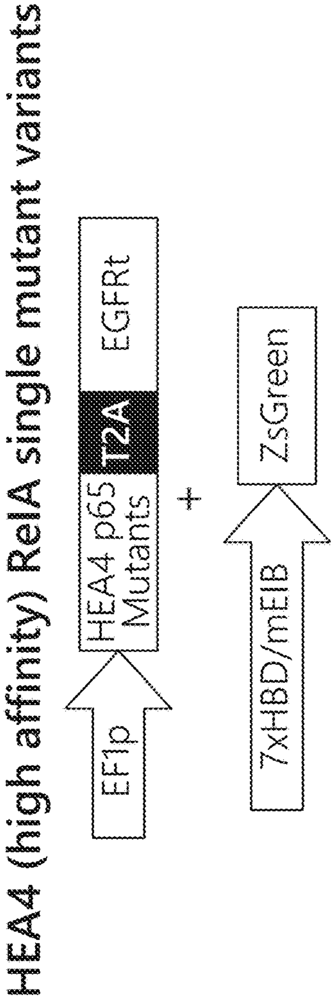
Figure 1C:
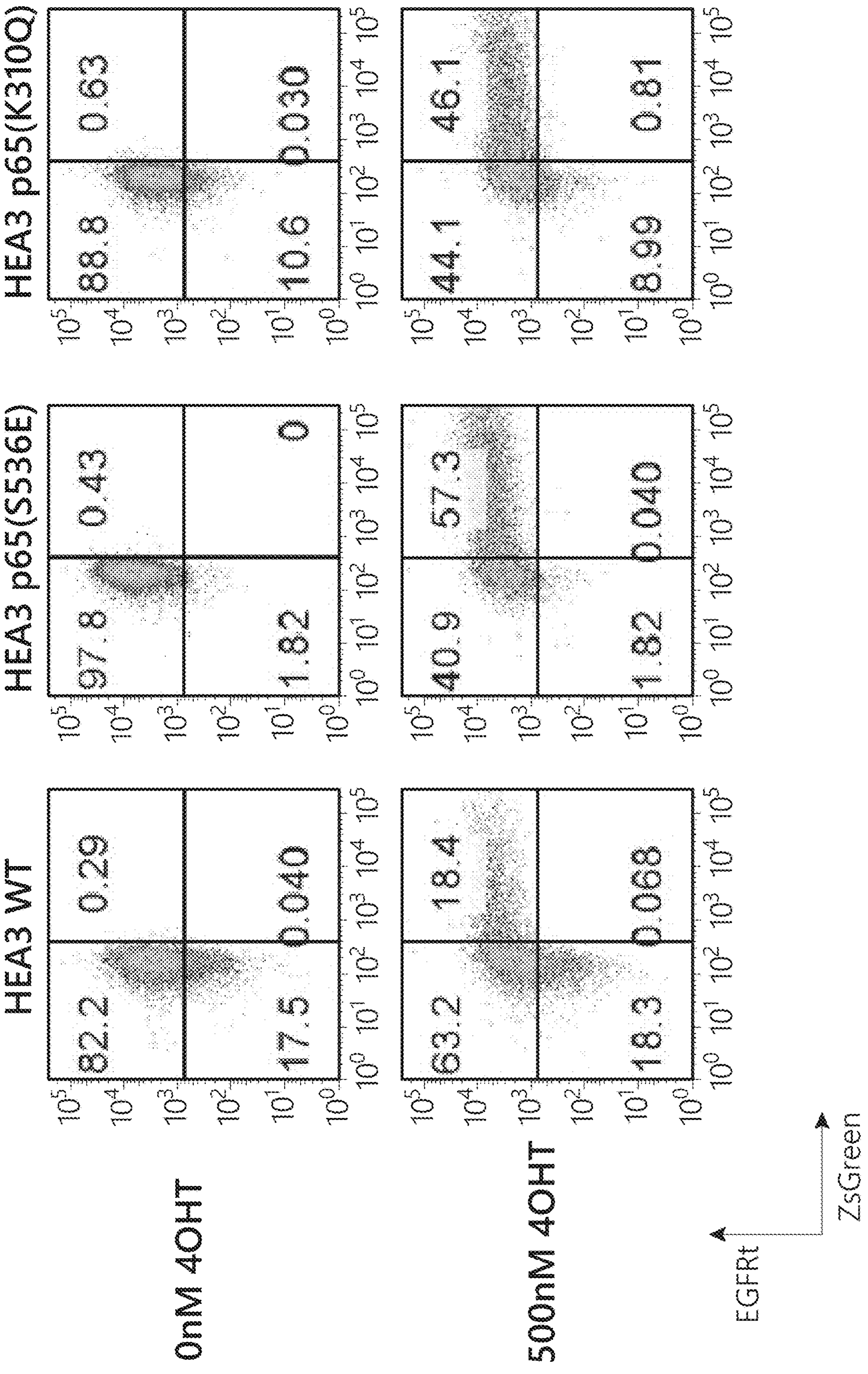
Figure 1D:
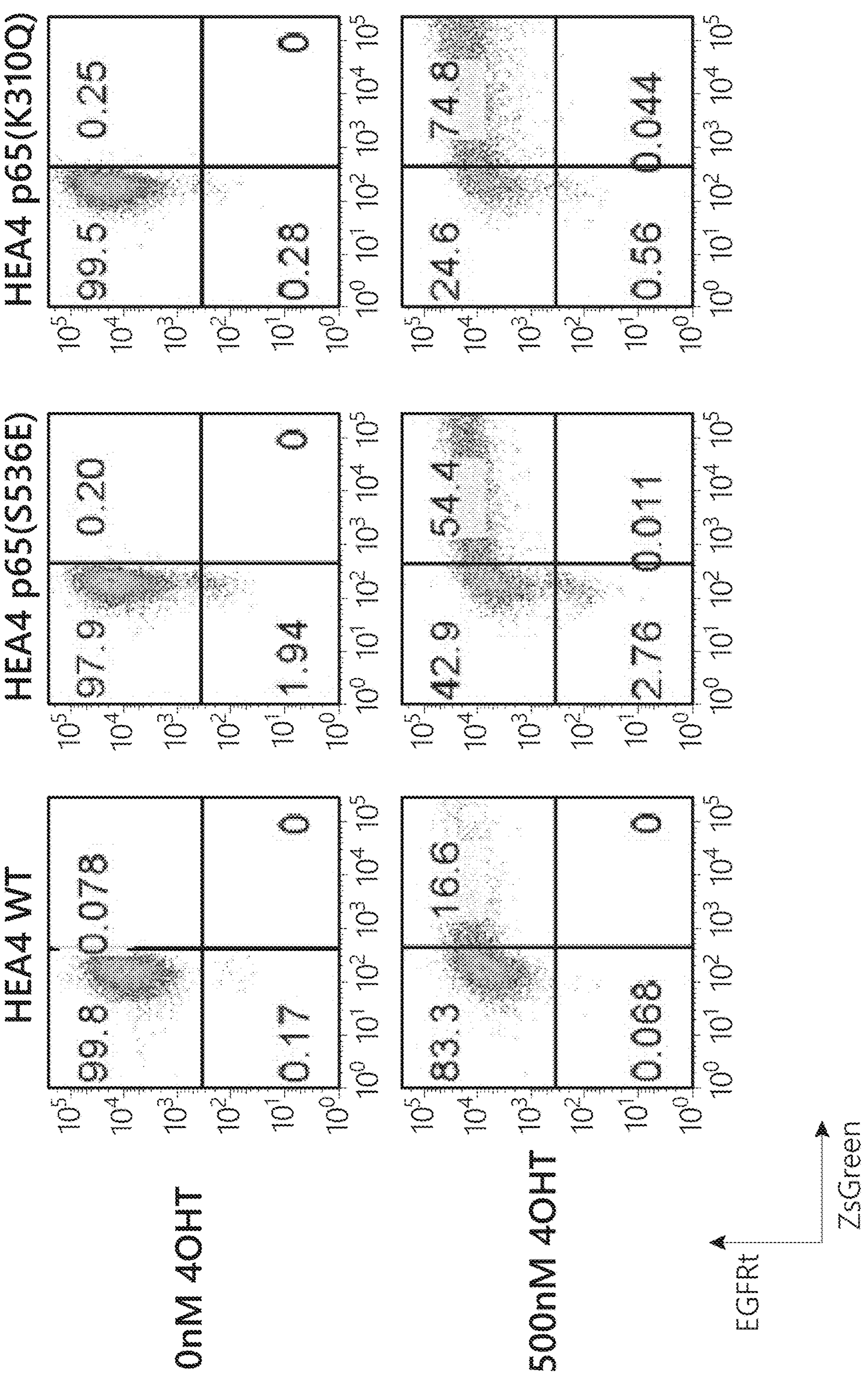
Figure 1E:
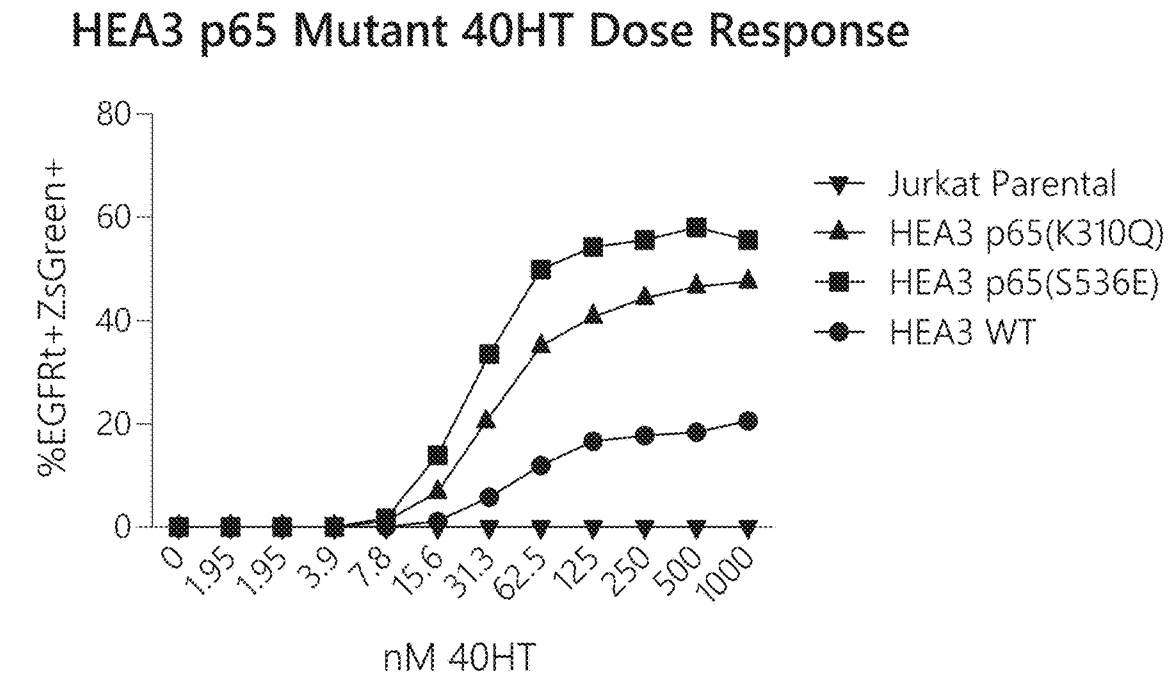
Figure 1E:
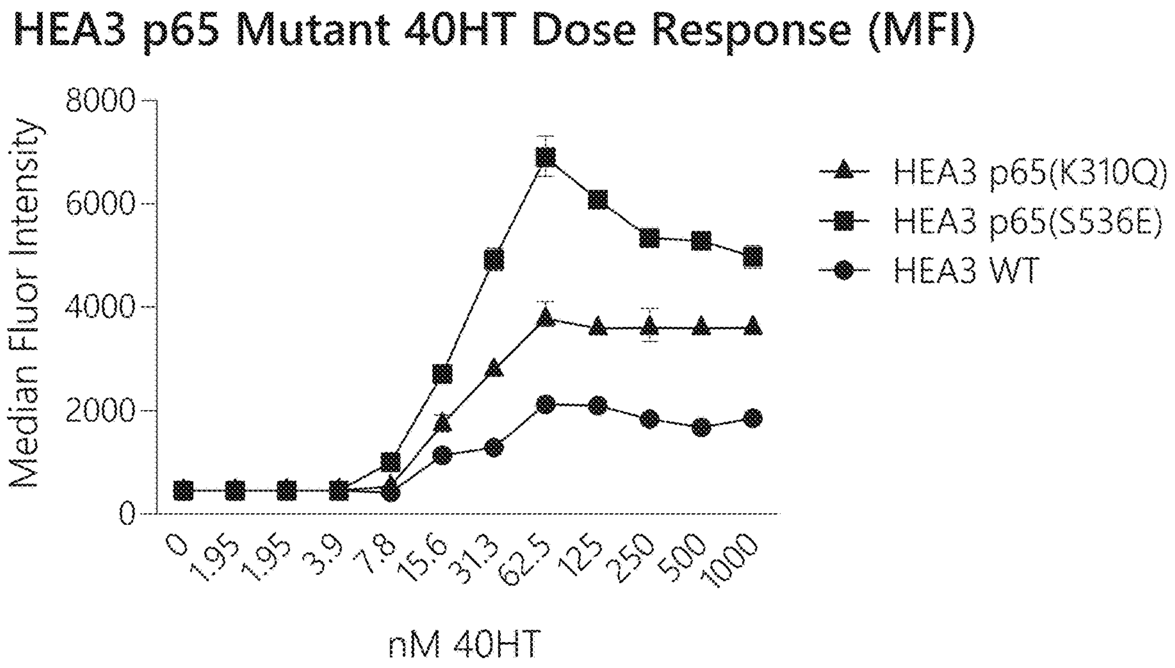
Figure 1F:
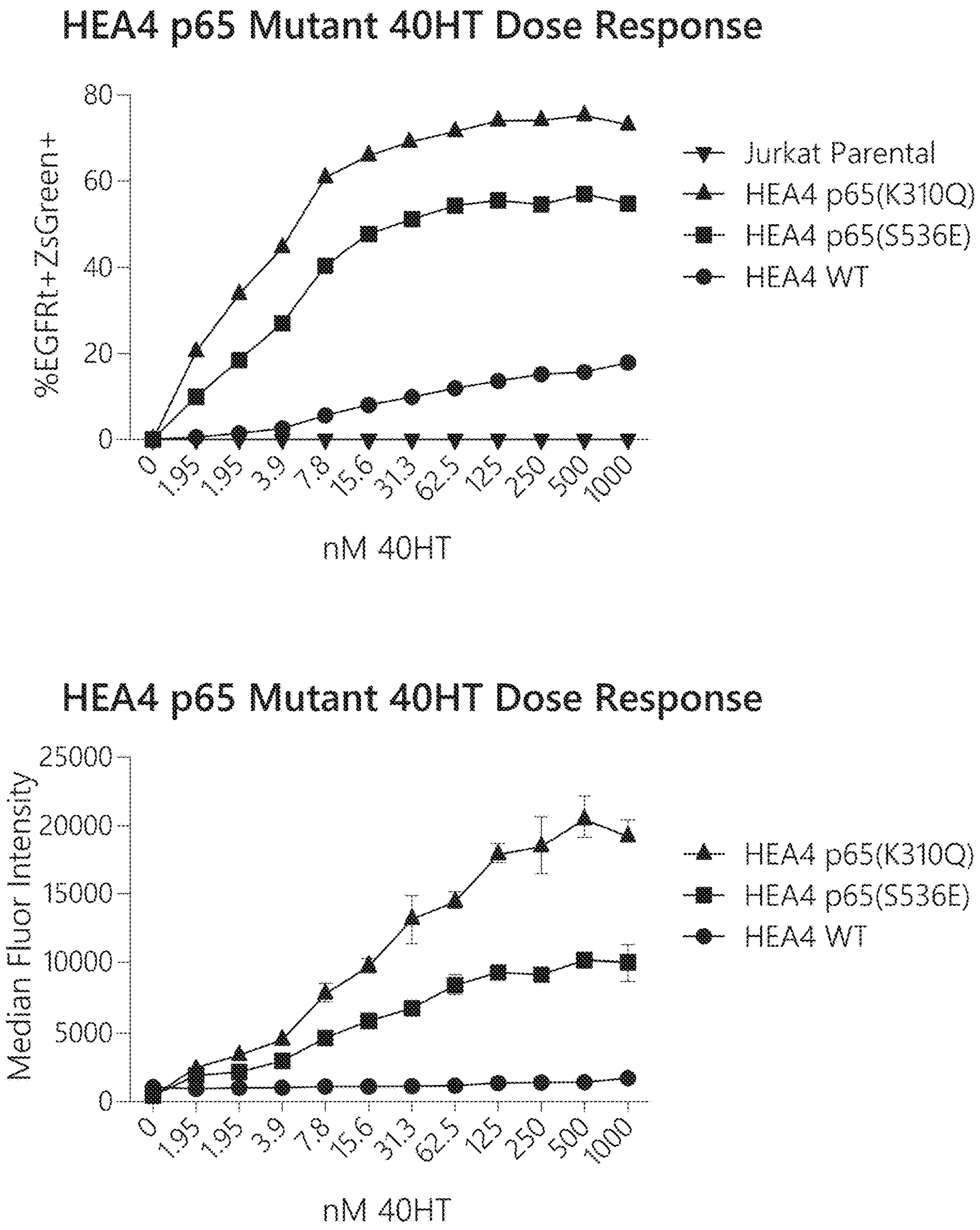

In the description that follows, the terms should be given their plain and ordinary meaning when read in light of the specification. One of skill in the art would understand the terms as used in view of the whole specification.

"About" has its plain and ordinary meaning when read in light of the specification, and may be used, for example, when referring to a measurable value and may be meant to encompass variations of ±20% or ±10%, more preferably ±5%, even more preferably ±1%, and still more preferably ±0.1% from the specified value.

"Antigen" or "Ag," have their plain and ordinary meaning when read in light of the specification, and may include but is not limited to, for example, a molecule that provokes an immune response. This immune response can involve either antibody production, or the activation of specific immunologically-competent cells, or both. It is readily apparent that an antigen can be generated synthesized, produced recombinantly or can be derived from a biological sample. Such a biological sample can include, but is not limited to a tissue sample, a tumor sample, a cell or a biological fluid such, for example, blood, plasma or ascites fluid. In some alternatives of the systems provided herein, the ligand recognized by a chimeric antigen receptor is an antigen, capable of provoking an immune response.

"Anti-tumor effect" has its plain and ordinary meaning when read in light of the specification, and may include but is not limited to, for example, a biological effect, which can be manifested by a decrease in tumor volume, a decrease in the number of tumor cells, a decrease in the number of metastases, an increase in life expectancy, or a decrease of various physiological symptoms associated with the cancerous condition. An "anti-tumor effect" can also be manifested by a decrease in recurrence or an increase in the time before recurrence.

"Chimeric receptor" has its plain and ordinary meaning when read in light of the specification, and may include but is not limited to, for example, a synthetically designed receptor comprising a ligand binding domain of an antibody or other protein sequence that binds to a molecule associated with the disease or disorder and is linked via a spacer domain to one or more intracellular signaling domains of a T cell or other receptors, such as a costimulatory domain. Chimeric receptor can also be referred to as artificial T cell receptors, chimeric T cell receptors, chimeric immunoreceptors, and chimeric antigen receptors (CARs). These CARs are engineered receptors that can graft an arbitrary specificity onto an immune receptor cell. The term chimeric antigen receptors or "CARs" are also considered by some investigators to include the antibody or antibody fragment, the spacer, signaling domain, and transmembrane region. Due to the surprising effects of modifying the different components or domains of the CAR described herein, such as the epitope binding region (for example, antibody fragment, scFv, or portion thereof), spacer, transmembrane domain, and/or signaling domain), the components of the CAR are frequently distinguished throughout this disclosure in terms of independent elements. The variation of the different elements of the CAR can, for example, lead to stronger binding affinity for a specific epitope or antigen.

A "single-chain variable fragment (scFv)" has its plain and ordinary meaning when read in light of the specification, and may include but is not limited to, for example, a fusion protein that can have variable regions of the heavy (VH) and light chains (VL) of immunoglobulins, connected with a short linker peptide of ten to 25 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. The scFv can be specific for an antigen. "Antigen" or "Ag" as used herein refers to a molecule that provokes an immune response. This immune response can involve either antibody production, or the activation of specific immunologically-competent cells, or both. An antigen can be generated, synthesized, produced recombinantly or can be derived from a biological sample. Such a biological sample can include, but is not limited to a tissue sample, a tumor sample, a cell or a biological fluid such, for example, blood, plasma or ascites fluid. In some alternatives of the CARs provided herein, the CAR comprises an antibody fragment, scFv, or portion thereof e.g., a polypeptide comprising the CDR domains. In some alternatives, the scFv specifically binds to CD19. This particular scFv is referred to as huCD19 scFv (G01S) and is encoded by SEQ ID NO: 40 (atgcttctcctggtgacaagccttctgctctgtgagt-
taccacacccagcattcctcctgatcccagaggtgcagctggtcgaatccgg
aggaggactggtccagcccggccggagcctgagactgagctgtgccgcttccg-
gattcacttttgacgattacgcaatgcattgggtg
aggcaggcccctggcaaggggctggaatgggtctccggaatctcttg-
gaacagtgggcgcattggatatgccgattctgtgaaggg ccgattcac-
tatctctcgggacaacgctaaaaatagtctgtttctgcagatgaat-
tccctgcgcgccgaggataccgccgtgtactattg
cgcccgagaccagggctaccactactatgatagcgccgaacatgcattcgacat-
ttggggacagggaactgtggtcaccgtgagctc cggaggaggaggaagcg-
gaggaggagggtccggaggcgggggatcacagagcgcactgacccagc-
cacggagcgtgagcg
gatttcctgggcagtctgtcaccattagttgcacaggcaccacatcagacgatgt-
gagctggtaccagcagcacccagggaaggctc cccagct-
gatgctgtatgacgtgtccaaaagaccttctggcgtcccacataggtttagtg-
gaagccggagcggccgggcagccagtc tgatcatttcagggctgcagacagaggacgaagctgattatttctgttctagt-tacgcaggcagatataactctgtgctgtttggcgggg gaacaaagctgactgtcctg). In some alternatives, the CAR comprises an scFv. In some alternatives, the scFv comprises an huCD19 scFv (G01S) amino acid sequence. In some alternatives, the scFv comprises an amino acid sequence set forth in SEQ ID NO: 41 (MLLLVTSLLLCELPHPAFLLIPE-VQLVESGGGLVQPGRSLRLSCAASGFTFDDYAMH WVRQAPGKGLEWVSGISWNSGRIG-YADSVKGRFTISRDNAKNSLFLQMNSLRAEDT AVYYCARDQGYHYYDSAE-HAFDIWGQGTVVTVSSGGGGSGGGGSGGGGSQ-SALTQ PRSVSGFPGQSVTISCTGTTSDDVSW YQQHPGKAPQLMLYDVSKRPSGVPHRFSGSR SGRAASLIISGLQTEDEADYFCSSYAGRYNS-VLFGGGTKLTVL). In some alternatives, the scFv is encoded by a nucleic acid sequence comprising a nucleic acid sequence encoding the amino acid sequence of SEQ ID NO: 41.

In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42 (Atgctgctgctggtgaccagcctgctgtgcgagctgccc-caccccgcctttctgctgatccccgacatccagatgacccagac cacctccagcctgagcgccagcctgggcgaccgggtgac-catcagctgccgggccagccaggacatcagcaagtacctgaactg gtatcagcagaagcccgacggcaccgtcaagctgctgatctac-cacaccagccggctgcacagcggcgtgcccagccggtttagc ggcagcggctccggcaccgactacagcctgaccatctccaacctggaacag-gaagatatcgccacctacttttgccagcagggcaa cacactgcccta-cacctttggcggcggaacaaagctggaaat-caccggcagcacctccggcagcggcaagcctggcagcggcga gggcagcaccaagggcgaggtgaagctgcag-gaaagcggccctggcctggtggcccccagccagagcctgagcgtgacctgca ccgtgagcggcgtgagcctgcccgactacggcgtgagctg-gatccggcagcccccaggaagggcctggaatggctgggcgtga tctggggcagcgagaccacctactacaacagcgccctgaagagccggctgac-catcatcaaggacaacagcaagagccaggtgtt cctgaagatgaacagcctgca-gaccgacgacaccgccatctactactgcgccaagcactactac-tacggcggcagctacgccatgg actactggggccagggcaccagcgtgaccgtgagcagc). In some alternatives, the scFv comprises an amino acid sequence set forth in SEQ ID NO: 43 (MLLLVTSLLLCELPHPAFL-LIPDIQMTQTTSSLSASLGDRVTISCRASQDISKY-LNWY QQKPDGTVKLLIYHTSRLHSGVPSRFSGSGSGTDYS-LTISNLEQEDIATYFCQQGNTLP YTFGGGTKLEITGST-SGSGKPGSGEGSTKGEVKLQESGPGLVAP-SQSLSVTCTVSGVS LPDYGVSWIRQPPRKGLEWLGVIWGSETTYYN-SALKSRLTIIKDNSKSQVFLKMNSL QTDDTAIYY-CAKHYYYGGSYAMDYWGQGTSVTVSS). In some alternatives, the scFv is encoded by a nucleic acid sequence comprising a nucleic acid sequence encoding the amino acid sequence of SEQ ID NO: 43.

In some alternatives, the scFv is encoded by a CD20 (CD20 (Leu16)) nucleic acid sequence. In some alternatives, the scFv is encoded by a sequence set forth in SEQ ID NO: 44 (atggagacagacacactcctgctatgggtgctgctgctctgggttccaggttc-cacaggtgacattgtgctgacccaatctccagctat cctgtctgcatctccaggg-gagaaggtcacaatgacttgcagggccagctcaagtgtaaatta-catggactggtaccagaagaagcc aggatcctcccccaaaccctggatttatgccacatccaacctggcttctg-gagtccctgctcgcttcagtggcagtgggtctgggacct cttactctct-cacaatcagcagagtggaggctgaagatgctgccacttattactgccagcagtg-gagttttaatccacccacgttcggag gggggaccaagctggaaataaaaggcagtactagcggtggtggct ccgggggcggttccggtgggggcggcagcagcgaggtg cagctgcagcagtctggggctgagctggtgaagcctggggcctcagtgaa-gatgtcctgcaaggcttctggctacacatttaccagtt acaatatgcactgggtaaagcagacacctggacagggcctggaatggattg-gagctatttatccaggaaatggtgatacttcctacaat cagaagtt-caaaggcaaggccacattgactgcagacaaatcctccagcacagccta-catgcagctcagcagcctgacatctgagga ctctgcggactattactgtgcaagatctaattattacggtagtactggttcttc-gatgtctggggcgcagggaccacggtcaccgt ctcctca). In some alternatives, the CD20 (Leu 16) scFv comprises an amino acid sequence set forth in SEQ ID NO: 45 (METDTLLL-WVLLLWVPGSTGDIVLTQSPAILSASPGEKVTMT-CRASSSVNYMDWY QKKPGSSPKPWIYATSN-LASGVPARFSGSGSGTSYSLTISRVEAEDAATYYCQQ WSF NPPTFGGGTKLEIKGSTSGGGSGGGSGGGGS-SEVQLQQSGAELVKPGASVKMSCKAS GYTFTSYN-MHWVKQTPGQGLEWIGAIYPGNGDTSYN-QKFKGKATLTADKSSSTAY MQLSSLTSEDSADYYCARSNYYGSSYWFFDVW-GAGTTVTVSS). In some alternatives, the scFv is encoded by a nucleic acid sequence comprising a nucleic acid sequence encoding the amino acid sequence of SEQ ID NO: 45.

In some alternatives, the scFv is encoded by a CD22 (m971) scFv nucleotide sequence. In some alternatives, the scFv specifically binds to CD22. In some alternatives, the scFv is encoded by a sequence set forth in SEQ ID NO: 46 (atgcttctcctggtgacaagccttctgctctgtgagttaccacacccagcat-tcctcctgatcccacaggtacagctgcagcagtcagg tccaggactggt-gaagccctcgcagaccctctcactcacctgtgc-catctccggggacagtgtctctagcaacagtgctgcttggaac tggatcaggcagtccccatcgagaggccttgagtggctgggaaggacatacta-caggtccaagtggtataatgattatgcagtatctgt gaaaagtcgaataaccat-caacccagacacatccaagaaccagttctccctgcagct-gaactctgtgactcccgaggacacggctgt gtattactgtgcaagagaagtgactggggatctcgaggatgcttttga-tatctggggccaagggacaatggtcaccgtctcctcaggc ggaggggggctctggcggcggaggatctgggggaggggggcagcgacatcca-gatgacccagtctccatcgtccctgtctgcatctgt aggagacagagtcaccat-cacttgccgggcaagccagaccatttggagctacttaaattggtatcagcaga-gaccagggaaagccc ctaacctcctgatctatgctgcatccagtttgcaaagtggggtcccat-caaggttcagtggcaggggatctgggacagatttcactctca ccatcagcagtctgcaagctgaagattttgcaacttactactgtcaacagagtta-cagtatccctcagacttttggccaggggaccaagc tggagatcaaacgaact). In some alternatives, the scFv comprises a CD22 (m971) scFv amino acid sequence. In some alternatives, the scFv comprises an amino acid sequence set forth in SEQ ID NO: 47 (MLLLVTSLLLCELPHPAFLLIPQVQLQQSGPGLVKP-SQTLSLTCAISGDSVSSNSAAW NWIRQSPSRGLEWL-GRTYYRSKWYNDYAVSVKSRIT-INPDTSKNQFSLQLNSVTPED TAVYYCAREVTGDLEDAFDIWGQGTMVTVSSGGG GSGGGGSGGGGSDIQMTQSPSS LSASVGDRVTIT-CRASQTIWSYLNWYQQRPGKAPNLLI-YAASSLQSGVPSRFSGRGS GTDFTLTISSLQAEDFA-TYYCQQSYSIPQTFGQGTKLEIKRT). In some alternatives, the scFv is encoded by a nucleic acid sequence comprising a nucleic acid sequence encoding the amino acid sequence of SEQ ID NO: 47.

In some alternatives, the scFv comprises a B7H3 (hBRCA84D) scFv nucleotide sequence. In some alternatives, the scFv binds specifically to the B7-H3 receptor. The B7-H3 receptor is known to be expressed on a variety of cancer cells. Without being limiting, these cancer cells can included gastric, ovarian and/or non-small cell lung cancers. In some alternatives, the CAR is used in the treatment or amelioration of cancer and/or inflammation. In some alternatives, the scFv is encoded by a sequence set forth in SEQ ID NO: 48 (atgctgcgtcggcggggcagccctggcatgggtgtg- catgtgggtgcagccctgggagcactgtggttctgcctcacaggagccc tggaggtccaggtccctgaagacccagtggtggcactggtgggcaccgatgc- caccctgtgctgctccttctcccctgagcctggctt cagcctggcacagct- caacctcatctggcagctgacagataccaaacagctggtgcacagctttgct- gagggccaggaccagggca gcgcctatgccaaccgcacggccctcttcccggacctgctggcacagggcaacg- catccctgaggctgcagcgcgtgcgtgtggc ggacgagggcagctt- cacctgcttcgtgagcatccgggat- ttcggcagcgctgccgtcagcctgcaggtggccgctccctactcgaa gcccagcatgaccctggagcc- caacaaggacctgcggccaggggacacggtgaccatcacgtgctccagc- taccagggctaccct gaggctgaggtgttctggcag- gatgggcagggtgtgccccctgactggcaacgtgaccacgtcgcagatggccaac gagcagggct tgtttgatgtgcacag- catcctgcgggtggtgctgggtgcaaatggcaccta- cagctgcctggtgcgcaaccccgtgctgcagcagg atgcgcacagctctgtcac- catcacagggcagcctatgacattcccccagaggccctgtgggtgaccgtgggg ctgtctgtctgtct cattgcactgctggtggccctggctttcgtgtgctggagaaa- gatcaaacagagctgtgaggaggagaatgcaggagctgaggacc aggatggg- gagggagaaggctccaagacagccctgcagcctct- gaaacactctgacagcaaagaagatgatggacaagaaatag cc). In some alternatives, the scFv comprises a B7H3 (hBRCA84D) scFv amino acid sequence. In some alternatives, the scFv comprises an amino acid sequence set forth in SEQ ID NO: 49 (MLRRRGSPGMGVHVGAALGALWFCLTGA- LEVQVPEDPVVALVGTDATLCCSFSPE PGFSLAQLN- LIWQLTDTKQLVHSFAEGQDQGSAYANRTALFPDL- LAQGNASLRLQR VRVADEGSFTCFVSIRDFGSAAVSLQVAAPY- SKPSMTLEPNKDLRPGDTVTITCSSYQ GYPE- AEVFWQDGQGVPLTGNVTTSQMA- NEQGLFDVHSILRVVLGANGTYSCLVRN PVLQQDAHSSVTITGQPMTFP- PEALWVTVGLSVCLIALLVALAFVCWRKIKQSCEEE NAGAEDQDGEGEGSKTALQPLKHSDSKEDDGQEIA). In some alternatives, the scFv is encoded by a nucleic acid sequence comprising a nucleic acid sequence encoding the amino acid sequence of SEQ ID NO: 49.

In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50 (atgctgctgctggtgaccagcctgctgctgtgcgagctgccc- caccccgcctttctgctgatcccccaggtgcagctgcagcagcct ggcgccgagctggtgaagccaggcgccagcgt- gaagctgtcctgcaaggccagcggctacaccttcaccggctactggatgcact gggtgaagcagagacccggccacggcctggaatggatcggcgagat- caaccccagcaacggccggaccaactacaacgagcgg ttcaagagcaaggc- caccctgaccgtggacaagagcagcaccaccgcctt- catgcagctgtccggcctgaccagcgaggacagcg ccgtgtacttctgcgccagggactactacggcaccagctacaacttcgac- tactggggccagggcaccacactgaccgtgagcagc ggcg- gagggggctctggcggcggaggatctgggggagggggcagcgacatcca- gatgacccagagcagcagcagcttcagcg tgagcctgggcgaccgggtgaccatcacctgtaaggccaacgaggacat- caacaaccggctggcctggtatcagcagacccccgg caacagccccaggctgctgatcagcggcgccac- caacctggtgaccggcgtgcccagccggtttagcggcagcggctccggcaa ggactacaccctgaccatcacaagcctgcaggccgaggacttcgccacctac- tactgccagcagtactggtccaccccccttcaccttc ggcagcggcaccgagctg- gaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFL- LIPQVQLQQPGAELVKPGASVKLSCK- ASGYTFTGYWM HWVKQRPGHGLEWIGEINPSN- GRTNYNERFKSKATLTVDKSSTTAFMQLSGLTSEDS AVYFCARDYYGTSYNFDYWGQGT- TLTVSSGGGGSGGGGSGGGGSDIQMTQSSSSFS VSLGDRVTITCKANEDINNRLAWYQQTPGNSPRLLIS- GATNLVTGVPSRFSGSGSGK DYTLTITSLQAEDFA- TYYCQQYWSTPFTFGSGTELEIK). In some alternatives, the scFv is encoded by a nucleic acid sequence comprising a nucleic acid sequence encoding the amino acid sequence of SEQ ID NO: 51.

In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52 (atgcttctcctggtgacaagccttctgctctgtgagttaccacacccag- cattcctcctgatcccacaggtgcagctgaaacagagcg gcccgggcctggtgcagccgagccagagcctgagcattacctgcaccgt- gagcggctttagcctgaccaactatggcgtgcattgg gtgcgccagagcccgggcaaaggcctggaatggctgggcgtgatttg- gagcggcggcaacaccgattataacaccccgtttacca gccgcctgagcat- taacaaagataacagcaaaagccaggtgtttttaaaat- gaacagcctgcagagcaacgataccgcgatttattat tgcgcgcgcgcgctgacctattatgattatgaatttgcgtat- tggggccagggcaccctggtgaccgtgagcgcgggcggcggcgg cagcggcggcggcggcagcggcggcggcggcagcgatat- tctgctgacccagagcccggtgattctgagcgtgagcccgggcg aacgcgt- gagctttagctgccgcgcgagccagagcattggcaccaacattcat- tggtatcagcagcgcaccaacggcagcccgcgc ctgctgattaaatatgcgagcgaaagcattagcggcattccgagccgctt- tagcggcagcggcagcggcaccgatttaccctgagc attaacagcgtg- gaaagcgaagatattgcggattattattgccagcagaacaacaactggccgac- cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL- CELPHPAFLLIPQVQLKQSGPGLVQPSQSL- SITCTVSGFSLTNYGVHW VRQSPGKGLEW- LGVIWSGGNTDYNTPFTSRLSINKDNSKSQVFFKMNS LQSNDTAIY YCARALTYYDYE- FAYWGQGTLVTVSAGGGGSGGGGSGGGGS- DILLTQSPVILSVSP GERVSFSCRASQSIGT- NIHWYQQRTNGSPRLLIKYASESISGIPSRFSGSGSGTD FTLSI NSVESEDI- ADYYCQQNNNWPTTFGAGTKLELKRT). In some alternatives, the scFv is encoded by a nucleic acid sequence comprising a nucleic acid sequence encoding the amino acid sequence of SEQ ID NO: 53.

In some alternatives, the scFv comprises the EGFRVIII (806) scFv nucleotide sequence. In some alternatives, the scFv is specific for EGFR. In some alternatives, the scFv is encoded by the nucleic acid sequence set forth in SEQ ID NO: 54 (atgctgctgctggtgacaagcctgctgctgtgcgagctgc- cacaccctgctttcctgctgatccctgatgtgcagctgcaggaatcag gcc- caagcctggtcaaaccctcccagtctctgagtctgacctgta- cagtgactgggtactccatcacatctgatttcgcatggaactgg attaggcagtttccaggcaataagctggagtggatgggctacatctcatatagcgg- gaacactcgctataatcccagtctgaaatcacg gatcagcattactaga- gacaccagcaagaaccagttctttctgcagctgaattccgtgaccattgagga- taccgccacatactattgcgt cacagctggcagaggctttccat- actggggacagggcacactggtgactgtcagcgccggctccacctctgggagtg- gaaaacctg gctccggggaaggatctacaaagggagacatcctgatgactcagtccccaagctccatgtcagtgagcctgggcgacaccgtctcta ttacatgtcactctagtcaggatatcaacagtaatat-tggctggctgcagcagcgacccggcaagtctttcaaagggctgatctatcatg gaactaacctggacgatgaagtgcctagcagattttccggctctgggagtg-gagctgattacagtctgaccatttcaagcctggagtca gaagacttcgcagattac-tattgcgtccagtatgcccagttcccctggacttttggcgggggaaccaagctg-gagatcaaacgg). In some alternatives, the scFv comprises the EGFRVIII (806) scFv amino acid sequence. In some alternatives, the scFv comprises the amino acid sequence set forth in SEQ ID NO: 55 (MLLLVTSLLLCELPHPAFL-LIPDVQLQESGPSLVKPSQSLSLTCTVTGYSITSD-FAWN WIRQFPGNKLEWMGYISYSGN-TRYNPSLKSRISITRDTSKNQFFLQLNSVTIEDTATY YCVTAGRGFPYWGQGTLVTVSAGST-SGSGKPGSGEGSTKGDILMTQSPSSMSVSLG DTVSITCHSSQDIN-SNIGWLQQRPGKSFKGLIYHGTNLD-DEVPSRFSGSGSGADYSLTI SSLESED-FADYYCVQYAQFPWTFGGGTKLEIKR). In some alternatives, the scFv is encoded by a nucleic acid sequence comprising a nucleic acid sequence encoding the amino acid sequence of SEQ ID NO: 55.

In some alternatives, the scFv is encoded by the EphA2 (2A4) scFv nucleotide sequence. In some alternatives, the scFv is encoded by the nucleic acid sequence set forth in SEQ ID NO: 56 (atgcttctcctggtgacaagccttctgctctgtgagttac-cacacccagcattcctcctgatcccacaggtgcagctgttggagtctggg ggaggcttggtacagcctggggtccctgagactctcctgtgcagcctctggatt-cacctttagagactataccatgtcttgggtgcg acaggcccctggacaagcgctt-gagtggatgggaaccattagtagtcgtggtacttacacctactatccagacagtgt-gaagggccg attcaccatctccagagacaacgccaagaactcactgtatctgcaaat-gaacagcctgagagccgaggacacggctgtgtattactgt gcgagagaagc-tatctttactcactggggccgtggcaccctggt-caccgtctcctcaggtggtggtggttctggcggcggcggctcc ggtggtggtggttctgacatccagttgacccagtctccatcctccctgtctg-catctgtaggagacagagtcaccatcacttgcaaggc gagtcaggacat-taataactatcacagctggtaccagcagaaacctggccaggctcccaggctcct-catctatcgtgcaaacagattg gtcgatggggtcccagacaggttcagtggcagcgggtatggaacagattt-taccctcacaattaataacatagaatctgaggatgctg catattacttctgtct-gaaatataatgtgtttccgtacacgttcggccaagggaccaaggtggagatcaaa). In some alternatives, the scFv comprises the EphA2 (2A4) scFv amino acid sequence. In some alternatives, the scFv comprises an amino acid sequence set forth in SEQ ID NO: 57 (MLLLVTSLLLCELPHPAFLLIPQVQLLESGG-GLVQPGGSLRLSCAASGFTFSSYTMS WVRQAPGQALEWMGTIS-SRGTYTYYPDSVKGRFTISRDNAKNSLYLQMNSL-RAEDT AVYYCAREAIFTHWGRGTLVTVSSGGGGSG GGGSGGGGSDIQLTQSPSSLSASVGDR VTITCK-ASQDINNYHSWYQQKPGQAPRLLIYRANRLVDGV PDRFSGSGYGTDFTLTI NNIESEDAAYYFCLKYNVFPYTFGQGTKVEIK). In some alternatives, the scFv is encoded by a nucleic acid sequence comprising a nucleic acid sequence encoding the amino acid sequence of SEQ ID NO: 57.

In some alternatives, the scFv is encoded by the EpHA2 (4H5) scFv nucleotide sequence. In some alternatives, the scFv is encoded by the nucleic acid sequence set forth in SEQ ID NO: 58 (atgcttctcctggtgacaagccttctgctctgtgagttac-cacacccagcattcctcctgatcccacaggtgcagctgttggagtctggg ggaggcttggtacagcctggggtccctgagactctcctgtgcagcctctggatt-cacctttgagagctataccatgtcttgggtgcg acaggcccctggacaagcgctt-gagtggatgggaaccattagtagtggtggtacttacacctactatccagacagtgt-gaagggccg attcaccatctccagagacaacgccaagaactcactgtatctgcaaat-gaacagcctgagagccgaggacacggctgtgtattactgt gcgagagaagc-tatctttacttactggggccgtggcaccctggt-caccgtctcctcaggtggtggtggttctggcggcggcggctccg gtggtggtggttctgacatccagttgacccagtctccatcctccctgtctg-catctgtaggagacagagtcaccatcacttgcaaggcg agtcaggacat-taataactatttaagctggtaccagcagaaacctggccaggctcccaggctcct-catctatcgtgcaaacagattggt agatggggtcccagacaggttcagtggcagcgggtatggaacagattttaccct-cacaattaataacatagaatctgaggatgctgcat attacttctgtctgaaatat-gatgtgtttccgtacacgttcggccaagggaccaaggtggagatcaaa). In some alternatives, the scFv comprises the EpHA2 (4H5) scFv amino acid sequence. In some alternatives, the scFv comprises an amino acid sequence set forth in SEQ ID NO: 59 (MLLLVTSLLLCELPHPAFLLIPQVQLLESGG-GLVQPGGSLRLSCAASGFTFSSYTMS WVRQAPGQALEWMGTIS-SGGTYTYYPDSVKGRFTISRDNAKNSLYLQMNSL-RAEDT AVYYCAREAIFTYWGRGTLVTVSSG GGGSGGGGSGGGGSDIQLTQSPSSLSASVGDR VTITCKASQDIN-NYLSWYQQKPGQAPRLLIYRANRLV DGVPDRFSGSGYGTDFTLTI NNIESEDAAYYFCL-KYDVFPYTFGQGTKVEIK). In some alternatives, the scFv is encoded by a nucleic acid sequence comprising a nucleic acid sequence encoding the amino acid sequence of SEQ ID NO: 59.

In some alternatives, the scFv is encoded by a FITC (E2) scFv nucleotide sequence. In some alternatives, the scFv is encoded by a nucleic acid sequence set forth in SEQ ID NO: 60 (atgcttctcctggtgacaagccttctgctctgtgagttaccacacccagcat-tcctcctgatcccaagcgtgctgacacagcctagctc cgtgtctgccgcccctggccagaaagtgac-catcagctgtagcggcagcaccagcaacatcggcaacaac-tacgtgtcctggtatca gcagcaccccggcaaggcccccaagctgatgatc-tacgacgtgtccaagcggcccagcggcgtgcccgatagattttccggcagc aagagcggcaacagcgccagcctggatatcagcggcctgcagtct-gaggacgaggccgactactattgcgccgcctgggacgata gcct-gagcgagttcctgtttggcaccggcaccaagctgacagtgctgggcggaggcg-gaggatctggcggcggaggaagtggcg gagggggatctcaggtgcagctggtg-gaaagcggcggcaacctggtgcagcctggcggatctctgagact-gagctgtgccgccag cggcttcaccttcggcagcttcagcat-gagctgggtgcgccaggctcctgggggaggactggaatgggtggcaggactgag cgcc agaagcagcctgacccactacgccgatagcgtgaagggccggttcac-catcagccgggacaacgccaagaacagcgtgtacctgc agat-gaacagcctgcgggtggaagataccgccgtgtactactgcgccagacggtcc-tacgacagcagcggctactggggccacttc tacagctacatggacgtgtggggccagggcaccctcgtgacagtgtct). In some alternatives, the scFv comprises the FITC (E2) scFv amino acid sequence. In some alternatives, the scFv comprises an amino acid sequences set forth in SEQ ID NO: 61 (MLLLVTSLLLCELPHPAFL-LIPSVLTQPSSVSAAPGQKVTISCSGSTS-NIGNNYVSWY QQHPGKAPKLMIYDV-SKRPSGVPDRFSGSKSGNSASLDISGLQSEDEADYYC AAWD DSLSEFLFGTGTKLTVLGGGGGSGG GGSGGGGSQVQLVESGGNLVQPGGSLRLSCA ASGFTFGSFSMSWVRQAPGGGLEWVAGL-SARSSLTHYADSVKGRFTISRDNAKNSV YLQMNSLRVEDTAVYY-CARRSYDSSGYWGHFYSYMDVWGQGTLVTVS). In some alternatives, the scFv is encoded by a nucleic acid sequence comprising a nucleic acid sequence encoding the amino acid sequence of SEQ ID NO: 61.

In some alternatives, the scFv is encoded by the GD2 (hu3F8) scFv nucleotide sequence. In some alternatives, the scFv is encoded by a nucleic acid sequence set forth in SEQ ID NO: 62 (atgcttctcctggtgacaagccttctgctctgtgagttac-cacacccagcattcctcctgatcccaagcatcgtgatgacccagacccc caagttcctgctggtgagcgccggcgacagggtgaccat-cacctgcaaggccagccagagcgtgagcaacgacgtgacctggtac cagcagaaggccggccagagcccccccaacaggta-cagcggcgtgcccgacaggttcaccggc agcggctacggcaccgccttcac-catcagcaccgtgcaggccaactggccgtgtacttctgccagcaggactacag cagcttcggcggcggcaccaagctggagatcaagagg). In some alternatives, the scFv comprises the GD2 (hu3F8) scFv amino acid sequence. In some alternatives, the scFv comprises an amino acid sequence set forth in SEQ ID NO: 63 (MLLLVTSLLL-CELPHPAFLLIPSIVMTQTPKFLLVSAGDRVTITCK-ASQSVSNDVTWY QQKAGQSPKLLIYSASN-RYSGVPDRFTGSGYGTAFTFTISTVQAEDLAVYFCQQ DYS SFGGGTKLEIKR). In some alternatives, the scFv is encoded by a nucleic acid sequence comprising a nucleic acid sequence encoding the amino acid sequence of SEQ ID NO: 63.

In some alternatives, the scFv is encoded by the Her2 (Herceptin) scFv nucleotide sequence. In some alternatives, the scFv is encoded by a nucleic acid sequence set forth in SEQ ID NO: 64 (atgcttctcctggtgacaagccttctgctctgtgagttac-cacacccagcattcctcctgatcccagatatccagatgacccagtccccg agctccctgtccgcctctgtgggcgatagggtcaccat-cacctgccgtgccagtcaggatgtgaatactgctgtagcctggtatcaaca gaaaccaggaaaagctccgaaactactgatttactcggcatccttcctctactctg-gagtcccttctcgcttctctggttccagatctggg acggatttcactctgac-catcagcagtctgcagccggaagacttcgcaacttattactgtcagcaacattatac-tactcctcccacgttcg gacagggtaccaaggtggagat-caaaggcagtactagcggcggtggctccgggggcg-gatccggtgggggcggcagcagcga ggttcagctggtg-gagtctggcggtggcctggtgcagccagggggctcactccgtttgtcctgtgcagc ttctggcttcaacattaaag acacctatata-cactgggtgcgtcaggccccgggtaagggcctggaatgggttgcaaggatt-tatcctacgaatggttatactagatat gccgatagcgtcaagggccgtttcac-tataagcgcagacacatccaaaaacacagcctacctgcagatgaacagcctgcgt gctga ggacactgccgtctattattgttctagatggggaggggacggcttctatgc-tatggactactggggtcaaggaaccctggtcaccgtct cgagt). In some alternatives, the scFv comprises the Her2 (Herceptin) scFv amino acid sequence. In some alternatives, the scFv comprises an amino acid sequence set forth in SEQ ID NO: 65 (MLLLVTSLLLCELPHPAFLLIPDIQMTQSPSSL-SASVGDRVTITCRASQDVNTAVAW YQQKPGKAPKLLIYSASFLY-SGVPSRFSGSRSGTDFTLTISSLQPEDFA-TYYCQQHYTT PPTFGQGTKVEIKGST-SGGGSGGGSGGGGSSEVQLVESGGGLVQPGGSLRLS-CAASG FNIKDTYIHWVRQAPGKGLEW-VARIYPTNGYTRYADSVKGRFTISADTSKNTAYLQ MNSLRAED-TAVYYCSRWGGDGFYAMDYWGQGTLVTVSS). In some alternatives, the scFv is encoded by a nucleic acid sequence comprising a nucleic acid sequence encoding the amino acid sequence of SEQ ID NO: 65.

In some alternatives, the scFv is encoded by the IL13R2a (hu08) VlVh scFv nucleotide sequence. In some alternatives, the scFv is encoded by a nucleic acid sequence set forth in SEQ ID NO: 66 (atgcttctcctggtgacaagccttctgctctgt-gagttaccacacccagcattcctcctgatcccagacatccagatgacccagtcccc ctcttctctgtctgcctctgtgggcgacagagtgaccat-cacctgtaaggccagtcaggatgtaggtactgctgtagcctggtatcagca gaagcctggcaaggctcccaagctgctgatctactcggcatcctaccggtc-cactggcgtgccttccagattctccggctctggctctg gcaccgattt-caccctgaccatctcctccctccagcctgaggatttcgccacctac-tactgccagcaccattatagtgctccgtggacgt ttggcggcggaacaaaggtggagat-caagggtggtggtggttctggcggcggcggctccggtggtggtggttct-gaggtgcagctg gtggagtctggcggcggactggtgcagcctggcggctctct-gagactgtcttgtgccgcctccggcttcaccttcagtaggaatggca tgtcttgggtgaggcaggcccctggcaagggcctggagtgggtggccaccgt-tagtagtggtggtagttacatctactatgcagaca gtgtgaagggggcggttcac-catctccagggacaacgccaagaactccctgtacctccagatgaactccct-gagggccgaggatacc gccgtgtactactgtgc). In some alternatives, the scFv comprises the IL13Ra2 (hu08) VlVh scFv amino acid sequence. In some alternatives, the scFv comprises an amino acid sequence set forth in SEQ ID NO: 67 (MLLL-VTSLLLCELPHPAFLLIPDIQMTQSPSSL-SASVGDRVTITCKASQDVGTAVAW YQQKPGKAPKLLIYSASYRSTGVPSRFSGSGSGTDFT LTISSLQPEDFATYYCQHHYS APWTFGGGTKVEIKGGGGSGGGGSGGGG-SEVQLVESGGGLVQPGGSLRLSCAASGF TFSRNGMSWVRQAPGKGLEWVATVSSGGSYIYY-ADSVKGRFTISRDNAKNSLYLQ MNSLRAED-TAVYYC). In some alternatives, the scFv is encoded by a nucleic acid sequence comprising a nucleic acid sequence encoding the amino acid sequence of SEQ ID NO: 67.

In some alternatives, the scFv is encoded by an IL13Ra2 (hu08) VhV1 scFv nucleotide sequence. In some alternatives, the scFv is encoded by a nucleic acid sequence set forth in SEQ ID NO: 68 (atgcttctcctggtgacaagccttctgctctgt-gagttaccacacccagcattcctcctgatcccagaggtgcagctggtggagtctgg cggcggactggtgcagcctggcggctctctga-gactgtcttgtgccgcctccggcttcaccttcagtaggaatggcatgtcttgggtga ggcaggcccctggcaagggcctggagtgggtggccaccgt-tagtagtggtggtagttacatctactatgcagacagtgtgaagggg cggttcac-catctccagggacaacgccaagaactccctgtacctccagatgaactccct-gagggccgaggataccgccgtgtactac tgtgccagacaagggactacggcactagctacgaggttcttc-gatgtctggggccagggcaccctggtgaccgtgtcctctggtggt ggtggttctggcggcggcggctccggtggtggtggttctgacatcca-gatgacccagtcccccctcttctctgtctgcctctgtgggcga cagagtgaccat-cacctgtaaggccagtcag-gatgtaggtactgctgtagcctggtatcagcagaagcctggcaaggctcccaagct gctgatctactcggcatcctaccggtccactggcgtgccttccagat-tctccggctctggctctggcaccgatttcaccctgaccatctc ctccctccagcct-gaggatttcgccacctactactgccagcaccat-tatagtgctccgtggacgtttggcggcggaacaaaggtggag atcaaggaatctaagta). In some alternatives, the scFv comprises an IL13Ra2 hu08 VhV1 scFv amino acid sequence. In some alternatives, the scFv comprises an amino acid sequence set forth in SEQ ID NO: 69 (MLLLVTSLLLCELPHPAFL-LIPEVQLVESGGGLVQPGGSLRLS-CAASGFTFSRNGMS WVRQAPGKGLEW-VATVSSGGSYIYYADSVKGRFTISRDNAKNSLYLQM-NSLRAEDT AVYYCARQGTTALA-TRFFDVWGQGTLVTVSSGGGGSGGGGSGGGGSDIQ-MTQSPSS LSASVGDRVTITCKASQDVGTA-VAWYQQKPGKAPKLLIYSASYRSTGVPSRFSGSGS GTDFTLTISSLQPEDFATYYCQHHYS-APWTFGGGTKVEIKESK). In some alternatives, the scFv is encoded by a nucleic acid sequence comprising a nucleic acid sequence encoding the amino acid sequence of SEQ ID NO: 69.

In some alternatives, the scFv is encoded by an IL13Ra2 (hu07) VlVh scFv nucleotide sequence. In some alternatives, the scFv is encoded by a nucleic acid sequence set forth in SEQ ID NO: 70 (atgcttctcctggtgacaagccttctgctctgt-gagttaccacacccagcattcctcctgatcccagatattcagatgacccagagccc gagcagcctgagcgcgagcgtgggcgatccgcgtgagcagcacctatctgcattggt atcagcagaaaccgggcaaagcgccgaaactgctgatt-tatagcaccagcaacctggcgagcggcgtgccgagccgctttagcgg cagcggcagcggcaccgattttaccctgaccattagcagcctgcagccggaa-gattttgcgacctattattgccatcagtatcatcgca gcccgctgacctttggcggcggcaccaaagtggaaat-taaaggtggtggtggttctggcggcggcggctccggtggtggtggttctg aagtgcagctggtg-gaaagcggcggcggcctggtgcagcggcggcgggcctggtgcgcggcgagcg gctttacct ttaccaaatatggcgtgcat-tgggtgcgccaggcgccgggcaaaggcctggaatgggtggcggt-gaaatgggcgggcggcagca ccgattataacagcgcgctgatgagccgctt-taccattagccgcgataacgcgaaaaacagcctgtatctgcagatgaacagcctgc gcgcggaagataccgcggtgtattattgcgcgcgcgatcatcgcgatgcgatg-gattattggggccagggcaccctggtgaccgtg agcagcgaatctaagta). In some alternatives, the scFv comprises an IL13Ra2 (hu07) VhV1 scFv amino acid sequence. In some alternatives, the scFv comprises an amino acid sequence set forth in SEQ ID NO: 71 (MLLLVTSLLLCELPHPAFLLIPDIQMTQSPSSL-SASVGDRVTITCTASLSVSSTYLHWY QQKPGKAPKLLIYSTSN-LASGVPSRFSGSGSGTDFTLTISSLQPEDFATYY-CHQYHRSP LTFGGGTKVEIKGGGGSGGGGSGGGG-SEVQLVESGGGLVQPGGSLRLSCAASGFTFT KYGVHWVRQAPGKGLEWVAVKWAGGSTDYN-SALMSRFTISRDNAKNSLYLQMNS LRAEDTAVYY-CARDHRDAMDYWGQGTLVTVSSESK). In some alternatives, the scFv is encoded by a nucleic acid sequence comprising a nucleic acid sequence encoding the amino acid sequence of SEQ ID NO: 71.

In some alternatives, the scFv is encoded by the IL13Ra2 (hu07) VhV1 scFv nucleotide sequence. In some alternatives, the scFv is encoded by a nucleic acid sequence set forth in SEQ ID NO: 72 (atgcttctcctggtgacaagccttctgctctgt-gagttaccacacccagcattcctcctgatcccagaagtgcagctggtggaaagcg gcggcggcctggtgcagccgggcggcagcctgcgcct-gagctgcgcggcgagcggctttacctttaccaaatatggcgtgcattgg gtgcgccaggcgccgggcaaaggcctggaatgggtggcggt-gaaatgggcgggcggcagcaccgattataacagcgcgctgat gagccgctt-taccattagccgcgataacgcgaaaaacagcctgtatctgcagat-gaacagcctgcgcgcggaagataccgcggtgt attattgcgcgcgcgatcatcgcgatgcgatggattat-tggggccagggcaccctggtgaccgtgagcagcggtggtggtggttctg gcggcggcggctccggtggtggtggttctgatattca-gatgacccagagcccgagcagcctgagcgcgagcgtgggcgatcgcgt gac-cattacctgcaccgcgagcctgagcgtgagcagcacctatctgcat-tggtatcagcagaaaccgggcaaagcgccgaaactgc tgatttatagcaccagcaacctggcgagcggcgtgccgagccgctt-tagcggcagcggcagcggcaccgattttaccctgaccatta gcagcctgcagccggaagattttgcgacctattattgccatcagtat-catcgcagcccgctgacctttggcggcggcaccaaagtgga aat-taaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFL-LIPEVQLVESGGGLVQPGGSLRLSCAASGFTFT-KYGVH WVRQAPGKGLEWVAVKWAGGSTDYN-SALMSRFTISRDNAKNSLYLQMNSLRAED TAVYYCARDHRDAMDYWGQGTLVTVSSGGGGS GGGGSGGGGSDIQMTQSPSSLSA SVGDRVTITC-TASLSVSSTYLHWYQQKPGKAPKLLIYSTSN-LASGVPSRFSGSGSGTD FTLTISSLQPEDFATYY-CHQYHRSPLTFGGGTKVEIKESK). In some alternatives, the scFv is encoded by a nucleic acid sequence comprising a nucleic acid sequence encoding the amino acid sequence of SEQ ID NO: 73.

In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74 (atgcttctcctggtgacaagccttctgctctgtgagttac-cacacccagcattcctcctgatcccaggccctgtgcctccctctacagcc ctcaggtacctcattgaggagctggtcaacat-cacccagaaccagaaggctccgctctgcaatggcagcatggtatggagcatcaac ctgacagctggcatgtactgtgcagccctggaatccctgat-caacgtgtcaggctgcagtgccatcgagaagacccagaggatgctg agcggat-tctgcccgcacaaggtctcagctgggcagttttccagcttgcatgtccgagacac-caaaatcgaggtggcccagtttgtaa aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFL-LIPGPVPPSTALRYLIEELVNITQNQKAPLCNG-SMVWSI NLTAGMYCAALESLINVSGC-SAIEKTQRMLSGFCPHKVSAGQFSSLHVRDTKIEVAQ FVKDLLLHLKKLFREGRF). In some alternatives, the scFv is encoded by a nucleic acid sequence comprising a nucleic acid sequence encoding the amino acid sequence of SEQ ID NO: 75.

In some alternatives, the scFv is encoded by an oaGD2 (8B6) VlVh scFv nucleotide sequence. In some alternatives, the scFv is encoded by a sequence set forth in SEQ ID NO: 76 (atgcttctcctggtgacaagccttctgctctgtgagttaccacacccagcat-tcctcctgatcccagatgttgtgatgacccaaactcca ctctccctgcctgtcagtcttggagatcaagcctcaatctcttgca-gatctagtcagagccttctaaaaaatggaaacaccttttaca ttggtacctgcagaagtcaggccagtctccaaagctccttatctacaaagtttc-caaccgactttctggggtcccagacaggttcagtgg cagtggatcagggacatat-ttcacactcaagatcagcagagtggaggctgaggatctgggagtttatttctgctct-caaagtacacatat tccgtacacattcggaggggggaccaagctcgagctgaaacgaggcg-gagggggctctggcggcggaggatctgggggagggg gcagcgaggt-gaaactggtggagtctggaggaggcttggtgctgcctggggattctctga-gactctcctgtgcaacttctgagttcac cttcactgattactacatgacttgggtccgccagcctccaagaaaggcactt-gagtggttgggttttattagaaacagagctaatggttac acaacagagtacaatc-catctgtgaagggtcggttcaccatttccagagataattcccaaagcatcctc-tatcttcaaatgaacaccctg agaactgaggacagtgccacttattactgtgcaagagtctctaactgggcctttgac-tactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77 (MLLLVTSLLLCELPHPAFL-LIPDVVMTQTPLSLPVSLGDQASIS-CRSSQSLLKNNGNT FLHWYLQKSGQSPKLLIYKVSNRLSGVPDRFSGSGSG TYFTLKISRVEAEDLGVYFCS QSTHIPY-TFGGGTKLELKRGGGGSGGGGSGGGGSEVKLVES-GGGLVLPGDSLRLSCA TSEFTFTDYYMTWVRQP-PRKALEWLGFIRNRANGYTTEYNPSVKGRFTISRDNS QSIL YLQMNTLRTEDSATYYCARVSN-WAFDYWGQGTTLTVSS). In some alternatives, the scFv is encoded by a nucleic acid sequence comprising a nucleic acid sequence encoding the amino acid sequence of SEQ ID NO: 77.

In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccc-caccccgcctttctgctgatcccccaggaacagctcgtcgaaagc ggcggcagactggtgacacctggcggcagcctgaccct-gagctgcaaggccagcggcttcgacttcagcgcctactacatgagctg ggtccgccaggcccctggcaagggactggaatggatcgccaccatc-taccccagcagcggcaagacctactacgccacctgggtg aacggacggttcac-catctccagcgacaacgcccagaacaccgtggacctgcagat-gaacagcctgacagccgccgaccgggcc acctacttttgcgccagagacagctacgccgacgacggcgccctgttcaa-catctggggccctggcaccctggtgacaatctctagc ggcggaggcg-gatctggtggcggaggaagtggcggcggaggatct-gagctggtgctgacccagagcccctctgtgtctgctgccc tgggaagccctgccaagatcacctgtaccctgagcagcgcccacaa-gaccgacaccatcgactggtatcagcagctgcagggcga ggcccccaga-tacctgatgcaggtgcagagcgacggcagctacac-caagaggccaggcgtgcccgaccggttcagcggatctag ctctggcgccgaccgctacctgatcatccccagcgtgcaggcc-gatgacgaggccgattactactgtggcgccgactacatcggcg gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESG-GRLVTPGGSLTLSCKASGFDFSAYYMSW VRQAPGKGLEWIATIYPSSGKTYYATWVNGRFTIS-SDNAQNTVDLQMNSLTAADRA TYFCARDSYADD-GALFNIWGPGTLVTISSGGGGSGGGGSGGGG-SELVLTQSPSVSAA LGSPAKITCTLS-SAHKTDTIDWYQQLQGEAPRYLMQVQSDG-SYTKRPGVPDRFSGSS SGADRYLIIPSVQADDEAD-YYCGADYIGGYVFGGGTQLTVTG). In some alternatives, the scFv is encoded by a nucleic acid sequence comprising a nucleic acid sequence encoding the amino acid sequence of SEQ ID NO: 79.

In some alternatives, the scFv comprises an amino acid sequence set forth in SEQ ID NO: 80 (CD33 (h2H12) VhVl scFv nucleotide sequence (atgcttctcctggtgacaagccttctgctctgtgagttaccacacccagcat-tcctcctgatcccacaggttcagctggtgcagtctgga gctgaggt-gaagaagcctggggcctcagtgaaggtctcctgcaaggcttctggttacacctt-taccaattatgatataaattgggtgag acaggcccctggacaagggcttgagtggattggatggatttatcctg-gagatggtagtaccaaatataatgagaaattcaaggccaag gctaccctgacagctgacacatccaccagcacagcctacatggagctgag-gagcctgagatctgatgacacagctgtgtattactgtg cttctggatatgaagatgc-tatggactactgggggcaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQS-GAEVKKPGASVKVSCKASGYTFTNYDIN WVRQAPGQGLEWIGWIYPGDGSTKYNEKFKAKATL-TADTSTSTAYMELRSLRSDDT AVYY-CASGYEDAMDYWGQGTTVTVSS). In some alternatives, the scFv is encoded by a nucleic acid sequence comprising a nucleic acid sequence encoding the amino acid sequence of SEQ ID NO: 81.

In some alternatives, the scFv is encoded by a sequence set forth in SEQ ID NO: 82 (CD33 (h2H12) VlVh scFv nucleotide sequence: atgcttctcctggtgacaagccttctgctctgtgagt-taccacacccagcattcctcctgatcccagacatccagatgacccagtctccat cctcactgtctgcatctgtaggagacagagtcaccatcaat-tgtaaggctagtcaggacattaatagctatttgagctggtttcagcaga aaccagg-gaaagcccctaagaccctgatctatagagcaaatagattggtagatggggtcccat-caaggttctctggcagtggatctgg gcaagattatactctcaccatcagcagcctgcagcctgaagattttgcaacttat-tactgcttgcagtatgatgagtttcctctcacatttgg aggagggaccaaggtg-gagatcaaa). In some alternatives, the scFv comprises an amino acid sequence set forth in SEQ ID NO: 83 (CD33 (h2H12) VlVh scFv amino acid sequence: MLLLVTSLLL-CELPHPAFLLIPDIQMTQSPSSLSASVGDRVTINCK-ASQDINSYLSWFQ QKPGKAPKTLIYRANRLVDGVPSRFS GSGSGQDYTLTISSLQPEDFATYYCLQYDEFP LTFGGGTKVEIK). In some alternatives, the scFv is encoded by a nucleic acid sequence comprising a nucleic acid sequence encoding the amino acid sequence of SEQ ID NO: 83.

In some alternatives, the scFv is encoded by a nucleic acid sequence set forth in SEQ ID NO: 84 (Mesothelin (P4) scFv nucleotide sequence: atgcttctcctggtgacaagccttctgctctgtgagt-taccacacccagcattcctcctgatcccacaggtacagctgcagcagtcaggt ccaggactcgtgacgccctcgcagaccctctcactcacctgtgc-catctccggggacagtgtctctagcaacagtgctacttggaact ggatcaggcagtccccatcgagaggccttgagtggctgggaaggacatacta-caggtccaagtggtataacgactatgcagtatctg tgaaaagtcgaatgagcat-caacccagacacatccaagaaccagttctccctgcagct-gaactctgtgactcccgaggacacggctg tgtattactgtgcaagaggaatgatgacttactattacggtatggacgtctggggc-caagggaccacggtcaccgtctcctcaggaatt ctaggatcc). In some alternatives, the scFv comprises an amino acid sequence set forth in SEQ ID NO: 85 (Mesothelin (P4) scFv amino acid sequence: MLLLVTSLLLCELPHPAFL-LIPQVQLQQSGPGLVTPSQTLSLTCAISGDSVSSN-SATWN WIRQSPSRGLEWLGRTYYRSKWYN-DYAVSVKSRMSINPDTSKNQFSLQLNSVTPED TAVYY-CARGMMTYYYGMDVWGQGTTVTVSSGILGS). In some alternatives, the scFv is encoded by a nucleic acid sequence comprising a nucleic acid sequence encoding the amino acid sequence of SEQ ID NO: 85.

In some alternatives, the scFv is encoded by a nucleic acid sequence set forth in SEQ ID NO: 86 (VAR2CSA (ID1-DBL2Xb) scFv nucleotide sequence: atgcttctcctggtgacaagccttctgctctgtgagttaccacacccagcat-tcctcctgatcccaagtctcacgaatgggtataagtgcg acaaatgcaaatcaggcacatcccggtccaaaaaaaaatggatctg-gaaaaagagcagcgggaatgaggagggcctgcaggaag aatacgctaacacaatcggactgccccctcgaactcaatctctgtaccttgg-gaacttgcctaaactggaaaacgtctgtgaagacgtc aaggacataaacttcga-tacgaaagagaagttcctggctggatgccttatcgtgagctttcacgagg-gaaagaatctgaagaaaggt acccacagaataaaaactctggcaataaagagaatttgtgcaaggccctg-gagtactcttttgcggactatggcgatctcataaagggc acaagcatctggga-taatgagtataccaaggatctggagctgaatctgcagaataactttgggaaat-tgtttgggaagtatattaaaaaa aataataccgccgagcaggacacatcctactcttccctcgacgagctgcgggagt-catggtggaacaccaacaaaaagtatatctgg acggcaatgaaacatggcgcg-gaaatgaatatcaccacttgtaatgcagacggctctgt-caccgggtccggttcttcttgcgatgatat accaaccatcgatttgattccgcagtatctgagatttctccaagagtgggtg-gaaaatttttgcgagcagaggcaagctaaggtcaagg acgtgatcaccaat-tgtaaaagttgcaaagaatcagggaacaagtgcaaaaccgagtgtaa-gacgaagtgcaaggacgaatgcgag aaatataaaaaattcatcgaggcttgtggaacagccgggggtgggat-tgggaccgcaggcagcccatggagcaagcggtgggacc aaatctataaacga-tacagcaagcacatcgaagatgccaagcg-gaaccgcaaagctggcacaaaaaactgtgggactagcagcac gactaatgccgcggcaagcactgatgaaaataaatgcgtgcaaagtga-catcgactctttcttcaaacacctgatcgatatcggtcttac tacgccaagcagc-tacctcagtaatgttctggatgataatatttgtggggcggacaaagcaccttggac-tacctacaccacctatacca caacagagaagtgtaataaagagagagacaaatcaaagtctcagagctctgata-cactggtcgttgtgaatgtgccaagccctttggg gaatacgccctacaga-tataaatac). In some alternatives, the scFv comprises an amino acid sequence set forth in SEQ ID NO: 87 (VAR2CSA (ID1-DBL2Xb) scFv amino acid sequence:

MLLLVTSLLLCELPHPAFLLIPSLTNGYKCDKCK-SGTSRSKKKWIWKKSSGNEEGLQ EEYANTIGLP-PRTQSLYLGNLPKLENVCEDVKDINFDTKEK-FLAGCLIVSFHEGKNLK KRYPQNKNSGNKENLCKALEYSFADYGD-LIKGTSIWDNEYTKDLELNLQNNFGKLF GKYIK-KNNTAEQDTSYSSLDELRESWWNTNKKYIWTAM-KHGAEMNITTCNADGSV TGSGSSCDDIP-TIDLIPQYLRFLQEWVENFCEQRQAKVKDVITNCK-SCKESGNKCKTE CKTKCKDECEKYKK-FIEACGTAGGGIGTAGSPWSKRWDQIYKRYSKHIEDA KRNRK AGTKNCGTSSTTNAAASTDENKCVQS-DIDSFFKHLIDIGLTTPSSYLSNVLDDNICGA DKAPWTTYTTYTTTEKCNKERDK-SKSQSSDTLVVVNVPSPLGNTPYRYKY). In some alternatives, the scFv is encoded by a nucleic acid sequence comprising a nucleic acid sequence encoding the amino acid sequence of SEQ ID NO: 87.

"Spacer", can also be referred to as a "linker," and has its plain and ordinary meaning when read in light of the specification, and may include but is not limited to, for example, residues which resides between the light and the heavy chains. The spacer can be 10 to 20 amino acids in length (e.g., at least, equal to 10, 11, 12, 13, 14, 15, 16, 17, 18, 19, or 20 amino acids or a length within a range defined by any two of the aforementioned lengths). The flexible spacer allows the scFv domain to orient in multiple directions in order to enable an optimized antigen binding specificity. The scFv domain can be preceded by a signal peptide so as to direct the nascent protein to the endoplasmic reticulum and subsequent surface expression, whereby cleavage can occur. A flexible spacer can also allow the scFv domain to orient in different directions to facilitate antigen binding. A good spacer for allowing specific binding of the scFv domain can be determined empirically and is dependent on the scFv domain antigen recognition domain. In some alternatives, the linker comprises optimized spacer lengths so as to improve binding of scFv domain to the target cell, which may increase cytotoxic efficacy. In some alternatives, the linker or spacer between the scFv domain and the transmembrane can be 25 to 55 amino acids in length (e.g., at least, equal to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids or a length within a range defined by any two of the aforementioned lengths. In some alternatives, the spacer is encoded by the nucleic acid sequence set forth in SEQ ID NO: 102 (IgG4 hinge nucleotide sequence: gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104 (IgG4-CH2(L235D, N297Q) nucleotide sequence; gcccccgagttcgacggcggacccagcgtgttcctgttccccccaagcc-caaggacaccctgatgatcagccggacccccgagg tgacctgcgtggtggtggacgtgagccaggaagatcccgaggtccagttcaat-tggtacgtggacggcgtggaagtgcacaacgcc aagaccaagcccagagag-gaacagttccagagcacc-taccgggtggtgtctgtgctgaccgtgctgcaccaggactggctgaacg gcaaagaatacaagtgcaaggtgtccaacaagggcctgcccagcag-catcgaaaagaccatcagcaaggccaag). In some alternatives, the spacer comprises an amino acid sequence set forth in SEQ ID NO: 105 (IgG4-CH2(L235D, N297Q) amino acid sequence; APEFDGGPSVFLFPPKPKDTLMISRTPE-VTCVVVDVSQEDPEVQFNWYVDGVEVHN AKTKPREEQFQSTYRVVSVLTVLHQDWLNGKEY KCKVSNKGLPSSIEKTISKAK). In some alternatives, the spacer is encoded by a nucleic acid sequence comprising a nucleic acid sequence encoding the amino acid sequence of SEQ ID NO: 105. In some alternatives, the spacer is encoded by a nucleic acid sequence set forth in SEQ ID NO: 106 (IgG4-CH3 nucleotide sequence: ggccagcctcgcgagccccaggtgtacaccctgcctccctcccag-gaagagatgaccaagaaccaggtgtccctgacctgcctggt gaagggcttc-taccccagcgacatcgccgtggagtgggagagcaacggccagcct-gagaacaactacaagaccacccctcccgtg ctggacagcgacggcagcttcttcctgta-cagccggctgaccgtggacaagagccggtggcaggaaggcaacgtctt-tagctgcag cgtgatgcacgaggccctgcacaaccacta-cacccagaagagcctgagcctgtccctgggcaag). In some alternatives, the spacer comprises an amino acid sequence set forth in SEQ ID NO: 107 (IgG4 CH3 amino acid sequence: GQPREPQVYTLPPSQEEMTKNQVSLTCLVKGFYPS-DIAVEWESNGQPENNYKTTPPV LDSDGSFFLY-SRLTVDKSRWQEGNVFSCSVMHEALHN-HYTQKSLSLSLGK). In some alternatives, the spacer is encoded by a nucleic acid sequence comprising a nucleic acid sequence encoding the amino acid sequence of SEQ ID NO: 107. In some alternatives, the spacer is encoded by a nucleic acid sequence set forth in SEQ ID NO: 108 (CD8 hinge/Transmembrane domain nucleotide sequence: gaatctaagtacggaccggccaagcctaccaccacccctgcccctagacctc-caacacccgccccaacaatcgccagccagcctct gtctct-gaggcccgaggcttgtagaccagctgctggcg-gagccgtgcacaccagaggactggatttcgcctgcgacatctacatctg ggcccctctggccggcacatgtggcgtgctgctgctgagcctcgtgatcacc). In some alternatives, the spacer comprises an amino acid sequence set forth in SEQ ID NO: 109 (CD8 hinge/Transmembrane domain amino acid sequence: ESKYGPAK-PTTTPAPRPPTPAPTIASQPLSLRPEACR-PAAGGAVHTRGLDFACDIYIW APLAGTCGVLLLSLVIT. In some alternatives, the spacer is encoded by a nucleic acid sequence comprising a nucleic acid sequence encoding the amino acid sequence of SEQ ID NO: 109.

"Transmembrane domain" has its plain and ordinary meaning when read in light of the specification, and may include but is not limited to, for example, a transmembrane region of a protein. This may be a single alpha helix, a transmembrane beta barrel, a beta-helix, or any other structure. In some alternatives herein, the transmembrane domain comprises CD28tm. In some alternatives, the transmembrane domain is encoded by a sequence set forth in SEQ ID NO: 110 (CD28 transmembrane domain nucleotide sequence: atgttctgggtgctggtggtggtcggaggcgtgctggcctgcta-cagcctgctggtcaccgtggccttcatcatcttttgggtg). In some alternatives, the transmembrane domain comprises an amino acid sequence set forth in SEQ ID NO: 111 (CD28 transmembrane domain amino acid sequence: MFWVLVVVGGVLA-CYSLLVTVAFIIFWV). In some alternatives, the transmembrane domain is encoded by a nucleic acid sequence comprising a nucleic acid sequence encoding the amino acid sequence of SEQ ID NO: 111. In some alternatives, the transmembrane domain is encoded by a sequence set forth in SEQ ID NO: 112 (CD8 hinge/Transmembrane domain nucleotide sequence: gaatctaagtacggaccggccaagcctaccac-cacccctgcccctagacctccaacacccgccccaacaatcgccagccagcctct gtctctgaggcccgaggcttgtagaccagctgctggcg-gagccgtgcacaccagaggactggatttcgcctgcgacatctacatctg ggcccctctggccggcacatgtggcgtgctgctgctgagcctcgtgatcacc). In some alternatives, the transmembrane domain comprises an amino acid sequence set forth in SEQ ID NO: 113 (CD8 hinge/Transmembrane domain amino acid sequence: ESKY-GPAKPTTTPAPRPPTPAPTIASQPLSLRPEACR-PAAGGAVHTRGLDFACDIYIW APLAGTCGVLLLSLVIT). In some alternatives, the transmembrane domain is encoded by a nucleic acid sequence comprising a nucleic acid sequence encoding the amino acid sequence of SEQ ID NO: 113.

A "chimeric cytokine receptor," has its plain and ordinary meaning when read in light of the specification, and may include but is not limited to, for example, a protein that has an amino acid sequence of a chemokine or portion thereof and is a fusion protein with another protein.

"Intracellular signaling domain," or "Co-stimulatory domain," has its plain and ordinary meaning when read in light of the specification, and may include but is not limited to, for example, a signaling moiety that provides to T cells a signal which, in addition to the primary signal provided by for instance the CD3 zeta chain of the TCR/CD3 complex, mediates a T cell response, including, but not limited to, activation, proliferation, differentiation, cytokine secretion, and the like. A co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, B7-H3, or a ligand that specifically binds with CD83. In some alternatives, the co-stimulatory domain is an intracellular signaling domain that interacts with other intracellular mediators to mediate a cell response including activation, proliferation, differentiation and cytokine secretion, and the like. In some alternatives of the signaling domain described herein, the signaling domain comprises CD3ζ, CD28 cytoplasmic domain, and/or 4-1BB. In some alternatives, the intracellular signaling domain is encoded by a nucleic acid sequence set forth in SEQ ID NO: 114 (CD3ζ Zeta nucleotide sequence: cgggtgaagttcagcagaagcgccgacgcccctgcc-taccagcagggccagaatcagctgtacaacgagctgaacctgggcaga agg-gaagagtacgacgtcctggataagcggagaggccgggaccct-gagatgggcggcaagcctcggcggaagaacccccagg aaggcctgtataacgaactgcagaaagacaagatggccgaggccta-cagcgagatcggcatgaagggcgagcggaggcggggc aagggc-cacgacggcctgtatcagggcctgtccaccgccaccaaggatacc-tacgacgccctgcacatgcaggccctgcccccaa gg). In some alternatives, the intracellular signaling domain comprises an amino acid sequence set forth in SEQ ID NO: 115 (CD3 Zeta amino acid sequence: RVKFSRSADAPAYQQGQNQLY-NELNLGRREEYDVLDKRRGRDPEMGGKPRRKNPQ EGLYNELQKDKMAEAYSEIGMKGERRRGKGHDG-LYQGLSTATKDTYDALHMQAL PPR). In some alternatives, the intracellular signaling domain is encoded by a nucleic acid sequence comprising a nucleic acid sequence encoding the amino acid sequence of SEQ ID NO: 115. In some alternatives, the intracellular signaling domain is encoded by a nucleic acid sequence set forth in SEQ ID NO: 116 (4-1BB nucleotide sequence: aaacggggcagaaagaaactcctgtatatattcaaacaaccatttatga-gaccagtacaaactactcaagaggaagatggctgtagct gccgat-ttccagaagaagaagaaggaggatgtgaactg). In some alternatives, the intracellular signaling domain comprises an amino acid sequence set forth in SEQ ID NO: 117 (4-1BB amino acid sequence: KRGRKKLLY-IFKQPFMRPVQTTQEEDGCSCRFPEEEEGGCEL). In some alternatives, the intracellular signaling domain is encoded by a nucleic acid sequence comprising a nucleic acid sequence encoding the amino acid sequence of SEQ ID NO: 117. In some alternatives, the intracellular signaling domain is encoded by a sequence set forth in SEQ ID NO: 118 (CD28 cytoplasmic domain nucleotide sequence: cgcagcaagcggagcagaggcggccacagcgactacatgaacatgacccccta-gacggcctggccccaccagaaagcactacca gccc-tacgcccctccccgggactttgccgcctacagaagc). In some alternatives, the intracellular signaling domain comprises an amino acid sequence set forth in SEQ ID NO: 119 (CD28 cytoplasmic domain amino acid sequence: RSKRSRGGH-SDYMNMTPRRPGPTRKHYQPYAPPRDFAAYRS). In some alternatives, the intracellular signaling domain is encoded by a nucleic acid sequence comprising a nucleic acid sequence encoding the amino acid sequence of SEQ ID NO: 119.

As used herein, "nucleic acid" or "nucleic acid molecule" has its plain and ordinary meaning when read in light of the specification, and may include but is not limited to, for example, deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

"DNA spacer" has its plain and ordinary meaning when read in light of the specification, and may include but is not limited to, for example, a spacer comprising nucleotides. A DNA spacer may reside in between a promoter and a gene that is to be expressed that is under control of the promoter, for example. In some alternatives, a DNA spacer is between the inducible promoter and the transgene. In some alternatives, the DNA spacer comprises a sequence set forth in SEQ ID NO: 120 (SEQ ID NO: 120; gctagcgtttaaact-taagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values.

"Coding for" and "encoding" has its plain and ordinary meaning when read in light of the specification, and may include but is not limited to, for example, property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "nucleic acid sequence coding for a polypeptide" includes all nucleotide sequences that are degenerate versions of each other and that code for the same amino acid sequence.

"Survivin," is also known as baculoviral inhibitor of apoptosis repeat-containing 5 or BIRC5, and has its plain and ordinary meaning when read in light of the specification, and may include but is not limited to, a protein that is a member of the inhibitor of apoptosis family. In some alternatives, Survivin is encoded by a sequence set forth in SEQ ID NO: 124 (Atgggtgccccgacgttgccccctgcctggcagccctttct-caaggaccaccgcatctctacattcaagaactggcccttcttggag ggctgcgcctgcaccccggagcggatggccgaggctggcttcatccactgccc-cactgagaacgagccagacttggcccagtgttt cttctgcttcaaggagctg-gaaggctgggagccagatgacgaccccatagaggaacataaaaagcat-tcgtccggttgcgctttccttt ctgtcaagaagcagtttgaagaattaacccttggtgaatttttt-gaaactggacagagaaagagccaagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD).

"Conditional" or "Inducible" has its plain and ordinary meaning when read in light of the specification, and may include but is not limited to, for example, nucleic acid construct that includes a promoter that provides for gene expression in the presence of an inducer and does not substantially provide for gene expression in the absence of the inducer.

"Constitutive" has its plain and ordinary meaning when read in light of the specification, and may include but is not limited to, for example, the nucleic acid construct that includes a promoter that is constitutive providing for expression of a polypeptide that is continuously produced.

"Specific" or "Specificity" has its plain and ordinary meaning when read in light of the specification, and may include but is not limited to, for example, the characteristic of a ligand for the binding partner or alternatively, the binding partner for the ligand, and can include complementary shape, charge and hydrophobic specificity for binding. Specificity for binding can include stereospecificity, regioselectivity and chemoselectivity. In some alternatives, a method of making a nucleic acid encoding a chimeric antigen receptor is provided such that a nucleic acid encoding a chimeric antigen receptor is generated, wherein the chimeric antigen receptor binds specifically to a desired or selected ligand.

"TamR-tf" has its plain and ordinary meaning when read in light of the specification, and may include but is not limited to, for example, tamoxifen regulated transcription factors. Without being limiting, tamoxifen regulated transcription factors can include wild-type HEA3, wild-type HEA4, mutant HEA3, mutant HEA4 and/or RelA variants.

"HEA3" has its plain and ordinary meaning when read in light of the specification, and may include but is not limited to, for example, a chimeric transcription factor composed of human subunits including the N-terminal DNA binding domain of Hepatocyte Nuclear Factor 1-alpha (HNF-1α) fused in frame to the mutant tamoxifen-specific ligand binding domain of the estrogen receptor ligand binding domain (ER-LBD) which contains 1 amino acid substitution (G521R), which ablates binding of estradiol but confers nanomolar estrogen analogues, that is in turn fused to the p65 activation domain of NF-κB (p65).

HEA-3 has been described by Roscilli et al. (Molecular Therapy, Vol. 6, Issue 5, pp. 653-663 (2002)) as a novel 4-hydroxytamoxifen (4-OHT) dependent regulator which was shown to have long term control of gene expression in mouse skeletal muscle (Roscilli et al.; included by reference in its entirety herein.)

"HEA4" has its plain and ordinary meaning when read in light of the specification, and may include but is not limited to, for example, a chimeric transcription factor composed of human subunits including the N-terminal DNA binding domain of Hepatocyte Nuclear Factor 1-alpha (HNF-1α) fused in frame to the tamoxifen-specific ligand binding domain of the estrogen receptor ligand binding domain (ER-LBD) which contains 3 amino acid substitutions (G400V, M543A, L544A) that ablate binding of estradiol but confers nanomolar sensitivity to estrogen analogues, that is in turn fused to the p65 activation domain of NF-κB (p65).

"Regulate" or "modulate" has its plain and ordinary meaning when read in light of the specification, and may include but is not limited to, for example, the act of controlling a biological process, or to exert a modifying or controlling influence on a biological or cellular process or pathway.

"Cytotoxic T lymphocyte" (CTL) has its plain and ordinary meaning when read in light of the specification, and may include but is not limited to, for example, a T lymphocyte that expresses CD8 on the surface thereof (e.g., a $CD8^+$ T cell). In some alternatives, such cells are preferably "memory" T cells (TM cells) that are antigen-experienced. In some alternatives, the host cells comprising the alternative systems provided herein are CTL cells.

"Central memory" T cell (or "TCM") has its plain and ordinary meaning when read in light of the specification, and may include but is not limited to, for example, an antigen experienced CTL that expresses CD62L, CCR-7 and/or CD45RO on the surface thereof, and does not express or has decreased expression of CD45RA, as compared to naïve cells. In some alternatives, central memory cells are positive for expression of CD62L, CCR7, CD28, CD127, CD45RO, and/or CD95, and may have decreased expression of CD54RA, as compared to naïve cells. "Effector memory" T cell (or "TEM") as used herein refers to an antigen experienced T cell that does not express or has decreased expression of CD62L on the surface thereof, as compared to central memory cells, and does not express or has a decreased expression of CD45RA, as compared to naïve cell. In some alternatives, effector memory cells are negative for expression of CD62L and/or CCR7, as compared to naïve cells or central memory cells, and may have variable expression of CD28 and/or CD45RA. In some alternatives, the host cells comprising the alternative systems provided herein are TCM cells. In some alternatives of the host cells provided herein, the host cell is a central memory T cell.

"Naïve" T cells has its plain and ordinary meaning when read in light of the specification, and may include but is not limited to, for example, a non-antigen experienced T lymphocyte that expresses CD62L and/or CD45RA, and does not express CD45RO−, as compared to central or effector memory cells. In some alternatives, naïve CD8+T lymphocytes are characterized by the expression of phenotypic markers of naïve T cells including CD62L, CCR7, CD28, CD127, and/or CD45RA. In some alternatives, the host cells comprising the alternative systems provided herein are naïve T cells.

"Effector" "$T_E$" T cells has its plain and ordinary meaning when read in light of the specification, and may include but is not limited to, for example, antigen experienced cytotoxic T lymphocyte cells that do not express or have decreased expression of CD62L, CCR7, and/or CD28, and are positive for granzyme B and/or perforin, as compared to central memory or naïve T cells. In some alternatives, the host cells comprising the alternative systems provided herein are effector T cells.

"Enriched" and "depleted" has its plain and ordinary meaning when read in light of the specification, and may include but is not limited to, for example, amounts of cell types in a mixture and subjecting of the mixture of the cells to a process or step, which results in an increase in the number of the "enriched" type and a decrease in the number of the "depleted" cells. Thus, depending upon the source of the original population of cells subjected to the enriching process, a mixture or composition may contain 60, 70, 80, 90, 95, or 99 percent or more (in number or count) of the "enriched" cells and/or 40, 30, 20, 10, 5 or 1 percent or less (in number or count) of the "depleted" cells. In some alternatives, an in vitro method for preparing a host cell of any one of any one of the alternatives is provided herein. The in vitro method comprises a) providing a system of any one of the alternatives described herein, and b) introducing the system into an isolated T lymphocyte population and expanding each T lymphocyte population in vitro. The process of expanding each T lymphocyte population is a process of enriching the T lymphocyte population.

"Epitope" has its plain and ordinary meaning when read in light of the specification, and may include but is not limited to, for example, a part of an antigen or molecule that is recognized by the immune system including antibodies, T cells, and/or B cells. Epitopes usually have at least 7 amino acids and can be linear or conformational. In some alternatives herein, an antibody or ligand binding domain can be optimized to bind a specific epitope. Techniques for optimizing binding can be appreciated by those skilled in the art. For example, a ligand binding motif can be optimized by point mutation in order to increase binding affinity and/or epitope recognition.

"Isolated," has its plain and ordinary meaning when read in light of the specification, and may include but is not limited to, for example, various polypeptides or nucleic acids that have been identified and separated and/or recovered from a component of its natural environment. Preferably, the isolated polypeptide or nucleic acid is free of association with all components with which it is naturally associated. Contaminant components of its natural environment are materials that would typically interfere with diagnostic or therapeutic uses for the polypeptide or nucleic acid, and can include enzymes, hormones, and other proteinaceous or non-proteinaceous solutes. Isolated can also be used to describe isolation of a subpopulation of cells, such as, for example isolation of subpopulations of CD4+ and/or CD8+T lymphocytes during methods of manufacturing cells for use.

"Intracellular signaling domain" has its plain and ordinary meaning when read in light of the specification, and may include but is not limited to, for example, all or a portion of one or more domains of a molecule (here the chimeric receptor molecule) that provides for activation of a lymphocyte. Intracellular domains of such molecules mediate a signal by interacting with cellular mediators to result in proliferation, differentiation, activation and other effector functions. In some alternatives, such molecules include all or portions of CD28, CD3, or 4-1BB, or combinations thereof.

"Ligand" has its plain and ordinary meaning when read in light of the specification, and may include but is not limited to, for example, a substance that binds specifically to another substance to form a complex. Examples of ligands include epitopes on antigens, molecules that bind to receptors, substrates, inhibitors, hormones, and/or activators. "Ligand binding domain" as used herein refers to substance or portion of a substance that binds to a ligand. Examples of ligand binding domains include antigen binding portions of antibodies, extracellular domains of receptors, and/or active sites of enzymes. "Operably linked" as used herein refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two proteins coding regions, in the same reading frame.

"Tumor specific molecule," has its plain and ordinary meaning when read in light of the specification, and may include but is not limited to, for example, tumor-typical antigens, proteins or molecules expressed by a tumor. In some of the alternatives described herein, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof.

A "viral molecule" or "viral specific molecule" has its plain and ordinary meaning when read in light of the specification, and may include but is not limited to, for example, a protein encoded by a viral RNA or DNA, or a molecule that is expressed by a cell in reaction to a viral infection. In some alternatives described herein the viral specific molecule is an HIV envelope protein or HIV envelope protein complex, Hepatitis C virus NS3 protein, HbcAg protein, HIV-1 GP120 protein, or Epstein-Barr virus early antigen protein.

"Percent (%) amino acid sequence identity" with respect to the chimeric receptor polypeptide sequences identified herein is defined as the percentage of amino acid residues in a candidate sequence that are identical with the amino acid residues in the reference sequence for each of the ligand binding domain, spacer, transmembrane domain, and/or the lymphocyte activating domain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program [Altschul et al., Methods in Enzymology, 266:460-480 (1996); herein incorporated by reference] uses several search parameters, most of which are set to the default values. Those that are not set to default values (i.e., the adjustable parameters) are set with the following values: overlap span=1, overlap fraction=0.125, word threshold (T)=11 and scoring matrix=BLOSUM62. A % amino acid sequence identity value is determined by dividing (a) the number of matching identical amino acid residues between each or all of the polypeptide amino acid sequence of the reference chimeric receptor sequence and the comparison amino acid sequence of interest as determined by WU-BLAST-2 by (b) the total number of amino acid residues of the polypeptide of interest. In some alternatives, the percent sequence identity of amino acids or nucleic acids are determined by computer software.

"Substantially purified" refers to a molecule that has 10%, 9%, 8%, 7%, 6%, 5%, 4%, 3%, 2%, or 1% or less other molecule types or other cell types. A substantially purified cell also refers to a cell, which has been separated from other cell types with which it is normally associated in its naturally occurring state. In some instances, a population of substantially purified cells refers to a homogenous population of cells.

"Not substantially found" when used in reference the presence of a tumor antigen or other molecules on normal cells refers to the percentage of a normal cell type that has the antigen or molecule, and/or the density of the antigen on the cells. In some alternatives, not substantially found means that the antigen or molecule is found on less than 50% of normal cell type and/or at a 50% less density as compared to the amount of cells or antigen found on a tumor cell or other diseased cell.

"T cells" or "T lymphocytes" has its plain and ordinary meaning when read in light of the specification, and may include but is not limited to, for example, can be T-cells from any mammal, preferably a primate, species, including monkeys, dogs, and/or humans. In some alternatives of the host cells provided herein, the host cells are T cells, wherein the T cells are allogeneic (from the same species but different donor) as the recipient subject; in some alternatives the T cells are autologous (the donor and the recipient are the same); in some alternatives the T cells are syngeneic (the donor and the recipients are different but are identical twins).

"Vector" or "construct" has its plain and ordinary meaning when read in light of the specification, and may include but is not limited to, for example, nucleic acid used to introduce heterologous nucleic acids into a cell that has regulatory elements to provide expression of the heterologous nucleic acids in the cell. Vectors include but are not limited to plasmid, minicircles, yeast, transposons, and viral genomes. In some alternatives, the vectors are plasmid, minicircles, yeast, transposons, or viral genomes. In some alternatives, the transposons are piggy bac transposons. In some alternatives of the systems provided herein, the first and/or second nucleic acid reside on a vector. In some alternatives, the vector is a viral vector.

"Transgene" has its plain and ordinary meaning when read in light of the specification, and may include but is not limited to, for example, a gene or genetic material that has been transferred naturally, or by any of a number of genetic engineering techniques from one organism to another. In some alternatives described herein, a method is provided for inducible expression of a transgene in cells, the system comprising: a) a first nucleic acid comprising a first promoter inducible by a drug, wherein the first nucleic acid is operably linked to a first polynucleotide that encodes the transgene; and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives, the transgene encodes a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity. In some alternatives, the transgene encodes a protein that modulates T cells.

A viral vector can be used to deliver genetic material into a cell. Delivery of the vector can be performed by transduction and the technique is known to those skilled in the art. In some alternatives herein, a vector for introducing the nucleic acid into a cell is an adenovirus viral vector or a lentivirus viral vector.

"Minicircles," have their plain and ordinary meaning when read in light of the specification, and may include but is not limited to, for example, small circular plasmid derivatives that have been freed or liberated from prokaryotic vector components. Minicircles can serve as an expression vector, where they have been applied as transgene carriers for the genetic modification of mammalian cells, with the advantage that, since they contain no bacterial DNA sequences, they are less likely to be perceived as foreign and destroyed. As such, typical transgene delivery methods involve plasmids, which contain foreign DNA. The smaller size of minicircles also extends their cloning capacity and facilitates their delivery into cells. Without being limiting, the preparation of minicircles can follow a two-step procedure, which can involve production of a parental plasmid (bacterial plasmid with eukaryotic inserts) in *E. coli* and induction of a site-specific recombinase at the end of this process but still in bacteria. These steps can be followed by the excision of prokaryotic vector parts via two recombinase-target sequences at both ends of the insert and recovery of the resulting minicircle (vehicle for the highly efficient modification of the recipient cell) and the miniplasmid by capillary gel electrophoresis (CGE).

The purified minicircle can be transferred into the recipient cell by transfection, by electroporation, or by other methods known to those skilled in the art. Conventional minicircles can lack an origin of replication, so they cannot replicate within the target cells and the encoded genes will disappear as the cell divides (which can be either an advantage or disadvantage depending on whether the application demands persistent or transient expression). Some alternatives utilize a gene delivery polynucleotide for stable insertion of a nucleic acid into a gene, wherein the nucleic acid for insertion is flanked by inverted terminal repeat gene sequences in the gene delivery polynucleotide, and wherein the gene delivery polynucleotide is selectable. In some alternatives, the gene delivery polynucleotide is a minicircle.

Plasmids containing transposon systems such as Sleeping Beauty (SB) or piggyBac offer a non-viral approach for stably introducing genes into T-cells. Recently, the piggyBac system was used to produce stably-transfected mammalian cells expressing multiple transgenes of interest by delivery of multiple transposons. The SB system, first reactivated for mammalian cell use by Ivics and coworkers, has been used as the gene delivery modality in clinical trials of T-cell immunotherapy. Gene integration by SB has weaker preference for transcriptional units and their regulatory sequences compared to the γ-retroviral and lentiviral vectors and is therefore considered to be safer. In some alternatives described herein, genetic modification by minicircles comprising the Sleeping Beauty system are contemplated. In some alternatives described herein, genetic modification by minicircles comprising the piggyBac system are contemplated. In some alternatives described herein, genetic modification by minicircles comprising the Sleeping Beauty system are contemplated.

"Apoptosis" has its plain and ordinary meaning when read in light of the specification, and may include but is not limited to, for example, the process of programmed cell death (PCD) that can occur in multicellular organisms. Biochemical events lead to characteristic cell changes (morphology) and death. These changes include blebbing, cell shrinkage, nuclear fragmentation, chromatin condensation, and chromosomal DNA fragmentation. In apoptosis, a cell initiates intracellular apoptotic signaling in response to stress, which can bring about cell suicide. The binding of nuclear receptors by glucocorticoids, heat, radiation, nutrient deprivation, viral infection, hypoxia and increased intracellular calcium concentration, for example, by damage to the membrane, can all trigger the release of intracellular apoptotic signals by a damaged cell. A number of cellular components, such as poly ADP ribose polymerase, can also help regulate apoptosis.

Before the actual process of cell death is precipitated by enzymes, apoptotic signals must cause regulatory proteins to initiate the apoptosis pathway. This step allows apoptotic signals to cause cell death, or the process to be stopped, should the cell no longer need to die. Several proteins are involved, but two main methods of regulation have been identified: targeting mitochondria functionality, or directly transducing the signal via adaptor proteins to the apoptotic mechanisms. Another extrinsic pathway for initiation identified in several toxin studies is an increase in calcium concentration within a cell caused by drug activity, which also can cause apoptosis via a calcium binding protease calpain.

Apoptosis can be regulated by many factors. These factors can include but are not limited to genes that can express IL-2, IL-7, IL-15, Chemokine receptors, Bcl2, CA-Akt, dn-TGFbetaRIII, dn-SHP1/2, and/or PD-1CD28 chimeras. IL-15 regulates T and natural killer cell activation and proliferation. In rodent lymphocytes, IL-15 was shown to prevent apoptosis by inducing an apoptosis inhibitor, BCL2L1/BCL-X(L). In humans with celiac disease, IL-15 similarly suppresses apoptosis in T-lymphocytes by inducing Bcl-2 and/or BCL-xL. Bcl-2 (B-cell lymphoma 2), encoded in humans by the BCL2 gene, is the founding member of the Bcl-2 family of regulator proteins that regulate cell death (apoptosis), by either inducing (pro-apoptotic) it or inhibiting it (anti-apoptotic). Bcl-2 is specifically considered as an important anti-apoptotic protein and is, thus classified as an oncogene. Protein kinase B (PKB), also known as Akt, is a serine/threonine-specific protein kinase that plays a key role in multiple cellular processes such as glucose metabolism, apoptosis, cell proliferation, transcription and cell migration. In some alternatives, a system for inducible expression of a gene that regulates a T cell function is provided, wherein the system comprises: a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity and b) a second nucleic acid comprising a second promoter, wherein the second nucleic acid is operably linked to third nucleic acid that encodes a transcriptional activator for the first promoter inducible by drug and wherein the system is configured to respond to an amount of the drug that is less than a comparable system utilizing a wild type HEA3 chimeric transcription factor, or the system has an enhanced transcriptional expression at a given concentration of the drug compared to a system utilizing a wild type HEA3. In some alternatives, the polypeptide that regulates apoptosis or modulates checkpoint signaling comprises IL-2, IL-7, IL-15, chemokine receptors, Bcl2, CA-Akt, dn-TGFbetaR-III, dn-SHP1/2 or PD-1CD28 chimeras.

"Checkpoint signaling" has its plain and ordinary meaning when read in light of the specification, and may include but is not limited to, for example, blocking the cell cycle at specific transition points, and/or checkpoints to ensure that the events of the cell cycle take place in the correct order. Checkpoint signaling can also be activated. By way of example and not of limitation, checkpoint signaling can occur by damage to the DNA so that the cell cycle does not have to proceed until the damage is repaired. "Cell cycle checkpoints" are control mechanisms in eukaryotic cells which ensure proper division of the cell. Each checkpoint serves as a potential halting point along the cell cycle, during which the conditions of the cell are assessed, with progression through the various phases of the cell cycle occurring when favorable conditions are met. Currently, there are three known checkpoints: the G1 checkpoint, also known as the restriction or start checkpoint; the G2/M checkpoint; and the metaphase checkpoint, also known as the spindle checkpoint. The biochemical pathways that restrain cell cycle transition and/or induce cell death after stress are known as cell cycle checkpoints. These checkpoints maintain the fidelity of DNA replication, repair, and division. Polypeptides that can regulate checkpoint signaling can include but are not limited to p53, p107, p130, and transcriptional repressor Rb. In some alternatives of the systems provided herein, the polypeptide that modulates checkpoint signaling comprises p53, p107, p130 or transcriptional repressor Rb.

"Negative checkpoint regulators" have their plain and ordinary meaning when read in light of the specification, and may include but is not limited to, for example, factors that can restrict the ability of T-cell responses to effectively attack tumors. They are also referred to as negative checkpoint signaling. In some alternatives, a system for inducible expression of a transgene is provided. In some alternatives, the transgene encodes a chimeric antigen receptor. In some alternatives, a system for inducible expression of chimeric antigen receptor in cells is provided. In some alternatives of the systems for inducible expression of a gene that regulates a T cell function, the polypeptide that modulates checkpoint signaling is a negative checkpoint regulator comprising PD-1, VISTA, LAG-3 or TIM3. In some alternatives, the system is inducible by an amount of the drug that is less than a comparable system utilizing a wild type HEA3 chimeric transcription factor, or the system has an enhanced transcriptional expression at a given concentration of the drug compared to a system utilizing a wild type HEA3.

In another example, cell cycle inhibitors mediating the growth inhibitory cues of upstream signaling pathways, the cyclin-CDK inhibitors of the Cip/Kip family p21Cip1, p27Kip1, and p57Kip2 have emerged as multifaceted proteins with functions beyond cell cycle regulation. In addition to regulating the cell cycle, Cip/Kip proteins can also play important roles in apoptosis, transcriptional regulation, cell fate determination, cell migration and cytoskeletal dynamics. A complex phosphorylation network modulates Cip/Kip protein functions by altering their subcellular localization, protein-protein interactions, and stability. These functions are essential for the maintenance of normal cell and tissue homeostasis, in processes ranging from embryonic development to tumor suppression. In some alternatives, a system for inducible expression of a transgene is provided. In some alternatives, the transgene encodes a chimeric antigen receptor. In some alternatives, a system for inducible expression of a transgene is provided. In some alternatives, the transgene encodes a chimeric antigen receptor. In some alternatives, a system for inducible expression of a chimeric antigen receptor in cells, such as mammalian cells, is provided. In some alternatives of the system for inducible expression of a gene that regulates a T cell function, the polypeptide modulates checkpoint signaling. In some alternatives, the polypeptide that modulates checkpoint signaling inhibits negative checkpoint regulators. In some alternatives, the negative checkpoint regulator comprises PD-1, VISTA, LAG-3 and/or TIM3.

"T cell precursors" have their plain and ordinary meaning when read in light of the specification, and may include but is not limited to, for example, lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8, and are therefore classed as double-negative ($CD4^-CD8^-$) cells. As they progress through their development, they become double-positive thymocytes ($CD4^+CD8^+$), and finally mature to single-positive ($CD4^+CD8^-$ or $CD4^-CD8^+$) thymocytes that are then released from the thymus to peripheral tissues.

About 98% of thymocytes die during the development processes in the thymus by failing either positive selection or negative selection, whereas the other 2% survive and leave the thymus to become mature immunocompetent T cells.

The double negative (DN) stage of the precursor T cell is focused on producing a functional β-chain whereas the double positive (DP) stage is focused on producing a functional α-chain, ultimately producing a functional αβ T cell receptor. As the developing thymocyte progresses through the four DN stages (DN1, DN2, DN3, and DN4), the T cell expresses an invariant α-chain but rearranges the β-chain locus. If the rearranged 3-chain successfully pairs with the invariant α-chain, signals are produced which cease rearrangement of the β-chain (and silence the alternate allele) and result in proliferation of the cell. Although these signals require this pre-TCR at the cell surface, they are dependent on ligand binding to the pre-TCR. These thymocytes will then express both CD4 and CD8 and progresses to the double positive (DP) stage where selection of the α-chain takes place. If a rearranged β-chain does not lead to any signaling (e.g. as a result of an inability to pair with the invariant α-chain), the cell may die by neglect (lack of signaling).

"Hematopoietic stem cells" or "HSC" have their plain and ordinary meaning when read in light of the specification, and may include but is not limited to, for example, precursor cells that can give rise to myeloid cells such as, for example, macrophages, monocytes, neutrophils, basophils, eosinophils, erythrocytes, megakaryocytes/platelets, dendritic cells and lymphoid lineages (such as, for example, T-cells, B-cells, NK-cells). HSCs have a heterogeneous population in which three classes of stem cells exist, which are distinguished by their ratio of lymphoid to myeloid progeny in the blood (L/M). In some alternatives described herein a host cell comprising a system of any one of the alternatives described herein is provided. In some alternatives of the host cells provided herein, the host cells are hematopoietic stem cells.

This disclosure provides for a system that has an inducible component for expression of transgenes and a constitutive component for expression of transgenes. The system can be tailored to provide for regulated expression of one or more transgenes to provide for functional characteristics in the transduced cells.

Although, T cell (CAR-T) adoptive therapy clinical trials (chimeric antigen receptor expressing T cells) can demonstrate potent anti-tumor activity, significant toxicities can arise, for example, by engraftment-induced cytokine storm (cytokine release syndrome), tumor lysis syndromes (TLS) and ongoing B cell cytopenias, each of which are attributable to unregulated functional outputs of constitutively expressed CARs. Such toxicities can threaten to limit the applicability of CAR-T cell adoptive therapy, in some patients. Clinical trials using transgene-modified adoptive T cell immunotherapies have tested T cells that can constitutively express the transgene, or are always in the "ON" state, contributing in large part to transgene associated side-effects. Methods to eliminate CAR-T cells such as suicide gene-mediated elimination of CAR-T cells, for example, can ameliorate such toxicities; however, this approach risks premature attenuation of anti-tumor activity and can significantly impact curative potential.

Current small molecule-regulated transgene expression technologies rely on a variety of drug inputs, which include, for example, macrolides, ecdysones and rapamycin analogs. However, use of these drugs may be limited due to the toxic off target effects, unfavorable biodistribution and pharmacodynamics profiles, limited output dynamic range, and/or limited availability as FDA-approved commercially available pharmaceuticals. Furthermore, many of these systems use chimeric transcriptional regulators built from xenogeneic components, thus introducing the complication of immunogenicity when applying these systems to human therapeutics.

Small molecule regulated transgene expression is a highly sought technology in biomedicine, particularly in CAR T cell immunotherapy. Competing systems typically use chimeric transcription factors composed of xenogeneic domains and drug inducers that are not currently FDA approved.

As such, there is a need to identify methods for controlling chimeric receptor expression that are important for therapeutic activity and cell populations that will provide enhanced survival and efficacy in vivo while minimizing adverse side effects of the drugs that induce chimeric antigen receptor expression. There is also a need for expression systems and methods for modulating cells for use in cell therapy, such as for modulating expression of recombinant antigen receptors such as CARs and/or other molecules expressed by such cells, such as to improve therapeutic activity, enhance survival and/or efficacy in vivo and/or minimize adverse side effects. Described herein, are methods that surprisingly led to enhanced survival and efficacy of the treatments in vivo, with minimized adverse side effects.

In some alternatives, a transgene under the control of the inducible promoter, is provided. In some alternatives, the transgene encodes a chimeric antigen receptor (CAR). The inducible promoter provides for the capacity to terminate CAR expression in cells while providing for reactivation of the cells at a later date (e.g. in the case of relapse). In addition, the cycling of CAR T cells through on and off periods can minimize exhaustion and/or energy due to chronic stimulation of the T cell receptors.

In some alternatives, a gene is under the control of the inducible promoter. In some alternatives, the gene encodes a chimeric cytokine receptor.

The design of the vectors also provides for additional transgenes that can enhance one or more functional characteristics of transduced cells, such as enhanced tumor potency, survival and proliferation of transduced cells. In some alternatives, these transgenes are under the control of an inducible promoter. Such transgenes include, without limitation, genes that promote survival and proliferation, genes that prevent apoptosis, and genes that regulate checkpoint signaling. Such genes include genes encoding IL-2, IL-15, chemokine receptors, Bcl2, CA-Akt, dn-TGFbetaR-III, dn-SHP1/2, and/or PD-1CD28 chimeras. In some alternatives, the transgenes are genes encoding IL-2, IL-7, IL-15, chemokine receptors, Bcl2, chimeric cytokine receptors, CA-Akt, dn-TGFbetaRIII, dn-SHP1/2, and/or PD-1CD28 chimeras. In some alternatives, the gene that modulates checkpoint signaling, encodes a polypeptide that inhibits negative checkpoint regulators. In some alternatives, the negative checkpoint regulator comprises PD-1, VISTA, LAG-3 and/or TIM3. In some alternatives, the gene is under a control of an inducible promoter. In some alternatives, the gene under control of an inducible promoter comprises a nucleic acid sequence set forth in SEQ ID NO: 88 (CCR (CD122) nucleotide sequence:
atgcttctcctggtgacaagccttctgctctgtgagttaccacacccagcat-
tcctcctgatcccagattgtgatattgaaggtaaagatg gcaaacaatat-
gagagtgttctaatggtcagcatcgatcaattattggacagcatgaaagaaat-
tggtagcaattgcctgaataatgaatt
taactttttaaaagacatatctgtgatgctaataaggaaggtatgtttttat-
tccgtgctgctcgcaagttgaggcaatttcttaaaatgaata gcactggtgatttt-
gatctccacttattaaaagtttcagaaggcacaacaatactgtt-
gaactgcactggccaggttaaaggaagaaaac
cagctgccctgggtgaagcccaaccaacaaagagtttggaagaaaataaatctt-
taaaggaacagaaaaaactgaatgacttgtgttt cctaaagagactatta-
caagagataaaaacttgttggaataaaattttgatgggcactaaagaacacg-
gaggcggtgggagcggagg
cggtgggagcatgacaattctaggtacaacttttggcatggtttttctttactt-
caagtcgtttctggagaaagtggctatgctcaaaatgg agacttggaa-
gatgcagaactggatgactactcattctcatgctatagccagttggaagtgaatg-
gatcgcagcactcactgacctgtg
cttttgaggacccagatgtcaacatcaccaatctggaattt-
gaaatatgtggggccctcgtggaggtaaagtgcctgaatttcaggaaa cta-
caagagatatatttcatcgagacaaagaaattcttactgattg-
gaaagagcaatatatgtgtgaaggttggagaaaagagtctaacc
tgcaaaaaaatagacctaaccactatagttaaacctgaggctccttttgacct-
gagtgtcatctatcgggaaggagccaatgactttgtg gtgacatttaatacat-
cacacttgcaaaagaagtatgtaaaagttttaatgcacgatgtagcttaccgccag-
gaaaaggatgaaaacaa
atggacgcatgtgaatttatccagcacaaaactgacactcctgcagagaaagctc-
caaccggcagcaatgtatgagattaaagttcga tccatccctgatcactattt-
taaaggcttctggagtgaatggagtccaagttattacttcagaactccagagat-
caataatagctcagggg
agatggatcctatcttactaaccatcagcatttt-
gagtttttctctgtcgctctgttggtcatcttggcctgtgtgttatggaactgcag-
gaac accgggccatggctgaagaaggtcctgaagtgtaacacccca-
gacccctcgaagttcttttcccagctgagctcagagcatggagga gacgtccagaagtggctctcttcgcccttcccct-
catcgtccttcagccctggcggcctggcacctgagatctcgccactagaagtgct
ggagagggacaaggtgacgcagctgctcctgcagcaggacaaggtgcct-
gagcccgcatccttaagcagcaaccactcgctgacc agctgcttcac-
caaccagggttacttcttcttccacctcccggatgccttggaga-
tagaggcctgccaggtgtactttacttacgacccct
actcagaggaagaccctgatgagggtgtggccggggcacc-
cacagggtcttccccccaacccctgcagcctctgtcaggggagga cgacgcc-
tactgcaccttcccctccagg-
gatgacctgctgctcttctcccccagtctcctcggtggccccagcccccccaagcact
gcc cctgggggcagtggggccggtgaagagag-
gatgccccccttctttgcaagaaagagtccccaga-
gactgggacccccagcccctgg ggcctcccaccccaggagtccca-
gacctggtggattttcagccacccccctgagctggtgctgcgagaggctggggagg
aggtccct gacgctggccccagggagg-
gagtcagtttcccctggtccaggcctcctgggcagggggagttcagggccct-
taatgctcgcctgcc cctgaacactgatgcctacttgtccctc-
caagaactccagggtcaggacccaactcacttggtg). In some alternatives, the sequence under control of an inducible promoter encodes for an amino acid sequence set forth in SEQ ID NO: 89 (CCR(CD122) amino acid sequence:
MLLLVTSLLLCELPHPAFLLIPDCDI-
EGKDGKQYESVLMVSIDQLLDSMKEIGSNCLN
NEFNFFKRHICDANKEGMFLFRAARKLRQFLKMN-
STGDFDLHLLKVSEGTTILLNCT GQVKGRKPAAL-
GEA-
QPTKSLEENKSLKEQKKLNDLCFLKRLLQEIKTCWN
KILMGT KEHGGGGSGGGGSM-
TILGTTFGMVFSLLQVVSGESGYAQNGDLEDAELD-
DYSFSCY SQLEVNGSQHSLTCAFEDPDVNITNLEFE-
ICGALVEVKCLNFRKLQEIYFIETKKFLLI
GKSNICVKVGEKSLTCKKIDLT-
TIVKPEAPFDLSVIYREGANDFVVTFNTSHLQKKYV
KVLMHDVAYRQEKDEN-
KWTHVNLSSTKLTLLQRKLQPAAMYEIKVR-
SIPDHYFKGF WSEWSPSYYFRT-
PEINNSSGEMDPILLTISILSFFSVALLVILACVLWNCR-
NTGPWLKK VLKCNTPDPSKFF-
SQLSSEHGGDVQKWLSSPFPSSSFSPGGLAPEISPLEV-
LERDKVTQ LLLQQDKVPEPASLSSNHSLT-
SCFTNQGYFFFHLPDALEIEACQVYFTYDPYSEEDPD
EGVAGAPTGSSPQPLQPLSGEDDAYCTFPSRDDLLLF-
SPSLLGGPSPPSTAPGGSGAGE ERM-
PPSLQERVPRDWDPQPLGPPTPGVPDLVDFQPPPEL-
VLREAGEEVPDAGPREGV
SFPWSRPPGQGEFRALNARLPLNTDAY-
LSLQELQGQDPTHLV). In some alternatives, the sequence under control of an inducible promoter is encoded by a nucleic acid sequence comprising a nucleic acid sequence encoding the amino acid sequence of SEQ ID NO: 89.

In some alternatives, the gene under control of an inducible promoter comprises the nucleic acid sequence set forth in SEQ ID NO: 90 (PD1ECD-IFNalpha nucleotide sequence nucleotide sequence: atgca-
gatccctcaggccccttggcctgtcgtgtgggctgtgctgcagctgg-
gatggcggcctggctggtttctggacagccccgac agaccctggaacccccta-
cattttcccctgccctgctggtcgtgaccgagggcgacaatgccaccttcacctgta
gcttcagcaaca ccagcgagagcttcgtgctgaactggtacagaat-
gagccccagcaaccagaccgacaagctggccgccttccccgaggatagatct
cagcccggccaggactgccggttcagagtgacccagctgcc-
caacggccgggacttccacatgtctgtcgtgcgggccagacgga
acgacagcggcacatatctgtgcggcgccatcagcctggcccccaaggccca-
gatcaaagagagcctgagagccgagctgagag
tgaccgagagaagggccgaagtgcctaccgcccaccctagcccatctccaagacctgccggccagttccagacactcgtgggcgg aggatgcgacctgcctca-gacacacagcctgggcagcagacggaccctgatgctgctggcccagatgcg-gaagatcagcctgttc agctgcctgaaggaccggcacgacttcggcttccctcag-gaagagttcggcaaccagtttcagaaggccgagacaatccccgtgct gcacgagatgatccagcagatcttcaacctgttctccac-caaggacagcagcgccgcctgggacgagacactgctggacaagttcta caccgagctgtaccagcagctgaatgacctggaagcctgcgt-gatccagggcgtgggcgtgacagagacacccctgatgaaggaa gatag-catcctggccgtgcgcaagtacttccagcggatcaccctgtacct-gaaagagaagaagtacagcccctgcgcctgggaggt cgtgcgcgccgagatcatgagaagcttcagcctgagcaccaacctgcag-gaaagcctgcggagcaaagaa). In some alternatives, the sequence under control of an inducible promoter encodes the amino acid sequence set forth in SEQ ID NO: 91 (PD1ECD-IFNalpha amino acid sequence: MQIPQAPWPVV-WAVLQLGWRPGWFLDSPDRPWNPPTFSPALL-VVTEGDNATFTCSF SNTSESFVLNWYRMSPSNQTDKLAAFPEDR-SQPGQDCRFRVTQLPNGRDFHMSVVR ARRNDSG-TYLCGAISLAPKAQIKESLRAELRVTERRAEVP-TAHPSPSPRPAGQFQTLV GGGCDLPQTHSLGSRRTLMLLAQMRKISLF-SCLKDRHDFGFPQEEFGNQFQKAETIP VLHEMIQQIFNLFSTKDSSAAWDETLLDKFYTE-LYQQLNDLEACVIQGVGVTETPLM KEDSI-LAVRKYFQRITLYLKEKKYSPCAWEVVRAE-IMRSFSLSTNLQESLRSKE). In some alternatives, the sequence under control of an inducible promoter is encoded by a nucleic acid sequence comprising a nucleic acid sequence encoding the amino acid sequence of SEQ ID NO: 91.

In some alternatives, the gene under control of an inducible promoter comprises the nucleic acid sequence set forth in SEQ ID NO: 92 (STAT5a nucleotide sequence:

```
atggcgggctggatccaggcccagcagctgcagggagacgcgctgcgccag
atgcaggtgctgtacggccagcacttccccatcgaggtccggcactacttg
gcccagtggattgagagccagccatgggatgccattgacttggacaatccc
caggacagagcccaagccacccagctcctggagggcctggtgcaggagctg
cagaagaaggcggagcaccaggtgggggaagatgggtttttactgaagatc
aagctggggcactacgccacgcagctccagaaaacatatgaccgctgcccc
ctggagctggtccgctgcatccggcacattctgtacaatgaacagaggctg
gtccgagaagccaacaattgcagctctccggctgggatcctggttgacgcc
atgtcccagaagcaccttcagatcaaccagacatttgaggagctgcgactg
gtcacgcaggacacagagaatgagctgaagaaactgcagcagactcaggag
tacttcatcatccagtaccaggagagcctgaggatccaagctcagtttgcc
cagctggcccagctgagcccccaggagcgtctgagccgggagacggccctc
cagcagaagcaggtgtctctggaggcctggttgcagcgtgaggcacagaca
ctgcagcagtaccgcgtggagctggccgagaagcaccagaagaccctgcag
ctgctgcggaagcagcagaccatcatcctggatgacgagctgatccagtgg
aagcggcggcagcagctggccgggaacggcgggcccccgagggcagcctg
gacgtgctacagtcctggtgtgagaagttggccgagatcatctggcagaac
cggcagcagatccgcagggctgagcacctctgccagcagctgcccatcccc
```

-continued

```
ggcccagtggaggagatgctggccgaggtcaacgccaccatcacggacatt
atctcagccctggtgaccagcacattcatcattgagaagcagcctcctcag
gtcctgaagacccagaccaagtttgcagccaccgtacgcctgctggtgggc
gggaagctgaacgtgcacatgaatcccccccaggtgaaggccaccatcatc
agtgagcagcaggccaagtctctgcttaaaaatgagaacacccgcaacgag
tgcagtggtgagatcctgaacaactgctgcgtgatggagtaccaccaagcc
acgggcaccctcagtgcccacttcaggaacatgtcactgaagaggatcaag
cgtgctgaccggcggggtgcagagtccgtgacagaggagaagttcacagtc
ctgtttgagtctcagttcagtgttggcagcaatgagcttgtgttccaggtg
aagactctgtccctacctgtggttgtcatcgtccacggcagccaggaccac
aatgccacggctactgtgctgtgggacaatgcctttgctgagccgggcagg
gtgccatttgccgtgcctgacaaagtgctgtggccgcagctgtgtgaggcg
ctcaacatgaaattcaaggccgaagtgcagagcaaccggggcctgaccaag
gagaacctcgtgttcctggcgcagaaactgttcaacaacagcagcagccac
ctggaggactacagtggcctgtccgtgtcctggtcccagttcaacagggag
aacttgccgggctggaactacaccttctggcagtggtttgacggggtgatg
gaggtgttgaagaagcaccacaagccccactggaatgatggggccatccta
ggttttgtgaataagcaacaggcccacgacctgctcatcaacaagcccgac
gggaccttcttgttgcgctttagtgactcagaaatcgggggcatcaccatc
gcctggaagtttgattccccggaacgcaacctgtggaacctgaaaccattc
accacgcgggatttctccatcaggtccctggctgaccggctgggggacctg
agctatctcatctatgtgtttcctgaccgccccaaggatgaggtcttctcc
aagtactacactcctgtgctggctaaagctgttgatggatatgtgaaacca
cagatcaagcaagtggtccctgagtttgtgaatgcatctgcagatgctggg
ggcagcagcgccacgtacatggaccaggcccctccccagctgtgtgcccc
caggctccctataacatgtacccacagaaccctgaccatgtactcgatcag
gatggagaattcgacctggatgagaccatggatgtggccaggcacgtggag
gaactcttacgccgaccaatggacagtcttgactcccgcctctcgcccccct
gccggtcttttcacctctgccagaggctccctctca).
```

In some alternatives, the sequence under control of an inducible promoter encodes for the amino acid sequence set forth in SEQ ID NO: 93 (STAT5a amino acid sequence: MAGWIQAQQLQGDALRQMQVLYGQHFPIEVRHY-LAQWIESQPWDAIDLDNPQDRA QATQL-LEGLVQELQKKAEHQVGEDGFLLKIKLGHYATQLQK TYDRCPLELVRCIRHI LYNEQRLVREANNCSSPAGIL-VDAMSQKHLQINQTFEELRLVTQDTENELKKLQQTQ EYFIIQYQESLRIQAQFAQLAQLSPQERLSRE-TALQQKQVSLEAWLQREAQTLQQYR VELAEKHQKTLQLLRKQQTIILDDELIQWKRRQQLA-GNGGPPEGSLDVLQSWCEKL AEIIWQNRQQIR-RAEHLCQQLPIPGPVEEMLAEVNATITDIISALVTST-FIIEKQPPQVL KTQTKFAATVRLLVGGKLNVHMNPPQVKATI-ISEQQAKSLLKNENTRNECSGEILNN CCVMEYHQATGTLSAHFRNMSLKRIKRADRR- GAESVTEEKFTVLFESQFSVGSNELV FQVKTLSLPVVVIVHGSQDHNATATVLWDNAFAE- PGRVPFAVPDKVLWPQLCEALN MKFKAEVQSNR- GLTKENLVFLAQKLFNNSSSHLEDYSGLSVSWSQFN- RENLPGWNY TFWQWFDGVMEVLKKHHKPHWND- GAILGFVNKQQAHDLLINKPDGTFLLRFSDSEI GGI- TIAWKFDSPERNLWNLKPFTTRDFSIRSLADRLGDL- SYLIYVFPDRPKDEVFSKY YTPVLAKAVDGYVKPQIKQVVPEFVNASADAGGS- SATYMDQAPSPAVCPQAPYNM YPQNPDHVLDQDGEFDLDETMDVAR- HVEELLRRPMDSLDSRLSPPAGLFTSARGSLS). In some alternatives, the sequence under control of an inducible promoter is encoded by a nucleic acid sequence comprising a nucleic acid sequence encoding the amino acid sequence of SEQ ID NO: 93.

In some alternatives, the gene under control of an inducible promoter comprises the nucleic acid sequence set forth in SEQ ID NO: 94 (Constitutively active-STAT5a nucleotide sequence:

```
atggcgggctggatccaggcccagcagctgcagggagacgcgctgcgccag
atgcaggtgctgtacggccagcacttccccatcgaggtccggcactacttg
gcccagtggattgagagccagccatgggatgccattgacttggacaatccc
caggacagagcccaagccacccagctcctggagggcctggtgcaggagctg
cagaagaaggcggagcaccaggtgggggaagatgggtttttactgaagatc
aagctggggcactacgccacgcagctccagaaaacatatgaccgctgcccc
ctggagctggtccgctgcatccggcacattctgtacaatgaacagaggctg
gtccgagaagccaacaattgcagctctccggctgggatcctggttgacgcc
atgtcccagaagcaccttcagatcaaccagacatttgaggagctgcgactg
gtcacgcaggacacagagaatgagctgaagaaactgcagcagactcaggag
tacttcatcatccagtaccaggagagcctgaggatccaagctcagtttgcc
cagctggcccagctgagcccccaggagcgtctgagccgggagacggccctc
cagcagaagcaggtgtctctggaggcctggttgcagcgtgaggcacagaca
ctgcagcagtaccgcgtggagctggccgagaagcaccagaagaccctgcag
ctgctgcggaagcagcagaccatcatcctggatgacgagctgatccagtgg
aagcggcggcagcagctggccgggaacggcgggcccccgagggcagcctg
gacgtgctacagtcctggtgtgagaagttggccgagatcatctggcagaac
cggcagcagatccgcagggctgagcgcctctgccagcagctgcccatcccc
ggcccagtggaggagatgctggccgaggtcaacgccaccatcacggacatt
atctcagccctggtgaccagcacattcatcattgagaagcagcctcctcag
gtcctgaagacccagaccaagtttgcagccaccgtacgcctgctggtgggc
gggaagctgaacgtgcacatgaatcccccccaggtgaaggccaccatcatc
agtgagcagcaggccaagtctctgcttaaaaatgagaacacccgcaacgag
tgcagtggtgagatcctgaacaactgctgcgtgatggagtaccaccaagcc
acgggcaccctcagtgcccacttcaggaacatgtcactgaagaggatcaag
cgtgctgaccggcggggtgcagagtccgtgacagaggagaagttcacagtc
ctgtttgagtctcagttcagtgttggcagcaatgagcttgtgttccaggtg
```

-continued

```
aagactctgtccctacctgtggttgtcatcgtccacggcagccaggaccac
aatgccacggctactgtgctgtgggacaatgcctttgctgagccgggcagg
gtgccatttgccgtgcctgacaaagtgctgtggccgcagctgtgtgaggcg
ctcaacatgaaattcaaggccgaagtgcagagcaaccggggcctgaccaag
gagaacctcgtgttcctggcgcagaaactgttcaacaacagcagcagccac
ctggaggactacagtggcctgtccgtgtcctggtcccagttcaacagggag
aacttgccgggctggaactacaccttctggcagtggtttgacggggtgatg
gaggtgttgaagaagcaccacaagccccactggaatgatggggccatccta
ggttttgtgaataagcaacaggcccacgacctgctcatcaacaagcccgac
gggaccttcttgttgcgctttagtgactcagaaatcgggggcatcaccatc
gcctggaagtttgattccccggaacgcaacctgtggaacctgaaaccattc
accacgcgggatttctccatcaggtccctggctgaccggctgggggacctg
agctatctcatctatgtgrncctgaccgccccaaggatgaggtcttctcca
agtactacactcctgtgctggctaaagctgttgatggatatgtgaaaccac
agatcaagcaagtggtccctgagrngtgaatgcatttgcagatgctggggg
cagcagcgccacgtacatggaccaggcccccctccccagctgtgtgcccccca
ggctccctataacatgtacccacagaaccctgaccatgtactcgatcagga
tggagaattcgacctggatgagaccatggatgtggccaggcacgtggagga
actcttacgccgaccaatggacagtcttgactcccgcctctcgccccctgc
cggtcttttcacctctgccagaggctccctctca).
```

In some alternatives, the sequence under control of an inducible promoter encodes for the amino acid sequence set forth in SEQ ID NO: 95 (Constitutively active-STAT5a amino acid sequence: MAGWIQAQQLQGDALRQMQVLYGQHFPIEVRHY- LAQWIESQPWDAIDLDNPQDRA QATQL- LEGLVQELQKKAEHQVGEDGFLLKIKLGHYAT QLQKTYDRCPLELVRCIRHI LYNEQRLVRE- ANNCSSPAGILVDAMSQKHLQINQT- FEELRLVTQDTENELKKLQQTQ EYFIIQYQESL- RIQAQFAQLAQLSPQERLSRETALQQKQVSLEAWLQ- REAQTLQQYR VELAEKHQKTLQLLRKQQTIILD- DELIQWKRRQQLAGNGGPPEGSLDVLQSWCEKL AEIIWQNRQQIRRAERLCQQLPIPGPVEEM- LAEVNATITDIISALVTSTFIIEKQPPQVL KTQTK- FAATVRLLVGGKLNVHMNPPQVKATI- ISEQQAKSLLKNENTRNECSGEILNN CCVMEYHQATGTLSAHFRNMSLKRIKRADRR- GAESVTEEKFTVLFESQFSVGSNELV FQVKTLSLPVVVIVHGSQDHNATATVLWDNAFAE- PGRVPFAVPDKVLWPQLCEALN MKFKAEVQSNR- GLTKENLVFLAQKLFNNSSSHLEDYSGLSVSWSQFN- RENLPGWNY TFWQWFDGVMEVLKKHHKPHWND- GAILGFVNKQQAHDLLINKPDGTFLLRFSDSEI GGI- TIAWKFDSPERNLWNLKPFTTRDFSIRSLADRLGDL- SYLIYVFPDRPKDEVFSKY YTPVLAKAVDGYVKPQIKQVVPEFVNAFADAGGS- SATYMDQAPSPAVCPQAPYNM YPQNPDHVLDQDGEFDLDETMDVAR- HVEELLRRPMDSLDSRLSPPAGLFTSARGSLS). In some alternatives, the sequence under control of an inducible promoter is encoded by a nucleic acid sequence comprising a nucleic acid sequence encoding the amino acid sequence of SEQ ID NO: 95.

In some alternatives, the gene under control of an inducible promoter comprises the nucleic acid sequence set forth in SEQ ID NO: 96 (Dominant negative TGFbRII nucleotide sequence:

```
atgggtcgggggctgctcaggggcctgtggccgctgcacatcgtcctgtgg
acgcgtatcgccagcacgatcccaccgcacgttcagaagtcggttaataac
gacatgatagtcactgacaacaacggtgcagtcaagtttccacaactgtgt
aaattttgtgatgtgagattttccacctgtgacaaccagaaatcctgcatg
agcaactgcagcatcacctccatctgtgagaagccacaggaagtctgtgtg
gctgtatggagaaagaatgacgagaacataacactagagacagtttgccat
gaccccaagctcccctaccatgactttattctggaagatgctgcttctcca
aagtgcattatgaaggaaaaaaaaaagcctggtgagactttcttcatgtgt
tcctgtagctctgatgagtgcaatgacaacatcatcttctcagaagaatat
aacaccagcaatcctgacttgttgctagtcatatttcaagtgacaggcatc
agcctcctgccaccactgggagttgccatatctgtcatcatcatcttctac
tgctaccgcgttaaccggcagcagaagctgagttcaacctgggaaaccggc
aagacgcggaagctcatggagttcagcgagcactgtgccatcatcctggaa
gatgaccgctctgacatcagctccacgtgtgccaacaacatcaaccacaac
acagagctgctgcccattgagctggacaccctggtggggaaaggtcgcttt
gctgaggtctataaggccaagctgaagcagaacacttcagagcagtttgag
acagtggcagtcaagatcttt).
```

In some alternatives, the sequence under control of an inducible promoter encodes for the amino acid sequence set forth in SEQ ID NO: 97 (Dominant negative TGFbRII amino acid sequence: MGRGLLRGLWPLHIVLWTRIAS-TIPPHVQKSVNNDMIVTDNNGAVKFPQLCKFCDV RFSTCDNQKSCMSNCSITSICEKPQEVCVAVWRKN-DENITLETVCHDPKLPYHDFILE DAASPKCI-MKEKKKPGETFFMCSCSSDECNDNIIF-SEEYNTSNPDLLLVIFQVTGISLLP PLGVAISVIII-FYCYRVNRQQKLSSTWETGKTRKLMEFSEH-CAIILEDDRSDISSTCAN NINHNTELLPIELD-TLVGKGRFAEVYKAKLKQNTSEQFETVAVKIF). In some alternatives, the sequence under control of an inducible promoter is encoded by a nucleic acid sequence comprising a nucleic acid sequence encoding the amino acid sequence of SEQ ID NO: 97.

In some alternatives, the gene under control of an inducible promoter comprises the nucleic acid sequence set forth in SEQ ID NO: 98 (Dominant negative SHP1 nucleotide sequence:

```
atggtgaggtggtttcaccgagacctcagtgggctggatgcagagaccctg
ctcaagggccgaggtgtccacggtagcttcctggctcggcccagtcgcaag
aaccagggtgacttctcgctctccgtcagggtggggatcaggtgacccat
attcggatccagaactcaggggatttctatgacctgtatggaggggagaag
```

-continued

```
tttgcgactctgacagagctggtggagtactacactcagcagcagggtgtc
ctgcaggaccgcgacggcaccatcatccacctcaagtacccgctgaactgc
tccgatcccactagtgagaggtggtaccatggccacatgtctggcgggcag
gcagagacgctgctgcaggccaagggcgagccctggacgtttcttgtgcgt
gagagcctcagccagcctggagacttcgtgctttctgtgctcagtgaccag
cccaaggctggcccaggctccccgctcagggtcacccacatcaaggtcatg
tgcgagggtggacgctacacagtgggtggtttggagaccttcgacagcctc
acggacctggtggagcatttcaagaagacggggattgaggaggcctcaggc
gcctttgtctacctgcggcagccgtactatgccacgagggtgaatgcggct
gacattgagaaccgagtgttggaactgaacaagaagcaggagtccgaggat
acagccaaggctggcttctgggaggagtttgagagtttgcagaagcaggag
gtgaagaacttgcaccagcgtctggaagggcagcggccagagaacaagggc
aagaaccgctacaagaacattctcccctttgaccacagccgagtgatcctg
cagggacgggacagtaacatccccgggtccgactacatcaatgccaactac
atcaagaaccagctgctaggccctgatgagaacgctaagacctacatcgcc
agccagggctgtctggaggccacggtcaatgacttctggcagatggcgtgg
caggagaacagccgtgtcatcgtcatgaccacccgagaggtggagaaaggc
cggaacaaatgcgtcccatactggcccgaggtgggcatgcagcgtgcttat
gggccctactctgtgaccaactgcggggagcatgacacaaccgaatacaaa
ctccgtaccttacaggtctccccgctggacaatggagacctgattcgggag
atctggcattaccagtacctgagctggcccgaccatggggtccccagtgag
cctgggggtgtcctcagcttcctggaccagatcaaccagcggcaggaaagt
ctgcctcacgcagggcccatcatcgtgcactccagcgccggcatcggccgc
acaggcaccatcattgtcatcgacatgctcatggagaacatctccaccaag
ggcctggactgtgacattgacatccagaagaccatccagatggtgcgggcg
cagcgctcgggcatggtgcagacggaggcgcagtacaagttcatctacgtg
gccatcgcccagttcattgaaaccactaagaagaagctggaggtcctgcag
tcgcagaagggccaggagtcggagtacgggaacatcacctatcccccagcc
atgaagaatgcccatgccaaggcctcccgcacctcgtccaaacacaaggag
gatgtgtatgagaacctgcacactaagaacaagagggaggagaaagtgaag
aagcagcggtcagcagacaaggagaagagcaagggttccctcaagaggaag
tga).
```

In some alternatives, the sequence under control of an inducible promoter encodes for the amino acid sequence set forth in SEQ ID NO: 99: Dominant negative SHP1 amino acid sequence: MVRWFHRDLSGL-DAETLLKGRGVHGS-FLARPSRKNQGDFSLSVRVGDQVTHIRIQN SGDFYD-LYGGEKFATLTELVEYYTQQQGVLQDRDGTIIHLKYP LNCSDPTSERWYH GHMSGGQAETLLQAKGEPWT-FLVRESLSQPGDFVLSVLSDQPKAGPGSPLRVTHIKV MCEGGRYTVGGLETFDSLTDLVEHFKKTGIEE-ASGAFVYLRQPYYATRVNAADIEN RVLELNKKQESEDTAKAGFWEEF-ESLQKQEVKNLHQRLEGQRPENKGKNRYKNILP FDHSRVILQGRDSNIPGSDYINANYIKNQLLGPDE-
NAKTYIASQGCLEATVNDFWQM AWQENSRVIVMTT-
REVEKGRNKCVPYWPE-
VGMQRAYGPYSVTNCGEHDTTEYKLR
TLQVSPLDNGDLI-
REIWHYQYLSWPDHGVPSEPGGVLSFLDQINQRQESL-
PHAGPIIV HSSAGIGRTGTIIVIDMLMENISTKGLDC-
DIDIQKTIQMVRAQRSGMVQTEAQYKFIY
VAIAQFIETTKKKLEVLQSQKGQESEYGNITYPPAMK-
NAHAKASRTSSKHKEDVYEN LHTKNK-
REEKVKKQRSADKEKSKGSLKRK). In some alternatives, the sequence under control of an inducible promoter is encoded by a nucleic acid sequence comprising a nucleic acid sequence encoding the amino acid sequence of SEQ ID NO: 99.

In some alternatives, the gene under control of an inducible promoter comprises a nucleic acid sequence set forth in SEQ ID NO: 100 (PD1TM-MyD88 nucleotide sequence:

```
atgcttctcctggtgacaagccttctgctctgtgagttaccacacccagca
ttcctcctgatcccaggcggaggagtgggagtcgtgggcggactgctggga
tctctggtgctgctcgtgtgggtgctggccgtgattggcggaggaatggct
gctggcggacctggcgctggatctgctgctcctgtgtctagcaccagcagc
ctgcctctggccgccctgaatatgagagtgcggcggagactgagcctgttc
ctgaacgtgcggacacaggtggccgccgattggacagctctggccgaggaa
atggacttcgagtacctggaaatccggcagctggaaacccaggccgaccct
acaggacgcctgctggatgcttggcagggcagaccaggcgcttctgtgggg
agactgctggaactgctgaccaagctgggccgggacgacgtgctgctggaa
ctgggccctagcatcgaagaggactgccagaagtacatcctgaagcagcag
caggaagaggccgagaagcctctgcaggtggcagccgtggatagcagcgtg
ccaagaacagctgagctggccggaatcaccaccctggacgatcctctgggc
cacatgcccgagagattcgacgccttcatctgctactgccccagcgacatc
cagttcgtgcaggaaatgatcagacagctggaacagaccaactaccggctg
aagctgtgcgtgtccgaccgggatgtgctgcctggcacctgtgtgtggtct
atcgccagcgagctgatcgagaagcggtgcagacggatggtcgtggtggtg
tccgacgactacctgcagtccaaagagtgcgacttccagaccaagttcgcc
ctgagcctgagccctggcgcccaccagaagagactgatccccatcaagtac
aaggccatgaagaaagagttccccagcatcctgcggttcatcaccgtgtgc
gactacaccaacccctgcaccaagtcctggttctggaccagactggccaag
gccctgtctctgcc).
```

In some alternatives, the gene under control of an inducible promoter encodes for an amino acid sequence set forth in SEQ ID NO: 101 (PD1TM-MyD88 amino acid sequence:
MLLLVTSLLLCELPHPAFLLIPGGGVGVVG-
GLLGSLVLLVWVLAVIGGGMAAGGPG
AGSAAPVSSTSSLPLAAL-
NMRVRRRLSLFLNVRTQVAADWTALAEEMDFEY-
LEIRQL ETQADPTGRLLDAWQGRPGASVGRL-
LELLTKLGRDDVLLELGPSIEEDCQKYILKQQ
QEEAEKPLQVAAVDSSVPRTAELAGIT-
TLDDPLGHMPERFDAFICYCPSDIQFVQEMI
RQLEQTNYRLKLCVSDRDVLPGTCVWSIASELIEKR-
CRRMVVVVSDDYLQSKECDF QTKFALSLSP-
GAHQKRLIPIKYKAMKKEFP-
SILRFITVCDYTNPCTKSWFWTRLAKAL SL). In some alternatives, the sequence under control of an inducible promoter is encoded by a nucleic acid sequence comprising a nucleic acid sequence encoding the amino acid sequence of SEQ ID NO: 101.

The disclosure provides for a system comprising first and second nucleic acids, and vectors and host cells including such nucleic acids. Each of the first and second nucleic acids comprise a number of modular components that can be excised and replaced with other components in order to customize the system for a specific target cell. In some alternatives, the first nucleic acid includes an inducible promoter for control of the expression of the genes (e.g., polynucleotide coding for a chimeric antigen receptor) in an on and off manner as needed, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In other alternatives, the second nucleic acid comprises a constitutive promoter that provides for expression of a transcriptional activator. In some alternatives, the gene encodes for a chimeric antigen receptor. In some alternatives, the gene encodes for a chimeric antigen receptor AND a transcriptional activator (encoded by one plasmid).

Inducible System.

The disclosure provides a system useful for providing regulated expression of transgenes in cells, such as mammalian cells. Such transgenes include, without limitation, T cell receptors, affinity matured T cell receptors, chimeric antigen receptors, chemokine receptors, chimeric chemokine receptors, cytokines, genes that inhibit apoptosis, and/or genes that modulate checkpoint signaling. In some alternatives, the polypeptide that modulates checkpoint signaling inhibits negative checkpoint regulators. In some alternatives, the negative checkpoint regulator comprises PD-1, VISTA, LAG-3 and/or TIM3. In some alternatives, the system contains a number of modular components that provide for easy substitution of elements of the nucleic acid. In some alternatives of the system, the system provides regulation of expression of transgenes in cells, such as mammalian cells, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives, the transgenes code for T cell receptors, affinity matured T cell receptors, chimeric antigen receptors, chemokine receptors, chimeric chemokine receptors, cytokines, genes that regulate apoptosis, and/or genes that modulate checkpoint signaling. In some alternatives, the gene that modulates checkpoint signaling encodes a polypeptide inhibits negative checkpoint regulators. In some alternatives, the negative checkpoint regulator comprises PD-1, VISTA, LAG-3 and/or TIM3.

In some alternatives, a system for inducible expression of a transgene is provided. In some alternatives, the transgene encodes a chimeric antigen receptor. In some alternatives, a system for inducible expression of a chimeric antigen receptor in cells, such as mammalian cells, is provided. In some alternatives, a system for inducible expression of a chimeric antigen receptor in cells, such as mammalian cells, comprises: a first nucleic acid comprising a first promoter inducible by a drug, wherein the first nucleic acid is operably linked to a first polynucleotide that encodes a chimeric antigen receptor which comprises a ligand binding domain that is specific for a ligand selected from a tumor specific molecule, viral molecule, or any other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain, and a fourth polynucleotide, which encodes an intracellular signaling domain, and a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives, the second promoter is constitutive or inducible.

In some alternatives, a polynucleotide coding for a chimeric antigen receptor comprises a polynucleotide coding for a ligand binding domain, wherein the target molecule is a tumor specific antigen, a polynucleotide coding for a polypeptide spacer wherein the spacer is optionally optimized; a polynucleotide coding for a transmembrane domain; and a polynucleotide coding for an intracellular signaling domain. In some alternatives, an expression vector comprises a first and/or second nucleic acid, as described herein. Polypeptides encoded by all of or a portion of the chimeric receptor nucleic acids are also included herein.

In other alternatives, a first nucleic acid comprises a first promoter inducible by a drug, wherein the first nucleic acid is operably linked to a polynucleotide coding for a gene that promotes cell survival and proliferation, a gene that regulates apoptosis, and/or a gene that modulates checkpoint signaling. Such genes include genes encoding IL-2, IL-7, IL-15, chemokine receptors, chimeric chemokine receptors, Bcl2, CA-Akt, dn-TGFbetaRIII, dn-SHP1/2, and/or PD-1CD28 chimeras. In some alternatives, the gene that modulates checkpoint signaling encodes a polypeptide that inhibits negative checkpoint regulators. In some alternatives, the negative checkpoint regulator comprises PD-1, VISTA, LAG-3 and/or TIM3.

In some alternatives, the system is for inducible expression of a gene that regulates a T cell function.

Inducible Promoters.

A system comprises a first nucleic acid comprising a first promoter inducible by a drug. By utilizing an inducible promoter, transgene expression can be turned on and off in order to avoid toxic side effects and/or to allow the cells to rest during remission. Another purpose of the inducible promoter system is to improve anti-tumor efficacy by turning on genes that enhance T cell function. Although several inducible promoter systems are known, clinical applicability of these systems is limited due to toxic off target effects, unfavorable biodistribution and pharmacodynamics profiles, limited output dynamic range, and/or limited availability as FDA-approved commercially available pharmaceuticals. Furthermore, many of these systems use chimeric transcriptional regulators built from xenogeneic components, thus introducing the complication of immunogenicity when applying these systems to human therapeutics. In some alternatives, the first nucleic acid comprises a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and other molecule expressed on a target cell population, wherein the ligand elicits recognition, modulation, inhibition, and/or elimination by a lymphocyte, a second polynucleotide, which encodes an optimized polypeptide spacer, a third polynucleotide, which encodes a transmembrane domain and a fourth polynucleotide, which encodes an intracellular signaling domain.

In some alternatives, a first promoter is inducible by a drug. The drug is selected based on safety record, favorable pharmacokinetic profile, tissue distribution, a low partition coefficient between the extracellular space and cytosol, low immunogenicity, low toxicities, and/or high expression in lymphocytes. In a specific alternative, a drug is selected that is FDA approved, provides for transgene expression in lymphocytes, does not activate other undesirable gene expression, and induces a promoter that does not contain any xenogeneic components. In some alternatives, the inducible promoter is activated by a transcriptional activator that interacts with a drug. The transcriptional activator is activated or able to bind to and activate the inducible promoter in the presence of the drug.

A specific alternative of a drug is a drug that binds to an estrogen receptor ligand binding domain of a transcriptional activator. In some alternatives, the drug includes tamoxifen, its metabolites, analogs, and pharmaceutically acceptable salts and/or hydrates or solvates thereof. In some alternatives, the drug includes tamoxifen and/or its metabolites, 4-hydroxytamoxifen, fulvestrant or other estrogen analogs, or CMP8.

Tamoxifen, CAS RN: 10540-29-1, useful in some approaches described herein, is also known as 2-(4-((1Z)-1,2-diphenyl-1-butenyl)phenoxy)-N,N-dimethyl-ethanamine, or (Z)-2-(para-(1,2-Diphenyl-1-butenyl)phenoxy)-N,N-dimethylamine (IUPAC), and has a molecular formula of C26H29NO and a molecular weight (M.W.) of 371.52 g/mol. Tamoxifen is a Selective Estrogen Receptor Modulator with tissue-specific activities. Tamoxifen acts as an anti-estrogen (inhibiting agent) agent in the mammary tissue, but as an estrogen (stimulating agent) in cholesterol metabolism, bone density, and cell proliferation in the endometrium. Tamoxifen is frequently administered orally as a pharmaceutically acceptable salt. For example, Tamoxifen citrate (RN 54965-24-1, M.W. 563.643) is indicated for treatment of metastatic breast cancer, and as an adjuvant for the treatment of breast cancer in women following mastectomy axillary dissection, and breast irradiation. Tamoxifen citrate is also indicated to reduce incidence of breast cancer in women at high risk for breast cancer.

Metabolites of tamoxifen in rat, mouse and human breast cancer patients, useful in some approaches described herein, include major metabolites N-desmethyltamoxifen (RN 31750-48-8, M.W. 357.494) and 4-hydroxytamoxifen (4-OHT) (RN 68392-35-8, M.W. 387.52, Afimoxifene), and are disclosed in Robinson et al. (Metabolites, pharmacodynamics, and pharmacokinetics of tamoxifen in rats and mice compared to the breast cancer patient. Drug Metab Dispos January 1991 19:36-43; incorporated by reference in its entirety herein). Additional cytochrome P-450 metabolites, useful in some approaches described herein, include cis-4-hydroxytamoxifen (RN 174592, M.W. 387.52; Afimoxifene, E-isomer), and 4'-hydroxytamoxifen ((Z)-4-(1-(4-(2-(dimethylamino)ethoxy)phenyl)-1-phenylbut-1-en-2-yl)phenol) as disclosed in Crewe et al. (Metabolism of Tamoxifen by recombinant human cytochrome P-450 enzymes: Formation of the 4-hydroxy, 4'-hydroxy and N-desmethyl metabolites and isomerization of trans-4-hydroxytamoxifen, Drug Metab Dispos, 30(8): 869-874, 2002, FIG. 1; incorporated by reference in its entirety herein).

Compounds with structural similarity to tamoxifen, useful in some approaches described herein, include, but are not limited to, cis-tamoxifen (RN 13002-65-8, M.W. 371.521), 4-methyltamoxifen (RN 73717-95-5, M.W. 385.548), N-desmethyltamoxifen (RN 31750-48-8, M.W. 357.494), (Z)-desethyl methyl tamoxifen (RN 15917-50-7, M.W. 357.494), (E)-desethyl methyl tamoxifen (RN 31750-45-5, M.W. 357.494), trans-4-hydoxytamoxifen (RN 68047-06-3, M.W. 387.52), Afimoxifene (RN 68392-35-8, M.W. 387.52, 4-hydroxytamoxifen), Afimoxifene, E-isomer (RN 174592-47-3, M.W. 387.52), 4-chlorotamoxifen (RN 77588-46-6, M.W. 405.966), 4-fluorotamoxifen (RN 73617-96-6, M.W. 389.511), Toremifene (RN 89778-26-7, M.W. 405.966), desethyl tamoxifen (RN 19957-51-8, M.W. 343.47), (E)-desethyl tamoxifen (RN 97151-10-5, M.W. 343.47), (Z)-desethyl tamoxifen (RN 97151-11-6, M.W. 343.47), Miproxifene (RN 129612-87-9, M.W. 429.6), 2-(p-(beta-ethyl-alpha-phenyl styryl)phenoxy)triethylamine (RN 749-86-0, M.W. 399.575), Droloxifene (RN 82413-20-5, M.W. 387.52), 4-iodo-tamoxifen (RN 116057-68-2, M.W. 497.413), dihydrotamoxifen (RN 109640-20-2, M.W. 373.537), (E)-N,N-dimethyl-2-(4-(1-(2-methylphenyl)-2-phenyl-1-butenyl)phenoxy)ethanamine (RN 97150-96-4, M.W. 385.548), or 4-hydroxytoremifene (RN 110503-62-3, M.W. 421.965); and/or pharmaceutically acceptable salts and/or hydrates or solvates thereof.

For example, citrate salts of tamoxifen, or citrate salts of compounds with structural similarity to tamoxifen, useful in some approaches described herein, include, but are not limited to tamoxifen citrate (RN 54965-24-1, M.W. 563.64), 2-(p-(1,2-diphenyl-1-butenyl)phenoxy)-N,N-dimethylethylamine citrate (RN 7244-97-5, 563.64), (E)-tamoxifen citrate (RN 76487-65-5, M.W. 563.64), Toremifene citrate (RN 89778-27-8, M.W. 598.088), Droloxifene citrate (RN 97752-20-0, M.W. 579.64), 2-(p-(1,2-bis(p-methoxyphenyl)-1-butenyl)phenoxy)triethylamine citrate (RN 42920-39-8, M.W. 651.748), 2-(4-(1,2-diphenylethenyl)phenoxy)-N,N-diethyl-ethanamine 2-hydroxy-1,2,3-propanetricarboxylate (RN 40297-42-5, M.W. 563.643), 2-(p-(alpha-phenyl styryl)phenoxy)triethylamine citrate (RN 102433-95-4, M.W. 563.64), 2-(p-(2-(p-methoxyphenyl)-1-phenyl-1-butenyl)phenoxy)triethylamine citrate (1:1) (RN 42824-34-0, M.W. 637.72), 2-(p-(1-(p-methoxyphenyl)-2-phenylpropenyl)phenoxy)triethylamine citrate (RN 13554-24-0, M.W. 607.696), 2-(p-(alpha-(p-methoxyphenyl)styryl)phenoxy)triethylamine citrate monohydrate (RN 13542-71-7, M.W. 593.669), 2-(p-(p-methoxy-alpha-phenylphenethyl) phenoxy)triethylamine citrate (RN 16421-72-0, M.W. 595.685), alpha-(p-(2-(diethylamino)ethoxy)phenyl)-beta-ethyl-p-methoxy-alpha-phenylphenethyl alcohol citrate (1:1) (RN 35263-93-5, M.W. 639.737), 1-(p-(2-(diethylamino)ethoxy)phenyl)-2-(p-methoxyphenyl)-1-phenylethanol citrate (M.W. 611.68), alpha-p-(2-(diethyl amino) ethoxy)phenyl)-beta-ethyl-alpha-(p-hydroxyphenyl)-p-methoxyphenethyl alcohol citrate (RN 35263-96-8, M.W. 655.737), and/or 2-(p-(p-methoxy-alpha-methylphenethyl) phenoxy)-triethylamine citrate (RN 15624-34-7, M.W. 533.614).

In some alternatives, an effective amount of the drug for inducing expression is an amount that provides for an increase in transgene expression over uninduced and/or basal level of expression. In some alternatives, this amount can be readily determined using known dosages and pharmacokinetic profile of the drug. In the systems provided herein, wherein the systems are inducible by the drug, the system is inducible by an amount of the drug that is less than a comparable system utilizing a wild type HEA3 chimeric transcription factor or a wild type HEA4 chimeric transcription factor.

In some alternatives, the inducible promoter has a low level of basal activity. When a lentiviral vector is used, the level of basal activity in uninduced cells is 20%, 15%, 10%, 5%, 4%, 3%, 2%, 1% or less, or any level of basal activity in between a range defined by any two aforementioned values, as compared to when cells are induced to express the gene. The level of basal activity can be determined by measuring the amount of the expression of the transgene (e.g. marker gene) in the absence of the inducer (e.g. drug) using flow cytometry.

In some alternatives, the inducible promoter provides for a high level of induced activity, as compared to uninduced or basal activity. In some alternatives, the level of activity in the induced state is 2, 4, 6, 8, or 10 fold or greater than the activity level in the uninduced state. In some alternatives, transgene expression under control of the inducible promoter is turned off in the absence of a transactivator in less than 10, 8, 6, 4, 2, or 1 days excluding 0 days.

In some alternatives, an inducible promoter can be designed and/or modified to provide for a low level of basal activity, a high level of inducibility, and/or a short time for reversibility. In some alternatives, the inducible promoter is the 7×HBD/mE1b promoter. An exemplary sequence for the promoter is set forth in SEQ ID NO: 23 (SEQ ID NO: 23; tagttaataatctacaatagttaataatctacaatagttaataatctacaatagt-taataatctacaatagttaataatctacaatagttaataat ctacaatagttaataatc-tacaagagctcagggtatataatg). For example, in the 7×HBD/mE1b promoter, mutations can be made to enhance the binding of the transcriptional activator. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values.

In some alternatives, the system employs a synthetic transcriptional activator which, in the presence of the drug (e.g., tamoxifen), binds a synthetic promoter upstream of a transgene to induce expression. In some alternatives, the transcriptional activator is HEA3. An exemplary amino acid sequence is set forth in SEQ ID NO: 1 (MVSKLSQLQ-TELLAALLESGLSKEALIQALGEPGPYLLAGEG-PLDKGESCGGGRGEL AELPNGLGETRGSEDE-TDDDGEDFTPPILKELENLSPEEAAHQKAVVETLLQE DPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKRMEH-LYSMKCKNVVPLYDLLLEMLDAHRLHAPTSRG-GASVE ETDQSHLATAGSTSSHSLQKYYITGEAE-GFPATVEFQYLPDTDDRHRIEEKRKRTYET FKSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFSSIADM DFSALLSQISS). Some alternatives include a nucleic acid comprising a nucleic acid sequence that encodes SEQ ID NO: 1. The mutant tamoxifen-specific ligand binding domain of the estrogen receptor ligand binding domain (ER-LBD) is found at amino acids 282-595 of the TamR-tf and has a mutation at position 521. The p65 activation domain of NF-κB (p65 or TAD) is found at amino acids 596 to 862. SEQ ID NO: 1 comprises one point mutation in the ER-LBD that ablates binding to endogenous estrogen, but confers nanomolar specificity to 4-OHT, fulvestrant and other estrogen analogs.

In some alternatives, the HEA3 transcription factor comprises at least one point mutation that ablates binding to the endogenous estrogen but confers nanomolar specificity tamoxifen metabolite, 4-hydroxytamoxifen, fulvestrant, and other estrogen analogs. In some alternatives, the one point mutation is at position 521 of the sequence of the wild-type HEA3. In some alternatives, the amino acid sequence comprises a sequence set forth in SEQ ID NO: 1 (MVSKLSQLQTELLAALLESGLSKEALIQALGEPGPYL-LAGEGPLDKGESCGGGRGEL AELPNGLGETRGSEDETDDDGEDFTPPILKELENL-SPEEAAHQKAVVETLLQEDPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKRMEH-LYSMKCKNVVPLYDLLLEMLDAHRLHAPTSRG-GASVE ETDQSHLATAGSTSSHSLQKYYITGEAE-GFPATVEFQYLPDTDDRHRIEEKRKRTYET FKSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFSSIADM DFSALLSQISS). SEQ ID NO: 1 comprises one point mutation in the ER-LBD that ablates binding to endogenous estrogen, but confers nanomolar specificity to 4-OHT, fulvestrant and other estrogen analogs.

In some alternatives, the HEA3 transcription factor comprises at least one point mutation in the p65 domain that enhances transcriptional activity. In some alternatives, the point mutation is at position 846 of the sequence of the wild-type HEA3 (position 536 in the RelA protein, which correspond to position 846 in HEA3). In some alternatives, the amino acid sequence comprises a sequence set forth in SEQ ID NO: 2 (SEQ ID NO: 2; MVSKLSQLQTEL-LAALLESGLSKEALIQALGEPGPYLLAGEG-PLDKGESCGGGRGEL AELPNGLGETRGSEDE-TDDDGEDFTPPILKELENLSPEEAAHQKAVVETLLQE DPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKRMEH-LYSMKCKNVVPLYDLLLEMLDAHRLHAPTSRG-GASVE ETDQSHLATAGSTSSHSLQKYYITGEAE-GFPATVEFQYLPDTDDRHRIEEKRKRTYET FKSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFESIADM DFSALLSQISS). Some alternatives include a nucleic acid comprising a nucleic acid sequence that encodes SEQ ID NO: 2. SEQ ID NO: 2 comprises a point mutation in HEA3, in the p65 domain which enhances transcriptional activity and is referred to as HEA3 (p65/S536E). The p65/S536E position in the RelA protein corresponds to position 846 in wild type HEA3 and wild type HEA4.

In some alternatives, the HEA3 transcription factor comprises at least one point mutation in the p65 domain that enhances transcriptional activity. In some alternatives, the point mutation is at position 621 of the sequence of the wild-type HEA3 (This is position 310 of the WT RelA protein). In some alternatives, the amino acid sequence comprises a sequence set forth in SEQ ID NO: 3 (SEQ ID NO: 3; MVSKLSQLQTELLAALLESGLSKEALIQAL-GEPGPYLLAGEGPLDKGESCGGGRGEL AEL-PNGLGETRGSEDETDDDGEDFTPPILKELENLSPEE-AAHQKAVVETLLQEDPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKRMEH- LYSMKCKNVVPLYDLLLEMLDAHRLHAPTSRG-GASVE ETDQSHLATAGSTSSHSLQKYYITGEAE-GFPATVEFQYLPDTDDRHRIEEKRKRTYET FQSSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFSSIADM DFSALLSQISS). Some alternatives include a nucleic acid comprising a nucleic acid sequence that encodes SEQ ID NO: 3. SEQ ID NO: 3 comprises a sequence of HEA3 containing one point mutation (K310Q positions in the RelA protein) in the p65 domain that enhances transcriptional activity. This is referred to as HEA3 (p65/K310Q). K310Q refers to position 310 of RelA. This position thus corresponds to position 621 of WT HEA3 AND WT HEA4.

In some alternatives, the HEA3 transcription factor comprises at least three point mutations in the estrogen receptor ligand binding domain that ablates binding to endogenous estrogen, and confer nanomolar sensitivity to CMP8 and 4-hydroxytamoxifen. In some alternatives, the point mutations are at positions 384, 421 and 521 of the sequence of the wild-type HEA3. In some alternatives, the amino acid sequence comprises a sequence set forth in SEQ ID NO: 8 (SEQ ID NO: 8; MVSKLSQLQTELLAALLESGLSKEAL-IQALGEPGPYLLAGEGPLDKGESCGGGRGEL AEL-PNGLGETRGSEDETDDDGEDFTPPILKELENLSPEE-AAHQKAVVETLLQEDPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWMEILMIGLV WRSMEHPGKLLFAPNLLLDRNQGKCVEGGVE-IFDMLLATSSRFRMMNLQGEEFVCL KSIILLNSGVYT-FLSSTLKSLEEKDHIHRVLDKITDTLIHLMAK-AGLTLQQQHQRLAQ LLLILSHIRHMSNKRMEH-LYSMKCKNVVPLYDLLLEMLDAHRLHAPTSRGGAS-VEE TDQSHLATAGSTSSHSLQKYYITGEAE-GFPATVEFQYLPDTDDRHRIEEKRKRTYETF KSIMKKSPFSGPTDPRPPPRRIAVPSRSSAS-VPKPAPQPYPFTSSLSTINYDEFPTMVFPS GQISQASALAPAPPQVLPQAPAPAPA-PAMVSALAQAPAPVPVLAPGPPQAVAPPAPK PTQAGEGTLSEALLQLQFDDEDLGALLGNSTD-PAVFTDLASVDNSEFQQLLNQGIPV APH-TTEPMLMEYPEAITRLVTGAQRPPDPAPAPL-GAPGLPNGLLSGDEDFSSIADMDF SALLSQISS). Some alternatives include a nucleic acid comprising a nucleic acid sequence that encodes SEQ ID NO: 8. SEQ ID No: 8 comprises the sequence of HEA3 containing three point mutations (L384M, M421G, G521R) in the ER-LBD that ablate binding to endogenous estrogen, and confer nanomolar sensitivity to CMP8 and 4-hydroxytamoxifen. This is referred to as CMP8-HEA3.

In some alternatives, the HEA3 transcription factor is a CMP8-responsive HEA3 transcription factor. In some alternatives, the CMP8-responsive HEA3 transcription factor comprises at least one point mutation in the p65 domain that enhances transcriptional activity. In some alternatives, the point mutation is at position 846 of the sequence of the CMP8-responsive HEA3 (position 536 in the RelA protein, which correspond to position 846 in HEA3). In some alternatives, the amino acid sequence comprises a sequence set forth in SEQ ID NO: 9 (SEQ ID NO: 9; MVSKLSQLQ-TELLAALLESGLSKEALIQALGEPGPYLLAGEG-PLDKGESCGGGRGEL AELPNGLGETRGSEDE-TDDDGEDFTPPILKELENLSPEEAAHQKAVVETLLQE DPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWMEILMIGLV WRSMEHPGKLLFAPNLLLDRNQGKCVEGGVE-IFDMLLATSSRFRMMNLQGEEFVCL KSIILLNSGVYT-FLSSTLKSLEEKDHIHRVLDKITDTLIHLMAK-AGLTLQQQHQRLAQ LLLILSHIRHMSNKRMEH-LYSMKCKNVVPLYDLLLEMLDAHRLHAPTSRGGAS-VEE TDQSHLATAGSTSSHSLQKYYITGEAE-GFPATVEFQYLPDTDDRHRIEEKRKRTYETF KSIMKKSPFSGPTDPRPPPRRIAVPSRSSAS-VPKPAPQPYPFTSSLSTINYDEFPTMVFPS GQISQASALAPAPPQVLPQAPAPAPA-PAMVSALAQAPAPVPVLAPGPPQAVAPPAPK PTQAGEGTLSEALLQLQFDDEDLGALLGNSTD-PAVFTDLASVDNSEFQQLLNQGIPV APH-TTEPMLMEYPEAITRLVTGAQRPPDPAPAPL-GAPGLPNGLLSGDEDFESIADMDF SALLSQISS). Some alternatives include a nucleic acid comprising a nucleic acid sequence that encodes SEQ ID NO: 9. SEQ ID NO: 9 is the sequence of CMP8-HEA3 containing one point mutation (S536E) in the p65 domain that enhances transcriptional activity. This is referred to as CMP8-HEA3 (p65/S536E positions in the RelA protein, which correspond to position 846 in HEA3).

In some alternatives, the HEA3 transcription factor is a CMP8-responsive HEA3 transcription factor. In some alternatives, the CMP8-responsive HEA3 transcription factor comprises at least one point mutation in the p65 domain that enhances transcriptional activity. In some alternatives, the point mutation is at position 310 of the sequence of the RelA protein which corresponds to position 621 of the wild-type HEA3 protein, and the wild-type HEA4 protein. In some alternatives, the amino acid sequence comprises a sequence set forth in SEQ ID NO: 10 (SEQ ID NO: 10; MVSK-LSQLQTELLAALLESGLSKEALIQALGEPGPYL-LAGEGPLDKGESCGGGRGEL AELPNGLGETRGSE-DETDDDGEDFTPPILKELENLSPEEAAHQKAVVETLL QEDPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWMEILMIGLV WRSMEHPGKLLFAPNLLLDRNQGKCVEGGVE- IFDMLLATSSRFRMMNLQGEEFVCL KSIILLNSGVYT-FLSSTLKSLEEKDHIHRVLDKITDTLIHLMAK-AGLTLQQQHQRLAQ LLLILSHIRHMSNKRMEH-LYSMKCKNVVPLYDLLLEMLDAHRLHAPTSRGGAS-VEE TDQSHLATAGSTSSHSLQKYYITGEAE-GFPATVEFQYLPDTDDRHRIEEKRKRTYETF QSIMKKSPFSGPTDPRPPPRRIAVPSRSSAS-VPKPAPQPYPFTSSLSTINYDEFPTMVFPS GQISQASALAPAPPQVLPQAPAPAPA-PAMVSALAQAPAPVPVLAPGPPQAVAPPAPK PTQAGEGTLSEALLQLQFDDEDLGALLGNSTD-PAVFTDLASVDNSEFQQLLNQGIPV APH-TTEPMLMEYPEAITRLVTGAQRPPDPAPAPL-GAPGLPNGLLSGDEDFSSIADMDF SALLSQISS). Some alternatives include a nucleic acid comprising a nucleic acid sequence that encodes SEQ ID NO: 10. SEQ ID NO: 10 is the sequence of CMP8-HEA3 containing one point mutation (K310Q positions in the RelA protein) in the p65 domain that enhances transcriptional activity. This is referred to as CMP8-HEA3 (p65/K310Q). Position 310 of the RelA protein is position 621 of wild-type HEA3 and wild-type HEA4.

In some alternatives, the HEA3 transcription factor is a CMP8-responsive HEA3 transcription factor. In some alternatives, the CMP8-responsive HEA3 transcription factor comprises at least two point mutations in the p65 domain that enhances transcriptional activity. In some alternatives, the point mutations are at positions 621 of the sequence of the wild-type HEA3 (The 310 position in the RelA protein corresponds to position 621 in wild type HEA3). In some alternatives, the amino acid sequence comprises a sequence set forth in SEQ ID NO: 11 (SEQ ID NO: 11; MVSK-LSQLQTELLAALLESGLSKEALIQALGEPGPYL-LAGEGPLDKGESCGGGRGEL AELPNGLGETRGSE-DETDDDGEDFTPPILKELENLSPEEAAHQKAVVETLL QEDPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWMEILMIGLV WRSMEHPGKLLFAPNLLLDRNQGKCVEGGVE-IFDMLLATSSRFRMMNLQGEEFVCL KSIILLNSGVYT-FLSSTLKSLEEKDHIHRVLDKITDTLIHLMAK-AGLTLQQQHQRLAQ LLLILSHIRHMSNKRMEH-LYSMKCKNVVPLYDLLLEMLDAHRLHAPTSRGGAS-VEE TDQSHLATAGSTSSHSLQKYYITGEAE-GFPATVEFQYLPDTDDRHRIEEKRKRTYETF QSIMKKSPFSGPTDPRPPPRRIAVPSRSSAS-VPKPAPQPYPFTSSLSTINYDEFPTMVFPS GQISQASALAPAPPQVLPQAPAPAPA-PAMVSALAQAPAPVPVLAPGPPQAVAPPAPK PTQAGEGTLSEALLQLQFDDEDLGALLGNSTD-PAVFTDLASVDNSEFQQLLNQGIPV APH-TTEPMLMEYPEAITRLVTGAQRPPDPAPAPL-GAPGLPNGLLSGDEDFESIADMDF SALLSQISS). Some alternatives include a nucleic acid comprising a nucleic acid sequence that encodes SEQ ID NO: 11. SEQ ID NO: 11 comprises the sequence of CMP8-HEA3 containing two point mutations (K310Q and S536E are positions in the RelA protein, which correspond to positions 621 (K310A of the RelA protein) and 846 (S536E of the RelA protein) in both HEA3 and HEA4) in the p65 domain that enhance transcriptional activity. This is referred to as CMP8-HEA3 (p65/S536E/K310Q positions in the RelA protein, which correspond to position 621 and 846 in both HEA3 and HEA4.

In some alternatives, the system employs a synthetic transcriptional activator which, in the presence of the drug, binds a synthetic promoter upstream of a transgene to induce expression. In some alternatives, the transcriptional activator is HEA4. HEA4 comprises an estrogen receptor ligand binding domain ((ER-LBD) and a p65 domain. In some alternatives, the HEA4 further comprises an HNF1alpha DNA binding domain. In some alternatives, the HEA4 comprises at last three point mutations in the ER-LBD that ablate binding to endogenous estrogen, and confer higher sensitivity to 4-hydroxytamoxifen, fulvestrant, and estrogen analogs compared to wild-type HEA3. In some alternatives, the positions of the three point mutations are at positions 400, 543 and 544 in HEA4 transcription factor. In some alternatives, the amino acid sequence of the HEA4 comprising the at least three mutations comprise an amino acid sequence set forth in SEQ ID NO: 4 (SEQ ID NO: 4; MVSKLSQLQTELLAALLESGLSKEALIQAL-GEPGPYLLAGEGPLDKGESCGGGRGEL AEL-PNGLGETRGSEDETDDDGEDFTPPILKELENLSPEE-AAHQKAVVETLLQEDPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPVKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKGMEHLYSMKCKNVVPLYDLL-LEAADAHRLHAPTSRGGASVE ETDQSHLATAGST-SSHSLQKYYITGEAE-GFPATVEFQYLPDTDDRHRIEEKRKRTYET FKSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFSSIADM DFSALLSQISS). Some alternatives include a nucleic acid comprising a nucleic acid sequence that encodes SEQ ID NO: 4. SEQ ID NO: 4 comprises the sequence of wild-type HEA4 containing three point mutations (G400V, M543A, L544A) in the ER-LBD that ablate binding to endogenous estrogen, and confer higher sensitivity to 4-hydroxytamoxifen, fulvestrant, and estrogen analogs compared to wild-type HEA3.

In some alternatives, the HEA4 transcription factor comprises at least one point mutation. In some alternatives, the at least one mutation is in the p65 domain and enhances transcriptional activity. In some alternatives, the at least one mutation is at position 846 of the wild type HEA4 transcription factor. In some alternatives, the amino acid sequence of the HEA4 comprising the at least one mutation comprises an amino acid sequence set forth in SEQ ID NO: 5 (SEQ ID NO: 5; MVSKLSQLQTELLAALLESGLSKEALIQAL-
GEPGPYLLAGEGPLDKGESCGGGRGEL AEL-
PNGLGETRGSEDETDDDGEDFTPPILKELENLSPEE-
AAHQKAVVETLLQEDPWR
VAKMVK-
SYLQQHNIPQREVVDTTGLNQSHLSQHLNKGTPMKT
QKRAALYTWYVR KQREVAQQFTHAGQG-
GLIEEPTGDELPTKKGRRNRFKWGPASQQILFQAY-
ERQKNP SKEERETLVEECNRAECIQRGVSP-
SQAQGLGSNLVTEVRVYNWFANRRKEEAFRHK
LSAGDMRAANLWPSPLMIKRSKKNSLALSL-
TADQMVSALLDAEPPILYSEYDPTRPF SEA-
SMMGLLTNLADRELVHMIN-
WAKRVPGFVDLTLHDQVHLLECAWLEILMIGLV
WRSMEHPVKLLFAPNLLLDRNQGKCVEGMVE-
IFDMLLATSSRFRMMNLQGEEFVC LKSIILLNSGVYT-
FLSSTLKSLEEKDHIHRVLDKITDTLIHLMAK-
AGLTLQQQHQRLA
QLLLILSHIRHMSNKGMEHLYSMKCKNVVPLYDLL-
LEAADAHRLHAPTSRGGASVE ETDQSHLATAGST-
SSHSLQKYYITGEAE-
GFPATVEFQYLPDTDDRHRIEEKRKRTYET
FKSIMKKSPFSGPTDPRPPPRRIAVPSRSSAS-
VPKPAPQPYPFTSSLSTINYDEFPTMVFP SGQ-
ISQASALAPAPPQVLPQAPAPAPA-
PAMVSALAQAPAPVPVLAPGPPQAVAPPAP
KPTQAGEGTLSEALLQLQFDDEDLGALLGNSTD-
PAVFTDLASVDNSEFQQLLNQGIP VAPH-
TTEPMLMEYPEAITRLVTGAQRPPDPAPAPL-
GAPGLPNGLLSGDEDFESIADM DFSALLSQISS). Some alternatives include a nucleic acid comprising a nucleic acid sequence that encodes SEQ ID NO: 5. SEQ ID NO: 5 comprises the sequence of HEA4 containing one point mutation (S536E positions in the RelA protein) in the p65 domain that enhances transcriptional activity. This is referred to as HEA4 (p65/S536E). The mutation S536E refers to the mutation at position 536 of WT RelA. This position translates to position 846 of HEA3. The mutation K310Q refers to the mutation at position 310 of WT RelA. This position translates to position 621 of HEA3.

In some alternatives, the HEA4 transcription factor comprises at least one point mutation. In some alternatives, the at least one mutation is in the p65 domain and enhances transcriptional activity. In some alternatives, the at least one mutation is at position 621 of the HEA4 transcription factor. In some alternatives, the amino acid sequence of the HEA4 comprising the at least one mutation comprises an amino acid sequence set forth in SEQ ID NO: 6 (SEQ ID NO: 6;
MVSKLSQLQTELLAALLESGLSKEALIQAL-
GEPGPYLLAGEGPLDKGESCGGGRGEL AEL-
PNGLGETRGSEDETDDDGEDFTPPILKELENLSPEE-
AAHQKAVVETLLQEDPWR
VAKMVK-
SYLQQHNIPQREVVDTTGLNQSHLSQHLNKGTPMKT
QKRAALYTWYVR KQREVAQQFTHAGQG-
GLIEEPTGDELPTKKGRRNRFKWGPASQQILFQAY-
ERQKNP SKEERETLVEECNRAECIQRGVSP-
SQAQGLGSNLVTEVRVYNWFANRRKEEAFRHK
LSAGDMRAANLWPSPLMIKRSKKNSLALSL-
TADQMVSALLDAEPPILYSEYDPTRPF SEA-
SMMGLLTNLADRELVHMIN-
WAKRVPGFVDLTLHDQVHLLECAWLEILMIGLV
WRSMEHPVKLLFAPNLLLDRNQGKCVEGMVE-
IFDMLLATSSRFRMMNLQGEEFVC LKSIILLNSGVYT-
FLSSTLKSLEEKDHIHRVLDKITDTLIHLMAK-
AGLTLQQQHQRLA
QLLLILSHIRHMSNKGMEHLYSMKCKNVVPLYDLL-
LEAADAHRLHAPTSRGGASVE ETDQSHLATAGST-
SSHSLQKYYITGEAE-
GFPATVEFQYLPDTDDRHRIEEKRKRTYET
FQSSIMKKSPFSGPTDPRPPPRRIAVPSRSSAS-
VPKPAPQPYPFTSSLSTINYDEFPTMVFP SGQ-
ISQASALAPAPPQVLPQAPAPAPA-
PAMVSALAQAPAPVPVLAPGPPQAVAPPAP
KPTQAGEGTLSEALLQLQFDDEDLGALLGNSTD-
PAVFTDLASVDNSEFQQLLNQGIP VAPH-
TTEPMLMEYPEAITRLVTGAQRPPDPAPAPL-
GAPGLPNGLLSGDEDFSSIADM DFSALLSQISS). Some alternatives include a nucleic acid comprising a nucleic acid sequence that encodes SEQ ID NO: 6. SEQ ID NO: 6 comprises the sequence of HEA4 containing one point mutation (K310Q positions in the RelA protein) in the p65 domain that enhances transcriptional activity. This is referred to as HEA4 (p65/K310Q). K310Q refers to the position in RelA, which corresponds to position 621 in WT HEA4.

In some alternatives, the HEA4 transcription factor comprises at least two point mutations. In some alternatives, the at least two mutations are in the p65 domain and enhances transcriptional activity. In some alternatives, at least two mutations are at positions 846 and 621 of the HEA4 transcription factor. In some alternatives, the amino acid sequence of the HEA4 comprising the at least two mutations comprise an amino acid sequence set forth in SEQ ID NO: 7 (SEQ ID NO: 7; MVSKLSQLQTELLAALLESGL-
SKEALIQALGEPGPYLLAGEGPLDKGESCGGGRGEL
AELPNGLGETRGSEDETDDDGEDFTPPILKELENL-
SPEEAAHQKAVVETLLQEDPWR VAKMVK-
SYLQQHNIPQREVVDTTGLNQSHLSQHLNKGTPMKT
QKRAALYTWYVR KQREVAQQFTHAGQG-
GLIEEPTGDELPTKKGRRNRFKWGPASQQILFQAY-
ERQKNP SKEERETLVEECNRAECIQRGVSP-
SQAQGLGSNLVTEVRVYNWFANRRKEEAFRHK
LSAGDMRAANLWPSPLMIKRSKKNSLALSL-
TADQMVSALLDAEPPILYSEYDPTRPF SEA-
SMMGLLTNLADRELVHMIN-
WAKRVPGFVDLTLHDQVHLLECAWLEILMIGLV
WRSMEHPVKLLFAPNLLLDRNQGKCVEGMVE-
IFDMLLATSSRFRMMNLQGEEFVC LKSIILLNSGVYT-
FLSSTLKSLEEKDHIHRVLDKITDTLIHLMAK-
AGLTLQQQHQRLA
QLLLILSHIRHMSNKGMEHLYSMKCKNVVPLYDLL-
LEAADAHRLHAPTSRGGASVE ETDQSHLATAGST-
SSHSLQKYYITGEAE-
GFPATVEFQYLPDTDDRHRIEEKRKRTYET
FQSSIMKKSPFSGPTDPRPPPRRIAVPSRSSAS-
VPKPAPQPYPFTSSLSTINYDEFPTMVFP SGQ-
ISQASALAPAPPQVLPQAPAPAPA-
PAMVSALAQAPAPVPVLAPGPPQAVAPPAP
KPTQAGEGTLSEALLQLQFDDEDLGALLGNSTD-
PAVFTDLASVDNSEFQQLLNQGIP VAPH-
TTEPMLMEYPEAITRLVTGAQRPPDPAPAPL-
GAPGLPNGLLSGDEDFESIADM DFSALLSQISS). Some alternatives include a nucleic acid comprising a nucleic acid sequence that encodes SEQ ID NO: 7. SEQ ID NO: 7 comprises the sequence of HEA4 containing two point mutations (K310Q and S536E, positions in the RelA protein) in the p65 domain that enhance transcriptional activity. This is referred to as HEA4 (p65/S536E/K310Q positions in the RelA protein). K310Q in RelA corresponds to position 621 in HEA4; S536E corresponds to position 846 in HEA4.

Additional chimeric transcription factors are also contemplated herein. In some alternatives, the HEA4 transcription factor comprises HNF1alpha, an ER-LBD that is the same as HEA4, and a VP64 activation domain instead of the p65 activation domain nucleotide sequence (referred herein as HEA4(VP64), and is encoded by SEQ ID NO: 24 (atggtgtc-caagctgtcccagctgcagacagaactgctggcagcactgctggaaagcggcct-gagcaaagaggccctgattcagg cactcggcgaacctggacct-tatctgctcgctggcgaaggccctctggataagggcgagagctgtggcggaggaa gaggagagct ggccgagctgcctaacggcctgggcga-gacaagaggcagcgaggacgagacagacgacgacggcgaggactt-cacccccccc atcctgaaagagctggaaaacctgagccccgaggaagccgcc-caccagaaagccgtggtggagacactgctgcaggaagatccc tggcgggtcgccaagatggtcaagagctacctgcagcagcacaa-catcccccagcgggaggtggtggacaccaccggcctgaac cagagccacct-gagccagcacctgaacaagggcacccccat-gaaaacccagaagagagccgccctgtacacttggtacgtgcgg aagcagagagaggtggcccagcagtttacacacgccggccagggcggcct-gatcgaggaacctaccggcgacgagctgcccac caagaagggcagacg-gaaccggtttaagtggggccctgcatctcagcagatcctgttccaggcc-tacgagcggcagaagaacccc agcaaagaggaacgggagacactggtggaagagtgcaaccgggccgagtg-catccagagaggcgtgagcccttctcaggctcag ggcctcggcagcaatctggt-caccgaagtgcgggtgtacaattggttcgccaaccggcggaaagag-gaagccttccggcacaagct gtctgctggcgatatgagagccgccaacctgtggcccagcccccctgatgat-caagcggagcaagaagaacagcctggccctgagc ctgaccgccgatca-gatggtgtccgctctgctggacgccgagccccctatcctgta-cagcgagtacgaccccaccagacccttcagc gaggccagcatgatgggcctgctgaccaacctggccgaccgggagctggtgca-catgatcaactgggccaagcgggtgcccggc ttcgtggacctgaccctgcacgaccaggtccacctgctggaatgtgcctggctg-gaaatcctgatgatcggcctcgtgtggagaagc atggaacaccccgt-gaagctgctgttcgcccccaacctgctcctggaccggaaccagg-gaaagtgcgtggagggcatggtggaga tcttcgacatgctgctggccacctccagccggttccggatgat-gaacctgcagggcgaggaattcgtgtgcctgaagtccatcatcct gct-gaacagcggcgtgtacaccttcctgtcatccaccctgaagtccctg-gaagagaaggaccacatccaccgggtgctggacaaga tcaccgacaccctgatccacctgatggc-caaggctggcctgacactccagcagcagcaccagagactggcccagctgctgct-gatc ctgagccacatccggcacatgagcaacaagggaatggaacacctgta-cagcatgaagtgcaagaacgtggtgcccctgtacgacct gctgctcgaggctgccgatgcccacagactgcacgcccctacaagcagaggcg-gagccagcgtggaggaaaccgaccagtctca cctggc-caccgccggcagcacaagcagccacagcctgcagaagtactacat-caccggcgaggccgagggattccctgccaccgt ggacgctctggacgacttcgaccttgacatgttgggttccgacgcgctggatgat-tttgatttggacatgctgggaagcgacgcactgg atgactttgatctcga-tatgctcggctctgacgcattggacgacttcgacttggatatgctgggttct; HEA4 (VP64)). In some alternatives, HEA4(VP64) comprises an amino acid sequence set forth in SEQ ID NO: (MVSKLSQLQTELLAALLESGLSKEALIQAL-GEPGPYLLAGEGPLDKGESCGGGRGEL AEL-PNGLGETRGSEDETDDDGEDFTPPILKELENLSPEE-AAHQKAVVETLLQEDPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPVKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKGMEHLYSMKCKNVVPLYDLL-LEAADAHRLHAPTSRGGASVE ETDQSHLATAGST-SSHSLQKYYITGEAEGFPATVDALDDFDLDMLGS-DALDDFDLD MLGSDALDDFDLDMLGSDALDDFDLDMLGS). Some alternatives include a nucleic acid sequence that encodes the amino acid sequence set forth in SEQ ID NO: 25. In some alternatives herein, the chimeric transcription factor is HEA4(VP64), and is encoded by SEQ ID NO: 24. In some alternatives, HEA4(VP64) comprises an amino acid sequence set forth in SEQ ID NO: 25.

In some alternatives, HEA4 comprises HNF1alpha, an ER-LBD that is the same as HEA4, and an HSF1 activation domain instead of a p65 activation domain. HEA4 (HSF-1) comprises HNF1alpha, ER-LBD that is the same as HEA4, and HSF1 activation domain instead of a p65 activation domain, and is encoded by SEQ ID NO: 26 (atggtgtc-caagctgtcccagctgcagacagaactgctggcagcactgctggaaagcggcct-gagcaaagaggccctgattcagg cactcggcgaacctggacct-tatctgctcgctggcgaaggccctctggataagggcgagagctgtggcggagga agaggagagct ggccgagctgcctaacggcctgggcga-gacaagaggcagcgaggacgagacagacgacgacggcgaggactt-cacccccccc atcctgaaagagctggaaaacctgagccccgaggaagccgcc-caccagaaagccgtggtggagacactgctgcaggaagatccc tggcgggtcgccaagatggtcaagagctacctgcagcagcacaa-catcccccagcgggaggtggtggacaccaccggcctgaac cagagccacct-gagccagcacctgaacaagggcacccccat-gaaaacccagaagagagccgccctgtacacttggtacgtgcgg aagcagagagaggtggcccagcagtttacacacgccggccagggcggcct-gatcgaggaacctaccggcgacgagctgcccac caagaagggcagacg-gaaccggtttaagtggggccctgcatctcagcagatcctgttccaggcc-tacgagcggcagaagaacccc agcaaagaggaacgggagacactggtggaagagtgcaaccgggccgagtg-catccagagaggcgtgagcccttctcaggctcag ggcctcggcagcaatctggt-caccgaagtgcgggtgtacaattggttcgccaaccggcggaaagag-gaagccttccggcacaagct gtctgctggcgatatgagagccgccaacctgtggcccagcccccctgatgat-caagcggagcaagaagaacagcctggccctgagc ctgaccgccgatca-gatggtgtccgctctgctggacgccgagccccctatcctgta-cagcgagtacgaccccaccagacccttcagc gaggccagcatgatgggcctgctgaccaacctggccgaccgggagctggtgca-catgatcaactgggccaagcgggtgcccggc ttcgtggacctgaccctgcacgaccaggtccacctgctggaatgtgcctggctg-gaaatcctgatgatcggcctcgtgtggagaagc atggaacaccccgt-gaagctgctgttcgcccccaacctgctcctggaccggaaccagg-gaaagtgcgtggagggcatggtggaga tcttcgacatgctgctggccacctccagccggttccggatgat-gaacctgcagggcgaggaattcgtgtgcctgaagtccatcatcct gct-gaacagcggcgtgtacaccttcctgtcatccaccctgaagtccctg-gaagagaaggaccacatccaccgggtgctggacaaga tcaccgacaccctgatccacctgatggc-caaggctggcctgacactccagcagcagcaccagagactggcccagctgctgct-gatc ctgagccacatccggcacatgagcaacaagggaatggaacacctgta-cagcatgaagtgcaagaacgtggtgcccctgtacgacct gctgctcgaggctgccgatgcccacagactgcacgcccctacaagcagaggcg-gagccagcgtggaggaaaccgaccagtctca cctggc-caccgccggcagcacaagcagccacagcctgcagaagtactacat-caccggcgaggccgagggattccctgccaccgt ggaaaagtgcctcagcgtagcctgcctggacaagaatgagctcagtgaccacttg-gatgctatggactccaacctggataacctgca gaccatgctgagcagc-cacggcttcagcgtggacaccagtgccctgctggacctgttcagcccctcggtgac cgtgcccgacatga gcctgcctgaccttgacagcagcctggccagtatccaagagctcctgtctccccaggagccccccaggcctcccgaggcagagaac agcagcccggattcagggaagcagctggtgcacta- cacagcgcagccgctgttcctgctggaccccggctccgtggacaccggga gcaacgacctgccggtgctgtttgagctgggagagggctcc- tacttctccgaaggggacggcttcgccgaggaccccaccatctcc ctgctgacaggctcggagcctcccaaagccaaggaccccactgtctcc). In some alternatives, herein the chimeric transcription factor is HEA4(HSF-1) and is encoded by SEQ ID NO: 26. In some alternatives, herein the chimeric transcription factor is HEA4(HSF-1) and comprises an amino acid sequence set forth in SEQ ID NO: 27 (MVSKLSQLQTELLAALLESGL- SKEALIQALGEPGPYLLAGEGPLDKGESCGGGRGEL AELPNGLGETRGSEDETDDDGEDFTPPILKELENL- SPEEAAHQKAVVETLLQEDPWR VAKMVK- SYLQQHNIPQREVVDTTGLNQSHLSQHLNKGTPMKT QKRAALYTWYVR KQREVAQQFTHAGQG- GLIEEPTGDELPTKKGRRNRFKWGPASQQILFQAY- ERQKNP SKEERETLVEECNRAECIQRGVSP- SQAQGLGSNLVTEVRVYNWFANRRKEEAFRHK LSAGDMRAANLWPSPLMIKRSKKNSLALSL- TADQMVSALLDAEPPILYSEYDPTRPF SEA- SMMGLLTNLADRELVHMIN- WAKRVPGFVDLTLHDQVHLLECAWLEILMIGLV WRSMEHPVKLLFAPNLLLDRNQGKCVEGMVE- IFDMLLATSSRFRMMNLQGEEFVC LKSIILLNSGVYT- FLSSTLKSLEEKDHIHRVLDKITDTLIHLMAK- AGLTLQQQHQRLA QLLLILSHIRHMSNKGMEHLYSMKCKNVVPLYDLL- LEAADAHRLHAPTSRGGASVE ETDQSHLATAGST- SSHSLQKYYITGEAEGFPATVEKCLSVACLDK- NELSDHLDAMDS NLDNLQTMLSSHGFSVDTSALLDLF- SPSVTVPDMSLPDLDSSLASIQELLSPQEPPRPP EAE- NSSPDSGKQLVHYTAQPLFLLDPGSVDTG- SNDLPVLFELGEGSYFSEGDGFAEDP TISLLTGSEPPKAKDPTVS). Some alternatives include a nucleic acid comprising a nucleic acid sequence that encodes SEQ ID NO: 27.

In some alternatives herein the chimeric transcription factor is HEA4(Arnt). HEA4(Arnt) comprises HNF1alpha, ER-LBD that is the same as HEA4, and an Arnt activation domain instead of an p65 activation domain amino acid sequence. In some alternatives, HEA4(Arnt) is encoded by a sequence set forth in SEQ ID NO: 28 (atggtgtc- caagctgtcccagctgcagacagaactgctggcagcactgctggaaagcggcct- gagcaaagaggccctgattcagg cactcggcgaacctggacct- tatctgctcgctggcgaaggccctctggataagggcgagagctgtggcggaggaa gaggagagct ggccgagctgcctaacggcctgggcga- gacaagaggcagcgaggacgagacagacgacgacggcgaggactt- cacccccccc atcctgaaagagctggaaaacctgagccccgaggaagccgcc- caccagaaagccgtggtggagacactgctgcaggaagatccc tggcgggtcgccaagatggtcaagagctacctgcagcagcacaa- catcccccagcgggaggtggtggacaccaccggcctgaac cagagccacct- gagccagcacctgaacaagggcacccccat- gaaaacccagaagagagccgccctgtacacttggtacgtgcgg aagcagagagaggtggcccagcagtttacacacgccggccagggcggcct- gatcgaggaacctaccggcgacgagctgcccac caagaagggcagacg- gaaccggtttaagtggggccctgcatctcagcagatcctgttccaggcc- tacgagcggcagaagaacccc agcaaagaggaacgggagacactggtggaagagtgcaaccgggccgagtg- catccagagaggcgtgagcccttctcaggctcag ggcctcggcagcaatctggt- caccgaagtgcgggtgtacaattggttcgccaaccggcggaaagag- gaagccttccggcacaagct gtctgctggcgatatgagagccgccaacctgtggcccagcccccctgatgat- caagcggagcaagaagaacagcctggccctgagc ctgaccgccgatca- gatggtgtccgctctgctggacgccgagccccctatcctgta- cagcgagtacgaccccaccagacccttcagc gaggccagcatgatgggcctgctgaccaacctggccgaccgggagctggtgca- catgatcaactgggccaagcgggtgcccggc ttcgtggacctgaccctgcacgaccaggtccacctgctggaatgtgcctggctg- gaaatcctgatgatcggcctcgtgtggagaagc atggaacaccccgt- gaagctgctgttcgcccccaacctgctcctggaccggaaccagg- gaaagtgcgtggagggcatggtggaga tcttcgacatgctgctggccacctccagccggttccggatgat- gaacctgcagggcgaggaattcgtgtgcctgaagtccatcatcct gct- gaacagcggcgtgtacaccttcctgtcatccaccctgaagtccctg- gaagagaaggaccacatccaccgggtgctggacaaga tcaccgacaccctgatccacctgatggc- caaggctggcctgacactccagcagcagcaccagagactggcccagctgctgct- gatc ctgagccacatccggcacatgagcaacaagggaatggaacacctgta- cagcatgaagtgcaagaacgtggtgcccctgtacgacct gctgctcgaggctgccgatgcccacagactgcacgcccctacaagcagaggcg- gagccagcgtggaggaaaccgaccagtctca cctggc- caccgccggcagcacaagcagccacagcctgcagaagtactacat- caccggcgaggccgagggattccctgccaccgt gcctgaggtcttccaggagatgctgtccatgctgggagatcagagcaacagcta- caacaatgaagaattccctgatctaactatgtttc ccccttttcagaa). In some alternatives, HEA4(Arnt) comprises an amino acid sequence set forth in SEQ ID NO: 29 (MVSKLSQLQTEL- LAALLESGLSKEALIQALGEPGPYLLAGEG- PLDKGESCGGGRGEL AELPNGLGETRGSEDE- TDDDGEDFTPPILKELENLSPEEAAHQKAVVETLLQE DPWR VAKMVK- SYLQQHNIPQREVVDTTGLNQSHLSQHLNKGTPMKT QKRAALYTWYVR KQREVAQQFTHAGQG- GLIEEPTGDELPTKKGRRNRFKWGPASQQILFQAY- ERQKNP SKEERETLVEECNRAECIQRGVSP- SQAQGLGSNLVTEVRVYNWFANRRKEEAFRHK LSAGDMRAANLWPSPLMIKRSKKNSLALSL- TADQMVSALLDAEPPILYSEYDPTRPF SEA- SMMGLLTNLADRELVHMIN- WAKRVPGFVDLTLHDQVHLLECAWLEILMIGLV WRSMEHPVKLLFAPNLLLDRNQGKCVEGMVE- IFDMLLATSSRFRMMNLQGEEFVC LKSIILLNSGVYT- FLSSTLKSLEEKDHIHRVLDKITDTLIHLMAK- AGLTLQQQHQRLA QLLLILSHIRHMSNKGMEHLYSMKCKNVVPLYDLL- LEAADAHRLHAPTSRGGASVE ETDQSHLATAGST- SSHSLQKYYITGEAEGFPATVPE- VFQEMLSMLGDQSNSYNNEEF PDLTMFPPFSE). Some alternatives include a nucleic acid comprising a nucleic acid sequence that encodes SEQ ID NO: 29.

"Selectable marker cassette," has its plain and ordinary meaning when read in light of the specification, and may be used, for example, to describe a gene that encodes a "selectable marker" and is introduced into a vector or a cell that confers a trait for artificial selection. A selectable marker cassette can be a screenable marker to allow a researcher to distinguish between wanted and unwanted cells, or to enrich for a specific cell type. In some alternatives, a gene delivery polynucleotide is provided. In some alternatives, the gene delivery polynucleotide comprises a selectable marker cassette. The selectable marker cassette as described herein, encodes a protein (the selectable marker) that is used for selecting or tracking a protein or cell that has a protein of interest. In the alternatives described herein, the fusion protein provided herein can comprise a marker sequence that can be selected in experiments, such as flow cytometry. In some alternatives, the marker is the protein Her2tG.

In some alternatives, the selectable marker is encoded by an EGFRt nucleotide sequence, wherein the selectable maker is encoded by a sequence set forth in SEQ ID NO: 30

(atgcttctcctggtgacaagccttctgctctgtgagttaccacacccagcattcctcctgatcccacgcaaagtgtgtaacggaataggt attggtgaatttaaagactcactctccataaatgctacgaatattaaacacttcaaaaactgcacctccatcagtggcgatctccacatcct gccggtggcatttaggggtgactccttcacacatactcctcctctggatccacaggaactggatattctgaaaaccgtaaaggaaatca cagggtttttgctgattcaggcttggcctgaaaacaggacggacctccatgcctttgagaacctagaaatcatacgcggcaggaccaa gcaacatggtcagttttctcttgcagtcgtcagcctgaacataacatccttgggattacgctccctcaaggagataagtgatggagatgt gataatttcaggaaacaaaaatttgtgctatgcaaatacaataaactggaaaaaactgtttgggacctccggtcagaaaaccaaaattat aagcaacagaggtgaaaacagctgcaaggccacaggccaggtctgccatgccttgtgctcccccgagggctgctggggcccgga gcccagggactgcgtctcttgccggaatgtcagccgaggcagggaatgcgtggacaagtgcaaccttctggagggtgagccaagg gagtttgtggagaactctgagtgcatacagtgccacccagagtgcctgcctcaggccatgaacatcacctgcacaggacggggacc agacaactgtatccagtgtgcccactacattgacggcccccactgcgtcaagacctgcccggcaggagtcatgggagaaaacaaca ccctggtctggaagtacgcagacgccggccatgtgtgccacctgtgccatccaaactgcacctacggatgcactgggccaggtcttg aaggctgtccaacgaatgggcctaagatcccgtccatcgccactgggatggtgggggccctcctcttgctgctggtggtggccctgg ggatcggcctcttcatgtga). In some alternatives, the selectable marker comprises an EGFRt amino acid sequence set forth in SEQ ID NO: 31 (MLLLVTSLLLCELPHPAFLLIPRKVCNGIGIGEFKDSLSINATNIKHFKNCTSISGDLHI LPVAFRGDSFTHTPPLDPQELDILKTVKEITGFLLIQAWPENRTDLHAFENLEIIRGRT KQHGQFSLAVVSLNITSLGLRSLKEISDGDVIISGNKNLCYANTINWKKLFGTSGQKT KIISNRGENSCKATGQVCHALCSPEGCWGPEPRDCVSCRNVSRGRECVDKCNLLEGE PREFVENSECIQCHPECLPQAMNITCTGRGPDNCIQCAHYIDGPHCVKTCPAGVMGE NNTLVWKYADAGHVCHLCHPNCTYGCTGPGLEGCPTNGPKIPSIATGMVGALLLLL VVALGIGLFM). Some alternatives include a nucleic acid comprising a nucleic acid sequence that encodes SEQ ID NO: 31.

In some alternatives, the selectable marker is encoded by a Her2t nucleotide sequence, set forth in SEQ ID NO: 32 (atgcttctcctggtgacaagccttctgctctgtgagttaccacacccagcattcctcctgatcccatgccaccctgagtgtcagcccca gaatggctcagtgacctgttttggaccggaggctgaccagtgtgtggcctgtgcccactataaggaccctcccttctgcgtggcccgct gccccagcggtgtgaaacctgacctctcctacatgcccatctggaagtttccagatgaggagggcgcatgccagccttgccccatca actgcacccactcctgtgtggacctggatgacaagggctgccccgccgagcagagagccagccctctgacgtccatcatctctgcg gtggttggcattctgctggtcgtggtcttggggggtggtctttgggatcctcatctga). In some alternatives, the selectable marker comprises the Her2t amino acid sequence set forth in SEQ ID NO: 33 (MLLLVTSLLLCELPHPAFLLIPCHPECQPQNGSVTCFGPEADQCVACAHYKDPPFCV ARCPSGVKPDLSYMPIWKFPDEEGACQPCPINCTHSCVDLDDKGCPAEQRASPLTSII SAVVGILLVVVLGVVFGILI). Some alternatives include a nucleic acid comprising a nucleic acid sequence that encodes SEQ ID NO: 33.

In some alternatives, the selectable marker is encoded by the Her2tG nucleotide sequence set forth in SEQ ID NO: 34 (atgcttctcctggtgacaagccttctgctctgtgagttaccacacccagcattcctcctgatcccatgccaccctgagtgtcagccccag aatggctcagtgacctgttttggaccggaggctgaccagtgtgtggcctgtgcccactataaggaccctcccttctgcgtggcccgctg ccccagcggtgtgaaacctgacctctcctacatgcccatctggaagtttccagatgaggagggcgcatgccagccttgccccatcaa ctgcacccactcctgtgtggacctggatgacaagggctgccccgccgagcagagagccagcccgttaacgggtggaggcagcgg aggtggctccatcatctctgcggtggttggcattctgctggtcgtggtcttgggggtggtctttgggatcctcatctga). In some alternatives, the selectable marker comprises the Her2tG amino acid sequence, set forth in SEQ ID NO: 35 (MLLLVTSLLLCELPHPAFLLIPCHPECQPQNGSVTCFGPEADQCVACAHYKDPPFCV ARCPSGVKPDLSYMPIWKFPDEEGACQPCPINCTHSCVDLDDKGCPAEQRASPLTGG GSGGGSIISAVVGILLVVVLGVVFGILI). Some alternatives include a nucleic acid comprising a nucleic acid sequence that encodes SEQ ID NO: 35.

In some alternatives, the selectable marker is encoded by the CD19t nucleotide sequence, set forth in SEQ ID NO: 36 (atgccacctcctcgcctcctcttcttcctcctcttcctcacccccatggaagtcaggcccgaggaacctctagtggtgaaggtggaag agggagataacgctgtgctgcagtgcctcaaggggacctcagatggcccactcagcagctgacctggtctcgggagtccccgctt aaacccttcttaaaactcagcctggggctgccaggcctgggaatccacatgaggcccctggccatctggcttttcatcttcaacgtctct caacagatgggggggcttctacctgtgccagccggggcccccctctgagaaggcctggcagcctggctggacagtcaatgtggagg gcagcggggagctgttccggtggaatgtttcggacctaggtggcctgggctgtggcctgaagaacaggtcctcagagggccccagc tccccttccgggaagctcatgagccccaagctgtatgtgtgggccaaagaccgccctgagatctgggagggaga gcctccgtgtgtc ccaccgagggacagcctgaaccagagcctcagccaggacctcaccatggcccctggctccacactctggctgtcctgtggggtacc ccctgactctgtgtccaggggccccctctcctggacccatgtgcacccaaggggcctaagtcattgctgagcctagagctgaagga cgatcgcccggccagagatatgtgggtaatggagacgggtctgttgttgccccgggccacagctcaagacgctggaaagtattattgt caccgtggcaacctgaccatgtcattccacctggagatcactgctcggccagtactatggcactggctgctgaggactggtggctgga aggtctcagctgtgactttggcttatctgatcttctgcctgtgttcccttgtgggcattcttcatcttcaaagagccctggtcctgaggagga aagataa). In some alternatives, the selectable marker comprises the CD19t amino acid sequence, set forth in SEQ ID NO: 37 (MPPPRLLFFLLFLTPMEVRPEEPLVVKVEEGDNAVLQCLKGTSDGPTQQLTWSRESP LKPFLKLSLGLPGLGIHMRPLAIWLFIFNVSQQMGGFYLC QPGPPSEKAWQPGWTVN VEGSGELFRWNVSDLGGLGCGLKNRSSEGPSSPSGKLMSPKLYVWAKDRPEIWEGE PPCVPPRDSLNQSLSQDLTMAPGSTLWLSCGVPPDSVSRGPLSWTHVHPKGPKSLLS LELKDDRPARDMWVMETGLLLPRATAQDAGKYYCHRGNLTMSFHLEITARPVLWH WLLRTGGWKVSAVTLAYLIFCLCSLVGILHLQRALVLRRKR). Some alternatives include a nucleic acid comprising a nucleic acid sequence that encodes SEQ ID NO: 37.

In some alternatives, the selectable marker is encoded by the DHFRdm nucleotide sequence set forth in SEQ ID NO: 38 (atggttggttcgctaaactgcatcgtcgctgtgtcccagaacatgggcatcggcaagaacggggacttcccctggccaccgctcag gaatgaatccagatatttccagagaatgaccacaacctcttcagtagaaggtaaacagaatctggtgattatgggtaagaagacctggt tctccattcctgagaagaatcgacctttaaagggtagaattaattagttctcagcagagaactcaaggaacctccacaaggagctcattt tctttccagaagtctagatgatgccttaaaacttactgaacaaccagaattagcaaataaagtagacatggtctggatagttggtggcagt tctgtttataaggaagccatgaatcacccaggccatcttaaactatttgtgacaaggatcatgcaagactttgaaagtgacacgtttttcc agaaattgatttgggagaaatataaacttctgccagaatacccaggtgttctctctgatgtccaggaggagaaaggcattaagtacaaattt gaagtatatgagaagaatgat). In some alternatives, the selectable marker comprises the DHFRdm amino acid sequence, set forth in SEQ ID NO: 39 (VGSLNCIVAVSQNMGIGKNGDFPWP-PLRNESRYFQRMTTTSSVEGKQNLVIMGKKT WFSI-PEKNRPLKGRINLVLSRELKEPPQGAHFLSRSLD-DALKLTEQPELANKVDMVW IVGGSSVYKEAMNHPGHLKLFVTRIMQDFESDTFF-PEIDLEKYKLLPEYPGVLSDVQE EKGIKYKFE-VYEKND). Some alternatives include a nucleic acid comprising a nucleic acid sequence that encodes SEQ ID NO: 39.

In some alternatives, a system for inducible expression of a chimeric antigen receptor is provided, wherein the system comprises a) a first nucleic acid comprising a first promoter inducible by a drug, wherein the first nucleic acid is operably linked to a first polynucleotide that encodes a chimeric antigen receptor comprising a ligand binding domain specific for a ligand selected from a tumor specific molecule, viral specific molecule, or any other selected molecule expressed on a target cell population, wherein the ligand can elicit recognition, modulation, inhibition, and/or elimination by a lymphocyte; a polynucleotide coding for a polypeptide spacer, wherein the spacer is preferably optimized; a polynucleotide coding for a transmembrane domain; and a polynucleotide coding for an intracellular signaling domain; and b) a second nucleic acid comprising a second promoter operably linked to nucleic acid coding for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives, the drug is tamoxifen and/or its metabolites. In some alternatives, the second promoter is constitutive or inducible. In some alternatives, the first promoter comprises a nucleic acid sequence of SEQ ID NO: 23 (SEQ ID NO: 23; tagttaataatctacaatagttaataatc-tacaatagttaataatctacaatagttaataatctacaatagttaataatctacaatagt-taataat ctacaatagttaataatctacaagagctcagggtatataatg). In some alternatives, the second promoter is a constitutive promoter. In some alternatives, the second promoter is the EF1αp. In some alternatives, the transcriptional activator comprises an amino acid sequence set forth in SEQ ID NO's: 1, 2, 3, 4, 5, 6, 7, 8, 9, 10 or 11. In some alternatives, the first nucleic acid further comprises a first vector and the second nucleic acid further comprises a second vector. In some alternatives, both vectors are packaged in a viral vector. In some alternatives, the viral vector is a lentivirus. In some alternatives, the first and second nucleic acid comprise a vector. In some alternatives, the first nucleic acid further comprises a nucleic acid sequence coding for a selectable marker. In some alternatives, the second nucleic acid further comprises a nucleic acid coding for a selectable marker. In some alternatives, a system for inducible expression is provided, wherein the system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity and b) a second nucleic acid comprising a second promoter, wherein the second nucleic acid is operably linked to third nucleic acid that encodes a transcriptional activator for the first promoter inducible by drug and wherein the system is configured to respond to an amount of the drug that is less than a comparable system utilizing a wild type HEA3 chimeric transcription factor or a wild type HEA4 chimeric transcription factor. In some alternatives, the transcriptional activator is HEA3 or HEA4. In some alternatives, HEA3 is a variant of a wild type HEA3 transcription factor. In some alternatives, HEA4 is a variant of a wild type HEA4 transcription factor. In some alternatives, HEA3 comprises an estrogen receptor ligand binding domain (ER-LBD) and a RelA (p65) transactivation domain, wherein the estrogen receptor ligand binding domain comprises mutations that allow selective binding to the drug ligand. In some alternatives, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives, HEA4 comprises an estrogen receptor ligand binding domain (ER-LBD) and a RelA (p65) transactivation domain, wherein the estrogen receptor ligand binding domain comprises at least three mutations that allow selective binding to the drug ligand, wherein HEA4 comprises an estrogen receptor ligand binding domain. In some alternatives, HEA4 comprises an estrogen receptor ligand binding domain (ER-LBD) and a RelA (p65) transactivation domain, wherein the RelA (p65) transactivation domain comprises at least one mutation that enhances transcriptional activity in response to the drug ligand. Mutations in the ER-LBD affect drug to receptor binding. In some alternatives, the HEA3 further comprises an HNF1alpha DNA binding domain. In some alternatives, HEA4 comprises an estrogen receptor ligand binding domain (ER-LBD) and a RelA (p65) transactivation domain, wherein the estrogen receptor ligand binding domain comprises at least one mutation that allows selective binding to the drug ligand, wherein HEA4 comprises an estrogen receptor ligand binding domain, wherein the estrogen receptor ligand binding domain comprises mutations that allow selective binding to the drug ligand. In some alternatives, the HEA4 further comprises an HNF1alpha DNA binding domain. In some alternatives, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives, HEA4 comprises three mutations in the ER-LBD that enhance sensitivity to drug compared to HEA3. In some alternatives, the variant of the HEA3 or HEA4 chimeric transcription factor comprises p65 phosphomimetic and/or acetylmimetic amino acid substitutions that enhance transcriptional activity in response to the drug ligand. In some alternatives, the variant of a wild type HEA3 transcription factor comprises at least one or more amino acid sequences set forth in SEQ ID Nos: 1-3, 8-11 and/or 121. In some alternatives, the wild type HEA3 transcription factor comprises an amino acid sequence set forth in SEQ ID No: 1 (MVSKLSQLQTELLAALLESGL-SKEALIQALGEPGPYLLAGEGPLDKGESCGGGRGEL AELPNGLGETRGSEDETDDDGEDFTPPILKELENL-SPEEAAHQKAVVETLLQEDPWR VAKMVK-SYLQQHNIPQREVVDTTGLNQSHLSQHLNKGTPMK-TQKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEASMMGLLTNLADRELVHMIN- WAKRVPGFVDLTLHDQVHLLECAWLEILMIGLV WRSMEHPGKLLFAPNLLLDRNQGKCVEGMVE- IFDMLLATSSRFRMMNLQGEEFVC LKSIILLNSGVYT- FLSSTLKSLEEKDHIHRVLDKITDTLIHLMAK- AGLTLQQQHQRLA QLLLILSHIRHMSNKRMEH- LYSMKCKNVVPLYDLLLEMLDAHRLHAPTSRG- GASVE ETDQSHLATAGSTSSHSLQKYYITGEAE- GFPATVEFQYLPDTDDRHRIEEKRKRTYET FKSIMKKSPFSGPTDPRPPPRRIAVPSRSSAS- VPKPAPQPYPFTSSLSTINYDEFPTMVFP SGQ- ISQASALAPAPPQVLPQAPAPAPA- PAMVSALAQAPAPVPVLAPGPPQAVAPPAP KPTQAGEGTLSEALLQLQFDDEDLGALLGNSTD- PAVFTDLASVDNSEFQQLLNQGIP VAPH- TTEPMLMEYPEAITRLVTGAQRPPDPAPAPL- GAPGLPNGLLSGDEDFSSIADM DFSALLSQISS). SEQ ID NO: 1 comprises one point mutation in the ER-LBD that ablates binding to endogenous estrogen, but confers nanomolar specificity to 4-OHT, fulvestrant and other estrogen analogs. In some alternatives, the variant of a wild type HEA3 transcription factor comprises an amino acid sequence set forth in SEQ ID No: 2 (SEQ ID NO: 2; MVSKLSQLQTELLAALLESGLSKEALIQAL- GEPGPYLLAGEGPLDKGESCGGGRGEL AEL- PNGLGETRGSEDETDDDGEDFTPPILKELENLSPEE- AAHQKAVVETLLQEDPWR VAKMVK- SYLQQHNIPQREVVDTTGLNQSHLSQHLNKGTPMKT QKRAALYTWYVR KQREVAQQFTHAGQG- GLIEEPTGDELPTKKGRRNRFKWGPASQQILFQAY- ERQKNP SKEERETLVEECNRAECIQRGVSP- SQAQGLGSNLVTEVRVYNWFANRRKEEAFRHK LSAGDMRAANLWPSPLMIKRSKKNSLALSL- TADQMVSALLDAEPPILYSEYDPTRPF SEA- SMMGLLTNLADRELVHMIN- WAKRVPGFVDLTLHDQVHLLECAWLEILMIGLV WRSMEHPGKLLFAPNLLLDRNQGKCVEGMVE- IFDMLLATSSRFRMMNLQGEEFVC LKSIILLNSGVYT- FLSSTLKSLEEKDHIHRVLDKITDTLIHLMAK- AGLTLQQQHQRLA QLLLILSHIRHMSNKRMEH- LYSMKCKNVVPLYDLLLEMLDAHRLHAPTSRG- GASVE ETDQSHLATAGSTSSHSLQKYYITGEAE- GFPATVEFQYLPDTDDRHRIEEKRKRTYET FKSIMKKSPFSGPTDPRPPPRRIAVPSRSSAS- VPKPAPQPYPFTSSLSTINYDEFPTMVFP SGQ- ISQASALAPAPPQVLPQAPAPAPA- PAMVSALAQAPAPVPVLAPGPPQAVAPPAP KPTQAGEGTLSEALLQLQFDDEDLGALLGNSTD- PAVFTDLASVDNSEFQQLLNQGIP VAPH- TTEPMLMEYPEAITRLVTGAQRPPDPAPAPL- GAPGLPNGLLSGDEDFESIADM DFSALLSQISS). SEQ ID NO: 2 comprises a point mutation in HEA3, in the p65 domain which enhances transcriptional activity and is referred to as HEA3 (p65/S536E positions in the RelA protein). In some alternatives, the variant of a wild type HEA3 transcription factor comprises an amino acid sequence set forth in SEQ ID NO: 3 (SEQ ID NO: 3; MVSKLSQLQTELLAALLESGLSKEALIQAL- GEPGPYLLAGEGPLDKGESCGGGRGEL AEL- PNGLGETRGSEDETDDDGEDFTPPILKELENLSPEE- AAHQKAVVETLLQEDPWR VAKMVK- SYLQQHNIPQREVVDTTGLNQSHLSQHLNKGTPMKT QKRAALYTWYVR KQREVAQQFTHAGQG- GLIEEPTGDELPTKKGRRNRFKWGPASQQILFQAY- ERQKNP SKEERETLVEECNRAECIQRGVSP- SQAQGLGSNLVTEVRVYNWFANRRKEEAFRHK LSAGDMRAANLWPSPLMIKRSKKNSLALSL- TADQMVSALLDAEPPILYSEYDPTRPF SEA- SMMGLLTNLADRELVHMIN- WAKRVPGFVDLTLHDQVHLLECAWLEILMIGLV WRSMEHPGKLLFAPNLLLDRNQGKCVEGMVE- IFDMLLATSSRFRMMNLQGEEFVC LKSIILLNSGVYT- FLSSTLKSLEEKDHIHRVLDKITDTLIHLMAK- AGLTLQQQHQRLA QLLLILSHIRHMSNKRMEH- LYSMKCKNVVPLYDLLLEMLDAHRLHAPTSRG- GASVE ETDQSHLATAGSTSSHSLQKYYITGEAE- GFPATVEFQYLPDTDDRHRIEEKRKRTYET FQSSIMKKSPFSGPTDPRPPPRRIAVPSRSSAS- VPKPAPQPYPFTSSLSTINYDEFPTMVFP SGQ- ISQASALAPAPPQVLPQAPAPAPA- PAMVSALAQAPAPVPVLAPGPPQAVAPPAP KPTQAGEGTLSEALLQLQFDDEDLGALLGNSTD- PAVFTDLASVDNSEFQQLLNQGIP VAPH- TTEPMLMEYPEAITRLVTGAQRPPDPAPAPL- GAPGLPNGLLSGDEDFSSIADM DFSALLSQISS). SEQ ID NO: 3 comprises a sequence of HEA3 containing one point mutation (K310Q positions in the RelA protein) in the p65 domain that enhances transcriptional activity. This is referred to as HEA3(p65/K310Q). In some alternatives, the variant of the wild type HEA3 transcription factor is encoded by at least one or more nucleic acid sequences set forth in SEQ ID NO: 12, 13, 14, 19, 20, 21, 22 or 122. In some alternatives, the variant of a wild type HEA4 transcription factor comprises at least one or more amino acid sequences set forth in SEQ ID Nos: 4-7. In some alternatives, the variant of the wild type HEA4 transcription factor is encoded by at least one or more nucleic acid sequences set forth in SEQ ID NO: 15, 16, 17 or 18. In some alternatives, the variant of a wild type HEA3 transcription factor comprises an amino acid sequence set forth in SEQ ID NO: 8 (SEQ ID NO: 8; MVSKLSQLQTELLAALLESGLSKEAL- IQALGEPGPYLLAGEGPLDKGESCGGGRGEL AEL- PNGLGETRGSEDETDDDGEDFTPPILKELENLSPEE- AAHQKAVVETLLQEDPWR VAKMVKSYLQQHNIPQREVVDTTGLNQSHL SQHLNKGTPMKTQKRAALYTWYVR KQREVAQQFTHAGQGGLIEEPTG- DELPTKKGRRNRFKWGPASQQILFQAYERQKNP SKEERETLVEECNRAECIQRGVSPSQAQGLG- SNLVTEVRVYNWFANRRKEEAFRHK LSAGDM- RAANLWPSPLMIKRSKKNSLALSLTADQMVSALL- DAEPPILYSEYDPTRPF SEASMMGLLTNLADRELVHMIN- WAKRVPGFVDLTLHDQVHLLECAWMEILMIGLV WRSMEHPGKLLFAPNLLLDRNQGKCVEGGVE- IFDMLLATSSRFRMMNLQGEEFVCL KSIILLNSGVYT- FLSSTLKSLEEKDHIHRVLDKITDTLIHLMAK- AGLTLQQQHQRLAQ LLLILSHIRHMSNKRMEH- LYSMKCKNVVPLYDLLLEMLDAHRLHAPTSRGGAS- VEE TDQSHLATAGSTSSHSLQKYYITGEAE- GFPATVEFQYLPDTDDRHRIEEKRKRTYETF KSIMKKSPFSGPTDPRPPPRRIAVPSRSSAS- VPKPAPQPYPFTSSLSTINYDEFPTMVFPS GQISQASALAPAPPQVLPQAPAPAPA- PAMVSALAQAPAPVPVLAPGPPQAVAPPAPK PTQAGEGTLSEALLQLQFDDEDLGALLGNSTD- PAVFTDLASVDNSEFQQLLNQGIPV APH- TTEPMLMEYPEAITRLVTGAQRPPDPAPAPL- GAPGLPNGLLSGDEDFSSIADMDF SALLSQISS). SEQ ID NO: 8 comprises the sequence of HEA3 containing three point mutations (L384M, M421G, G521R) in the ER-LBD that ablate binding to endogenous estrogen, and confer nanomolar sensitivity to CMP8 and 4-hydroxytamoxifen. This is referred to as CMP8-HEA3. In some alternatives, the variant of a wild type HEA3 transcription factor comprises an amino acid sequence set forth in SEQ ID NO: 9 (SEQ ID NO: 9; MVSKLSQLQTELLAALLESGLSKEALIQAL-GEPGPYLLAGEGPLDKGESCGGGRGEL AEL-PNGLGETRGSEDETDDDGEDFTPPILKELENLSPEE-AAHQKAVVETLLQEDPWR VAKMVK-SYLQQHNIPQREVVDTTGLNQSHLSQHLNKGTPMK-TQKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWMEILMIGLV WRSMEHPGKLLFAPNLLLDRNQGKCVEGGVE-IFDMLLATSSRFRMMNLQGEEFVCL KSIILLNSGVYT-FLSSTLKSLEEKDHIHRVLDKITDTLIHLMAK-AGLTLQQQHQRLAQ LLLILSHIRHMSNKRMEH-LYSMKCKNVVPLYDLLLEMLDAHRLHAPTSRGGAS-VEE TDQSHLATAGSTSSHSLQKYYITGEAE-GFPATVEFQYLPDTDDRHRIEEKRKRTYETF KSIMKKSPFSGPTDPRPPPRRIAVPSRSSAS-VPKPAPQPYPFTSSLSTINYDEFPTMVFPS GQISQASALAPAPPQVLPQAPAPAPA-PAMVSALAQAPAPVPVLAPGPPQAVAPPAPK PTQAGEGTLSEALLQLQFDDEDLGALLGNSTD-PAVFTDLASVDNSEFQQLLNQGIPV APH-TTEPMLMEYPEAITRLVTGAQRPPDPAPAPL-GAPGLPNGLLSGDEDFESIADMDF SALLSQISS). SEQ ID NO: 9 is the sequence of CMP8-HEA3 containing one point mutation (S536E positions in the RelA protein) in the p65 domain that enhances transcriptional activity. This is referred to as CMP8-HEA3(p65/S536E positions in the RelA protein). In some alternatives, the variant of a wild type HEA3 transcription factor comprises an amino acid sequence set forth in SEQ ID NO: 10 (SEQ ID NO: 10; MVSKLSQLQTELLAALLESGLSKEALIQAL-GEPGPYLLAGEGPLDKGESCGGGRGEL AEL-PNGLGETRGSEDETDDDGEDFTPPILKELENLSPEE-AAHQKAVVETLLQEDPWR VAKMVK-SYLQQHNIPQREVVDTTGLNQSHLSQHLNKGTPMK-TQKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWMEILMIGLV WRSMEHPGKLLFAPNLLLDRNQGKCVEGGVE-IFDMLLATSSRFRMMNLQGEEFVCL KSIILLNSGVYT-FLSSTLKSLEEKDHIHRVLDKITDTLIHLMAK-AGLTLQQQHQRLAQ LLLILSHIRHMSNKRMEH-LYSMKCKNVVPLYDLLLEMLDAHRLHAPTSRGGAS-VEE TDQSHLATAGSTSSHSLQKYYITGEAE-GFPATVEFQYLPDTDDRHRIEEKRKRTYETF QSIMKKSPFSGPTDPRPPPRRIAVPSRSSAS-VPKPAPQPYPFTSSLSTINYDEFPTMVFPS GQISQASALAPAPPQVLPQAPAPAPA-PAMVSALAQAPAPVPVLAPGPPQAVAPPAPK PTQAGEGTLSEALLQLQFDDEDLGALLGNSTD-PAVFTDLASVDNSEFQQLLNQGIPV APH-TTEPMLMEYPEAITRLVTGAQRPPDPAPAPL-GAPGLPNGLLSGDEDFSSIADMDF SALLSQISS). SEQ ID NO: 10 is the sequence of CMP8-HEA3 containing one point mutation (K310Q positions in the RelA protein) in the p65 domain that enhances transcriptional activity. This is referred to as CMP8-HEA3(p65/K310Q positions in the RelA protein). In some alternatives, the variant of a wild type HEA3 transcription factor comprises an amino acid sequence set forth in SEQ ID NO: 11 (SEQ ID NO: 11; MVSKLSQLQTELLAALLESGLSKEALIQAL-GEPGPYLLAGEGPLDKGESCGGGRGEL AEL-PNGLGETRGSEDETDDDGEDFTPPILKELENLSPEE-AAHQKAVVETLLQEDPWR VAKMVKSYLQQHNIPQREVVDTTGLNQSHLS QHLNKGTPMKTQKRAALYTWYVR KQREVAQQFTHAGQGGLIEEPTG-DELPTKKGRRNRFKWGPASQQILFQAYERQKNP SKEERETLVEECNRAECIQRGVSPSQAQGLG-SNLVTEVRVYNWFANRRKEEAFRHK LSAGDM-RAANLWPSPLMIKRSKKNSLALSLTADQMVSALL-DAEPPILYSEYDPTRPF SEASMMGLLTNLADRELVHMIN-WAKRVPGFVDLTLHDQVHLLECAWMEILMIGLV WRSMEHPGKLLFAPNLLLDRNQGKCVEGGVE-IFDMLLATSSRFRMMNLQGEEFVCL KSIILLNSGVYT-FLSSTLKSLEEKDHIHRVLDKITDTLIHLMAK-AGLTLQQQHQRLAQ LLLILSHIRHMSNKRMEH-LYSMKCKNVVPLYDLLLEMLDAHRLHAPTSRGGAS-VEE TDQSHLATAGSTSSHSLQKYYITGEAE-GFPATVEFQYLPDTDDRHRIEEKRKRTYETF QSIMKKSPFSGPTDPRPPPRRIAVPSRSSAS-VPKPAPQPYPFTSSLSTINYDEFPTMVFPS GQISQASALAPAPPQVLPQAPAPAPA-PAMVSALAQAPAPVPVLAPGPPQAVAPPAPK PTQAGEGTLSEALLQLQFDDEDLGALLGNSTD-PAVFTDLASVDNSEFQQLLNQGIPV APH-TTEPMLMEYPEAITRLVTGAQRPPDPAPAPL-GAPGLPNGLLSGDEDFESIADMDF SALLSQISS). SEQ ID NO: 11 comprises the sequence of CMP8-HEA3 containing two point mutations (K310Q and S536E positions in the RelA protein) in the p65 domain that enhance transcriptional activity. This is referred to as CMP8-HEA3(p65/S536E/K310Q positions in the RelA protein). In some alternatives, the polypeptide that modulates checkpoint signaling inhibits negative checkpoint regulators. In some alternatives, the negative checkpoint regulator comprises PD-1, VISTA, LAG-3 and/or TIM3. In some alternatives, the second promoter is constitutive or inducible. In some alternatives, the second nucleic acid further comprises a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte, a polynucleotide coding for a polypeptide spacer, wherein the spacer is optimized, a polynucleotide coding for a transmembrane domain and a polynucleotide encoding an intracellular signaling domain. In some alternatives, the first promoter is in opposite orientation to the second promoter. In some alternatives, the ligand binding domain is an antibody fragment, preferably a binding fragment thereof. In some alternatives, the ligand binding domain is a single chain variable fragment. In some alternatives, the tumor specific molecule is CD19, CD20, CD22, CD23, CD123, CS-1, ROR1, CE7, EGFR, hB7H3, mesothelin, c-Met, PSMA, Her2, GD-2, or MAGE A3 TCR or combinations thereof. In some alternatives, the system employs a synthetic transcriptional activator which, in the presence of a drug binds a synthetic promoter upstream of a transgene to induce expression. In some alternatives, the transcriptional activator is HEA3. In some alternatives, the drug is tamoxifen. In some alternatives, the viral specific molecule is an HIV envelope protein or HIV envelope protein complex, Hepatitis C virus NS3 protein, HbcAg protein, HIV-1 GP120 protein, or Epstein-Barr virus early antigen protein.

Additional changes can be made to the transcriptional activator to increase the properties of the transcription factor including, without limitation, altering one or more amino acids in the estrogen receptor ligand binding domain and/or altering one or more amino acids in the p65 transactivating domain. Altering amino acids in the estrogen receptor binding domain can provide for more specific and higher sensitivity binding of the drug to the transcriptional activator. In some alternatives, HEA4 comprises at least three point mutations. For example, mutations can be made at amino acid position 400, 543, and 544. In some alternatives, the wild type HEA4 comprises the sequence set forth in SEQ ID NO: 4 (SEQ ID NO: 4; MVSKLSQLQTELLAALLESGLSKEALIQALGEPGPYLLAGEGPLDKGESCGGGRGEL AELPNGLGETRGSEDETDDDGEDFTPPILKELENLSPEEAAHQKAVVETLLQEDPWR VAKMVKSYLQQHNIPQREVVDTTGLNQSHLSQHLNKGTPMK TQKRAALYTWYVR KQREVAQQFTHAGQGGLIEEPTGDELPTKKGRRNRFKWGPASQQILFQAYERQKNP SKEERETLVEECNRAECIQRGVSPSQAQGLGSNLVTEVRVYNWFANRRKEEAFRHK LSAGDMRAANLWPSPLMIKRSKKNSLALSLTADQMVSALLDAEPPILYSEYDPTRPF SEASMMGLLTNLADRELVHMINWAKRVPGFVDLTLHDQVHLLECAWLEILMIGLV WRSMEHPVKLLFAPNLLLDRNQGKCVEGMVEIFDMLLATSSRFRMMNLQGEEFVC LKSIILLNSGVYTFLSSTLKSLEEKDHIHRVLDKITDTLIHLMAKAGLTLQQQHQRLA QLLLILSHIRHMSNKGMEHLYSMKCKNVVPLYDLLLEAADAHRLHAPTSRGGASVE ETDQSHLATAGSTSSHSLQKYYITGEAEGFPATVEFQYLPDTDDRHRIEEKRKRTYET FKSIMKKSPFSGPTDPRPPPRRIAVPSRSSASVPKPAPQPYPFTSSLSTINYDEFPTMVFP SGQISQASALAPAPPQVLPQAPAPAPAPAMVSALAQAPAPVPVLAPGPPQAVAPPAP KPTQAGEGTLSEALLQLQFDDEDLGALLGNSTDPAVFTDLASVDNSEFQQLLNQGIP VAPHTTEPMLMEYPEAITRLVTGAQRPPDPAPAPLGAPGLPNGLLSGDEDFSSIADM DFSALLSQISS). SEQ ID NO: 4 comprises the sequence of wild-type HEA4 containing three point mutations (G400V, M543A, L544A) in the ER-LBD that ablate binding to endogenous estrogen, and confer higher sensitivity to 4-hydroxytamoxifen, fulvestrant, and estrogen analogs compared to wild-type HEA3. The transcriptional activator with altered sequence has increased affinity for tamoxifen or 4-hydroxytamoxifen, fulvestrant, and estrogen analogs compared to wild-type HEA3. Altering amino acids in the p65 transactivating domain can provide for increased expression of the transgene in the absence of activation of the transduced cells (SEQ ID NO: 5 and SEQ ID NO: 6).

In the absence of tamoxifen, TamR-tf is excluded from the nucleus by binding of cytosolic heat-shock protein 90 (HSP90) to the tamoxifen binding active site and transgene expression is in the "OFF" state. Nanomolar concentrations of cytosolic tamoxifen actively outcompete HSP90 for ER-LBD binding, resulting in TamR-tf translocation to the nucleus. Upon nuclear translocation, TamR-tf is readily available to bind its restricted synthetic promoter. In the presence of tamoxifen, binding of TamR-tf to 7×HBD/mE1B promoter induces the "ON" state of transgene expression. In some alternatives, this transcriptional regulator can be modified to provide for varying level of control of transgene expression. Amino acid substitutions in the LBD of TamR-tf (HEA3) permit selective responsiveness to tamoxifen and its metabolites, where 4-hydroxy tamoxifen (4-OHT) is the most pharmacologically active metabolite, with respect to TamR-tf (HEA3) activity, while lacking interaction with endogenous estrogen.

In some alternatives, a system for inducible expression of a transgene is provided. In some alternatives, the transgene encodes a chimeric antigen receptor. In some alternatives, a system for inducible expression of a chimeric antigen receptor in cells, such as mammalian cells, is provided. In some alternatives, a system for inducible expression of a chimeric antigen receptor in cells, such as mammalian cells, is provided, the system comprises: a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral specific molecule, or other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives, the transcriptional activator is HEA3 or HEA4. In some alternatives, HEA3 is a variant of a wild type HEA3 transcription factor. In some alternatives, HEA4 is a variant of a wild type HEA4 transcription factor. In some alternatives, HEA3 comprises an estrogen receptor ligand binding domain (ER-LBD) and a RelA (p65) transactivation domain, wherein the estrogen receptor ligand binding domain comprises at least one mutation that allows selective and high sensitivity binding to the drug ligand. In some alternatives, the HEA3 further comprises an HNF1alpha DNA binding domain. Mutations in the ER-LBD affect drug-to-receptor binding. In some alternatives, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives, HEA4 comprises an estrogen receptor ligand binding domain (ER-LBD) and a RelA (p65) transactivation domain, wherein the estrogen receptor ligand binding domain comprises at least one mutation that allows selective and high sensitivity binding to the drug ligand. In some alternatives, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives, the HEA4 further comprises an HNF1alpha DNA binding domain. In some alternatives, HEA4 comprises three mutations in the ER-LBD that enhance sensitivity to drug compared to HEA3. Mutations in the ER-LBD affect drug-to-receptor binding. In some alternatives, the variant of the HEA3 or HEA4 chimeric transcription factor comprises p65 phosphomimetic and/or acetylmimetic amino acid substitutions that enhance transcriptional activity in response to the drug ligand. In some alternatives, the variant of the wild type HEA3 transcription factor comprises at least one or more amino acid sequences set forth in SEQ ID Nos: 1-3, 8-11 and/or 121. In some alternatives, the HEA3 transcription factor is encoded by a nucleic acid sequence set forth in SEQ ID NO: 12 (SEQ ID NO: 12; atggtgtccaagctgtcccagctgca-
gacagaactgctggcagcactgctggaaagcggcctgagcaaagaggccct-
gattcaggc actcggcgaacctggaccttatctgctcgctggcgaaggccctctg-
gataagggcgagagctgtggcggaggaagaggagagctg
gccgagctgcctaacggcctgggcgagacaagaggcagcgaggacgagaca-
gacgacgacggcgaggacttcacccccccccat cctgaaagagctggaaaacct-
gagccccgaggaagccgcccaccagaaagccgtggtggagacactgctgcag-
gaagatccctg
gcgggtcgccaagatggtcaagagctacctgcagcagcacaa-
catcccccagcgggaggtggtggacaccaccggcctgaacca gagccacct-
gagccagcacctgaacaagggcacccccat-
gaaaacccagaagagagccgccctgtacacttggtacgtgcggaa
gcagagagaggtggcccagcagtttacaccggccagggcggcct-
gatccggccagggcggccgacgaggaaccaccggcgacgagctgcccacca
agaagggcagacggaaccggtttaagtggggccctgcatctcagca-
gatcctgttccaggcctacgagcggcagaagaaccccag caaagaggaacgg-
gagacactggtggaagagtgcaaccgggccgagtgcatccagagaggcgt-
gagcccttctcaggctcaggg
cctcggcagcaatctggtcaccgaagtgcgggtgtacaattggttcgc-
caaccggcggaaagaggaagccttccggcacaagctgt ctgctggcgatat-
gagagccgccaacctgtggcccagcccccctgatgatcaagcg-
gagcaagaagaacagcctggccctgagcct
gaccgccgatcagatggtgtccgctctgctggacgccgagccccctatcctgta-
cagcgagtacgaccccaccagacccttcagcg aggccagcat-
gatgggcctgctgaccaacctggccgaccgggagctggtgcacatgat-
caactgggccaagcgggtgcccggctt
cgtggacctgaccctgcacgaccaggtccacctgctggaatgtgcctggctg-
gaaatcctgatgatcggcctcgtgtggagaagcat
ggaacaccccggcaagctgctgttcgcccccaacctgctcctggaccg-
gaaccagggaaagtgcgtggagggcatggtggagatc ttcga-
catgctgctggccacctccagccggttccggatgatgaacctgcagggcgag-
gaattcgtgtgcctgaagtccatcatcctgc
tgaacagcggcgtgtacaccttcctgtcatccaccctgaagtccctg-
gaagagaaggaccacatccaccgggtgctggacaagatca ccgacaccct-
gatccacctgatggccaaggctggcctgacactccagcagcagcaccaga-
gactggcccagctgctgctgatcctg
agccacatccggcacatgagcaacaagcggatggaacacctgtacagcat-
gaagtgcaagaacgtggtgcccctgtacgacctgct gctcgagatgctg-
gatgcccacagactgcacgcccctacaagcagaggcggagccagcgtggag-
gaaaccgaccagtctcacct
ggccaccgccggcagcacaagcagccacagcctgcagaagtactacat-
caccggcgaggccgagggattccctgccaccgtgga
gttccagtacctgcccgacaccgacgaccggcaccggatcgaggaaaagcg-
gaagcggacctacgagacattcaagagcatcatg
aagaagtccccccttcagcggccccaccgatccca-
gacccccccctagaagaatcgccgtgcccagcagatctagcgccagcgtgc
ccaagcctgccccccagccctaccctttcaccatcaactacgacgagttccc-
taccagggccccgcg gccagatctctcaggcctctgctctggcacctgctc-
cacctcaggtgctgcctcaggcccctgctccagccccagcccctgccatggt
gtctgcactggcccaggctccagctcctgtgcctgtgctggcccctggacctcctc
aggctgtggcccctcctgcccctaaacctacc caggccggggagg-
gaacactgtctgaggccctgctgcagctccagttcgacgacgaggatctgg-
gagcactgctgggcaatagca ccgaccccgccgtgtt-
taccgacctggcctccgtggacaacagcgagttccagcagctcctcaaccagggc
atccctgtcgcccca cacaccaccgagcccatgctgatggaataccccgaggc-
catcaccagactggtcacaggcgcccagaggcctccagatccagcac cagctc-
cactgggagcccctggcctgcctaatgggctgctgtctggcgacgag
gacttctccagcattgccgacatggacttcagcg ccctgctgtccca-
gatcagcagc). In some alternatives, the variant of the wild type HEA3 transcription factor is encoded by a nucleic acid sequence set forth in SEQ ID NO: 13 (SEQ ID NO: 13;
atggtgtccaagctgtcccagctgcagacagaactgctggcagcactgctg-
gaaagcggcctgagcaaagaggccctgattcaggc
actcggcgaacctggaccttatctgctcgctggcgaaggccctctgga-
taagggcgagagctgtggcggaggaagaggagagctg
gccgagctgcctaacggcctgggcgagacaagaggcagcgaggacgagaca-
gacgacgacggcgaggacttcacccccccccat cctgaaagagctggaaaacct-
gagccccgaggaagccgcccaccagaaagccgtggtggagacactgctgcag-
gaagatccctg
gcgggtcgccaagatggtcaagagctacctgcagcagcacaa-
catcccccagcgggaggtggtggacaccaccggcctgaacca gagccacct-
gagccagcacctgaacaagggcacccccat-
gaaaacccagaagagagccgccctgtacacttggtacgtgcggaa
gcagagagaggtggcccagcagtttacacacggccagggcggcct-
gatccggccagggcggcctgatcgaggaacctaccggcgacgagctgcc-
cacca agaagggcagacggaaccggtttaagtggggccctgcatctcagca-
gatcctgttccaggcctacgagcggcagaagaaccccag
caaagaggaacgggagacactggtggaagagtgcaaccgggccgagtg-
catccagagaggcgtgagcccttctcaggctcaggg cctcggcagcaatctggt-
caccgaagtgcgggtgtacaattggttcgccaaccggcggaaagag-
gaagccttccggcacaagctgt
ctgctggcgatatgagagccgccaacctgtggcccagcccccctgatgat-
caagcggagcaagaagaacagcctggccctgagcct gaccgccgatca-
gatggtgtccgctctgctggacgccgagccccctatcctgta-
cagcgagtacgaccccaccagacccttcagcg
aggccagcatgatgggcctgctgaccaacctggccgaccgggagctggtgca-
catgatcaactgggccaagcgggtgcccggctt
cgtggacctgaccctgcacgaccaggtccacctgctggaatgtgcctggctg-
gaaatcctgatgatcggcctcgtgtggagaagcat
ggaacaccccggcaagctgctgttcgcccccaacctgctcctggaccg-
gaaccagggaaagtgcgtggagggcatggtggagatc ttcga-
catgctgctggccacctccagccggttccggatgatgaacctgcagggcgag-
gaattcgtgtgcctgaagtccatcatcctgc
tgaacagcggcgtgtacaccttcctgtcatccaccctgaagtccctg-
gaagagaaggaccacatccaccgggtgctggacaagatca ccgacaccct-
gatccacctgatggccaaggctggcctgacactccagcagcagcaccaga-
gactggcccagctgctgctgatcctg
agccacatccggcacatgagcaacaagcggatggaacacctgtacagcat-
gaagtgcaagaacgtggtgcccctgtacgacctgct gctcgagatgctg-
gatgcccacagactgcacgcccctacaagcagaggcggagccagcgtggag-
gaaaccgaccagtctcacct
ggccaccgccggcagcacaagcagccacagcctgcagaagtactacat-
caccggcgaggccgagggattccctgccaccgtgga
gttccagtacctgcccgacaccgacgaccggcaccggatcgaggaaaagcg-
gaagcggacctacgagacattcaagagcatcatg
aagaagtccccccttcagcggccccaccgatccca-
gacccccccctagaagaatcgccgtgcccagcagatctagcgccagcgtgc
ccaagcctgccccccagccctaccctttcaccagcagcctgagcaccatcaac-
tacgacgagttccctaccatggtgttccccagcg gcca-
gatctctcaggcctctgctctggcacctgctc-
cacctcaggtgctgcctcaggcccctgctccagccccagcccctgccatggt
gtctgcactggcccaggctccagctcctgtgcctgtgctggcccctggacctcctc
aggctgtggcccctcctgcccctaaacctacc caggccggggagg-
gaacactgtctgaggccctgctgcagctccagttcgacgacgaggatctgg gagcactgctgggcaatagca ccgaccccgccgtgtt-
taccgacctggcctccgtggacaacagcgagttccagcagctcctcaaccagggc
atccctgtcgcccca cacaccaccgagcccatgctgatggaataccccgaggc-
catcaccagactggtcacaggcgcccagaggcctccagatccagcac cagctc-
cactgggagcccctggcctgcctaatgggctgctgtctggcgacga
ggacttcgagagcattgccgacatggacttcagcg ccctgctgtccca-
gatcagcagc). In some alternatives, the variant of the wild type HEA3 transcription factor is encoded by a nucleic acid sequence set forth in SEQ ID NO: 14 (SEQ ID NO: 14;
atggtgtccaagctgtcccagctgcagacagaactgctggcagcactgctg-
gaaagcggcctgagcaaagaggccctgattcaggc
actcggcgaacctggaccttatctgctcgctggcgaaggccctctgga-
taagggcgagagctgtggcggaggaagaggagagctg
gccgagctgcctaacggcctgggcgagacaagaggcagcgaggacgagaca-
gacgacgacggcgaggacttcacccccccccat cctgaaagagctggaaaacct-
gagccccgaggaagccgcccaccagaaagccgtggtggagacactgctgcag-
gaagatccctg
gcgggtcgccaagatggtcaagagctacctgcagcagcacaa-
catcccccagcgggaggtggtggacaccaccggcctgaacca gagccacct-
gagccagcacctgaacaagggcacccccat-
gaaaacccagaagagagccgccctgtacacttggtacgtgcggaa
gcagagagaggtggcccagcagtttacacacggccagggcggcct-
gatccggccagggcggcctgatcgaggaacctaccggcgacgagctgcc-
cacca agaagggcagacggaaccggtttaagtggggccctgcatctcagca-
gatcctgttccaggcctacgagcggcagaagaaccccag
caaagaggaacgggagacactggtggaagagtgcaaccgggccgagtg-
catccagagaggcgtgagcccttctcaggctcaggg cctcggcagcaatctggt-
caccgaagtgcgggtgtacaattggttcgccaaccggcggaaagag-
gaagccttccggcacaagctgt
ctgctggcgatatgagagccgccaacctgtggcccagcccccctgatgat-
caagcggagcaagaagaacagcctggccctgagcct gaccgccgatca-
gatggtgtccgctctgctggacgccgagccccctatcctgta-
cagcgagtacgaccccaccagacccttcagcg
aggccagcatgatgggcctgctgaccaacctggccgaccgggagctggtgca-
catgatcaactgggccaagcgggtgcccggctt
cgtggacctgaccctgcacgaccaggtccacctgctggaatgtgcctggctg-
gaaatcctgatgatcggcctcgtgtggagaagcat
ggaacaccccggcaagctgctgttcgcccccaacctgctcctggaccg-
gaaccagggaaagtgcgtggagggcatggtggagatc ttcga-
catgctgctggccacctccagccggttccggatgatgaacctgcagggcgag-
gaattcgtgtgcctgaagtccatcatcctgc
tgaacagcggcgtgtacaccttcctgtcatccaccctgaagtccctg-
gaagagaaggaccacatccaccgggtgctggacaagatca ccgacaccct-
gatccacctgatggccaaggctggcctgacactccagcagcagcaccaga-
gactggcccagctgctgctgatcctg
agccacatccggcacatgagcaacaagcggatggaacacctgtacagcat-
gaagtgcaagaacgtggtgcccctgtacgacctgct gctcgagatgctg-
gatgcccacagactgcacgcccctacaagcagaggcggagccagcgtggag-
gaaaccgaccagtctcacct
ggccaccgccggcagcacaagcagccacagcctgcagaagtactacat-
caccggcgaggccgagggattccctgccaccgtgga
gttccagtacctgcccgacaccgacgaccggcaccggatcgaggaaaagcg-
gaagcggacctacgagacattccagagcatcatg
aagaagtccccccttcagcggccccaccgatccca-
gacccccccctagaagaatcgccgtgcccagcagatctagcgccagcgtgc
ccaagcctgccccccagccctaccctttcaccagcagcctgagcaccatcaac-
tacgacgagttccctaccatggtgttccccagcg gcca-
gatctctcaggcctctgctctggcacctgctc-
cacctcaggtgctgcctcaggcccctgctccagccccagcccctgccatggt
gtctgcactggcccaggctccagctcctgtgcctgtgctggcccctggacctcctc
aggctgtggcccctcctgcccctaaacctacc caggccggggagg-
gaacactgtctgaggccctgctgcagctccagttcgacgacgaggatctgg-
gagcactgctgggcaatagca ccgaccccgccgtgtt-
taccgacctggcctccgtggacaacagcgagttccagcagctcctcaaccagggc
atccctgtcgcccca cacaccaccgagcccatgctgatggaataccccgaggc-
catcaccagactggtcacaggcgcccagaggcctccagatccagcac cagctc-
cactgg-
gagcccctggcctgcctaatgggctgctgtctggcgacgaggacttctccagcatt
gccgacatggacttcagcg ccctgctgtcccagatcagcagc). In some alternatives, the variant of the wild type HEA3 transcription factor is encoded by a nucleic acid sequence set forth in SEQ ID NO: 19 (SEQ ID NO: 19; atggtgtccaagctgtcccagctgca-
gacagaactgctggcagcactgctggaaagcggcctgagcaaagaggccct-
gattcaggc actcggcgaacctggaccttatctgctcgctggcgaaggccctctg-
gataagggcgagagctgtggcggaggaagaggagagctg
gccgagctgcctaacggcctgggcgagacaagaggcagcgaggacgagaca-
gacgacgacggcgaggacttcacccccccccat cctgaaagagctggaaaacct-
gagccccgaggaagccgcccaccagaaagccgtggtggagacactgctgcag-
gaagatccctg
gcgggtcgccaagatggtcaagagctacctgcagcagcacaa-
catcccccagcgggaggtggtggacaccaccggcctgaacca gagccacct-
gagccagcacctgaacaagggcacccccat-
gaaaacccagaagagagccgccctgtacacttggtacgtgcggaa
gcagagagaggtggcccagcagtttacacacggccagggcggcct-
gatccggccagggcggcctgatcgaggaacctaccggcgacgagctgcc-
cacca agaagggcagacggaaccggtttaagtggggccctgcatctcagca-
gatcctgttccaggcctacgagcggcagaagaaccccag
caaagaggaacgggagacactggtggaagagtgcaaccgggccgagtg-
catccagagaggcgtgagcccttctcaggctcaggg cctcggcagcaatctggt-
caccgaagtgcgggtgtacaattggttcgccaaccggcggaaagag-
gaagccttccggcacaagctgt
ctgctggcgatatgagagccgccaacctgtggcccagcccccctgatgat-
caagcggagcaagaagaacagcctggccctgagcct gaccgccgatca-
gatggtgtccgctctgctggacgccgagccccctatcctgta-
cagcgagtacgaccccaccagacccttcagcg
aggccagcatgatgggcctgctgaccaacctggccgaccgggagctggtgca-
catgatcaactgggccaagcgggtgcccggctt
cgtggacctgaccctgcacgaccaggtccacctgctggaatgtgcctggatg-
gaaatcctgatgatcggcctcgtgtggagaagcat
ggaacaccccggcaagctgctgttcgcccccaacctgctcctggaccg-
gaaccagggaaagtgcgtggagggcggcgtggagat cttcga-
catgctgctggccacctccagccggttccggatgatgaacctgcagggcgag-
gaattcgtgtgcctgaagtccatcatcctg
ctgaacagcggcgtgtacaccttcctgtcatccaccctgaagtccctg-
gaagagaaggaccacatccaccgggtgctggacaagatc accgacaccct-
gatccacctgatggccaaggctggcctgacactccagcagcagcaccaga-
gactggcccagctgctgctgatcct
gagccacatccggcacatgagcaacaagcggatggaacacctgtacagcat-
gaagtgcaagaacgtggtgcccctgtacgacctg ctgctcgagatgctg-
gatgcccacagactgcacgcccctacaagcagaggcggagccagcgtggag-
gaaaccgaccagtctcac
ctggccaccgccggcagcacaagcagccacagcctgcagaagtactacat-
caccggcgaggccgagggattccctgccaccgtg
gagttccagtacctgcccgacaccgacgaccggcaccggatcgaggaaaagcg-
gaagcggacctacgagacattcaagagcatc
atgaagaagtccccccttcagcggccccaccgatccca-
gacccccccctagaagaatcgccgtgcccagcagatctagcgccagcgt gcc-
caagcctgccccccagccctaccctttcaccagcagcctgagcaccatcaac-
tacgacgagttccctaccatggtgttccccag
cggccagatctctcaggcctctgctctggcacctgctc-
cacctcaggtgctgcctcaggcccctgctccagccccagcccctgccatg
gtgtctgcactggcccaggctccagctcctgtgcctgtgctggcccctggacctcct
caggctgtggcccctcctgcccctaaaccta cccaggccggggagg-
gaacactgtctgaggccctgctgcagctccagttcgacgacgaggatctgg-
gagcactgctgggcaatag caccgaccccgccgtgtt-
taccgacctggcctccgtggacaacagcgagttccagcagctcctcaaccagggc
atccctgtcgccc cacacaccaccgagcccatgctgatggaataccccgaggc-
catcaccagactggtcacaggcgcccagaggcctccagatccagc accagctc-
cactgggagcccctggcctgcctaatgggctgctgtctggcgacgagga
cttctccagcattgccgacatggacttcag cgccctgctgtcccagatcagcagc). In some alternatives, the variant of the wild type HEA3 transcription factor is encoded by a nucleic acid sequence set forth in SEQ ID NO: 20 (SEQ ID NO: 20; atggtgtc-
caagctgtcccagctgcagacagaactgctggcagcactgctggaaagcggcctgagcaaagaggccctgattcaggc actcggcgaacctggacct-
tatctgctcgctggcgaaggccctctggataagggcgagagctgtggcggagga
agaggagagctg gccgagctgcctaacggcctgggcga-
gacaagaggcagcgaggacgagacagacgacgacggcgaggactt-
cacccccccat cctgaaagagctggaaaacctgagccccgaggaagccgcc-
caccagaaagccgtggtggagacactgctgcaggaagatccctg
gcgggtcgccaagatggtcaagagctacctgcagcagcacaa-
catcccccagcgggaggtggtggacaccaccggcctgaacca gagccacct-
gagccagcacctgaacaagggcaccccccat-
gaaaacccagaagagagccgccctgtacacttggtacgtgcggaa
gcagagagaggtggcccagcagtttacacacggccagggcggcct-
gatccggccagggcggcctgatcgaggaacctaccggcgacgagctgcc-
cacca agaagggcagacggaaccggtttaagtggggccctgcatctcagca-
gatcctgttccaggcctacgagcggcagaagaaccccag
caaagaggaacgggagacactggtggaagagtgcaaccgggccgagtg-
catccagagaggcgtgagcccttctcaggctcaggg cctcggcagcaatctggt-
caccgaagtgcgggtgtacaattggttcgccaaccggcggaaagag-
gaagccttccggcacaagctgt
ctgctggcgatatgagagccgccaacctgtggcccagccccctgatgat-
caagcggagcaagaagaacagcctggccctgagcct gaccgccgatca-
gatggtgtccgctctgctggacgccgagccccctatcctgta-
cagcgagtacgaccccaccagacccttcagcg
aggccagcatgatgggcctgctgaccaacctggccgaccgggagctggtgca-
catgatcaactgggccaagcgggtgcccggctt
cgtggacctgaccctgcacgaccaggtccacctgctggaatgtgcctggatg-
gaaatcctgatgatcggcctcgtgtggagaagcat
ggaacaccccggcaagctgctgttcgcccccaacctgctcctggaccg-
gaaccagggaaagtgcgtggagggcggcgtggagat cttcga-
catgctgctggccacctccagccggttccggatgatgaacctgcagggcgag-
gaattcgtgtgcctgaagtccatcatcctg
ctgaacagcggcgtgtacaccttcctgtcatccaccctgaagtccctg-
gaagagaaggaccacatccaccgggtgctggacaagatc accgacaccct-
gatccacctgatggccaaggctggcctgacactccagcagcagcaccaga-
gactggcccagctgctgctgatcct
gagccacatccggcacatgagcaacaagcggatggaacacctgtacagcat-
gaagtgcaagaacgtggtgcccctgtacgacctg ctgctcgagatgctg-
gatgcccacagactgcacgcccctacaagcagaggcggagccagcgtggag-
gaaaccgaccagtctcac
ctggccaccgccggcagcacaagcagccacagcctgcagaagtactacat-
caccggcgaggccgagggattccctgccaccgtg
gagttccagtacctgcccgacaccgacgaccggcaccggatcgaggaaaagcg-
gaagcggacctacgagacattcaagagcatc
atgaagaagtccccttcagcggccccaccgatccca-
gacccccccctagaagaatcgccgtgcccagcagatctagcgccagcgt gcc-
caagcctgcccccagccctaccctttcaccagcagcctgagcaccatcaac-
tacgacgagttccctaccatggtgttccccag
cggccagatctctcaggcctctgctctggcacctgctc-
cacctcaggtgctgcctcaggcccctgctccagccccagcccctgccatg
gtgtctgcactggcccaggctccagctcctgtgcctgtgctggcccctggacctcc
tcaggctgtggcccctcctgccctaaaccta cccaggccggggagg-
gaacactgtctgaggccctgctgcagctccagttcgacgacgaggatctgg-
gagcactgctgggcaatag caccgaccccgccgtgtt-
taccgacctggcctccgtggacaacagcgagttccagcagctcctcaaccaggg
catccctgtcgccc cacacaccaccgagcccatgctgatggaatacccgaggc-
catcaccagactggtcacaggcgcccagaggcctccagatccagc accagctc-
cactgggagcccctggcctgcctaatgggctgctgtctggcgacgagg
acttcgagagcattgccgacatggacttcag cgccctgctgtccca-
gatcagcagc). In some alternatives, the variant of the wild type HEA3 transcription factor is encoded by a nucleic acid sequence set forth in SEQ ID NO: 21 (SEQ ID NO: 21;
atggtgtccaagctgtcccagctgcagacagaactgctggcagcactgctg-
gaaagcggcctgagcaaagaggccctgattcaggc
actcggcgaacctggaccttatctgctcgctggcgaaggccctctgga-
taagggcgagagctgtggcggaggaagaggagagctg
gccgagctgcctaacggcctgggcgagacaagaggcagcgaggacgagaca-
gacgacgacggcgaggacttcacccccccat cctgaaagagctggaaaacct-
gagccccgaggaagccgcccaccagaaagccgtggtggagacactgctgcag-
gaagatccctg
gcgggtcgccaagatggtcaagagctacctgcagcagcacaa-
catcccccagcgggaggtggtggacaccaccggcctgaacca gagccacct-
gagccagcacctgaacaagggcaccccccat-
gaaaacccagaagagagccgccctgtacacttggtacgtgcggaa
gcagagagaggtggcccagcagtttacacacggccagggcggcct-
gatccggccagggcggcctgatcgaggaacctaccggcgacgagctgcc-
cacca agaagggcagacggaaccggtttaagtggggccctgcatctcagca-
gatcctgttccaggcctacgagcggcagaagaaccccag
caaagaggaacgggagacactggtggaagagtgcaaccgggccgagtg-
catccagagaggcgtgagcccttctcaggctcaggg cctcggcagcaatctggt-
caccgaagtgcgggtgtacaattggttcgccaaccggcggaaagag-
gaagccttccggcacaagctgt
ctgctggcgatatgagagccgccaacctgtggcccagccccctgatgat-
caagcggagcaagaagaacagcctggccctgagcct gaccgccgatca-
gatggtgtccgctctgctggacgccgagccccctatcctgta-
cagcgagtacgaccccaccagacccttcagcg
aggccagcatgatgggcctgctgaccaacctggccgaccgggagctggtgca-
catgatcaactgggccaagcgggtgcccggctt
cgtggacctgaccctgcacgaccaggtccacctgctggaatgtgcctggatg-
gaaatcctgatgatcggcctcgtgtggagaagcat
ggaacaccccggcaagctgctgttcgcccccaacctgctcctggaccg-
gaaccagggaaagtgcgtggagggcggcgtggagat cttcga-
catgctgctggccacctccagccggttccggatgatgaacctgcagggcgag-
gaattcgtgtgcctgaagtccatcatcctg
ctgaacagcggcgtgtacaccttcctgtcatccaccctgaagtccctg-
gaagagaaggaccacatccaccgggtgctggacaagatc accgacaccct-
gatccacctgatggccaaggctggcctgacactccagcagcagcaccaga-
gactggcccagctgctgctgatcct
gagccacatccggcacatgagcaacaagcggatggaacacctgtacagcat-
gaagtgcaagaacgtggtgcccctgtacgacctg ctgctcgagatgctg-
gatgcccacagactgcacgcccctacaagcagaggcggagccagcgtggag-
gaaaccgaccagtctcac
ctggccaccgccggcagcacaagcagccacagcctgcagaagtactacat-
caccggcgaggccgagggattccctgccaccgtg
gagttccagtacctgcccgacaccgacgaccggcaccggatcgaggaaaagcg-
gaagcggacctacgagacattccagagcatc
atgaagaagtccccttcagcggccccaccgatccca-
gacccccccctagaagaatcgccgtgcccagcagatctagcgccagcgt gcc-
caagcctgcccccagccctaccctttcaccagcagcctgagcaccatcaac-
tacgacgagttccctaccatggtgttccccag
cggccagatctctcaggcctctgctctggcacctgctc-
cacctcaggtgctgcctcaggcccctgctccagccccagcccctgccatg
gtgtctgcactggcccaggctccagctcctgtgcctgtgctggcccctggacctcct
caggctgtggcccctcctgccctaaaccta cccaggccggggagg-
gaacactgtctgaggccctgctgcagctccagttcgacgacgaggatctgg-
gagcactgctgggcaatag caccgaccccgccgtgtt-
taccgacctggcctccgtggacaacagcgagttccagcagctcctcaaccagggc
atccctgtcgccc cacacaccaccgagcccatgctgatggaatacccgaggc-
catcaccagactggtcacaggcgcccagaggcctccagatccagc accagctc-
cactgggagcccctggcctgcctaatgggctgctgtctggcgacga
ggacttctccagcattgccgacatggacttcag cgccctgctgtccca-
gatcagcagc). In some alternatives, the variant of the wild type HEA3 transcription factor is encoded by a nucleic acid sequence set forth in SEQ ID NO: 22 (SEQ ID NO: 22;
atggtgtccaagctgtcccagctgcagacagaactgctggcagcactgctg-
gaaagcggcctgagcaaagaggccctgattcaggc
actcggcgaacctggaccttatctgctcgctggcgaaggccctctgga-
taagggcgagagctgtggcggaggaagaggagagctg
gccgagctgcctaacggcctgggcgagacaagaggcagcgaggacgagaca-
gacgacgacggcgaggacttcacccccccat cctgaaagagctggaaaacct-
gagccccgaggaagccgcccaccagaaagccgtggtggagacactgctgcag-
gaagatccctg
gcgggtcgccaagatggtcaagagctacctgcagcagcacaa-
catcccccagcgggaggtggtggacaccaccggcctgaacca gagccacct-
gagccagcacctgaacaagggcaccccccat-
gaaaacccagaagagagccgccctgtacacttggtacgtgcggaa
gcagagagaggtggcccagcagtttacacacggccagggcggcct-
gatccggccagggcggcctgatcgaggaacctaccggcgacgagctgcccacca agaagggcagacggaaccggtttaagtggggccctgcatctcagca-
gatcctgttccaggcctacgagcggcagaagaaccccag
caaagaggaacgggagacactggtggaagagtgcaaccgggccgagtg-
catccagagaggcgtgagcccttctcaggctcaggg cctcggcagcaatctggt-
caccgaagtgcgggtgtacaattggttcgccaaccggcggaaagag-
gaagccttccggcacaagctgt
ctgctggcgatatgagagccgccaacctgtggcccagccccctgatgat-
caagcggagcaagaagaacagcctggccctgagcct gaccgccgatca-
gatggtgtccgctctgctggacgccgagccccctatcctgta-
cagcgagtacgaccccaccagacccttcagcg
aggccagcatgatgggcctgctgaccaacctggccgaccgggagctggtgca-
catgatcaactgggccaagcgggtgcccggctt
cgtggacctgaccctgcacgaccaggtccacctgctggaatgtgcctggatg-
gaaatcctgatgatcggcctcgtgtggagaagcat
ggaacaccccggcaagctgctgttcgcccccaacctgctcctggaccg-
gaaccagggaaagtgcgtggagggcggcgtggagat cttcga-
catgctgctggccacctccagccggttccggatgatgaacctgcagggcgag-
gaattcgtgtgcctgaagtccatcatcctg
ctgaacagcggcgtgtacaccttcctgtcatccaccctgaagtccctg-
gaagagaaggaccacatccaccgggtgctggacaagatc accgacaccct-
gatccacctgatggccaaggctggcctgacactccagcagcagcaccaga-
gactggcccagctgctgctgatcct
gagccacatccggcacatgagcaacaagcggatggaacacctgtacagcat-
gaagtgcaagaacgtggtgcccctgtacgacctg ctgctcgagatgctg-
gatgcccacagactgcacgcccctacaagcagaggcggagccagcgtggag-
gaaaccgaccagtctcac
ctggccaccgccggcagcacaagcagccacagcctgcagaagtactacat-
caccggcgaggccgagggattccctgccaccgtg
gagttccagtacctgcccgacaccgacgaccggcaccggatcgaggaaaagcg-
gaagcggacctacgagacattccagagcatc
atgaagaagtccccttcagcggccccaccgatccca-
gacccccccctagaagaatcgccgtgcccagcagatctagcgccagcgt gcc-
caagcctgcccccagccctaccctttcaccagcagcctgagcaccatcaac-
tacgacgagttccctaccatggtgttccccag
cggccagatctctcaggcctctgctctggcacctgctc-
cacctcaggtgctgcctcaggcccctgctccagccccagcccctgccatg
gtgtctgcactggcccaggctccagctcctgtgcctgtgctggcccctggacctcc
tcaggctgtggcccctcctgcccctaaaccta cccaggccggggagg-
gaacactgtctgaggccctgctgcagctccagttcgacgacgaggatctgg-
gagcactgctgggcaatag caccgaccccgccgtgtt-
taccgacctggcctccgtggacaacagcgagttccagcagctcctcaaccagggc
atccctgtcgccc cacacaccaccgagcccatgctgatggaataccccgaggc-
catcaccagactggtcacaggcgcccagaggcctccagatccagc accagctc-
cactgggagcccctggcctgcctaatgggctgctgtctggcgacg
aggacttcgagagcattgccgacatggacttcag cgccctgctgtccca-
gatcagcagc). In some alternatives, the variant of a wild type HEA4 transcription factor comprises at least one or more amino acid sequences set forth in SEQ ID Nos: 4-7. In some alternatives, the variant of the wild type HEA4 transcription factor is encoded by a nucleic acid sequence set forth in SEQ ID NO: 15 (SEQ ID NO: 15; atggtgtccaagctgtcccagctgca-
gacagaactgctggcagcactgctggaaagcggcctgagcaaagaggccct-
gattcaggc actcggcgaacctggaccttatctgctcgctggcgaaggccctctg-
gataagggcgagagctgtggcggaggaagaggagagctg
gccgagctgcctaacggcctgggcgagacaagaggcagcgaggacgagaca-
gacgacgacggcgaggacttcaccccccccat cctgaaagagctggaaaacct-
gagccccgaggaagccgcccaccagaaagccgtggtggagacactgctgcag-
gaagatccctg
gcgggtcgccaagatggtcaagagctacctgcagcagcacaa-
catcccccagcgggaggtggtggacaccaccggcctgaacca gagccacct-
gagccagcacctgaacaagggcacccccat-
gaaaacccagaagagagccgccctgtacacttggtacgtgcggaa
gcagagagaggtggcccagcagtttacacacggccagggcggcct-
gatccggccagggcggcctgatcgaggaacctaccggcgacgagctgcc-
cacca agaagggcagacggaaccggtttaagtggggccctgcatctcagca-
gatcctgttccaggcctacgagcggcagaagaaccccag
caaagaggaacgggagacactggtggaagagtgcaaccgggccgagtg-
catccagagaggcgtgagcccttctcaggctcaggg cctcggcagcaatctggt-
caccgaagtgcgggtgtacaattggttcgccaaccggcggaaagag-
gaagccttccggcacaagctgt
ctgctggcgatatgagagccgccaacctgtggcccagccccctgatgat-
caagcggagcaagaagaacagcctggccctgagcct gaccgccgatca-
gatggtgtccgctctgctggacgccgagccccctatcctgta-
cagcgagtacgaccccaccagacccttcagcg
aggccagcatgatgggcctgctgaccaacctggccgaccgggagctggtgca-
catgatcaactgggccaagcgggtgcccggctt
cgtggacctgaccctgcacgaccaggtccacctgctggaatgtgcctggctg-
gaaatcctgatgatcggcctcgtgtggagaagcat ggaacaccccgt-
gaagctgctgttcgcccccaacctgctcctggaccggaaccagg-
gaaagtgcgtggagggcatggtggagatc
ttcgacatgctgctggccacctccagccggttccggatgat-
gaacctgcagggcgaggaattcgtgtgcctgaagtccatcatcctgc
tgaacagcggcgtgtacaccttcctgtcatccaccctgaagtccctg-
gaagagaaggaccacatccaccgggtgctggacaagatca ccgacaccct-
gatccacctgatggccaaggctggcctgacactccagcagcagcaccaga-
gactggcccagctgctgctgatcctg
agccacatccggcacatgagcaacaagggaatggaacacctgtacagcat-
gaagtgcaagaacgtggtgcccctgtacgacctgct gctcgaggctgcc-
gatgcccacagactgcacgcccctacaagcagaggcggagccagcgtggag-
gaaaccgaccagtctcacct
ggccaccgccggcagcacaagcagccacagcctgcagaagtactacat-
caccggcgaggccgagggattccctgccaccgtgga
gttccagtacctgcccgacaccgacgaccggcaccggatcgaggaaaagcg-
gaagcggacctacgagacattcaagagcatcatg
aagaagtccccttcagcggccccaccgatccca-
gacccccccctagaagaatcgccgtgcccagcagatctagcgccagcgtgc
ccaagcctgcccccagccctaccctttccccccaccatcaac-
tacgacgagttccctaccagggccccgcg gcca-
gatctctcaggcctctgctctggcacctgctc-
cacctcaggtgctgcctcaggcccctgctccagccccagcccctgccatggt
gtctgcactggcccaggctccagctcctgtgcctgtgctggcccctggacctcctc
aggctgtggcccctcctgcccctaaacctacc caggccggggagg-
gaacactgtctgaggccctgctgcagctccagttcgacgacgaggatctgg-
gagcactgctgggcaatagca ccgaccccgccgtgtt-
taccgacctggcctccgtggacaacagcgagttccagcagctcctcaaccagggc
atccctgtcgcccca cacaccaccgagcccatgctgatggaataccccgaggc-
catcaccagactggtcacaggcgcccagaggcctccagatccagcac cagctc-
cactgggagcccctggcctgcctaatgggctgctgtctggcgacgaggacttct
ccagcattgccgacatggacttcagcg ccctgctgtcccagatcagcagc). In some alternatives, the variant of the wild type HEA4 transcription factor is encoded by a nucleic acid sequence set forth in SEQ ID NO: 16 (SEQ ID NO: 16; atggtgtc-
caagctgtcccagctgcagacagaactgctggcagcactgctggaaagcggcct-
gagcaaagaggccctgattcaggc actcggcgaacctggacct-
tatctgctcgctggcgaaggccctctggataagggcgagagctgtggcggagga
agaggagagctg gccgagctgcctaacggcctgggcga-
gacaagaggcagcgaggacgagacagacgacgacggcgaggactt-
caccccccccat cctgaaagagctggaaaacctgagccccgaggaagccgcc-
caccagaaagccgtggtggagacactgctgcaggaagatccctg
gcgggtcgccaagatggtcaagagctacctgcagcagcacaa-
catcccccagcgggaggtggtggacaccaccggcctgaacca gagccacct-
gagccagcacctgaacaagggcacccccat-
gaaaacccagaagagagccgccctgtacacttggtacgtgcggaa
gcagagagaggtggcccagcagtttacacacggccagggcggcct-
gatccggccagggcggcctgatcgaggaacctaccggcgacgagctgcc-
cacca agaagggcagacggaaccggtttaagtggggccctgcatctcagca-
gatcctgttccaggcctacgagcggcagaagaaccccag
caaagaggaacgggagacactggtggaagagtgcaaccgggccgagtg-
catccagagaggcgtgagcccttctcaggctcaggg cctcggcagcaatctggt-
caccgaagtgcgggtgtacaattggttcgccaaccggcggaaagag-
gaagccttccggcacaagctgt
ctgctggcgatatgagagccgccaacctgtggcccagccccctgatgat-
caagcggagcaagaagaacagcctggccctgagcct gaccgccgatca-
gatggtgtccgctctgctggacgccgagccccctatcctgtacagcgagtacgaccccaccagacccttcagcg
aggccagcatgatgggcctgctgaccaacctggccgaccgggagctggtgca-
catgatcaactgggccaagcgggtgcccggctt
cgtggacctgaccctgcacgaccaggtccacctgctggaatgtgcctggctg-
gaaatcctgatgatcggcctcgtgtggagaagcat ggaacaccccgt-
gaagctgctgttcgcccccaacctgctcctggaccggaaccagg-
gaaagtgcgtggagggcatggtggagatc
ttcgacatgctgctggccacctccagccggttccggatgat-
gaacctgcagggcgaggaattcgtgtgcctgaagtccatcatcctgc
tgaacagcggcgtgtacaccttcctgtcatccaccctgaagtccctg-
gaagagaaggaccacatccaccgggtgctggacaagatca ccgacaccct-
gatccacctgatggccaaggctggcctgacactccagcagcagcaccaga-
gactggcccagctgctgctgatcctg
agccacatccggcacatgagcaacaagggaatggaacacctgtacagcat-
gaagtgcaagaacgtggtgcccctgtacgacctgct gctcgaggctgcc-
gatgcccacagactgcacgcccctacaagcagaggcggagccagcgtggag-
gaaaccgaccagtctcacct
ggccaccgccggcagcacaagcagccacagcctgcagaagtactacat-
caccggcgaggccgagggattccctgccaccgtgga
gttccagtacctgcccgacaccgacgaccggcaccggatcgaggaaaagcg-
gaagcggacctacgagacattcaagagcatcatg
aagaagtccccttcagcggccccaccgatccca-
gacccccccctagaagaatcgccgtgcccagcagatctagcgccagcgtgc
ccaagcctgccccccagccctaccctttcccccccaccatcaac-
tacgacgagttccctaccagggccccgcg gcca-
gatctctcaggcctctgctctggcacctgctc-
cacctcaggtgctgcctcaggcccctgctccagccccagcccctgccatggt
gtctgcactggcccaggctccagctcctgtgcctgtgctggcccctggacctcctca
ggctgtggcccctcctgccccctaaacctacc caggccggggagg-
gaacactgtctgaggccctgctgcagctccagttcgacgacgaggatctgg-
gagcactgctgggcaatagca ccgacccccgccgtgtt-
taccgacctggcctccgtggacaacagcgagttccagcagctcctcaaccagggc
atccctgtcgcccca cacaccaccgagcccatgctgatggaataccccgaggc-
catcaccagactggtcacaggcgcccagaggcctccagatccagcac cagctc-
cactgggagcccctggcctgcctaatgggctgctgtctggcgacgaggac
ttcgagagcattgccgacatggacttcagcg ccctgctgtcccagatcagcagc).

In some alternatives, the variant of the wild type HEA4 transcription factor is encoded by a nucleic acid sequence set forth in SEQ ID NO: 17 (SEQ ID NO: 17; atggtgtc-
caagctgtcccagctgcagacagaactgctggcagcactgctggaaagcggcct-
gagcaaagaggccctgattcaggc actcggcgaacctggacct-
tatctgctcgctggcgaaggccctctggataagggcgagagctgtggcggaggaa
gaggagagctg gccgagctgcctaacggcctgggcga-
gacaagaggcagcgaggacgagacagacgacgacggcgaggactt-
cacccccccccat cctgaaagagctggaaaacctgagccccgaggaagccgcc-
caccagaaagccgtggtggagacactgctgcaggaagatccctg
gcgggtcgccaagatggtcaagagctacctgcagcagcacaa-
catcccccagcgggaggtggtggacaccaccggcctgaacca gagccacct-
gagccagcacctgaacaagggcacccccat-
gaaaacccagaagagagccgccctgtacacttggtacgtgcggaa
gcagagagaggtggcccagcagtttacacacggccagggcggcct-
gatccggccagggcggcctgatcgaggaacctaccggcgacgagctgcc-
cacca agaagggcagacggaaccggtttaagtggggccctgcatctcagca-
gatcctgttccaggcctacgagcggcagaagaaccccag
caaagaggaacgggagacactggtggaagagtgcaaccgggccgagtg-
catccagagaggcgtgagcccttctcaggctcaggg cctcggcagcaatctggt-
caccgaagtgcgggtgtacaattggttcgccaaccggcggaaagag-
gaagccttccggcacaagctgt
ctgctggcgatatgagagccgccaacctgtggcccagccccctgatgat-
caagcggagcaagaagaacagcctggccctgagcct gaccgccgatca-
gatggtgtccgctctgctggacgccgagccccctatcctgta-
cagcgagtacgaccccaccagacccttcagcg
aggccagcatgatgggcctgctgaccaacctggccgaccgggagctggtgca-
catgatcaactgggccaagcgggtgcccggctt
cgtggacctgaccctgcacgaccaggtccacctgctggaatgtgcctggctg-
gaaatcctgatgatcggcctcgtgtggagaagcat ggaacaccccgt-
gaagctgctgttcgcccccaacctgctcctggaccggaaccagg-
gaaagtgcgtggagggcatggtggagatc
ttcgacatgctgctggccacctccagccggttccggatgat-
gaacctgcagggcgaggaattcgtgtgcctgaagtccatcatcctgc
tgaacagcggcgtgtacaccttcctgtcatccaccctgaagtccctg-
gaagagaaggaccacatccaccgggtgctggacaagatca ccgacaccct-
gatccacctgatggccaaggctggcctgacactccagcagcagcaccaga-
gactggcccagctgctgctgatcctg
agccacatccggcacatgagcaacaagggaatggaacacctgtacagcat-
gaagtgcaagaacgtggtgcccctgtacgacctgct gctcgaggctgcc-
gatgcccacagactgcacgcccctacaagcagaggcggagccagcgtggag-
gaaaccgaccagtctcacct
ggccaccgccggcagcacaagcagccacagcctgcagaagtactacat-
caccggcgaggccgagggattccctgccaccgtgga
gttccagtacctgcccgacaccgacgaccggcaccggatcgaggaaaagcg-
gaagcggacctacgagacattccagagcatcatg
aagaagtccccttcagcggccccaccgatccca-
gacccccccctagaagaatcgccgtgcccagcagatctagcgccagcgtgc
ccaagcctgccccccagccctaccctttcccccccaccatcaac-
tacgacgagttccctaccagggccccgcg gcca-
gatctctcaggcctctgctctggcacctgctc-
cacctcaggtgctgcctcaggcccctgctccagccccagcccctgccatggt
gtctgcactggcccaggctccagctcctgtgcctgtgctggcccctggacctcctca
ggctgtggcccctcctgccccctaaacctacc caggccggggagg-
gaacactgtctgaggccctgctgcagctccagttcgacgacgaggatctgg-
gagcactgctgggcaatagca ccgacccccgccgtgtt-
taccgacctggcctccgtggacaacagcgagttccagcagctcctcaaccagggc
atccctgtcgcccca cacaccaccgagcccatgctgatggaataccccgaggc-
catcaccagactggtcacaggcgcccagaggcctccagatccagcac cagctc-
cactgggagcccctggcctgcctaatgggctgctgtctggcgacgagga
cttctccagcattgccgacatggacttcagcg ccctgctgtcccagatcagcagc).

In some alternatives, the variant of the wild type HEA4 transcription factor is encoded by a nucleic acid sequence set forth in SEQ ID NO: 18 (SEQ ID NO: 18; atggtgtc-
caagctgtcccagctgcagacagaactgctggcagcactgctggaaagcggcct-
gagcaaagaggccctgattcaggc actcggcgaacctggacct-
tatctgctcgctggcgaaggccctctggataagggcgagagctgtggcggagga
agaggagagctg gccgagctgcctaacggcctgggcga-
gacaagaggcagcgaggacgagacagacgacgacggcgaggactt-
cacccccccccat cctgaaagagctggaaaacctgagccccgaggaagccgcc-
caccagaaagccgtggtggagacactgctgcaggaagatccctg
gcgggtcgccaagatggtcaagagctacctgcagcagcacaa-
catcccccagcgggaggtggtggacaccaccggcctgaacca gagccacct-
gagccagcacctgaacaagggcacccccat-
gaaaacccagaagagagccgccctgtacacttggtacgtgcggaa
gcagagagaggtggcccagcagtttacacacggccagggcggcct-
gatccggccagggcggcctgatcgaggaacctaccggcgacgagctgcc-
cacca agaagggcagacggaaccggtttaagtggggccctgcatctcagca-
gatcctgttccaggcctacgagcggcagaagaaccccag
caaagaggaacgggagacactggtggaagagtgcaaccgggccgagtg-
catccagagaggcgtgagcccttctcaggctcaggg cctcggcagcaatctggt-
caccgaagtgcgggtgtacaattggttcgccaaccggcggaaagag-
gaagccttccggcacaagctgt
ctgctggcgatatgagagccgccaacctgtggcccagccccctgatgat-
caagcggagcaagaagaacagcctggccctgagcct gaccgccgatca-
gatggtgtccgctctgctggacgccgagccccctatcctgta-
cagcgagtacgaccccaccagacccttcagcg
aggccagcatgatgggcctgctgaccaacctggccgaccgggagctggtgca-
catgatcaactgggccaagcgggtgcccggctt
cgtggacctgaccctgcacgaccaggtccacctgctggaatgtgcctggctg-
gaaatcctgatgatcggcctcgtgtggagaagcat ggaacaccccgt-
gaagctgctgttcgcccccaacctgctcctggaccggaaccagg-
gaaagtgcgtggagggcatggtggagatc
ttcgacatgctgctggccacctccagccggttccggatgat-
gaacctgcagggcgaggaattcgtgtgcctgaagtccatcatcctgc
tgaacagcggcgtgtacaccttcctgtcatccaccctgaagtccctg-
gaagagaaggaccacatccaccgggtgctggacaagatca ccgacaccct-
gatccacctgatggccaaggctggcctgacactccagcagcagcaccagagactggcccagctgctgctgatcctg agccacatccggcacatgagcaacaagggaatggaacacctgtacagcat-gaagtgcaagaacgtggtgcccctgtacgacctgct gctcgaggctgcc-gatgcccacagactgcacgcccctacaagcagaggcggagccagcgtggag-gaaaccgaccagtctcacct ggccaccgccggcagcacaagcagccacagcctgcagaagtactacat-caccggcgaggccgagggattccctgccaccgtgga gttccagtacctgcccgacaccgacgaccggcaccggatcgaggaaaagcg-gaagcggacctacgagacattccagagcatcatg aagaagtccccc ttcagcggccccaccgatccca-gacccccccctagaagaatcgccgtgcccagcagatctagcgccagcgtgc ccaagcctgcccccccagccctaccctttcccccccaccatcaac-tacgacgagttccctaccagggccccgcg gcca-gatctctcaggcctctgctctggcacctgctc-cacctcaggtgctgcctcaggcccctgctccagccccagcccctgccatggt gtctgcactggcccaggctccagctcctgtgcctgtgctggcccctggacctcctc aggctgtggcccctcctgcccctaaacctacc caggccggggagg-gaacactgtctgaggccctgctgcagctccagttcgacgacgaggatctgg-gagcactgctgggcaatagca ccgaccccgccgtgtt-taccgacctggcctccgtggacaacagcgagttccagcagctcctcaaccaggg catccctgtcgcccca cacaccaccgagcccatgctgatggaataccccgaggc-catcaccagactggtcacaggcgcccagaggcctccagatccagcac cagctc-cactgggagcccctggcctgcctaatgggctgctgtctggcgacgaggactt cgagagcattgccgacatggacttcagcg ccctgctgtcccagatcagcagc). In some alternatives, the drug is tamoxifen and/or its metabolites, 4-hydroxytamoxifen, fulvestrant or other estrogen analogs, or CMP8.

In some alternatives, the inducible promoter functions in a lentiviral construct and/or in lymphocytes.

Chimeric Antigen Receptors.

A system with an enhanced sensitivity to a drug ligand for inducible expression of a chimeric antigen receptor in cells, such as mammalian cells, comprises: a first promoter inducible by a drug, wherein the first nucleic acid is operably linked to a first polynucleotide that encodes a chimeric antigen receptor, which comprises a ligand binding domain that is specific for a ligand selected from a tumor specific molecule, a viral specific molecule, or any other selected molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and a second nucleic acid comprising a second promoter that is operably linked to a nucleic acid encoding a transcriptional activator for the first promoter inducible by drug, wherein the system is inducible by an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In other alternatives, another polynucleotide coding for a chimeric antigen receptor is under the control of a constitutive promoter. In some alternatives, the drug is tamoxifen and/or its metabolites, 4-hydroxytamoxifen, fulvestrant or other estrogen analogs, or CMP8.

Ligand Binding Domain.

In some alternatives, the chimeric receptor nucleic acid comprises a polynucleotide coding for a ligand binding domain. In some alternatives, the ligand binding domain specifically binds to a tumor a viral molecule, or other molecule expressed on a target or selected cell population, and it may be humanized. In some alternatives, a ligand binding domain, includes without limitation, receptors or portions thereof, small peptides, peptidomimetics, substrates, cytokines, and the like. In some alternatives, the ligand binding domain is an antibody or fragment thereof, preferably a binding fragment thereof, any of which may be humanized. A nucleic acid sequence coding for an antibody or antibody fragment can readily be determined. In a specific alternative, the polynucleotide codes for a scFv that specifically binds CD19. In other specific alternatives, the polynucleotide codes for a single chain Fv that specifically binds HER2, CE7, hB7H3, or EGFR and, optionally, said polynucleotide encodes a humanized version thereof. The sequences of these antibodies and binding domains thereof are known to or can readily be determined by those of skill in the art. In some alternatives, the polynucleotide codes for a single scFv that specifically binds with CD19, CD20, CD22, EGFRvIII, EGFR, EphA2, IL13Ra2, L1CAM, oaGD2, Her2, B7H3, CD33, Mesothelin, ROR-1, FITC or VAR2CSA.

Tumor antigens are proteins that are produced by tumor cells that elicit an immune response. The selection of the ligand binding domain of the invention will depend on the type of cancer to be treated, and can target tumor antigens or other tumor cell surface molecules. A tumor sample from a subject can be characterized for the presence of certain biomarkers or cell surface markers. For example, breast cancer cells from a subject can be positive or negative for each of Her2Neu, Estrogen receptor, and/or the Progesterone receptor. A tumor antigen or cell surface molecule that is found on the individual subject's tumor cells is selected. Tumor antigens and cell surface molecules are well known in the art and include, for example, carcinoembryonic antigen (CEA), prostate specific antigen, PSMA, Her2/neu, estrogen receptor, progesterone receptor, ephrinB2, CD19, CD20, CD22, CD23, CD123, CS-1, CE7, hB7H3, ROR1, mesothelin, c-Met, GD-2, and/or MAGE A3 TCR. In some alternatives, the tumor antigen or tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR and/or any combinations thereof. In some alternatives, a target molecule is a cell surface molecule that is found on tumor cells and is not substantially found on normal tissues, or restricted in its expression to non-vital normal tissues.

In some alternatives, the target is CD19, CD20, CD22, EGFRvIII, EGFR, EphA2, IL13Ra2, L1CAM, oaGD2, GD2, Her2, B7H3, CD33, Mesothelin, ROR-1, FITC, and/or VAR2CSA.

In one alternative, the target molecule on the tumor comprises one or more epitopes associated with a malignant tumor. Malignant tumors express a number of proteins that can serve as target antigens for T cell receptor or chimeric receptor mediated recognition. Other target molecules belong to the group of cell transformation-related molecules such as the oncogene HER-2/Neu/ErbB2. In some alternatives, the tumor antigen is selectively expressed or overexpressed on the tumor cells as compared to control cells of the same tissue type. In other alternatives, the tumor antigen is a cell surface polypeptide.

Once a tumor cell surface molecule that may be targeted with a chimeric receptor is identified, an epitope of the target molecule is selected and characterized. Antibodies that specifically bind a tumor cell surface molecule can be prepared using methods of obtaining monoclonal antibodies, methods of phage display, methods to generate human or humanized antibodies, or methods using a transgenic animal or plant engineered to produce human antibodies. Phage display libraries of partially or fully synthetic antibodies are available and can be screened for an antibody or fragment thereof that can bind to the target molecule. Phage display libraries of human antibodies are also available. In some alternatives, antibodies specifically bind to a tumor cell surface molecule and do not cross react with nonspecific components such as bovine serum albumin or other unrelated antigens. Once identified, the amino acid sequence or polynucleotide sequence coding for the antibody can be isolated and/or determined.

Antibodies or antigen binding fragments include all or a portion of polyclonal antibodies, a monoclonal antibody, a human antibody, a humanized antibody, a synthetic antibody, a chimeric antibody, a bispecific antibody, a minibody, and a linear antibody. "Antibody fragments" has its plain and ordinary meaning when read in light of the specification, and may be used, for example, to described a portion of an intact antibody, preferably the antigen binding or variable region of the intact antibody and can readily be prepared. Examples of antibody fragments include Fab, Fab', F(ab')2, and Fv fragments; diabodies; linear antibodies; single-chain antibody molecules; and multispecific antibodies formed from antibody fragments. In some alternatives, the antibody fragments are Fab, Fab', F(ab')2, and Fv fragments; diabodies; linear antibodies; single-chain antibody molecules; or multispecific antibodies formed from antibody fragments. Any of such aforementioned antibodies or antibody fragments can be humanized and used with the compositions and methods described herein.

In some alternatives, a number of different antibodies that bind to a particular tumor cell surface molecule can be isolated and characterized. In some alternatives, the antibodies are characterized based on epitope specificity of the targeted molecule. In addition, in some cases, antibodies that bind to the same epitope can be selected based on the affinity of the antibody for that epitope. In some alternatives, an antibody has an affinity of at least 1 mM, and preferably <50 nM. In some alternatives, the antibody has an affinity of 50 nM, 100 nM, 200 nM, 300 nM 400 nM, 500 nM, 1 uM, 100 uM, 200 uM, 300 uM, 400 uM, 500 uM, 600 uM, 700 uM, 800 uM, 900 uM or 1 mM or an affinity within a range defined by any two of the aforementioned values. In some alternatives, an antibody is selected that has a higher affinity for the epitope, as compared to other antibodies. For example, an antibody is selected that has at least a 2 fold, at least a 5 fold, at least a 10 fold, at least a 20 fold, at least a 30 fold, at least a 40 fold, or at least a 50 fold greater affinity than a reference antibody that binds to the same epitope or an affinity that is greater than a reference antibody within a range defined by any two of the aforementioned values.

In some alternatives, target molecules are CD19, CD20, CD22, CD23, CE7, hB7H3, EGFR, CD123, CS-1, ROR1, mesothelin, Her2, c-Met, PSMA, GD-2, or MAGE A3 TCR or any combination thereof. In some alternatives, the antibody or binding fragment there of specific for these target molecules is humanized.

In specific alternatives, the target antigen is CD19, CD20, CD22, EGFRvIII, EphA2, L13Ra2, oaGD2, GD2, CD33, Mesothelin, ROR-1, and/or VAR2CSA. A number of antibodies specific for CD19, CD20, CD22, EGFRvIII, EphA2, L13Ra2, oaGD2, GD2, CD33, Mesothelin, ROR-1 and/or VAR2CSA are known to those of skill in the art and can be readily characterized for sequence, epitope binding, and affinity. The disclosure also contemplates variable regions that have at least 90%, 91%, 92%, 93%, 94%, 95%, 96%, 97%, 98%, or 99% amino acid sequence identity to that of the scFv for CD19, CD20, CD22, EGFRvIII, EphA2, IL13Ra2, oaGD2, GD2, CD33, Mesothelin, ROR-1 and/or VAR2CSA.

"Humanized antibodies," has its plain and ordinary meaning when read in light of the specification, and may be used, for example, and may refer to antibodies from non-human species whose protein sequences have been modified to increase their similarity to antibody variants produced naturally in humans. The process of "humanization" can be applied to monoclonal antibodies developed for administration to humans (for example, antibodies developed as anticancer drugs). Humanization can be desirable when the process of developing a specific antibody involves utilization of a non-human immune system (such as that in mice). The protein sequences of antibodies produced in this way are partially distinct from homologous antibodies occurring naturally in humans, and are therefore potentially immunogenic when administered to human patients. Humanized antibodies are distinct from chimeric antibodies, in that they have the protein sequences made more similar to human antibodies but can carry a larger stretch of non-human protein. A derivative of a humanized antibody can refer to a segment of an antibody or sequence that is derived from a humanized antibody. In some alternatives, the ligand binding domain comprises a humanized antibody or portion thereof. In some alternatives, the ligand binding domain comprises a scFv. In some alternatives, the scFv is a humanized scFv.

In some alternatives, the scFv binds specifically to CD19, CD22, CD20, B7H3 receptor, L1CAM, EGFR, EGFRVIII, EphA2, FITC(E2), GD2, Her2, IL13R2a (hu08) VlVh, IL13Ra2, IL13Ra2, oaGD2, ROR1, CD33, Mesothelin, and/or VAR2CSA.

Humanization can be desirable in some alternatives for reducing the immunogenicity of monoclonal antibodies that are derived from xenogeneic sources, such as, for example, rodents. Humanization is also desirable in some alternatives so as to improve the interaction of the antibody or a fragment thereof with the human immune system. Due to the development of hybridoma technology, a large number of xenogeneic antibodies are highly immunogenic in humans, which can ultimately limit their clinical applications especially when administration may need to be repeated. Additionally, they can be rapidly removed from the circulation and can cause systemic inflammatory effects as well. Therefore, humanization strategies are desirable in some alternatives to circumvent these situations. Techniques for antibody humanization are known to those skilled in the art.

In some alternatives, a polynucleotide coding for a ligand binding domain is operably linked to a polynucleotide coding for a spacer region. In some alternatives, the polynucleotide coding for a ligand binding domain can also have one or more restriction enzyme sites at the 5' and/or 3' ends of the coding sequence in order to provide for easy excision and replacement of the polynucleotide with another polynucleotide coding for a ligand binding domain coding for a different antigen or that has different binding characteristics. For example, a restriction site, NheI, is encoded upstream of the leader sequence; and a 3' RsrII located within the hinge region allows subcloning of any desirable scFv into a chimeric receptor vector. In some alternatives, the polynucleotide is codon optimized for expression in mammalian cells, such as humans. Subcloning into a restriction site of a desired vector is a technique that is appreciated by those skilled in the art.

In some alternatives, the polynucleotide coding for a ligand binding domain is operably linked to a signal peptide.

In some alternatives, the signal peptide is a signal peptide for granulocyte colony stimulating factor. Polynucleotides coding for other signal peptides such as CD8 alpha can be utilized. In some alternatives, the polynucleotide codes for CD8 alpha.

In some alternatives, the polynucleotide coding for a ligand binding domain is operably linked to a promoter. A promoter is selected that provides for expression of the chimeric antigen receptor in a mammalian cell, such as a human cell. In a specific alternative, the promoter is an inducible promoter.

Spacer

In some alternatives, the chimeric receptor nucleic acid comprises a polynucleotide coding for a spacer region. Typically, a spacer region is found between the ligand binding domain and the transmembrane domain of the chimeric receptor. In some alternatives, a spacer region provides for flexibility of the ligand binding domain and allows for high expression levels in lymphocytes. For example, a CD19-specific chimeric receptor having a spacer domain of 229 amino acids had less antitumor activity than a CD19-specific chimeric receptor with a short spacer region comprised of the modified IgG4 hinge only. In some alternatives, the spacer is optimized for increased T cell proliferation and/or cytokine production in response to the ligand as compared to a reference chimeric receptor.

In some alternatives, a spacer region has at least 10 to 229 amino acids, 10 to 200 amino acids, 10 to 175 amino acids, 10 to 150 amino acids, 10 to 125 amino acids, 10 to 100 amino acids, 10 to 75 amino acids, 10 to 50 amino acids, 10 to 40 amino acids, 10 to 30 amino acids, 10 to 20 amino acids, or 10 to 15 amino acids, or a length within a range defined by any two of the aforementioned lengths. In some alternatives, a spacer region has 12 amino acids or less, 119 amino acids or less, or 229 amino acids or less but greater than 1 or 2 amino acids. In some alternatives, the spacer is optimized for increased T cell proliferation and/or cytokine production in response to the ligand as compared to a reference chimeric receptor.

In some alternatives, the spacer region is derived from a hinge region of an immunoglobulin molecule. In some alternatives, a spacer region comprises all or a portion of the hinge region from a human IgG1, human IgG2, a human IgG3, or a human IgG4, and can contain one or more amino acid substitutions. In some alternatives, a portion of the hinge region includes the upper hinge amino acids found between the variable heavy chain and the core, and the core hinge amino acids including a polyproline region. In some alternatives, the spacer is optimized for increased T cell proliferation and/or cytokine production in response to the ligand as compared to a reference chimeric receptor.

In some alternatives, a short spacer region has 12 amino acids or less and comprises all or a portion of a IgG4 hinge region sequence or variant thereof, an intermediate spacer region has 119 amino acids or less and comprises all or a portion of a IgG4 hinge region sequence and a CH3 region or variant thereof, and a long spacer has 229 amino acids or less but not zero and comprises all or a portion of a IgG4 hinge region sequence, a CH2 region, and a CH3 region or variant thereof. In some alternatives, a short spacer region has 1, 2, 3, 4, 5, 6, 7, 8, 9, 10, 11 or 12 amino acids or a size within a range defined by any two of the aforementioned amino acid lengths. In some alternatives, a medium spacer region has 13, 20, 30, 40, 50, 60, 70, 80, 90, 100, 110 or 119 amino acids or a size within a range defined by any two of the aforementioned amino acid lengths. In some alternatives, a spacer region has 120, 130, 140, 150, 160, 170, 180, 190, 200, 210 or 219 amino acids or a size within a range defined by any two of the aforementioned amino acid lengths.

A polynucleotide coding for a spacer region can be readily prepared by synthetic or recombinant methods from the amino acid sequence. In some alternatives, a polynucleotide coding for a spacer region is operably linked to a polynucleotide coding for a transmembrane region. In some alternatives, the polynucleotide coding for the spacer region can also have one or more restriction enzyme sites at the 5' and/or 3' ends of the coding sequence in order to provide for easy excision and replacement of the polynucleotide with another polynucleotide coding for a different spacer region. In some alternatives, the polynucleotide coding for the spacer region is codon optimized for expression in mammalian cells, such as human cells.

In an alternative, the spacer region is a hinge region sequence from IgG1, IgG2, IgG3, or IgG4 or a portion thereof, a hinge region sequence from IgG1, IgG2, IgG3, or IgG4 in combination with all or a portion of a CH2 region or variant thereof, a hinge region sequence from IgG1, IgG2, IgG3, or IgG4 in combination with all or a portion of a CH3 region or variant thereof, and a hinge region sequence from IgG1, IgG2, IgG3, or IgG4 in combination with all or a portion of a CH2 region or variant thereof, and/or a CH3 region or variant thereof. In some alternatives, a short spacer region is a modified IgG4 hinge sequence having 12 amino acids or less but greater than one or two amino acids, an intermediate sequence is a IgG4 hinge sequence with a CH3 sequence having 119 amino acids or less but greater than one or two amino acids; or a IgG4 hinge sequence with a CH2 and CH3 region having 229 amino acids or less but greater than one or two amino acids.

Transmembrane Domain.

In some alternatives, the chimeric receptor nucleic acid comprises a polynucleotide coding for a transmembrane domain. The transmembrane domain provides for anchoring of the chimeric receptor in the membrane.

In an alternative, the transmembrane domain that naturally is associated with one of the domains in the chimeric receptor is used. In some cases, the transmembrane domain can be selected or modified by amino acid substitution to avoid binding of such domains to the transmembrane domains of the same or different surface membrane proteins to minimize interactions with other members of the receptor complex.

The transmembrane domain can be derived either from a natural or a synthetic source. When the source is natural, the domain can be derived from any membrane-bound or transmembrane protein.

Transmembrane regions in some alternatives comprise at least the transmembrane region(s) of the alpha, beta or zeta chain of the T-cell receptor, CD28, CD3, CD45, CD4, CD8, CD9, CD16, CD22; CD33, CD37, CD64, CD80, CD86, CD134, CD137 and/or CD154.

A transmembrane domain can be synthetic or a variant of a naturally occurring transmembrane domain. In some alternatives, synthetic or variant transmembrane domains comprise predominantly hydrophobic residues such as leucine and valine, for example. In some alternatives, a transmembrane domain can have at least 80%, 85%, 90%, 95%, or 100% amino acid sequence identity with a transmembrane domain as set forth in SEQ ID NO: 110-113 or an amino acid sequence identity that is within a range defined by any two of the aforementioned values. Variant transmembrane domains preferably have a hydrophobic score of at least 50 as calculated by Kyte Doolittle.

A polynucleotide coding for a transmembrane domain can be readily prepared by synthetic or recombinant methods. In some alternatives, a polynucleotide coding for a transmembrane domain is operably linked to a polynucleotide coding for an intracellular signaling region. In some alternatives, the polynucleotide coding for a transmembrane domain can also have one or more restriction enzyme sites at the 5' and/or 3' ends of the coding sequence in order to provide for easy excision and replacement of the polynucleotide coding for a transmembrane domain with another polynucleotide coding for a different transmembrane domain. In some alternatives, the polynucleotide coding for a transmembrane domain is codon optimized for expression in mammalian cells, such as human cells.

Intracellular Signaling Domain.

In some alternatives, the chimeric receptor nucleic acid comprises a polynucleotide coding for an intracellular signaling domain. The intracellular signaling domain provides for activation of one function of the transduced cell expressing the chimeric receptor upon binding to the ligand expressed on tumor cells. In some alternatives, the intracellular signaling domain contains one or more intracellular signaling domains. In some alternatives, the intracellular signaling domain is a portion of and/or a variant of an intracellular signaling domain that provides for activation of at least one function of the transduced cell.

Examples of intracellular signaling domains for use in a chimeric receptor of the disclosure include the cytoplasmic sequences of the CD3 zeta chain, and/or co-receptors that act in concert to initiate signal transduction following chimeric receptor engagement, as well as any derivative or variant of these sequences and any synthetic sequence that has the same functional capability. T cell activation can be said to be mediated by two distinct classes of cytoplasmic signaling sequence: those that initiate antigen-dependent primary activation and provide a T cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner can contain signaling motifs, which are known as receptor tyrosine-based activation motifs or ITAMs. Examples of ITAM containing primary cytoplasmic signaling sequences suitable for use with alternatives described herein include those derived from CD3 zeta, FcR gamma, CD3 gamma, CD3 delta, CD3 epsilon, CD5, CD22, CD79a, CD79b, and/or CD66d.

In a preferred alternative, the intracellular signaling domain of the chimeric receptor can be designed to comprise the CD3-zeta signaling domain by itself or combined with any other desired cytoplasmic domain(s). For example, the intracellular signaling domain of the chimeric receptor can comprise a CD3zeta chain and a costimulatory signaling region.

The costimulatory signaling region refers to a portion of the chimeric receptor comprising the intracellular domain of a costimulatory molecule. A costimulatory molecule is a cell surface molecule other than an antigen receptor or their ligands that is required for a response of lymphocytes to an antigen. Examples of such molecules suitable for use in the alternatives described herein include CD27, CD28, 4-1BB (CD 137), OX40, CD30, CD40, lymphocyte function-associated antigen-1 (LFA-1), CD2, CD7, LIGHT, NKG2C, B7-H3, zeta chain associated protein kinase (ZAP70), and/or a ligand that specifically binds with CD83.

The intracellular signaling sequences of the chimeric receptor can be linked to each other in a random or specified order. In some alternatives, a short oligo- or polypeptide linker, preferably between 2 and 10 amino acids in length, such as 2, 3, 4, 5, 6, 7, 8, 9, or 10 amino acids in length, can form the linkage. In one alternative, the intracellular signaling domains comprises all or a portion of the signaling domain of CD3-zeta or variant thereof and all or a portion of the signaling domain of CD28 or a variant thereof. In another alternative, the intracellular signaling domain comprises all or a portion of the signaling domain of CD3-zeta or variant thereof and all or a portion of the signaling domain of 4-1BB or variant thereof. In yet another alternative, the intracellular signaling domain comprises all or a portion of the signaling domain of CD3-zeta or variant thereof, all or a portion of the signaling domain of CD28 or variant thereof, and all or a portion of the signaling domain of 4-1BB or variant thereof. In a specific alternative, the amino acid sequence of the intracellular signaling domain comprises a variant of CD3zeta and a portion of the 4-1BB intracellular signaling domain.

In an alternative, a polynucleotide coding for an intracellular signaling domain comprises a 4-1BB intracellular domain linked to a portion of a CD3zeta domain. In other alternatives, a 4-1BB intracellular domain and a CD28 intracellular domain are linked to a portion of a CD3 zeta domain.

In some alternatives, the intracellular domain is encoded by a sequence set forth in SEQ ID NO: 114. In some alternatives, the intracellular domain is encoded by a sequence set forth in SEQ ID NO: 116. In some alternatives, the intracellular domain is encoded by a sequence set forth in SEQ ID NO: 118. In some alternatives, the intracellular domain comprises an amino acid sequence set forth in SEQ ID NO: 115. In some alternatives, the intracellular domain comprises an amino acid sequence set forth in SEQ ID NO: 117. In some alternatives, the intracellular domain comprises an amino acid sequence set forth in SEQ ID NO: 119.

A polynucleotide coding for an intracellular signaling domain can be readily prepared by synthetic or recombinant methods from the amino acid sequence. In some alternatives, the polynucleotide coding for an intracellular signaling domain can also have one or more restriction enzyme sites at the 5' and/or 3' ends of the coding sequence in order to provide for easy excision and replacement of the polynucleotide coding for an intracellular signaling domain with another polynucleotide coding for a different intracellular signaling domain. In some alternatives, the polynucleotide coding for an intracellular signaling domain is codon optimized for expression in mammalian cells. In some alternatives, the mammalian cells are human cells.

Marker Sequences.

In some alternatives, the system further comprises one or more marker sequences under the control of an inducible promoter. A marker sequence can provide for selection of transduced cells, and/or identification of transduced cells. In some alternatives, the marker sequence is for a selection of transduced cells and/or identification of transduced cells. In some alternatives, the marker sequence is operably linked to a polynucleotide sequence coding for a linker sequence. In some alternatives, the linker sequence is a cleavable linker sequence. In some alternatives, the linker is 2A linker such as, for example, T2A, P2A or F2A. In some alternatives, the linker is a cleavable T2A linker.

A number of different marker sequences can be employed. Typically, a marker sequence has a functional characteristic that allows for selection of transduced cells and/or detection of transduced cells. In some alternatives, the marker sequence is compatible with transduction of human lymphocytes. In some alternatives, the marker sequence allows for selection of transduced cells and/or detection of transduced cells.

The positive selectable marker can be a gene, which upon being introduced into the host cell, expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5, which codes for resistance to the antibiotic G418, the double mutant of the dihydrofolate reductase (DHFR) gene, which provides resistance to methotrexate, DHFR dm. Transduced cells cultured in the presence of these agents will survive and be selected.

In an alternative, a first nucleic acid further comprises a polynucleotide coding for a marker sequence. In an alternative, the marker sequence is a truncated epidermal growth factor receptor (EGFRt). In some alternatives, the marker sequence is a truncated Her2 sequence (Her2t). Selectable marker sequences that can be used in the alternatives set forth in this disclosure are provided below.

Selectable Marker Sequences

EGFRt nucleotide sequence:
(SEQ ID NO: 30)
Atgcttctcctggtgacaagccttctgctctgtgagttaccacacccagca
ttcctcctgatcccacgcaaagtgtgtaacggaataggtattggtgaattt
aaagactcactctccataaatgctacgaatattaaacacttcaaaaactgc
acctccatcagtggcgatctccacatcctgccggtggcatttaggggtgac
tccttcacacatactcctcctctggatccacaggaactggatattctgaaa
accgtaaaggaaatcacagggtttttgctgattcaggcttggcctgaaaac
aggacggacctccatgcctttgagaacctagaaatcatacgcggcaggacc
aagcaacatggtcagttttctcttgcagtcgtcagcctgaacataacatcc
ttgggattacgctccctcaaggagataagtgatggagatgtgataatttca
ggaaacaaaaatttgtgctatgcaaatacaataaactggaaaaaactgttt
gggacctccggtcagaaaaccaaaattataagcaacagaggtgaaaacagc
tgcaaggccacaggccaggtctgccatgccttgtgctcccccgagggctgc
tggggcccggagcccagggactgcgtctcttgccggaatgtcagccgaggc
agggaatgcgtggacaagtgcaaccttctggagggtgagccaagggagttt
gtggagaactctgagtgcatacagtgccacccagagtgcctgcctcaggcc
atgaacatcacctgcacaggacggggaccagacaactgtatccagtgtgcc
cactacattgacggcccccactgcgtcaagacctgcccggcaggagtcatg
ggagaaaacaacaccctggtctggaagtacgcagacgccggccatgtgtgc
cacctgtgccatccaaactgcacctacggatgcactgggccaggtcttgaa
ggctgtccaacgaatgggcctaagatcccgtccatcgccactgggatggtg
ggggccctcctcttgctgctggtggtggccctggggatcggcctcttcatg
tga;

EGFRt amino acid sequence:
(SEQ ID NO: 31)
MLLLVTSLLLCELPHPAFLLIPRKVCNGIGIGEFKDSLSINATNIKHFKNC
TSISGDLHILPVAFRGDSFTHTPPLDPQELDILKTVKEITGFLLIQAWPEN -continued RTDLHAFENLEIIRGRTKQHGQFSLAVVSLNITSLGLRSLKEISDGDVIIS
GNKNLCYANTINWKKLFGTSGQKTKIISNRGENSCKATGQVCHALCSPEGC
WGPEPRDCVSCRNVSRGRECVDKCNLLEGEPREFVENSECIQCHPECLPQA
MNITCTGRGPDNCIQCAHYIDGPHCVKTCPAGVMGENNTLVWKYADAGHVC
HLCHPNCTYGCTGPGLEGCPTNGPKIPSIATGMVGALLLLLVVALGIGLF
M;

Her2t nucleotide sequence:
(SEQ ID NO: 32)
Atgcttctcctggtgacaagccttctgctctgtgagttaccacacccagca
ttcctcctgatcccatgccaccctgagtgtcagccccagaatggctcagtg
acctgttttggaccggaggctgaccagtgtgtggcctgtgcccactataag
gaccctcccttctgcgtggcccgctgccccagcggtgtgaaacctgacctc
tcctacatgcccatctggaagtttccagatgaggagggcgcatgccagcct
tgccccatcaactgcacccactcctgtgtggacctggatgacaagggctgc
cccgccgagcagagagccagccctctgacgtccatcatctctgcggtggtt
ggcattctgctggtcgtggtcttgggggtggtctttgggatcctcatctg
a;

Her2t amino acid sequence:
(SEQ ID NO: 33)
MLLLVTSLLLCELPHPAFLLIPCHPECQPQNGSVTCFGPEADQCVACAHYK
DPPFCVARCPSGVKPDLSYMPIWKFPDEEGACQPCPINCTHSCVDLDDKGC
PAEQRASPLTSITSAVVGILLVVVLGVVFGILI;

Her2tG nucleotide sequence:
(SEQ ID NO: 34)
Atgcttctcctggtgacaagccttctgctctgtgagttaccacacccagca
ttcctcctgatcccatgccaccctgagtgtcagccccagaatggctcagtg
acctgttttggaccggaggctgaccagtgtgtggcctgtgcccactataag
gaccctcccttctgcgtggcccgctgccccagcggtgtgaaacctgacctc
tcctacatgcccatctggaagtttccagatgaggagggcgcatgccagcct
tgccccatcaactgcacccactcctgtgtggacctggatgacaagggctgc
cccgccgagcagagagccagcccgttaacgggtggaggcagcggaggtggc
tccatcatctctgcggtggttggcattctgctggtcgtggtcttgggggtg
gtattgggatcctcatctga;

Her2tG amino acid sequence:
(SEQ ID NO: 35)
MLLLVTSLLLCELPHPAFLLIPCHPECQPQNGSVTCFGPEADQCVACAHYK
DPPFCVARCPSGVKPDLSYMPIWKFPDEEGACQPCPINCTHSCVDLDDKGC
PAEQRASPLTGGGSGGGSIISAVVGILLVVVLGVVFGILI;

CD19t nucleotide sequence:
(SEQ ID NO: 36)
Atgccacctcctcgcctcctcttcttcctcctcttcctcacccccatggaa
gtcaggcccgaggaacctctagtggtgaaggtggaagagggagataacgct
gtgctgcagtgcctcaaggggacctcagatggccccactcagcagctgacc
tggtctcgggagtccccgcttaaacccttcttaaaactcagcctggggctg
ccaggcctgggaatccacatgaggcccctggccatctggcttttcatcttc -continued aacgtctctcaacagatggggggcttctacctgtgccagccggggcccccc
tctgagaaggcctggcagcctggctggacagtcaatgtggagggcagcggg
gagctgttccggtggaatgtttcggacctaggtggcctgggctgtggcctg
aagaacaggtcctcagagggccccagctccccttccgggaagctcatgagc
cccaagctgtatgtgtgggccaaagaccgccctgagatctgggagggagag
cctccgtgtgtcccaccgagggacagcctgaaccagagcctcagccaggac
ctcaccatggcccctggctccacactctggctgtcctgtggggtaccccct
gactctgtgtccaggggccccctctcctggacccatgtgcaccccaagggg
cctaagtcattgctgagcctagagctgaaggacgatcgcccggccagagat
atgtgggtaatggagacgggtctgttgttgccccgggccacagctcaagac
gctggaaagtattattgtcaccgtggcaacctgaccatgtcattccacctg
gagatcactgctcggccagtactatggcactggctgctgaggactggtggc
tggaaggtctcagctgtgactttggcttatctgatcttctgcctgtgttcc
cttgtgggcattcttcatcttcaaagagccctggtcctgaggaggaaaaga
taa;

CD19t amino acid sequence:
(SEQ ID NO: 37)
MPPPRLLFFLLFLTPMEVRPEEPLVVKVEEGDNAVLQCLKGTSDGPTQQLT
WSRESPLKPFLKLSLGLPGLGIHMRPLAIWLFIFNVSQQMGGFYLCQPGPP
SEKAWQPGWTVNVEGSGELFRWNVSDLGGLGCGLKNRSSEGPSSPSGKLMS
PKLYVWAKDRPEIWEGEPPCVPPRDSLNQSLSQDLTMAPGSTLWLSCGVPP
DSVSRGPLSWTHVHPKGPKSLLSLELKDDRPARDMWVMETGLLLPRATAQD
AGKYYCHRGNLTMSFHLEITARPVLWHWLLRTGGWKVSAVTLAYLIFCLCS
LVGILHLQRALVLRRKR DHFRdm nucleotide sequence:
(SEQ ID NO: 38)
Atggttggttcgctaaactgcatcgtcgctgtgtcccagaacatgggcatc
ggcaagaacggggacttcccctggccaccgctcaggaatgaatccagatat
ttccagagaatgaccacaacctcttcagtagaaggtaaacagaatctggtg
attatgggtaagaagacctggttctccattcctgagaagaatcgacctttta
aagggtagaattaatttagttctcagcagagaactcaaggaacctccacaa
ggagctcatttttctttccagaagtctagatgatgccttaaaacttactgaa
caaccagaattagcaaataaagtagacatggtctggatagttggtggcagt
tctgtttataaggaagccatgaatcacccaggccatcttaaactatttgtg
acaaggatcatgcaagactttgaaagtgacacgtttttttccagaaattgat
ttggagaaatataaacttctgccagaatacccaggtgttctctctgatgtc
caggaggagaaaggcattaagtacaaatttgaagtatatgagaagaatga
t;
and DHFRdm amino acid sequence:
(SEQ ID NO: 39)
VGSLNCIVAVSQNMGIGKNGDFPWPPLRNESRYFQRMTTTSSVEGKQNLVI
MGKKTWFSIPEKNRPLKGRINLVLSRELKEPPQGAHFLSRSLDDALKLTEQ
PELANKVDMVWIVGGSSVYKEAMNHPGHLKLFVTRIMQDFESDTFFPEIDL
EKYKLLPEYPGVLSDVQEEKGIKYKFEVYEKND.

DNA spacer sequence:
(SEQ ID NO: 120)
Gctagcgtttaaacttaagcttggtaccgagctcggatccgccacc.
The DNA spacer sequence may be described also as the 7xHBD/mE1B_DNA spacer.

In some alternatives herein, the DNA spacer, a 46 base pair sequence, may reside in between the 7×HBD/mE1B promoter and inducible transgene. The DNA spacer which comprises SEQ ID NO: 120, allows enhanced gene expression of the transgene. In some alternatives herein, a vector construct comprising a DNA spacer between a promoter and a transgene showed an increase in transcription of the transgene as compared to a vector that had the promoter and the transgene without a DNA spacer. In some alternatives herein, the DNA spacer enhanced transgene expression as compared to a vector that did not have a DNA spacer between the promoter and the transgene. In some alternatives, a DNA spacer is between the mE1B promoter and the transgene.

In some alternatives, the polynucleotide coding for the marker sequence is operably linked to a polynucleotide coding for a linker sequence. In some alternatives, the linker is a 2A linker, such as, for example, T2A, P2A, E2A or F2A.

A polynucleotide coding for marker sequence can be readily prepared by synthetic or recombinant methods from the amino acid sequence. In some alternatives, a polynucleotide coding for a marker sequence is operably linked to a polynucleotide coding for an intracellular signaling domain. In some alternatives, the polynucleotide coding for a marker sequence can also have one or more restriction enzyme sites at the 5' and/or 3' ends of the coding sequence in order to provide for easy excision and replacement of the polynucleotide coding for a marker sequence with another polynucleotide coding for a different marker sequence. In some alternatives, the polynucleotide coding for a marker sequence is codon optimized for expression in mammalian cells, preferably humans.

In some alternatives, two or more marker sequences can be employed. In some alternatives, a first marker sequence is under control of a constitutive promoter and provides for an indication that the transduced cell is expressing the transgene. In other alternatives, a second marker sequence is under the control of the inducible promoter and provides an indication that the transgene expression has been induced. In some alternatives, the marker under the control of the inducible promoter can be used to select for cells in which noninduced or basal expression is much lower than in other cells by selecting cells that have a lower expression of the marker sequence under the control of the inducible promoter and expand those cells for further applications. In some alternatives, the transgene encodes a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity. In some alternatives, the transgene encodes a protein that modulates T cells. In some alternatives, the transgene encodes a chimeric antigen receptor.

Other Genetic Components Under Control of Inducible Promoter.

In some alternatives, the first nucleic acid comprises a polynucleotide sequence coding for genes that promote survival and proliferation, genes that prevent apoptosis, and/or genes that inhibit negative checkpoint signaling under the control of an inducible promoter. Such genes include genes encoding IL-2, IL-7, IL-15, chemokine receptors, Bcl2, CA-Akt, dn-TGFbetaRIII, dn-SHP1/2, PD-1-IFNalpha and/or PD-1CD28 chimeras. These genes are also placed under the control of an inducible promoter as described herein. In some alternatives, the genes encode IL-2, IL-7, IL-15, chemokine receptors, chimeric cytokine receptors, Bcl2, CA-Akt, dn-TGFbetaRII, dn-SHP1/2, PD-1-IFNalpha, and/or PD-1CD28 chimeras. In some alternatives, the gene that modulates checkpoint signaling encodes a polypeptide that inhibits negative checkpoint regulators. In some alternatives, the negative checkpoint regulator comprises PD-1, VISTA, LAG-3 and/or TIM3.

In some alternatives, a first nucleic acid comprises a first inducible promoter linked to a polynucleotide coding for a cytokine, chemokine receptor, or chimeric cytokine receptor. chemokines, also referred to as chemotactic cytokines, are a group of structurally related proteins that regulate cell trafficking of lymphocytes. In some alternatives, the chemokines are homeostatic or inflammatory. Chemokine receptors include CCR2, CCR7, or CCR15. Cytokines include interleukins such as IL2, IL-12, IL-7, and/or Il-15, interferons, such as interferon 6, tumor necrosis factor, and a TLR4 agonist. Chimeric cytokine receptors can also include CCR (CD122). In some alternatives, the chemokine receptors comprise CCR2, CCR7, and/or CCR15. In some alternatives, the chemokine receptors include CCR2, CCR7, or CCR15. In some alternatives, the cytokines include interleukins, wherein the interleukins are 1L2, IL-12, IL-7 and/or 11-15 or interferons, wherein the interferons comprise interferon 6, tumor necrosis factor, or a TLR4 agonist.

In some alternatives, a first nucleic acid comprises a first inducible promoter linked to a polynucleotide coding for a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttct-caaggaccaccgcatctctacattcaagaactggcccttcttggag ggctgcgcctgcaccccggagcggatggccgaggctggcttcatccactgccc-cactgagaacgagccagacttggcccagtgttt cttctgcttcaaggagctg-gaaggctgggagccagatgacgaccccatagaggaacataaaaagcat-tcgtccggttgcgctttccttt ctgtcaagaagcagtttgaagaattaacccttggtgaatttt-gaaactggacagagaaagagccaagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD).

In some alternatives, a first nucleic acid comprises a first inducible promoter linked to a polynucleotide coding for a polypeptide that modulates checkpoint signaling. Such genes include dn-TGFbetaRII, dn-SHP1/2, PD-1-IFNalpha, and/or PD-1CD28 chimeras. In some alternatives, the polypeptide is dn-TGFbetaRII, dn-SHP1/2, PD-1-IFNalpha, and/or PD-1CD28 chimeras. In some alternatives, the polypeptide that modulates checkpoint signaling inhibits negative checkpoint regulators. In some alternatives, the negative checkpoint regulator comprises PD-1, VISTA, LAG-3 and/or TIM3.

Any number of nucleic acids can be placed under the control of an inducible promoter including those coding for chimeric antigen receptor, a marker sequences, a cytokine, a chemokine, an inhibitor of apoptosis, and/or an inhibitor of negative checkpoint signaling. In some alternatives, one or more inducible promoters can be utilized to provide for an adequate expression level of each of the nucleic acids. In some alternatives, constructs can be prepared with a gene such as a cytokine under the control of an inducible promoter and a construct comprising a chimeric antigen receptor under the control of a constitutive promoter. Such constructs are useful to provide for cell survival and proliferation of transduced cells, for example lymphocytes expressing a chimeric antigen receptor.

In the systems provided herein, the systems are inducible by an amount of the drug that is less than a comparable system utilizing a wild type HEA3 chimeric transcription factor or a wild type HEA4 chimeric transcription factor.

In some alternatives, HEA3 comprises two amino acid mutations, wherein the sequence is encoded by a sequence set forth in SEQ ID NO: 122 (atggtgtccaagctgtcccagctgca-gacagaactgctggcagcactgctggaaagcggcctgagcaaagaggccct-gattcagg cactcggcgaacctggaccttatctgctcgctggcgaaggccctctg-gataagggcgagagctgtggcggaggaagaggagagct ggccgagctgcctaacggcctgggcgagacaagaggcagcgaggacga-gacagacgacgacggcgaggacttcacccccccc atcctgaaagagctg-gaaaacctgagccccgaggaagccgcccaccagaaagccgtggtgga-gacactgctgcaggaagatccc tggcgggtcgccaagatggtcaagagctacctgcagcagcacaa-catcccccagcgggaggtggtggacaccaccggcctgaac cagagccacct-gagccagcacctgaacaagggcacccccat-gaaaacccagaagagagccgccctgtacacttggtacgtgcgg aagcagagagaggtggcccagcagtttacacacgccggccagggcggcct-gatcgaggaacctaccggcgacgagctgcccac caagaagggcagacg-gaaccggtttaagtggggccctgcatctcagcagatcctgttccaggcc-tacgagcggcagaagaacccc agcaaagaggaacgggagacactggtggaagagtgcaaccgggccgagtg-catccagagaggcgtgagcccttctcaggctcag ggcctcggcagcaatctggt-caccgaagtgcgggtgtacaattggttcgccaaccggcggaaagag-gaagccttccggcacaagct gtctgctggcgatatgagagccgccaacctgtggcccagcccccctgatgat-caagcggagcaagaagaacagcctggccctgagc ctgaccgccgatca-gatggtgtccgctctgctggacgccgagccccctatcctgta-cagcgagtacgaccccaccagacccttcagc gaggccagcatgatgggcctgctgaccaacctggccgaccgggagctggtgca-catgatcaactgggccaagcgggtgcccggc ttcgtggacctgaccctgcacgaccaggtccacctgctggaatgtgcctggctg-gaaatcctgatgatcggcctcgtgtggagaagc atg-gaacaccccggcaagctgctgttcgcccccaacctgctcctggaccg-gaaccagggaaagtgcgtggagggcatggtggaga tcttcgacatgctgctggccacctccagccggttccggatgat-gaacctgcagggcgaggaattcgtgtgcctgaagtccatcatcct gct-gaacagcggcgtgtacaccttcctgtcatccaccctgaagtccctg-gaagagaaggaccacatccaccgggtgctggacaaga tcaccgacaccctgatccacctgatggc-caaggctggcctgacactccagcagcagcaccagagactggcccagctgctgct-gatc ctgagccacatccggcacatgagcaacaagcggatggaacacctgta-cagcatgaagtgcaagaacgtggtgcccctgtacgacct gctgctcgagatgctggatgcccacagactgcacgcccctacaagcagaggcg-gagccagcgtggaggaaaccgaccagtctca cctggc-caccgccggcagcacaagcagccacagcctgcagaagtactacat-caccggcgaggccgagggattccctgccaccgt ggagttccagtacctgcccgacaccgacgaccggcaccggatcgag-gaaaagcggaagcggacctacgagacattccagagcat catgaagaagtccccttcagcggccccaccgatccca- gacccccccctagaagaatcgccgtgcccagcagatctagcgccagc gtgcccaagcctgccccccagccctaccctttcaccagcagcctgagcaccat- caactacgacgagttccctaccatggtgttcccca gcggcca- gatctctcaggcctctgctctggcacctgctc- cacctcaggtgctgcctcaggcccctgctccagccccagcccctgccat ggtgtctgcactggcccaggctccagctcctgtgcctgtgctggcccctggacctc ctcaggctgtggcccctcctgcccctaaacct acccaggccggggagg- gaacactgtctgaggccctgctgcagctccagttcgacgacgaggatctgg- gagcactgctgggcaata gcaccgaccccgccgtgtt- taccgacctggcctccgtggacaacagcgagttccagcagctcctcaaccagggc atccctgtcgcc ccacacaccaccgagcccatgctgatggaataccccgaggc- catcaccagactggtcacaggcgcccagaggcctccagatccag caccagctc- cactgggagcccctggcctgcctaatgggctgctgtctggcgacgaggactt cgagagcattgccgacatggacttca gcgccctgctgtcccagatcagcagc). In some alternatives, the HEA3 comprises an amino acid sequence set forth in SEQ ID NO: 121 (MVSKLSQLQ- TELLAALLESGLSKEALIQALGEPGPYLLAGEG- PLDKGESCGGGRGEL AELPNGLGETRGSEDE- TDDDGEDFTPPILKELENLSPEEAAHQKAVVETLLQE DPWR VAKMVK- SYLQQHNIPQREVVDTTGLNQSHLSQHLNKGTPMKT QKRAALYTWYVR KQREVAQQFTHAGQG- GLIEEPTGDELPTKKGRRNRFKWGPASQQILFQAY- ERQKNP SKEERETLVEECNRAECIQRGVSP- SQAQGLGSNLVTEVRVYNWFANRRKEEAFRHK LSAGDMRAANLWPSPLMIKRSKKNSLALSL- TADQMVSALLDAEPPILYSEYDPTRPF SEA- SMMGLLTNLADRELVHMIN- WAKRVPGFVDLTLHDQVHLLECAWLEILMIGLV WRSMEHPGKLLFAPNLLLDRNQGKCVEGMVE- IFDMLLATSSRFRMMNLQGEEFVC LKSIILLNSGVYT- FLSSTLKSLEEKDHIHRVLDKITDTLIHLMAK- AGLTLQQQHQRLA QLLLILSHIRHMSNKRMEH- LYSMKCKNVVPLYDLLLEMLDAHRLHAPTSRG- GASVE ETDQSHLATAGSTSSHSLQKYYITGEAE- GFPATVEFQYLPDTDDRHRIEEKRKRTYET FQSSIMKKSPFSGPTDPRPPPRRIAVPSRSSAS- VPKPAPQPYPFTSSLSTINYDEFPTMVFP SGQ- ISQASALAPAPPQVLPQAPAPAPA- PAMVSALAQAPAPVPVLAPGPPQAVAPPAP KPTQAGEGTLSEALLQLQFDDEDLGALLGNSTD- PAVFTDLASVDNSEFQQLLNQGIP VAPH- TTEPMLMEYPEAITRLVTGAQRPPDPAPAPL- GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3.

Constitutive Promoter Systems.

In other alternatives, a system comprises a second nucleic acid that comprises a constitutive promoter or a second inducible promoter linked to a transcriptional activator. In other alternatives, a system comprises a second nucleic acid that comprises a promoter linked to a transcriptional activator. In some alternatives, the promoter is a constitutive promoter or an inducible promoter. In some alternatives, a constitutive promoter includes EF1α promoter, actin promoter, the myosin promoter, the hemoglobin promoter, and the creatine kinase promoter. In some alternatives, viral promoters such as the CMV promoter are excluded. In some alternatives, the constitutive promoter can be linked to one or more of a polynucleotide coding for marker, or a chimeric antigen receptor as described herein.

Constitutive Promoters.

A constitutive promoter provides for continuous gene expression of the gene under the control of the promoter. In some alternatives, the constitutive promoter is a promoter that provides for gene expression in a lentiviral construct and/or in lymphocytes. In some alternatives, the promoter is not derived from a xenogenic source such as a plant or a virus.

In a specific alternative, the constitutive promoter comprises EF1α promoter, actin promoter, the myosin promoter, the hemoglobin promoter, and/or the creatine kinase promoter. In some alternatives, viral promoters such as the CMV promoter are excluded.

Transcriptional Activators.

In some alternatives, the constitutive promoter is operably linked to a transcriptional activator. In some alternatives, the transcriptional activator activates an inducible promoter in the presence of the inducer (e.g. drug).

In some alternatives, an inducible promoter is induced in the presence of a transcriptional activator. In some alternatives, the transcriptional activator preferentially binds to the promoter in the presence of the drug. In some alternatives, the transcriptional activator is TamR-tf (HEA3 or HEA4). Modification of the transcriptional activator can be made in the amino acid sequence that can affect the ability of an activator to bind to the drug, the promoter, or both. For example, binding in the ER ligand binding domain would affect the binding of the drug to the transcriptional activator. In some alternatives, HEA3 comprises two amino acid mutations, wherein the sequence is encoded by a sequence set forth in SEQ ID NO: 122 (atggtgtccaagctgtcccagctgca- gacagaactgctggcagcactgctggaaagcggcctgagcaaagaggccct- gattcagg cactcggcgaacctggaccttatctgctcgctggcgaaggccctctg- gataagggcgagagctgtggcggaggaagaggagagct ggccgagctgcctaacggcctgggcgagacaagaggcagcgaggacga- gacagacgacgacggcgaggacttcacccccccc atcctgaaagagctg- gaaaacctgagccccgaggaagccgcccaccagaaagccgtggtgga- gacactgctgcaggaagatccc tggcgggtcgccaagatggtcaagagctacctgcagcagcacaa- catcccccagcgggaggtggtggacaccaccggcctgaac cagagccacct- gagccagcacctgaacaagggcacccccat- gaaaacccagaagagagccgccctgtacacttggtacgtgcgg aagcagagagaggtggcccagcagtttacacacgccggccagggcggcct- gatcgaggaacctaccggcgacgagctgcccac caagaagggcagacg- gaaccggtttaagtggggccctgcatctcagcagatcctgttccaggcc- tacgagcggcagaagaacccc agcaaagaggaacgggagacactggtggaagagtgcaaccgggccgagtg- catccagagaggcgtgagcccttctcaggctcag ggcctcggcagcaatctggt- caccgaagtgcgggtgtacaattggttcgccaaccggcggaaagag- gaagccttccggcacaagct gtctgctggcgatatgagagccgccaacctgtggcccagccccctgatgat- caagcggagcaagaagaacagcctggccctgagc ctgaccgccgatca- gatggtgtccgctctgctggacgccgagccccctatcctgta- cagcgagtacgaccccaccagacccttcagc gaggccagcatgatgggcctgctgaccaacctggccgaccgggagctggtgca- catgatcaactgggccaagcgggtgcccggc ttcgtggacctgaccctgcacgaccaggtccacctgctggaatgtgcctggctg- gaaatcctgatgatcggcctcgtgtggagaagc atg- gaacaccccggcaagctgctgttcgcccccaacctgctcctggaccg- gaaccagggaaagtgcgtggagggcatggtggaga tcttcgacatgctgctggccacctccagccggttccggatgat- gaacctgcagggcgaggaattcgtgtgcctgaagtccatcatcct gct- gaacagcggcgtgtacaccttcctgtcatccaccctgaagtccctg- gaagagaaggaccacatccaccgggtgctggacaaga tcaccgacaccctgatccacctgatggc- caaggctggcctgacactccagcagcagcaccagagactggcccagctgctgct- gatc ctgagccacatccggcacatgagcaacaagcggatggaacacctgtacagcatgaagtgcaagaacgtggtgcccctgtacgacct gctgctcgagatgctggatgcccacagactgcacgcccctacaagcagaggcg-gagccagcgtggaggaaaccgaccagtctca cctggc-caccgccggcagcacaagcagccacagcctgcagaagtactacat-caccggcgaggccgagggattccctgccaccgt ggagttccagtacctgcccgacaccgacgaccggcaccggatcgag-gaaaagcggaagcggacctacgagacattccagagcat cat-gaagaagtccccttcagcggccccaccgatccca-gacccccccctagaagaatcgccgtgcccagcagatctagcgccagc gtgcccaagcctgccccccagccctaccctttcaccagcagcctgagcaccat-caactacgacgagttccctaccatggtgttcccca gcggcca-gatctctcaggcctctgctctggcacctgctc-cacctcaggtgctgcctcaggcccctgctccagccccagcccctgccat ggtgtctgcactggcccaggctccagctcctgtgcctgtgctggcccctggacctc ctcaggctgtggcccctcctgcccctaaacct acccaggccggggagg-gaacactgtctgaggccctgctgcagctccagttcgacgacgaggatctgg-gagcactgctgggcaata gcaccgaccccgccgtgtt-taccgacctggcctccgtggacaacagcgagttccagcagctcctcaaccagggc atccctgtcgcc ccacacaccaccgagcccatgctgatggaatacccgaggc-catcaccagactggtcacaggcgcccagaggcctccagatccag caccagctc-cactgggagcccctggcctgcctaatgggctgctgtctggcgacgagga cttcgagagcattgccgacatggacttca gcgccctgctgtccca-gatcagcagc). In some alternatives, the HEA3 comprises an amino acid sequence set forth in SEQ ID NO: 121 (MVSK-LSQLQTELLAALLESGLSKEALIQALGEPGPYL-LAGEGPLDKGESCGGGRGEL AELPNGLGETRGSE-DETDDDGEDFTPPILKELENLSPEEAAHQKAVVETLL QEDPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKRMEH-LYSMKCKNVVPLYDLLLEMLDAHRLHAPTSRG-GASVE ETDQSHLATAGSTSSHSLQKYYITGEAE-GFPATVEFQYLPDTDDRHRIEEKRKRTYET FQSSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3.

In some alternatives, the system employs a synthetic transcriptional activator which, in the presence of the drug (e.g. tamoxifen), binds a synthetic promoter upstream of a transgene to induce expression. In some alternatives, it is a variant of a wild type "TamR-tf" HEA3 transcription factor. In some alternatives, it is a variant of a wild type "TamR-tf" HEA4 transcription factor. An exemplary amino acid sequence is provided in SEQ ID NO: 1 (MVSKLSQLQ-TELLAALLESGLSKEALIQALGEPGPYLLAGEG-PLDKGESCGGGRGEL AELPNGLGETRGSEDE-TDDDGEDFTPPILKELENLSPEEAAHQKAVVETLLQE DPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKRMEH-LYSMKCKNVVPLYDLLLEMLDAHRLHAPTSRG-GASVE ETDQSHLATAGSTSSHSLQKYYITGEAE-GFPATVEFQYLPDTDDRHRIEEKRKRTYET FKSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFSSIADM DFSALLSQISS). The mutant tamoxifen-specific ligand binding domain of the estrogen receptor ligand binding domain (ER-LBD) is found at amino acids 282-595 of the HEA3 and has a mutation at position 521 (SEQ ID NO: 1; MVSKLSQLQTEL-LAALLESGLSKEALIQALGEPGPYLLAGEG-PLDKGESCGGGRGEL AELPNGLGETRGSEDE-TDDDGEDFTPPILKELENLSPEEAAHQKAVVETLLQE DPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKRMEH-LYSMKCKNVVPLYDLLLEMLDAHRLHAPTSRG-GASVE ETDQSHLATAGSTSSHSLQKYYITGEAE-GFPATVEFQYLPDTDDRHRIEEKRKRTYET FKSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFSSIADM DFSALLSQISS). The p65 activation domain of NF-κB (p65 or TAD) is found at amino acids 596 to 862. SEQ ID NO: 1 comprises one point mutation in the ER-LBD that ablates binding to endogenous estrogen, but confers nanomolar specificity to 4-OHT, fulvestrant and other estrogen analogs. In some alternatives, HEA3 comprises two amino acid mutations, wherein the sequence is encoded by a sequence set forth in SEQ ID NO: 122 (atggtgtccaagctgtcccagctgca- gacagaactgctggcagcactgctggaaagcggcctgagcaaagaggccct- gattcagg cactcggcgaacctggaccttatctgctcgctggcgaaggccctctg- gataagggcgagagctgtggcggaggaagaggagagct ggccgagctgcctaacggcctgggcgagacaagaggcagcgaggacga- gacagacgacgacggcgaggacttcaccccccc atcctgaaagagctg- gaaaacctgagccccgaggaagccgcccaccagaaagccgtggtgga- gacactgctgcaggaagatccc tggcgggtcgccaagatggtcaagagctacctgcagcagcacaa- catcccccagcgggaggtggtggacaccaccggcctgaac cagagccacct- gagccagcacctgaacaagggcaccccccat- gaaaacccagaagagagccgccctgtacacttggtacgtgcgg aagcagagagaggtggcccagcagtttacacacgccggccagggcggcct- gatcgaggaacctaccggcgacgagctgcccac caagaagggcagacg- gaaccggtttaagtggggccctgcatctcagcagatcctgttccaggcc- tacgagcggcagaagaacccc agcaaagaggaacgggagacactggtggaagagtgcaaccgggccgagtg- catccagagaggcgtgagcccttctcaggctcag ggcctcggcagcaatctggt- caccgaagtgcgggtgtacaattggttcgccaaccggcggaaagag- gaagccttccggcacaagct gtctgctggcgatatgagagccgccaacctgtggcccagcccccctgatgat- caagcggagcaagaagaacagcctggccctgagc ctgaccgccgatca- gatggtgtccgctctgctggacgccgagccccctatcctgta- cagcgagtacgaccccaccagacccttcagc gaggccagcatgatgggcctgctgaccaacctggccgaccgggagctggtgca- catgatcaactgggccaagcgggtgcccggc ttcgtggacctgaccctgcacgaccaggtccacctgctggaatgtgcctggctg- gaaatcctgatgatcggcctcgtgtggagaagc atg- gaacacccccggcaagctgctgttcgcccccaacctgctcctggaccg- gaaccagggaaagtgcgtggagggcatggtggaga tcttcgacatgctgctggccacctccagccggttccggatgat- gaacctgcagggcgaggaattcgtgtgcctgaagtccatcatcct gct- gaacagcggcgtgtacaccttcctgtcatccaccctgaagtccctg- gaagagaaggaccacatccaccgggtgctggacaaga tcaccgacaccctgatccacctgatggc- caaggctggcctgacactccagcagcagcaccagagactggcccagctgctgct- gatc ctgagccacatccggcacatgagcaacaagcggatggaacacctgta- cagcatgaagtgcaagaacgtggtgcccctgtacgacct gctgctcgagatgctggatgcccacagactgcacgcccctacaagcagaggcg- gagccagcgtggaggaaaccgaccagtctca cctggc- caccgccggcagcacaagcagccacagcctgcagaagtactacat- caccggcgaggccgagggattccctgccaccgt ggagttccagtacctgcccgacaccgacgaccggcaccggatcgag- gaaaagcggaagcggacctacgagacattccagagcat cat- gaagaagtccccttcagcggccccaccgatccca- gaccccccccctagaagaatcgccgtgcccagcagatctagcgccagc gtgcccaagcctgccccccagccctaccctttcaccagcagcctgagcaccat- caactacgacgagttccctaccatggtgttcccca gcggcca- gatctctcaggcctctgctctggcacctgctc- cacctcaggtgctgcctcaggcccctgctccagccccagcccctgccat ggtgtctgcactggcccaggctccagctcctgtgcctgtgctggcccctggacctc ctcaggctgtggcccctcctgcccctaaacct acccaggccggggagg- gaacactgtctgaggccctgctgcagctccagttcgacgacgaggatctgg- gagcactgctgggcaata gcaccgaccccgccgtgtt- taccgacctggcctccgtggacaacagcgagttccagcagctcctcaaccagggc atccctgtcgcc ccacacaccaccgagcccatgctgatggaatacccccgaggc- catcaccagactggtcacaggcgcccagaggcctccagatccag caccagctc- cactgggagcccctggcctgcctaatgggctgctgtctggcgacgag gacttcgagagcattgccgacatggacttca gcgccctgctgtccca- gatcagcagc). In some alternatives, the HEA3 comprises an amino acid sequence set forth in SEQ ID NO: 121 (MVSK- LSQLQTELLAALLESGLSKEALIQALGEPGPYL- LAGEGPLDKGESCGGGRGEL AELPNGLGETRGSE- DETDDDGEDFTPPILKELENLSPEEAAHQKAVVETLL QEDPWR VAKMVK- SYLQQHNIPQREVVDTTGLNQSHLSQHLNKGTPMKT QKRAALYTWYVR KQREVAQQFTHAGQG- GLIEEPTGDELPTKKGRRNRFKWGPASQQILFQAY- ERQKNP SKEERETLVEECNRAECIQRGVSP- SQAQGLGSNLVTEVRVYNWFANRRKEEAFRHK LSAGDMRAANLWPSPLMIKRSKKNSLALSL- TADQMVSALLDAEPPILYSEYDPTRPF SEA- SMMGLLTNLADRELVHMIN- WAKRVPGFVDLTLHDQVHLLECAWLEILMIGLV WRSMEHPGKLLFAPNLLLDRNQGKCVEGMVE- IFDMLLATSSRFRMMNLQGEEFVC LKSIILLNSGVYT- FLSSTLKSLEEKDHIHRVLDKITDTLIHLMAK- AGLTLQQQHQRLA QLLLILSHIRHMSNKRMEH- LYSMKCKNVVPLYDLLLEMLDAHRLHAPTSRG- GASVE ETDQSHLATAGSTSSHSLQKYYITGEAE- GFPATVEFQYLPDTDDRHRIEEKRKRTYET FQSIMKKSPFSGPTDPRPPPRRIAVPSRSSAS- VPKPAPQPYPFTSSLSTINYDEFPTMVFP SGQ- ISQASALAPAPPQVLPQAPAPAPA- PAMVSALAQAPAPVPVLAPGPPQAVAPPAP KPTQAGEGTLSEALLQLQFDDEDLGALLGNSTD- PAVFTDLASVDNSEFQQLLNQGIP VAPH- TTEPMLMEYPEAITRLVTGAQRPPDPAPAPL- GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3.

Additional changes can be made to the transcriptional activator to increase the properties of the transcription factor including, without limitation, altering one or more amino acids in the estrogen receptor ligand binding domain and/or altering one or more amino acids in the p65 transactivating domain. Altering amino acids in the estrogen receptor binding domain can provide for more specific and sensitive binding of the drug to the transcriptional activator. For example, mutations are made at amino acid position 400, 543, and 544 of SEQ ID NO: 4 (SEQ ID NO: 4; MVSK- LSQLQTELLAALLESGLSKEALIQALGEPGPYL- LAGEGPLDKGESCGGGRGEL AELPNGLGETRGSE- DETDDDGEDFTPPILKELENLSPEEAAHQKAVVETLL QEDPWR VAKMVK- SYLQQHNIPQREVVDTTGLNQSHLSQHLNKGTPMKT QKRAALYTWYVR KQREVAQQFTHAGQG- GLIEEPTGDELPTKKGRRNRFKWGPASQQILFQAY- ERQKNP SKEERETLVEECNRAECIQRGVSP- SQAQGLGSNLVTEVRVYNWFANRRKEEAFRHK LSAGDMRAANLWPSPLMIKRSKKNSLALSL- TADQMVSALLDAEPPILYSEYDPTRPF SEA- SMMGLLTNLADRELVHMIN- WAKRVPGFVDLTLHDQVHLLECAWLEILMIGLV WRSMEHPVKLLFAPNLLLDRNQGKCVEGMVE- IFDMLLATSSRFRMMNLQGEEFVC LKSIILLNSGVYT- FLSSTLKSLEEKDHIHRVLDKITDTLIHLMAK- AGLTLQQQHQRLA QLLLILSHIRHMSNKGMEHLYSMKCKNVVPLYDLL- LEAADAHRLHAPTSRGGASVE ETDQSHLATAGST- SSHSLQKYYITGEAE- GFPATVEFQYLPDTDDRHRIEEKRKRTYET FKSIMKKSPFSGPTDPRPPPRRIAVPSRSSAS- VPKPAPQPYPFTSSLSTINYDEFPTMVFP SGQ- ISQASALAPAPPQVLPQAPAPAPA- PAMVSALAQAPAPVPVLAPGPPQAVAPPAP KPTQAGEGTLSEALLQLQFDDEDLGALLGNSTD- PAVFTDLASVDNSEFQQLLNQGIP VAPHTTEPMLMEYPEAITRLVTGAQRPPDPAPAPLGAPGLPNGLLSGDEDFSSIADM DFSALLSQISS). SEQ ID NO: 4 comprises the sequence of wild-type HEA4 containing three point mutations (G400V, M543A, L544A) in the ER-LBD that ablate binding to endogenous estrogen, and confer higher sensitivity to 4-hydroxytamoxifen, fulvestrant, and estrogen analogs compared to wild-type HEA3. The transcriptional activator with altered sequence has increased affinity for tamoxifen or 4-OHT. Altering amino acids in the p65 transactivating domain can provide for increased expression of the transgene in the absence of activation of the transduced cells. In some alternatives, the transgene encodes a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity. In some alternatives, the transgene encodes a protein that modulates T cells. In some alternatives, the transgene encodes a chimeric antigen receptor.

Marker

In some alternatives, the constitutive promoter is operably linked to a polynucleotide coding for a marker polypeptide. Such marker polypeptides are described herein, and include EGFRt, Her2t, and/or DHFRdm.

In some alternatives, the marker is encoded by a sequence set forth in SEQ ID NO's: 30, 32, 34, 36 or 38. In some alternatives, the marker comprises an amino acid sequence set forth in SEQ ID NO's: 31, 33, 35, 37 or 39.

Chimeric Antigen Receptor

In some alternatives, the constitutive promoter is operably linked to a polynucleotide coding for a chimeric antigen receptor. In some alternatives, the chimeric antigen receptor comprises a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; a polynucleotide coding for a transmembrane domain; and a polynucleotide coding for an intracellular signaling domain. In some alternatives, the spacer is optimized to provide for increased T cell proliferation and/or cytokine production in response to the ligand as compared to a reference chimeric receptor.

Vectors

A variety of vector combinations can be constructed to provide for efficiency of transduction and transgene expression. In some alternatives, the vector is a dual packaged or single (all in one) viral vector. In other alternatives, the vectors can include a combination of viral vectors and plasmid vectors. Other viral vectors include foamy virus, adenoviral vectors, retroviral vectors, and lentiviral vectors. In some alternatives, the vector is a lentiviral vector. In some alternatives, the vector is a foamy viral vector, adenoviral vectors, retroviral vectors or lentiviral vectors.

In some alternatives, a plasmid vector or a viral vector comprises a first nucleic acid comprising an inducible promoter linked to a polynucleotide coding for a chimeric antigen receptor. In some alternatives, a plasmid vector or viral vector comprises a first nucleic acid sequence comprising a polynucleotide coding for a gene that enhances cell survival or proliferation, a gene that regulates apoptosis, and/or a gene that modulates checkpoint signaling. In some alternatives, the modulation of checkpoint signaling inhibits negative checkpoint regulators. In some alternatives, the negative checkpoint regulator comprises PD-1, VISTA, LAG-3 and/or TIM3. Such polynucleotides code for a cytokine, a chimeric cytokine receptor, or a chemokine receptor. In some alternatives, a plasmid vector or a viral vector comprises a first nucleic acid comprising an inducible promoter linked to a polynucleotide coding for a marker sequence. In some alternatives, the marker sequence is compatible with transduction of human lymphocytes. In some alternatives, the marker sequence allows for selection of transduced cells and/or detection of transduced cells. In some alternatives, the marker is a gene that can include inter alia, hygromycin-B phosphotransferase gene (hph), which confers resistance to hygromycin B, the amino glycoside phosphotransferase gene (neo or aph) from Tn5, which codes for resistance to the antibiotic G418, the mutated dihydrofolate reductase (DHFR) gene, which provides resistance to methotrexate, DHFRdm, the pac gene that provides resistance to puromycin, Sh ble gene, which inactivates zeocin, the adenosine deaminase gene (ADA), and/or the multi-drug resistance (MDR) gene. A first nucleic acid can include a number of different polynucleotide sequences all under the control of the inducible promoter. For example, a polynucleotide coding for a chimeric antigenic receptor can be linked to a polynucleotide coding for a marker polypeptide and/or a polynucleotide coding for cytokine or chemokine receptor. In some alternatives, a gene is under the control of the inducible promoter. In some alternatives, the gene encodes a chimeric cytokine receptor.

In some alternatives, a lentiviral vector comprises a second nucleic acid comprising a constitutive promoter linked to a nucleic acid sequence coding for transcriptional activator that binds to drug and activates expression of an inducible promoter. In some alternatives, a lentiviral vector with a constitutive promoter can also include a nucleic acid sequence including a marker gene, piggybac transposase, and/or a polynucleotide coding for a chimeric antigen receptor. Each element of the nucleic acid can be separated from one another with a sequence such as a T2A self-cleaving sequence. In some alternatives, the elements of the nucleic acid are separated from one another with a sequence self-cleaving sequence. In some alternatives, the self-cleaving sequence is a 2A linker. In some alternatives, the linker is T2A, P2A, E2A or F2A.

In other alternatives, the heterogeneous (heterogeneous to the vector, e,g, lentiviral vector) nucleic acid sequence is limited by the amount of additional genetic components that can be packaged in the vector. In some alternatives, a construct contains at least two genes heterogenous to the viral vector. In some alternatives, the construct contains no more than 4 genes heterogenous to the viral vector. The number of genes heterogenous to the viral vector that can be packaged in the vector can be determined by detecting the expression of one or more transgenes, and selecting vector constructs that provide for transduction of at least 10% of the cells and/or detectable expression levels of the transgene in at least 10% of the cells. In some alternatives, the transgene encodes a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity. In some alternatives, the transgene encodes a protein that modulates T cells. In some alternatives, the transgene encodes a chimeric antigen receptor.

In some alternatives, a lentivirus is a dual packaged virus. A dual packaged virus contains at least one conditional construct comprising an inducible promoter operably linked to a polynucleotide coding for a chimeric antigen receptor. Optionally the conditional construct comprises a marker gene, a nucleic acid for a cytokine, a nucleic acid for a chimeric cytokine receptor, a nucleic acid for a chemokine receptor. In some alternatives, a dual packaged lentivirus contains a constitutive construct comprising a constitutive promoter. In an alternative, the constitutive construct comprises a constitutive promoter linked to a transcriptional activator for the inducible promoter. In some alternatives, the constitutive construct also includes a marker gene and/or a polynucleotide encoding a cytokine or chemokine. In some alternatives of a system with two constructs, each construct can be packaged in a separate viral vector and the viral vectors can be mixed together for transduction in a cell population.

When the constitutive and conditional constructs both contain a marker gene, the marker gene on each construct is the same or different from one another. In some alternatives, when the constitutive and conditional constructs both contain a polynucleotide coding for a chimeric antigen receptor, the chimeric antigen receptor can be targeted to the same antigen but have different ligand binding domains, can be targeted to the same antigen but different epitopes, or can be targeted to different antigens.

In some alternatives, the vector is a minicircle. Minicircles are episomal DNA vectors that are produced as circular expression cassettes devoid of any bacterial plasmid DNA backbone. Their smaller molecular size enables more efficient transfections and offers sustained expression over a period of weeks as compared to standard plasmid vectors that only work for a few days. In some alternatives, a minicircle contains a drug inducible promoter linked to a polynucleotide coding for a chimeric antigen receptor. In some alternatives, the inducible promoter can be linked to chemokine receptor, a marker gene, and/or a cytokine. One or more minicircles can be employed. In some alternatives, a minicircle comprises an inducible promoter linked to a polynucleotide coding for a first chimeric antigen receptor, another minicircle comprises an inducible promoter linked to a polynucleotide coding for a second and different chimeric antigen receptor, and/or a minicircle comprises an inducible promoter linked to a polynucleotide coding for a chemokine receptor, a chimeric antigen receptor, and a marker gene. Each element of the constructs is separated by a nucleic acid, such as that coding for a self-cleaving T2A sequence. In some alternatives, each element of the constructs is separated by a nucleic acid, such as that coding for a self-cleaving T2A sequence. In some alternatives, each minicircle differs from one another in the chimeric antigen receptor including but not limited to the spacer length and sequence, the intracellular signaling domain, and/or the marker sequence. The minicircle vector can be used with a constitutive lentivirus vector coding for a transcriptional activator for the inducible promoter. In some alternatives, the minicircle vector is used with a constitutive lentivirus vector coding for a transcriptional activator for the inducible promoter. In the systems provided herein, the systems are inducible by an amount of the drug that is less than a comparable system utilizing a wild type HEA3 chimeric transcription factor or a wild type HEA4 chimeric transcription factor.

In some alternatives, the vector is a piggy bac transposon. The PiggyBac (PB) transposon is a mobile genetic element that efficiently transposes between vectors and chromosomes via a "cut and paste" mechanism. During transposition, the PB transposase recognizes transposon-specific inverted terminal repeat sequences (ITRs) located on both ends of the transposon vector and efficiently moves the contents from the original sites and efficiently integrates them into TTAA chromosomal sites. The powerful activity of the PiggyBac transposon system enables genes of interest between the two ITRs in the PB vector to be easily mobilized into target genomes.

In some alternatives, a PB contains a drug inducible promoter linked to a polynucleotide coding for a chimeric antigen receptor. In some alternatives, the inducible promoter can be linked to chemokine receptor, a marker gene, and/or a cytokine. One or more PB transposons can be employed. In some alternatives, a PB comprises an inducible promoter linked to a polynucleotide coding for a first chimeric antigen receptor, another PB comprises an inducible promoter linked to a polynucleotide coding for a second and different chimeric antigen receptor, and/or a PB comprises an inducible promoter linked to a polynucleotide coding for a chemokine receptor, a chimeric antigen receptor, and a marker gene. Each element of the constructs is separated by a nucleic acid, such as that coding for a self-cleaving T2A sequence. In some alternatives, each PB differs from one another in the chimeric antigen receptor including but not limited to the spacer length and sequence, the intracellular signaling domain, and/or the marker sequence. The PB vector can be used with a constitutive lentivirus vector coding for a transcriptional activator for the inducible promoter and constitutive vector comprising the piggyback transposase linked to a constitutive promoter.

Some alternatives concern a first nucleic acid comprising a first promoter inducible by a drug, wherein the first nucleic acid is operably linked to a polynucleotide coding for chimeric antigen receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte; a polynucleotide coding for a polypeptide spacer, wherein the spacer is optimized; and a polynucleotide coding for an intracellular signaling domain; and a second nucleic acid comprising a second constitutive or inducible promoter operably linked to nucleic acid coding for a transcriptional activator for the inducible promoter. In some alternatives, the first and second nucleic acid are in a single lentivirus vector. In some alternatives, the spacer is optimized for increased T cell proliferation and/or cytokine production in response to the ligand as compared to a reference chimeric receptor. In some alternatives, the first nucleic acid further comprises a marker gene. In some alternatives, the second nucleic acid further comprises polynucleotide coding for a second and different chimeric antigen receptor. The first and second chimeric antigen receptor can differ from one another in the ligand binding domain, the target antigen, an epitope of the target antigen, the spacer domain in length and sequence (short medium or long), and in the intracellular signaling domains. In some alternatives, in a single lentivirus construct the first and second nucleic acids can be separated by a genomic insulator nucleic acid such as the sea urchin insulator chromatin domain. In other alternatives, the inducible promoter of the first nucleic acid and the constitutive promoter of the second nucleic acid are in opposite orientation. One or more of these vectors can be used in conjunction with one another to transduce target cells and provide for inducible expression of a chimeric antigen receptor.

Host Cells and Compositions: T Lymphocyte Populations.

The compositions described herein provide for genetically modified host cells with the vectors and/or constructs as described herein. In some alternatives, the host cells are CD4+ and/or CD8+T lymphocytes.

T lymphocytes can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques or variations thereof that will be apparent to those skilled in the art. In some alternatives, the T cells are autologous T cells obtained from the patient.

For example, the desired T cell population or subpopulation can be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). The non-dividing feeder cells can comprise gamma-irradiated PBMC feeder cells. In some alternatives, the PBMC are irradiated with gamma rays in the range of 3000 to 3600 rads to prevent cell division. In some alternatives, the PBMC are irradiated with gamma rays of 3000, 3100, 3200, 3300, 3400, 3500 or 3600 rads or any value of rads between any two endpoints of any of the listed values to prevent cell division. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least 25 degrees Celsius, preferably at least 30 degrees, more preferably 37 degrees. In some alternatives, the temperature for the growth of human T lymphocytes is 22, 24, 26, 28, 30, 32, 34, 36, 37 degrees Celsius or any other temperature between a range defined by any two endpoints of any of the listed values.

The T lymphocytes expanded include $CD8^+$ cytotoxic T lymphocytes (CTL) and $CD4^+$ helper T lymphocytes that can be specific for an antigen present on a human tumor or a pathogen. In some alternatives, the cells include precursor T cells. In some alternatives, the cells are hematopoietic stem cells.

In some alternatives, the expansion method can further comprise adding non-dividing EBV-transformed lymphoblastoid cells (LCL) as feeder cells. LCL can be irradiated with gamma rays in the range of 6000 to 10,000 rads. In some alternatives, the LCL are irradiated with gamma rays in of 6000, 6500, 7000, 7500, 8000, 8500, 9000, 9500 or 10,000 rads or any amount of rads in between a range defined by any two endpoints of any of the listed values. The LCL feeder cells can be provided in any suitable amount, such as a ratio of LCL feeder cells to initial T lymphocytes of at least 10:1.

In some alternatives, the expansion method can further comprise adding anti-CD3 and/or anti CD28 antibody to the culture medium (e.g., at a concentration of at least 0.5 ng/ml). In some alternatives, the expansion method can further comprise adding IL-2 and/or IL-7 and/or IL-15 to the culture medium (e.g., wherein the concentration of IL-2 is at least 10 units/ml).

After isolation of T lymphocytes both cytotoxic and helper T lymphocytes can be sorted into naïve, memory, and effector T cell subpopulations either before or after expansion.

CD8+ cells can be obtained by using standard methods. In some alternatives, CD8+ cells are further sorted into naïve, central memory, and effector memory cells by identifying cell surface antigens that are associated with each of those types of CD8+ cells. In some alternatives, memory T cells are present in both CD62L+ and CD62L-subsets of CD8+ peripheral blood lymphocytes. PBMC are sorted into CD62L-CD8+ and CD62L+CD8+ fractions after staining with anti-CD8 and anti-CD62L antibodies. In some alternatives, the expression of phenotypic markers of central memory TCM include CD45RO, CD62L, CCR7, CD28, CD3, and/or CD127 and are negative or low for granzyme B. In some alternatives, central memory T cells are CD45RO+, CD62L+, and/or CD8+ T cells. In some alternatives, effector $T_E$ are negative for CD62L, CCR7, CD28, and/or CD127, and positive for granzyme B and/or perforin. In some alternatives, naïve CD8+T lymphocytes are characterized by the expression of phenotypic markers of naïve T cells including CD62L, CCR7, CD28, CD3, CD127, and/or CD45RA.

CD4+T helper cells are sorted into naïve, central memory, and effector cells by identifying cell populations that have cell surface antigens. CD4+ lymphocytes can be obtained by standard methods. In some alternatives, naïve CD4+T lymphocytes are CD45RO−, CD45RA+, CD62L+, and/or CD4+ T cells. In some alternatives, central memory CD4+ cells are CD62L+ and/or CD45RO+. In some alternatives, effector CD4+ cells are CD62L− and/or CD45RO−.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some alternatives, a decrease in expression of one or markers refers to loss of 1 log 10 in the mean fluorescence intensity and/or decrease of percentage of cells that exhibit the marker of at least 20% of the cells, 25% of-the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells or any % between 20 and 100% when compared to a reference cell population. In some alternatives, a cell population positive for one or markers refers to a percentage of cells that exhibit the marker of at least 50% of the cells, 55% of the cells, 60% of the cells, 65% of the cells, 70% of the cells, 75% of the cells, 80% of the cells, 85% of the cells, 90% of the cell, 95% of the cells, or 100% of the cells or any % between 50 and 100% when compared to a reference cell population.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some alternatives, a decrease in expression of one or markers refers to loss of 1 log 10 in the mean fluorescence intensity and/or decrease of percentage of cells that exhibit the marker of at least 20% of the cells, 25% of-the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells or any % between 20 and 100% when compared to a reference cell population. In some alternatives, an increase refers to an increase in mean or median fluorescence intensity and/or to an increase in the number of cells in a cell population that are positive for one or a given marker, such as a population in which s refers to a percentage of cells that exhibit the marker of at least 50% of the cells, 55% of the cells, 60% of the cells, 65% of the cells, 70% of the cells, 75% of the cells, 80% of the cells, 85% of the cells, 90% of the cell, 95% of the cells, or 100% of the cells or any % between 50 and 100% exhibit the marker, e.g., when compared to a reference cell population.

In some alternatives, populations of CD4+ and CD8+ that are antigen specific can be obtained by stimulating naïve or antigen specific T lymphocytes with antigen. For example, antigen-specific T cell lines or clones can be generated to Cytomegalovirus antigens by isolating T cells from infected subjects and stimulating the cells in vitro with the same antigen. Naïve T cells can also be used. Any number of antigens from tumor cells can be utilized as targets to elicit T cell responses. In some alternatives, the adoptive cellular immunotherapy compositions are useful in the treatment of a disease or disorder including a solid tumor, hematologic malignancy, breast cancer or melanoma.

Modification of T Lymphocyte Populations.

In some alternatives, it can be desired to introduce functional genes into the T cells to be used in immunotherapy in accordance with the present disclosure. For example, the introduced gene or genes can improve the efficacy of therapy by promoting the viability and/or function of transferred T cells; or they can provide a genetic marker to permit selection and/or evaluation of in vivo survival or migration; or they can incorporate functions that improve the safety of immunotherapy, for example, by making the cell susceptible to controlled expression of the transgene. This can be carried out in accordance with known techniques that will be apparent to those skilled in the art based upon the present disclosure.

In some alternatives, T cells are modified with a vector coding for drug inducible chimeric receptors as described herein. In some alternatives, the T cells are modified with a vector coding for drug inducible transgenes. In some alternatives, the transgene encodes a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity. In some alternatives, the transgene encodes a protein that modulates T cells. In some alternatives, the transgene encodes a chimeric antigen receptor. In some alternatives, cells are modified with a vector comprising a polynucleotide coding for a chimeric antigen receptor under control of an inducible promoter. In other alternatives, cells are modified with a vector comprising a polynucleotide coding for a cytokine, a chimeric cytokine receptor, chemokine receptor, a gene that regulates apoptosis, or a gene that modulates checkpoint signaling under the control of an inducible promoter. In some alternatives, the T cells are obtained from the subject to be treated, in other alternatives the lymphocytes are obtained from allogeneic human donors, preferably healthy human donors. In some alternatives, the modulation of checkpoint signaling inhibits negative checkpoint regulators. In some alternatives, the negative checkpoint regulator comprises PD-1, VISTA, LAG-3 and/or TIM3.

Chimeric receptors can be constructed with a specificity for any cell surface marker by utilizing antigen binding fragments or antibody variable domains of, for example, antibody molecules. The antigen binding molecules can be linked to one or more cell signaling modules. In some alternatives, cell signaling modules include CD3 transmembrane domains, CD3 intracellular signaling domains, and/or CD28 transmembrane domains. In some alternatives, the intracellular signaling domain comprises a CD28 transmembrane and signaling domain linked to a CD3 zeta intracellular domain. In some alternatives, a chimeric receptor can also include a transduction marker such as EGFRt.

In some alternatives, the same or a different chimeric receptor can be introduced into each of population of CD4+ and/or CD8+T lymphocytes. In some alternatives, the chimeric receptor in each of these populations has a ligand binding domain that specifically binds to the same ligand on the tumor or infected cell or a different antigen or epitope. The cellular signaling modules can differ. In some alternatives, the intracellular signaling domain of the CD8+ cytotoxic T cells is the same as the intracellular signaling domain of the CD4+ helper T cells. In other alternatives, the intracellular signaling domain of the CD8+ cytotoxic T cells is different than the intracellular signaling domain of the CD4+ helper T cells.

In some alternatives, each of the CD4 or CD8 T lymphocytes can be sorted into naïve, central memory, effector memory or effector cells prior to transduction, as described herein. In some alternatives, each of the CD4 or CD8 T lymphocytes can be sorted into naïve, central memory, effector memory, or effector cells after transduction.

As described herein, in some alternatives, naïve CD4+ cells are CD45RO−, CD45RA+, CD62L+, and/or CD4+ positive T cells. In some alternatives, central memory CD4+ cells are CD62L positive and/or CD45RO positive. In some alternatives, effector CD4+ cells are CD62L negative and/or CD45RO positive. Each of these populations can be independently modified with a chimeric receptor.

As described, in some alternatives, memory T cells are present in both CD62L+ and CD62L− subsets of CD8+ peripheral blood lymphocytes. PBMC are sorted into CD62L−CD8+ and CD62L+CD8+ fractions after staining with anti-CD8 and anti-CD62L antibodies. In some alternatives, the expression of phenotypic markers of central memory T cells (TCM) include CD62L, CCR7, CD28, CD3, and/or CD127 and are negative or low for granzyme B. In some alternatives, central memory T cells are CD45RO+, CD62L+, and/or CD8+ T cells. In some alternatives, effector T cells ($T_E$) are negative for CD62L, CCR7, CD28, and/or CD127, and positive for granzyme B and/or perforin. In some alternatives, naïve CD8+T lymphocytes are characterized by CD8+, CD62L+, CD45RO+, CCR7+, CD28+ CD127+, and/or CD45RO+. Each of these populations can be independently modified with a chimeric receptor.

Various transduction techniques have been developed, which utilize recombinant infectious virus particles for gene delivery. This represents a currently preferred approach to the transduction of T lymphocytes of the present invention. The viral vectors, which have been used in this way include virus vectors derived from simian virus 40, adenoviruses, adeno-associated virus (AAV), lentiviral vectors, and/or retroviruses. Thus, gene transfer and expression methods are numerous but essentially function to introduce and express genetic material in mammalian cells. Several of the above techniques have been used to transduce hematopoietic or lymphoid cells, including calcium phosphate transfection, protoplast fusion, electroporation, and infection with recombinant adenovirus, adeno-associated virus and retrovirus vectors. Primary T lymphocytes have been successfully transduced by electroporation and by retroviral or lentiviral infection.

Retroviral and lentiviral vectors provide a highly efficient method for gene transfer into eukaryotic cells. Moreover, retroviral or lentiviral integration takes place in a controlled fashion and results in the stable integration of one or a few copies of the new genetic information per cell.

It is contemplated that overexpression of a stimulatory factor (for example, a lymphokine or a cytokine) can be toxic to the treated individual. Therefore, it is within the scope of the invention to include gene segments that cause the T cells of the invention to be susceptible to negative selection in vivo. By "negative selection" has its plain and ordinary meaning when read in light of the specification, and may be used, for example, when an infused cell is eliminated as a result of a change in the in vivo condition of the individual. The negative selectable phenotype can result from the insertion of a gene that confers sensitivity to an administered agent, for example, a compound. Negative selectable genes are known in the art, and include, inter alia the following: the Herpes simplex virus type I thymidine kinase (HSV-I TK) gene, which confers ganciclovir sensitivity; the cellular hypoxanthine phosphribosyltransferase (HPRT) gene, the cellular adenine phosphoribosyltransferase (APRT) gene, and bacterial cytosine deaminase.

In some alternatives, it can be useful to include in the T cells a positive marker that enables the selection of cells of the negative selectable phenotype in vitro. The positive selectable marker can be a gene that upon being introduced into the host cell expresses a dominant phenotype permitting positive selection of cells carrying the gene. Genes of this type are known in the art, and include, inter alia, hygromycin-B phosphotransferase gene (hph), which confers resistance to hygromycin B, the amino glycoside phosphotransferase gene (neo or aph) from Tn5, which codes for resistance to the antibiotic G418, the double mutant of the dihydrofolate reductase (DHFRdm) gene, the adenosine deaminase gene (ADA), and/or the multi-drug resistance (MDR) gene.

A variety of methods can be employed for transducing T lymphocytes, as is well known in the art. In some alternatives, transduction is carried out using lentiviral vectors.

In some alternatives, CD4+ and CD8+ cells each can separately be modified with an expression vector encoding a chimeric receptor to form defined populations. In some alternatives, cells can be separately modified with a vector comprising a polynucleotide under the control of a constitutive promoter and a vector comprising a polynucleotide coding for a cytokine or chemokine receptor under control of an inducible promoter.

In some alternatives, these cells are further sorted into subpopulations of naïve, central memory and effector cells as described above, by sorting for cell surface antigens unique to each of those cell populations. In addition, CD4+ or CD8+ cell populations can be selected by their cytokine profile or proliferative activities. For example, CD4+T lymphocytes that have enhanced production of cytokines such as IL-2, IL-4, IL-10, TNFα, and/or IFNγ, as compared to sham transduced cells or transduced CD8+ cells when stimulated with antigen can be selected. In other alternatives, naïve or central memory CD4+ T cells that have enhanced production of IL-2 and/or TNFα are selected. Likewise, CD8+ cells that have enhanced IFNγ production are selected, as compared to sham transduced CD8+ cells.

In some alternatives, CD4+ and CD8+ cells are selected that are cytotoxic for antigen bearing cells. In some alternatives, CD4+ are expected to be weakly cytotoxic as compared to CD8+ cells. In a preferred alternative, transduced lymphocytes, such as CD8+ central memory cells, are selected that provide for tumor cell killing in vivo using an animal model established for the particular type of cancer.

In yet other alternatives, transduced chimeric receptor expressing T cells are selected that can persist in vivo using an animal model established for the particular type of cancer. In some alternatives, transduced chimeric receptor CD8+ central memory cells with a short spacer region have been shown to persist in vivo after introduction into the animal for 3 days or more, 10 days or more, 20 days or more, 30 days or more, 40 days or more, or 50 days or more.

The disclosure contemplates that combinations of CD4+ and CD8+ T cells will be utilized in the compositions. In one alternative, combinations of chimeric receptor transduced CD4+ cells can be combined with chimeric receptor transduced CD8+ cells of the same ligand specificity or combined with $CD8^+$ T cells that are specific for a distinct tumor ligand. In other alternatives, chimeric receptor transduced CD8+ cells are combined with chimeric receptor transduced CD4+ cells specific for a different ligand expressed on the tumor. In yet another alternative, chimeric receptor modified CD4+ and CD8+ cells are combined. In some alternatives, CD8+ and CD4+ cells can be combined in different ratios for example, a 1:1 ratio of CD8+ and CD4+, a ratio of 10:1 of CD8+ to CD4+, or a ratio of 100:1 of CD8+ to CD4+, or any other ratio of CD8+ to CD4+ that is between a range defined by any of the listed ratios. In some alternatives, the combined population is tested for cell proliferation in vitro and/or in vivo, and the ratio of cells that provides for proliferation of cells is selected.

After transduction and/or selection for chimeric receptor bearing cells, the cell populations are preferably expanded in vitro until a sufficient number of cells are obtained to provide for at least one infusion into a human subject, typically around $10^4$ cells/kg to $10^9$ cells/kg. In some alternatives, the transduced cells are cultured in the presence of antigen bearing cells, anti CD3, anti CD28, and IL 2, IL-7, IL 15, or IL-21 or any combination thereof.

In some alternatives, CD4+ and CD8+ cells that proliferate in response to cytokine stimulation, antigen or tumor targets in vitro or in vivo are selected. For example, CD4+ or CD8+ transduced cells that proliferate vigorously when stimulated with antiCD3 and/or anti-CD28 are selected. In some alternatives, stimulation of transduced cells provides for enhanced transgene expression in the presence of an inducer (e.g. drug) of those trans genes under the control of an inducible promoter. In some alternatives, the transgene encodes a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity. In some alternatives, the transgene encodes a protein that modulates T cells. In some alternatives, the transgene encodes a chimeric antigen receptor.

Each of the subpopulations of CD4+ and CD8+ cells can be combined with one another. In a specific alternative, modified naïve or central memory CD4+ cells are combined with modified central memory CD8+ T cells to provide a synergistic cytotoxic effect on antigen bearing cells, such as tumor cells.

Compositions.

The disclosure provides for an adoptive cellular immunotherapy composition comprising a genetically modified T lymphocyte cell preparation as described herein. In some alternatives, the T lymphocyte cell preparation comprises CD4+ T cells that have a chimeric receptor comprising an extracellular antibody variable domain specific for a ligand associated with the disease or disorder, a spacer region, a transmembrane domain, and an intracellular signaling domain of a T cell receptor or other receptors under the control of a drug inducible promoter as described herein. In other alternatives, an adoptive cellular immunotherapy composition further comprises a chimeric receptor modified tumor-specific CD8+ cytotoxic T lymphocyte cell preparation that provides a cellular immune response, wherein the cytotoxic T lymphocyte cell preparation comprises CD8+ T cells that have a chimeric receptor comprising an extracellular single chain antibody specific for a ligand associated with the disease or disorder, a spacer region, a transmembrane domain, and an intracellular signaling domain of a T cell receptor under the control of a drug inducible promoter as described herein. In some alternatives, the chimeric receptor modified T cell population of the disclosure can persist in vivo for at least 3 days or longer. In an alternative, each of these populations can be combined with one another or other cell types to provide a composition. In some alternatives, the T cell population can express genes that modulate the T cell function. In some alternatives, the genes encode cytokines, chemokine receptors and proteins that can modulate T cell function.

In some alternatives, the CD4+T helper lymphocyte cell is naïve CD4+ T cells, central memory CD4+ T cells, effector memory CD4+ T cells, or bulk CD4+ T cells. In some alternatives, CD4+ helper lymphocyte cell is a naïve CD4+ T cell, wherein the naïve CD4+ T cell comprises a CD45RO−, CD45RA+, and/or is a CD62L+CD4+ T cell.

In some alternatives, the CD8+T cytotoxic lymphocyte cell is a naïve CD8+ T cell, central memory CD8+ T cell, effector memory CD8+ T cell and/or bulk CD8+ T cell. In some alternatives, the CD8+ cytotoxic T lymphocyte cell is a central memory T cell, wherein the central memory T cell comprises a CD45RO+, CD62L+, and/or CD8+ T cell. In yet other alternatives, the CD8+ cytotoxic T lymphocyte cell is a central memory T cell and the CD4+ helper T lymphocyte cell is a naïve or central memory CD4+ T cell.

In some alternatives, the compositions comprise T cell precursors. In some alternatives, the compositions comprise hematopoietic stem cells. In some alternatives, the composition comprises a host cell wherein the host cell is a CD8+T cytotoxic lymphocyte cell selected from the group consisting of naïve CD8+ T cells, central memory CD8+ T cells, effector memory CD8+ T cells and bulk CD8+ T cells or a CD4+T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell. In some alternatives, the precursor T cell is a hematopoietic stem cell.

Methods

The disclosure provides methods of making adoptive immunotherapy compositions and uses or methods of using these compositions for performing cellular immunotherapy in a subject having a disease or disorder. In some alternatives, a method of manufacturing the compositions comprises obtaining a modified naïve or central memory CD4+T helper cell, wherein the modified helper T lymphocyte cell preparation comprises CD4+ T cells that have a chimeric receptor comprising a ligand binding domain specific for a tumor cell surface molecule, a spacer domain, a transmembrane domain, and an intracellular signaling domain under control of an inducible promoter as described herein. In other alternatives, CD4+ cells have a cytokine or chemokine receptor under the control of an inducible promoter. CD4+ cells can also have other genes under control of the inducible promoter (genes that control apoptosis, alter extracellular environment etc).

In another alternative, a method further comprises obtaining a modified CD8+ central memory T cell, wherein the modified central memory CD8 T lymphocyte cell preparation comprises CD8+ cells that have a chimeric receptor comprising a ligand binding domain, wherein the ligand binding domain is specific for a ligand, wherein the ligand is a tumor specific molecule, viral specific molecule, or any other selected molecule expressed on a target cell population, wherein the ligand can elicit recognition, modulation, inhibition, and/or elimination by a lymphocyte, a spacer domain, a transmembrane domain, and an intracellular signaling domain under control of the inducible promoter as described herein. In other alternatives, CD8+ cells have a cytokine or chemokine receptor under the control of an inducible promoter.

The drug inducible promoter in both modified CD4+ T cells and modified CD8+ cytotoxic T cells can be the same or different. In some alternatives, in one population of cells the promoter linked to the chimeric antigen receptor is a constitutive promoter and in the other population it is an inducible promoter. For example, modified CD4+ T cells that have a chimeric receptor comprising a ligand binding domain specific for a tumor cell surface molecule, a spacer domain, a transmembrane domain, and an intracellular signaling domain under control of an constitutive promoter, while the CD8+ cytotoxic T cell comprises CD8+ cells that have a chimeric receptor comprising a ligand binding domain specific for a tumor cell surface molecule, a spacer domain, a transmembrane domain, and an intracellular signaling domain under control of the inducible promoter. In some alternatives, the genes being controlled by the constitutive or inducible promoter are genes encoding cytokines, chemokine receptors and apoptosis regulators.

In some alternatives, the polynucleotide can code for a chimeric antigen receptor that differs in the CD4+ versus the CD8+ cell population. The difference between the two constructs can include the specificity or affinity of the ligand binding domain for an antigen or epitope, the length and sequence of the spacer region, and the intracellular signaling components.

The preparation of the CD4+ and CD8+ cells that are modified with a chimeric receptor is described throughout this disclosure. Antigen specific T lymphocytes can be obtained from a patient having the disease or disorder or can be prepared by in vitro stimulation of T lymphocytes in the presence of antigen. Subpopulations of CD4+ and/or CD8+T lymphocytes that are not selected for antigen specificity can also be isolated as described herein and combined in the methods of manufacturing.

In some alternatives, the combination of cell populations can be evaluated for uniformity of cell surface makers, the ability to proliferate through at least two generations, to have a uniform cell differentiation status. Quality control can be performed by co-culturing a cell line expressing the target ligand with chimeric receptor modified T cells and the drug that induces expression of the chimeric antigen receptor to determine if the chimeric receptor modified T cells recognize the cell line using cytotoxicity, proliferation, or cytokine production assays in the presence of the inducer that are known in the field. Cell differentiation status and cell surface markers on the chimeric receptor modified T cells can be determined by flow cytometry. In some alternatives, the markers and cell differentiation status on the CD8+ cells include CD3, CD8, CD62L, CD28, CD27, CD69, CD25, PD-1, CTLA-4, CD45RO, and/or CD45RA. In some alternatives, the markers and the cell differentiation status on the CD4+ cells include CD3, CD4, CD62L, CD28, CD27, CD69, CD25, PD-1, CTLA-4 CD45RO, and/or CD45RA.

In some alternatives, the chimeric receptor modified T cells as described herein are able to persist in vivo for at least 3 days, or at least 10 days. In some alternatives, the chimeric receptor modified T cells as described herein, can proliferate in vivo through at least 2, or at least 3 generations as determined by CFSE dye dilution. Proliferation and persistence of the chimeric receptor modified T cells can be determined by using an animal model of the disease or disorder and administering the cells and determining persistence and/or proliferative capacity of the transferred cells. In other alternatives, proliferation and activation can be tested in vitro by going through multiple cycles of activation with antigen bearing cells.

The disclosure also provides methods of performing cellular immunotherapy in a subject having a disease or disorder comprising: administering a composition of lymphocytes expressing a chimeric receptor under the control of a drug inducible promoter as described herein, and administering the drug.

In some alternatives, the drug is tamoxifen, variants, derivatives, pharmaceutical salts, solvates, and hydrates thereof as described herein. In some alternatives, the drug is delivered prior to, at the same time as the composition, or at later time points after the composition has been administered.

In some alternatives, the drug is administered with the composition, and if a toxic effect of the composition is observed the drug is withdrawn until the toxic effects diminish. After the symptoms of toxicity diminish, the drug is administered again. In some alternatives, a drug can be administered again once symptoms of toxicity diminish.

In some alternatives, the drug is administered with the composition but once the subject has a decrease in the tumor load or cancer cells, the drug is withdrawn for a period of time to allow the modified cells to rest and if there is no activity of the modified cells, the modified cells are not needed because of remission of the cancer.

In other alternatives, a method comprises administering to the subject a genetically modified cytotoxic T lymphocyte cell preparation that provides a cellular immune response, wherein the cytotoxic T lymphocyte cell preparation comprises CD8+ T cells that have a chimeric receptor comprising a ligand binding domain, wherein the ligand binding domain is specific for a ligand, wherein the ligand is a tumor specific molecule, viral molecule, or any other molecule expressed on a target cell population, wherein the ligand can elicit recognition, modulation, inhibition, and/or elimination by a lymphocyte, a spacer domain, a transmembrane domain, and an intracellular signaling domain under the control of a drug inducible promoter as described herein, and/or a genetically modified helper T lymphocyte cell preparation that elicits direct tumor recognition and enhances the genetically modified cytotoxic T lymphocyte cell preparations ability to mediate a cellular immune response, wherein the helper T lymphocyte cell preparation comprises CD4+ T cells that have a chimeric receptor comprising a ligand binding domain, wherein the ligand binding domain is specific for a ligand, wherein the ligand is a tumor specific molecule, viral specific molecule, or any other molecule expressed on a target cell population, wherein the ligand can elicit recognition, modulation, inhibition, and/or elimination by a lymphocyte, a spacer domain, a transmembrane domain, and an intracellular signaling domain under control of a constitutive or drug inducible promoter as described herein and administering the drug that induces the inducible promoter. In some alternatives, the administering of the drug is performed after administering of the composition or host cells, wherein administering is performed 1 day, 2 days, 3 days, 4 days, 5 days, 6 days, 7 days, 2 weeks, 4 weeks or two months, or any time in between any two values of time listed. In some alternatives of the methods, the systems are inducible by an amount of the drug that is less than a comparable system utilizing a wild type HEA3 chimeric transcription factor or a wild type HEA4 chimeric transcription factor.

In other alternatives, a method comprises administering to the subject a genetically modified cytotoxic T lymphocyte cell preparation that provides a cellular immune response, wherein the cytotoxic T lymphocyte cell preparation comprises CD8+ T cells that have a chimeric receptor comprising a ligand binding domain specific for a tumor cell surface molecule, a spacer domain, a transmembrane domain, and an intracellular signaling domain under the control of a constitutive promoter as described herein, and/or a genetically modified helper T lymphocyte cell preparation that elicits direct tumor recognition and enhances the genetically modified cytotoxic T lymphocyte cell preparations ability to mediate a cellular immune response, wherein the helper T lymphocyte cell preparation comprises CD4+ T cells that have a chimeric receptor comprising a ligand binding domain specific for a tumor cell surface molecule, a spacer domain, a transmembrane domain, and an intracellular signaling domain under control of a constitutive or drug inducible promoter as described herein and administering the drug that induces the inducible promoter. In some alternatives, the tumor specific molecule is a tumor surface molecule.

In other alternatives, a method comprises administering to the subject a genetically modified cytotoxic T lymphocyte cell preparation that provides a cellular immune response, wherein the cytotoxic T lymphocyte cell preparation comprises CD8+ T cells that express a cytokine, chemokine receptor, a polypeptide that regulates apoptosis, and/or a polypeptide that modulates checkpoint signaling under the control of an inducible promoter as described herein, and/or a genetically modified helper T lymphocyte cell preparation that elicits direct tumor recognition and enhances the genetically modified cytotoxic T lymphocyte cell preparations ability to mediate a cellular immune response, wherein the helper T lymphocyte cell preparation comprises CD4+ T cells that express a cytokine, chemokine receptor, a polypeptide that regulates apoptosis, and/or a polypeptide that modulates checkpoint signaling under control of a constitutive or drug inducible promoter as described herein and administering the drug that induces the inducible promoter. In some alternatives, one or more of the cell populations expresses a chimeric antigen receptor under the control of a constitutive promoter. In some alternatives, the modulation of checkpoint signaling inhibits negative checkpoint regulators. In some alternatives, the negative checkpoint regulator comprises PD-1, VISTA, LAG-3 and/or TIM3.

An effective amount of the drug for induction is an amount of the drug that provides for induction of the chimeric antigen receptor in at least 5%, at least 10%, at least 20%, at least 30%, at least 40%, at least 50%, at least 60%, at least 70%, at least 80%, at least 90%, at least 100% or any number in between a range defined by any of the listed percent values of the transduced cells as described herein. In the methods provided herein, the systems are inducible by an amount of the drug that is less than a comparable system utilizing a wild type HEA3 chimeric transcription factor or a wild type HEA4 chimeric transcription factor.

Another alternative describes a method of performing cellular immunotherapy in a subject having a disease or disorder comprising: analyzing a biological sample of the subject for the presence of a target molecule associated with the disease or disorder and administering the adoptive immunotherapy compositions described herein and administering the drug that induces the inducible promoter, wherein the chimeric receptor specifically binds to the target molecule.

Subjects that can be treated in accordance with alternatives described herein are, in general, human and other primate subjects, such as monkeys and apes for veterinary medicine purposes. The subjects can be male or female and can be any suitable age, including infant, juvenile, adolescent, adult, and geriatric subjects.

The methods are useful in the treatment or inhibition of, for example, hematologic malignancy, melanoma, breast cancer, brain cancer, and other epithelial malignancies or solid tumors. In some alternatives, the molecule associated with the disease or disorder is an orphan tyrosine kinase receptor ROR1, Her2, EGFR, CE7, hB7H3, CD19, CD20, CD22, mesothelin, CEA, or a hepatitis B surface antigen.

Subjects that can be addressed using the methods described herein include subjects identified or selected as having cancer, including but not limited to colon, lung, liver, breast, renal, prostate, ovarian, skin (including melanoma), bone, and brain cancer, etc. Such identification and/or selection can be made by clinical or diagnostic evaluation. In some alternatives, the tumor associated antigens or molecules to which alternatives are directed are antigens associated with melanoma, breast cancer, brain cancer, squamous cell carcinoma, colon cancer, leukemia, myeloma, and/or prostate cancer. In other alternatives the tumor associated molecules can be targeted with genetically modified T cells expressing an engineered chimeric receptor. Examples include but are not limited to B cell lymphoma, breast cancer, brain cancer, prostate cancer, and/or leukemia.

Cells prepared as described above can be utilized in methods and compositions for adoptive immunotherapy in accordance with known techniques, or variations thereof that will be apparent to those skilled in the art based on the instant disclosure.

In some alternatives, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin, fetal bovine serum or other human serum components.

In some alternatives, a treatment or inhibitory effective amount of cells in the composition is a transduced CD4 or CD8 cell or at least 2 cell subsets (for example, 1 CD8+ central memory T cell subset and 1 CD4+ helper T cell subset) or is more typically greater than $10^2$ cells, and up to $10^6$, up to and including $10^8$ or $10^9$ cells and can be more than $10^{10}$ cells. The number of cells will depend upon the ultimate use for which the composition is intended as will the type of cells included therein. For example, if cells that are specific for a particular antigen are desired, then the population will contain greater than 70%, generally greater than 80%, 85% and 90-95% of such cells. For uses provided herein, the cells are generally in a volume of a liter or less, can be 500 mls or less, even 250 mls or 100 mls or less or a volume in between a range defined by any two listed volume values. Hence the density of the desired cells is typically greater than $10^4$ cells/ml and generally is greater than $10^7$ cells/ml, generally $10^8$ cells/ml or greater. The clinically relevant number of immune cells can be apportioned into multiple infusions that cumulatively equal or exceed $10^6$, $10^7$, $10^8$, $10^8$, $10^9$, $10^{10}$ or $10^{11}$ cells or any amount of cells in between a range defined by any two endpoints of any of the listed values.

In some alternatives, the lymphocytes of the invention can be used to confer immunity to individuals. "Immunity" has its plain and ordinary meaning when read in light of the specification, and may be used, for example, to mean a lessening of one or more physical symptoms associated with a response to infection by a pathogen, or to a tumor, to which the lymphocyte response is directed. The amount of cells administered is usually in the range present in normal individuals with immunity to the pathogen. Thus, the cells are usually administered by infusion, with each infusion in a range of from 2 cells, up to at least $10^6$ to $3\times10^{10}$ cells, preferably in the range of at least $10^7$ to $10^9$ cells. The T cells can be administered by a single infusion, or by multiple infusions over a range of time. However, since different individuals are expected to vary in responsiveness, the type and amount of cells infused, as well as the number of infusions and the time range over which multiple infusions are given are determined by the attending physician, and can be determined by routine examination. The generation of sufficient levels of T lymphocytes (including cytotoxic T lymphocytes and/or helper T lymphocytes) is readily achievable using the rapid expansion method of the present invention, as exemplified herein.

In some alternatives, a composition as described herein is administered to an identified or selected subject, such as a subject identified or selected as having melanoma, breast cancer, brain cancer, squamous cell carcinoma, colon cancer, leukemia, myeloma, and/or prostate cancer, intravenously, intraperitoneally, intratumorly, into the bone marrow, into the lymph node, and/or into cerebrospinal fluid. In some alternatives, the chimeric receptor engineered compositions are delivered to the site of the tumor. Alternatively, the compositions as described herein can be combined with a compound that targets the cells to the tumor or the immune system compartments and avoid sites such as the lung.

In some alternatives, the compositions as described herein are administered with chemotherapeutic agents and/or immunosuppressants. In an alternative, a patient is first administered a chemotherapeutic agent that inhibits or destroys other immune cells followed by the compositions described herein. In some cases, chemotherapy can be avoided entirely.

In some alternatives, a method comprising administering the modified T cells as described herein in combination with the inducer (e.g. inducible drug) until the tumor burden is diminished. Once the tumor burden is diminished, the inducer drug can be withdrawn in order to switch the expression of the chimeric antigen receptor off and decrease the number of T cells expressing the receptor. In other alternatives, the inducer drug can be administered at a different time in order to switch the expression of the chimeric antigen receptor on in the event of a relapse or increase in tumor growth.

In other alternatives, the inducer drug can be given for a period of time of days, weeks, or months, and then withdrawn for days, weeks or months, followed by re-administration of the inducer drug for days, weeks or months to allow for cycling of the expression of the chimeric antigen receptor to avoid anergy or nonresponsiveness due to chronic stimulation of the cells.

More Alternatives.

In some alternatives, a system for inducible expression of a transgene is provided. In some alternatives, the transgene encodes a chimeric antigen receptor. In some alternatives, a system for inducible expression of a chimeric antigen receptor in cells, such as mammalian cells, is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttctcaaggaccaccg-catctctacattcaagaactggcccttcttggag ggctgcgcctgcaccccg-gagcggatggccgaggctggcttcatccactgccccactgagaacgagcca-gacttggcccagtgttt cttctgcttcaaggagctggaaggctgggagccagatgacgaccccatagag-gaacataaaaagcattcgtccggttgcgctttcctttctgtcaagaagcagttt-gaagaattaacccttggtgaatttttgaaactggacagagaaagagc-caagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD). In some alternatives, the polypeptide that regulates apoptosis is Survivin. In some alternatives, Survivin is encoded by a sequence set forth in SEQ ID NO: 124. In some alternatives, Survivin comprises an amino acid sequence set forth in SEQ ID NO: 123. The system comprises a) a first nucleic acid comprising a first promoter inducible by a drug, wherein the first nucleic acid is operably linked to a first polynucleotide that encodes a transgene, which comprises a ligand binding domain that is specific for a ligand selected from the group consisting of a tumor specific molecule, a viral specific molecule, and any other selected molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and any other selected molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the chimeric antigen receptor comprises a scFv. In some alternatives, the scFv specifically binds to CD19. In some alternatives, the scFv comprises an huCD19 scFv (G01S) amino acid sequence. In some alternatives, the scFv comprises an amino acid sequence set forth in SEQ ID NO: 41 (MLLLVTSLLL-CELPHPAFLLIPEVQLVESGGGLVQPGRSLRLS-CAASGFTFDDYAMH WVRQAPGKGLEWVSGISWNS-GRIGYADSVKGRFTISRDNAKNSLFLQMNSLRAEDT AVYYCARDQGYHYYDSAE-HAFDIWGQGTVVTVSSGGGGSGGGGSGGGGSQ-SALTQ PRSVSGFPGQSVTISCTGTTSDDVSWY QQHPGKAPQLMLYDVSKRPSGVPHRFSGSR SGRAASLIISGLQTEDEADYFCSSYAGRYNS-VLFGGGTKLTVL). In some alternatives, the scFv is encoded by a nucleic acid sequence comprising a nucleic acid sequence encoding the amino acid sequence of SEQ ID NO: 41. In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42 (Atgctgctgctggtgaccagcctgctgtgcgagctgccc-caccccgcctttctgctgatccccgacatccagatgacccagac cacctccagcctgagcgccagcctgggcgaccgggtgac-catcagctgccgggccagccaggacatcagcaagtacctgaactg gtatcagcagaagcccgacggcaccgtcaagctgctgatctac-cacaccagccggctgcacagcggcgtgcccagccggtttagc ggcagcggctccggcaccgactacagcctgaccatctccaacctggaacag-gaagatatcgccacctacttttgccagcagggcaa cacactgcccta-cacctttggcggcggaacaaagctggaaat-caccggcagcacctccggcagcggcaagcctggcagcggcga gggcagcaccaagggcgaggtgaagctgcag-gaaagcggccctggcctggtggcccccagccagagcctgagcgtgacctgca ccgtgagcggcgtgagcctgcccgactacggcgtgagctg-gatccggcagcccccaggaagggcctggaatggctgggcgtga tctggggcagcgagaccacctactacaacagcgccctgaagagccggctgac-catcatcaaggacaacagcaagagccaggtgtt cctgaagatgaacagcctgca-gaccgacgacaccgccatctactactgcgccaagcactactac-tacggcggcagctacgccatgg actactggggccagggcaccagcgtgaccgtgagcagc). In some alternatives, the scFv comprises an amino acid sequence set forth in SEQ ID NO: 43 (MLLLVTSLLLCELPHPAFL-LIPDIQMTQTTSSLSASLGDRVTISCRASQDISKY-LNWY QQKPDGTVKLLIYHTSRLHSGVPSRFSGSGSGTDYS-LTISNLEQEDIATYFCQQGNTLP YTFGGGTKLEITGST-SGSGKPGSGEGSTKGEVKLQESGPGLVAP-SQSLSVTCTVSGVS LPDYGVSWIRQPPRKGLEWLGVIWGSETTYYN-SALKSRLTIIKDNSKSQVFLKMNSL QTDDTAIYY-CAKHYYYGGSYAMDYWGQGTSVTVSS). In some alternatives, the scFv is encoded by a nucleic acid sequence comprising a nucleic acid sequence encoding the amino acid sequence of SEQ ID NO: 43. some alternatives, the scFv comprises a B7H3 (hBRCA84D) scFv nucleotide sequence. In some alternatives, the scFv binds specifically to the B7-H3 receptor. In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50

(atgctgctgctggtgaccagcctgctgctgtgcgagctgccc-caccccgcctttctgctgatcccccaggtgcagctgcagcagcct ggcgccgagctggtgaagccaggcgccagcgt-gaagctgtcctgcaaggccagcggctacaccttcaccggctactggatgcact gggtgaagcagagacccggccacggcctggaatggatcggcgagat-caaccccagcaacggccggaccaactacaacgagcgg ttcaagagcaaggc-caccctgaccgtggacaagagcagcaccaccgcctt-catgcagctgtccggcctgaccagcgaggacagcg ccgtgtacttctgcgccagggactactacggcaccagctacaacttcgac-tactggggccagggcaccacactgaccgtgagcagc ggcg-gagggggctctggcggcggaggatctgggggagggggcagcgacatcca-gatgacccagagcagcagcagcttcagcg tgagcctgggcgaccgggtgaccatcacctgtaaggccaacgaggacat-caacaaccggctggcctggtatcagcagacccccgg caacagccccaggctgctgatcagcggcgccac-caacctggtgaccggcgtgcccagccggtttagcggcagcggctccggcaa ggactacaccctgaccatcacaagcctgcaggccgaggacttcgccacctac-tactgccagcagtactggtccacccccttcaccttc ggcagcggcaccgagctg-gaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFL-LIPQVQLQQPGAELVKPGASVKLSCK-ASGYTFTGYWM HWVKQRPGHGLEWIGEINPSN-GRTNYNERFKSKATLTVDKSSTTAFMQLSGLTSEDS AVYFCARDYYGTSYNFDYWGQGT-TLTVSSGGGGSGGGGSGGGGSDIQMTQSSSSFS VSLGDRVTITCKANEDINNRLAWYQQTPGNSPRLLIS-GATNLVTGVPSRFSGSGSGK DYTLTITSLQAEDFA-TYYCQQYWSTPFTFGSGTELEIK). In some alternatives, the scFv is encoded by a nucleic acid sequence comprising a nucleic acid sequence encoding the amino acid sequence of SEQ ID NO: 51. In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52 (atgcttctcctggtgacaagccttctgctctgtgagttaccacacccagcat-tcctcctgatcccacaggtgcagctgaaacagagcg gcccgggcctggtgcagccgagccagagcctgagcattacctgcaccgt-gagcggctttagcctgaccaactatggcgtgcattgg gtgcgccagagcccgggcaaaggcctggaatggctgggcgtgatttg-gagcggcggcaacaccgattataacaccccgtttacca gccgcctgagcat-taacaaagataacagcaaaagccaggtgtttttaaaat-gaacagcctgcagagcaacgataccgcgatttattat tgcgcgcgcgcgctgacctattatgattatgaatttgcgtat-tggggccagggcaccctggtgaccgtgagcgcgggcggcggcgg cagcggcggcggcggcagcggcggcggcggcagcgatat-tctgctgacccagagcccggtgattctgagcgtgagcccgggcg aacgcgt-gagctttagctgccgcgcgagccagagcattggcaccaacattcat-tggtatcagcagcgcaccaacggcagcccgcgc ctgctgattaaatatgcgagcgaaagcattagcggcattccgagccgctt-tagcggcagcggcagcggcaccgattttaccctgagc attaacagcgtg-gaaagcgaagatattgcggattattattgccagcagaacaacaactggccgac-cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL-CELPHPAFLLIPQVQLKQSGPGLVQPSQSL-SITCTVSGFSLTNYGVHW VRQSPGKGLEW-LGVIWSGGNTDYNTPFTSRLSINKDNSKSQVFFKMN SLQSNDTAIY YCARALTYYDYE-FAYWGQGTLVTVSAGGGGSGGGGSGGGGS-DILLTQSPVILSVSP GERVSFSCRASQSIGT-NIHWYQQRTNGSPRLLIKYASESISGIPSRFSGSGSGT DFTLSI NSVESEDI-ADYYCQQNNNWPTTFGAGTKLELKRT). In some alternatives, the scFv is encoded by a nucleic acid sequence comprising a nucleic acid sequence encoding the amino acid sequence of SEQ ID NO: 53. In some alternatives, the scFv comprises the EGFRVIII (806) scFv nucleotide sequence. In some alternatives, the scFv is specific for EGFR. In some alternatives, the scFv is encoded by the EphA2 (2A4) scFv nucleotide sequence. In some alternatives, the scFv is encoded by the nucleic acid sequence set forth in SEQ ID NO: 56. In some alternatives, the scFv is encoded by the EpHA2 (4H5) scFv nucleotide sequence. In some alternatives, the scFv is encoded by the nucleic acid sequence set forth in SEQ ID NO: 58. In some alternatives, the scFv is encoded by a FITC (E2) scFv nucleotide sequence. In some alternatives, the scFv is encoded by a nucleic acid sequence set forth in SEQ ID NO: 60. In some alternatives, the scFv is encoded by an IL13Ra2 (hu08) VhVl scFv nucleotide sequence. In some alternatives, the scFv is encoded by a nucleic acid sequence set forth in SEQ ID NO: 68. In some alternatives, the scFv comprises an IL13Ra2 hu08 VhVl scFv amino acid sequence. In some alternatives, the scFv comprises an amino acid sequence set forth in SEQ ID NO: 69 (MLLLVTSLLLCELPHPAFLLIPEVQLVESGG-GLVQPGGSLRLSCAASGFTFSRNGMS WVRQAPGK-GLEWVATVSSGGSYIYYADSVKGRFTISRDNAKNS-LYLQMNSLRAEDT AVYYCARQGTTALATRFFDVWGQGTLVTVSSGGGG SGGGGSGGGGSDIQMTQSPSS LSASVGDRVTITCK-ASQDVGTA-VAWYQQKPGKAPKLLIYSASYRSTGVPSRFSGSGS GTDFTLTISSLQPEDFATYYCQHHYS-APWTFGGGTKVEIKESK). In some alternatives, the scFv is encoded by a nucleic acid sequence comprising a nucleic acid sequence encoding the amino acid sequence of SEQ ID NO: 69. In some alternatives, the scFv is encoded by an IL13Ra2 (hu07) VlVh scFv nucleotide sequence. In some alternatives, the scFv is encoded by a nucleic acid sequence set forth in SEQ ID NO: 70 (atgcttctcctggtgacaagccttctgctctgtgagttaccacacccagcat-tcctcctgatcccagatattcagatgacccagagccc gagcagcct-gagcgcgagcgtgggcgatccgcgtgagcagcacctatctgcattggt atcagcagaaaccgggcaaagcgccgaaactgctgatt-tatagcaccagcaacctggcgagcggcgtgccgagccgctttagcgg cagcggcagcggcaccgattttaccctgaccattagcagcctgcagccggaa-gattttgcgacctattattgccatcagtatcatcgca gcccgctgacctttggcggcggcaccaaagtggaaat-taaaggtggtggtggttctggcggcggcggctccggtggtggtggttctg aagtgcagctggtg-gaaagcggcggcggcctggtgcagcggcggcgggcctggtgcgcggcgagc ggctttacct ttaccaaatatggcgtgcat-tgggtgcgccaggcgccgggcaaaggcctggaatgggtggcggt-gaaatgggcgggcggcagca ccgattataacagcgcgctgatgagccgctt-taccattagccgcgataacgcgaaaaacagcctgtatctgcagatgaacagcctgc gcgcggaagataccgcggtgtattattgcgcgcgcgatcatcgcgatgcgatg-gattattggggccagggcaccctggtgaccgtg agcagcgaatctaagta). In some alternatives, the scFv comprises an IL13Ra2 (hu07) VhVl scFv amino acid sequence. In some alternatives, the scFv comprises an amino acid sequence set forth in SEQ ID NO: 71 (MLLLVTSLLLCELPHPAFLLIPDIQMTQSPSSL-SASVGDRVTITCTASLSVSSTYLHWY QQKPGKAPKLLIYSTSN-LASGVPSRFSGSGSGTDFTLTISSLQPEDFATYY-CHQYHRSP LTFGGGTKVEIKGGGGSGGGGSGGGG-SEVQLVESGGGLVQPGGSLRLSCAASGFTFT KYGVHWVRQAPGKGLEWVAVKWAGGSTDYN-SALMSRFTISRDNAKNSLYLQMNS LRAEDTAVYY- CARDHRDAMDYWGQGTLVTVSSESK). In some alternatives, the scFv is encoded by a nucleic acid sequence comprising a nucleic acid sequence encoding the amino acid sequence of SEQ ID NO: 71. In some alternatives, the scFv is encoded by the IL13Ra2 (hu07) VhVl scFv nucleotide sequence. In some alternatives, the scFv is encoded by a nucleic acid sequence set forth in SEQ ID NO: 72 (atgcttctcctggtgacaagccttctgctctgtgagttaccacacccagcat-tcctcctgatcccagaagtgcagctggtggaaagcg gcggcggcctggtgcagccgggcggcagcctgcgcct-gagctgcgcggcgagcggctttacctttaccaaatatggcgtgcattgg gtgcgccaggcgccgggcaaaggcctggaatgggtggcggt-gaaatgggcgggcggcagcaccgattataacaggcgctgat gagccgctttac-cattagccgcgataacgcgaaaaacagcctgtatctgcagat-gaacagcctgcgcgcggaagataccgcggtgt attattgcgcgcgcgatcatcgcgatgcgatggattat-tggggccagggcaccctggtgaccgtgagcagcggtggtggtggttctg gcggcggcggctccggtggtggtggttctgatattca-gatgacccagagcccgagcagcctgagcgcgagcgtgggcgatcgcgt gac-cattacctgcaccgcgagcctgagcgtgagcagcacctatctgcat-tggtatcagcagaaaccgggcaaagcgccgaaactgc tgatttatagcaccagcaacctggcgagcggcgtgccgagccgctt-tagcggcagcggcagcggcaccgatttaccctgaccatta gcagcctgcagccggaagattttgcgacctattattgccatcagtat-catcgcagcccgctgacctttggcggcggcaccaaagtgga aat-taaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFL-LIPEVQLVESGGGLVQPGGSLRLSCAASGFTFT-KYGVH WVRQAPGKGLEWVAVKWAGGSTDYN-SALMSRFTISRDNAKNSLYLQMNSLRAED TAVYYCARDHR-DAMDYWGQGTLVTVSSGGGGSGGGGSGGGGSDIQ MTQSPSSLSA SVGDRVTITCTASLSVS-STYLHWYQQKPGKAPKLLIYSTSN-LASGVPSRFSGSGSGTD FTLTISSLQPEDFATYY-CHQYHRSPLTFGGGTKVEIKESK). In some alternatives, the scFv is encoded by a nucleic acid sequence comprising a nucleic acid sequence encoding the amino acid sequence of SEQ ID NO: 73. In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74 (atgcttctcctggtgacaagccttctgctctgtgagttaccacacccagcat-tcctcctgatcccaggccctgtgcctccctctacagcc ctcaggtacctcattgag-gagctggtcaacatcacccagaaccagaaggctccgctctgcaatggcag-catggtatggagcatcaac ctgacagctggcatgtactgtgcagccctggaatccctgat-caacgtgtcaggctgcagtgccatcgagaagacccagaggatgctg agcggat-tctgcccgcacaaggtctcagctgggcagttttccagcttgcatgtccgagacac-caaaatcgaggtggcccagtttgtaa aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFL-LIPGPVPPSTALRYLIEELVNITQNQKAPLCNG-SMVWSI NLTAGMYCAALESLINVSGC-SAIEKTQRMLSGFCPHKVSAGQFSSLHVRDTKIEVAQ FVKDLLLHLKKLFREGRF). In some alternatives, the scFv is encoded by a nucleic acid sequence comprising a nucleic acid sequence encoding the amino acid sequence of SEQ ID NO: 75. In some alternatives, the scFv is encoded by an oaGD2 (8B6) VlVh scFv nucleotide sequence. In some alternatives, the scFv is encoded by a sequence set forth in SEQ ID NO: 76 (atgcttctcctggtgacaagccttctgctctgt-gagttaccacacccagcattcctcctgatcccagatgttgtgatgacccaaactcca ctctccctgcctgtcagtcttggagatcaagcctcaatctcttgca-gatctagtcagagccttctaaaaaatggaaacaccttttttaca ttggtacctgcagaagtcaggccagtctccaaagctccttatctacaaagtttc-caaccgactttctggggtcccagacaggttcagtgg cagtggatcagggacatat-ttcacactcaagatcagcagagtggaggctgaggatctgggagtttatttctgctct-caaagtacacatat tccgtacacattcggagggggggaccaagctcgagctgaaacgaggcg-gaggggggctctggcggcggaggatctgggggagggg gcagcgaggt-gaaactggtggagtctggaggaggcttggtgctgcctggggattctctga-gactctcctgtgcaacttctgagttcac cttcactgattactacatgacttgggtccgccagcctccaagaaaggcactt-gagtggttgggttttattagaaacagagctaatggttac acaacagagtacaatc-catctgtgaagggtcggttcaccatttccagagataattcccaaagcatcctc-tatcttcaaatgaacaccctg agaactgaggacagtgccacttattactgtgcaagagtctctaactgggcctttgac-tactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77 (MLLLVTSLLLCELPHPAFL-LIPDVVMTQTPLSLPVSLGDQASIS-CRSSQSLLKNNGNT FLHWYLQKSGQSPKLLIYKVSNRLSGVPDRFSGSGS GTYFTLKISRVEAEDLGVYFCS QSTHIPY-TFGGGTKLELKRGGGGSGGGGSGGGGSEVKLVES-GGGLVLPGDSLRLSCA TSEFTFTDYYMTWVRQP-PRKALEWLGFIRNRANGYTTEYNPSVKGRFTISRDNS QSIL YLQMNTLRTEDSATYYCAR VSN-WAFDYWGQGTTLTVSS). In some alternatives, the scFv is encoded by a nucleic acid sequence comprising a nucleic acid sequence encoding the amino acid sequence of SEQ ID NO: 77. In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccc-caccccgcctttctgctgatcccccaggaacagctcgtcgaaagc ggcggca-gactggtgacacctggcggcagcctgaccct-gagctgcaaggccagcggcttcgacttcagcgcctactacatgagctg ggtccgccaggcccctggcaagggactggaatggatcgccaccatc-taccccagcagcggcaagacctactacgccacctgggtg aacggacggttcac-catctccagcgacaacgcccagaacaccgtggacctgcagat-gaacagcctgacagccgccgaccgggcc acctacttttgcgccagagacagctacgccgacgacggcgccctgttcaa-catctggggccctggcaccctggtgacaatctctagc ggcggaggcg-gatctggtggcggaggaagtggcggcggaggatct-gagctggtgctgacccagagcccctctgtgtctgctgccc tgggaagccctgccaagatcacctgtaccctgagcagcgcccacaa-gaccgacaccatcgactggtatcagcagctgcagggcga ggcccccaga-tacctgatgcaggtgcagagcgacggcagctacac-caagaggccaggcgtgcccgaccggttcagcggatctag ctctggcgccgaccgctacctgatcatccccagcgtgcaggcc-gatgacgaggccgattactactgtggcgccgactacatcggcg gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESG-GRLVTPGGSLTLSCKASGFDFSAYYMSW VRQAPGKGLEWIATIYPSSGKTYYATWVNGRFTIS-SDNAQNTVDLQMNSLTAADRA TYFCARDSYADD-GALFNIWGPGTLVTISSGGGGSGGGGSGGGG-SELVLTQSPSVSAA LGSPAKITCTLS-SAHKTDTIDWYQQLQGEAPRYLMQVQSDG-SYTKRPGVPDRFSGSS SGADRYLIIPSVQADDEAD- YYCGADYIGGYVFGGGTQLTVTG). In some alternatives, the scFv is encoded by a nucleic acid sequence comprising a nucleic acid sequence encoding the amino acid sequence of SEQ ID NO: 79. In some alternatives, the scFv comprises an amino acid sequence set forth in SEQ ID NO: 80 (CD33 (h2H12) VhVl scFv nucleotide sequence (atgcttctcctggtgacaagccttctgctctgtgagttaccacacccagcattcctcctgatcccacaggttcagctggtgcagtctgga gctgaggtgaagaagcctggggcctcagtgaaggtctcctgcaaggcttctggttacaccttaccaattatgatataaattgggtgag acaggcccctggacaagggcttgagtggattggatggatttatcctggagatggtagtaccaaatataatgagaaattcaaggccaag gctaccctgacagctgacacatccaccagcacagcctacatggagctgaggagcctgagatctgatgacacagctgtgtattactgtg cttctggatatgaagatgctatggactactgggggcaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQSGAEVKKPGASVKVSCKASGYTFTNYDIN WVRQAPGQGLEWIGWIYPGDGSTKYNEKFKAKATLTADTSTSTAYMELRSLRSDDT AVYYCASGYEDAMDYWGQGTTVTVSS). In some alternatives, the scFv is encoded by a nucleic acid sequence comprising a nucleic acid sequence encoding the amino acid sequence of SEQ ID NO: 81. In some alternatives, the scFv is encoded by a sequence set forth in SEQ ID NO: 82 (CD33 (h2H12) VlVh scFv nucleotide sequence: atgcttctcctggtgacaagccttctgctctgtgagttaccacacccagcattcctcctgatcccagacatccagatgacccagtctccat cctcactgtctgcatctgtaggagacagagtcaccatcaattgtaaggctagtcaggacattaatagctatttgagctggtttcagcaga aaccagggaaagcccctaagaccctgatctatagagcaaatagattggtagatggggtcccatcaaggttctctggcagtggatctgg gcaagattatactctcaccatcagcagcctgcagcctgaagattttgcaacttattactgcttgcagtatgatgagtttcctctcacatttgg aggagggaccaaggtggagatcaaa). In some alternatives, the scFv comprises an amino acid sequence set forth in SEQ ID NO: 83 (CD33 (h2H12) VlVh scFv amino acid sequence: MLLLVTSLLLCELPHPAFLLIPDIQMTQSPSSLSASVGDRVTINCKASQDINSYLSWFQ QKPGKAPKTLIYRANRLVDGVPSRFSGSGSGQDYTL TISSLQPEDFATYYCLQYDEFP LTFGGGTKVEIK). In some alternatives, the scFv is encoded by a nucleic acid sequence comprising a nucleic acid sequence encoding the amino acid sequence of SEQ ID NO: 83. In some alternatives, the scFv is encoded by a nucleic acid sequence set forth in SEQ ID NO: 84. In some alternatives, the scFv is encoded by a nucleic acid sequence set forth in SEQ ID NO: 86. In some alternatives, the scFv comprises an amino acid sequence set forth in SEQ ID NO: 87. In some alternatives, the spacer is encoded by the nucleic acid sequence set forth in SEQ ID NO: 102 (IgG4 hinge nucleotide sequence: gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, HEA3 comprises two amino acid mutations, wherein the sequence is encoded by a sequence set forth in SEQ ID NO: 122 (atggtgtccaagctgtcccagctgcagacagaactgctggcagcactgctggaaagcggcctgagcaaagaggccctgattcagg cactcggcgaacctggaccttatctgctcgctggcgaaggccctctggataagggcgagagctgtggcggagga agaggagagct ggccgagctgcctaacggcctgggcgagacaagaggcagcgaggacgagacagacgacgacggcgaggacttcacccccccc atcctgaaagagctggaaaacctgagccccgaggaagccgcccaccagaaagccgtggtggagacactgctgcaggaagatccc tggcgggtcgccaagatggtcaagagctacctgcagcagcacaacatcccccagcgggaggtggtggacaccaccggcctgaac cagagccacctgagccagcacctgaacaagggcacccccatgaaaacccagaagagagccgccctgtacacttggtacgtgcgg aagcagagagaggtggcccagcagtttacacacgccggccagggcggcctgatcgaggaacctaccggcgacgagctgcccac caagaagggcagacggaaccggtttaagtggggccctgcatctcagcagatcctgttccaggcctacgagcggcagaagaacccc agcaaagaggaacgggagacactggtggaagagtgcaaccgggccgagtgcatccagagaggcgtgagcccttctcaggctcag ggcctcggcagcaatctggtcaccgaagtgcgggtgtacaattggttcgccaaccggcggaaagaggaagccttccggcacaagct gtctgctggcgatatgagagccgccaacctgtggcccagcccccctgatgatcaagcggagcaagaagaacagcctggccctgagc ctgaccgccgatcagatggtgtccgctctgctggacgccgagccccctatcctgtacagcgagtacgaccccaccagacccttcagc gaggccagcatgatgggcctgctgaccaacctggccgaccgggagctggtgcacatgatcaactgggccaagcgggtgcccggc ttcgtggacctgaccctgcacgaccaggtccacctgctggaatgtgcctggctggaaatcctgatgatcggcctcgtgtggagaagc atggaacaccccggcaagctgctgttcgcccccaacctgctcctggaccggaaccagggaaagtgcgtggagggcatggtggaga tcttcgacatgctgctggccacctccagccggttccggatgatgaacctgcagggcgaggaattcgtgtgcctgaagtccatcatcct gctgaacagcggcgtgtacaccttcctgtcatccaccctgaagtccctggaagagaaggaccacatccaccgggtgctggacaaga tcaccgacaccctgatccacctgatggccaaggctggcctgacactccagcagcagcaccagagactggcccagctgctgctgatc ctgagccacatccggcacatgagcaacaagcggatggaacacctgtacagcatgaagtgcaagaacgtggtgcccctgtacgacct gctgctcgagatgctggatgcccacagactgcacgcccctacaagcagaggcggagccagcgtggaggaaaccgaccagtctca cctggccaccgccggcagcacaagcagccacagcctgcagaagtactacatcaccggcgaggccgagggattccctgccaccgt ggagttccagtacctgcccgacaccgacgaccggcaccggatcgaggaaaagcggaagcggacctacgagacattccagagcat catgaagaagtccccccttcagcggcccccaccgatcccagaccccccccctagaagaatcgccgtgcccagcagatctagcgccagc gtgcccaagcctgcccccccagccctaccctttcaccagcagcctgagcaccatcaactacgacgagttccctaccatggtgttcccca gcggccagatctctcaggcctctgctctggcacctgctccacctcaggtgctgcctcaggcccctgctccagccccagcccctgccat ggtgtctgcactggcccaggctccagctcctgtgcctgtgctggcccctggacctc ctcaggctgtggcccctcctgcccctaaacct acccaggccggggagggaacactgtctgaggccctgctgcagctccagttcgacgacgaggatctgggagcactgctgggcaata gcaccgaccccgccgtgtttaccgacctggcctccgtggacaacagcgagttccagcagctcctcaaccagggc atccctgtcgcc ccacacaccaccgagcccatgctgatggaatacccgaggccatcaccagactggtcacaggcgcccagaggcctccagatccag caccagctccactgggagcccctggcctgcctaatgggctgctgtctggcgacgagga cttcgagagcattgccgacatggacttca gcgccctgctgtcccagatcagcagc). In some alternatives, the HEA3 comprises an amino acid sequence set forth in SEQ ID NO: 121 (MVSKLSQLQTELLAALLESGLSKEALIQALGEPGPYLLAGEGPLDKGESCGGGRGEL AELPNGLGETRGSE- DETDDDGEDFTPPILKELENLSPEEAAHQKAVVETLL QEDPWR VAKMVK-SYLQQHNIPQREVVDTTGLNQSHLSQHLNKGTPMK TQKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEG-MVEFDMLLATSSRFRMMNLQGEEFVC LKSIILLNSGVYTFLSSTLKSLEEKDHIHRVLDKITDT-LIHLMAKAGLTLQQQHQRLA QLLLILSHIRHMSNK-RMEHLYSMKCKNVVPLYDLLLEMLDAHRLHAP-TSRGGASVE ETDQSHLATAGSTSSHSLQKYYITGEAE-GFPATVEFQYLPDTDDRHRIEEKRKRTYET FQS-SIMKKSPFSGPTDPRPPPRRIAVPSRSSAS-VPKPAPQPYPFTSSLSTINYDEFPTMVFP SGQISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3. In some alternatives, a system for inducible expression of a chimeric antigen receptor in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgcccccctgcctggcagccctttctcaaggaccaccg-catctctacattcaagaactggcccttcttggag ggctgcgcctgcaccccg-gagcggatggccgaggctggcttcatccactgccccactgagaacgagcca-gacttggcccagtgttt cttctgcttcaaggagctggaaggctgggagccagatgacgaccccatagag-gaacataaaaagcattcgtccggttgcgctttcctttt ctgtcaagaagcagttt-gaagaattaacccttggtgaatttttgaaactggacagagaaagagc-caagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD).

In some alternatives, a system for inducible expression of a chimeric antigen receptor in cells is provided. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and any other selected molecule expressed on a target cell population, wherein the ligand elicits recognition, modulation, inhibition, and/or elimination by a lymphocyte; a second polynucleotide, which encodes a spacer, preferably an optimized polypeptide spacer; a third polynucleotide, which encodes a transmembrane domain; and a fourth polynucleotide, which encodes an intracellular signaling domain; and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives, the transcriptional activator is HEA3 or HEA4. In some alternatives, HEA3 is a variant of a wild type HEA3 transcription factor. In some alternatives, HEA4 is a variant of a wild type HEA4 transcription factor. In some alternatives, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives, the variant of the HEA3 or HEA4 chimeric transcription factor comprises p65 phosphomimetic and/or acetylmimetic amino acid substitutions that enhance transcriptional activity in response to the drug ligand. In some alternatives, the variant of the wild type HEA3 transcription factor comprises an amino acid sequence set forth in SEQ ID Nos: 1-3, 8-11 and/or 121. In some alternatives, the variant of the wild type HEA3 transcription factor is encoded by a nucleic acid sequence set forth in SEQ ID NO: 12, 13, 14, 19, 20, 21, 22 or 122. In some alternatives, the variant of a wild type HEA4 transcription factor comprises an amino acid sequence set forth in SEQ ID Nos: 4-7. In some alternatives, the variant of the wild type HEA4 transcription factor is encoded by a nucleic acid sequence set forth in SEQ ID NO: 15, 16, 17 or 18. In some alternatives, the drug is tamoxifen and/or its metabolites, 4-hydroxytamoxifen, fulvestrant or other estrogen analogs, or CMP8. In some alternatives, the first promoter comprises a nucleic acid sequence set forth in SEQ ID NO: 23. In some alternatives, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives, the drug induces expression of the chimeric antigen receptor at a non-toxic dosing of drug at less than 10 nM drug but not zero. In some alternatives, the non-toxic dosing of drug decreases, eliminates or prevents drug side effects in comparison to a dosage amount for inducing expression with a wild type HEA3 or wild type HEA4 chimeric transcription factor. In some alternatives, the side effects are cataracts, constipation, diarrhea, edema, fatigue, fluid retention, flushing, headache, hot flashes, high blood pressure, muscle pain, nausea, shortness of breath, vomiting or weight loss. In some alternatives, the signaling domain comprises a CD28, 4-1BB and/or CD3ζ domain. In some alternatives, the second promoter is an inducible promoter. In some alternatives, the second promoter is a constitutive promoter. In some alternatives, the second promoter is the EF1αp. In some alternatives, the transcriptional activator comprises at least one amino acid sequence set forth in SEQ ID NO: 1-11 or 121. In some alternatives, the transcriptional activator is encoded by at least one nucleic acid sequence set forth in SEQ ID NO: 12-22 or 122. In some alternatives, the first nucleic acid further comprises a first vector and the second nucleic acid further comprises a second vector. In some alternatives, both vectors are packaged in a viral vector. In some alternatives, the viral vector is an adeno-associated virus or a lentivirus. In some alternatives, the first nucleic acid further comprises a fifth polynucleotide that encodes a selectable marker. In some alternatives, the second nucleic acid further comprises a sixth polynucleotide that encodes a selectable marker. In some alternatives, the selectable marker is EGFRt and/or HER2t. In some alternatives, the selectable marker confers drug resistance. In some alternatives, the first nucleic acid further comprises a seventh polynucleotide that encodes a self-cleaving peptide. In some alternatives, the self-cleaving peptide comprises a P2A, T2A, E2A or F2A peptide. In some alternatives, the spacer is optimized for increased T cell proliferation and/or cytokine production in response to the ligand as compared to a reference chimeric receptor. In some alternatives, the first nucleic acid further comprises a DNA spacer, wherein the spacer is operably linked to the first promoter and operably linked to the first polynucleotide that encodes the chimeric antigen receptor. In some alternatives, the DNA spacer is between the first promoter and the first polynucleotide that encodes the chimeric antigen receptor. In some alternatives, the DNA spacer comprises a sequence set forth in SEQ ID NO: 120. In some alternatives, the DNA spacer comprises a sequence that has 95%, 90%, 85% or 80% sequence identity to SEQ ID NO: 120 or any percent sequence identity in between a range defined by any two aforementioned values. In some alternatives, the DNA spacer enhances gene expression of the chimeric antigen receptor.

In some alternatives, a system for inducible expression of a gene that regulates a T cell function is provided. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the chimeric antigen receptor comprises a scFv. In some alternatives, the scFv specifically binds to CD19. In some alternatives, the scFv comprises an huCD19 scFv (G01S) amino acid sequence. In some alternatives, the scFv comprises an amino acid sequence set forth in SEQ ID NO: 41 (MLLLVTSLLLCELPHPAFLLIPEVQLVESGG-GLVQPGRSLRLSCAASGFTFDDYAMH WVRQAPGK-GLEWVSGISWNSGRIGYADSVKGRFTISRD-NAKNSLFLQMNSLRAEDT AVYYCARDQGYHYYDSAE-HAFDIWGQGTVVTVSSGGGGSGGGGSGGGGSQ-SALTQ PRSVSGFPGQSVTISCTGTTSDDVSWYQ QHPGKAPQLMLYDVSKRPSGVPHRFSGSR SGRAAS-LIISGLQTEDEADYFCSSYAGRYNS-VLFGGGTKLTVL). In some alternatives, the scFv is encoded by a nucleic acid sequence comprising a nucleic acid sequence encoding the amino acid sequence of SEQ ID NO: 41. In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42 (Atgctgctgctggtgaccagcctgctgtgcgagctgccc-caccccgcctttctgctgatccccgacatccagatgacccagac cacctccagcctgagcgccagcctgggcgaccgggtgac-catcagctgccgggccagccaggacatcagcaagtacctgaactg gtatcagcagaagcccgacggcaccgtcaagctgctgatctac-cacaccagccggctgcacagcggcgtgcccagccggtttagc ggcagcggctccggcaccgactacagcctgaccatctccaacctggaacag-gaagatatcgccacctacttttgccagcagggcaa cacactgccctacacctttggcggcggaacaaagctggaaat-caccggcagcacctccggcagcggcaagcctggcagcggcga gggcagcaccaagggcgaggtgaagctgcag-gaaagcggccctggcctggtggcccccagccagagcctgagcgtgacctgca ccgtgagcggcgtgagcctgcccgactacggcgtgagctg-gatccggcagcccccccaggaagggcctggaatggctgggcgtga tctggggcagcgagaccacctactacaacagcgccctgaagagccggctgac-catcatcaaggacaacagcaagagccaggtgtt cctgaagatgaacagcctgca-gaccgacgacaccgccatctactactgcgccaagcactactac-tacggcggcagctacgccatgg actactggggccagggcaccagcgtgaccgtgagcagc). In some alternatives, the scFv comprises an amino acid sequence set forth in SEQ ID NO: 43 (MLLLVTSLLLCELPHPAFL-LIPDIQMTQTTSSLSASLGDRVTISCRASQDISKY-LNWY QQKPDGTVKLLIYHTSRLHSGVPSRFSGSGSGTDYS-LTISNLEQEDIATYFCQQGNTLP YTFGGGTKLEITGST-SGSGKPGSGEGSTKGEVKLQESGPGLVAP-SQSLSVTCTVSGVS LPDYGVSWIRQPPRKGLEWLGVIWGSETTYYN-SALKSRLTIIKDNSKSQVFLKMNSL QTDDTAIYY-CAKHYYYGGSYAMDYWGQGTSVTVSS). In some alternatives, the scFv is encoded by a nucleic acid sequence comprising a nucleic acid sequence encoding the amino acid sequence of SEQ ID NO: 43. some alternatives, the scFv comprises a B7H3 (hBRCA84D) scFv nucleotide sequence. In some alternatives, the scFv binds specifically to the B7-H3 receptor. In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50 (atgctgctgctggtgaccagcctgctgctgtgcgagctgccc-caccccgcctttctgctgatcccccaggtgcagctgcagcagcct ggcgccgagctggtgaagccaggcgccagcgt-gaagctgtcctgcaaggccagcggctacaccttcaccggctactggatgcact gggtgaagcagagacccggccacggcctggaatggatcggcgagat-caaccccagcaacggccggaccaactacaacgagcgg ttcaagagcaaggc-caccctgaccgtggacaagagcagcaccaccgcctt-catgcagctgtccggcctgaccagcgaggacagcg ccgtgtacttctgcgccagggactactacggcaccagctacaacttcgac-tactggggccagggcaccacactgaccgtgagcagc ggcg-gagggggctctggcggcggaggatctgggggagggggcagcgacatcca-gatgacccagagcagcagcagcttcagcg tgagcctgggcgaccgggtgaccatcacctgtaaggccaacgaggacat-caacaaccggctggcctggtatcagcagacccccgg caacagccccaggctgctgatcagcggcgccac-caacctggtgaccggcgtgcccagccggtttagcggcagcggctccggcaa ggactacaccctgaccatcacaagcctgcaggccgaggacttcgccacctac-tactgccagcagtactggtccaccccccttcaccttc ggcagcggcaccgagctg-gaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFL- LIPQVQLQQPGAELVKPGASVKLSCK- ASGYTFTGYWM HWVKQRPGHGLEWIGEINPSN- GRTNYNERFKSKATLTVDKSSTTAFMQLSGLTSEDS AVYFCARDYYGTSYNFDYWGQGT- TLTVSSGGGGSGGGGSGGGGSDIQMTQSSSSFS VSLGDRVTITCKANEDINNRLAWYQQTPGNSPRLLIS- GATNLVTGVPSRFSGSGSGK DYTLTITSLQAEDFA- TYYCQQYWSTPFTFGSGTELEIK). In some alternatives, the scFv is encoded by a nucleic acid sequence comprising a nucleic acid sequence encoding the amino acid sequence of SEQ ID NO: 51. In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52 (atgcttctcctggtgacaagccttctgctctgtgagttaccacacccagcat- tcctcctgatcccacaggtgcagctgaaacagagcg gcccgggcctggtgcagccgagccagagcctgagcattacctgcaccgt- gagcggctttagcctgaccaactatggcgtgcattgg gtgcgccagagcccgggcaaaggcctggaatggctgggcgtgatttg- gagcggcggcaacaccgattataacaccccgtttacca gccgcctgagcat- taacaaagataacagcaaaagccaggtgtttttaaaat- gaacagcctgcagagcaacgataccgcgatttattat tgcgcgcgcgcgctgacctattatgattatgaatttgcgtat- tggggccagggcaccctggtgaccgtgagcgcgggcggcggcgg cagcggcggcggcggcagcggcggcggcggcagcgatat- tctgctgacccagagcccggtgattctgagcgtgagcccgggcg aacgcgt- gagctttagctgccgcgcgagccagagcattggcaccaacattcat- tggtatcagcagcgcaccaacggcagcccgcgc ctgctgattaaatatgcgagcgaaagcattagcggcattccgagccgctt- tagcggcagcggcagcggcaccgattttaccctgagc attaacagcgtg- gaaagcgaagatattgcggattattattgccagcagaacaacaactggccgac- cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL- CELPHPAFLLIPQVQLKQSGPGLVQPSQSL- SITCTVSGFSLTNYGVHW VRQSPGKGLEW- LGVIWSGGNTDYNTPFTSRLSINKDNSKSQVFFKMN SLQSNDTAIY YCARALTYYDYE- FAYWGQGTLVTVSAGGGGSGGGGSGGGGS- DILLTQSPVILSVSP GERVSFSCRASQSIGT- NIHWYQQRTNGSPRLLIKYASESISGIPSRFSGSGSGTD FTLSI NSVESEDI- ADYYCQQNNNWPTTFGAGTKLELKRT). In some alternatives, the scFv is encoded by a nucleic acid sequence comprising a nucleic acid sequence encoding the amino acid sequence of SEQ ID NO: 53. In some alternatives, the scFv comprises the EGFRVIII (806) scFv nucleotide sequence. In some alternatives, the scFv is specific for EGFR. In some alternatives, the scFv is encoded by the EphA2 (2A4) scFv nucleotide sequence. In some alternatives, the scFv is encoded by the nucleic acid sequence set forth in SEQ ID NO: 56. In some alternatives, the scFv is encoded by the EpHA2 (4H5) scFv nucleotide sequence. In some alternatives, the scFv is encoded by the nucleic acid sequence set forth in SEQ ID NO: 58. In some alternatives, the scFv is encoded by a FITC (E2) scFv nucleotide sequence. In some alternatives, the scFv is encoded by a nucleic acid sequence set forth in SEQ ID NO: 60. In some alternatives, the scFv is encoded by an IL13Ra2 (hu08) VhVl scFv nucleotide sequence. In some alternatives, the scFv is encoded by a nucleic acid sequence set forth in SEQ ID NO: 68. In some alternatives, the scFv comprises an IL13Ra2 hu08 VhVl scFv amino acid sequence. In some alternatives, the scFv comprises an amino acid sequence set forth in SEQ ID NO: 69 (MLLLVTSLLLCELPHPAFLLIPEVQLVESGG- GLVQPGGSLRLSCAASGFTFSRNGMS WVRQAPGK- GLEWVATVSSGGSYIYYADSVKGRFTISRDNAKNS- LYLQMNSLRAEDT AVYYCARQGTTALATRFFDVWGQGTLVTV SSGGGGSGGGGSGGGGSDIQMTQSPSS LSASVGDRVTITCKASQDVGTA- VAWYQQKPGKAPKLLIYSASYRSTGVPSRFSGSGS GTDFTLTISSLQPEDFATYYCQHHYS- APWTFGGGTKVEIKESK). In some alternatives, the scFv is encoded by a nucleic acid sequence comprising a nucleic acid sequence encoding the amino acid sequence of SEQ ID NO: 69. In some alternatives, the scFv is encoded by an IL13Ra2 (hu07) VlVh scFv nucleotide sequence. In some alternatives, the scFv is encoded by a nucleic acid sequence set forth in SEQ ID NO: 70 (atgcttctcctggtgacaagccttctgctctgtgagttaccacacccagcat- tcctcctgatcccagatattcagatgacccagagccc gagcagcct- gagcgcgagcgtgggcgatccgcgtgagcagcacctatctgcattggt atcagcagaaaccgggcaaagcgccgaaactgctgatt- tatagcaccagcaacctggcgagcggcgtgccgagccgctttagcgg cagcggcagcggcaccgattttaccctgaccattagcagcctgcagccggaa- gattttgcgacctattattgccatcagtatcatcgca gcccgctgacctttggcggcggcaccaaagtggaaat- taaaggtggtggtggttctggcggcggcggctccggtggtggtggttctg aagtgcagctggtg- gaaagcggcggcggcctggtgcagcggcggcgggcctggtgcgcggcgagcg gctttacct ttaccaaatatggcgtgcat- tgggtgcgccaggcgccgggcaaaggcctggaatgggtggcggt- gaaatgggcgggcggcagca ccgattataacagcgcgctgatgagccgctt- taccattagccgcgataacgcgaaaaacagcctgtatctgcagatgaacagcctgc gcgcggaagataccgcggtgtattattgcgcgcgcgatcatcgcgatgcgatg- gattattggggccagggcaccctggtgaccgtg agcagcgaatctaagta). In some alternatives, the scFv comprises an IL13Ra2 (hu07) VhVl scFv amino acid sequence. In some alternatives, the scFv comprises an amino acid sequence set forth in SEQ ID NO: 71 (MLLLVTSLLLCELPHPAFLLIPDIQMTQSPSSL- SASVGDRVTITCTASLSVSSTYLHWY QQKPGKAPKLLIYSTSN- LASGVPSRFSGSGSGTDFTLTISSLQPEDFATYY- CHQYHRSP LTFGGGTKVEIKGGGGSGGGGSGGGG- SEVQLVESGGGLVQPGGSLRLSCAASGFTFT KYGVHWVRQAPGKGLEWVAVKWAGGSTDYN- SALMSRFTISRDNAKNSLYLQMNS LRAEDTAVYY- CARDHRDAMDYWGQGTLVTVSSESK). In some alternatives, the scFv is encoded by a nucleic acid sequence comprising a nucleic acid sequence encoding the amino acid sequence of SEQ ID NO: 71. In some alternatives, the scFv is encoded by the IL13Ra2 (hu07) VhVl scFv nucleotide sequence. In some alternatives, the scFv is encoded by a nucleic acid sequence set forth in SEQ ID NO: 72 (atgcttctcctggtgacaagccttctgctctgtgagttaccacacccagcat- tcctcctgatcccagaagtgcagctggtggaaagcg gcggcggcctggtgcagccgggcggcagcctgcgcct- gagctgcgcggcgagcggctttacctttaccaaatatggcgtgcattgg gtgcgccaggcgccgggcaaaggcctggaatgggtggcggt- gaaatgggcgggcggcagcaccgattataacagcgcgctgat gagccgctt- taccattagccgcgataacgcgaaaaacagcctgtatctgcagat- gaacagcctgcgcgcggaagataccgcggtgt attattgcgcgcgcgatcatcgcgatgcgatggattat- tggggccagggcaccctggtgaccgtgagcagcggtggtggtggttctg gcggcggcggctccggtggtggtggttctgatattca- gatgacccagagcccgagcagcctgagcgcgagcgtgggcgatcgcgt gac- cattacctgcaccgcgagcctgagcgtgagcagcacctatctgcat-tggtatcagcagaaaccgggcaaagcgccgaaactgc tgatttatagcaccagcaacctggcgagcggcgtgccgagccgcttagcggcagcggcagcggcaccgatttaccctgaccatta gcagcctgcagccggaagattttgcgacctattattgccatcagtatcatcgcagcccgctgacctttggcggcggcaccaaagtgga aataaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFLLIPEVQLVESGGGLVQPGGSLRLSCAASGFTFTKYGVH WVRQAPGKGLEWVAVKWAGGSTDYNSALMSRFTISRDNAKNSLYLQMNSLRAED TAVYYCARDHRDAMDYWGQGTLVTVSSGGGGSGGGGSGGGGSDIQ MTQSPSSLSA SVGDRVTITCTASLSVSSTYLHWYQQKPGKAPKLLIYSTSNLASGVPSRFSGSGSGTD FTLTISSLQPEDFATYYCHQYHRSPLTFGGGTKVEIKESK). In some alternatives, the scFv is encoded by a nucleic acid sequence comprising a nucleic acid sequence encoding the amino acid sequence of SEQ ID NO: 73. In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74 (atgcttctcctggtgacaagccttctgctctgtgagttaccacacccagcattcctcctgatcccaggccctgtgcctccctctacagcc ctcaggtacctcattgaggagctggtcaacatcacccagaaccagaaggctccgctctgcaatggcagcatggtatggagcatcaac ctgacagctggcatgtactgtgcagccctggaatccctgatcaacgtgtcaggctgcagtgccatcgagaagacccagaggatgctg agcggattctgcccgcacaaggtctcagctgggcagttttccagcttgcatgtccgagacaccaaaatcgaggtggcccagtttgtaa aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFLLIPGPVPPSTALRYLIEELVNITQNQKAPLCNGSMVWSI NLTAGMYCAALESLINVSGCSAIEKTQRMLSGFCPHKVSAGQFSSLHVRDTKIEVAQ FVKDLLLHLKKLFREGRF). In some alternatives, the scFv is encoded by a nucleic acid sequence comprising a nucleic acid sequence encoding the amino acid sequence of SEQ ID NO: 75. In some alternatives, the scFv is encoded by an oaGD2 (8B6) VlVh scFv nucleotide sequence. In some alternatives, the scFv is encoded by a sequence set forth in SEQ ID NO: 76 (atgcttctcctggtgacaagccttctgctctgtgagttaccacacccagcattcctcctgatcccagatgttgtgatgacccaaactcca ctctccctgcctgtcagtcttggagatcaagcctcaatctcttgcagatctagtcagagccttctaaaaaatggaaacaccttttaca ttggtacctgcagaagtcaggccagtctccaaagctccttatctacaaagtttccaaccgactttctggggtcccagacaggttcagtgg cagtggatcagggacatatttcacactcaagatcagcagagtggaggctgaggatctgggagtttatttctgctctcaaagtacacatat tccgtacacattcggaggggggaccaagctcgagctgaaacgaggcggaggggggctctggcggcggaggatctgggggagggg gcagcgaggtgaaactggtggagtctggaggaggcttggtgctgcctggggattctctgagactctcctgtgcaacttctgagttcac cttcactgattactacatgacttgggtccgccagcctccaagaaaggcacttgagtggttgggttttattagaaacagagctaatggttac acaacagagtacaatccatctgtgaagggtcggttcaccatttccagagataattcccaaagcatcctctatcttcaaatgaacaccctg agaactgaggacagtgccacttattactgtgcaagagtctctaactgggcctttgactactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77 (MLLLVTSLLLCELPHPAFLLIPDVVMTQTPLSLPVSLGDQASISCRSSQSLLKNNGNT FLHWYLQKSGQSPKLLIYKVSNRLSGVPDRFSGSGS GTYFTLKISRVEAEDLGVYFCS QSTHIPYTFGGGTKLELKRGGGGSGGGGSGGGGSEVKLVESGGGLVLPGDSLRLSCA TSEFTFTDYYMTWVRQPPRKALEWLGFIRNRANGYTTEYNPSVKGRFTISRDNS QSIL YLQMNTLRTEDSATYYCARVSNWAFDYWGQGTTLTVSS). In some alternatives, the scFv is encoded by a nucleic acid sequence comprising a nucleic acid sequence encoding the amino acid sequence of SEQ ID NO: 77. In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccccaccccgcctttctgctgatcccccaggaacagctcgtcgaaagc ggcggcagactggtgacacctggcggcagcctgaccctgagctgcaaggccagcggcttcgacttcagcgcctactacatgagctg ggtccgccaggcccctggcaagggactggaatggatcgccaccatctaccccagcagcggcaagacctactacgccacctgggtg aacggacggttcaccatctccagcgacaacgcccagaacaccgtggacctgcagatgaacagcctgacagccgccgaccgggcc acctacttttgcgccagagacagctacgccgacgacggcgccctgttcaacatctggggccctggcaccctggtgacaatctctagc ggcggaggcggatctggtggcggaggaagtggcggcggaggatctgagctggtgctgacccagagcccctctgtgtctgctgccc tgggaagccctgccaagatcacctgtaccctgagcagcgcccacaagaccgacaccatcgactggtatcagcagctgcagggcga ggcccccagatacctgatgcaggtgcagagcgacggcagctacaccaagaggccaggcgtgcccgaccggttcagcggatctag ctctggcgccgaccgctacctgatcatccccagcgtgcaggccgatgacgaggccgattactactgtggcgccgactacatcggcg gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESGGRLVTPGGSLTLSCKASGFDFSAYYMSW VRQAPGKGLEWIATIYPSSGKTYYATWVNGRFTISSDNAQNTVDLQMNSLTAADRA TYFCARDSYADDGALFNIWGPGTLVTISSGGGGSGGGGSGGGGSELVLTQSPSVSAA LGSPAKITCTLSSAHKTDTIDWYQQLQGEAPRYLMQVQSDGSYTKRPGVPDRFSGSS SGADRYLIIPSVQADDEADYYCGADYIGGYVFGGGTQLTVTG). In some alternatives, the scFv is encoded by a nucleic acid sequence comprising a nucleic acid sequence encoding the amino acid sequence of SEQ ID NO: 79. In some alternatives, the scFv comprises an amino acid sequence set forth in SEQ ID NO: 80 (CD33 (h2H12) VhVl scFv nucleotide sequence (atgcttctcctggtgacaagccttctgctctgtgagttaccacacccagcattcctcctgatcccacaggttcagctggtgcagtctgga gctgaggtgaagaagcctggggcctcagtgaaggtctcctgcaaggcttctggttacaccttcaccaattatgatataaattgggtgag acaggcccctggacaagggcttgagtggattggatggatttatcctggagatggtagtaccaaatataatgagaaattcaaggccaag gctaccctgacagctgacacatccaccagcacagcctacatggagctgaggagcctgagatctgatgacacagctgtgtattactgtg cttctggatatgaagatgctatggactactgggggcaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQSGAEVKKPGASVKVSCKASGYTFTNYDIN WVRQAPGQGLEWIGWIYPGDGSTKYNEKFKAKATLTADTSTSTAYMELRSLRSDDT AVYYCASGYEDAMDYWGQGTTVTVSS). In some alternatives, the scFv is encoded by a nucleic acid sequence comprising a nucleic acid sequence encoding the amino acid sequence of SEQ ID NO: 81. In some alternatives, the scFv is encoded by a sequence set forth in SEQ ID NO: 82 (CD33 (h2H12) VlVh scFv nucleotide sequence: atgcttctcctggtgacaagccttctgctctgtgagttaccacacccagcattcctcctgatcccagacatccagatgacccagtctccat cctcactgtctgcatctgtaggagacagagtcaccatcaattgtaaggctagtcaggacattaatagctatttgagctggtttcagcaga aaccagggaaagcccctaagaccctgatctatagagcaaatagattggtagatggggtcccatcaaggttctctggcagtggatctgg gcaagattatactctcaccatcagcagcctgcagcctgaagattttgcaacttattactgcttgcagtatgatgagtttcctctcacatttgg aggagggaccaaggtggagatcaaa). In some alternatives, the scFv comprises an amino acid sequence set forth in SEQ ID NO: 83 (CD33 (h2H12) VlVh scFv amino acid sequence: MLLLVTSLLLCELPHPAFLLIPDIQMTQSPSSLSASVGDRVTINCKASQDINSYLSWFQ QKPGKAPKTLIYRANRLVDGVPSRFS GSGSGQDYTLTISSLQPEDFATYYCLQYDEFP LTFGGGTKVEIK). In some alternatives, the scFv is encoded by a nucleic acid sequence comprising a nucleic acid sequence encoding the amino acid sequence of SEQ ID NO: 83. In some alternatives, the scFv is encoded by a nucleic acid sequence set forth in SEQ ID NO: 84. In some alternatives, the scFv is encoded by a nucleic acid sequence set forth in SEQ ID NO: 86. In some alternatives, the scFv comprises an amino acid sequence set forth in SEQ ID NO: 87. In some alternatives, the spacer is encoded by the nucleic acid sequence set forth in SEQ ID NO: 102 (IgG4 hinge nucleotide sequence: gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, HEA3 comprises two amino acid mutations, wherein the sequence is encoded by a sequence set forth in SEQ ID NO: 122 (atggtgtccaagctgtcccagctgcagacagaactgctggcagcactgctggaaagcggcctgagcaaagaggccctgattcagg cactcggcgaacctggaccttatctgctcgctggcgaaggccctctggataagggcgagagctgtggcggaggaa gaggagagct ggccgagctgcctaacggcctgggcgagacaagaggcagcgaggacgagacagacgacgacggcgaggacttcacccccccc atcctgaaagagctggaaaacctgagccccgaggaagccgcccaccagaaagccgtggtggagacactgctgcaggaagatccc tggcgggtcgccaagatggtcaagagctacctgcagcagcacaacatcccccagcgggaggtggtggacaccaccggcctgaac cagagccacctgagccagcacctgaacaagggcacccccatgaaaacccagaagagagccgccctgtacacttggtacgtgcgg aagcagagagaggtggcccagcagtttacacacgccggccagggcggcctgatcgaggaacctaccggcgacgagctgcccac caagaagggcagacggaaccggtttaagtggggccctgcatctcagcagatcctgttccaggcctacgagcggcagaagaacccc agcaaagaggaacgggagacactggtggaagagtgcaaccgggccgagtgcatccagagaggcgtgagcccttctcaggctcag ggcctcggcagcaatctggtcaccgaagtgcgggtgtacaattggttcgccaaccggcggaaagaggaagccttccggcacaagct gtctgctggcgatatgagagccgccaacctgtggcccagcccccctgatgatcaagcggagcaagaagaacagcctggccctgagc ctgaccgccgatcagatggtgtccgctctgctggacgccgagccccctatcctgtacagcgagtacgaccccaccagacccttcagc gaggccagcatgatgggcctgctgaccaacctggccgaccgggagctggtgcacatgatcaactgggccaagcgggtgcccggc ttcgtggacctgaccctgcacgaccaggtccacctgctggaatgtgcctggctggaaatcctgatgatcggcctcgtgtggagaagc atggaacaccccggcaagctgctgttcgcccccaacctgctcctggaccggaaccagggaaagtgcgtggagggcatggtggaga tcttcgacatgctgctggccacctccagccggttccggatgatgaacctgcagggcgaggaattcgtgtgcctgaagtccatcatcct gctgaacagcggcgtgtacaccttcctgtcatccaccctgaagtccctggaagagaaggaccacatccaccgggtgctggacaaga tcaccgacaccctgatccacctgatggccaaggctggcctgacactccagcagcagcaccagagactggcccagctgctgctgatc ctgagccacatccggcacatgagcaacaagcggatggaacacctgtacagcatgaagtgcaagaacgtggtgcccctgtacgacct gctgctcgagatgctggatgcccacagactgcacgcccctacaagcagaggcggagccagcgtggaggaaaccgaccagtctca cctggccaccgccggcagcacaagcagccacagcctgcagaagtactacatcaccggcgaggccgagggattccctgccaccgt ggagttccagtacctgcccgacaccgacgaccggcaccggatcgaggaaaagcggaagcggacctacgagacattccagagcat catgaagaagtccccccttcagcggccccaccgatcccagacccccccctagaagaatcgccgtgcccagcagatctagcgccagc gtgcccaagcctgccccccagccctaccctttcaccagcagcctgagcaccatcaactacgacgagttccctaccatggtgttcccca gcggccagatctctcaggcctctgctctggcacctgctccacctcaggtgctgcctcaggcccctgctccagccccagcccctgccat ggtgtctgcactggcccaggctccagctcctgtgcctgtgctggcccctggacctc ctcaggctgtggcccctcctgcccctaaacct acccaggccggggagggaacactgtctgaggccctgctgcagctccagttcgacgacgaggatctgggagcactgctgggcaata gcaccgaccccgccgtgtttaccgacctggcctccgtggacaacagcgagttccagcagctcctcaaccagggc atccctgtcgcc ccacacaccaccgagcccatgctgatggaataccccgaggccatcaccagactggtcacaggcgcccagaggcctccagatccag caccagctccactgggagcccctggcctgcctaatgggctgctgtctggcgacga ggacttcgagagcattgccgacatggacttca gcgccctgctgtcccagatcagcagc). In some alternatives, the HEA3 comprises an amino acid sequence set forth in SEQ ID NO: 121 (MVSKLSQLQTELLAALLESGLSKEALIQALGEPGPYLLAGEGPLDKGESCGGGRGEL AELPNGLGETRGSEDETDDDGEDFTPPILKELENLSPEEAAHQKAVVETLL QEDPWR VAKMVKSYLQQHNIPQREVVDTTGLNQSHLSQHLNKGTPMKT QKRAALYTWYVR KQREVAQQFTHAGQGGLIEEPTGDELPTKKGRRNRFKWGPASQQILFQAYERQKNP SKEERETLVEECNRAECIQRGVSPSQAQGLGSNLVTEVRVYNWFANRRKEEAFRHK LSAGDMRAANLWPSPLMIKRSKKNSLALSLTADQMVSALLDAEPPILYSEYDPTRPF SEASMMGLLTNLADRELVHMINWAKRVPGFVDLTLHDQVHLLECAWLEILMIGLV WRSMEHPGKLLFAPNLLLDRNQGKCVEGMVEIFDMLLATSSRFRMMNLQGEEFVC LKSIILLNSGVYTFLSSTLKSLEEKDHIHRVLDKITDTLIHLMAKAGLTLQQQHQRLA QLLLILSHIRHMSNKRMEHLYSMKCKNVVPLYDLLLEMLDAHRLHAPTSRGGASVE ETDQSHLATAGSTSSHSLQKYYITGEAEGFPATVEFQYLPDTDDRHRIEEKRKRTYET FQSSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3. In some alternatives, a system for inducible expression of a chimeric antigen receptor in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttctcaaggaccaccg-catctctacattcaagaactggcccttcttggag ggctgcgcctgcaccccg-gagcggatggccgaggctggcttcatccactgccccactgagaacgagcca-gacttggcccagtgttt cttctgcttcaaggagctggaaggctgggagccagatgacgaccccatagag-gaacataaaaagcattcgtccggttgcgctttccttt ctgtcaagaagcagttt-gaagaattaacccttggtgaatttttgaaactggacagagaaagagc-caagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD). In some alternatives, a system for inducible expression of a transgene in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttct-caaggaccaccgcatctctacattcaagaactggcccttcttggag ggctgcgcctgcaccccggagcggatggccgaggctggcttcatccactgccc-cactgagaacgagccagacttggcccagtgttt cttctgcttcaaggagctg-gaaggctgggagccagatgacgaccccatagaggaacataaaaagcat-tcgtccggttgcgctttccttt ctgtcaagaagcagtttgaagaattaacccttggtgaatttttt-gaaactggacagagaaagagccaagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD).

In some alternatives, a chimeric receptor polypeptide coded for by the first nucleic acid of the system of any one of the alternatives herein or the second nucleic acid of the system of any one of the alternatives is provided. In some alternatives, the system is for inducible expression of a chimeric antigen receptor in cells, such as mammalian cells, The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and any other selected molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the chimeric antigen receptor comprises a scFv. In some alternatives, the scFv specifically binds to CD19. In some alternatives, the scFv comprises an huCD19 scFv (G01S) amino acid sequence. In some alternatives, the scFv comprises an amino acid sequence set forth in SEQ ID NO: 41 (MLLLVTSLLLCELPHPAFLLIPEVQLVESGG-GLVQPGRSLRLSCAASGFTFDDYAMH WVRQAPGK-GLEWVSGISWNSGRIGYADSVKGRFTISRD-NAKNSLFLQMNSLRAEDT AVYYCARDQGYHYYDSAE-HAFDIWGQGTVVTVSSGGGGSGGGGSGGGGSQ-SALTQ PRSVSGFPGQSVTISCTGTTSDDVSWYQQHPGKAPQL MLYDVSKRPSGVPHRFSGSR SGRAASLIISGLQT-EDEADYFCSSYAGRYNSVLFGGGTKLTVL). In some alternatives, the scFv is encoded by a nucleic acid sequence comprising a nucleic acid sequence encoding the amino acid sequence of SEQ ID NO: 41. In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42 (Atgctgctgctggtgaccagcctgctgtgcgagctgccc-caccccgcctttctgctgatccccgacatccagatgacccagac cacctccagcctgagcgccagcctgggcgaccgggtgac-catcagctgccgggccagccaggacatcagcaagtacctgaactg gtatcagcagaagcccgacggcaccgtcaagctgctgatctac-cacaccagccggctgcacagcggcgtgcccagccggtttagc ggcagcggctccggcaccgactacagcctgaccatctccaacctggaacag-gaagatatcgccacctacttttgccagcagggcaa cacactgccctacacctttggcggcggaacaaagctggaaat-caccggcagcacctccggcagcggcaagcctggcagcggcga gggcagcaccaagggcgaggtgaagctgcag-gaaagcggccctggcctggtggcccccagccagagcctgagcgtgacctgca ccgtgagcggcgtgagcctgcccgactacggcgtgagctg-gatccggcagcccccccaggaagggcctggaatggctgggcgtga tctggggcagcgagaccacctactacaacagcgccctgaagagccggctgac-catcatcaaggacaacagcaagagccaggtgtt cctgaagatgaacagcctgca-gaccgacgacaccgccatctactactgcgccaagcactactac-tacggcggcagctacgccatgg actactggggccagggcaccagcgtgaccgtgagcagc). In some alternatives, the scFv comprises an amino acid sequence set forth in SEQ ID NO: 43 (MLLLVTSLLLCELPHPAFL-LIPDIQMTQTTSSLSASLGDRVTISCRASQDISKY-LNWY QQKPDGTVKLLIYHTSRLHSGVPSRFSGSGSGTDYS-LTISNLEQEDIATYFCQQGNTLP YTFGGGTKLEITGST-SGSGKPGSGEGSTKGEVKLQESGPGLVAP-SQSLSVTCTVSGVS LPDYGVSWIRQPPRKGLEWLGVIWGSETTYYN-SALKSRLTIIKDNSKSQVFLKMNSL QTDDTAIYY-CAKHYYYGGSYAMDYWGQGTSVTVSS). In some alternatives, the scFv is encoded by a nucleic acid sequence comprising a nucleic acid sequence encoding the amino acid sequence of SEQ ID NO: 43. some alternatives, the scFv comprises a B7H3 (hBRCA84D) scFv nucleotide sequence. In some alternatives, the scFv binds specifically to the B7-H3 receptor. In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50 (atgctgctgctggtgaccagcctgctgctgtgcgagctgccc- caccccgcctttctgctgatcccccaggtgcagctgcagcagcct ggcgccgagctggtgaagccaggcgccagcgt- gaagctgtcctgcaaggccagcggctacaccttcaccggctactggatgcact gggtgaagcagagacccggccacggcctggaatggatcggcgagat- caaccccagcaacggccggaccaactacaacgagcgg ttcaagagcaaggc- caccctgaccgtggacaagagcagcaccaccgcctt- catgcagctgtccggcctgaccagcgaggacagcg ccgtgtacttctgcgccagggactactacggcaccagctacaacttcgac- tactggggccagggcaccacactgaccgtgagcagc ggcg- gagggggctctggcggcggaggatctgggggagggggcagcgacatcca- gatgacccagagcagcagcagcttcagcg tgagcctgggcgaccgggtgaccatcacctgtaaggccaacgaggacat- caacaaccggctggcctggtatcagcagacccccgg caacagccccaggctgctgatcagcggcgccac- caacctggtgaccggcgtgcccagccggtttagcggcagcggctccggcaa ggactacaccctgaccatcacaagcctgcaggccgaggacttcgccacctac- tactgccagcagtactggtccaccccccttcaccttc ggcagcggcaccgagctg- gaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFL- LIPQVQLQQPGAELVKPGASVKLSCK- ASGYTFTGYWM HWVKQRPGHGLEWIGEINPSN- GRTNYNERFKSKATLTVDKSSTTAFMQLSGLTSEDS AVYFCARDYYGTSYNFDYWGQGT- TLTVSSGGGGSGGGGSGGGGSDIQMTQSSSSFS VSLGDRVTITCKANEDINNRLAWYQQTPGNSPRLLIS- GATNLVTGVPSRFSGSGSGK DYTLTITSLQAEDFA- TYYCQQYWSTPFTFGSGTELEIK). In some alternatives, the scFv is encoded by a nucleic acid sequence comprising a nucleic acid sequence encoding the amino acid sequence of SEQ ID NO: 51. In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52 (atgcttctcctggtgacaagccttctgctctgtgagttaccacacccagcat- tcctcctgatcccacaggtgcagctgaaacagagcg gcccgggcctggtgcagccgagccagagcctgagcattacctgcaccgt- gagcggctttagcctgaccaactatggcgtgcattgg gtgcgccagagcccgggcaaaggcctggaatggctgggcgtgatttg- gagcggcggcaacaccgattataacaccccgtttacca gccgcctgagcat- taacaaagataacagcaaaagccaggtgtttttaaaat- gaacagcctgcagagcaacgataccgcgatttattat tgcgcgcgcgcgctgacctattatgattatgaatttgcgtat- tggggccagggcaccctggtgaccgtgagcgcgggcggcggcgg cagcggcggcggcggcagcggcggcggcggcagcgatat- tctgctgacccagagcccggtgattctgagcgtgagcccgggcg aacgcgt- gagctttagctgccgcgcgagccagagcattggcaccaacattcat- tggtatcagcagcgcaccaacggcagcccgcgc ctgctgattaaatatgcgagcgaaagcattagcggcattccgagccgctt- tagcggcagcggcagcggcaccgattttaccctgagc attaacagcgtg- gaaagcgaagatattgcggattattattgccagcagaacaacaactggccgac- cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL- CELPHPAFLLIPQVQLKQSGPGLVQPSQSL- SITCTVSGFSLTNYGVHW VRQSPGKGLEW- LGVIWSGGNTDYNTPFTSRLSINKDNSKSQVFFKMN SLQSNDTAIY YCARALTYYDYE- FAYWGQGTLVTVSAGGGGSGGGGSGGGGS- DILLTQSPVILSVSP GERVSFSCRASQSIGT- NIHWYQQRTNGSPRLLIKYASESISGIPSRFSGSGSGTD FTLSI NSVESEDI- ADYYCQQNNNWPTTFGAGTKLELKRT). In some alternatives, the scFv is encoded by a nucleic acid sequence comprising a nucleic acid sequence encoding the amino acid sequence of SEQ ID NO: 53. In some alternatives, the scFv comprises the EGFRVIII (806) scFv nucleotide sequence. In some alternatives, the scFv is specific for EGFR. In some alternatives, the scFv is encoded by the EphA2 (2A4) scFv nucleotide sequence. In some alternatives, the scFv is encoded by the nucleic acid sequence set forth in SEQ ID NO: 56. In some alternatives, the scFv is encoded by the EpHA2 (4H5) scFv nucleotide sequence. In some alternatives, the scFv is encoded by the nucleic acid sequence set forth in SEQ ID NO: 58. In some alternatives, the scFv is encoded by a FITC (E2) scFv nucleotide sequence. In some alternatives, the scFv is encoded by a nucleic acid sequence set forth in SEQ ID NO: 60. In some alternatives, the scFv is encoded by an IL13Ra2 (hu08) VhVl scFv nucleotide sequence. In some alternatives, the scFv is encoded by a nucleic acid sequence set forth in SEQ ID NO: 68. In some alternatives, the scFv comprises an IL13Ra2 hu08 VhVl scFv amino acid sequence. In some alternatives, the scFv comprises an amino acid sequence set forth in SEQ ID NO: 69 (MLLLVTSLLLCELPHPAFLLIPEVQLVESGG- GLVQPGGSLRLSCAASGFTFSRNGMS WVRQAPGK- GLEWVATVSSGGSYIYYADSVKGRFTISRDNAKNS- LYLQMNSLRAEDT AVYYCARQGTTALA- TRFFDVWGQGTLVTVSSGGGGSGGGGSGGGGSDIQ MTQSPSS LSASVGDRVTITCKASQDVGTA- VAWYQQKPGKAPKLLIYSASYRSTGVPSRFSGSGS GTDFTLTISSLQPEDFATYYCQHHYS- APWTFGGGTKVEIKESK). In some alternatives, the scFv is encoded by a nucleic acid sequence comprising a nucleic acid sequence encoding the amino acid sequence of SEQ ID NO: 69. In some alternatives, the scFv is encoded by an IL13Ra2 (hu07) VlVh scFv nucleotide sequence. In some alternatives, the scFv is encoded by a nucleic acid sequence set forth in SEQ ID NO: 70 (atgcttctcctggtgacaagccttctgctctgtgagttaccacacccagcat- tcctcctgatcccagatattcagatgacccagagccc gagcagcct- gagcgcgagcgtgggcgatccgcgtgagcagcacctatctgcattggt atcagcagaaaccgggcaaagcgccgaaactgctgatt- tatagcaccagcaacctggcgagcggcgtgccgagccgctttagcgg cagcggcagcggcaccgattttaccctgaccattagcagcctgcagccggaa- gattttgcgacctattattgccatcagtatcatcgca gcccgctgacctttggcggcggcaccaaagtggaaat- taaaggtggtggtggttctggcggcggcggctccggtggtggtggttctg aagtgcagctggtg- gaaagcggcggcggcctggtgcagcggcggcgggcctggtgcgcggcgagc ggctttacct ttaccaaatatggcgtgcat- tgggtgcgccaggcgccgggcaaaggcctggaatgggtggcggt- gaaatgggcgggcggcagca ccgattataacagcgcgctgatgagccgctt- taccattagccgcgataacgcgaaaaacagcctgtatctgcagatgaacagcctgc gcgcggaagataccgcggtgtattattgcgcgcgcgatcatcgcgatgcgatg- gattattggggccagggcaccctggtgaccgtg agcagcgaatctaagta). In some alternatives, the scFv comprises an IL13Ra2 (hu07) VhVl scFv amino acid sequence. In some alternatives, the scFv comprises an amino acid sequence set forth in SEQ ID NO: 71 (MLLLVTSLLLCELPHPAFLLIPDIQMTQSPSSL- SASVGDRVTITCTASLSVSSTYLHWY QQKPGKAPKLLIYSTSN- LASGVPSRFSGSGSGTDFTLTISSLQPEDFATYY- CHQYHRSP LTFGGGTKVEIKGGGGSGGGGSGGGG- SEVQLVESGGGLVQPGGSLRLSCAASGFTFT KYGVHWVRQAPGKGLEWVAVKWAGGSTDYN- SALMSRFTISRDNAKNSLYLQMNS LRAEDTAVYYCARDHRDAMDYWGQGTLVTVSSESK). In some alternatives, the scFv is encoded by a nucleic acid sequence comprising a nucleic acid sequence encoding the amino acid sequence of SEQ ID NO: 71. In some alternatives, the scFv is encoded by the IL13Ra2 (hu07) VhVl scFv nucleotide sequence. In some alternatives, the scFv is encoded by a nucleic acid sequence set forth in SEQ ID NO: 72 (atgcttctcctggtgacaagccttctgctctgtgagttaccacacccagcattcctcctgatcccagaagtgcagctggtggaaagcg gcggcggcctggtgcagccgggcggcagcctgcgcctgagctgcgcggcgagcggctttacctttaccaaatatggcgtgcattgg gtgcgccaggcgccgggcaaaggcctggaatgggtggcggtgaaatgggcgggcggcagcaccgattataacagcgcgctgat gagccgctttaccattagccgcgataacgcgaaaaacagcctgtatctgcagatgaacagcctgcgcgcggaagataccgcggtgt attattgcgcgcgcgatcatcgcgatgcgatggattattggggccagggcaccctggtgaccgtgagcagcggtggtggtggttctg gcggcggcggctccggtggtggtggttctgatattcagatgacccagagcccgagcagcctgagcgcgagcgtgggcgatcgcgt gaccattacctgcaccgcgagcctgagcgtgagcagcacctatctgcattggtatcagcagaaaccgggcaaagcgccgaaactgc tgatttatagcaccagcaacctggcgagcggcgtgccgagccgctttagcggcagcggcagcggcaccgatttaccctgaccatta gcagcctgcagccggaagattttgcgacctattattgccatcagtatcatcgcagcccgctgacctttggcggcggcaccaaagtgga aattaaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFLLIPEVQLVESGGGLVQPGGSLRLSCAASGFTFTKYGVH WVRQAPGKGLEWVAVKWAGGSTDYNSALMSRFTISRDNAKNSLYLQMNSLRAED TAVYYCARDHRDAMDYWGQGTLVTVSSGGGGSGGGGSGGGGSDIQM TQSPSSLSA SVGDRVTITCTASLSVSSTYLHWYQQKPGKAPKLLIYSTSNLASGVPSRFSGSGSGTD FTLTISSLQPEDFATYYCHQYHRSPLTFGGGTKVEIKESK). In some alternatives, the scFv is encoded by a nucleic acid sequence comprising a nucleic acid sequence encoding the amino acid sequence of SEQ ID NO: 73. In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74 (atgcttctcctggtgacaagccttctgctctgtgagttaccacacccagcattcctcctgatcccaggccctgtgcctccctctacagcc ctcaggtacctcattgaggagctggtcaacatcacccagaaccagaaggctccgctctgcaatggcagcatggtatggagcatcaac ctgacagctggcatgtactgtgcagccctggaatccctgatcaacgtgtcaggctgcagtgccatcgagaagacccagaggatgctg agcggattctgcccgcacaaggtctcagctgggcagttttccagcttgcatgtccgagacaccaaaatcgaggtggcccagtttgtaa aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFLLIPGPVPPSTALRYLIEELVNITQNQKAPLCNGSMVWSI NLTAGMYCAALESLINVSGCSAIEKTQRMLSGFCPHKVSAGQFSSLHVRDTKIEVAQ FVKDLLLHLKKLFREGRF). In some alternatives, the scFv is encoded by a nucleic acid sequence comprising a nucleic acid sequence encoding the amino acid sequence of SEQ ID NO: 75. In some alternatives, the scFv is encoded by an oaGD2 (8B6) VlVh scFv nucleotide sequence. In some alternatives, the scFv is encoded by a sequence set forth in SEQ ID NO: 76 (atgcttctcctggtgacaagccttctgctctgtgagttaccacacccagcattcctcctgatcccagatgttgtgatgacccaaactcca ctctccctgcctgtcagtcttggagatcaagcctcaatctcttgcagatctagtcagagccttctaaaaaatggaaacacctttttaca ttggtacctgcagaagtcaggccagtctccaaagctccttatctacaaagtttccaaccgactttctggggtcccagacaggttcagtgg cagtggatcagggacatatttcacactcaagatcagcagagtggaggctgaggatctgggagtttatttctgctctcaaagtacacatat tccgtacacattcggaggggggaccaagctcgagctgaaacgaggcggaggggggctctggcggcggaggatctgggggagggg gcagcgaggtgaaactggtggagtctggaggaggcttggtgctgcctggggattctctgagactctcctgtgcaacttctgagttcac cttcactgattactacatgacttgggtccgccagcctccaagaaaggcacttgagtggttgggttttattagaaacagagctaatggttac acaacagagtacaatccatctgtgaagggtcggttcaccatttccagagataattcccaaagcatcctctatcttcaaatgaacaccctg agaactgaggacagtgccacttattactgtgcaagagtctctaactgggcctttgactactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77 (MLLLVTSLLLCELPHPAFLLIPDVVMTQTPLSLPVSLGDQASISCRSSQSLLKNNGNT FLHWYLQKSGQSPKLLIYKVSNRLSGVPDRFSGSGSG TYFTLKISRVEAEDLGVYFCS QSTHIPYTFGGGTKLELKRGGGGSGGGGSGGGGSEVKLVESGGGLVLPGDSLRLSCA TSEFTFTDYYMTWVRQPPRKALEWLGFIRNRANGYTTEYNPSVKGRFTISRDNS QSIL YLQMNTLRTEDSATYYCARVSNWAFDYWGQGTTLTVSS). In some alternatives, the scFv is encoded by a nucleic acid sequence comprising a nucleic acid sequence encoding the amino acid sequence of SEQ ID NO: 77. In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccccaccccgcctttctgctgatcccccaggaacagctcgtcgaaagc ggcggcagactggtgacacctggcggcagcctgaccctgagctgcaaggccagcggcttcgacttcagcgcctactacatgagctg ggtccgccaggcccctggcaagggactggaatggatcgccaccatctaccccagcagcggcaagacctactacgccacctgggtg aacggacggttcaccatctccagcgacaacgcccagaacaccgtggacctgcagatgaacagcctgacagccgccgaccgggcc acctacttttgcgccagagacagctacgccgacgacggcgccctgttcaacatctggggccctggcaccctggtgacaatctctagc ggcggaggcggatctggtggcggaggaagtggcggcggaggatctgagctggtgctgacccagagcccctctgtgtctgctgccc tgggaagccctgccaagatcacctgtaccctgagcagcgcccacaagaccgacaccatcgactggtatcagcagctgcagggcga ggcccccagatacctgatgcaggtgcagagcgacggcagctacaccaagaggccaggcgtgcccgaccggttcagcggatctag ctctggcgccgaccgctacctgatcatccccagcgtgcaggccgatgacgaggccgattactactgtggcgccgactacatcggcg gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESGGRLVTPGGSLTLSCKASGFDFSAYYMSW VRQAPGKGLEWIATIYPSSGKTYYATWVNGRFTISSDNAQNTVDLQMNSLTAADRA TYFCARDSYADDGALFNIWGPGTLVTISSGGGGSGGGGSGGGGSELVLTQSPSVSAA LGSPAKITCTLSSAHKTDTIDWYQQLQGEAPRYLMQVQSDG- SYTKRPGVPDRFSGSS SGADRYLIIPSVQADDEADYYCGADYIGGYVFGGGTQLTVTG). In some alternatives, the scFv is encoded by a nucleic acid sequence comprising a nucleic acid sequence encoding the amino acid sequence of SEQ ID NO: 79. In some alternatives, the scFv comprises an amino acid sequence set forth in SEQ ID NO: 80 (CD33 (h2H12) VhVl scFv nucleotide sequence (atgcttctcctggtgacaagccttctgctctgtgagttaccacacccagcattcctcctgatcccacaggttcagctggtgcagtctgga gctgaggtgaagaagcctggggcctcagtgaaggtctcctgcaaggcttctggttacaccttaccaattatgatataaattgggtgag acaggcccctggacaagggcttgagtggattggatggatttatcctggagatggtagtaccaaatataatgagaaattcaaggccaag gctaccctgacagctgacacatccaccagcacagcctacatggagctgaggagcctgagatctgatgacacagctgtgtattactgtg cttctggatatgaagatgctatggactactgggggcaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQSGAEVKKPGASVKVSCKASGYTFTNYDIN WVRQAPGQGLEWIGWIYPGDGSTKYNEKFKAKATLTADTSTSTAYMELRSLRSDDT AVYYCASGYEDAMDYWGQGTTVTVSS). In some alternatives, the scFv is encoded by a nucleic acid sequence comprising a nucleic acid sequence encoding the amino acid sequence of SEQ ID NO: 81. In some alternatives, the scFv is encoded by a sequence set forth in SEQ ID NO: 82 (CD33 (h2H12) VlVh scFv nucleotide sequence: atgcttctcctggtgacaagccttctgctctgtgagttaccacacccagcattcctcctgatcccagacatccagatgacccagtctccat cctcactgtctgcatctgtaggagacagagtcaccatcaattgtaaggctagtcaggacattaatagctatttgagctggtttcagcaga aaccagggaaagcccctaagaccctgatctatagagcaaatagattggtagatggggtcccatcaaggttctctggcagtggatctgg gcaagattatactctcaccatcagcagcctgcagcctgaagattttgcaacttattactgcttgcagtatgatgagtttcctctcacatttgg aggagggaccaaggtggagatcaaa). In some alternatives, the scFv comprises an amino acid sequence set forth in SEQ ID NO: 83 (CD33 (h2H12) VlVh scFv amino acid sequence: MLLLVTSLLLCELPHPAFLLIPDIQMTQSPSSLSASVGDRVTINCKASQDINSYLSWFQ QKPGKAPKTLIYRANRLVDGVPSRFSGSGSGQDYTL TISSLQPEDFATYYCLQYDEFP LTFGGGTKVEIK). In some alternatives, the scFv is encoded by a nucleic acid sequence comprising a nucleic acid sequence encoding the amino acid sequence of SEQ ID NO: 83. In some alternatives, the scFv is encoded by a nucleic acid sequence set forth in SEQ ID NO: 84. In some alternatives, the scFv is encoded by a nucleic acid sequence set forth in SEQ ID NO: 86. In some alternatives, the scFv comprises an amino acid sequence set forth in SEQ ID NO: 87. In some alternatives, the spacer is encoded by the nucleic acid sequence set forth in SEQ ID NO: 102 (IgG4 hinge nucleotide sequence: gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, HEA3 comprises two amino acid mutations, wherein the sequence is encoded by a sequence set forth in SEQ ID NO: 122 (atggtgtccaagctgtcccagctgcagacagaactgctggcagcactgctggaaagcggcctgagcaaagaggccctgattcagg cactcggcgaacctggacctatctgctcgctggcgaaggccctctggataagggcgagagctgtggcggaggaa gaggagagct ggccgagctgcctaacggcctgggcgagacaagaggcagcgaggacgagacagacgacgacggcgaggacttcacccccccc atcctgaaagagctggaaaacctgagccccgaggaagccgcccaccagaaagccgtggtggagacactgctgcaggaagatccc tggcgggtcgccaagatggtcaagagctacctgcagcagcacaacatcccccagcgggaggtggtggacaccaccggcctgaac cagagccacctgagccagcacctgaacaagggcacccccatgaaaacccagaagagagagccgccctgtacacttggtacgtgcgg aagcagagagaggtggcccagcagtttacacacgccggccagggcggcctgatcgaggaacctaccggcgacgagctgcccac caagaagggcagacggaaccggtttaagtggggccctgcatctcagcagatcctgttccaggcctacgagcggcagaagaacccc agcaaagaggaacgggagacactggtggaagagtgcaaccgggccgagtgcatccagagaggcgtgagcccttctcaggctcag ggcctcggcagcaatctggtcaccgaagtgcgggtgtacaattggttcgccaaccggcggaaagaggaagccttccggcacaagct gtctgctggcgatatgagagccgccaacctgtggcccagccccctgatgatcaagcggagcaagaagaacagcctggccctgagc ctgaccgccgatcagatggtgtccgctctgctggacgccgagccccctatcctgtacagcgagtacgaccccaccagacccttcagc gaggccagcatgatgggcctgctgaccaacctggccgaccgggagctggtgcacatgatcaactgggccaagcgggtgcccggc ttcgtggacctgaccctgcacgaccaggtccacctgctggaatgtgcctggctggaaatcctgatgatcggcctcgtgtggagaagc atggaacaccccggcaagctgctgttcgcccccaacctgctcctggaccggaaccagggaaagtgcgtggagggcatggtggaga tcttcgacatgctgctggccacctccagccggttccggatgatgaacctgcagggcgaggaattcgtgtgcctgaagtccatcatcct gctgaacagcggcgtgtacaccttcctgtcatccaccctgaagtccctggaagagaaggaccacatccaccgggtgctggacaaga tcaccgacaccctgatccacctgatggccaaggctggcctgacactccagcagcagcaccagagactggcccagctgctgctgatc ctgagccacatccggcacatgagcaacaagcggatggaacacctgtacagcatgaagtgcaagaacgtggtgcccctgtacgacct gctgctcgagatgctggatgcccacagactgcacgcccctacaagcagaggcggagccagcgtggaggaaaccgaccagtctca cctggccaccgccggcagcacaagcagccacagcctgcagaagtactacatcaccggcgaggccgagggattccctgccaccgt ggagttccagtacctgcccgacaccgacgaccggcaccggatcgaggaaaagcggaagcggacctacgagacattccagagcat catgaagaagtccccccttcagcggccccaccgatcccagacccccccctagaagaatcgccgtgcccagcagatctagcgccagc gtgcccaagcctgccccccagccctaccctttcaccagcagcctgagcaccatcaactacgacgagttccctaccatggtgttcccca gcggccagatctctcaggcctctgctctggcacctgctccacctcaggtgctgcctcaggcccctgctccagccccagcccctgccat ggtgtctgcactggcccaggctccagctcctgtgcctgtgctggcccctggacctc ctcaggctgtggcccctcctgcccctaaacct acccaggccggggagggaacactgtctgaggccctgctgcagctccagttcgacgacgaggatctgggagcactgctgggcaata gcaccgaccccgccgtgtttaccgacctggcctccgtggacaacagcgagttccagcagctcctcaaccagggc atccctgtcgcc ccacacaccaccgagcccatgctgatggaataccccgaggccatcaccagactggtcacaggcgcccagaggcctccagatccag caccagctccactgggagcccctggcctgcctaatgggctgctgtctggcgacgaggactt cgagagcattgccgacatggacttca gcgccctgctgtcccagatcagcagc). In some alternatives, the HEA3 comprises an amino acid sequence set forth in SEQ ID NO: 121 (MVSKLSQLQTELLAALLESGLSKEALIQALGEPGPYLLAGEG- PLDKGESCGGGRGEL AELPNGLGETRGSEDE-TDDDGEDFTPPILKELENLSPEEAAHQKAVVETLLQE DPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKRMEH-LYSMKCKNVVPLYDLLLEMLDAHRLHAPTSRG-GASVE ETDQSHLATAGSTSSHSLQKYYITGEAE-GFPATVEFQYLPDTDDRHRIEEKRKRTYET FQSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3. In some alternatives, a system for inducible expression of a chimeric antigen receptor in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttctcaaggaccaccg-catctctacattcaagaactggcccttcttggag ggctgcgcctgcaccccg-gagcggatggccgaggctggcttcatccactgccccactgagaacgagcca-gacttggcccagtgttt cttctgcttcaaggagctggaaggctgggagccagatgacgaccccatagag-gaacataaaaagcattcgtccggttgcgctttcctttctgtcaagaagcagttt-gaagaattaacccttggtgaatttttgaaactggacagagaaagagc-caagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD).

In some alternatives, a host cell, such as a mammalian cell, comprising a system of any one of the alternatives herein is provided. In some alternatives, the system is for inducible expression of a chimeric antigen receptor in cells, such as mammalian cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives, the system is for inducible expression of a transgene in cells, such as mammalian cells. The system comprises a) a first nucleic acid comprising a first promoter inducible by a drug, wherein the first nucleic acid is operably linked to a first polynucleotide that encodes a transgene and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the host cell is a precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the chimeric antigen receptor comprises a scFv. In some alternatives, the scFv specifically binds to CD19. In some alternatives, the scFv comprises an huCD19 scFv (G01S) amino acid sequence. In some alternatives, the scFv comprises an amino acid sequence set forth in SEQ ID NO: 41 (MLLLVTSLLLCEL-
PHPAFLLIPEVQLVESGGGLVQPGRSLRLS-
CAASGFTFDDYAMH WVRQAPGKGLEWVSGISWNS-
GRIGYADSVKGRFTISRDNAKNSLFLQMNSLRAEDT
AVYYCARDQGYHYYDSAE-
HAFDIWGQGTVVTVSSGGGGSGGGGSGGGGSQ-
SALTQ
PRSVSGFPGQSVTISCTGTTSDDVSWYQQHPGKAPQL
MLYDVSKRPSGVPHRFSGSR SGRAASLIISGLQT-
EDEADYFCSSYAGRYNSVLFGGGTKLTVL). In some alternatives, the scFv is encoded by a nucleic acid sequence comprising a nucleic acid sequence encoding the amino acid sequence of SEQ ID NO: 41. In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42
(Atgctgctgctggtgaccagcctgctgtgcgagctgccc-
caccccgcctttctgctgatccccgacatccagatgacccagac
cacctccagcctgagcgccagcctgggcgaccgggtgac-
catcagctgccgggccagccaggacatcagcaagtacctgaactg
gtatcagcagaagcccgacggcaccgtcaagctgctgatctac-
cacaccagccggctgcacagcggcgtgcccagccggtttagc
ggcagcggctccggcaccgactacagcctgaccatctccaacctggaacag-
gaagatatcgccacctacttttgccagcagggcaa cacactgcccta-
cacctttggcggcggaacaaagctggaaat-
caccggcagcacctccggcagcggcaagcctggcagcggcga
gggcagcaccaagggcgaggtgaagctgcag-
gaaagcggccctggcctggtggcccccagccagagcctgagcgtgacctgca
ccgtgagcggcgtgagcctgcccgactacggcgtgagctg-
gatccggcagcccccccaggaagggcctggaatggctgggcgtga
tctggggcagcgagaccacctactacaacagcgccctgaagagccggctgac-
catcatcaaggacaacagcaagagccaggtgtt cctgaagatgaacagcctgca-
gaccgacgacaccgccatctactactgcgccaagcactactac-
tacggcggcagctacgccatgg
actactggggccagggcaccagcgtgaccgtgagcagc). In some alternatives, the scFv comprises an amino acid sequence set forth in SEQ ID NO: 43 (MLLLVTSLLLCELPHPAFL-
LIPDIQMTQTTSSLSASLGDRVTISCRASQDISKY-
LNWY
QQKPDGTVKLLIYHTSRLHSGVPSRFSGSGSGTDYS-
LTISNLEQEDIATYFCQQGNTLP YTFGGGTKLEITGST-
SGSGKPGSGEGSTKGEVKLQESGPGLVAP-
SQSLSVTCTVSGVS
LPDYGVSWIRQPPRKGLEWLGVIWGSETTYYN-
SALKSRLTIIKDNSKSQVFLKMNSL QTDDTAIYY-
CAKHYYYGGSYAMDYWGQGTSVTVSS). In some alternatives, the scFv is encoded by a nucleic acid sequence comprising a nucleic acid sequence encoding the amino acid sequence of SEQ ID NO: 43. some alternatives, the scFv comprises a B7H3 (hBRCA84D) scFv nucleotide sequence. In some alternatives, the scFv binds specifically to the B7-H3 receptor. In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50
(atgctgctgctggtgaccagcctgctgctgtgcgagctgccc-
cacccccgcctttctgctgatcccccaggtgcagctgcagcagcct
ggcgccgagctggtgaagccaggcgccagcgt-
gaagctgtcctgcaaggccagcggctacaccttcaccggctactggatgcact
gggtgaagcagagacccggccacggcctggaatggatcggcgagat-
caaccccagcaacggccggaccaactacaacgagcgg ttcaagagcaaggc-
caccctgaccgtggacaagagcagcaccaccgcctt-
catgcagctgtccggcctgaccagcgaggacagcg
ccgtgtacttctgcgccagggactactacggcaccagctacaacttcgac-
tactggggccagggcaccacactgaccgtgagcagc ggcg-
gagggggctctggcggcggaggatctgggggagggggcagcgacatcca-
gatgacccagagcagcagcagcttcagcg
tgagcctgggcgaccgggtgaccatcacctgtaaggccaacgaggacat-
caacaaccggctggcctggtatcagcagacccccgg
caacagccccaggctgctgatcagcggcgccac-
caacctggtgaccggcgtgcccagccggtttagcggcagcggctccggcaa
ggactacaccctgaccatcacaagcctgcaggccgaggacttcgccacctac-
tactgccagcagtactggtccaccccccttcaccttc ggcagcggcaccgagctg-
gaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFL-
LIPQVQLQQPGAELVKPGASVKLSCK-
ASGYTFTGYWM HWVKQRPGHGLEWIGEINPSN-
GRTNYNERFKSKATLTVDKSSTTAFMQLSGLTSEDS
AVYFCARDYYGTSYNFDYWGQGT-
TLTVSSGGGGSGGGGSGGGGSDIQMTQSSSSFS
VSLGDRVTITCKANEDINNRLAWYQQTPGNSPRLLIS-
GATNLVTGVPSRFSGSGSGK DYTLTITSLQAEDFA-
TYYCQQYWSTPFTFGSGTELEIK). In some alternatives, the scFv is encoded by a nucleic acid sequence comprising a nucleic acid sequence encoding the amino acid sequence of SEQ ID NO: 51. In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52
(atgcttctcctggtgacaagccttctgctctgtgagttaccacacccagcat-
tcctcctgatcccacaggtgcagctgaaacagagcg
gcccgggcctggtgcagccgagccagagcctgagcattacctgcaccgt-
gagcggctttagcctgaccaactatggcgtgcattgg
gtgcgccagagcccgggcaaaggcctggaatggctgggcgtgatttg-
gagcggcggcaacaccgattataacaccccgtttacca gccgcctgagcat-
taacaaagataacagcaaaagccaggtgtttttaaaat-
gaacagcctgcagagcaacgataccgcgatttattat
tgcgcgcgcgcgctgacctattatgattatgaatttgcgtat-
tggggccagggcaccctggtgaccgtgagcgcgggcggcggcgg
cagcggcggcggcggcagcggcggcggcggcagcgatat-
tctgctgacccagagcccggtgattctgagcgtgagcccgggcg aacgcgt-
gagctttagctgccgcgcgagccagagcattggcaccaacattcat-
tggtatcagcagcgcaccaacggcagcccgcgc
ctgctgattaaatatgcgagcgaaagcattagcggcattccgagccgctt-
tagcggcagcggcagcggcaccgattttaccctgagc attaacagcgtg-
gaaagcgaagatattgcggattattattgccagcagaacaacaactggccgac-
cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL-
CELPHPAFLLIPQVQLKQSGPGLVQPSQSL-
SITCTVSGFSLTNYGVHW VRQSPGKGLEW-
LGVIWSGGNTDYNTPFTSRLSINKDNSKSQVFFKMN-
SLQSNDTAIY YCARALTYYDYE-
FAYWGQGTLVTVSAGGGGSGGGGSGGGGS-
DILLTQSPVILSVSP GERVSFSCRASQSIGT-
NIHWYQQRTNGSPRLLIKYASESISGIPSRFSGSGSGT-
DFTLSI NSVESEDI-
ADYYCQQNNNWPTTFGAGTKLELKRT). In some alternatives, the scFv is encoded by a nucleic acid sequence comprising a nucleic acid sequence encoding the amino acid sequence of SEQ ID NO: 53. In some alternatives, the scFv comprises the EGFRVIII (806) scFv nucleotide sequence. In some alternatives, the scFv is specific for EGFR. In some alternatives, the scFv is encoded by the EphA2 (2A4) scFv nucleotide sequence. In some alternatives, the scFv is encoded by the nucleic acid sequence set forth in SEQ ID NO: 56. In some alternatives, the scFv is encoded by the EpHA2 (4H5) scFv nucleotide sequence. In some alternatives, the scFv is encoded by the nucleic acid sequence set forth in SEQ ID NO: 58. In some alternatives, the scFv is encoded by a FITC (E2) scFv nucleotide sequence. In some alternatives, the scFv is encoded by a nucleic acid sequence set forth in SEQ ID NO: 60. In some alternatives, the scFv is encoded by an IL13Ra2 (hu08) VhVl scFv nucleotide sequence. In some alternatives, the scFv is encoded by a nucleic acid sequence set forth in SEQ ID NO: 68. In some alternatives, the scFv comprises an IL13Ra2 hu08 VhVl scFv amino acid sequence. In some alternatives, the scFv comprises an amino acid sequence set forth in SEQ ID NO: 69 (MLLLVTSLLLCELPHPAFLLIPEVQLVESGG-
GLVQPGGSLRLSCAASGFTFSRNGMS WVRQAPGK-
GLEWVATVSSGGSYIYYADSVKGRFTISRDNAKNS-
LYLQMNSLRAEDT
AVYYCARQGTTALA-
TRFFDVWGQGTLVTVSSGGGGSGGGGSGGGGSDIQ-
MTQSPSS LSASVGDRVTITCKASQDVGTA-
VAWYQQKPGKAPKLLIYSASYRSTGVPSRFSGSGS
GTDFTLTISSLQPEDFATYYCQHHYS-
APWTFGGGTKVEIKESK). In some alternatives, the scFv is encoded by a nucleic acid sequence comprising a nucleic acid sequence encoding the amino acid sequence of SEQ ID NO: 69. In some alternatives, the scFv is encoded by an IL13Ra2 (hu07) VlVh scFv nucleotide sequence. In some alternatives, the scFv is encoded by a nucleic acid sequence set forth in SEQ ID NO: 70
(atgcttctcctggtgacaagccttctgctctgtgagttaccacacccagcat-
tcctcctgatcccagatattcagatgacccagagccc gagcagcct-
gagcgcgagcgtgggcgatccgcgtgagcagcacctatctgcattggt
atcagcagaaaccgggcaaagcgccgaaactgctgatt-
tatagcaccagcaacctggcgagcggcgtgccgagccgctttagcgg
cagcggcagcggcaccgattttaccctgaccattagcagcctgcagccggaa-
gattttgcgacctattattgccatcagtatcatcgca
gcccgctgacctttggcggcggcaccaaagtggaaattaaaggtggtggtggttctggcggcggcggctccggtggtggtggttctg aagtgcagctggtg-gaaagcggcggcggcctggtgcagcggcggcgggcctggtgcgcggcgagc ggctttacct ttaccaaatatggcgtgcat-tgggtgcgccaggcgccgggcaaaggcctggaatgggtggcggt-gaaatgggcgggcggcagca ccgattataacagcgcgctgatgagccgctt-taccattagccgcgataacgcgaaaaacagcctgtatctgcagatgaacagcctgc gcgcggaagataccgcggtgtattattgcgcgcgcgatcatcgcgatgcgatg-gattattggggccagggcaccctggtgaccgtg agcagcgaatctaagta). In some alternatives, the scFv comprises an IL13Ra2 (hu07) VhVl scFv amino acid sequence. In some alternatives, the scFv comprises an amino acid sequence set forth in SEQ ID NO: 71 (MLLLVTSLLLCELPHPAFLLIPDIQMTQSPSSL-SASVGDRVTITCTASLSVSSTYLHWY QQKPGKAPKLLIYSTSN-LASGVPSRFSGSGSGTDFTLTISSLQPEDFATYY-CHQYHRSP LTFGGGTKVEIKGGGGSGGGGSGGGG-SEVQLVESGGGLVQPGGSLRLSCAASGFTFT KYGVHWVRQAPGKGLEWVAVKWAGGSTDYN-SALMSRFTISRDNAKNSLYLQMNS LRAEDTAVYY-CARDHRDAMDYWGQGTLVTVSSESK). In some alternatives, the scFv is encoded by a nucleic acid sequence comprising a nucleic acid sequence encoding the amino acid sequence of SEQ ID NO: 71. In some alternatives, the scFv is encoded by the IL13Ra2 (hu07) VhVl scFv nucleotide sequence. In some alternatives, the scFv is encoded by a nucleic acid sequence set forth in SEQ ID NO: 72 (atgcttctcctggtgacaagccttctgctctgtgagttaccacacccagcat-tcctcctgatcccagaagtgcagctggtggaaagcg gcggcggcctggtgcagccgggcggcagcctgcgcct-gagctgcgcggcgagcggctttacctttaccaaatatggcgtgcattgg gtgcgccaggcgccgggcaaaggcctggaatgggtggcggt-gaaatgggcgggcggcagcaccgattataacagcgcgctgat gagccgctt-taccattagccgcgataacgcgaaaaacagcctgtatctgcagat-gaacagcctgcgcgcggaagataccgcggtgt attattgcgcgcgcgatcatcgcgatgcgatggattat-tggggccagggcaccctggtgaccgtgagcagcggtggtggtggttctg gcggcggcggctccggtggtggtggttctgatattca-gatgacccagagcccgagcagcctgagcgcgagcgtgggcgatcgcgt gac-cattacctgcaccgcgagcctgagcgtgagcagcacctatctgcat-tggtatcagcagaaaccgggcaaagcgccgaaactgc tgatttatagcaccagcaacctggcgagcggcgtgccgagccgctt-tagcggcagcggcagcggcaccgattttaccctgaccatta gcagcctgcagccggaagattttgcgacctattattgccatcagtat-catcgcagcccgctgacctttggcggcggcaccaaagtgga aat-taaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFL-LIPEVQLVESGGGLVQPGGSLRLSCAASGFTFT-KYGVH WVRQAPGKGLEWVAVKWAGGSTDYN-SALMSRFTISRDNAKNSLYLQMNSLRAED TAVYYCARDHR-DAMDYWGQGTLVTVSSGGGGSGGGGSGGGGSDIQ-MTQSPSSLSA SVGDRVTITCTASLSVS-STYLHWYQQKPGKAPKLLIYSTSN-LASGVPSRFSGSGSGTD FTLTISSLQPEDFATYY-CHQYHRSPLTFGGGTKVEIKESK). In some alternatives, the scFv is encoded by a nucleic acid sequence comprising a nucleic acid sequence encoding the amino acid sequence of SEQ ID NO: 73. In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74 (atgcttctcctggtgacaagccttctgctctgtgagttaccacacccagcat-tcctcctgatcccaggccctgtgcctccctctacagcc ctcaggtacctcattgag-gagctggtcaacatcacccagaaccagaaggctccgctctgcaatggcag-catggtatggagcatcaac ctgacagctggcatgtactgtgcagccctggaatccctgat-caacgtgtcaggctgcagtgccatcgagaagacccagaggatgctg agcggat-tctgcccgcacaaggtctcagctgggcagttttccagcttgcatgtccgagacac-caaaatcgaggtggcccagtttgtaa aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFL-LIPGPVPPSTALRYLIEELVNITQNQKAPLCNG-SMVWSI NLTAGMYCAALESLINVSGC-SAIEKTQRMLSGFCPHKVSAGQFSSLHVRDTKIEVAQ FVKDLLLHLKKLFREGRF). In some alternatives, the scFv is encoded by a nucleic acid sequence comprising a nucleic acid sequence encoding the amino acid sequence of SEQ ID NO: 75. In some alternatives, the scFv is encoded by an oaGD2 (8B6) VlVh scFv nucleotide sequence. In some alternatives, the scFv is encoded by a sequence set forth in SEQ ID NO: 76 (atgcttctcctggtgacaagccttctgctctgt-gagttaccacacccagcattcctcctgatcccagatgttgtgatgacccaaactcca ctctccctgcctgtcagtcttggagatcaagcctcaatctcttgca-gatctagtcagagccttctaaaaaatggaaacacctttttaca ttggtacctgcagaaagtcaggccagtctccaaagctccttatctacaaagtttc-caaccgactttctggggtcccagacaggttcagtgg cagtggatcagggacatat-ttcacactcaagatcagcagagtggaggctgaggatctgggagtttatttctgctct-caaagtacacatat tccgtacacattcggaggggggaccaagctcgagctgaaacgaggcg-gaggggggctctggcggcggaggatctgggggagggg gcagcgaggt-gaaactggtggagtctggaggaggcttggtgctgcctggggattctctga-gactctcctgtgcaacttctgagttcac cttcactgattactacatgacttgggtccgccagcctccaagaaaggcactt-gagtggttgggttttattagaaacagagctaatggttac acaacagagtacaatc-catctgtgaagggtcggttcaccatttccagagataattcccaaagcatcctc-tatcttcaaatgaacaccctg agaactgaggacagtgccacttattactgtgcaagagtctctaactgggcctttgac-tactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77 (MLLLVTSLLLCELPHPAFL-LIPDVVMTQTPLSLPVSLGDQASIS-CRSSQSLLKNNGNT FLHWYLQKSGQSPKLLIYKVSNRLSGVPDRFSGSGS-GTYFTLKISRVEAEDLGVYFCS QSTHIPY-TFGGGTKLELKRGGGGSGGGGSGGGGSEVKLVES-GGGLVLPGDSLRLSCA TSEFTFTDYYMTWVRQP-PRKALEWLGFIRNRANGYTTEYNPSVKGRFTISRDN-SQSIL YLQMNTLRTEDSATYYCARVSN-WAFDYWGQGTTLTVSS). In some alternatives, the scFv is encoded by a nucleic acid sequence comprising a nucleic acid sequence encoding the amino acid sequence of SEQ ID NO: 77. In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccc-caccccgcctttctgctgatcccccaggaacagctcgtcgaaagc ggcggca-gactggtgacacctggcggcagcctgaccct-gagctgcaaggccagcggcttcgacttcagcgcctactacatgagctg ggtccgccaggcccctggcaagggactggaatggatcgccaccatc-taccccagcagcggcaagacctactacgccacctgggtg aacggacggttcac-catctccagcgacaacgcccagaacaccgtggacctgcagat-gaacagcctgacagccgccgaccgggcc acctacttttgcgccagagacagctacgccgacgacggcgccctgttcaa-catctggggccctggcaccctggtgacaatctctagc ggcggaggcggatctggtggcggaggaagtggcggcggaggatctgagctggtgctgacccagagcccctctgtgtctgctgccc tgggaagccctgccaagatcacctgtaccctgagcagcgcccacaagaccgacaccatcgactggtatcagcagctgcagggcga ggcccccagatacctgatgcaggtgcagagcgacggcagctacaccaagaggccaggcgtgcccgaccggttcagcggatctag ctctggcgccgaccgctacctgatcatccccagcgtgcaggccgatgacgaggccgattactactgtggcgccgactacatcggcg gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESGGRLVTPGGSLTLSCKASGFDFSAYYMSW VRQAPGKGLEWIATIYPSSGKTYYATWVNGRFTISSDNAQNTVDLQMNSLTAADRA TYFCARDSYADDGALFNIWGPGTLVTISSGGGGSGGGGSGGGGSELVLTQSPSVSAA LGSPAKITCTLSSAHKTDTIDWYQQLQGEAPRYLMQVQSDGSYTKRPGVPDRFSGSS SGADRYLIIPSVQADDEADYYCGADYIGGYVFGGGTQLTVTG). In some alternatives, the scFv is encoded by a nucleic acid sequence comprising a nucleic acid sequence encoding the amino acid sequence of SEQ ID NO: 79. In some alternatives, the scFv comprises an amino acid sequence set forth in SEQ ID NO: 80 (CD33 (h2H12) VhVl scFv nucleotide sequence (atgcttctcctggtgacaagccttctgctctgtgagttaccacacccagcattcctcctgatcccacaggttcagctggtgcagtctgga gctgaggtgaagaagcctggggcctcagtgaaggtctcctgcaaggcttctggttacaccttcaccaattatgatataaattgggtgag acaggcccctggacaagggcttgagtggattggatggatttatcctggagatggtagtaccaaatataatgagaaattcaaggccaag gctaccctgacagctgacacatccaccagcacagcctacatggagctgaggagcctgagatctgatgacacagctgtgtattactgtg cttctggatatgaagatgctatggactactggggggcaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQSGAEVKKPGASVKVSCKASGYTFTNYDIN WVRQAPGQGLEWIGWIYPGDGSTKYNEKFKAKATLTADTSTSTAYMELRSLRSDDT AVYYCASGYEDAMDYWGQGTTVTVSS). In some alternatives, the scFv is encoded by a nucleic acid sequence comprising a nucleic acid sequence encoding the amino acid sequence of SEQ ID NO: 81. In some alternatives, the scFv is encoded by a sequence set forth in SEQ ID NO: 82 (CD33 (h2H12) VlVh scFv nucleotide sequence: atgcttctcctggtgacaagccttctgctctgtgagttaccacacccagcattcctcctgatcccagacatccagatgacccagtctccat cctcactgtctgcatctgtaggagacagagtcaccatcaattgtaaggctagtcaggacattaatagctatttgagctggtttcagcaga aaccagggaaagcccctaagaccctgatctatagagcaaatagattggtagatggggtcccatcaaggttctctggcagtggatctgg gcaagattatactctcaccatcagcagcctgcagcctgaagattttgcaacttattactgcttgcagtatgatgagtttcctctcacatttgg aggagggaccaaggtggagatcaaa). In some alternatives, the scFv comprises an amino acid sequence set forth in SEQ ID NO: 83 (CD33 (h2H12) VlVh scFv amino acid sequence: MLLLVTSLLLCELPHPAFLLIPDIQMTQSPSSLSASVGDRVTINCKASQDINSYLSWFQ QKPGKAPKTLIYRANRLVDGVPSRFSGSGSGQDYTLTISSLQPEDFATYYCLQYDEFP LTFGGGTKVEIK). In some alternatives, the scFv is encoded by a nucleic acid sequence comprising a nucleic acid sequence encoding the amino acid sequence of SEQ ID NO: 83. In some alternatives, the scFv is encoded by a nucleic acid sequence set forth in SEQ ID NO: 84. In some alternatives, the scFv is encoded by a nucleic acid sequence set forth in SEQ ID NO: 86. In some alternatives, the scFv comprises an amino acid sequence set forth in SEQ ID NO: 87. In some alternatives, the spacer is encoded by the nucleic acid sequence set forth in SEQ ID NO: 102 (IgG4 hinge nucleotide sequence: gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, HEA3 comprises two amino acid mutations, wherein the sequence is encoded by a sequence set forth in SEQ ID NO: 122 (atggtgtccaagctgtcccagctgcagacagaactgctggcagcactgctggaaagcggcctgagcaaagaggccctgattcagg cactcggcgaacctggacctatctgctcgctggcgaaggccctctggataagggcgagagctgtggcggaggaagaggagagct ggccgagctgcctaacggcctgggcgagacaagaggcagcgaggacgagacagacgacgacggcgaggacttcaccccccccc atcctgaaagagctggaaaacctgagccccgaggaagccgcccaccagaaagccgtggtggagacactgctgcaggaagatccc tggcgggtcgccaagatggtcaagagctacctgcagcagcacaacatcccccagcgggaggtggtggacaccaccggcctgaac cagagccacctgagccagcacctgaacaagggcacccccatgaaaacccagaagagagagccgccctgtacacttggtacgtgcgg aagcagagagaggtggcccagcagtttacacacgccggccagggcggcctgatcgaggaacctaccggcgacgagctgcccac caagaagggcagacggaaccggtttaagtggggccctgcatctcagcagatcctgttccaggcctacgagcggcagaagaacccc agcaaagaggaacgggagacactggtggaagagtgcaaccgggccgagtgcatccagagaggcgtgagcccttctcaggctcag ggcctcggcagcaatctggtcaccgaagtgcgggtgtacaattggttcgccaaccggcggaaagaggaagccttccggcacaagct gtctgctggcgatatgagagccgccaacctgtggcccagcccccctgatgatcaagcggagcaagaagaacagcctggccctgagc ctgaccgccgatcagatggtgtccgctctgctggacgccgagccccctatcctgtacagcgagtacgaccccaccagacccttcagc gaggccagcatgatgggcctgctgaccaacctggccgaccgggagctggtgcacatgatcaactgggccaagcgggtgcccggc ttcgtggacctgaccctgcacgaccaggtccacctgctggaatgtgcctggctggaaatcctgatgatcggcctcgtgtggagaagc atggaacaccccggcaagctgctgttcgcccccaacctgctcctggaccggaaccagggaaagtgcgtggagggcatggtggaga tcttcgacatgctgctggccacctccagccggttccggatgatgaacctgcagggcgaggaattcgtgtgcctgaagtccatcatcct gctgaacagcggcgtgtacaccttcctgtcatccaccctgaagtccctggaagagaaggaccacatccaccgggtgctggacaaga tcaccgacaccctgatccacctgatggccaaggctggcctgacactccagcagcagcaccagagactggcccagctgctgctgatc ctgagccacatccggcacatgagcaacaagcggatggaacacctgtacagcatgaagtgcaagaacgtggtgcccctgtacgacct gctgctcgagatgctggatgcccacagactgcacgcccctacaagcagaggcggagccagcgtggaggaaaccgaccagtctca cctggccaccgccggcagcacaagcagccacagcctgcagaagtactacatcaccggcgaggccgagggattccctgccaccgt ggagttccagtacctgcccgacaccgacgaccggcaccggatcgag- gaaaagcggaagcggacctacgagacattccagagcat cat- gaagaagtccccttcagcggccccaccgatccca- gacccccccctagaagaatcgccgtgcccagcagatctagcgccagc gtgcccaagcctgcccccagccctaccctttcaccagcagcctgagcaccat- caactacgacgagttccctaccatggtgttcccca gcggcca- gatctctcaggcctctgctctggcacctgctc- cacctcaggtgctgcctcaggcccctgctccagccccagcccctgccat ggtgtctgcactggcccaggctccagctcctgtgcctgtgctggcccctggacctc ctcaggctgtggcccctcctgcccctaaacct acccaggccggggagg- gaacactgtctgaggccctgctgcagctccagttcgacgacgaggatctgg- gagcactgctgggcaata gcaccgaccccgccgtgtt- taccgacctggcctccgtggacaacagcgagttccagcagctcctcaaccaggg catccctgtcgcc ccacacaccaccgagcccatgctgatggaataccccgaggc- catcaccagactggtcacaggcgcccagaggcctccagatccag caccagctc- cactgggagcccctggcctgcctaatgggctgctgtctggcg acgaggacttcgagagcattgccgacatggacttca gcgccctgctgtccca- gatcagcagc). In some alternatives, the HEA3 comprises an amino acid sequence set forth in SEQ ID NO: 121 (MVSK- LSQLQTELLAALLESGLSKEALIQALGEPGPYL- LAGEGPLDKGESCGGGRGEL AELPNGLGETRGSE- DETDDDGEDFTPPILKELENLSPEEAAHQKAVVETLL QEDPWR VAKMVK- SYLQQHNIPQREVVDTTGLNQSHLSQHLNKGTPMKT QKRAALYTWYVR KQREVAQQFTHAGQG- GLIEEPTGDELPTKKGRRNRFKWGPASQQILFQAY- ERQKNP SKEERETLVEECNRAECIQRGVSP- SQAQGLGSNLVTEVRVYNWFANRRKEEAFRHK LSAGDMRAANLWPSPLMIKRSKKNSLALSL- TADQMVSALLDAEPPILYSEYDPTRPF SEA- SMMGLLTNLADRELVHMIN- WAKRVPGFVDLTLHDQVHLLECAWLEILMIGLV WRSMEHPGKLLFAPNLLLDRNQGKCVEGMVE- IFDMLLATSSRFRMMNLQGEEFVC LKSIILLNSGVYT- FLSSTLKSLEEKDHIHRVLDKITDTLIHLMAK- AGLTLQQQHQRLA QLLLILSHIRHMSNKRMEH- LYSMKCKNVVPLYDLLLEMLDAHRLHAPTSRG- GASVE ETDQSHLATAGSTSSHSLQKYYITGEAE- GFPATVEFQYLPDTDDRHRIEEKRKRTYET FQSIMKKSPFSGPTDPRPPPRRIAVPSRSSAS- VPKPAPQPYPFTSSLSTINYDEFPTMVFP SGQ- ISQASALAPAPPQVLPQAPAPAPA- PAMVSALAQAPAPVPVLAPGPPQAVAPPAP KPTQAGEGTLSEALLQLQFDDEDLGALLGNSTD- PAVFTDLASVDNSEFQQLLNQGIP VAPH- TTEPMLMEYPEAITRLVTGAQRPPDPAPAPL- GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3. In some alternatives, a system for inducible expression of a chimeric antigen receptor in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttctcaaggaccaccg- catctctacattcaagaactggcccttcttggag ggctgcgcctgcaccccg- gagcggatggccgaggctggcttcatccactgccccactgagaacgagcca- gacttggcccagtgttt cttctgcttcaaggagctggaaggctgggagccagatgacgaccccatagag- gaacataaaaagcattcgtccggttgcgctttccttt ctgtcaagaagcagttt- gaagaattaacccttggtgaatttttgaaactggacagagaaagagc- caagaacaaaattgcaaaggaaac caacaataagaagaaagaatttgaggaaactgtgaagaaagtgcgccgtgc- catcgagcagctggctgcaatggat). In some alternatives, Survivin comprises the amino acid sequence set forth in SEQ ID NO: 123 (MGAPTLPPAWQPFLKDHRISTFKNWP- FLEGCACTPERMAEAGFIHCPTENEPDLAQC FFCFKELEGWEPDDDPIEEHKKHSSGCAFLSVKKQ- FEELTLGEFLKLDRERAKNKIAK ETNNKKKE- FEETVKKVRRAIEQLAAMD).

In some alternatives, a composition comprising a host cell, such as a mammalian cell, of any one or more of the alternatives herein is provided, in a pharmaceutically acceptable excipient. In some alternatives, the host cell, such as a mammalian cell, comprises a system of any one of the alternatives herein. In some alternatives, the system is for inducible expression of a chimeric antigen receptor in cells, such as mammalian cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral molecule, and other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optionally optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment, such as a binding fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the host cell is a precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell, wherein the host cell is a precursor T cell and a host cell wherein the host cell is a hematopoietic stem cell. In some alternatives, the composition comprises a host cell, wherein the host cell is a precursor T cell or a hematopoietic stem cell and a host cell that is a CD8+T cytotoxic lymphocyte cell selected from the group consisting of naïve CD8+ T cells, central memory CD8+ T cells, effector memory CD8+ T cells and bulk CD8+ T cells or a CD4+ T cell selected from naïve CD4+ T cells, central memory CD4+ T cells, effector memory CD4+ T cells, and bulk CD4+ T cells. In some alternatives, the chimeric antigen receptor comprises a scFv. In some alternatives, the scFv specifically binds to CD19. In some alternatives, the scFv comprises an huCD19 scFv (G01S) amino acid sequence. In some alternatives, the scFv comprises an amino acid sequence set forth in SEQ ID NO: 41 (MLLLVTSLLLCELPHPAFLLIPEVQLVESGG-GLVQPGRSLRLSCAASGFTFDDYAMH WVRQAPGK-GLEWVSGISWNSGRIGYADSVKGRFTISRD-NAKNSLFLQMNSLRAEDT AVYYCARDQGYHYYDSAE-HAFDIWGQGTVVTVSSGGGGSGGGGSGGGGSQ-SALTQ PRSVSGFPGQSVTISCTGTTSDDVSWYQQHPGKAPQ LMLYDVSKRPSGVPHRFSGSR SGRAASLIISGLQT-EDEADYFCSSYAGRYNSVLFGGGTKLTVL). In some alternatives, the scFv is encoded by a nucleic acid sequence comprising a nucleic acid sequence encoding the amino acid sequence of SEQ ID NO: 41. In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42 (Atgctgctgctggtgaccagcctgctgtgcgagctgccc-caccccgcctttctgctgatccccgacatccagatgacccagac cacctccagcctgagcgccagcctgggcgaccgggtgaccatcagctgccgggccagccaggacatcagcaagtacctgaactg gtatcagcagaagcccgacggcaccgtcaagctgctgatctac-cacaccagccggctgcacagcggcgtgcccagccggtttagc ggcagcggctccggcaccgactacagcctgaccatctccaacctggaacag-gaagatatcgccacctacttttgccagcagggcaa cacactgccctacacctttggcggcggaacaaagctggaaat-caccggcagcacctccggcagcggcaagcctggcagcggcga gggcagcaccaagggcgaggtgaagctgcag-gaaagcggccctggcctggtggcccccagccagagcctgagcgtgacctgca ccgtgagcggcgtgagcctgcccgactacggcgtgagctg-gatccggcagcccccaggaagggcctggaatggctgggcgtga tctggggcagcgagaccacctactacaacagcgccctgaagagccggctgac-catcatcaaggacaacagcaagagccaggtgtt cctgaagatgaacagcctgca-gaccgacgacaccgccatctactactgcgccaagcactactac-tacggcggcagctacgccatgg actactggggccagggcaccagcgtgaccgtgagcagc). In some alternatives, the scFv comprises an amino acid sequence set forth in SEQ ID NO: 43 (MLLLVTSLLLCELPHPAFL-LIPDIQMTQTTSSLSASLGDRVTISCRASQDISKY-LNWY QQKPDGTVKLLIYHTSRLHSGVPSRFSGSGSGTDYS-LTISNLEQEDIATYFCQQGNTLPYTFGGGTKLEITGST-SGSGKPGSGEGSTKGEVKLQESGPGLVAP-SQSLSVTCTVSGVS LPDYGVSWIRQPPRKGLEWLGVIWGSETTYYN-SALKSRLTIIKDNSKSQVFLKMNSL QTDDTAIYY-CAKHYYYGGSYAMDYWGQGTSVTVSS). In some alternatives, the scFv is encoded by a nucleic acid sequence comprising a nucleic acid sequence encoding the amino acid sequence of SEQ ID NO: 43. some alternatives, the scFv comprises a B7H3 (hBRCA84D) scFv nucleotide sequence. In some alternatives, the scFv binds specifically to the B7-H3 receptor. In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50 (atgctgctgctggtgaccagcctgctgctgtgcgagctgccc-cacccccgcctttctgctgatcccccaggtgcagctgcagcagcct ggcgccgagctggtgaagccaggcgccagcgt-gaagctgtcctgcaaggccagcggctacaccttcaccggctactggatgcact gggtgaagcagagacccggccacggcctggaatggatcggcgagat-caaccccagcaacggccggaccaactacaacgagcgg ttcaagagcaaggc-caccctgaccgtggacaagagcagcaccaccgcctt-catgcagctgtccggcctgaccagcgaggacagcg ccgtgtacttctgcgccagggactactacggcaccagctacaacttcgac-tactggggccagggcaccacactgaccgtgagcagc ggcg-gagggggctctggcggcggaggatctggggggagggggcagcgacatcca-gatgacccagagcagcagcagcttcagcg tgagcctgggcgaccgggtgaccatcacctgtaaggccaacgaggacat-caacaaccggctggcctggtatcagcagacccccgg caacagccccaggctgctgatcagcggcgccac-caacctggtgaccggcgtgcccagccggtttagcggcagcggctccggcaa ggactacaccctgaccatcacaagcctgcaggccgaggacttcgccacctac-tactgccagcagtactggtccaccccctttcacttc ggcagcggcaccgagctg-gaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFL-LIPQVQLQQPGAELVKPGASVKLSCK-ASGYTFTGYWM HWVKQRPGHGLEWIGEINPSN-GRTNYNERFKSKATLTVDKSSTTAFMQLSGLTSEDS AVYFCARDYYGTSYNFDYWGQGT-TLTVSSGGGGSGGGGSGGGGSDIQMTQSSSSFS VSLGDRVTITCKANEDINNRLAWYQQTPGNSPRLLIS-GATNLVTGVPSRFSGSGSGK DYTLTITSLQAEDFA-TYYCQQYWSTPFTFGSGTELEIK). In some alternatives, the scFv is encoded by a nucleic acid sequence comprising a nucleic acid sequence encoding the amino acid sequence of SEQ ID NO: 51. In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52 (atgcttctcctggtgacaagccttctgctctgtgagttaccacacccagcat-tcctcctgatcccacaggtgcagctgaaacagagcg gcccgggcctggtgcagccgagccagagcctgagcattacctgcaccgt-gagcggctttagcctgaccaactatggcgtgcattgg gtgcgccagagcccgggcaaaggcctggaatggctgggcgtgatttg-gagcggcggcaacaccgattataacaccccgtttacca gccgcctgagcat-taacaaagataacagcaaaagccaggtgtttttaaaat-gaacagcctgcagagcaacgataccgcgatttattat tgcgcgcgcgcgctgacctattatgattatgaatttgcgtat-tggggccagggcaccctggtgaccgtgagcgcgggcggcggcgg cagcggcggcggcggcagcggcggcggcggcagcgatat-tctgctgacccagagcccggtgattctgagcgtgagcccgggcg aacgcgt-gagctttagctgccgcgcgagccagagcattggcaccaacattcat-tggtatcagcagcgcaccaacggcagcccgcgc ctgctgattaaatatgcgagcgaaagcattagcggcattccgagccgctt-tagcggcagcggcagcggcaccgattttaccctgagc attaacagcgtg-gaaagcgaagatattgcggattattattgccagcagaacaacaactggccgac-cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL-CELPHPAFLLIPQVQLKQSGPGLVQPSQSL-SITCTVSGFSLTNYGVHW VRQSPGKGLEW-LGVIWSGGNTDYNTPFTSRLSINKDNSKSQVFFKMN SLQSNDTAIY YCARALTYYDYE-FAYWGQGTLVTVSAGGGGSGGGGSGGGGS-DILLTQSPVILSVSP GERVSFSCRASQSIGT-NIHWYQQRTNGSPRLLIKYASESISGIPSRFSGSGSGTD FTLSI NSVESEDI-ADYYCQQNNNWPTTFGAGTKLELKRT). In some alternatives, the scFv is encoded by a nucleic acid sequence comprising a nucleic acid sequence encoding the amino acid sequence of SEQ ID NO: 53. In some alternatives, the scFv comprises the EGFRVIII (806) scFv nucleotide sequence. In some alternatives, the scFv is specific for EGFR. In some alternatives, the scFv is encoded by the EphA2 (2A4) scFv nucleotide sequence. In some alternatives, the scFv is encoded by the nucleic acid sequence set forth in SEQ ID NO: 56. In some alternatives, the scFv is encoded by the EpHA2 (4H5) scFv nucleotide sequence. In some alternatives, the scFv is encoded by the nucleic acid sequence set forth in SEQ ID NO: 58. In some alternatives, the scFv is encoded by a FITC (E2) scFv nucleotide sequence. In some alternatives, the scFv is encoded by a nucleic acid sequence set forth in SEQ ID NO: 60. In some alternatives, the scFv is encoded by an IL13Ra2 (hu08) VhVl scFv nucleotide sequence. In some alternatives, the scFv is encoded by a nucleic acid sequence set forth in SEQ ID NO: 68. In some alternatives, the scFv comprises an IL13Ra2 hu08 VhVl scFv amino acid sequence. In some alternatives, the scFv comprises an amino acid sequence set forth in SEQ ID NO: 69 (MLLLVTSLLLCELPHPAFLLIPEVQLVESGG-GLVQPGGSLRLSCAASGFTFSRNGMS WVRQAPGK-GLEWVATVSSGGSYIYYADSVKGRFTISRDNAKNS-LYLQM-NSLRAEDT AVYYCARQGTTALA-TRFFDVWGQGTLVTVSSGGGGSGGGGSGGGGSDIQ-MTQSPSS LSASVGDRVTITCKASQDVGTA- VAWYQQKPGKAPKLLIYSASYRSTGVPSRFSGSGS GTDFTLTISSLQPEDFATYYCQHHYS-APWTFGGGTKVEIKESK). In some alternatives, the scFv is encoded by a nucleic acid sequence comprising a nucleic acid sequence encoding the amino acid sequence of SEQ ID NO: 69. In some alternatives, the scFv is encoded by an IL13Ra2 (hu07) VlVh scFv nucleotide sequence. In some alternatives, the scFv is encoded by a nucleic acid sequence set forth in SEQ ID NO: 70 (atgcttctcctggtgacaagccttctgctctgtgagttaccacacccagcat-tcctcctgatcccagatattcagatgacccagagccc gagcagcct-gagcgcgagcgtgggcgatcgcgtgagcagcacctatctgcattggt atcagcagaaaccgggcaaagcgccgaaactgctgatt-tatagcaccagcaacctggcgagcggcgtgccgagccgctttagcgg cagcggcagcggcaccgattttaccctgaccattagcagcctgcagccggaa-gattttgcgacctattattgccatcagtatcatcgca gcccgctgacctttggcggcggcaccaaagtggaaat-taaaggtggtggtggttctggcggcggcggctccggtggtggtggttctg aagtgcagctggtg-gaaagcggcggcggcctggtgcagcggcggcgggcctggtgcgcggcgagc ggctttacct ttaccaaatatggcgtgcat-tgggtgcgccaggcgccgggcaaaggcctggaatgggtggcggt-gaaatgggcgggcggcagca ccgattataacagcgcgctgatgagccgctt-taccattagccgcgataacgcgaaaaacagcctgtatctgcagatgaacagcctgc gcgcggaagataccgcggtgtattattgcgcgcgcgatcatcgcgatgcgatg-gattattggggccagggcaccctggtgaccgtg agcagcgaatctaagta). In some alternatives, the scFv comprises an IL13Ra2 (hu07) VhVl scFv amino acid sequence. In some alternatives, the scFv comprises an amino acid sequence set forth in SEQ ID NO: 71 (MLLLVTSLLLCELPHPAFLLIPDIQMTQSPSSL-SASVGDRVTITCTASLSVSSTYLHWY QQKPGKAPKLLIYSTSN-LASGVPSRFSGSGSGTDFTLTISSLQPEDFATYY-CHQYHRSP LTFGGGTKVEIKGGGGSGGGGSGGGG-SEVQLVESGGGLVQPGGSLRLSCAASGFTFT KYGVHWVRQAPGKGLEWVAVKWAGGSTDYN-SALMSRFTISRDNAKNSLYLQMNS LRAEDTAVYY-CARDHRDAMDYWGQGTLVTVSSESK). In some alternatives, the scFv is encoded by a nucleic acid sequence comprising a nucleic acid sequence encoding the amino acid sequence of SEQ ID NO: 71. In some alternatives, the scFv is encoded by the IL13Ra2 (hu07) VhVl scFv nucleotide sequence. In some alternatives, the scFv is encoded by a nucleic acid sequence set forth in SEQ ID NO: 72 (atgcttctcctggtgacaagccttctgctctgtgagttaccacacccagcat-tcctcctgatcccagaagtgcagctggtggaaagcg gcggcggcctggtgcagccgggcggcagcctgcgcct-gagctgcgcggcgagcggctttacctttaccaaatatggcgtgcattgg gtgcgccaggcgccgggcaaaggcctggaatgggtggcggt-gaaatgggcgggcggcagcaccgattataacagcgcgctgat gagccgctt-taccattagccgcgataacgcgaaaaacagcctgtatctgcagat-gaacagcctgcgcgcggaagataccgcggtgt attattgcgcgcgcgatcatcgcgatgcgatggattat-tggggccagggcaccctggtgaccgtgagcagcggtggtggtggttctg gcggcggcggctccggtggtggtggttctgatattca-gatgacccagagcccgagcagcctgagcgcgagcgtgggcgatcgcgt gac-cattacctgcaccgcgagcctgagcgtgagcagcacctatctgcat-tggtatcagcagaaaccgggcaaagcgccgaaactgc tgatttatagcaccagcaacctggcgagcggcgtgccgagccgctt-tagcggcagcggcagcggcaccgattttaccctgaccatta gcagcctgcagccggaagattttgcgacctattattgccatcagtat-catcgcagcccgctgacctttggcggcggcaccaaagtgga aat-taaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFL-LIPEVQLVESGGGLVQPGGSLRLSCAASGFTFT-KYGVH WVRQAPGKGLEWVAVKWAGGSTDYN-SALMSRFTISRDNAKNSLYLQMNSLRAED TAVYYCARDHR-DAMDYWGQGTLVTVSSGGGGSGGGGSGGGGSDIQ-MTQSPSSLSA SVGDRVTITCTASLSVS-STYLHWYQQKPGKAPKLLIYSTSN-LASGVPSRFSGSGSGTD FTLTISSLQPEDFATYY-CHQYHRSPLTFGGGTKVEIKESK). In some alternatives, the scFv is encoded by a nucleic acid sequence comprising a nucleic acid sequence encoding the amino acid sequence of SEQ ID NO: 73. In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74 (atgcttctcctggtgacaagccttctgctctgtgagttaccacacccagcat-tcctcctgatcccaggccctgtgcctccctctacagcc ctcaggtacctcattgag-gagctggtcaacatcacccagaaccagaaggctccgctctgcaatggcag-catggtatggagcatcaac ctgacagctggcatgtactgtgcagccctggaatccctgat-caacgtgtcaggctgcagtgccatcgagaagacccagaggatgctg agcggat-tctgcccgcacaaggtctcagctgggcagttttccagcttgcatgtccgagacac-caaaatcgaggtggcccagtttgtaa aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFL-LIPGPVPPSTALRYLIEELVNITQNQKAPLCNG-SMVWSI NLTAGMYCAALESLINVSGC-SAIEKTQRMLSGFCPHKVSAGQFSSLHVRDTKIEVAQ FVKDLLLHLKKLFREGRF). In some alternatives, the scFv is encoded by a nucleic acid sequence comprising a nucleic acid sequence encoding the amino acid sequence of SEQ ID NO: 75. In some alternatives, the scFv is encoded by an oaGD2 (8B6) VlVh scFv nucleotide sequence. In some alternatives, the scFv is encoded by a sequence set forth in SEQ ID NO: 76 (atgcttctcctggtgacaagccttctgctctgt-gagttaccacacccagcattcctcctgatcccagatgttgtgatgacccaaactcca ctctccctgcctgtcagtcttggagatcaagcctcaatctcttgca-gatctagtcagagccttctaaaaaatggaaacacctttttaca ttggtacctgcagaagtcaggccagtctccaaagctccttatctacaaagtttc-caaccgactttctggggtcccagacaggttcagtgg cagtggatcagggacatat-ttcacactcaagatcagcagagtggaggctgaggatctgggagtttatttctgctct-caaagtacacatat tccgtacacattcggagggggggaccaagctcgagctgaaacgaggcg-gagggggctctggcggcggaggatctgggggagggg gcagcgaggt-gaaactggtggagtctggaggaggcttggtgctgcctggggattctctga-gactctcctgtgcaacttctgagttcac cttcactgattactacatgacttgggtccgccagcctccaagaaaggcactt-gagtggttgggttttattagaaacagagctaatggttac acaacagagtacaatc-catctgtgaagggtcggttcaccatttccagagataattcccaaagcatcctc-tatcttcaaatgaacaccctg agaactgaggacagtgccacttattactgtgcaagagtctctaactgggcctttgac-tactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77 (MLLLVTSLLLCELPHPAFL-LIPDVVMTQTPLSLPVSLGDQASIS-CRSSQSLLKNNGNT FLHWYLQKSGQSPKLLIYKVSNRLSGVPDRFSGSGS-GTYFTLKISRVEAEDLGVYFCS QSTHIPY-TFGGGTKLELKRGGGGSGGGGSGGGGSEVKLVES-GGGLVLPGDSLRLSCA TSEFTFTDYYMTWVRQP-PRKALEWLGFIRNRANGYTTEYNPSVKGRFTISRDN- SQSIL YLQMNTLRTEDSATYYCARVSNWAFDYWGQGTTLTVSS). In some alternatives, the scFv is encoded by a nucleic acid sequence comprising a nucleic acid sequence encoding the amino acid sequence of SEQ ID NO: 77. In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccccaccccgcctttctgctgatcccccaggaacagctcgtcgaaagc ggcggcagactggtgacacctggcggcagcctgaccctgagctgcaaggccagcggcttcgacttcagcgcctactacatgagctg ggtccgccaggcccctggcaagggactggaatggatcgccaccatctaccccagcagcggcaagacctactacgccacctgggtg aacggacggttcaccatctccagcgacaacgcccagaacaccgtggacctgcagatgaacagcctgacagccgccgaccgggcc acctacttttgcgccagagacagctacgccgacgacggcgccctgttcaacatctggggccctggcaccctggtgacaatctctagc ggcggaggcggatctggtggcggaggaagtggcggcggaggatctgagctggtgctgacccagagcccctctgtgtctgctgccc tgggaagccctgccaagatcacctgtaccctgagcagcgcccacaagaccgacaccatcgactggtatcagcagctgcagggcga ggcccccagatacctgatgcaggtgcagagcgacggcagctacaccaagaggccaggcgtgcccgaccggttcagcggatctag ctctggcgccgaccgctacctgatcatccccagcgtgcaggccgatgacgaggccgattactactgtggcgccgactacatcggcg gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESGGRLVTPGGSLTLSCKASGFDFSAYYMSW VRQAPGKGLEWIATIYPSSGKTYYATWVNGRFTISSDNAQNTVDLQMNSLTAADRA TYFCARDSYADDGALFNIWGPGTLVTISSGGGGSGGGGSGGGGSELVLTQSPSVSAA LGSPAKITCTLSSAHKTDTIDWYQQLQGEAPRYLMQVQSDGSYTKRPGVPDRFSGSS SGADRYLIIPSVQADDEADYYCGADYIGGYVFGGGTQLTVTG). In some alternatives, the scFv is encoded by a nucleic acid sequence comprising a nucleic acid sequence encoding the amino acid sequence of SEQ ID NO: 79. In some alternatives, the scFv comprises an amino acid sequence set forth in SEQ ID NO: 80 (CD33 (h2H12) VhVl scFv nucleotide sequence (atgcttctcctggtgacaagccttctgctctgtgagttaccacacccagcattcctcctgatcccacaggttcagctggtgcagtctgga gctgaggtgaagaagcctggggcctcagtgaaggtctcctgcaaggcttctggttacaccttaccaattatgatataaattgggtgag acaggcccctggacaagggcttgagtggattggatggatttatcctggagatggtagtaccaaatataatgagaaattcaaggccaag gctaccctgacagctgacacatccaccagcacagcctacatggagctgaggagcctgagatctgatgacacagctgtgtattactgtg cttctggatatgaagatgctatggactactggggggcaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQSGAEVKKPGASVKVSCKASGYTFTNYDIN WVRQAPGQGLEWIGWIYPGDGSTKYNEKFKAKATLTADTSTSTAYMELRSLRSDDT AVYYCASGYEDAMDYWGQGTTVTVSS). In some alternatives, the scFv is encoded by a nucleic acid sequence comprising a nucleic acid sequence encoding the amino acid sequence of SEQ ID NO: 81. In some alternatives, the scFv is encoded by a sequence set forth in SEQ ID NO: 82 (CD33 (h2H12) VlVh scFv nucleotide sequence: atgcttctcctggtgacaagccttctgctctgtgagttaccacacccagcattcctcctgatcccagacatccagatgacccagtctccat cctcactgtctgcatctgtaggagacagagtcaccatcaattgtaaggctagtcaggacattaatagctatttgagctggtttcagcaga aaccagggaaagcccctaagaccctgatctatagagcaaatagattggtagatggggtcccatcaaggttctctggcagtggatctgg gcaagattatactctcaccatcagcagcctgcagcctgaagattttgcaacttattactgcttgcagtatgatgagtttcctctcacatttgg aggagggaccaaggtggagatcaaa). In some alternatives, the scFv comprises an amino acid sequence set forth in SEQ ID NO: 83 (CD33 (h2H12) VlVh scFv amino acid sequence: MLLLVTSLLLCELPHPAFLLIPDIQMTQSPSSLSASVGDRVTINCKASQDINSYLSWFQ QKPGKAPKTLIYRANRLVDGVPSR FSGSGSGQDYTLTISSLQPEDFATYYCLQYDEFP LTFGGGTKVEIK). In some alternatives, the scFv is encoded by a nucleic acid sequence comprising a nucleic acid sequence encoding the amino acid sequence of SEQ ID NO: 83. In some alternatives, the scFv is encoded by a nucleic acid sequence set forth in SEQ ID NO: 84. In some alternatives, the scFv is encoded by a nucleic acid sequence set forth in SEQ ID NO: 86. In some alternatives, the scFv comprises an amino acid sequence set forth in SEQ ID NO: 87. In some alternatives, the spacer is encoded by the nucleic acid sequence set forth in SEQ ID NO: 102 (IgG4 hinge nucleotide sequence: gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, HEA3 comprises two amino acid mutations, wherein the sequence is encoded by a sequence set forth in SEQ ID NO: 122 (atggtgtccaagctgtcccagctgcagacagaactgctggcagcactgctggaaagcggcctgagcaaagaggccctgattcagg cactcggcgaacctggacctatctgctcgctggcgaaggccctctggataagggcgagagctgtggcggaggaagaggagagct ggccgagctgcctaacggcctgggcgagacaagaggcagcgaggacgagacagacgacgacggcgaggacttcacccccccc atcctgaaagagctggaaaacctgagccccgaggaagccgcccaccagaaagccgtggtggagacactgctgcaggaagatccc tggcgggtcgccaagatggtcaagagctacctgcagcagcacaacatcccccagcgggaggtggtggacaccaccggcctgaac cagagccacctgagccagcacctgaacaagggcacccccatgaaaacccagaagagagccgccctgtacacttggtacgtgcgg aagcagagagaggtggcccagcagtttacacacgccggccagggcggcctgatcgaggaacctaccggcgacgagctgcccac caagaagggcagacggaaccggtttaagtggggccctgcatctcagcagatcctgttccaggcctacgagcggcagaagaacccc agcaaagaggaacgggagacactggtggaagagtgcaaccgggccgagtgcatccagagaggcgtgagcccttctcaggctcag ggcctcggcagcaatctggtcaccgaagtgcgggtgtacaattggttcgccaaccggcggaaagaggaagccttccggcacaagct gtctgctggcgatatgagagccgccaacctgtggcccagccccctgatgatcaagcggagcaagaagaacagcctggccctgagc ctgaccgccgatcagatggtgtccgctctgctggacgccgagcccccctatcctgtacagcgagtacgaccccaccagacccttcagc gaggccagcatgatgggcctgctgaccaacctggccgaccgggagctggtgcacatgatcaactgggccaagcgggtgcccggc
ttcgtggacctgaccctgcacgaccaggtccacctgctggaatgtgcctggctg-
gaaatcctgatgatcggcctcgtgtggagaagc atg-
gaacaccccggcaagctgctgttcgcccccaacctgctcctggaccg-
gaaccagggaaagtgcgtggagggcatggtggaga
tcttcgacatgctgctggccacctccagccggttccggatgat-
gaacctgcagggcgaggaattcgtgtgcctgaagtccatcatcct gct-
gaacagcggcgtgtacaccttcctgtcatccaccctgaagtccctg-
gaagagaaggaccacatccaccgggtgctggacaaga
tcaccgacaccctgatccacctgatggc-
caaggctggcctgacactccagcagcagcaccagagactggcccagctgctgct-
gatc ctgagccacatccggcacatgagcaacaagcggatggaacacctgta-
cagcatgaagtgcaagaacgtggtgcccctgtacgacct
gctgctcgagatgctggatgcccacagactgcacgcccctacaagcagaggcg-
gagccagcgtggaggaaaccgaccagtctca cctggc-
caccgccggcagcacaagcagccacagcctgcagaagtactacat-
caccggcgaggccgagggattccctgccaccgt
ggagttccagtacctgcccgacaccgacgaccggcaccggatcgag-
gaaaagcggaagcggacctacgagacattccagagcat cat-
gaagaagtccccttcagcggccccaccgatccca-
gacccccccctagaagaatcgccgtgcccagcagatctagcgccagc
gtgcccaagcctgccccccagccctacccttcaccagcagcctgagcaccat-
caactacgacgagttccctaccatggtgttcccca gcggcca-
gatctctcaggcctctgctctggcacctgctc-
cacctcaggtgctgcctcaggcccctgctccagccccagcccctgccat
ggtgtctgcactggcccaggctccagctcctgtgcctgtgctggcccctggacctc
ctcaggctgtggcccctcctgcccctaaacct acccaggccggggagg-
gaacactgtctgaggccctgctgcagctccagttcgacgacgaggatctgg-
gagcactgctgggcaata gcaccgaccccgccgtgtt-
taccgacctggcctccgtggacaacagcgagttccagcagctcctcaaccaggg
catccctgtcgcc ccacacaccaccgagcccatgctgatggaataccccgaggc-
catcaccagactggtcacaggcgcccagaggcctccagatccag caccagctc-
cactgggagcccctggcctgcctaatgggctgctgtctggcgacgag
gacttcgagagcattgccgacatggacttca gcgccctgctgtccca-
gatcagcagc). In some alternatives, the HEA3 comprises an amino acid sequence set forth in SEQ ID NO: 121 (MVSK-
LSQLQTELLAALLESGLSKEALIQALGEPGPYL-
LAGEGPLDKGESCGGGRGEL AELPNGLGETRGSE-
DETDDDGEDFTPPILKELENLSPEEAAHQKAVVETLL
QEDPWR VAKMVK-
SYLQQHNIPQREVVDTTGLNQSHLSQHLNKGTPMKT
QKRAALYTWYVR KQREVAQQFTHAGQG-
GLIEEPTGDELPTKKGRRNRFKWGPASQQILFQAY-
ERQKNP SKEERETLVEECNRAECIQRGVSP-
SQAQGLGSNLVTEVRVYNWFANRRKEEAFRHK
LSAGDMRAANLWPSPLMIKRSKKNSLALSL-
TADQMVSALLDAEPPILYSEYDPTRPF SEA-
SMMGLLTNLADRELVHMIN-
WAKRVPGFVDLTLHDQVHLLECAWLEILMIGLV
WRSMEHPGKLLFAPNLLLDRNQGKCVEGMVE-
IFDMLLATSSRFRMMNLQGEEFVC LKSIILLNSGVYT-
FLSSTLKSLEEKDHIHRVLDKITDTLIHLMAK-
AGLTLQQQHQRLA
QLLLILSHIRHMSNKRMEH-
LYSMKCKNVVPLYDLLLEMLDAHRLHAPTSRG-
GASVE ETDQSHLATAGSTSSHSLQKYYITGEAE-
GFPATVEFQYLPDTDDRHRIEEKRKRTYET
FQSIMKKSPFSGPTDPRPPPRRIAVPSRSSAS-
VPKPAPQPYPFTSSLSTINYDEFPTMVFP SGQ-
ISQASALAPAPPQVLPQAPAPAPA-
PAMVSALAQAPAPVPVLAPGPPQAVAPPAP
KPTQAGEGTLSEALLQLQFDDEDLGALLGNSTD-
PAVFTDLASVDNSEFQQLLNQGIP VAPH-
TTEPMLMEYPEAITRLVTGAQRPPDPAPAPL-
GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3. In some alternatives, a system for inducible expression of a chimeric antigen receptor in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttctcaaggaccaccg-
catctctacattcaagaactggcccttcttggag ggctgcgcctgcaccccg-
gagcggatggccgaggctggcttcatccactgccccactgagaacgagcca-
gacttggcccagtgttt
cttctgcttcaaggagctggaaggctgggagccagatgacgaccccatagag-
gaacataaaaagcattcgtccggttgcgctttccttt ctgtcaagaagcagttt-
gaagaattaacccttggtgaatttttgaaactggacagagaaagagc-
caagaacaaaattgcaaaggaaac
caacaataagaagaaagaatttgaggaaactgtgaagaaagtgcgccgtgc-
catcgagcagctggctgcaatggat). In some alternatives, Survivin comprises the amino acid sequence set forth in SEQ ID NO: 123 (MGAPTLPPAWQPFLKDHRISTFKNWP-
FLEGCACTPERMAEAGFIHCPTENEPDLAQC
FFCFKELEGWEPDDDPIEEHKKHSSGCAFLSVKKQ-
FEELTLGEFLKLDRERAKNKIAK ETNNKKKE-
FEETVKKVRRAIEQLAAMD).

In some alternatives, an in vitro method for preparing a host cell of any one of alternatives herein is provided. The method comprises a) providing a system of any one of the alternatives herein; and b) introducing the system into an isolated T lymphocyte population and expanding each T lymphocyte population in vitro. In some alternatives, the T lymphocytes are expanded, and wherein the method further comprises culturing the cells in the presence of anti-CD3 and/or anti CD28, and at least one homeostatic cytokine until the cells expand sufficiently for use as a cell infusion. In some alternatives, the isolated T lymphocyte population comprises precursor T cells. In some alternatives, the precursor T cells are hematopoietic stem cells. In some alternatives, the lymphocyte is CD8+ or CD4+. In some alternatives, the system is for inducible expression of a chimeric antigen receptor in cells, such as mammalian cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the chimeric antigen receptor comprises a scFv. In some alternatives, the scFv specifically binds to CD19. In some alternatives, the scFv comprises an huCD19 scFv (G01S) amino acid sequence. In some alternatives, the scFv comprises an amino acid sequence set forth in SEQ ID NO: 41 (MLLLVTSLLLCELPHPAFLLIPEVQLVESGG-GLVQPGRSLRLSCAASGFTFDDYAMH WVRQAPGK-GLEWVSGISWNSGRIGYADSVKGRFTISRD-NAKNSLFLQMNSLRAEDT AVYYCARDQGYHYYDSAE-HAFDIWGQGTVVTVSSGGGGSGGGGSGGGGSQ-SALTQ PRSVSGFPGQSVTISCTGTTSDDVS-WYQQHPGKAPQLMLYDVSKRPSGVPHRFSGSR SGRAASLIISGLQTEDEADYFCSSYAGRYNS-VLFGGGTKLTVL). In some alternatives, the scFv is encoded by a nucleic acid sequence comprising a nucleic acid sequence encoding the amino acid sequence of SEQ ID NO: 41. In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42 (Atgctgctgctggtgaccagcctgctgtgcgagctgccc-caccccgcctttctgctgatccccgacatccagatgacccagac cacctccagcctgagcgccagcctgggcgaccgggtgac-catcagctgccgggccagccaggacatcagcaagtacctgaactg gtatcagcagaagcccgacggcaccgtcaagctgctgatctac-cacaccagccggctgcacagcggcgtgcccagccggtttagc ggcagcggctccggcaccgactacagcctgaccatctccaacctggaacag-gaagatatcgccacctacttttgccagcagggcaa cacactgccctacacctttggcggcggaacaaagctggaaat-caccggcagcacctccggcagcggcaagcctggcagcggcga gggcagcaccaagggcgaggtgaagctgcag-gaaagcggccctggcctggtggcccccagccagagcctgagcgtgacctgca ccgtgagcggcgtgagcctgcccgactacggcgtgagctg-gatccggcagcccccaggaagggcctggaatggctgggcgtga tctggggcagcgagaccacctactacaacagcgccctgaagagccggctgac-catcatcaaggacaacagcaagagccaggtgtt cctgaagatgaacagcctgca-gaccgacgacaccgccatctactactgcgccaagcactactac-tacggcggcagctacgccatgg actactggggccagggcaccagcgtgaccgtgagcagc). In some alternatives, the scFv comprises an amino acid sequence set forth in SEQ ID NO: 43 (MLLLVTSLLLCELPHPAFL-LIPDIQMTQTTSSLSASLGDRVTISCRASQDISKY-LNWY QQKPDGTVKLLIYHTSRLHSGVPSRFSGSGSGTDYS-LTISNLEQEDIATYFCQQGNTLP YTFGGGTKLEITGST-SGSGKPGSGEGSTKGEVKLQESGPGLVAP-SQSLSVTCTVSGVS LPDYGVSWIRQPPRKGLEWLGVIWGSETTYYN-SALKSRLTIIKDNSKSQVFLKMNSL QTDDTAIYY-CAKHYYYGGSYAMDYWGQGTSVTVSS). In some alternatives, the scFv is encoded by a nucleic acid sequence comprising a nucleic acid sequence encoding the amino acid sequence of SEQ ID NO: 43. some alternatives, the scFv comprises a B7H3 (hBRCA84D) scFv nucleotide sequence. In some alternatives, the scFv binds specifically to the B7-H3 receptor. In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50 (atgctgctgctggtgaccagcctgctgctgtgcgagctgccc-caccccgcctttctgctgatcccccaggtgcagctgcagcagcct ggcgccgagctggtgaagccaggcgccagcgt-gaagctgtcctgcaaggccagcggctacaccttcaccggctactggatgcact gggtgaagcagagacccggccacggcctggaatggatcggcgagat-caaccccagcaacggccggaccaactacaacgagcgg ttcaagagcaaggc-caccctgaccgtggacaagagcagcaccaccgcctt-catgcagctgtccggcctgaccagcgaggacagcg ccgtgtacttctgcgccagggactactacggcaccagctacaacttcgac-tactggggccagggcaccacactgaccgtgagcagc ggcg-gaggggctctggcggcggaggatctggggagggggcagcgacatcca-gatgacccagagcagcagcagcttcagcg tgagcctgggcgaccgggtgaccatcacctgtaaggccaacgaggacat-caacaaccggctggcctggtatcagcagacccccgg caacagccccaggctgctgatcagcggcgccac-caacctggtgaccggcgtgcccagccggtttagcggcagcggctccggcaa ggactacaccctgaccatcacaagcctgcaggccgaggacttcgccacctac-tactgccagcagtactggtccacccccttcacctc ggcagcggcaccgagctg-gaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFL-LIPQVQLQQPGAELVKPGASVKLSCK-ASGYTFTGYWM HWVKQRPGHGLEWIGEINPSN-GRTNYNERFKSKATLTVDKSSTTAFMQLSGLTSEDS AVYFCARDYYGTSYNFDYWGQGT-TLTVSSGGGGSGGGGSGGGGSDIQMTQSSSSFS VSLGDRVTITCKANEDINNRLAWYQQTPGNSPRLLIS-GATNLVTGVPSRFSGSGSGK DYTLTITSLQAEDFA-TYYCQQYWSTPFTFGSGTELEIK). In some alternatives, the scFv is encoded by a nucleic acid sequence comprising a nucleic acid sequence encoding the amino acid sequence of SEQ ID NO: 51. In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52 (atgcttctcctggtgacaagccttctgctctgtgagttaccacacccagcat-tcctcctgatcccacaggtgcagctgaaacagagcg gcccgggcctggtgcagccgagccagagcctgagcattacctgcaccgt-gagcggctttagcctgaccaactatggcgtgcattgg gtgcgccagagcccgggcaaaggcctggaatggctgggcgtgatttg-gagcggcggcaacaccgattataacaccccgtttacca gccgcctgagcat-taacaaagataacagcaaaagccaggtgtttttaaaat-gaacagcctgcagagcaacgataccgcgatttattat tgcgcgcgcgcgctgacctattatgattatgaatttgcgtat-tggggccagggcaccctggtgaccgtgagcgcgggcggcggcgg cagcggcggcggcggcagcggcggcggcggcagcgatat-tctgctgacccagagcccggtgattctgagcgtgagcccgggcg aacgcgt-gagctttagctgccgcgcgagccagagcattggcaccaacattcat-tggtatcagcagcgcaccaacggcagcccgcgc ctgctgattaaatatgcgagcgaaagcattagcggcattccgagccgctt-tagcggcagcggcagcggcaccgatttaccctgagc attaacagcgtg-gaaagcgaagatattgcggattattattgccagcagaacaacaactggccgac-cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL-CELPHPAFLLIPQVQLKQSGPGLVQPSQSL-SITCTVSGFSLTNYGVHW VRQSPGKGLEW-LGVIWSGGNTDYNTPFTSRLSINKDNSKSQVFFKMN-SLQSNDTAIY YCARALTYYDYE-FAYWGQGTLVTVSAGGGGSGGGGSGGGGS-DILLTQSPVILSVSP GERVSFSCRASQSIGT-NIHWYQQRTNGSPRLLIKYASESISGIPSRFSGSGSGT-DFTLSI NSVESEDI-ADYYCQQNNNWPTTFGAGTKLELKRT). In some alternatives, the scFv is encoded by a nucleic acid sequence comprising a nucleic acid sequence encoding the amino acid sequence of SEQ ID NO: 53. In some alternatives, the scFv comprises the EGFRVIII (806) scFv nucleotide sequence. In some alternatives, the scFv is specific for EGFR. In some alternatives, the scFv is encoded by the EphA2 (2A4) scFv nucleotide sequence. In some alternatives, the scFv is encoded by the nucleic acid sequence set forth in SEQ ID NO: 56. In some alternatives, the scFv is encoded by the EpHA2 (4H5) scFv nucleotide sequence. In some alternatives, the scFv is encoded by the nucleic acid sequence set forth in SEQ ID NO: 58. In some alternatives, the scFv is encoded by a FITC (E2) scFv nucleotide sequence. In some alternatives, the scFv is encoded by a nucleic acid sequence set forth in SEQ ID NO: 60. In some alternatives, the scFv is encoded by an IL13Ra2 (hu08) VhVl scFv nucleotide sequence. In some alternatives, the scFv is encoded by a nucleic acid sequence set forth in SEQ ID NO: 68. In some alternatives, the scFv comprises an IL13Ra2 hu08 VhVl scFv amino acid sequence. In some alternatives, the scFv comprises an amino acid sequence set forth in SEQ ID NO: 69 (MLLLVTSLLLCELPHPAFLLIPEVQLVESGG-GLVQPGGSLRLSCAASGFTFSRNGMS WVRQAPGK-GLEWVATVSSGGSYIYYADSVKGRFTISRDNAKNS-LYLQM-NSLRAEDT AVYYCARQGTTALATRFFDVWGQGTLVTVSSGGGG SGGGGSGGGGSDIQMTQSPSS LSASVGDRVTITCK- ASQDVGTAVAWYQQKPGKAPKLLIYS ASYRSTGVPSRFSGSGS GTDFTLTISSLQPEDFATYYCQHHYSAPWTFGGGTKVEIKESK). In some alternatives, the scFv is encoded by a nucleic acid sequence comprising a nucleic acid sequence encoding the amino acid sequence of SEQ ID NO: 69. In some alternatives, the scFv is encoded by an IL13Ra2 (hu07) VlVh scFv nucleotide sequence. In some alternatives, the scFv is encoded by a nucleic acid sequence set forth in SEQ ID NO: 70 (atgcttctcctggtgacaagccttctgctctgtgagttaccacacccagcattcctcctgatcccagatattcagatgacccagagccc gagcagcctgagcgcgagcgtgggcgatcgcgtgagcagcacctatctgcattggt atcagcagaaaccgggcaaagcgccgaaactgctgatttatagcaccagcaacctggcgagcggcgtgccgagccgctttagcgg cagcggcagcggcaccgatttaccctgaccattagcagcctgcagccggaagattttgcgacctattattgccatcagtatcatcgca gcccgctgacctttggcggcggcaccaaagtggaaattaaaggtggtggtggttctggcggcggcggctccggtggtggtggttctg aagtgcagctggtggaaagcggcggcggcctggtgcagcggcggcgggc ctggtgcgcggcgagcggctttacct ttaccaaatatggcgtgcattgggtgcgccaggcgccgggcaaaggcctggaatgggtggcggtgaaatgggcgggcggcagca ccgattataacagcgcgctgatgagccgctttaccattagccgcgataacgcgaaaaacagcctgtatctgcagatgaacagcctgc gcgcggaagataccgcggtgtattattgcgcgcgcgatcatcgcgatgcgatggattattggggccagggcaccctggtgaccgtg agcagcgaatctaagta). In some alternatives, the scFv comprises an IL13Ra2 (hu07) VhVl scFv amino acid sequence. In some alternatives, the scFv comprises an amino acid sequence set forth in SEQ ID NO: 71 (MLLLVTSLLLCELPHPAFLLIPDIQMTQSPSSLSASVGDRVTITCTASLSVSSTYLHWY QQKPGKAPKLLIYSTSNLASGVPSRFSGSGSGTDFTLTISSLQPEDFATYYCHQYHRSP LTFGGGTKVEIKGGGGSGGGGSGGGGSEVQLVESGGGLVQPGGSLRLSCAASGFTFT KYGVHWVRQAPGKGLEWVAVKWAGGSTDYNSALMSRFTISRDNAKNSLYLQMNS LRAEDTAVYYCARDHRDAMDYWGQGTLVTVSSESK). In some alternatives, the scFv is encoded by a nucleic acid sequence comprising a nucleic acid sequence encoding the amino acid sequence of SEQ ID NO: 71. In some alternatives, the scFv is encoded by the IL13Ra2 (hu07) VhVl scFv nucleotide sequence. In some alternatives, the scFv is encoded by a nucleic acid sequence set forth in SEQ ID NO: 72 (atgcttctcctggtgacaagccttctgctctgtgagttaccacacccagcattcctcctgatcccagaagtgcagctggtggaaagcg gcggcggcctggtgcagccgggcggcagcctgcgcctgagctgcgcggcgagcggctttacctttaccaaatatggcgtgcattgg gtgcgccaggcgccgggcaaaggcctggaatgggtggcggtgaaatgggcgggcggcagcaccgattataacagcgcgctgat gagccgctttaccattagccgcgataacgcgaaaaacagcctgtatctgcagatgaacagcctgcgcgcggaagataccgcggtgt attattgcgcgcgcgatcatcgcgatgcgatggattattggggccagggcaccctggtgaccgtgagcagcggtggtggtggttctg gcggcggcggctccggtggtggtggttctgatattcagatgacccagagcccgagcagcctgagcgcgagcgtgggcgatcgcgt gaccattacctgcaccgcgagcctgagcgtgagcagcacctatctgcattggtatcagcagaaaccgggcaaagcgccgaaactgc tgatttatagcaccagcaacctggcgagcggcgtgccgagccgctttagcggcagcggcagcggcaccgatttaccctgaccatta gcagcctgcagccggaagattttgcgacctattattgccatcagtatcatcgcagcccgctgacctttggcggcggcaccaaagtgga aataaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFLLIPEVQLVESGGGLVQPGGSLRLSCAASGFTFTKYGVH WVRQAPGKGLEWVAVKWAGGSTDYNSALMSRFTISRDNAKNSLYLQMNSLRAED TAVYYCARDHRDAMDYWGQGTLVTVSSGGGGSGGGGSGGGGSDIQMTQSPSSLSA SVGDRVTITCTASLSVSSTYLHWYQQKPGKAPKLLIYSTSNLASGVPSRFSGSGSGTD FTLTISSLQPEDFATYYCHQYHRSPLTFGGGTKVEIKESK). In some alternatives, the scFv is encoded by a nucleic acid sequence comprising a nucleic acid sequence encoding the amino acid sequence of SEQ ID NO: 73. In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74 (atgcttctcctggtgacaagccttctgctctgtgagttaccacacccagcattcctcctgatcccaggccctgtgcctccctctacagcc ctcaggtacctcattgaggagctggtcaacatcacccagaaccagaaggctccgctctgcaatggcagcatggtatggagcatcaac ctgacagctggcatgtactgtgcagccctggaatccctgatcaacgtgtcaggctgcagtgccatcgagaagacccagaggatgctg agcggattctgcccgcacaaggtctcagctgggcagttttccagcttgcatgtccgagacaccaaaatcgaggtggcccagtttgtaa aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFLLIPGPVPPSTALRYLIEELVNITQNQKAPLCNGSMVWSI NLTAGMYCAALESLINVSGCSAIEKTQRMLSGFCPHKVSAGQFSSLHVRDTKIEVAQ FVKDLLLHLKKLFREGRF). In some alternatives, the scFv is encoded by a nucleic acid sequence comprising a nucleic acid sequence encoding the amino acid sequence of SEQ ID NO: 75. In some alternatives, the scFv is encoded by an oaGD2 (8B6) VlVh scFv nucleotide sequence. In some alternatives, the scFv is encoded by a sequence set forth in SEQ ID NO: 76 (atgcttctcctggtgacaagccttctgctctgtgagttaccacacccagcattcctcctgatcccagatgttgtgatgacccaaactcca ctctccctgcctgtcagtcttggagatcaagcctcaatctcttgcagatctagtcagagccttctaaaaaatggaaacacctttttaca ttggtacctgcagaagtcaggccagtctccaaagctccttatctacaaagtttccaaccgactttctggggtcccagacaggttcagtgg cagtggatcagggacatatttcacactcaagatcagcagagtggaggctgaggatctgggagtttatttctgctctcaaagtacacatat tccgtacacattcggaggggggaccaagctcgagctgaaacgaggcggaggggggctctggcggcggaggatctgggggagggg gcagcgaggtgaaactggtggagtctggaggaggcttggtgctgcctggggattctctgagactctcctgtgcaacttctgagttcac cttcactgattactacatgacttgggtccgccagcctccaagaaaggcacttgagtggttgggttttattagaaacagagctaatggttac acaacagagtacaatccatctgtgaagggtcggttcaccatttccagagataattcccaaagcatcctctatcttcaaatgaacaccctg agaactgaggacagtgccacttattactgtgcaagagtctctaactgggcctttgactactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77 (MLLLVTSLLLCELPHPAFLLIPDVVMTQTPLSLPVSLGDQASISCRSSQSLLKNNGNT FLHWYLQKSGQSPKLLIYKVSNRLSGVPDRFSGSGSGTYFTLKISRVEAEDLGVYFCS QSTHIPYTFGGGTKLELKRGGGGSGGGGSGGGGSEVKLVESGGGLVLPGDSLRLSCA TSEFTFTDYYMTWVRQPPRKALEWLGFIRNRANGYTTEYNPSVKGRFTISRDNS QSIL YLQMNTLRTEDSATYY CARVSN- WAFDYWGQGTTLTVSS). In some alternatives, the scFv is encoded by a nucleic acid sequence comprising a nucleic acid sequence encoding the amino acid sequence of SEQ ID NO: 77. In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccccaccccgcctttctgctgatcccccaggaacagctcgtcgaaagc ggcggcagactggtgacacctggcggcagcctgaccctgagctgcaaggccagcggcttcgacttcagcgcctactacatgagctg ggtccgccaggcccctggcaagggactggaatggatcgccaccatctaccccagcagcggcaagacctactacgccacctgggtg aacggacggttcaccatctccagcgacaacgcccagaacaccgtggacctgcagatgaacagcctgacagccgccgaccgggcc acctacttttgcgccagagacagctacgccgacgacggcgccctgttcaacatctggggccctggcaccctggtgacaatctctagc ggcggaggcggatctggtggcggaggaagtggcggcggaggatctgagctggtgctgacccagagccccctctgtgtctgctgccc tgggaagccctgccaagatcacctgtaccctgagcagcgcccacaagaccgacaccatcgactggtatcagcagctgcagggcga ggcccccagatacctgatgcaggtgcagagcgacggcagctacaccaagaggccaggcgtgcccgaccggttcagcggatctag ctctggcgccgaccgctacctgatcatccccagcgtgcaggccgatgacgaggccgattactactgtggcgccgactacatcggcg gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESGGRLVTPGGSLTLSCKASGFDFSAYYMSW VRQAPGKGLEWIATIYPSSGKTYYATWVNGRFTISSDNAQNTVDLQMNSLTAADRA TYFCARDSYADDGALFNIWGPGTLVTISSGGGGSGGGGSGGGGSELVLTQSPSVSAA LGSPAKITCTLSSAHKTDTIDWYQQLQGEAPRYLMQVQSDGSYTKRPGVPDRFSGSS SGADRYLIIPSVQADDEADYYCGADYIGGYVFGGGTQLTVTG). In some alternatives, the scFv is encoded by a nucleic acid sequence comprising a nucleic acid sequence encoding the amino acid sequence of SEQ ID NO: 79. In some alternatives, the scFv comprises an amino acid sequence set forth in SEQ ID NO: 80 (CD33 (h2H12) VhVl scFv nucleotide sequence (atgcttctcctggtgacaagccttctgctctgtgagttaccacacccagcattcctcctgatcccacaggttcagctggtgcagtctgga gctgaggtgaagaagcctggggcctcagtgaaggtctcctgcaaggcttctggttacaccttcaccaattatgatataaattgggtgag acaggcccctggacaagggcttgagtggattggatggatttatcctggagatggtagtaccaaatataatgagaaattcaaggccaag gctaccctgacagctgacacatccaccagcacagcctacatggagctgaggagcctgagatctgatgacacagctgtgtattactgtg cttctggatatgaagatgctatggactactggggccaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQSGAEVKKPGASVKVSCKASGYTFTNYDIN WVRQAPGQGLEWIGWIYPGDGSTKYNEKFKAKATLTADTSTSTAYMELRSLRSDDT AVYYCASGYEDAMDYWGQGTTVTVSS). In some alternatives, the scFv is encoded by a nucleic acid sequence comprising a nucleic acid sequence encoding the amino acid sequence of SEQ ID NO: 81. In some alternatives, the scFv is encoded by a sequence set forth in SEQ ID NO: 82 (CD33 (h2H12) VlVh scFv nucleotide sequence: atgcttctcctggtgacaagccttctgctctgtgagttaccacacccagcattcctcctgatcccagacatccagatgacccagtctccat cctcactgtctgcatctgtaggagacagagtcaccatcaattgtaaggctagtcaggacattaatagctatttgagctggtttcagcaga aaccagggaaagcccctaagaccctgatctatagagcaaatagattggtagatggggtcccatcaaggttctctggcagtggatctgg gcaagattatactctcaccatcagcagcctgcagcctgaagattttgcaacttattactgcttgcagtatgatgagtttcctctcacatttgg aggagggaccaaggtggagatcaaa). In some alternatives, the scFv comprises an amino acid sequence set forth in SEQ ID NO: 83 (CD33 (h2H12) VlVh scFv amino acid sequence: MLLLVTSLLLCELPHPAFLLIPDIQMTQSPSSLSASVGDRVTINCKASQDINSYLSWFQ QKPGKAPKTLIYRANRLVDGVPSRFSG SGSGQDYTLTISSLQPEDFATYYCLQYDEFP LTFGGGTKVEIK). In some alternatives, the scFv is encoded by a nucleic acid sequence comprising a nucleic acid sequence encoding the amino acid sequence of SEQ ID NO: 83. In some alternatives, the scFv is encoded by a nucleic acid sequence set forth in SEQ ID NO: 84. In some alternatives, the scFv is encoded by a nucleic acid sequence set forth in SEQ ID NO: 86. In some alternatives, the scFv comprises an amino acid sequence set forth in SEQ ID NO: 87. In some alternatives, the spacer is encoded by the nucleic acid sequence set forth in SEQ ID NO: 102 (IgG4 hinge nucleotide sequence: gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, HEA3 comprises two amino acid mutations, wherein the sequence is encoded by a sequence set forth in SEQ ID NO: 122 (atggtgtccaagctgtcccagctgcagacagaactgctggcagcactgctggaaagcggcctgagcaaagaggccctgattcagg cactcggcgaacctggacctatctgctcgctggcgaaggcccctctggataagggcgagagctgtggcggagga agaggagagct ggccgagctgcctaacggcctgggcgagacaagaggcagcgaggacgagacagacgacgacggcgaggacttcaccccccccc atcctgaaagagctggaaaacctgagccccgaggaagccgcccaccagaaagccgtggtggagacactgctgcaggaagatccc tggcgggtcgccaagatggtcaagagctacctgcagcagcacaacatcccccagcgggaggtggtggacaccaccggcctgaac cagagccacctgagccagcacctgaacaagggcacccccatgaaaacccagaagagagccgccctgtacacttggtacgtgcgg aagcagagagaggtggcccagcagtttacacacgccggccagggcggcctgatcgaggaacctaccggcgacgagctgcccac caagaagggcagacggaaccggtttaagtggggccctgcatctcagcagatcctgttccaggcctacgagcggcagaagaacccc agcaaagaggaacgggagacactggtggaagagtgcaaccgggccgagtgcatccagagaggcgtgagcccttctcaggctcag ggcctcggcagcaatctggtcaccgaagtgcgggtgtacaattggttcgccaaccggcggaaagaggaagccttccggcacaagct gtctgctggcgatatgagagccgccaacctgtggcccagccccctgatgatcaagcggagcaagaagaacagcctggccctgagc ctgaccgccgatcagatggtgtccgctctgctggacgccgagccccctatcctgtacagcgagtacgaccccaccagacccttcagc gaggccagcatgatgggcctgctgaccaacctggccgaccgggagctggtgcacatgatcaactgggccaagcgggtgcccggc ttcgtggacctgaccctgcacgaccaggtccacctgctggaatgtgcctggctg-gaaatcctgatgatcggcctcgtgtggagaagc atg-gaacaccccggcaagctgctgttcgcccccaacctgctcctggaccg-gaaccagggaaagtgcgtggagggcatggtggaga tcttcgacatgctgctggccacctccagccggttccggatgat-gaacctgcagggcgaggaattcgtgtgcctgaagtccatcatcct gct-gaacagcggcgtgtacaccttcctgtcatccaccctgaagtccctg-gaagagaaggaccacatccaccgggtgctggacaaga tcaccgacaccctgatccacctgatggc-caaggctggcctgacactccagcagcagcaccagagactggcccagctgctgct-gatc ctgagccacatccggcacatgagcaacaagcggatggaacacctgta-cagcatgaagtgcaagaacgtggtgcccctgtacgacct gctgctcgagatgctggatgcccacagactgcacgcccctacaagcagaggcg-gagccagcgtggaggaaaccgaccagtctca cctggc-caccgccggcagcacaagcagccacagcctgcagaagtactacat-caccggcgaggccgagggattccctgccaccgt ggagttccagtacctgcccgacaccgacgaccggcaccggatcgag-gaaaagcggaagcggacctacgagacattccagagcat cat-gaagaagtcccccttcagcggccccaccgatccca-gacccccccctagaagaatcgccgtgcccagcagatctagcgccagc gtgcccaagcctgccccccagccctaccctttcaccagcagcctgagcaccat-caactacgacgagttccctaccatggtgttcccca gcggcca-gatctctcaggcctctgctctggcacctgctc-cacctcaggtgctgcctcaggcccctgctccagccccagcccctgccat ggtgtctgcactggcccaggctccagctcctgtgcctgtgctggcccctggacctc ctcaggctgtggcccctcctgcccctaaacct acccaggccggggagg-gaacactgtctgaggccctgctgcagctccagttcgacgacgaggatctgg-gagcactgctgggcaata gcaccgaccccgccgtgtt-taccgacctggcctccgtggacaacagcgagttccagcagctcctcaaccaggg catccctgtcgcc ccacacaccaccgagcccatgctgatggaatacccgaggc-catcaccagactggtcacaggcgcccagaggcctccagatccag caccagctc-cactgggagcccctggcctgcctaatgggctgctgtctggcgacg aggacttcgagagcattgccgacatggacttca gcgccctgctgtccca-gatcagcagc). In some alternatives, the HEA3 comprises an amino acid sequence set forth in SEQ ID NO: 121 (MVSK-LSQLQTELLAALLESGLSKEALIQALGEPGPYL-LAGEGPLDKGESCGGGRGEL AELPNGLGETRGSE-DETDDDGEDFTPPILKELENLSPEEAAHQKAVVETLL QEDPWR VAKMVK-SYLQQHNIPQREVVDTTGLNQSHLSQHLNKGTPMKT QKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKRMEH-LYSMKCKNVVPLYDLLLEMLDAHRLHAPTSRG-GASVE ETDQSHLATAGSTSSHSLQKYYITGEAE-GFPATVEFQYLPDTDDRHRIEEKRKRTYET FQSSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3. In some alternatives, a system for inducible expression of a chimeric antigen receptor in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttctcaaggaccaccg-catctctacattcaagaactggcccttcttggag ggctgcgcctgcaccccg-gagcggatggccgaggctggcttcatccactgccccactgagaacgagcca-gacttggcccagtgttt cttctgcttcaaggagctggaaggctgggagccagatgacgaccccatagag-gaacataaaaagcattcgtccggttgcgctttccttt ctgtcaagaagcagttt-gaagaattaacccttggtgaatttttgaaactggacagagaaagagc-caagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD).

In some alternatives, a method of treating, inhibiting, or ameliorating a disease in a subject in need thereof is provided. The method comprises administering to the subject the host cell, such as a mammalian cell, of any one of the alternatives herein, or at least one composition or product combination of any one or more of the alternatives herein. In some alternatives, the host cell, such as a mammalian cell, comprising a system of any one of the alternatives herein. In some alternatives, the system is for inducible expression of a chimeric antigen receptor in cells, such as mammalian cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and any other selected molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment, such as a binding fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the host cell is a precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises the host cell, such as a mammalian cell, of any one or more of the alternatives herein is provided, in a pharmaceutically acceptable excipient. In some alternatives, the host cell, such as a mammalian cell, comprises a system of any one of the alternatives herein. In some alternatives, the system is for inducible expression of a chimeric antigen receptor in cells, such as mammalian cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral molecule, and other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the host cell is a precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell, wherein the host cell is a precursor T cell and a host cell wherein the host cell is a hematopoietic stem cell. In some alternatives, the composition comprises a host cell, wherein the host cell is a precursor T cell or a hematopoietic stem cell and a host cell that is a CD8+T cytotoxic lymphocyte cell selected from the group consisting of naïve CD8+ T cells, central memory CD8+ T cells, effector memory CD8+ T cells and bulk CD8+ T cells or a CD4+ T cell selected from naïve CD4+ T cells, central memory CD4+ T cells, effector memory CD4+ T cells, and bulk CD4+ T cells. In some alternatives, the disease is cancer or a viral disease. In some alternatives, the subject is identified or selected to receive an anti-cancer therapy. In some alternatives, the subject is identified or selected to receive an anti-viral therapy. In some alternatives, the method further comprises measuring or evaluating an inhibition of the disease. In some alternatives, the method further comprises providing said subject an additional anti-cancer therapy or anti-viral therapy before, during, or after administration of the cells of any one or more of the alternatives herein or at least one composition or product combination of any one or more of the alternatives herein. In some alternatives, the cells, such as mammalian cells, of any one or more of the aforementioned alternatives or at least one composition or product combination of any one or more of aforementioned alternatives are administered to said subject by adoptive cell transfer. In some alternatives, the host cells of any one or more of aforementioned alternatives or at least one composition or product combination of any one or more of the aforementioned alternatives are administered to said subject after said subject has received another form of anti-cancer therapy or anti-viral therapy. In some alternatives, the method further comprises administering a drug that induces expression of a transgene in the host cell or composition for the treatment of cancer or a viral infection. In some alternatives, the drug is tamoxifen and/or its metabolites, fulvestrant and/or other estrogen analogs or CMP8. In some alternatives, tamoxifen is administered at a dose range of 10, 11, 12, 13, 14, 15, 16, 17, 18, 19 or 20 mg/dose or within a range defined by any two of the aforementioned values. In some alternatives, the fulvestrant is administered at a dose range of 250, 300, 350, 400, 450 or 500 mg/dose mg/dose or within a range defined by any two of the aforementioned values. In some alternatives, the CMP8 is administered at a dose range to provide 30, 40 or 50 nM of drug levels in serum, or within a range defined by any two of the aforementioned values. In some alternatives, the cancer is a solid tumor or hematologic malignancy. In some alternatives, the solid tumor is selected from the group consisting of a breast cancer, brain cancer, lung cancer, colon cancer, renal cancer, pancreatic cancer, prostate cancer, and ovarian cancer. In some alternatives, the chimeric antigen receptor comprises a scFv. In some alternatives, the scFv specifically binds to CD19. In some alternatives, the scFv comprises an huCD19 scFv (G01S) amino acid sequence. In some alternatives, the scFv comprises an amino acid sequence set forth in SEQ ID NO: 41 (MLLLVTSLLL-CELPHPAFLLIPEVQLVESGGGLVQPGRSLRLS-CAASGFTFDDYAMH WVRQAPGKGLEWVSGISWNS-GRIGYADSVKGRFTISRDNAKNSLFLQMNSLRAEDT AVYYCARDQGYHYYDSAE-HAFDIWGQGTVVTVSSGGGGSGGGGSGGGGSQ-SALTQ PRSVSGFPGQSVTISCTGTTSDDVSWYQQHPGKAPQ-LMLYDVSKRPSGVPHRFSGSR SGRAASLIISGLQT-EDEADYFCSSYAGRYNSVLFGGGTKLTVL). In some alternatives, the scFv is encoded by a nucleic acid sequence comprising a nucleic acid sequence encoding the amino acid sequence of SEQ ID NO: 41. In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42 (Atgctgctgctggtgaccagcctgctgtgcgagctgccc-caccccgcctttctgctgatccccgacatccagatgacccagac cacctccagcctgagcgccagcctgggcgaccgggtgac-catcagctgccgggccagccaggacatcagcaagtacctgaactg gtatcagcagaagcccgacggcaccgtcaagctgctgatctac-cacaccagccggctgcacagcggcgtgcccagccggtttagc ggcagcggctccggcaccgactacagcctgaccatctccaacctggaacag-gaagatatcgccacctacttttgccagcagggcaa cacactgcccta-cacctttggcggcggaacaaagctggaaat-caccggcagcacctccggcagcggcaagcctggcagcggcga gggcagcaccaagggcgaggtgaagctgcag-gaaagcggccctggcctggtggcccccagccagagcctgagcgtgacctgca ccgtgagcggcgtgagcctgcccgactacggcgtgagctg-gatccggcagcccccaggaagggcctggaatggctgggcgtga tctggggcagcgagaccacctactacaacagcgccctgaagagccggctgac-catcatcaaggacaacagcaagagccaggtgtt cctgaagatgaacagcctgca-gaccgacgacaccgccatctactactgcgccaagcactactac-tacggcggcagctacgccatgg actactggggccagggcaccagcgtgaccgtgagcagc). In some alternatives, the scFv comprises an amino acid sequence set forth in SEQ ID NO: 43 (MLLLVTSLLLCELPHPAFL-LIPDIQMTQTTSSLSASLGDRVTISCRASQDISKY-LNWY QQKPDGTVKLLIYHTSRLHSGVPSRFSGSGSGTDYS-LTISNLEQEDIATYFCQQGNTLP YTFGGGTKLEITGST-SGSGKPGSGEGSTKGEVKLQESGPGLVAP-SQSLSVTCTVSGVS LPDYGVSWIRQPPRKGLEWLGVIWGSETTYYN-SALKSRLTIIKDNSKSQVFLKMNSL QTDDTAIYY-CAKHYYYGGSYAMDYWGQGTSVTVSS). In some alternatives, the scFv is encoded by a nucleic acid sequence comprising a nucleic acid sequence encoding the amino acid sequence of SEQ ID NO: 43. some alternatives, the scFv comprises a B7H3 (hBRCA84D) scFv nucleotide sequence. In some alternatives, the scFv binds specifically to the B7-H3 receptor. In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50 (atgctgctgctggtgaccagcctgctgctgtgcgagctgccc-caccccgcctttctgctgatcccccaggtgcagctgcagcagcct ggcgccgagctggtgaagccaggcgccagcgt-gaagctgtcctgcaaggccagcggctacaccttcaccggctactggatgcact gggtgaagcagagacccggccacggcctggaatggatcggcgagat-caaccccagcaacggccggaccaactacaacgagcgg ttcaagagcaaggc-caccctgaccgtggacaagagcagcaccaccgcctt-catgcagctgtccggcctgaccagcgaggacagcg ccgtgtacttctgcgccagggactactacggcaccagctacaacttcgac-tactggggccagggcaccacactgaccgtgagcagc ggcg-gagggggctctggcggcggaggatctgggggagggggcagcgacatcca-gatgacccagagcagcagcagcttcagcg tgagcctgggcgaccgggtgaccatcacctgtaaggccaacgaggacat-caacaaccggctggcctggtatcagcagacccccgg caacagccccaggctgctgatcagcggcgccac-caacctggtgaccggcgtgcccagccggtttagcggcagcggctccggcaa ggactacaccctgaccatcacaagcctgcaggccgaggacttcgccacctac-tactgccagcagtactggtccacccccttcaccttc ggcagcggcaccgagctg-gaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFL-LIPQVQLQQPGAELVKPGASVKLSCK-ASGYTFTGYWM HWVKQRPGHGLEWIGEINPSN-GRTNYNERFKSKATLTVDKSSTTAFMQLSGLTSEDS AVYFCARDYYGTSYNFDYWGQGT-TLTVSSGGGGSGGGGSGGGGSDIQMTQSSSSFS VSLGDRVTITCKANEDINNRLAWYQQTPGNSPRLLIS-GATNLVTGVPSRFSGSGSGK DYTLTITSLQAEDFA-TYYCQQYWSTPFTFGSGTELEIK). In some alternatives, the scFv is encoded by a nucleic acid sequence comprising a nucleic acid sequence encoding the amino acid sequence of SEQ ID NO: 51. In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52 (atgcttctcctggtgacaagccttctgctctgtgagttaccacacccagcat-tcctcctgatcccacaggtgcagctgaaacagagcg gcccgggcctggtgcagccgagccagagcctgagcattacctgcaccgt-gagcggctttagcctgaccaactatggcgtgcattgg gtgcgccagagcccgggcaaaggcctggaatggctgggcgtgatttg-gagcggcggcaacaccgattataacaccccgtttacca gccgcctgagcat-taacaaagataacagcaaaagccaggtgtttttaaaat-gaacagcctgcagagcaacgataccgcgatttattat tgcgcgcgcgcgctgacctattatgattatgaatttgcgtat-tggggccagggcaccctggtgaccgtgagcgcgggcggcggcgg cagcggcggcggcggcagcggcggcggcggcagcgatat-tctgctgacccagagcccggtgattctgagcgtgagcccgggcg aacgcgt-gagctttagctgccgcgcgagccagagcattggcaccaacattcat-tggtatcagcagcgcaccaacggcagcccgcgc ctgctgattaaatatgcgagcgaaagcattagcggcattccgagccgctt-tagcggcagcggcagcggcaccgattttaccctgagc attaacagcgtg-gaaagcgaagatattgcggattattattgccagcagaacaacaactggccgac-cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL-CELPHPAFLLIPQVQLKQSGPGLVQPSQSL-SITCTVSGFSLTNYGVHW VRQSPGKGLEW-LGVIWSGGNTDYNTPFTSRLSINKDNSKSQVFFKMN-SLQSNDTAIY YCARALTYYDYE-FAYWGQGTLVTVSAGGGGSGGGGSGGGGS-DILLTQSPVILSVSP GERVSFSCRASQSIGT-NIHWYQQRTNGSPRLLIKYASESISGIPSRFSGSGSGT-DFTLSI NSVESEDIADYYCQQNNNWPTTF GAGTKLELKRT). In some alternatives, the scFv is encoded by a nucleic acid sequence comprising a nucleic acid sequence encoding the amino acid sequence of SEQ ID NO: 53. In some alternatives, the scFv comprises the EGFRVIII (806) scFv nucleotide sequence. In some alternatives, the scFv is specific for EGFR. In some alternatives, the scFv is encoded by the EphA2 (2A4) scFv nucleotide sequence. In some alternatives, the scFv is encoded by the nucleic acid sequence set forth in SEQ ID NO: 56. In some alternatives, the scFv is encoded by the EpHA2 (4H5) scFv nucleotide sequence. In some alternatives, the scFv is encoded by the nucleic acid sequence set forth in SEQ ID NO: 58. In some alternatives, the scFv is encoded by a FITC (E2) scFv nucleotide sequence. In some alternatives, the scFv is encoded by a nucleic acid sequence set forth in SEQ ID NO: 60. In some alternatives, the scFv is encoded by an IL13Ra2 (hu08) VhVl scFv nucleotide sequence. In some alternatives, the scFv is encoded by a nucleic acid sequence set forth in SEQ ID NO: 68. In some alternatives, the scFv comprises an IL13Ra2 hu08 VhVl scFv amino acid sequence. In some alternatives, the scFv comprises an amino acid sequence set forth in SEQ ID NO: 69 (MLLLVTSLLL-CELPHPAFLLIPEVQLVESGGGLVQPGGSLRLS-CAASGFTFSRNGMS WVRQAPGKGLEW-VATVSSGGSYIYYADSVKGRFTISRDNAKNSLYLQM-NSLRAEDT AVYYCARQGTTALA-TRFFDVWGQGTLVTVSSGGGGSGGGGSGGGGSDIQ-MTQSPSS LSASVGDRVTITCKASQDVGTA-VAWYQQKPGKAPKLLIYSASYRSTGVPSRFSGSGS GTDFTLTISSLQPEDFATYYCQHHYS-APWTFGGGTKVEIKESK). In some alternatives, the scFv is encoded by a nucleic acid sequence comprising a nucleic acid sequence encoding the amino acid sequence of SEQ ID NO: 69. In some alternatives, the scFv is encoded by an IL13Ra2 (hu07) VlVh scFv nucleotide sequence. In some alternatives, the scFv is encoded by a nucleic acid sequence set forth in SEQ ID NO: 70 (atgcttctcctggtgacaagccttctgctctgtgagttaccacacccagcat-tcctcctgatcccagatattcagatgacccagagccc gagcagcct-gagcgcgagcgtgggcgatccgcgtgagcagcacctatctgcattggt atcagcagaaaccgggcaaagcgccgaaactgctgatt-tatagcaccagcaacctggcgagcggcgtgccgagccgctttagcgg cagcggcagcggcaccgattttaccctgaccattagcagcctgcagccggaa-gattttgcgacctattattgccatcagtatcatcgca gcccgctgacctttggcggcggcaccaaagtggaaat-taaaggtggtggtggttctggcggcggcggctccggtggtggtggttctg aagtgcagctggtg-gaaagcggcggcggcctggtgcagccgggcggcagcctgcgcct-gagctgcgcggcgagcggctttacct ttaccaaatatggcgtgcat-tgggtgcgccaggcgccgggcaaaggcctggaatgggtggcggtgaaatggg-cgggcggcagca ccgattataacagcgcgctgatgagccgctttaccatt-agccgcgataacgcgaaaaacagcctgtatctgcagatgaacagcctgc gcgcggaagataccgcggtgtattattgcgcgcgcgatcatcgcgatgcgatg-gattattggggccagggcaccctggtgaccgtg agcagcgaatctaagta). In some alternatives, the scFv comprises an IL13Ra2 (hu07) VhVl scFv amino acid sequence. In some alternatives, the scFv comprises an amino acid sequence set forth in SEQ ID NO: 71 (MLLLVTSLLLCELPHPAFLLIPDIQMTQSPSSL-SASVGDRVTITCTASLSVSSTYLHWY QQKPGKAPKLLIYSTSN-LASGVPSRFSGSGSGTDFTLTISSLQPEDFATYY-CHQYHRSP LTFGGGTKVEIKGGGGSGGGGSGGGG-SEVQLVESGGGLVQPGGSLRLSCAASGFTFT KYGVHWVRQAPGKGLEWVAVKWAGGSTDYN-SALMSRFTISRDNAKNSLYLQMNS LRAEDTAVYY-CARDHRDAMDYWGQGTLVTVSSESK). In some alternatives, the scFv is encoded by a nucleic acid sequence comprising a nucleic acid sequence encoding the amino acid sequence of SEQ ID NO: 71. In some alternatives, the scFv is encoded by the IL13Ra2 (hu07) VhVl scFv nucleotide sequence. In some alternatives, the scFv is encoded by a nucleic acid sequence set forth in SEQ ID NO: 72 (atgcttctcctggtgacaagccttctgctctgtgagttaccacacccagcat-tcctcctgatcccagaagtgcagctggtggaaagcg gcggcggcctggtgcagccgggcggcagcctgcgcct-gagctgcgcggcgagcggctttacctttaccaaatatggcgtgcattgg gtgcgccaggcgccgggcaaaggcctggaatgggtggcggt-gaaatgggcgggcggcagcaccgattataacagcgcgctgat gagccgctt-taccattagccgcgataacgcgaaaaacagcctgtatctgcagat-gaacagcctgcgcgcggaagataccgcggtgt attattgcgcgcgcgatcatcgcgatgcgatggattat-tggggccagggcaccctggtgaccgtgagcagcggtggtggtggttctg gcggcggcggctccggtggtggtggttctgatattca-gatgacccagagcccgagcagcctgagcgcgagcgtgggcgatcgcgt gac-cattacctgcaccgcgagcctgagcgtgagcagcacctatctgcat-tggtatcagcagaaaccgggcaaagcgccgaaactgc tgatttatagcaccagcaacctggcgagcggcgtgccgagccgctt-tagcggcagcggcagcggcaccgattttaccctgaccatta gcagcctgcagccggaagattttgcgacctattattgccatcagtat-catcgcagcccgctgacctttggcggcggcaccaaagtgga aat-taaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFL-LIPEVQLVESGGGLVQPGGSLRLSCAASGFTFT-KYGVH WVRQAPGKGLEWVAVKWAGGSTDYN-SALMSRFTISRDNAKNSLYLQMNSLRAED TAVYYCARDHR-DAMDYWGQGTLVTVSSGGGGSGGGGSG-GGGSDIQMTQSPSSLSA SVGDRVTITCTASLSVS-STYLHWYQQKPGKAPKLLIYSTSN-LASGVPSRFSGSGSGTD FTLTISSLQPEDFATYY-CHQYHRSPLTFGGGTKVEIKESK). In some alternatives, the scFv is encoded by a nucleic acid sequence comprising a nucleic acid sequence encoding the amino acid sequence of SEQ ID NO: 73. In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74 (atgcttctcctggtgacaagccttctgctctgtgagttaccacacccagcat-tcctcctgatcccaggccctgtgcctccctctacagcc ctcaggtacctcattgag-gagctggtcaacatcacccagaaccagaaggctccgctctgcaatggcag-catggtatggagcatcaac ctgacagctggcatgtactgtgcagccctggaatccctgat-caacgtgtcaggctgcagtgccatcgagaagacccagaggatgctg agcggat-tctgcccgcacaaggtctcagctgggcagttttccagcttgcatgtccgagacac-caaaatcgaggtggcccagtttgtaa aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFL-LIPGPVPPSTALRYLIEELVNITQNQKAPLCNG-SMVWSI NLTAGMYCAALESLINVSGC-SAIEKTQRMLSGFCPHKVSAGQFSSLHVRDTKIEVAQ FVKDLLLHLKKLFREGRF). In some alternatives, the scFv is encoded by a nucleic acid sequence comprising a nucleic acid sequence encoding the amino acid sequence of SEQ ID NO: 75. In some alternatives, the scFv is encoded by an oaGD2 (8B6) VlVh scFv nucleotide sequence. In some alternatives, the scFv is encoded by a sequence set forth in SEQ ID NO: (atgcttctcctggtgacaagccttctgctctgtgagt-taccacacccagcattcctcctgatcccagatgttgtgatgacccaaactcca ctctccctgcctgtcagtcttggagatcaagcctcaatctcttgca-gatctagtcagagccttctaaaaaatggaaacaccttttttaca ttggtacctgcagaagtcaggccagtctccaaagctccttatctacaaagtttc-caaccgactttctggggtcccagacaggttcagtgg cagtggatcagggacatat-ttcacactcaagatcagcagagtggaggctgaggatctgggagtttatttctgctct-caaagtacacatat tccgtacacattcggagggggggaccaagctcgagctgaaacgaggcg-gagggggctctggcggcggaggatctgggggagggg gcagcgaggt-gaaactggtggagtctggaggaggcttggtgctgcctggggattctctga-gactctcctgtgcaacttctgagttcac cttcactgattactacatgacttgggtccgccagcctccaagaaaggcactt-gagtggttgggttttattagaaacagagctaatggttac acaacagagtacaatc-catctgtgaagggtcggttcaccatttccagagataattcccaaagcatcctc-tatcttcaaatgaacaccctg agaactgaggacagtgccacttattactgtgcaagagtctctaactgggcctttgac-tactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77 (MLLLVTSLLLCELPHPAFL-LIPDVVMTQTPLSLPVSLGDQASIS-CRSSQSLLKNNGNT FLHWYLQKSGQSPKLLIYKVSNRLSGVPDRFSGSGS-GTYFTLKISRVEAEDLGVYFCS QSTHIPY-TFGGGTKLELKRGGGGSGGGGSGGGGSEVKLVES-GGGLVLPGDSLRLSCA TSEFTFTDYYMTWVRQP-PRKALEWLGFIRNRANGYTTEYNPSVKGRFTISRDN-SQSIL YLQMNTLRTEDSATYYCARVSN-WAFDYWGQGTTLTVSS). In some alternatives, the scFv is encoded by a nucleic acid sequence comprising a nucleic acid sequence encoding the amino acid sequence of SEQ ID NO: 77. In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccc-caccccgcctttctgctgatcccccaggaacagctcgtcgaaagc ggcggca-gactggtgacacctggcggcagcctgaccct-gagctgcaaggccagcggcttcgacttcagcgcctactacatgagctg ggtccgccaggcccctggcaagggactggaatggatcgccaccatc-taccccagcagcggcaagacctactacgccacctgggtg aacggacggttcac-catctccagcgacaacgcccagaacaccgtggacctgcagat-gaacagcctgacagccgccgaccgggcc acctacttttgcgccagagacagctacgccgacgacggcgccctgttcaa-catctggggccctggcaccctggtgacaatctctagc ggcggaggcg-gatctggtggcggaggaagtggcggcggaggatct-gagctggtgctgacccagagcccctctgtgtctgctgccc tgggaagccctgccaagatcacctgtaccctgagcagcgcccacaa-gaccgacaccatcgactggtatcagcagctgcagggcga ggcccccaga-tacctgatgcaggtgcagagcgacggcagctacac-caagaggccaggcgtgcccgaccggttcagcggatctag ctctggcgccgaccgctacctgatcatccccagcgtgcaggcc-gatgacgaggccgattactactgtggcgccgactacatcggcg gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESG-GRLVTPGGSLTLSCKASGFDFSAYYMSW VRQAPGKGLEWIATIYPSSGKTYYATWVNGRFTIS-SDNAQNTVDLQMNSLTAADRA TYFCARDSYADD-GALFNIWGPGTLVTISSGGGGSGGGGSGGGG-SELVLTQSPSVSAA LGSPAKITCTLS-SAHKTDTIDWYQQLQGEAPRYLMQVQSDG-SYTKRPGVPDRFSGSS SGADRYLIIPSVQADDEAD-YYCGADYIGGYVFGGGTQLTVTG). In some alternatives, the scFv is encoded by a nucleic acid sequence comprising a nucleic acid sequence encoding the amino acid sequence of SEQ ID NO: 79. In some alternatives, the scFv comprises an amino acid sequence set forth in SEQ ID NO: 80 (CD33 (h2H12) VhVl scFv nucleotide sequence (atgcttctcctggtgacaagccttctgctctgtgagttaccacacccagcat-tcctcctgatcccacaggttcagctggtgcagtctgga gctgaggt-gaagaagcctggggcctcagtgaaggtctcctgcaaggcttctggttacacctt-taccaattatgatataaattgggtgag acaggcccctggacaagggcttgagtggattggatggatttatcctg-gagatggtagtaccaaatataatgagaaattcaaggccaag gctaccctgacagctgacacatccaccagcacagcctacatggagctgag-gagcctgagatctgatgacacagctgtgtattactgtg cttctggatatgaagatgc-tatggactactgggggcaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQS-GAEVKKPGASVKVSCKASGYTFTNYDIN WVRQAPGQGLEWIGWIYPGDGSTKYNEKFKAKATL- TADTSTSTAYMELRSLRSDDT AVYY-
CASGYEDAMDYWGQGTTVTVSS). In some alternatives, the scFv is encoded by a nucleic acid sequence comprising a nucleic acid sequence encoding the amino acid sequence of SEQ ID NO: 81. In some alternatives, the scFv is encoded by a sequence set forth in SEQ ID NO: 82 (CD33 (h2H12) VlVh scFv nucleotide sequence:
atgcttctcctggtgacaagccttctgctctgtgagttaccacacccagcat-
tcctcctgatcccagacatccagatgacccagtctccat cctcactgtctg-
catctgtaggagacagagtcaccatcaattgtaaggctagtcaggacattaatagc-
tatttgagctggtttcagcaga
aaccagggaaagcccctaagaccctgatctatagagcaaatagattggta-
gatggggtcccatcaaggttctctggcagtggatctgg gcaagattatactctcac-
catcagcagcctgcagcctgaagattttgcaacttattactgcttgcagtatgat-
gagtttcctctcacatttgg aggagggaccaaggtggagatcaaa). In some alternatives, the scFv comprises an amino acid sequence set forth in SEQ ID NO: 83 (CD33 (h2H12) VlVh scFv amino acid sequence: MLLLVTSLLLCELPHPAFL-
LIPDIQMTQSPSSLSASVGDRVTINCKASQDIN-
SYLSWFQ QKPGKAPKTLIYRANRLVDGVPSR-
FSGSGSGQDYTLTISSLQPEDFATYYCLQYDEFP
LTFGGGTKVEIK). In some alternatives, the scFv is encoded by a nucleic acid sequence comprising a nucleic acid sequence encoding the amino acid sequence of SEQ ID NO: 83. In some alternatives, the scFv is encoded by a nucleic acid sequence set forth in SEQ ID NO: 84. In some alternatives, the scFv is encoded by a nucleic acid sequence set forth in SEQ ID NO: 86. In some alternatives, the scFv comprises an amino acid sequence set forth in SEQ ID NO: 87. In some alternatives, the spacer is encoded by the nucleic acid sequence set forth in SEQ ID NO: 102 (IgG4 hinge nucleotide sequence:
gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcg-
gatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, HEA3 comprises two amino acid mutations, wherein the sequence is encoded by a sequence set forth in SEQ ID NO: 122 (atggtgtc-
caagctgtcccagctgcagacagaactgctggcagcactgctggaaagcggcct-
gagcaaagaggccctgattcagg cactcggcgaacctggacct-
tatctgctcgctggcgaaggccctctggataagggcgagagctgtggcggagga-
agaggagagct ggccgagctgcctaacggcctgggcga-
gacaagaggcagcgaggacgagacagacgacgacggcgaggactt-
caccccccccc atcctgaaagagctggaaaacctgagccccgaggaagccgcc-
caccagaaagccgtggtggagacactgctgcaggaagatccc
tggcgggtcgccaagatggtcaagagctacctgcagcagcacaa-
catcccccagcgggaggtggtggacaccaccggcctgaac cagagccacct-
gagccagcacctgaacaagggcacccccat-
gaaaacccagaagagagccgccctgtacacttggtacgtgcgg
aagcagagagaggtggcccagcagtttacacacgccggccagggcggcct-
gatcgaggaacctaccggcgacgagctgcccac caagaagggcagacg-
gaaccggtttaagtggggccctgcatctcagcagatcctgttccaggcc-
tacgagcggcagaagaacccc
agcaaagaggaacgggagacactggtggaagagtgcaaccgggccgagtg-
catccagagaggcgtgagcccttctcaggctcag ggcctcggcagcaatctggt-
caccgaagtgcgggtgtacaattggttcgccaaccggcggaaagag-
gaagccttccggcacaagct
gtctgctggcgatatgagagccgccaacctgtggcccagcccccctgatgat-
caagcggagcaagaagaacagcctggccctgagc ctgaccgccgatca-
gatggtgtccgctctgctggacgccgagccccctatcctgta-
cagcgagtacgaccccaccagacccttcagc
gaggccagcatgatgggcctgctgaccaacctggccgaccgggagctggtgca-
catgatcaactgggccaagcgggtgcccggc
ttcgtggacctgaccctgcacgaccaggtccacctgctggaatgtgcctggctg-
gaaatcctgatgatcggcctcgtgtggagaagc atg-
gaacaccccggcaagctgctgttcgcccccaacctgctcctggaccg-
gaaccagggaaagtgcgtggagggcatggtggaga
tcttcgacatgctgctggccacctccagccggttccggatgat-
gaacctgcagggcgaggaattcgtgtgcctgaagtccatcatcct gct-
gaacagcggcgtgtacaccttcctgtcatccaccctgaagtccctg-
gaagagaaggaccacatccaccgggtgctggacaaga
tcaccgacaccctgatccacctgatggc-
caaggctggcctgacactccagcagcagcaccagagactggcccagctgctgct-
gatc ctgagccacatccggcacatgagcaacaagcggatggaacacctgta-
cagcatgaagtgcaagaacgtggtgcccctgtacgacct
gctgctcgagatgctggatgcccacagactgcacgcccctacaagcagaggcg-
gagccagcgtggaggaaaccgaccagtctca cctggc-
caccgccggcagcacaagcagccacagcctgcagaagtactacat-
caccggcgaggccgagggattccctgccaccgt
ggagttccagtacctgcccgacaccgacgaccggcaccggatcgag-
gaaaagcggaagcggacctacgagacattccagagcat cat-
gaagaagtccccccttcagcggccccaccgatccca-
gaccccccccctagaagaatcgccgtgcccagcagatctagcgccagc
gtgcccaagcctgcccccccagccctaccctttcaccagcagcctgagcaccat-
caactacgacgagttccctaccatggtgttcccca gcggcca-
gatctctcaggcctctgctctggcacctgctc-
cacctcaggtgctgcctcaggcccctgctccagccccagcccctgccat
ggtgtctgcactggcccaggctccagctcctgtgcctgtgctggcccctggacctc-
ctcaggctgtggcccctcctgcccctaaacct acccaggccggggagg-
gaacactgtctgaggccctgctgcagctccagttcgacgacgaggatctgg-
gagcactgctgggcaata gcaccgaccccgccgtgtt-
taccgacctggcctccgtggacaacagcgagttccagcagctcctcaaccaggg-
catccctgtcgcc ccacacaccaccgagcccatgctgatggaataccccgaggc-
catcaccagactggtcacaggcgcccagaggcctccagatccag caccagctc-
cactgggagcccctggcctgcctaatgggctgctgtctggcgacgag-
gacttcgagagcattgccgacatggacttca gcgccctgctgtccca-
gatcagcagc). In some alternatives, the HEA3 comprises an amino acid sequence set forth in SEQ ID NO: 121 (MVSK-
LSQLQTELLAALLESGLSKEALIQALGEPGPYL-
LAGEGPLDKGESCGGGRGEL AELPNGLGETRGSE-
DETDDDGEDFTPPILKELENLSPEEAAHQKAVVETLL-
QEDPWR VAKMVK-
SYLQQHNIPQREVVDTTGLNQSHLSQHLNKGTPMK-
TQKRAALYTWYVR KQREVAQQFTHAGQG-
GLIEEPTGDELPTKKGRRNRFKWGPASQQILFQAY-
ERQKNP SKEERETLVEECNRAECIQRGVSP-
SQAQGLGSNLVTEVRVYNWFANRRKEEAFRHK
LSAGDMRAANLWPSPLMIKRSKKNSLALSL-
TADQMVSALLDAEPPILYSEYDPTRPF SEA-
SMMGLLTNLADRELVHMIN-
WAKRVPGFVDLTLHDQVHLLECAWLEILMIGLV
WRSMEHPGKLLFAPNLLLDRNQGKCVEGMVE-
IFDMLLATSSRFRMMNLQGEEFVC LKSIILLNSGVYT-
FLSSTLKSLEEKDHIHRVLDKITDTLIHLMAK-
AGLTLQQQHQRLA
QLLLILSHIRHMSNKRMEH-
LYSMKCKNVVPLYDLLLEMLDAHRLHAPTSRG-
GASVE ETDQSHLATAGSTSSHSLQKYYITGEAE-
GFPATVEFQYLPDTDDRHRIEEKRKRTYET
FQSSIMKKSPFSGPTDPRPPPRRIAVPSRSSAS- VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3. In some alternatives, a system for inducible expression of a chimeric antigen receptor in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttctcaaggaccaccg-catctctacattcaagaactggcccttcttggag ggctgcgcctgcaccccg-gagcggatggccgaggctggcttcatccactgccccactgagaacgagcca-gacttggcccagtgttt cttctgcttcaaggagctggaaggctgggagccagatgacgaccccatagag-gaacataaaaagcattcgtccggttgcgctttccttt ctgtcaagaagcagttt-gaagaattaacccttggtgaatttttgaaactggacagagaaagagc-caagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD).

In some alternatives, a use of the host cell, such as a mammalian cell, of any one of or more of the alternatives or at least one composition or product combination of any one or more of the alternatives in combination with a drug that induces expression of a transgene in the host cell, such as a mammalian cell, or composition for the treatment of cancer or a viral infection is provided. In some alternatives, the host cell, such as a mammalian cell comprises a system of any one of the alternatives herein. In some alternatives, the system is for inducible expression of a chimeric antigen receptor in cells, such as mammalian cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral molecule, and other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optionally optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the host cell is a precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell, such as a mammalian cell, of any one or more of the alternatives herein is provided, in a pharmaceutically acceptable excipient. In some alternatives, the host cell, preferably a mammalian cell, comprises a system of any one of the alternatives herein. In some alternatives, the system is for inducible expression of a chimeric antigen receptor in cells, such as mammalian cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral molecule, and other molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment, such as a binding fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the host cell is a precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell, wherein the host cell is a precursor T cell and a host cell wherein the host cell is a hematopoietic stem cell. In some alternatives, the composition comprises a host cell, wherein the host cell is a precursor T cell or a hematopoietic stem cell and a host cell that is a CD8+T cytotoxic lymphocyte cell selected from the group consisting of naïve CD8+ T cells, central memory CD8+ T cells, effector memory CD8+ T cells and bulk CD8+ T cells or a CD4+ T cell selected from naïve CD4+ T cells, central memory CD4+ T cells, effector memory CD4+ T cells, and bulk CD4+ T cells. In some alternatives, the drug is tamoxifen and/or its metabolites, fulvestrant and/or other estrogen analogs or CMP8. In some alternatives, tamoxifen is administered at a dose range of 10, 11, 12, 13, 14, 15, 16, 17, 18, 19 or 20 mg/dose or within a range defined by any two of the aforementioned values. In some alternatives, the fulvestrant is administered at a dose range of 250, 300, 350, 400, 450 or 500 mg/dose or within a range defined by any two of the aforementioned values. In some alternatives, the CMP8 is administered at a dose range to provide 30, 40 or 50 nM of drug levels in serum, or within a range defined by any two of the aforementioned values. In some alternatives, the cancer is a solid tumor or hematologic malignancy. In some alternatives, the solid tumor is selected from the group consisting of a breast cancer, brain cancer, lung cancer, colon cancer, renal cancer, pancreatic cancer, prostate cancer, and ovarian cancer. In some alternatives, the chimeric antigen receptor comprises a scFv. In some alternatives, the scFv specifically binds to CD19. In some alternatives, the scFv comprises an huCD19 scFv (G01S) amino acid sequence. In some alternatives, the scFv comprises an amino acid sequence set forth in SEQ ID NO: 41 (MLLLVTSLLL-CELPHPAFLLIPEVQLVESGGGLVQPGRSLRLS-CAASGFTFDDYAMH WVRQAPGKGLEWVSGISWNS-GRIGYADSVKGRFTISRDNAKNSLFLQMNSLRAEDT AVYYCARDQGYHYYDSAE-HAFDIWGQGTVVTVSSGGGGSGGGGSGGGGSQ-SALTQ PRSVSGFPGQSVTISCTGTTSD-DVSWYQQHPGKAPQLMLYDVSKRPSGVPHRFSGSR SGRAASLIISGLQTEDEADYFCSSYAGRYNS-VLFGGGTKLTVL). In some alternatives, the scFv is encoded by a nucleic acid sequence comprising a nucleic acid sequence encoding the amino acid sequence of SEQ ID NO: 41. In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42 (Atgctgctgctggtgaccagcctgctgtgcgagctgccc-caccccgcctttctgctgatccccgacatccagatgacccagac cacctccagcctgagcgccagcctgggcgaccgggtgac-catcagctgccgggccagccaggacatcagcaagtacctgaactg gtatcagcagaagcccgacggcaccgtcaagctgctgatctac-cacaccagccggctgcacagcggcgtgcccagccggtttagc ggcagcggctccggcaccgactacagcctgaccatctccaacctggaacag-gaagatatcgccacctacttttgccagcagggcaa cacactgcccta-cacctttggcggcggaacaaagctggaaat-caccggcagcacctccggcagcggcaagcctggcagcggcga gggcagcaccaagggcgaggtgaagctgcag-gaaagcggccctggcctggtggcccccagccagagcctgagcgtgacctgca ccgtgagcggcgtgagcctgcccgactacggcgtgagctg-gatccggcagcccccccaggaagggcctggaatggctgggcgtga tctggggcagcgagaccacctactacaacagcgccctgaagagccggctgac-catcatcaaggacaacagcaagagccaggtgtt cctgaagatgaacagcctgca-gaccgacgacaccgccatctactactgcgccaagcactactac-tacggcggcagctacgccatgg actactggggccagggcaccagcgtgaccgtgagcagc). In some alternatives, the scFv comprises an amino acid sequence set forth in SEQ ID NO: 43 (MLLLVTSLLLCELPHPAFL-LIPDIQMTQTTSSLSASLGDRVTISCRASQDISKY-LNWY QQKPDGTVKLLIYHTSRLHSGVPSRFSGSGSGTDYS-LTISNLEQEDIATYFCQQGNTLP YTFGGGTKLEITGST-SGSGKPGSGEGSTKGEVKLQESGPGLVAP-SQSLSVTCTVSGVS LPDYGVSWIRQPPRKGLEWLGVIWGSETTYYN-SALKSRLTIIKDNSKSQVFLKMNSL QTDDTAIYY-CAKHYYYGGSYAMDYWGQGTSVTVSS). In some alternatives, the scFv is encoded by a nucleic acid sequence comprising a nucleic acid sequence encoding the amino acid sequence of SEQ ID NO: 43. some alternatives, the scFv comprises a B7H3 (hBRCA84D) scFv nucleotide sequence. In some alternatives, the scFv binds specifically to the B7-H3 receptor. In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50 (atgctgctgctggtgaccagcctgctgctgtgcgagctgccc-caccccgcctttctgctgatcccccaggtgcagctgcagcagcct ggcgccgagctggtgaagccaggcgccagcgt-gaagctgtcctgcaaggccagcggctacaccttcaccggctactggatgcact gggtgaagcagagacccggccacggcctggaatggatcggcgagat-caaccccagcaacggccggaccaactacaacgagcgg ttcaagagcaaggc-caccctgaccgtggacaagagcagcaccaccgcctt-catgcagctgtccggcctgaccagcgaggacagcg ccgtgtacttctgcgccagggactactacggcaccagctacaacttcgac-tactggggccagggcaccacactgaccgtgagcagc ggcg-gagggggctctggcggcggaggatctgggggagggggcagcgacatcca-gatgacccagagcagcagcagcttcagcg tgagcctgggcgaccgggtgaccatcacctgtaaggccaacgaggacat-caacaaccggctggcctggtatcagcagacccccgg caacagccccaggctgctgatcagcggcgccac-caacctggtgaccggcgtgcccagccggtttagcggcagcggctccggcaa ggactacaccctgaccatcacaagcctgcaggccgaggacttcgccacctac-tactgccagcagtactggtccaccccttcaccttc ggcagcggcaccgagctg-gaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFL-LIPQVQLQQPGAELVKPGASVKLSCK-ASGYTFTGYWM HWVKQRPGHGLEWIGEINPSN-GRTNYNERFKSKATLTVDKSSTTAFMQLSGLTSEDS AVYFCARDYYGTSYNFDYWGQGT-TLTVSSGGGGSGGGGSGGGGSDIQMTQSSSSFS VSLGDRVTITCKANEDINNRLAWYQQTPGNSPRLLIS-GATNLVTGVPSRFSGSGSGK DYTLTITSLQAEDFA-TYYCQQYWSTPFTFGSGTELEIK). In some alternatives, the scFv is encoded by a nucleic acid sequence comprising a nucleic acid sequence encoding the amino acid sequence of SEQ ID NO: 51. In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52 (atgcttctcctggtgacaagccttctgctctgtgagttaccacacccagcat-tcctcctgatcccacaggtgcagctgaaacagagcg gcccgggcctggtgcagccgagccagagcctgagcattacctgcaccgt-gagcggctttagcctgaccaactatggcgtgcattgg gtgcgccagagcccgggcaaaggcctggaatggctgggcgtgatttg-gagcggcggcaacaccgattataacaccccgtttacca gccgcctgagcat-taacaaagataacagcaaaagccaggtgtttttaaaat-gaacagcctgcagagcaacgataccgcgatttattat tgcgcgcgcgcgctgacctattatgattatgaatttgcgtat-tggggccagggcaccctggtgaccgtgagcgcgggcggcggcgg cagcggcggcggcggcagcggcggcggcggcagcgatat-tctgctgacccagagcccggtgattctgagcgtgagcccgggcg aacgcgt-gagctttagctgccgcgcgagccagagcattggcaccaacattcat-tggtatcagcagcgcaccaacggcagcccgcgc ctgctgattaaatatgcgagcgaaagcattagcggcattccgagccgctt-tagcggcagcggcagcggcaccgattttaccctgagc attaacagcgtg-gaaagcgaagatattgcggattattattgccagcagaacaacaactggccgac-cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL-CELPHPAFLLIPQVQLKQSGPGLVQPSQSL-SITCTVSGFSLTNYGVHW VRQSPGKGLEW-LGVIWSGGNTDYNTPFTSRLSINKDNSKSQVFFKMN-SLQSNDTAIY YCARALTYYDYE-FAYWGQGTLVTVSAGGGGSGGGGSGGGGS-DILLTQSPVILSVSP GERVSFSCRASQSIGT-NIHWYQQRTNGSPRLLIKYASESISGIPSRFSGSGSGT-DFTLSI NSVESEDI-ADYYCQQNNNWPTTFGAGTKLELKRT). In some alternatives, the scFv is encoded by a nucleic acid sequence comprising a nucleic acid sequence encoding the amino acid sequence of SEQ ID NO: 53. In some alternatives, the scFv comprises the EGFRVIII (806) scFv nucleotide sequence. In some alternatives, the scFv is specific for EGFR. In some alternatives, the scFv is encoded by the EphA2 (2A4) scFv nucleotide sequence. In some alternatives, the scFv is encoded by the nucleic acid sequence set forth in SEQ ID NO: 56. In some alternatives, the scFv is encoded by the EpHA2 (4H5) scFv nucleotide sequence. In some alternatives, the scFv is encoded by the nucleic acid sequence set forth in SEQ ID NO: 58. In some alternatives, the scFv is encoded by a FITC (E2) scFv nucleotide sequence. In some alternatives, the scFv is encoded by a nucleic acid sequence set forth in SEQ ID NO: 60. In some alternatives, the scFv is encoded by an IL13Ra2 (hu08) VhVl scFv nucleotide sequence. In some alternatives, the scFv is encoded by a nucleic acid sequence set forth in SEQ ID NO: 68. In some alternatives, the scFv comprises an IL13Ra2 hu08 VhVl scFv amino acid sequence. In some alternatives, the scFv comprises an amino acid sequence set forth in SEQ ID NO: 69 (MLLLVTSLLLCELPHPAFLLIPEVQLVESGG-GLVQPGGSLRLSCAASGFTFSRNGMS WVRQAPGK-GLEWVATVSSGGSYIYYADSVKGRFTISRDNAKNS-LYLQMNSLRAEDT AVYYCARQGTTALA-TRFFDVWGQGTLVTVSSGGGGSGGGGSGGGGSDIQ-MTQSPSS LSASVGDRVTITCKASQDVGTA-VAWYQQKPGKAPKLLIYSASYRSTGVPSRFSGSGS GTDFTLTISSLQPEDFATYYCQHHYS-APWTFGGGTKVEIKESK). In some alternatives, the scFv is encoded by a nucleic acid sequence comprising a nucleic acid sequence encoding the amino acid sequence of SEQ ID NO: 69. In some alternatives, the scFv is encoded by an IL13Ra2 (hu07) VlVh scFv nucleotide sequence. In some alternatives, the scFv is encoded by a nucleic acid sequence set forth in SEQ ID NO: 70 (atgcttctcctggtgacaagccttctgctctgtgagttaccacacccagcat- tcctcctgatcccagatattcagatgacccagagccc gagcagcct- gagcgcgagcgtgggcgatccgcgtgagcagcacctatctgcattggt atcagcagaaaccgggcaaagcgccgaaactgctgatt- tatagcaccagcaacctggcgagcggcgtgccgagccgctttagcgg cagcggcagcggcaccgatttaccctgaccattagcagcctgcagccggaa- gattttgcgacctattattgccatcagtatcatcgca gcccgctgacctttggcggcggcaccaaagtggaaat- taaaggtggtggtggttctggcggcggcggctccggtggtggtggttctg aagtgcagctggtg- gaaagcggcggcggcctggtgcagcggcggcgggcctggtgcgcggcgagc- ggctttacct ttaccaaatatggcgtgcat- tgggtgcgccaggcgccgggcaaaggcctggaatgggtggcggt- gaaatgggcgggcggcagca ccgattataacagcgcgctgatgagccgctt- taccattagccgcgataacgcgaaaaacagcctgtatctgcagatgaacagcctgc gcgcggaagataccgcggtgtattattgcgcgcgcgatcatcgcgatgcgatg- gattattggggccagggcaccctggtgaccgtg agcagcgaatctaagta). In some alternatives, the scFv comprises an IL13Ra2 (hu07) VhVl scFv amino acid sequence. In some alternatives, the scFv comprises an amino acid sequence set forth in SEQ ID NO: 71 (MLLLVTSLLLCELPHPAFLLIPDIQMTQSPSSL- SASVGDRVTITCTASLSVSSTYLHWY QQKPGKAPKLLIYSTSN- LASGVPSRFSGSGSGTDFTLTISSLQPEDFATYY- CHQYHRSP LTFGGGTKVEIKGGGGSGGGGSGGGG- SEVQLVESGGGLVQPGGSLRLSCAASGFTFT KYGVHWVRQAPGKGLEWVAVKWAGGSTDYN- SALMSRFTISRDNAKNSLYLQMNS LRAEDTAVYY- CARDHRDAMDYWGQGTLVTVSSESK). In some alternatives, the scFv is encoded by a nucleic acid sequence comprising a nucleic acid sequence encoding the amino acid sequence of SEQ ID NO: 71. In some alternatives, the scFv is encoded by the IL13Ra2 (hu07) VhVl scFv nucleotide sequence. In some alternatives, the scFv is encoded by a nucleic acid sequence set forth in SEQ ID NO: 72 (atgcttctcctggtgacaagccttctgctctgtgagttaccacacccagcat- tcctcctgatcccagaagtgcagctggtggaaagcg gcggcggcctggtgcagccgggcggcagcctgcgcct- gagctgcgcggcgagcggctttacctttaccaaatatggcgtgcattgg gtgcgccaggcgccgggcaaaggcctggaatgggtggcggt- gaaatgggcgggcggcagcaccgattataacagcgcgctgat gagccgctt- taccattagccgcgataacgcgaaaaacagcctgtatctgcagat- gaacagcctgcgcgcggaagataccgcggtgt attattgcgcgcgcgatcatcgcgatgcgatggattat- tggggccagggcaccctggtgaccgtgagcagcggtggtggtggttctg gcggcggcggctccggtggtggtggttctgatattca- gatgacccagagcccgagcagcctgagcgcgagcgtgggcgatcgcgt gac- cattacctgcaccgcgagcctgagcgtgagcagcacctatctgcat- tggtatcagcagaaaccgggcaaagcgccgaaactgc tgatttatagcaccagcaacctggcgagcggcgtgccgagccgctt- tagcggcagcggcagcggcaccgatttaccctgaccatta gcagcctgcagccggaagattttgcgacctattattgccatcagtat- catcgcagcccgctgacctttggcggcggcaccaaagtgga aat- taaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFL- LIPEVQLVESGGGLVQPGGSLRLSCAASGFTFT- KYGVH WVRQAPGKGLEWVAVKWAGGSTDYN- SALMSRFTISRDNAKNSLYLQMNSLRAED TAVYYCARDHR- DAMDYWGQGTLVTVSSGGGGSGGGGSGGGGSDIQ- MTQSPSSLSA SVGDRVTITCTASLSVS- STYLHWYQQKPGKAPKLLIYSTSN- LASGVPSRFSGSGSGTD FTLTISSLQPEDFATYY- CHQYHRSPLTFGGGTKVEIKESK). In some alternatives, the scFv is encoded by a nucleic acid sequence comprising a nucleic acid sequence encoding the amino acid sequence of SEQ ID NO: 73. In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74 (atgcttctcctggtgacaagccttctgctctgtgagttaccacacccagcat- tcctcctgatcccaggccctgtgcctccctctacagcc ctcaggtacctcattgag- gagctggtcaacatcacccagaaccagaaggctccgctctgcaatggcag- catggtatggagcatcaac ctgacagctggcatgtactgtgcagccctggaatccctgat- caacgtgtcaggctgcagtgccatcgagaagacccagaggatgctg agcggat- tctgcccgcacaaggtctcagctgggcagttttccagcttgcatgtccgagacac- caaaatcgaggtggcccagtttgtaa aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFL- LIPGPVPPSTALRYLIEELVNITQNQKAPLCNG- SMVWSI NLTAGMYCAALESLINVSGC- SAIEKTQRMLSGFCPHKVSAGQFSSLHVRDTKIEVAQ FVKDLLLHLKKLFREGRF). In some alternatives, the scFv is encoded by a nucleic acid sequence comprising a nucleic acid sequence encoding the amino acid sequence of SEQ ID NO: 75. In some alternatives, the scFv is encoded by an oaGD2 (8B6) VlVh scFv nucleotide sequence. In some alternatives, the scFv is encoded by a sequence set forth in SEQ ID NO: 76 (atgcttctcctggtgacaagccttctgctctgt- gagttaccacacccagcattcctcctgatcccagatgttgtgatgacccaaactcca ctctccctgcctgtcagtcttggagatcaagcctcaatctcttgca- gatctagtcagagccttctaaaaaatggaaacaccttttttaca ttggtacctgcagaagtcaggccagtctccaaagctccttatctacaaagtttc- caaccgactttctggggtcccagacaggttcagtgg cagtggatcagggacatat- ttcacactcaagatcagcagagtggaggctgaggatctgggagtttatttctgctct- caaagtacacatat tccgtacacattcggaggggggaccaagctcgagctgaaacgaggcg- gaggggggctctggcggcggaggatctgggggagggg gcagcgaggt- gaaactggtggagtctggaggaggcttggtgctgcctggggattctctga- gactctcctgtgcaacttctgagttcac cttcactgattactacatgacttgggtccgccagcctccaagaaaggcactt- gagtggttgggttttattagaaacagagctaatggttac acaacagagtacaatc- catctgtgaagggtcggttcaccatttccagagataattcccaaagcatcctc- tatcttcaaatgaacaccctg agaactgaggacagtgccacttattactgtgcaagagtctctaactgggcctttgac- tactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77 (MLLLVTSLLLCELPHPAFL- LIPDVVMTQTPLSLPVSLGDQASIS- CRSSQSLLKNNGNT FLHWYLQKSGQSPKLLIYKVSNRLSGVPDRFSGSGS- GTYFTLKISRVEAEDLGVYFCS QSTHIPY- TFGGGTKLELKRGGGGSGGGGSGGGGSEVKLVES- GGGLVLPGDSLRLSCA TSEFTFTDYYMTWVRQP- PRKALEWLGFIRNRANGYTTEYNPSVKGRFTISRDN- SQSIL YLQMNTLRTEDSATYYCARVSN- WAFDYWGQGTTLTVSS). In some alternatives, the scFv is encoded by a nucleic acid sequence comprising a nucleic acid sequence encoding the amino acid sequence of SEQ ID NO: 77. In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccccaccccgcctttctgctgatcccccaggaacagctcgtcgaaagc ggcggcagactggtgacacctggcggcagcctgaccctgagctgcaaggccagcggcttcgacttcagcgcctactacatgagctg ggtccgccaggcccctggcaagggactggaatggatcgccaccatctaccccagcagcggcaagacctactacgccacctgggtg aacggacggttcaccatctccagcgacaacgcccagaacaccgtggacctgcagatgaacagcctgacagccgccgaccgggcc acctacttttgcgccagagacagctacgccgacgacggcgccctgttcaacatctggggccctggcaccctggtgacaatctctagc ggcggaggcggatctggtggcggaggaagtggcggcggaggatctgagctggtgctgacccagagcccctctgtgtctgctgccc tgggaagccctgccaagatcacctgtaccctgagcagcgcccacaagaccgacaccatcgactggtatcagcagctgcagggcga ggcccccagatacctgatgcaggtgcagagcgacggcagctacaccaagaggccaggcgtgcccgaccggttcagcggatctag ctctggcgccgaccgctacctgatcatccccagcgtgcaggccgatgacgaggccgattactactgtggcgccgactacatcggcg gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESGGRLVTPGGSLTLSCKASGFDFSAYYMSW VRQAPGKGLEWIATIYPSSGKTYYATWVNGRFTISSDNAQNTVDLQMNSLTAADRA TYFCARDSYADDGALFNIWGPGTLVTISSGGGGSGGGGSGGGGSELVLTQSPSVSAA LGSPAKITCTLSSAHKTDTIDWYQQLQGEAPRYLMQVQSDGSYTKRPGVPDRFSGSS SGADRYLIIPSVQADDEADYYCGADYIGGYVFGGGTQLTVTG). In some alternatives, the scFv is encoded by a nucleic acid sequence comprising a nucleic acid sequence encoding the amino acid sequence of SEQ ID NO: 79. In some alternatives, the scFv comprises an amino acid sequence set forth in SEQ ID NO: 80 (CD33 (h2H12) VhVl scFv nucleotide sequence (atgcttctcctggtgacaagccttctgctctgtgagttaccacacccagcattcctcctgatcccacaggttcagctggtgcagtctgga gctgaggtgaagaagcctggggcctcagtgaaggtctcctgcaaggcttctggttacacctttaccaattatgatataaattgggtgag acaggcccctggacaagggcttgagtggattggatggatttatcctggagatggtagtaccaaatataatgagaaattcaaggccaag gctaccctgacagctgacacatccaccagcacagcctacatggagctgaggagcctgagatctgatgacacagctgtgtattactgtg cttctggatatgaagatgctatggactactgggggcaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQSGAEVKKPGASVKVSCKASGYTFTNYDIN WVRQAPGQGLEWIGWIYPGDGSTKYNEKFKAKATLTADTSTSTAYMELRSLRSDDT AVYYCASGYEDAMDYWGQGTTVTVSS). In some alternatives, the scFv is encoded by a nucleic acid sequence comprising a nucleic acid sequence encoding the amino acid sequence of SEQ ID NO: 81. In some alternatives, the scFv is encoded by a sequence set forth in SEQ ID NO: 82 (CD33 (h2H12) VlVh scFv nucleotide sequence: atgcttctcctggtgacaagccttctgctctgtgagttaccacacccagcattcctcctgatcccagacatccagatgacccagtctccat cctcactgtctgcatctgtaggagacagagtcaccatcaattgtaaggctagtcaggacattaatagctatttgagctggtttcagcaga aaccagggaaagcccctaagaccctgatctatagagcaaatagattggtagatggggtcccatcaaggttctctggcagtggatctgg gcaagattatactctcaccatcagcagcctgcagcctgaagattttgcaacttattactgcttgcagtatgatgagtttcctctcacatttgg aggagggaccaaggtggagatcaaa). In some alternatives, the scFv comprises an amino acid sequence set forth in SEQ ID NO: 83 (CD33 (h2H12) VlVh scFv amino acid sequence: MLLLVTSLLLCELPHPAFLLIPDIQMTQSPSSLSASVGDRVTINCKASQDINSYLSWFQ QKPGKAPKTLIYRANRLVDGVPSRFSGSGSGQDYTLTISSLQPEDFATYYCLQYDEFP LTFGGGTKVEIK). In some alternatives, the scFv is encoded by a nucleic acid sequence comprising a nucleic acid sequence encoding the amino acid sequence of SEQ ID NO: 83. In some alternatives, the scFv is encoded by a nucleic acid sequence set forth in SEQ ID NO: 84. In some alternatives, the scFv is encoded by a nucleic acid sequence set forth in SEQ ID NO: 86. In some alternatives, the scFv comprises an amino acid sequence set forth in SEQ ID NO: 87. In some alternatives, the spacer is encoded by the nucleic acid sequence set forth in SEQ ID NO: 102 (IgG4 hinge nucleotide sequence: gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, HEA3 comprises two amino acid mutations, wherein the sequence is encoded by a sequence set forth in SEQ ID NO: 122 (atggtgtccaagctgtcccagctgcagacagaactgctggcagcactgctggaaagcggcctgagcaaagaggccctgattcagg cactcggcgaacctggaccttatctgctcgctggcgaaggccctctggataagggcgagagctgtggcggaggaagaggagagct ggccgagctgcctaacggcctgggcgagacaagaggcagcgaggacgagacagacgacgacggcgaggacttcacccccccc atcctgaaagagctggaaaacctgagccccgaggaagccgcccaccagaaagccgtggtggagacactgctgcaggaagatccc tggcgggtcgccaagatggtcaagagctacctgcagcagcacaacatcccccagcgggaggtggtggacaccaccggcctgaac cagagccacctgagccagcacctgaacaagggcacccccatgaaaacccagaagagagccgccctgtacacttggtacgtgcgg aagcagagagaggtggcccagcagtttacacacgccggccagggcggcctgatcgaggaacctaccggcgacgagctgcccac caagaagggcagacggaaccggtttaagtggggccctgcatctcagcagatcctgttccaggcctacgagcggcagaagaacccc agcaaagaggaacgggagacactggtggaagagtgcaaccgggccgagtgcatccagagaggcgtgagcccttctcaggctcag ggcctcggcagcaatctggtcaccgaagtgcgggtgtacaattggttcgccaaccggcggaaagaggaagccttccggcacaagct gtctgctggcgatatgagagccgccaacctgtggcccagcccccctgatgatcaagcggagcaagaagaacagcctggccctgagc ctgaccgccgatcagatggtgtccgctctgctggacgccgagccccctatcctgtacagcgagtacgaccccaccagacccttcagc gaggccagcatgatgggcctgctgaccaacctggccgaccgggagctggtgcacatgatcaactgggccaagcgggtgcccggc ttcgtggacctgaccctgcacgaccaggtccacctgctggaatgtgcctggctggaaatcctgatgatcggcctcgtgtggagaagc atggaacaccccggcaagctgctgttcgcccccaacctgctcctggaccggaaccagggaaagtgcgtggagggcatggtggaga tcttcgacatgctgctggccacctccagccggttccggatgatgaacctgcagggcgaggaattcgtgtgcctgaagtccatcatcct gctgaacagcggcgtgtacaccttcctgtcatccaccctgaagtccctg-gaagagaaggaccacatccaccgggtgctggacaaga tcaccgacaccctgatccacctgatggc-caaggctggcctgacactccagcagcagcaccagagactggcccagctgctgct-gatc ctgagccacatccggcacatgagcaacaagcggatggaacacctgta-cagcatgaagtgcaagaacgtggtgcccctgtacgacct gctgctcgagatgctggatgcccacagactgcacgcccctacaagcagaggcg-gagccagcgtggaggaaaccgaccagtctca cctggc-caccgccggcagcacaagcagccacagcctgcagaagtactacat-caccggcgaggccgagggattccctgccaccgt ggagttccagtacctgcccgacaccgacgaccggcaccggatcgag-gaaaagcggaagcggacctacgagacattccagagcat cat-gaagaagtccccctcagcggccccaccgatccca-gacccccccctagaagaatcgccgtgcccagcagatctagcgccagc gtgcccaagcctgcccccagccctaccctttcaccagcagcctgagcaccat-caactacgacgagttccctaccatggtgttcccca gcggcca-gatctctcaggcctctgctctggcacctgctc-cacctcaggtgctgcctcaggcccctgctccagccccagcccctgccat ggtgtctgcactggcccaggctccagctcctgtgcctgtgctggcccctggacct-cctcaggctgtggcccctcctgcccctaaacct acccaggccggggagg-gaacactgtctgaggccctgctgcagctccagttcgacgacgaggatctgg-gagcactgctgggcaata gcaccgaccccgccgtgtt-taccgacctggcctccgtggacaacagcgagttccagcagctcctcaaccagggc atccctgtcgcc ccacacaccaccgagcccatgctgatggaataccccgaggc-catcaccagactggtcacaggcgcccagaggcctccagatccag caccagctc-cactgggagcccctggcctgcctaatgggctgctgtctggcgacg aggacttcgagagcattgccgacatggacttca gcgccctgctgtccca-gatcagcagc). In some alternatives, the HEA3 comprises an amino acid sequence set forth in SEQ ID NO: 121 (MVSK-LSQLQTELLAALLESGLSKEALIQALGEPGPYL-LAGEGPLDKGESCGGGRGEL AELPNGLGETRGSE-DETDDDGEDFTPPILKELENLSPEEAAHQKAVVETLL QEDPWR VAKMVK-SYLQQHNIPQREVVDTTGLNQSHLSQHLNKGTPMK-TQKRAALYTWYVR KQREVAQQFTHAGQG-GLIEEPTGDELPTKKGRRNRFKWGPASQQILFQAY-ERQKNP SKEERETLVEECNRAECIQRGVSP-SQAQGLGSNLVTEVRVYNWFANRRKEEAFRHK LSAGDMRAANLWPSPLMIKRSKKNSLALSL-TADQMVSALLDAEPPILYSEYDPTRPF SEA-SMMGLLTNLADRELVHMIN-WAKRVPGFVDLTLHDQVHLLECAWLEILMIGLV WRSMEHPGKLLFAPNLLLDRNQGKCVEGMVE-IFDMLLATSSRFRMMNLQGEEFVC LKSIILLNSGVYT-FLSSTLKSLEEKDHIHRVLDKITDTLIHLMAK-AGLTLQQQHQRLA QLLLILSHIRHMSNKRMEH-LYSMKCKNVVPLYDLLLEMLDAHRLHAPTSRG-GASVE ETDQSHLATAGSTSSHSLQKYYITGEAE-GFPATVEFQYLPDTDDRHRIEEKRKRTYET FQSSIMKKSPFSGPTDPRPPPRRIAVPSRSSAS-VPKPAPQPYPFTSSLSTINYDEFPTMVFP SGQ-ISQASALAPAPPQVLPQAPAPAPA-PAMVSALAQAPAPVPVLAPGPPQAVAPPAP KPTQAGEGTLSEALLQLQFDDEDLGALLGNSTD-PAVFTDLASVDNSEFQQLLNQGIP VAPH-TTEPMLMEYPEAITRLVTGAQRPPDPAPAPL-GAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3. In some alternatives, a system for inducible expression of a chimeric antigen receptor in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttctcaaggaccaccg-catctctacattcaagaactggcccttcttggag ggctgcgcctgcaccccg-gagcggatggccgaggctggcttcatccactgccccactgagaacgagcca-gacttggcccagtgttt cttctgcttcaaggagctggaaggctgggagccagatgacgaccccatagag-gaacataaaaagcattcgtccggttgcgctttccttt ctgtcaagaagcagttt-gaagaattaacccttggtgaatttttgaaactggacagagaaagagc-caagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD).

In some alternatives, a method of performing cellular immunotherapy in a subject having cancer or a viral infection is provided. The method comprises administering the host cells, such as mammalian cells, of any one or more of the alternatives herein or at least one composition or product combination of any one or more of the alternatives herein to the subject and administering a drug that induces expression of a transgene in the composition or the host cells, such as mammalian cells. In some alternatives, the host cell, such as a mammalian cell, comprises a system of any one of the alternatives herein. In some alternatives, the system is for inducible expression of a chimeric antigen receptor in cells, such as mammalian cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral molecule, and other molecule expressed on a target cell population, wherein the ligand elicits recognition, modulation, inhibition, and/or elimination by a lymphocyte, a second polynucleotide, which encodes a spacer preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER- LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the host cell is a precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell, such as a mammalian cell, of any one or more of the alternatives herein, in a pharmaceutically acceptable excipient. In some alternatives, the host cell, such as a mammalian cell, comprises a system of any one of the alternatives herein. In some alternatives, the system is for inducible expression of a chimeric antigen receptor in cells, such as mammalian cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and other molecule expressed on a target cell population, wherein the ligand elicits recognition, modulation, inhibition, and/or elimination by a lymphocyte, a second polynucleotide, which encodes an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment, such as a binding fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the host cell is a precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell, wherein the host cell is a precursor T cell and a host cell wherein the host cell is a hematopoietic stem cell. In some alternatives, the composition comprises a host cell, wherein the host cell is a precursor T cell or a hematopoietic stem cell and a host cell that is a CD8+T cytotoxic lymphocyte cell selected from the group consisting of naïve CD8+ T cells, central memory CD8+ T cells, effector memory CD8+ T cells and bulk CD8+ T cells or a CD4+ T cell selected from naïve CD4+ T cells, central memory CD4+ T cells, effector memory CD4+ T cells, and bulk CD4+ T cells. In some alternatives, the cancer is selected from a solid tumor or hematologic malignancy. In some alternatives, the solid tumor is selected from the group consisting of a breast cancer, brain cancer, lung cancer, colon cancer, renal cancer, pancreatic cancer, prostate cancer, and ovarian cancer. In some alternatives, the chimeric antigen receptor comprises a scFv. In some alternatives, the scFv specifically binds to CD19. In some alternatives, the scFv comprises an huCD19 scFv (G01S) amino acid sequence. In some alternatives, the scFv comprises an amino acid sequence set forth in SEQ ID NO: 41 (MLLLVTSLLLCELPHPAFLLIPEVQLVESGG-GLVQPGRSLRLSCAASGFTFDDYAMH WVRQAPGK-GLEWVSGISWNSGRIGYADSVKGRFTISRD-NAKNSLFLQMNSLRAEDT AVYYCARDQGYHYYDSAE-HAFDIWGQGTVVTVSSGGGGSGGGGSGGGGSQ-SALTQ PRSVSGFPGQSVTISCTGTTSDDVSW YQQHPGKAPQLMLYDVSKRPSGVPHRFSGSR SGRAASLIISGLQTEDEADYFCSSYAGRYNS-VLFGGGTKLTVL). In some alternatives, the scFv is encoded by a nucleic acid sequence comprising a nucleic acid sequence encoding the amino acid sequence of SEQ ID NO: 41. In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42 (Atgctgctgctggtgaccagcctgctgtgcgagctgccc-caccccgcctttctgctgatccccgacatccagatgacccagac cacctccagcctgagcgccagcctgggcgaccgggtgac-catcagctgccgggccagccaggacatcagcaagtacctgaactg gtatcagcagaagcccgacggcaccgtcaagctgctgatctac-cacaccagccggctgcacagcggcgtgcccagccggtttagc ggcagcggctccggcaccgactacagcctgaccatctccaacctggaacag-gaagatatcgccacctacttttgccagcagggcaa cacactgcccta-cacctttggcggcggaacaaagctggaaat-caccggcagcacctccggcagcggcaagcctggcagcggcga gggcagcaccaagggcgaggtgaagctgcag-gaaagcggccctggcctggtggcccccagccagagcctgagcgtgacctgca ccgtgagcggcgtgagcctgcccgactacggcgtgagctg-gatccggcagccccccaggaagggcctggaatggctgggcgtga tctggggcagcgagaccacctactacaacagcgccctgaagagccggctgac-catcatcaaggacaacagcaagagccaggtgtt cctgaagatgaacagcctgca-gaccgacgacaccgccatctactactgcgccaagcactactac-tacggcggcagctacgccatgg actactggggccagggcaccagcgtgaccgtgagcagc). In some alternatives, the scFv comprises an amino acid sequence set forth in SEQ ID NO: 43 (MLLLVTSLLLCELPHPAFL-LIPDIQMTQTTSSLSASLGDRVTISCRASQDISKY-LNWY QQKPDGTVKLLIYHTSRLHSGVPSRFSGSGSGTDYS-LTISNLEQEDIATYFCQQGNTLP YTFGGGTKLEITGST-SGSGKPGSGEGSTKGEVKLQESGPGLVAP-SQSLSVTCTVSGVS LPDYGVSWIRQPPRKGLEWLGVIWGSETTYYN-SALKSRLTIIKDNSKSQVFLKMNSL QTDDTAIYY-CAKHYYYGGSYAMDYWGQGTSVTVSS). In some alternatives, the scFv is encoded by a nucleic acid sequence comprising a nucleic acid sequence encoding the amino acid sequence of SEQ ID NO: 43. some alternatives, the scFv comprises a B7H3 (hBRCA84D) scFv nucleotide sequence. In some alternatives, the scFv binds specifically to the B7-H3 receptor. In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50 (atgctgctgctggtgaccagcctgctgctgtgcgagctgccc-caccccgcctttctgctgatcccccaggtgcagctgcagcagcct ggcgccgagctggtgaagccaggcgccagcgt-gaagctgtcctgcaaggccagcggctacaccttcaccggctactggatgcact gggtgaagcagagacccggccacggcctggaatggatcggcgagat-caaccccagcaacggccggaccaactacaacgagcgg ttcaagagcaaggc-caccctgaccgtggacaagagcagcaccaccgcctt-catgcagctgtccggcctgaccagcgaggacagcg ccgtgtacttctgcgccagggactactacggcaccagctacaacttcgac-tactggggccagggcaccacactgaccgtgagcagc ggcg-gagggggctctggcggcggaggatctgggggagggggcagcgacatcca-gatgacccagagcagcagcagcttcagcg tgagcctgggcgaccgggtgaccatcacctgtaaggccaacgaggacat-caacaaccggctggcctggtatcagcagacccccgg caacagccccaggctgctgatcagcggcgccac-caacctggtgaccggcgtgcccagccggtttagcggcagcggctccggcaa ggactacaccctgaccatcacaagcctgcaggccgaggacttcgccacctac-tactgccagcagtactggtccaccccctcaccttc ggcagcggcaccgagctg-gaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFL-LIPQVQLQQPGAELVKPGASVKLSCK-ASGYTFTGYWM HWVKQRPGHGLEWIGEINPSN-GRTNYNERFKSKATLTVDKSSTTAFMQLSGLTSEDS AVYFCARDYYGTSYNFDYWGQGT-TLTVSSGGGGSGGGGSGGGGSDIQMTQSSSSFS VSLGDRVTITCKANEDINNRLAWYQQTPGNSPRLLIS-GATNLVTGVPSRFSGSGSGK DYTLTITSLQAEDFA-TYYCQQYWSTPFTFGSGTELEIK). In some alternatives, the scFv is encoded by a nucleic acid sequence comprising a nucleic acid sequence encoding the amino acid sequence of SEQ ID NO: 51. In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52 (atgcttctcctggtgacaagccttctgctctgtgagttaccacacccagcat-tcctcctgatcccacaggtgcagctgaaacagagcg gcccgggcctggtgcagccgagccagagcctgagcattacctgcaccgt-gagcggctttagcctgaccaactatggcgtgcattgg gtgcgccagagcccgggcaaaggcctggaatggctgggcgtgatttg-gagcggcggcaacaccgattataacaccccgtttacca gccgcctgagcat-taacaaagataacagcaaaagccaggtgtttttaaaat-gaacagcctgcagagcaacgataccgcgatttattat tgcgcgcgcgcgctgacctattatgattatgaatttgcgtat-tggggccagggcaccctggtgaccgtgagcgcgggcggcggcgg cagcggcggcggcggcagcggcggcggcggcagcgatat-tctgctgacccagagcccggtgattctgagcgtgagcccgggcg aacgcgt-gagctttagctgccgcgcgagccagagcattggcaccaacattcat-tggtatcagcagcgcaccaacggcagcccgcgc ctgctgattaaatatgcgagcgaaagcattagcggcattccgagccgctt-tagcggcagcggcagcggcaccgattttaccctgagc attaacagcgtg-gaaagcgaagatattgcggattattattgccagcagaacaacaactggccgac-cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL-CELPHPAFLLIPQVQLKQSGPGLVQPSQSL-SITCTVSGFSLTNYGVHW VRQSPGKGLEW-LGVIWSGGNTDYNTPFTSRLSINKDNSKSQVFFKMN-SLQSNDTAIY YCARALTYYDYE- FAYWGQGTLVTVSAGGGGSGGGGSGGGGSDILLTQSPVILSVSP GERVSFSCRASQSIGTNIHWYQQRTNGSPRLLIKYASESISGIPSRFSGSGSGTDFTLSI NSVESEDIADYYCQQNNNWPTTFGAGTKLELKRT). In some alternatives, the scFv is encoded by a nucleic acid sequence comprising a nucleic acid sequence encoding the amino acid sequence of SEQ ID NO: 53. In some alternatives, the scFv comprises the EGFRVIII (806) scFv nucleotide sequence. In some alternatives, the scFv is specific for EGFR. In some alternatives, the scFv is encoded by the EphA2 (2A4) scFv nucleotide sequence. In some alternatives, the scFv is encoded by the nucleic acid sequence set forth in SEQ ID NO: 56. In some alternatives, the scFv is encoded by the EpHA2 (4H5) scFv nucleotide sequence. In some alternatives, the scFv is encoded by the nucleic acid sequence set forth in SEQ ID NO: 58. In some alternatives, the scFv is encoded by a FITC (E2) scFv nucleotide sequence. In some alternatives, the scFv is encoded by a nucleic acid sequence set forth in SEQ ID NO: 60. In some alternatives, the scFv is encoded by an IL13Ra2 (hu08) VhVl scFv nucleotide sequence. In some alternatives, the scFv is encoded by a nucleic acid sequence set forth in SEQ ID NO: 68. In some alternatives, the scFv comprises an IL13Ra2 hu08 VhVl scFv amino acid sequence. In some alternatives, the scFv comprises an amino acid sequence set forth in SEQ ID NO: 69 (MLLLVTSLLLCELPHPAFLLIPEVQLVESGGGLVQPGGSLRLSCAASGFTFSRNGMS WVRQAPGKGLEWVATVSSGGSYIYYADSVKGRFTISRDNAKNSLYLQMNSLRAEDT AVYYCARQGTTALATRFFDVWGQGTLVTVSSGGGGSGGGGSGGGGSDIQMTQSPSS LSASVGDRVTITCKASQDVGTAVAWYQQKPGKAPKLLIYSASYRSTGVPSRFSGSGS GTDFTLTISSLQPEDFATYYCQHHYSAPWTFGGGTKVEIKESK). In some alternatives, the scFv is encoded by a nucleic acid sequence comprising a nucleic acid sequence encoding the amino acid sequence of SEQ ID NO: 69. In some alternatives, the scFv is encoded by an IL13Ra2 (hu07) VlVh scFv nucleotide sequence. In some alternatives, the scFv is encoded by a nucleic acid sequence set forth in SEQ ID NO: 70 (atgcttctcctggtgacaagccttctgctctgtgagttaccacacccagcattcctcctgatcccagatattcagatgacccagagccc gagcagcctgagcgcgagcgtgggcgatccgcgtgagcagcacctatctgcattggt atcagcagaaaccgggcaaagcgccgaaactgctgatttatagcaccagcaacctggcgagcggcgtgccgagccgctttagcgg cagcggcagcggcaccgatttaccctgaccattagcagcctgcagccggaagattttgcgacctattattgccatcagtatcatcgca gcccgctgacctttggcggcggcaccaaagtggaaattaaaggtggtggtggttctggcggcggcggctccggtggtggtggttctg aagtgcagctggtggaaagcggcggcggcctggtgcagcggcggcgggcctggtgcgcggcgagc ggctttacct ttaccaaatatggcgtgcattgggtgcgccaggcgccgggcaaaggcctggaatgggtggcggtgaaatgggcgggcggcagca ccgattataacagcgcgctgatgagccgctttaccattagccgcgataacgcgaaaaacagcctgtatctgcagatgaacagcctgc gcgcggaagataccgcggtgtattattgcgcgcgcgatcatcgcgatgcgatggattattggggccagggcaccctggtgaccgtg agcagcgaatctaagta). In some alternatives, the scFv comprises an IL13Ra2 (hu07) VhVl scFv amino acid sequence. In some alternatives, the scFv comprises an amino acid sequence set forth in SEQ ID NO: 71 (MLLLVTSLLLCELPHPAFLLIPDIQMTQSPSSLSASVGDRVTITCTASLSVSSTYLHWY QQKPGKAPKLLIYSTSNLASGVPSRFSGSGSGTDFTLTISSLQPEDFATYYCHQYHRSP LTFGGGTKVEIKGGGGSGGGGSGGGGSEVQLVESGGGLVQPGGSLRLSCAASGFTFT KYGVHWVRQAPGKGLEWVAVKWAGGSTDYNSALMSRFTISRDNAKNSLYLQMNS LRAEDTAVYYCARDHRDAMDYWGQGTLVTVSSESK). In some alternatives, the scFv is encoded by a nucleic acid sequence comprising a nucleic acid sequence encoding the amino acid sequence of SEQ ID NO: 71. In some alternatives, the scFv is encoded by the IL13Ra2 (hu07) VhVl scFv nucleotide sequence. In some alternatives, the scFv is encoded by a nucleic acid sequence set forth in SEQ ID NO: 72 (atgcttctcctggtgacaagccttctgctctgtgagttaccacacccagcattcctcctgatcccagaagtgcagctggtggaaagcg gcggcggcctggtgcagccgggcggcagcctgcgcctgagctgcgcggcgagcggctttacctttaccaaatatggcgtgcattgg gtgcgccaggcgccgggcaaaggcctggaatgggtggcggtgaaatgggcgggcggcagcaccgattataacagcgcgctgat gagccgctttaccattagccgcgataacgcgaaaaacagcctgtatctgcagatgaacagcctgcgcgcggaagataccgcggtgt attattgcgcgcgcgatcatcgcgatgcgatggattattggggccagggcaccctggtgaccgtgagcagcggtggtggtggttctg gcggcggcggctccggtggtggtggttctgatattcagatgacccagagcccgagcagcctgagcgcgagcgtgggcgatcgcgt gaccattacctgcaccgcgagcctgagcgtgagcagcacctatctgcattggtatcagcagaaaccgggcaaagcgccgaaactgc tgatttatagcaccagcaacctggcgagcggcgtgccgagccgctttagcggcagcggcagcggcaccgattttaccctgaccatta gcagcctgcagccggaagattttgcgacctattattgccatcagtatcatcgcagcccgctgacctttggcggcggcaccaaagtgga aattaaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFLLIPEVQLVESGGGLVQPGGSLRLSCAASGFTFTKYGVH WVRQAPGKGLEWVAVKWAGGSTDYNSALMSRFTISRDNAKNSLYLQMNSLRAED TAVYYCARDHRDAMDYWGQGTLVTVSSGGGGSGGGGSGGGGSDIQ MTQSPSSLSA SVGDRVTITCTASLSVSSTYLHWYQQKPGKAPKLLIYSTSNLASGVPSRFSGSGSGTD FTLTISSLQPEDFATYYCHQYHRSPLTFGGGTKVEIKESK). In some alternatives, the scFv is encoded by a nucleic acid sequence comprising a nucleic acid sequence encoding the amino acid sequence of SEQ ID NO: 73. In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74 (atgcttctcctggtgacaagccttctgctctgtgagttaccacacccagcattcctcctgatcccaggccctgtgcctccctctacagcc ctcaggtacctcattgaggagctggtcaacatcacccagaaccagaaggctccgctctgcaatggcagcatggtatggagcatcaac ctgacagctggcatgtactgtgcagccctggaatccctgatcaacgtgtcaggctgcagtgccatcgagaagacccagaggatgctg agcggattctgcccgcacaaggtctcagctgggcagttttccagcttgcatgtccgagacaccaaaatcgaggtggcccagtttgtaa aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFLLIPGPVPPSTALRYLIEELVNITQNQKAPLCNGSMVWSI NLTAGMYCAALESLINVSGCSAIEKTQRMLSGFCPHKVSAGQFSSLHVRDTKIEVAQ FVKDLLLHLKKLFREGRF). In some alternatives, the scFv is encoded by a nucleic acid sequence comprising a nucleic acid sequence encoding the amino acid sequence of SEQ ID NO: 75. In some alternatives, the scFv is encoded by an oaGD2 (8B6) VlVh scFv nucleotide sequence. In some alternatives, the scFv is encoded by a sequence set forth in SEQ ID NO: 76 (atgcttctcctggtgacaagccttctgctctgt-gagttaccacacccagcattcctcctgatcccagatgttgtgatgacccaaactcca ctctccctgcctgtcagtcttggagatcaagcctcaatctcttgca-gatctagtcagagccttctaaaaaatggaaacacctttttaca ttggtacctgcagaagtcaggccagtctccaaagctccttatctacaaagtttc-caaccgactttctggggtcccagacaggttcagtgg cagtggatcagggacatat-ttcacactcaagatcagcagagtggaggctgaggatctgggagtttatttctgctct-caaagtacacatat tccgtacacattcggaggggggaccaagctcgagctgaaacgaggcg-gagggggctctggcggcggaggatctgggggagggg gcagcgaggt-gaaactggtggagtctggaggaggcttggtgctgcctggggattctctga-gactctcctgtgcaacttctgagttcac cttcactgattactacatgacttgggtccgccagcctccaagaaaggcactt-gagtggttgggttttattagaaacagagctaatggttac acaacagagtacaatc-catctgtgaagggtcggttcaccatttccagagataattcccaaagcatcctc-tatcttcaaatgaacaccctg agaactgaggacagtgccacttattactgtgcaagagtctctaactgggcctttgac-tactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77 (MLLLVTSLLLCELPHPAFL-LIPDVVMTQTPLSLPVSLGDQASIS-CRSSQSLLKNNGNT FLHWYLQKSGQSPKLLIYKVSNRLSGVPDRFSGSGS GTYFTLKISRVEAEDLGVYFCS QSTHIPY-TFGGGTKLELKRGGGGSGGGGSGGGGSEVKLVES-GGGLVLPGDSLRLSCA TSEFTFTDYYMTWVRQP-PRKALEWLGFIRNRANGYTTEYNPSVKGRFTISRDNSQ-SIL YLQMNTLRTEDSATYYCARVSNWAFDYWGQGT-TLTVSS). In some alternatives, the scFv is encoded by a nucleic acid sequence comprising a nucleic acid sequence encoding the amino acid sequence of SEQ ID NO: 77. In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccc-caccccgcctttctgctgatcccccaggaacagctcgtcgaaagc ggcggca-gactggtgacacctggcggcagcctgaccct-gagctgcaaggccagcggcttcgacttcagcgcctactacatgagctg ggtccgccaggcccctggcaagggactggaatggatcgccaccatc-taccccagcagcggcaagacctactacgccacctgggtg aacggacggttcac-catctccagcgacaacgcccagaacaccgtggacctgcagat-gaacagcctgacagccgccgaccgggcc acctacttttgcgccagagacagctacgccgacgacggcgccctgttcaa-catctggggccctggcaccctggtgacaatctctagc ggcggaggcg-gatctggtggcggaggaagtggcggcggaggatct-gagctggtgctgacccagagcccctctgtgtctgctgccc tgggaagccctgccaagatcacctgtaccctgagcagcgcccacaa-gaccgacaccatcgactggtatcagcagctgcagggcga ggcccccaga-tacctgatgcaggtgcagagcgacggcagctacac-caagaggccaggcgtgcccgaccggttcagcggatctag ctctggcgccgaccgctacctgatcatccccagcgtgcaggcc-gatgacgaggccgattactactgtggcgccgactacatcggcg gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESG-GRLVTPGGSLTLSCKASGFDFSAYYMSW VRQAPGKGLEWIATIYPSSGKTYYATWVNGRFTIS-SDNAQNTVDLQMNSLTAADRA TYFCARDSYADD-GALFNIWGPGTLVTISSGGGGSGGGGSGGGG-SELVLTQSPSVSAA LGSPAKITCTLS-SAHKTDTIDWYQQLQGEAPRYLMQVQSDG-SYTKRPGVPDRFSGSS SGADRYLIIPSVQADDEAD-YYCGADYIGGYVFGGGTQLTVTG). In some alternatives, the scFv is encoded by a nucleic acid sequence comprising a nucleic acid sequence encoding the amino acid sequence of SEQ ID NO: 79. In some alternatives, the scFv comprises an amino acid sequence set forth in SEQ ID NO: 80 (CD33 (h2H12) VhVl scFv nucleotide sequence (atgcttctcctggtgacaagccttctgctctgtgagttaccacacccagcat-tcctcctgatcccacaggttcagctggtgcagtctgga gctgaggt-gaagaagcctggggcctcagtgaaggtctcctgcaaggcttctggttacacctt-taccaattatgatataaattgggtgag acaggcccctggacaagggcttgagtggattggatggatttatcctg-gagatggtagtaccaaatataatgagaaattcaaggccaag gctaccctgacagctgacacatccaccagcacagcctacatggagctgag-gagcctgagatctgatgacacagctgtgtattactgtg cttctggatatgaagatgc-tatggactactgggggcaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQS-GAEVKKPGASVKVSCKASGYTFTNYDIN WVRQAPGQGLEWIGWIYPGDGSTKYNEKFKAKATL-TADTSTSTAYMELRSLRSDDT AVYY-CASGYEDAMDYWGQGTTVTVSS). In some alternatives, the scFv is encoded by a nucleic acid sequence comprising a nucleic acid sequence encoding the amino acid sequence of SEQ ID NO: 81. In some alternatives, the scFv is encoded by a sequence set forth in SEQ ID NO: 82 (CD33 (h2H12) VlVh scFv nucleotide sequence: atgcttctcctggtgacaagccttctgctctgtgagttaccacacccagcat-tcctcctgatcccagacatccagatgacccagtctccat cctcactgtctg-catctgtaggagacagagtcaccatcaattgtaaggctagtcaggacattaatagc-tatttgagctggtttcagcaga aaccagggaaagcccctaagaccctgatctatagagcaaatagattggta-gatggggtcccatcaaggttctctggcagtggatctgg gcaagattatactctcac-catcagcagcctgcagcctgaagattttgcaacttattactgcttgcagtatgat-gagtttcctctcacatttgg aggagggaccaaggtggagatcaaa). In some alternatives, the scFv comprises an amino acid sequence set forth in SEQ ID NO: 83 (CD33 (h2H12) VlVh scFv amino acid sequence: MLLLVTSLLLCELPHPAFL-LIPDIQMTQSPSSLSASVGDRVTINCKASQDIN-SYLSWFQ QKPGKAPKTLIYRANRLVDGVPSRFSGSGSGQDYTL TISSLQPEDFATYYCLQYDEFP LTFGGGTKVEIK). In some alternatives, the scFv is encoded by a nucleic acid sequence comprising a nucleic acid sequence encoding the amino acid sequence of SEQ ID NO: 83. In some alternatives, the scFv is encoded by a nucleic acid sequence set forth in SEQ ID NO: 84. In some alternatives, the scFv is encoded by a nucleic acid sequence set forth in SEQ ID NO: 86. In some alternatives, the scFv comprises an amino acid sequence set forth in SEQ ID NO: 87. In some alternatives, the spacer is encoded by the nucleic acid sequence set forth in SEQ ID NO: 102 (IgG4 hinge nucleotide sequence: gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, HEA3 comprises two amino acid mutations, wherein the sequence is encoded by a sequence set forth in SEQ ID NO: 122 (atggtgtccaagctgtcccagctgcagacagaactgctggcagcactgctggaaagcggcctgagcaaagaggccctgattcagg cactcggcgaacctggacctatctgctcgctggcgaaggccctctggataagggcgagagctgtggcggagga agaggagagct ggccgagctgcctaacggcctgggcgagacaagaggcagcgaggacgagacagacgacgacggcgaggacttcacccccccc atcctgaaagagctggaaaacctgagccccgaggaagccgcccaccagaaagccgtggtggagacactgctgcaggaagatccc tggcgggtcgccaagatggtcaagagctacctgcagcagcacaacatcccccagcgggaggtggtggacaccaccggcctgaac cagagccacctgagccagcacctgaacaagggcacccccatgaaaacccagaagagagccgccctgtacacttggtacgtgcgg aagcagagagaggtggcccagcagtttacacacgccggccagggcggcctgatcgaggaacctaccggcgacgagctgcccac caagaagggcagacggaaccggtttaagtggggccctgcatctcagcagatcctgttccaggcctacgagcggcagaagaacccc agcaaagaggaacgggagacactggtggaagagtgcaaccgggccgagtgcatccagagaggcgtgagccctctcaggctcag ggcctcggcagcaatctggtcaccgaagtgcgggtgtacaattggttcgccaaccggcggaaagaggaagccttccggcacaagct gtctgctggcgatatgagagccgccaacctgtggcccagcccccctgatgatcaagcggagcaagaagaacagcctggccctgagc ctgaccgccgatcagatggtgtccgctctgctggacgccgagccccctatcctgtacagcgagtacgaccccaccagacccttcagc gaggccagcatgatgggcctgctgaccaacctggccgaccgggagctggtgcacatgatcaactgggccaagcgggtgcccggc ttcgtggacctgaccctgcacgaccaggtccacctgctggaatgtgcctggctggaaatcctgatgatcggcctcgtgtggagaagc atgaacaccccggcaagctgctgttcgcccccaacctgctcctggaccggaaccagggaaagtgcgtggagggcatggtggaga tcttcgacatgctgctggccacctccagccggttccggatgatgaacctgcagggcgaggaattcgtgtgcctgaagtccatcatcct gctgaacagcggcgtgtacaccttcctgtcatccaccctgaagtccctggaagagaaggaccacatccaccgggtgctggacaaga tcaccgacaccctgatccacctgatggccaaggctggcctgacactccagcagcagcaccagagactggcccagctgctgctgatc ctgagccacatccggcacatgagcaacaagcggatggaacacctgtacagcatgaagtgcaagaacgtggtgcccctgtacgacct gctgctcgagatgctggatgcccacagactgcacgcccctacaagcagaggcggagccagcgtggaggaaaccgaccagtctca cctggccaccgccggcagcacaagcagccacagcctgcagaagtactacatcaccggcgaggccgagggattccctgccaccgt ggagttccagtacctgcccgacaccgacgaccggcaccggatcgaggaaaagcggaagcggacctacgagacattccagagcat catgaagaagtccccettcagcggccccaccgatcccagacccccccctagaagaatcgccgtgcccagcagatctagcgccagc gtgcccaagcctgcccccagccctaccctttcaccagcagcctgagcaccatcaactacgacgagttccctaccatggtgttcccca gcggccagatctctcaggcctctgctctggcacctgctccacctcaggtgctgcctcaggcccctgctccagccccagcccctgccat ggtgtctgcactggcccaggctccagctcctgtgcctgtgctggcccctggacctc ctcaggctgtggcccctcctgcccctaaacct acccaggccggggagggaacactgtctgaggccctgctgcagctccagttcgacgacgaggatctgggagcactgctgggcaata gcaccgaccccgccgtgtttaccgacctggcctccgtggacaacagcgagttccagcagctcctcaaccaggg catccctgtcgcc ccacacaccaccgagcccatgctgatggaataccccgaggccatcaccagactggtcacaggcgcccagaggcctccagatccag caccagctccactgggagcccctggcctgcctaatgggctgctgtctggcgacgag gacttcgagagcattgccgacatggacttca gcgccctgctgtcccagatcagcagc). In some alternatives, the HEA3 comprises an amino acid sequence set forth in SEQ ID NO: 121 (MVSKLSQLQTELLAALLESGLSKEALIQALGEPGPYLLAGEGPLDKGESCGGGRGEL AELPNGLGETRGSEDETDDDGEDFTPPILKELENLSPEEAAHQKAVVETLLQEDPWR VAKMVKSYLQQHNIPQREVVDTTGLNQSHLSQHLNKGTPMKTQKRAALYTWYVR KQREVAQQFTHAGQGGLIEEPTGDELPTKKGRRNRFKWGPASQQILFQAYERQKNP SKEERETLVEECNRAECIQRGVSPSQAQGLGSNLVTEVRVYNWFANRRKEEAFRHK LSAGDMRAANLWPSPLMIKRSKKNSLALSLTADQMVSALLDAEPPILYSEYDPTRPF SEASMMGLLTNLADRELVHMINWAKRVPGFVDLTLHDQVHLLECAWLEILMIGLV WRSMEHPGKLLFAPNLLLDRNQGKCVEGMVEIFDMLLATSSRFRMMNLQGEEFVC LKSIILLNSGVYTFLSSTLKSLEEKDHIHRVLDKITDTLIHLMAKAGLTLQQQHQRLA QLLLILSHIRHMSNKRMEHLYSMKCKNVVPLYDLLLEMLDAHRLHAPTSRGGASVE ETDQSHLATAGSTSSHSLQKYYITGEAEGFPATVEFQYLPDTDDRHRIEEKRKRTYET FQSSIMKKSPFSGPTDPRPPPRRIAVPSRSSASVPKPAPQPYPFTSSLSTINYDEFPTMVFP SGQISQASALAPAPPQVLPQAPAPAPAPAMVSALAQAPAPVPVLAPGPPQAVAPPAP KPTQAGEGTLSEALLQLQFDDEDLGALLGNSTDPAVFTDLASVDNSEFQQLLNQGIP VAPHTTEPMLMEYPEAITRLVTGAQRPPDPAPAPLGAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3; S536E corresponds to position 846 in HEA3. In some alternatives, a system for inducible expression of a chimeric antigen receptor in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgccccctgcctggcagccctttctcaaggaccaccgcatctctacattcaagaactggcccttcttggag ggctgcgcctgcaccccggagcggatggccgaggctggcttcatccactgccccactgagaacgagccagacttggcccagtgttt cttctgcttcaaggagctggaaggctgggagccagatgacgaccccatagaggaacataaaaagcattcgtccggttgcgctttccttt ctgtcaagaagcagtttgaagaattaaccettggtgaatttttgaaactggacagagaaagagccaagaacaaaattgcaaaggaaac caacaataagaagaaagaatttgaggaaactgtgaagaaagtgcgccgtgccatcgagcagctggctgcaatggat). In some alternatives, Survivin comprises the amino acid sequence set forth in SEQ ID NO: 123 (MGAPTLPPAWQPFLKDHRISTFKNWPFLEGCACTPERMAEAGFIHCPTENEPDLAQC FFCFKELEGWEPDDDPIEEHKKHSSGCAFLSVKKQFEELTLGEFLKLDRERAKNKIAK ETNNKKKEFEETVKKVRRAIEQLAAMD).

In some alternatives, a use of the host cell, such as a mammalian cell, of any one of or more of the alternatives herein or at least one composition or product combination of any one or more of alternatives herein as a medicament, is provided. In some alternatives, the host cell, such as a mammalian cell, comprises a system of any one of the alternatives herein. In some alternatives, the system is for inducible expression of a chimeric antigen receptor in cells, such as mammalian cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and any other selected molecule expressed on a target cell population, wherein the ligand elicits recognition, modulation, inhibition, and/or elimination by a lymphocyte, a second polynucleotide, which encodes a spacer, preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the host cell is a precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell of any one or more of the alternatives herein is provided, in a pharmaceutically acceptable excipient. In some alternatives, the host cell comprises a system of any one of the alternatives herein. In some alternatives, the system is for inducible expression of a chimeric antigen receptor in cells. The system comprises a) a first nucleic acid comprising a first promoter inducible by a drug, wherein the first nucleic acid is operably linked to a first polynucleotide that encodes a chimeric antigen receptor, which comprises a ligand binding domain that is specific for a ligand selected from the group consisting of a tumor specific molecule, a viral specific molecule, and other molecule expressed on a target cell population, wherein the ligand elicits recognition, modulation, inhibition, and/or elimination by a lymphocyte, a second polynucleotide, which encodes a spacer preferably an optimized polypeptide spacer, a third polynucleotide, which encodes a transmembrane domain and a fourth polynucleotide, which encodes an intracellular signaling domain and b) a second nucleic acid comprising a second promoter that is operably linked to a nucleic acid encoding a transcriptional activator for the first promoter inducible by a drug, wherein the system is inducible by an amount of the drug that is less than a comparable system utilizing a wild type HEA3 chimeric transcription factor, or the system has an enhanced transcriptional expression at a given concentration of the drug compared to a system utilizing a wild type HEA3, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of the wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the drug is tamoxifen and/or its metabolites, 4-hydroxytamoxifen, fulvestrant or other estrogen analogs, or CMP8. In some alternatives of the system, the first promoter comprises a nucleic acid sequence set forth in SEQ ID NO: 23. In some alternatives of the system, the drug induces a high expression of the chimeric antigen receptor, such as at a concentration of at least 4, 6, 8, 10, 20, 30, 40, 50, 60, 70, 80, 90, 100, 200, 300, 400 or 500 nM of drug or a concentration that is within a range defined by any two of the aforementioned values, as compared to a wild type HEA3 or a wild type HEA4 chimeric transcription factor. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage amount for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the signaling domain comprises a CD28, 4-1BB and/or CD3ζ domain. In some alternatives of the system, the second promoter is an inducible promoter. In some alternatives of the system, the second promoter is a constitutive promoter. In some alternatives of the system, the second promoter is the EF1αp. In some alternatives of the system, the transcriptional activator comprises at least one amino acid sequence set forth in SEQ ID NO: 1-11 or 121. In some alternatives of the system, the transcriptional activator is encoded by at least one nucleic acid sequence set forth in SEQ ID NO: 12-22 or 122. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives of the system, the first nucleic acid further comprises a fifth polynucleotide that encodes a selectable marker. In some alternatives of the system, the second nucleic acid further comprises a sixth polynucleotide that encodes a selectable marker. In some alternatives of the system, selectable marker is EGFRt and/or HER2t. In some alternatives of the system, the selectable marker confers drug resistance. In some alternatives of the system, the first nucleic acid further comprises a seventh polynucleotide that encodes a self-cleaving peptide. In some alternatives of the system, the self-cleaving peptide comprises a P2A, T2A, E2A or F2A peptide. In some alternatives of the system, the spacer is optimized for increased T cell proliferation and/or cytokine production in response to the ligand as compared to a reference chimeric receptor. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence of 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some that has alternatives, the system is for inducible expression of a gene that regulates a T cell function. The system comprises a) a first nucleic acid comprising a first promoter inducible by a drug, wherein the first nucleic acid is operably linked to a first polynucleotide, which encodes a cytokine, a chemokine receptor, a chimeric cytokine receptor, a polypeptide that regulates apoptosis, a polypeptide that modulates the extracellular environment, a polypeptide that modulates checkpoint signaling, a microRNA product that regulates growth, a microRNA product that regulates survival, or a microRNA product that regulates cytolytic capacity; and b) a second nucleic acid comprising a second promoter, wherein the second nucleic acid is operably linked to a third nucleic acid that encodes a transcriptional activator for the first promoter inducible by drug; and wherein the system is configured to respond to an amount of the drug that is less than a comparable system utilizing a wild type HEA3 chimeric transcription factor or a wild type HEA4 chimeric transcription factor, or the system has an enhanced transcriptional expression at a given concentration of the drug compared to a system utilizing a wild type HEA3. In some alternatives of the system, the transcriptional activator is HEA3 or HEA4. In some alternatives of the system, HEA3 is a variant of a wild type HEA3 transcription factor. In some alternatives of the system, HEA4 is a variant of a wild type HEA4 transcription factor. In some alternatives of the system, HEA3 comprises an estrogen receptor ligand binding domain (ER-LBD) and a RelA (p65) transactivation domain, and wherein the estrogen receptor ligand binding domain comprises at least one mutation that allows selective binding to the drug ligand. In some alternatives of the system, HEA3 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, HEA4 comprises an estrogen receptor ligand binding domain (ER-LBD) and a RelA (p65) transactivation domain, wherein the estrogen receptor ligand binding domain comprises at least one mutation that allows selective binding to the drug ligand. In some alternatives of the system, HEA4 comprises an estrogen receptor ligand binding domain (ER-LBD) and a RelA (p65) transactivation domain, wherein the RelA (p65) transactivation domain comprises at least one mutation that enhances transcriptional activity in response to a drug. In some alternatives of the system, the variant of the HEA3 or HEA4 chimeric transcription factor comprises p65 phosphomimetic and/or acetylmimetic amino acid substitutions that enhance transcriptional activity in response to the drug ligand. In some alternatives of the system, the variant of a wild type HEA3 transcription factor comprises an amino acid sequence set forth in SEQ ID Nos: 1-3, 8-11 and/or 121. In some alternatives of the system, the variant of the wild type HEA3 transcription factor is encoded by a nucleic acid sequence set forth in SEQ ID NO: 12, 13, 14, 19, 20, 21, 22 or 122. In some alternatives of the system, the variant of a wild type HEA4 transcription factor comprises an amino acid sequence set forth in SEQ ID Nos: 4-7. In some alternatives of the system, the variant of the wild type HEA4 transcription factor is encoded by a nucleic acid sequence set forth in SEQ ID NO: 15, 16, 17 or 18. In some alternatives of the system, the transcriptional regulator is a variant of a HEA3 chimeric transcription factor, and wherein the variant comprises amino acid substitutions that allow selective binding to the drug. In some alternatives of the system, the drug is tamoxifen and/or its metabolites, 4-hydroxytamoxifen, fulvestrant or other estrogen analogs, or CMP8. In some alternatives of the system, the drug induces a level of expression of the chimeric antigen receptor that is greater than a wild type HEA3 or wild type HEA4 chimeric transcription factor at a concentration of the drug that is at least 4, 6, 8, 10, 20, 30, 40, 50, 60, 70, 80, 90, 100, 200, 300, 400 or 500 nM of the drug or at a concentration that is within a range defined by any two of the aforementioned values. In some alternatives of the system, the drug induces expression of the chimeric antigen receptor at a non-toxic dosing of drug at less than 10 nM drug but not zero. In some alternatives of the system, the non-toxic dosing of drug decreases, eliminates or prevents drug side effects in comparison to a dosage for inducing expression with a wild type HEA3 or wild type HEA4 chimeric transcription factor. In some alternatives of the system, the side effects are cataracts, constipation, diarrhea, edema, fatigue, fluid retention, flushing, headache, hot flashes, high blood pressure, muscle pain, nausea, shortness of breath, vomiting or weight loss. In some alternatives of the system, the second nucleic acid further comprises: a polynucleotide encoding a chimeric antigen receptor comprising a ligand binding domain, which is a tumor specific molecule, viral molecule, or another molecule expressed on a target cell population, wherein the ligand elicits recognition, modulation, inhibition, and/or elimination by a lymphocyte; a polynucleotide coding for a polypeptide spacer, wherein the spacer is optimized; a polynucleotide coding for a transmembrane domain; and a polynucleotide encoding an intracellular signaling domain. In some alternatives of the system, the first promoter is in opposite orientation to the second promoter. In some alternatives of the system, the ligand binding domain is an antibody fragment. In some alternatives of the system, the ligand binding domain is a single chain variable fragment. In some alternatives of the system, the tumor specific molecule is selected from the group consisting of CD19, CD20, CD22, CD23, CD123, CS-1, ROR1, CE7, EGFR, hB7H3, mesothelin, c-Met, PSMA, Her2, GD-2, and MAGE A3 TCR or any combination thereof. In some alternatives of the system, the viral specific molecule is an HIV envelope protein or HIV envelope protein complex, Hepatitis C virus NS3 protein, HbcAg protein, HIV-1 GP120 protein, or Epstein-Barr virus early antigen protein. In some alternatives of the system, the ligand binding domain specifically binds with CD19, CD20, CD22, EGFRvIII, EGFR, EphA2, IL13Ra2, L1CAM, oaGD2, Her2, B7H3, CD33, Mesothelin, ROR-1, FITC and/or VAR2CSA. In some alternatives of the system, the spacer comprises IgG4, IgG4-CH2(L235D, N297Q) or IgG4-CH3. In some alternatives of the system, the first nucleic acid further comprises a DNA spacer, wherein the spacer is operably linked to the first promoter and operably linked to the first polynucleotide that encodes the chimeric antigen receptor. In some alternatives of the system, the DNA spacer is between the first promoter and the first polynucleotide that encodes the chimeric antigen receptor. In some alternatives of the system, the DNA spacer comprises a sequence set forth in SEQ ID NO: 120. In some alternatives of the system, the DNA spacer comprises a sequence that has 95%, 90%, 85% or 80% sequence identity to SEQ ID NO: 120 or any percent sequence identity in between a range defined by any two aforementioned values. In some alternatives of the system, the DNA spacer enhances gene expression of the chimeric antigen receptor. In some alternatives of the system, the first nucleic acid further comprises a first vector and the second nucleic acid further comprises a second vector. In some alternatives of the system, both vectors are packaged in a viral vector. In some alternatives of the system, the viral vector is an adeno-associated virus or a lentivirus. In some alternatives, the host cell is a precursor T cell. In some alternatives, the precursor T cell is a hematopoietic stem cell. In some alternatives, the host cell is a CD8+T cytotoxic lymphocyte cell selected from the group consisting of naïve CD8+ T cells, central memory CD8+ T cells, effector memory CD8+ T cells and bulk CD8+ T cells. In some alternatives, the host cell is a CD4+T helper lymphocyte cell that is selected from the group consisting of naïve CD4+ T cells, central memory CD4+ T cells, effector memory CD4+ T cells, and bulk CD4+ T cells. In some alternatives, the composition comprises a host cell, wherein the host cell is a precursor T cell and a host cell wherein the host cell is a hematopoietic stem cell. In some alternatives, the composition comprises a host cell, wherein the host cell is a precursor T cell or a hematopoietic stem cell and a host cell that is a CD8+T cytotoxic lymphocyte cell selected from the group consisting of naïve CD8+ T cells, central memory CD8+ T cells, effector memory CD8+ T cells and bulk CD8+ T cells or a CD4+ T cell selected from naïve CD4+ T cells, central memory CD4+ T cells, effector memory CD4+ T cells, and bulk CD4+ T cells. In some alternatives, the chimeric antigen receptor comprises a scFv. In some alternatives, the scFv specifically binds to CD19. In some alternatives, the scFv comprises an huCD19 scFv (G01S) amino acid sequence. In some alternatives, the scFv comprises an amino acid sequence set forth in SEQ ID NO: 41 (MLLLVTSLLLCELPHPAFLLIPEVQLVESGGGLVQPGRSLRLSCAASGFTFDDYAMH WVRQAPGKGLEWVSGISWNSGRIGYADSVKGRFTISRDNAKNSLFLQMNSLRAEDT AVYYCARDQGYHYYDSAEHAFDIWGQGTVVTVSSGGGGSGGGGSGGGGSQSALTQ PRSVSGFPGQSVTISCTGTTSDDVSWYQQHPGKAPQ LMLYDVSKRPSGVPHRFSGSR SGRAASLIISGLQTEDEADYFCSSYAGRYNSVLFGGGTKLTVL). In some alternatives, the scFv is encoded by a nucleic acid sequence comprising a nucleic acid sequence encoding the amino acid sequence of SEQ ID NO: 41. In some alternatives, the scFv is encoded by the muCD19 (FMC63) scFv nucleotide sequence. In some alternatives, the scFv specifically binds to CD19. In some alternatives, the scFv is encoded by a sequence set forth in SEQ ID NO: 42 (AtgctgctgctggtgaccagcctgctgtgcgagctgcccCaccccgcctttctgctgatccccgacatccagatgacccagac cacctccagcctgagcgccagcctgggcgaccgggtgaccatcagctgccgggccagccaggacatcagcaagtacctgaactg gtatcagcagaagcccgacggcaccgtcaagctgctgatctaccacaccagccggctgcacagcggcgtgcccagccggtttagc ggcagcggctccggcaccgactacagcctgaccatctccaacctggaacaggaagatatcgccacctacttttgccagcagggcaa cacactgccctacacctttggcggcggaacaaagctggaaatcaccggcagcacctccggcagcggcaagcctggcagcggcgagggcagcaccaagggcgaggtgaagctgcaggaaagcggccctggcctggtggcccccagccagagcctgagcgtgacctgca ccgtgagcggcgtgagcctgcccgactacggcgtgagctggatccggcagcccccaggaagggcctggaatggctgggcgtgatctggggcagcgagaccacctactacaacagcgccctgaagagccggctgaccatcatcaaggacaacagcaagagccaggtgtt cctgaagatgaacagcctgcagaccgacgacaccgccatctactactgcgccaagcactactactacggcggcagctacgccatgg actactggggccagggcaccagcgtgaccgtgagcagc). In some alternatives, the scFv comprises an amino acid sequence set forth in SEQ ID NO: 43 (MLLLVTSLLLCELPHPAFLLIPDIQMTQTTSSLSASLGDRVTISCRASQDISKYLNWY QQKPDGTVKLLIYHTSRLHSGVPSRFSGSGSGTDYSLTISNLEQEDIATYFCQQGNTLP YTFGGGTKLEITGSTSGSGKPGSGEGSTKGEVKLQESGPGLVAPSQSLSVTCTVSGVS LPDYGVSWIRQPPRKGLEWLGVIWGSETTYYNSALKSRLTIIKDNSKSQVFLKMNSL QTDDTAIYYCAKHYYYGGSYAMDYWGQGTSVTVSS). In some alternatives, the scFv is encoded by a nucleic acid sequence comprising a nucleic acid sequence encoding the amino acid sequence of SEQ ID NO: 43. some alternatives, the scFv comprises a B7H3 (hBRCA84D) scFv nucleotide sequence. In some alternatives, the scFv binds specifically to the B7-H3 receptor. In some alternatives, the scFv comprises the L1CAM (CE7) scFv nucleotide sequence. In some alternatives, the scFv is specific for the epitope, CE7 epitope, of L1CAM. In some alternatives, the scFv is encoded by a sequence set forth in SEQ ID NO: 50 (atgctgctgctggtgaccagcctgctgctgtgcgagctgccccaccccgcctttctgctgatcccccaggtgcagctgcagcagcct ggcgccgagctggtgaagccaggcgccagcgtgaagctgtcctgcaaggccagcggctacaccttcaccggctactggatgcact gggtgaagcagagacccggccacggcctggaatggatcggcgagatcaaccccagcaacggccggaccaactacaacgagcgg ttcaagagcaaggccaccctgaccgtggacaagagcagcaccaccgccttcatgcagctgtccggcctgaccagcgaggacagcg ccgtgtacttctgcgccagggactactacggcaccagctacaacttcgactactggggccagggcaccacactgaccgtgagcagc ggcggaggggggctctggcggcggaggatctgggggagggggcagcgacatccagatgacccagagcagcagcagcttcagcg tgagcctgggcgaccgggtgaccatcacctgtaaggccaacgaggacatcaacaaccggctggcctggtatcagcagacccccgg caacagccccaggctgctgatcagcggcgccaccaacctggtgaccggcgtgcccagccggtttagcggcagcggctccggcaa ggactacaccctgaccatcacaagcctgcaggccgaggacttcgccacctactactgccagcagtactggtccaccccccttcaccttc ggcagcggcaccgagctggaaatcaaa). In some alternatives, the scFv comprises the L1CAM (CE7) scFv amino acid sequence. In some alternatives, the scFv comprises an amino acid sequence set forth in SEQ ID NO: 51 (MLLLVTSLLLCELPHPAFLLIPQVQLQQPGAELVKPGASVKLSCKASGYTFTGYWM HWVKQRPGHGLEWIGEINPSNGRTNYNERFKSKATLTVDKSSTTAFMQLSGLTSEDS AVYFCARDYYGTSYNFDYWGQGTTLTVSSGGGGSGGGGSGGGGSDIQMTQSSSSFS VSLGDRVTITCKANEDINNRLAWYQQTPGNSPRLLISGATNLVTGVPSRFSGSGSGK DYTLTITSLQAEDFATYYCQQYWSTPFTFGSGTELEIK). In some alternatives, the scFv is encoded by a nucleic acid sequence comprising a nucleic acid sequence encoding the amino acid sequence of SEQ ID NO: 51. In some alternatives, the scFv is encoded by the EGFR (cetuximab) scFv nucleotide sequence. In some alternatives, the scFv is specific for EGFR. In some alternatives, the scFv is encoded by a nucleic acid sequence set forth in SEQ ID NO: 52 (atgcttctcctggtgacaagccttctgctctgtgagttaccacacccagcat- tcctcctgatcccacaggtgcagctgaaacagagcg gcccgggcctggtgcagccgagccagagcctgagcattacctgcaccgt- gagcggctttagcctgaccaactatggcgtgcattgg gtgcgccagagcccgggcaaaggcctggaatggctgggcgtgatttg- gagcggcggcaacaccgattataacaccccgtttacca gccgcctgagcat- taacaaagataacagcaaaagccaggtgtttttaaaat- gaacagcctgcagagcaacgataccgcgatttattat tgcgcgcgcgcgctgacctattatgattatgaatttgcgtat- tggggccagggcaccctggtgaccgtgagcgcgggcggcggcgg cagcggcggcggcggcagcggcggcggcggcagcgatat- tctgctgacccagagcccggtgattctgagcgtgagcccgggcg aacgcgt- gagctttagctgccgcgcgagccagagcattggcaccaacattcat- tggtatcagcagcgcaccaacggcagcccgcgc ctgctgattaaatatgcgagcgaaagcattagcggcattccgagccgctt- tagcggcagcggcagcggcaccgattttaccctgagc attaacagcgtg- gaaagcgaagatattgcggattattattgccagcagaacaacaactggccgac- cacctttggcgcgggcaccaaa ctggaactgaaacgcacc). In some alternatives, the scFv comprises the EGFR scFv amino acid sequence. In some alternatives, the scFv comprises an amino acid sequence set forth in SEQ ID NO: 53 (MLLLVTSLLL- CELPHPAFLLIPQVQLKQSGPGLVQPSQSL- SITCTVSGFSLTNYGVHW VRQSPGKGLEW- LGVIWSGGNTDYNTPFTSRLSINKDNSKSQVFFKMN SLQSNDTAIY YCARALTYYDYE- FAYWGQGTLVTVSAGGGGSGGGGSGGGGS- DILLTQSPVILSVSP GERVSFSCRASQSIGT- NIHWYQQRTNGSPRLLIKYASESISGIPSRFSGSGSGT DFTLSI NSVESEDI- ADYYCQQNNNWPTTFGAGTKLELKRT). In some alternatives, the scFv is encoded by a nucleic acid sequence comprising a nucleic acid sequence encoding the amino acid sequence of SEQ ID NO: 53. In some alternatives, the scFv comprises the EGFRVIII (806) scFv nucleotide sequence. In some alternatives, the scFv is specific for EGFR. In some alternatives, the scFv is encoded by the EphA2 (2A4) scFv nucleotide sequence. In some alternatives, the scFv is encoded by the nucleic acid sequence set forth in SEQ ID NO: 56. In some alternatives, the scFv is encoded by the EpHA2 (4H5) scFv nucleotide sequence. In some alternatives, the scFv is encoded by the nucleic acid sequence set forth in SEQ ID NO: 58. In some alternatives, the scFv is encoded by a FITC (E2) scFv nucleotide sequence. In some alternatives, the scFv is encoded by a nucleic acid sequence set forth in SEQ ID NO: 60. In some alternatives, the scFv is encoded by an IL13Ra2 (hu08) VhVl scFv nucleotide sequence. In some alternatives, the scFv is encoded by a nucleic acid sequence set forth in SEQ ID NO: 68. In some alternatives, the scFv comprises an IL13Ra2 hu08 VhVl scFv amino acid sequence. In some alternatives, the scFv comprises an amino acid sequence set forth in SEQ ID NO: 69 (MLLLVTSLLLCELPHPAFLLIPEVQLVESGG- GLVQPGGSLRLSCAASGFTFSRNGMS WVRQAPGK- GLEWVATVSSGGSYIYYADSVKGRFTISRDNAKNS- LYLQMNSLRAEDT AVYYCARQGTTALA- TRFFDVWGQGTLVTVSSGGGGSGG GGSGGGGSDIQMTQSPSS LSASVGDRVTITCK- ASQDVGTA- VAWYQQKPGKAPKLLIYSASYRSTGVPSRFSGSGS GTDFTLTISSLQPEDFATYYCQHHYS- APWTFGGGTKVEIKESK). In some alternatives, the scFv is encoded by a nucleic acid sequence comprising a nucleic acid sequence encoding the amino acid sequence of SEQ ID NO: 69. In some alternatives, the scFv is encoded by an IL13Ra2 (hu07) VlVh scFv nucleotide sequence. In some alternatives, the scFv is encoded by a nucleic acid sequence set forth in SEQ ID NO: 70 (atgcttctcctggtgacaagccttctgctctgtgagttaccacacccagcat- tcctcctgatcccagatattcagatgacccagagccc gagcagcct- gagcgcgagcgtgggcgatccgcgtgagcagcacctatctgcattggt atcagcagaaaccgggcaaagcgccgaaactgctgatt- tatagcaccagcaacctggcgagcggcgtgccgagccgctttagcgg cagcggcagcggcaccgattttaccctgaccattagcagcctgcagccggaa- gattttgcgacctattattgccatcagtatcatcgca gcccgctgacctttggcggcggcaccaaagtggaaat- taaaggtggtggtggttctggcggcggcggctccggtggtggtggttctg aagtgcagctggtg- gaaagcggcggcggcctggtgcagcggcggcgggcctggtgcgcggcgagc ggctttacct ttaccaaatatggcgtgcat- tgggtgcgccaggcgccgggcaaaggcctggaatgggtggcggt- gaaatgggcgggcggcagca ccgattataacagcgcgctgatgagccgctt- taccattagccgcgataacgcgaaaaacagcctgtatctgcagatgaacagcctgc gcgcggaagataccgcggtgtattattgcgcgcgcgatcatcgcgatgcgatg- gattattggggccagggcaccctggtgaccgtg agcagcgaatctaagta). In some alternatives, the scFv comprises an IL13Ra2 (hu07) VhVl scFv amino acid sequence. In some alternatives, the scFv comprises an amino acid sequence set forth in SEQ ID NO: 71 (MLLLVTSLLLCELPHPAFLLIPDIQMTQSPSSL- SASVGDRVTITCTASLSVSSTYLHWY QQKPGKAPKLLIYSTSN- LASGVPSRFSGSGSGTDFTLTISSLQPEDFATYY- CHQYHRSP LTFGGGTKVEIKGGGGSGGGGSGGGG- SEVQLVESGGGLVQPGGSLRLSCAASGFTFT KYGVHWVRQAPGKGLEWVAVKWAGGSTDYN- SALMSRFTISRDNAKNSLYLQMNS LRAEDTAVYY- CARDHRDAMDYWGQGTLVTVSSESK). In some alternatives, the scFv is encoded by a nucleic acid sequence comprising a nucleic acid sequence encoding the amino acid sequence of SEQ ID NO: 71. In some alternatives, the scFv is encoded by the IL13Ra2 (hu07) VhVl scFv nucleotide sequence. In some alternatives, the scFv is encoded by a nucleic acid sequence set forth in SEQ ID NO: 72 (atgcttctcctggtgacaagccttctgctctgtgagttaccacacccagcat- tcctcctgatcccagaagtgcagctggtggaaagcg gcggcggcctggtgcagccgggcggcagcctgcgcct- gagctgcgcggcgagcggctttacctttaccaaatatggcgtgcattgg gtgcgccaggcgccgggcaaaggcctggaatgggtggcggt- gaaatgggcgggcggcagcaccgattataacagcgcgctgat gagccgctt- taccattagccgcgataacgcgaaaaacagcctgtatctgcagat- gaacagcctgcgcgcggaagataccgcggtgt attattgcgcgcgcgatcatcgcgatgcgatggattat- tggggccagggcaccctggtgaccgtgagcagcggtggtggtggttctg gcggcggcggctccggtggtggtggttctgatattca- gatgacccagagcccgagcagcctgagcgcgagcgtgggcgatcgcgt gac- cattacctgcaccgcgagcctgagcgtgagcagcacctatctgcat- tggtatcagcagaaaccgggcaaagcgccgaaactgc tgatttatagcaccagcaacctggcgagcggcgtgccgagccgctt- tagcggcagcggcagcggcaccgattttaccctgaccatta gcagcctgcagccggaagattttgcgacctattattgccatcagtat- catcgcagcccgctgacctttggcggcggcaccaaagtgga aat- taaagaatctaagta). In some alternatives, the scFv comprises an IL13Ra2 (hu07) VhVl scFv amino acid sequence. In some alternatives, the scFv comprises an amino acid sequence set forth in SEQ ID NO: 73 (MLLLVTSLLLCELPHPAFL- LIPEVQLVESGGGLVQPGGSLRLSCAASGFTFT- KYGVH WVRQAPGKGLEWVAVKWAGGSTDYN- SALMSRFTISRDNAKNSLYLQMNSLRAED TAVYYCARDHRDAMDYWGQGTLVTVSSGGGG
SGGGGSGGGGSDIQMTQSPSSLSA SVGDRVTITC-
TASLSVSSTYLHWYQQKPGKAPKLLIYSTSN-
LASGVPSRFSGSGSGTD FTLTISSLQPEDFATYY-
CHQYHRSPLTFGGGTKVEIKESK). In some alternatives, the scFv is encoded by a nucleic acid sequence comprising a nucleic acid sequence encoding the amino acid sequence of SEQ ID NO: 73. In some alternatives, the antibody or portion thereof or scFv is encoded by the Anti-IL13Ra2 (IL13 zetakine) nucleotide sequence. In some alternatives, the antibody or portion thereof or scFv is encoded by a sequence set forth in SEQ ID NO: 74
(atgcttctcctggtgacaagccttctgctctgtgagttaccacacccagcat-
tcctcctgatcccaggccctgtgcctccctctacagcc ctcaggtacctcattgag-
gagctggtcaacatcacccagaaccagaaggctccgctctgcaatggcag-
catggtatggagcatcaac
ctgacagctggcatgtactgtgcagccctggaatccctgat-
caacgtgtcaggctgcagtgccatcgagaagacccagaggatgctg agcggat-
tctgcccgcacaaggtctcagctgggcagttttccagcttgcatgtccgagacac-
caaaatcgaggtggcccagtttgtaa
aggacctgctcttacatttaaagaaactttttcgcgagggacggttcaa). In some alternatives, the antibody or portion thereof or scFv comprises an Anti-IL13Ra2 (IL13 zetakine) amino acid sequence. In some alternatives, the antibody or portion thereof or scFv comprises an amino acid sequence set forth in SEQ ID NO: 75 (MLLLVTSLLLCELPHPAFL-
LIPGPVPPSTALRYLIEELVNITQNQKAPLCNG-
SMVWSI NLTAGMYCAALESLINVSGC-
SAIEKTQRMLSGFCPHKVSAGQFSSLHVRDTKIEVAQ
FVKDLLLHLKKLFREGRF). In some alternatives, the scFv is encoded by a nucleic acid sequence comprising a nucleic acid sequence encoding the amino acid sequence of SEQ ID NO: 75. In some alternatives, the scFv is encoded by an oaGD2 (8B6) VlVh scFv nucleotide sequence. In some alternatives, the scFv is encoded by a sequence set forth in SEQ ID NO: 76 (atgcttctcctggtgacaagccttctgctctgt-
gagttaccacacccagcattcctcctgatcccagatgttgtgatgacccaaactcca
ctctccctgcctgtcagtcttggagatcaagcctcaatctcttgca-
gatctagtcagagccttctaaaaaatggaaacacctttttaca
ttggtacctgcagaagtcaggccagtctccaaagctccttatctacaaagtttc-
caaccgactttctggggtcccagacaggttcagtgg cagtggatcagggacatat-
ttcacactcaagatcagcagagtggaggctgaggatctgggagtttatttctgctct-
caaagtacacatat
tccgtacacattcggagggggggaccaagctcgagctgaaacgaggcg-
gagggggctctggcggcggaggatctgggggagggg gcagcgaggt-
gaaactggtggagtctggaggaggcttggtgctgcctggggattctctga-
gactctcctgtgcaacttctgagttcac
cttcactgattactacatgacttgggtccgccagcctccaagaaaggcactt-
gagtggttgggttttattagaaacagagctaatggttac acaacagagtacaatc-
catctgtgaagggtcggttcaccatttccagagataattcccaaagcatcctc-
tatcttcaaatgaacaccctg
agaactgaggacagtgccacttattactgtgcaagagtctctaactgggcctttgac-
tactggggccaaggcaccactctcacagtctc ctca). In some alternatives, the scFv comprises the oaGD2 (8B6) VlVh scFv amino acid sequence. In some alternatives, the scFv comprises an amino acid sequence set forth in SEQ ID NO: 77
(MLLLVTSLLLCELPHPAFL-
LIPDVVMTQTPLSLPVSLGDQASIS-
CRSSQSLLKNNGNT
FLHWYLQKSGQSPKLLIYKVSNRLSGVPDRFSGSGS-
GTYFTLKISRVEAEDLGVYFCS QSTHIPY-
TFGGGTKLELKRGGGGSGGGGSGGGGSEVKLVES-
GGGLVLPGDSLRLSCA TSEFTFTDYYMTWVRQP-
PRKALEWLGFIRNRANGYTTEYNPSVKGRFTISRDN-
SQSIL YLQMNTLRTEDSATYYCARVSN-
WAFDYWGQGTTLTVSS). In some alternatives, the scFv is encoded by a nucleic acid sequence comprising a nucleic acid sequence encoding the amino acid sequence of SEQ ID NO: 77. In some alternatives, the scFv is encoded by an ROR1 (R12) scFv nucleotide sequence. In some alternatives, the scFv is encoded by a sequence set forth in SEQ ID NO: 78 (atgctgctgctggtgacaagcctgctgctgtgcgagctgccc-
caccccgcctttctgctgatcccccaggaacagctcgtcgaaagc ggcggca-
gactggtgacacctggcggcagcctgaccct-
gagctgcaaggccagcggcttcgacttcagcgcctactacatgagctg
ggtccgccaggcccctggcaagggactggaatggatcgccaccatc-
taccccagcagcggcaagacctactacgccacctgggtg aacggacggttcac-
catctccagcgacaacgcccagaacaccgtggacctgcagat-
gaacagcctgacagccgccgaccgggcc
acctacttttgcgccagagacagctacgccgacgacggcgccctgttcaa-
catctggggccctggcaccctggtgacaatctctagc ggcggaggcg-
gatctggtggcggaggaagtggcggcggaggatct-
gagctggtgctgacccagagcccctctgtgtctgctgccc
tgggaagccctgccaagatcacctgtaccctgagcagcgcccacaa-
gaccgacaccatcgactggtatcagcagctgcagggcga ggcccccaga-
tacctgatgcaggtgcagagcgacggcagctacac-
caagaggccaggcgtgcccgaccggttcagcggatctag
ctctggcgccgaccgctacctgatcatccccagcgtgcaggcc-
gatgacgaggccgattactactgtggcgccgactacatcggcg
gctacgtgttcggcggaggcacccagctgaccgtgaccggc). In some alternatives, the scFv comprises an amino acid sequence set forth in SEQ ID NO: 79 (ROR1 (R12) scFv amino acid sequence; MLLLVTSLLLCELPHPAFLLIPQEQLVESG-
GRLVTPGGSLTLSCKASGFDFSAYYMSW
VRQAPGKGLEWIATIYPSSGKTYYATWVNGRFTIS-
SDNAQNTVDLQMNSLTAADRA TYFCARDSYADD-
GALFNIWGPGTLVTISSGGGGSGGGGSGGGG-
SELVLTQSPSVSAA
LGSPAKITCTLS-
SAHKTDTIDWYQQLQGEAPRYLMQVQSDG-
SYTKRPGVPDRFSGSS SGADRYLIIPSVQADDEAD-
YYCGADYIGGYVFGGGTQLTVTG). In some alternatives, the scFv is encoded by a nucleic acid sequence comprising a nucleic acid sequence encoding the amino acid sequence of SEQ ID NO: 79. In some alternatives, the scFv comprises an amino acid sequence set forth in SEQ ID NO: 80 (CD33 (h2H12) VhVl scFv nucleotide sequence
(atgcttctcctggtgacaagccttctgctctgtgagttaccacacccagcat-
tcctcctgatcccacaggttcagctggtgcagtctgga gctgaggt-
gaagaagcctggggcctcagtgaaggtctcctgcaaggcttctggttacacctt-
taccaattatgatataaattgggtgag
acaggcccctggacaagggcttgagtggattggatggatttatcctg-
gagatggtagtaccaaatataatgagaaattcaaggccaag
gctaccctgacagctgacacatccaccagcacagcctacatggagctgag-
gagcctgagatctgatgacacagctgtgtattactgtg cttctggatatgaagatgc-
tatggactactgggggcaagggaccacagtcacagtctcctca). In some alternatives, the scFv is specific for CD33. In some alternatives, the scFv comprises an amino acid sequence set forth in SEQ ID NO: 81 (CD33 (h2H12) VhVl scFv amino acid sequence; MLLLVTSLLLCELPHPAFLLIPQVQLVQS-
GAEVKKPGASVKVSCKASGYTFTNYDIN
WVRQAPGQGLEWIGWIYPGDGSTKYNEKFKAKATL-
TADTSTSTAYMELRSLRSDDT AVYY-
CASGYEDAMDYWGQGTTVTVSS). In some alternatives, the scFv is encoded by a nucleic acid sequence comprising a nucleic acid sequence encoding the amino acid sequence of SEQ ID NO: 81. In some alternatives, the scFv is encoded by a sequence set forth in SEQ ID NO: 82 (CD33 (h2H12) VlVh scFv nucleotide sequence:
atgcttctcctggtgacaagccttctgctctgtgagttaccacacccagcat-
tcctcctgatcccagacatccagatgacccagtctccat cctcactgtctg-
catctgtaggagacagagtcaccatcaattgtaaggctagtcaggacattaatagc-
tatttgagctggtttcagcaga
aaccagggaaagcccctaagaccctgatctatagagcaaatagattggtagatggggtcccatcaaggttctctggcagtggatctgg gcaagattatactctcaccatcagcagcctgcagcctgaagattttgcaacttattactgcttgcagtatgatgagtttcctctcacatttgg aggagggaccaaggtggagatcaaa). In some alternatives, the scFv comprises an amino acid sequence set forth in SEQ ID NO: 83 (CD33 (h2H12) VlVh scFv amino acid sequence: MLLLVTSLLLCELPHPAFLLIPDIQMTQSPSSLSASVGDRVTINCKASQDINSYLSWFQ QKPGKAPKTLIYRANRLVDGVPSRFSGSGSGQDYTLTISSLQPEDFATYYCLQYDEFP LTFGGGTKVEIK). In some alternatives, the scFv is encoded by a nucleic acid sequence comprising a nucleic acid sequence encoding the amino acid sequence of SEQ ID NO: 83. In some alternatives, the scFv is encoded by a nucleic acid sequence set forth in SEQ ID NO: 84. In some alternatives, the scFv is encoded by a nucleic acid sequence set forth in SEQ ID NO: 86. In some alternatives, the scFv comprises an amino acid sequence set forth in SEQ ID NO: 87. In some alternatives, the spacer is encoded by the nucleic acid sequence set forth in SEQ ID NO: 102 (IgG4 hinge nucleotide sequence: gagagcaagtacggaccgccctgccccccttgccct). In some alternatives, the spacer comprises an amino acid sequence set forth in SEQ ID NO: 103 (IgG4 hinge amino acid sequence: ESKYGPPCPPCP). In some alternatives, the spacer is encoded by a nucleic acid sequence comprising a nucleic acid sequence encoding the amino acid sequence of SEQ ID NO: 103. In some alternatives, the spacer is encoded by a nucleic acid sequence set forth in SEQ ID NO: 104. In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, HEA3 comprises two amino acid mutations, wherein the sequence is encoded by a sequence set forth in SEQ ID NO: 122 (atggtgtccaagctgtcccagctgcagacagaactgctggcagcactgctggaaagcggcctgagcaaagaggccctgattcagg cactcggcgaacctggacctatctgctcgctggcgaaggccctctggataagggcgagagctgtggcggaggaagaggagagct ggccgagctgcctaacggcctgggcgagacaagaggcagcgaggacgagacagacgacgacggcgaggacttcacccccccc atcctgaaagagctggaaaacctgagccccgaggaagccgcccaccagaaagccgtggtggagacactgctgcaggaagatccc tggcgggtcgccaagatggtcaagagctacctgcagcagcacaacatcccccagcgggaggtggtggacaccaccggcctgaac cagagccacctgagccagcacctgaacaagggcacccccatgaaaacccagaagagagccgccctgtacacttggtacgtgcgg aagcagagagaggtggcccagcagtttacacacgccggccagggcggcctgatcgaggaacctaccggcgacgagctgcccac caagaagggcagacggaaccggtttaagtggggccctgcatctcagcagatcctgttccaggcctacgagcggcagaagaacccc agcaaagaggaacgggagacactggtggaagagtgcaaccgggccgagtgcatccagagaggcgtgagcccttctcaggctcag ggcctcggcagcaatctggtcaccgaagtgcgggtgtacaattggttcgccaaccggcggaaagaggaagccttccggcacaagct gtctgctggcgatatgagagccgccaacctgtggcccagccccctgatgatcaagcggagcaagaagaacagcctggccctgagc ctgaccgccgatcagatggtgtccgctctgctggacgccgagccccctatcctgtacagcgagtacgaccccaccagacccttcagc gaggccagcatgatgggcctgctgaccaacctggccgaccgggagctggtgcacatgatcaactgggccaagcgggtgcccggc ttcgtggacctgaccctgcacgaccaggtccacctgctggaatgtgcctggctggaaatcctgatgatcggcctcgtgtggagaagc atggaacaccccggcaagctgctgttcgcccccaacctgctcctggaccggaaccagggaaaagtgcgtggagggcatggtggaga tcttcgacatgctgctggccacctccagccggttccggatgatgaacctgcagggcgaggaattcgtgtgcctgaagtccatcatcct gctgaacagcggcgtgtacaccttcctgtcatccaccctgaagtccctggaagagaaggaccacatccaccgggtgctggacaaga tcaccgacaccctgatccacctgatggccaaggctggcctgacactccagcagcagcaccagagactggcccagctgctgctgatc ctgagccacatccggcacatgagcaacaagcggatggaacacctgtacagcatgaagtgcaagaacgtggtgcccctgtacgacct gctgctcgagatgctggatgcccacagactgcacgcccctacaagcagaggcggagccagcgtggaggaaaccgaccagtctca cctggccaccgccggcagcacaagcagccacagcctgcagaagtactacatcaccggcgaggccgagggattccctgccaccgt ggagttccagtacctgcccgacaccgacgaccggcaccggatcgaggaaaagcggaagcggacctacgagacattccagagcat catgaagaagtccccttcagcggccccaccgatcccagacccccccctagaagaatcgccgtgcccagcagatctagcgccagc gtgcccaagcctgccccccagccctaccctttcaccagcagcctgagcaccatcaactacgacgagttccctaccatggtgttcccca gcggccagatctctcaggcctctgctctggcacctgctccacctcaggtgctgcctcaggcccctgctccagccccagcccctgccat ggtgtctgcactggcccaggctccagctcctgtgcctgtgctggcccctggacctc ctcaggctgtggcccctcctgcccctaaacct acccaggccggggagggaacactgtctgaggccctgctgcagctccagttcgacgacgaggatctgggagcactgctgggcaata gcaccgaccccgccgtgtttaccgacctggcctccgtggacaacagcgagttccagcagctcctcaaccagggc atccctgtcgcc ccacacaccaccgagcccatgctgatggaatacccccgaggccatcaccagactggtcacaggcgcccagaggcctccagatccag caccagctccactgggagcccctggcctgcctaatgggctgctgtctggcgac gaggacttcgagagcattgccgacatggacttca gcgccctgctgtcccagatcagcagc). In some alternatives, the HEA3 comprises an amino acid sequence set forth in SEQ ID NO: 121 (MVSKLSQLQTELLAALLESGLSKEALIQALGEPGPYLLAGEGPLDKGESCGGGRGEL AELPNGLGETRGSEDETDDDGEDFTPPILKELENLSPEEAAHQKAVVETLLQEDPWR VAKMVKSYLQQHNIPQREVVDTTGLNQSHLSQHLNKGTPMKTQKRAALYTWYVR KQREVAQQFTHAGQGGLIEEPTGDELPTKKGRRNRFKWGPASQQILFQAYERQKNP SKEERETLVEECNRAECIQRGVSPSQAQGLGSNLVTEVRVYNWFANRRKEEAFRHK LSAGDMRAANLWPSPLMIKRSKKNSLALSLTADQMVSALLDAEPPILYSEYDPTRPF SEASMMGLLTNLADRELVHMINWAKRVPGFVDLTLHDQVHLLECAWLEILMIGLV WRSMEHPGKLLFAPNLLLDRNQGKCVEGMVEIFDMLLATSSRFRMMNLQGEEFVC LKSIILLNSGVYTFLSSTLKSLEEKDHIHRVLDKITDTLIHLMAKAGLTLQQQHQRLA QLLLILSHIRHMSNKRMEHLYSMKCKNVVPLYDLLLEMLDAHRLHAPTSRGGASVE ETDQSHLATAGSTSSHSLQKYYITGEAEGFPATVEFQYLPDTDDRHRIEEKRKRTYET FQSSIMKKSPFSGPTDPRPPRRIAVPSRSSASVPKPAPQPYPFTSSLSTINYDEFPTMVFP SGQISQASALAPAPPQVLPQAPAPAPAPAMVSALAQAPAPVPVLAPGPPQAVAPPAP KPTQAGEGTLSEALLQLQFDDEDLGALLGNSTDPAVFTDLASVDNSEFQQLLNQGIP VAPHTTEPMLMEYPEAITRLVTGAQRPPDPAPAPLGAPGLPNGLLSGDEDFESIADM DFSALLSQISS). This sequence comprises the sequence of HEA3 containing two point mutations (K310Q and S536E, positions in the RelA protein) in the p65 domain that enhance transcriptional activity. This is referred to as HEA3(p65/S536E/K310Q). K310Q in RelA corresponds to position 621 in HEA3;

S536E corresponds to position 846 in HEA3. In some alternatives, a system for inducible expression of a chimeric antigen receptor in cells is provided. In some alternatives, the transgene encodes a polypeptide that regulates apoptosis. In some alternatives, genes that inhibit apoptosis include, for example, Bcl2, and/or CA-Akt. In some alternatives, the polypeptide is Bcl2 or CA-Akt. In some alternatives, genes that inhibit apoptosis include, for example, Survivin, Bcl2, CA-Akt, and/or dnCaspase3. In some alternatives, the polypeptide is Survivin, Bcl2, or CA-Akt and/or dnCaspase 3. In some alternatives, Survivin is encoded by a sequence set forth in SEQ ID NO: 124 (Atgggtgccccgacgttgcccccctgcctggcagccctttctcaaggaccaccg-catctctacattcaagaactggccctcttggag ggctgcgcctgcaccccg-gagcggatggccgaggctggcttcatccactgccccactgagaacgagcca-gacttggcccagtgttt cttctgcttcaaggagctggaaggctgggagccagatgacgaccccatagag-gaacataaaaagcattcgtccggttgcgctttcctttt ctgtcaagaagcagttt-gaagaattaacccttggtgaatttttgaaactggacagagaaagagc-caagaacaaaattgcaaaggaaac caacaataagaagaaagaatttgaggaaactgtgaagaaagtgcgccgtgc-catcgagcagctggctgcaatggat). In some alternatives, Survivin comprises the amino acid sequence set forth in SEQ ID NO: 123 (MGAPTLPPAWQPFLKDHRISTFKNWP-FLEGCACTPERMAEAGFIHCPTENEPDLAQC FFCFKELEGWEPDDDPIEEHKKHSSGCAFLSVKKQ-FEELTLGEFLKLDRERAKNKIAK ETNNKKKE-FEETVKKVRRAIEQLAAMD).

Vector Construction and Preparation of Dual Packaged Lentivirus.

An inducible lentiviral vector encoding constitutively expressed drug-inducible transcription factors was constructed. The constructs encoded HEA3 single RelA variants, HEA4 single RelA variants, HEA4 double RelA variants (SEQ ID NO: 12-21) wild type HEA3, or wild type HEA4 and a ZsGreen fluorescent reporter.

A conditional lentiviral vector encoding 7×HBD/mE1B-ZsGreen-epHIV7 was constructed. The synthetic promoter 7×HBD/mE1B was constructed by combining seven minimal Hepatocyte Nuclear Factor 1-alpha (HNF1α) binding sites cloned from the human albumin promoter and the E1B TATA box. In this way, only in the presence of tamoxifen does binding of HEA3 or HEA4 to 7×HBD/mE1B promoter induce the "ON" state of transgene expression.

The transcriptional regulator, HEA3, is a chimeric transcription factor composed of human subunits including the N-terminal DNA binding domain of Hepatocyte Nuclear Factor 1-alpha (HNF-1α) fused in frame to the mutant tamoxifen-specific ligand binding domain of the estrogen receptor ligand binding domain (ER-LBD), that is in turn fused to the p65 activation domain of NF-κβ (p65). In the absence of tamoxifen, HEA3 is excluded from the nucleus by binding of cytosolic heat-shock protein 90 (HSP90) to the tamoxifen binding active site and transgene expression is in the "OFF" state. Nanomolar concentrations of cytosolic tamoxifen actively outcompete HSP90 for ER-LBD binding, resulting in HEA3 translocation to the nucleus. Upon nuclear translocation, HEA3 is readily available to bind its restricted synthetic promoter. Transcriptional responsiveness to HEA3 in the presence of tamoxifen is achieved when transgenes are placed behind an HEA3 responsive synthetic promoter (7×HBD/mE1B). In some alternatives, a DNA spacer is between the inducible promoter and the transgene. In some alternatives, the transgene encodes a chimeric antigen receptor. In some alternatives, the DNA spacer comprises a sequence set forth in SEQ ID NO: 120 (SEQ ID NO: 120; gctagcgtttaaacttaagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values.

The transcriptional regulator, HEA4, is a chimeric transcription factor composed of human subunits including the N-terminal DNA binding domain of Hepatocyte Nuclear Factor 1-alpha (HNF-1α) fused in frame to the mutant tamoxifen-specific ligand binding domain of the estrogen receptor ligand binding domain (ER-LBD) containing 3 amino acid substitutions that abolish sensitivity to estradiol, that is in turn fused to the p65 activation domain of NF-κβ (p65). Single or double mutations in the p65 activation domain have been constructed to enhance transcriptional activity. In the absence of tamoxifen, HEA4 is excluded from the nucleus by binding of cytosolic heat-shock protein 90 (HSP90) to the tamoxifen binding active site and transgene expression is in the "OFF" state. Nanomolar concentrations of cytosolic tamoxifen actively outcompete HSP90 for ER-LBD binding, resulting in HEA4 translocation to the nucleus. Upon nuclear translocation, HEA4 is readily available to bind its restricted synthetic promoter. Transcriptional responsiveness to HEA4 in the presence of tamoxifen is achieved when transgenes are placed behind an HEA4 responsive synthetic promoter (7×HBD/mE1B). In some alternatives, a DNA spacer is between the inducible promoter and the transgene. In some alternatives, the DNA spacer comprises a sequence set forth in SEQ ID NO: 120 (SEQ ID NO: 120; gctagcgtttaaacttaagcttggtaccgagctcg-gatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, the transgene encodes a chimeric antigen receptor.

The synthetic promoter 7×HBD/mE1B consists of seven minimal Hepatocyte Nuclear Factor-1 (HNF-1α) binding sites cloned from the human albumin promoter and the mE1B promoter TATA box. In this way, only in the presence of tamoxifen does binding of HEA3 or HEA4 to 7×HBD/mE1B promoter induce the "ON" state of transgene expression. In some alternatives, a DNA spacer is between the inducible promoter and the transgene. In some alternatives, the DNA spacer comprises a sequence set forth in SEQ ID NO: 120 (SEQ ID NO: 120; gctagcgtttaaact-taagcttggtaccgagctcggatccgccacc). In some alternatives, the DNA spacer comprises a sequence that has 95%, 90%, 85% or 80% sequence identity to SEQ ID NO: 120 or any percent sequence identity in between a range defined by any two aforementioned values. In some alternatives, the transgene encodes a chimeric antigen receptor.

The nucleic acid sequences encoding the chimeric transcription factors were constructed under the control of an EF1a constitutive promoter. The nucleic acid sequences encoding chimeric transcription factors were linked with sequences encoding the self-cleaving T2A sequence and a marker sequence EGFRt and cloned into an epHIV7.2 lentiviral backbone.

Lentivirus housing constitutive chimeric transcription factors and the inducible 7×HBD/mE1B-ZsGreen were produced in 293T cells co-transfected at a 1:2 (HEA3 or HEA4:7×HBD/mE1B) molar ratio with packaging vectors pCHGP-2, pCMV-Rev2 and pCMV-G using Lipofectamine 2000 (Life Technologies). Medium was changed 16 hours after transfection and virus was collected after 72 hours. Virus was concentrated at 24,500 rpm for 1 hour and 34 minutes at 4 C.

Generation of Jurkat Lines Expressing ZsGreen when Induced with Tamoxifen.

Jurkat cells were transduced with lentiviral supernatant (MOI≥3) supplemented with 1 μg/mL protamine sulfate (Seattle Children's Hospital Pharmacy). Transduced Jurkat cells were expanded in RPMI, 10% FBS and 2 mM L-glutamine. 10-30 days following transduction, EGFRt+ cells were enriched using biotinylated cetuximab and anti-biotin magnetic microbeads (Miltenyi). Cells were cultured in RPMI, 10% FBS and 2 mM L-glutamine until use in cellular assays.

Schematic of Dual-Packaged Lentiviral Constructs Housing the Constitutively Expressed Drug-Inducible Transcription Factors Jurkat cells expressing HEA3 (FIG. 1A) or (FIG. 1B) HEA4 single mutant RelA variants (S536E or K310Q or WT [wild-type]), and a ZsGreen fluorescent reporter vectors were constructed.

Characterization of "ON" and "OFF" States of HEA3 and HEA4 Single Mutant RelA Variants Jurkat cells were seeded at 5.0E5 cells/mL in the presence or absence of 500 nM 4-OHT. After 24 hours, cells were collected and stained with biotinylated cetuximab and Streptavidin-APC in HBSS containing 2% FBS and 0.1% $NaN_3$ and fixed in PBS with paraformaldehyde. EGFRt and ZsGreen reporter expression was obtained on a MACSQuant (Miltenyi). Data was analyzed using FlowJo Version 10. ZsGreen reporter expression in Jurkat cells expressing (FIG. 1C) HEA3 or (FIG. 1D) HEA4 single mutant RelA (S536E or K310Q) variants following 24 hours of culture with 500 nM 4-OHT are shown.

Characterization of 4-OHT Dose Response of HEA3 and HEA4 Single Mutant RelA Variants Jurkat cells expressing (FIG. 1A) HEA3 or (FIG. 1B) HEA4 single mutant RelA variants (S536E or K310Q or WT [wild-type]), and a ZsGreen fluorescent reporter vectors were seeded at 5.0E5 cells/mL with increasing doses of 4-OHT. After 24 hours, cells were collected and stained with biotinylated cetuximab and Streptavidin-APC in HBSS containing 2% FBS and 0.1% and fixed in PBS with paraformaldehyde. EGFRt and ZsGreen reporter expression was obtained on a MACSQuant (Miltenyi). Data was analyzed using FlowJo Version 10. 4-OHT dose response are shown: Percentage of EGFRt+ZsGreen+ cells and ZsGreen median fluorescent intensity of (FIG. 1E) HEA3 or (FIG. 1F) HEA4 RelA variant expressing Jurkat cells.

Figure 2A:
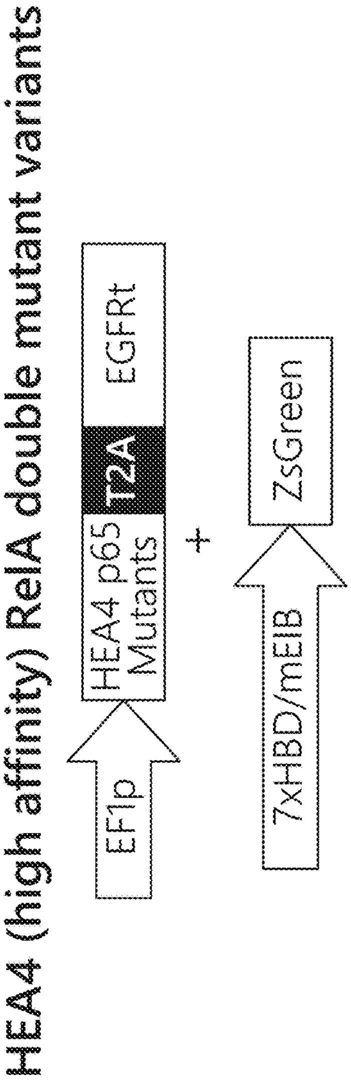
FIGS. 2A to 2E show HEA4 (high affinity) RelA double mutant variants and CMP8-responsive HEA3 RelA variants and their response when dosed with 4-OHT and CMP8, respectively, when they are transduced into cells. Shown in the figures is a schematic of dual-packaged lentiviral constructs housing the constitutively expressed drug-inducible transcription factors, (FIG. 2A) HEA4 double mutant RelA variant (S536E/K310Q positions in the RelA protein domain, which correspond to position S846E and K621Q in HEA3 and HEA4, respectively) or (FIG. 2B) CMP8-responsive HEA3 single mutant RelA variant (S563E), and a ZsGreen fluorescent reporter. ZsGreen reporter expression in Jurkat cells expressing the (FIG. 2C) HEA4 double mutant RelA variant or the (FIG. 2D) CMP8-responsive HEA3 RelA variant, following 24 hours of culture with 500 nM 4-OHT and CMP8. 4-OHT and CMP8 dose response: Percentage of EGFRt+ZsGreen+ cells and ZsGreen median fluorescent intensity of Jurkat cells expressing the (FIG. 2E) HEA4 double mutant RelA variant or (FIG. 2F) CMP8-responsive HEA3 single mutant RelA variant.
Figure 2B:
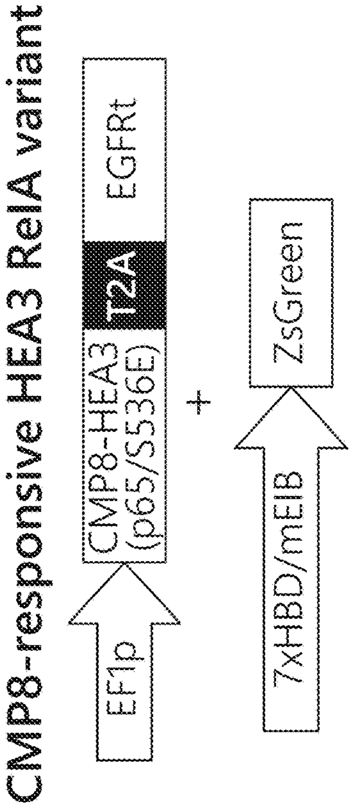

Schematic of Dual-Packaged Lentiviral Constructs Housing the Constitutively Expressed Drug-Inducible Transcription Factors Jurkat cells expressing an HEA4 (FIG. 2A) double mutant RelA (S536E/K310Q) variant or a CMP8-responsive (FIG. 2B) HEA3 single mutant RelA (S536E) variant and a ZsGreen fluorescent reporter vector were constructed.

Figure 2C:
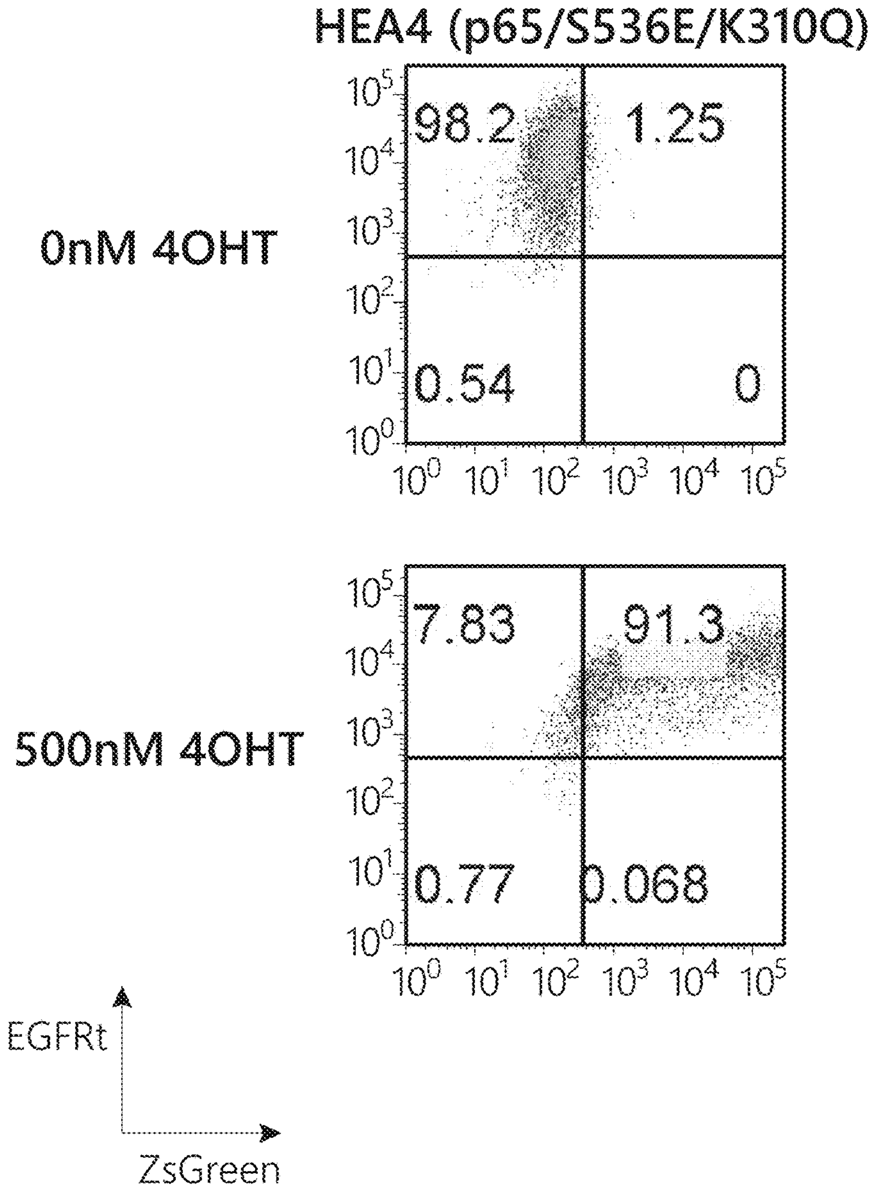
Figure 2D:
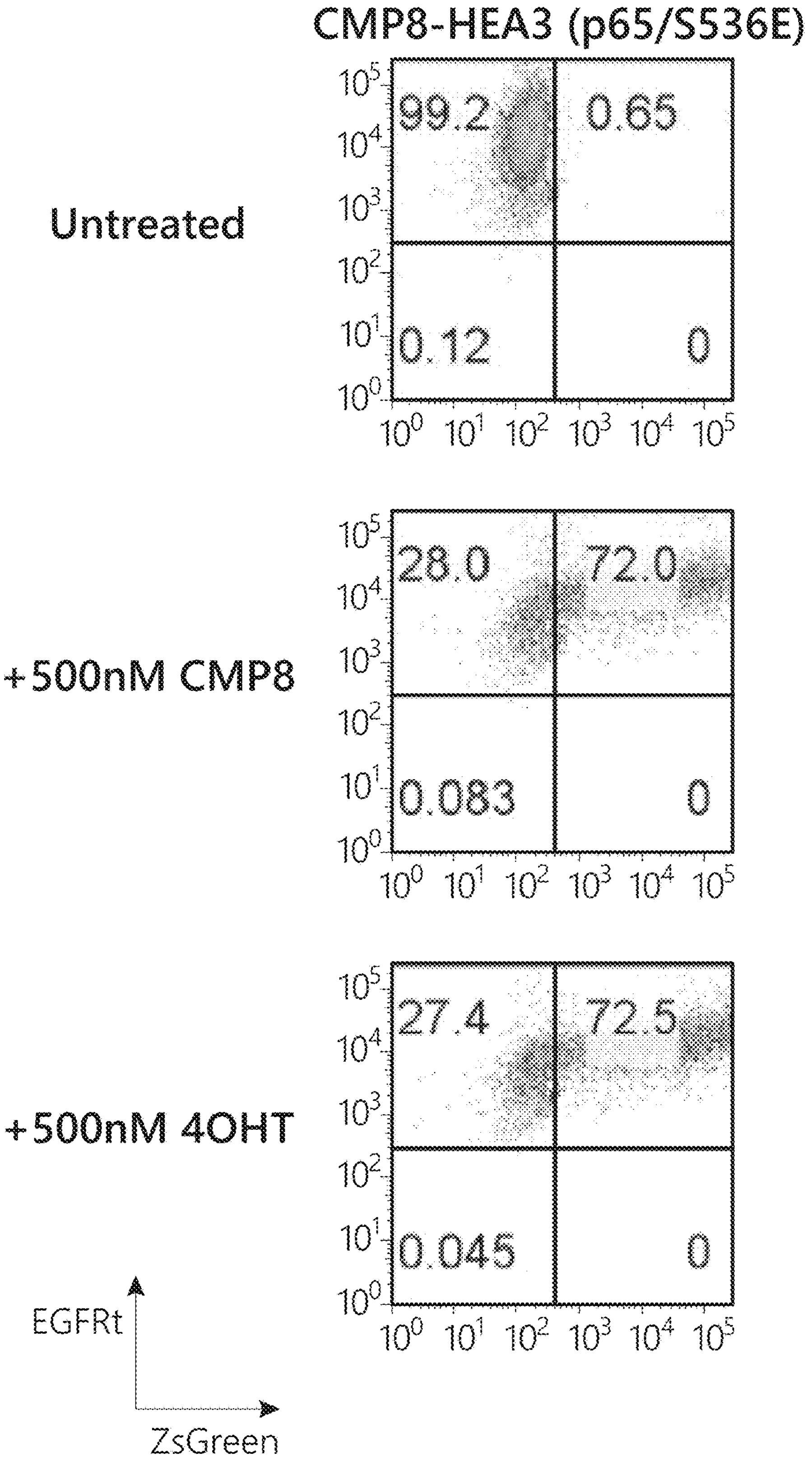

Characterization of "ON" and "OFF" States of HEA4 Double Mutant RelA Variants and CMP8-Responsive HEA3 Single Mutant RelA Variants Jurkat cells were seeded at 5.0E5 cells/mL in the presence or absence of 500 nM 4-OHT (FIG. 2C) or CMP8 (FIG. 2D). After 24 hours, cells were collected and stained with biotinylated cetuximab and Streptavidin-APC in HBSS containing 2% FBS and 0.1% and fixed in PBS with paraformaldehyde. EGFRt and ZsGreen reporter expression was obtained on a MACSQuant (Miltenyi). Data was analyzed using FlowJo Version 10. ZsGreen reporter expression in Jurkat cells expressing (FIG. 2C) the HEA4 double mutant RelA (S536E/K310Q) variant or (FIG. 2D) CMP8-responsive HEA3 single mutant RelA (S536E) variant following 24 hours of culture with 500 nM 4-OHT or 500 nM CMP8 are shown.

Figure 2E:
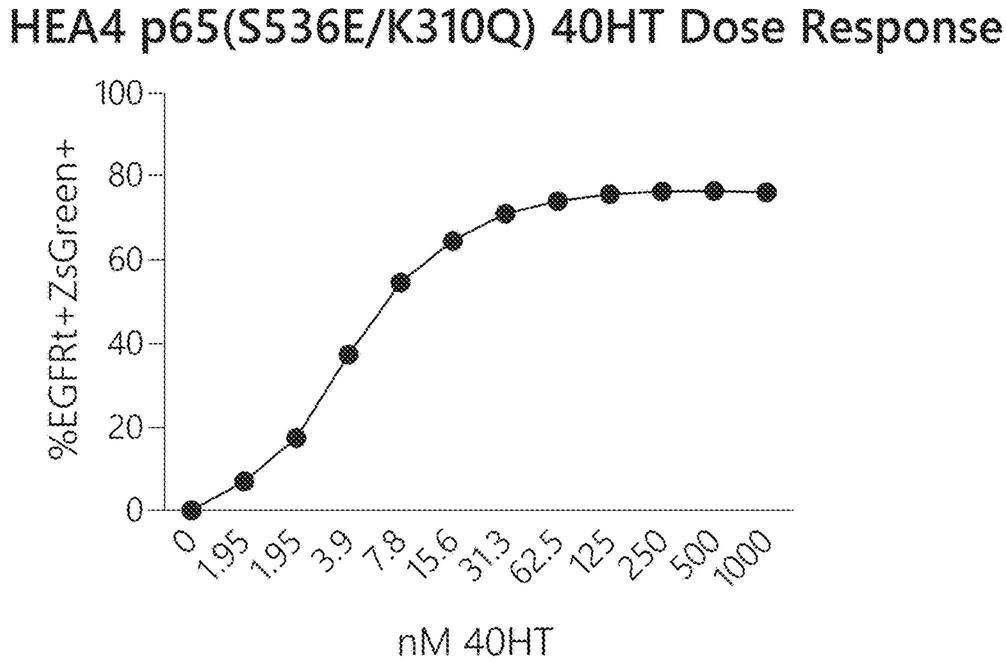
Figure 2E:
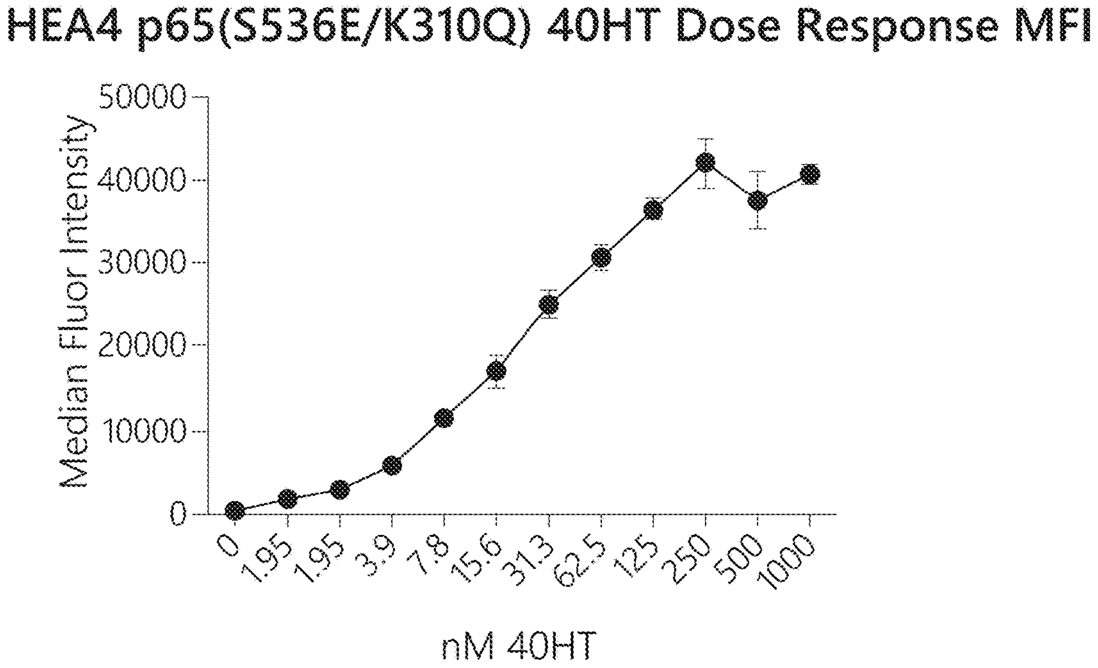
Figure 2F:
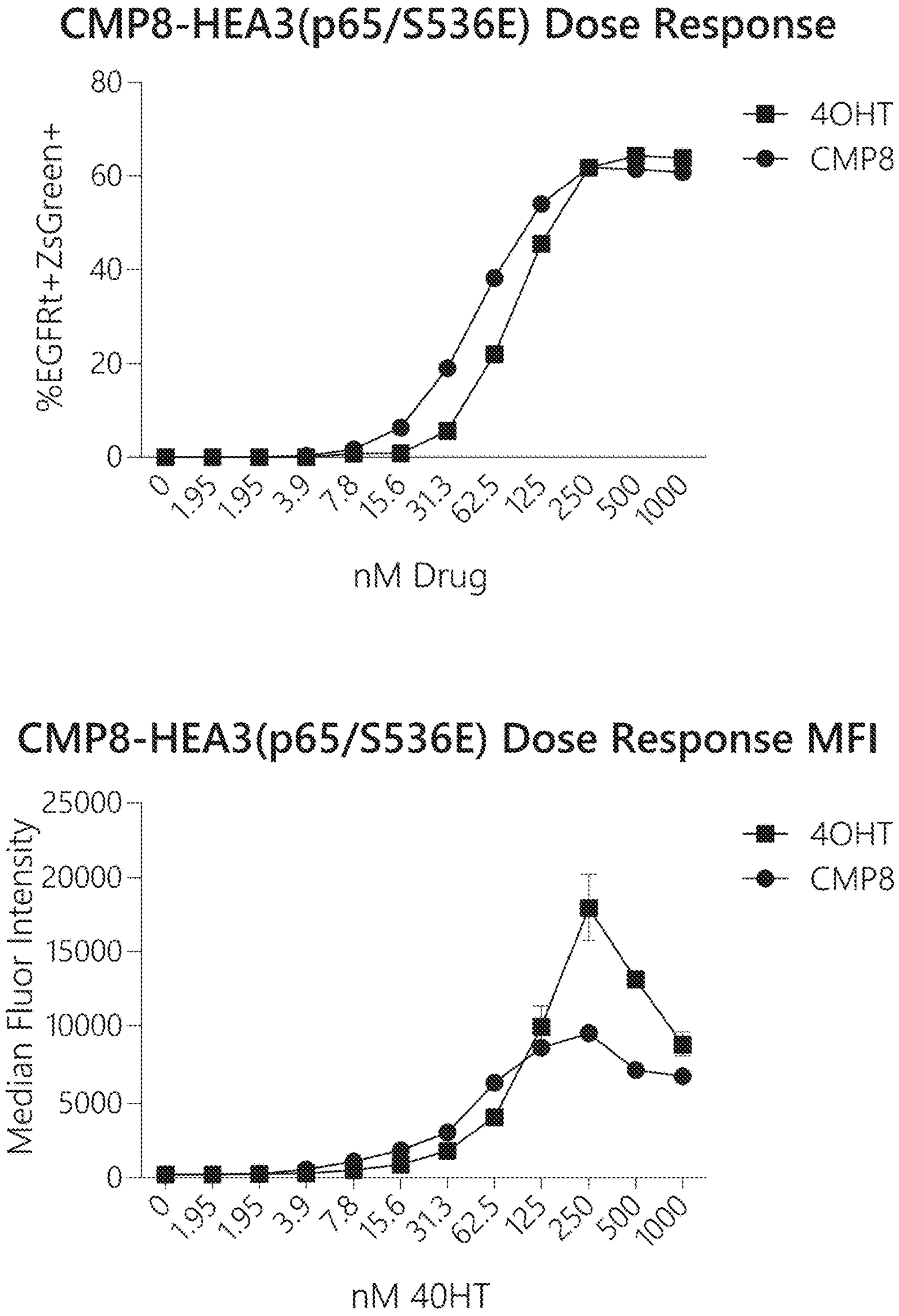

Characterization of 4-OHT Dose Response of HEA4 Double Mutant RelA Variants and CMP8-Responsive HEA3 Single Mutant RelA Variants Jurkat cells expressing (FIG. 2A) HEA4 double mutant RelA variants (S536E/K310Q) or (FIG. 2B) CMP8-responsive HEA3 single mutant RelA variants, and a ZsGreen fluorescent reporter vectors were seeded at Jurkat cells were seeded at 5.0E5 cells/mL with increasing doses of 4-OHT or CMP8. After 24 hours, cells were collected and stained with biotinylated cetuximab and Streptavidin-APC in HBSS containing 2% FBS and 0.1% and fixed in PBS with paraformaldehyde. EGFRt and ZsGreen reporter expression was obtained on a MACSQuant (Miltenyi). Data was analyzed using FlowJo Version 10. 4-OHT dose response are shown: Percentage of EGFRt+ZsGreen+ cells and ZsGreen median fluorescent intensity of (FIG. 2E) the HEA4 double mutant RelA (S536E/K310Q) variant or (FIG. 2F) CMP8-responsive HEA3 single mutant RelA (S536E) variant expressing Jurkat cells.

Lentiviral Vectors Comprising a DNA Spacer.

Jurkat cells expressing an HEA4 double mutant RelA (S536E/K310Q) variant or a CMP8-responsive HEA3 single mutant RelA (S536E) variant and a ZsGreen fluorescent reporter vector were constructed. For comparison of expression levels, Jurkat cells expressing an HEA4 double mutant RelA (S536E/K310Q) variant comprising a DNA spacer between the promoter and transgene or a CMP8-responsive HEA3 single mutant RelA (S536E) variant comprising a DNA spacer between the promoter and transgene and a ZsGreen fluorescent reporter vector were also constructed.

Jurkat cells were seeded at 5.0E5 cells/mL in the presence or absence of 500 nM 4-OHT (FIG. 2C) or CMP8. After 24 hours, cells were collected and stained with biotinylated cetuximab and Streptavidin-APC in HBSS containing 2% FBS and 0.1% and fixed in PBS with paraformaldehyde. EGFRt and ZsGreen reporter expression was obtained on a MACSQuant (Miltenyi). Data was analyzed using FlowJo Version 10. ZsGreen reporter expression in Jurkat cells expressing the HEA4 double mutant RelA (S536E/K310Q) variant or CMP8-responsive HEA3 single mutant RelA (S536E) variant following 24 hours of culture with 500 nM 4-OHT or 500 nM CMP8 were compared to the expression of Jurkat cells expressing the HEA4 double mutant RelA (S536E/K310Q) variant that had the DNA spacer and the CMP8-responsive HEA3 single mutant RelA (S536E) variant that had the DNA spacer following 24 hours of culture with 500 nM 4-OHT or 500 nM CMP8. It is expected that the expression of the transgenes increased 1.5 to 2.0 fold as compared to the vectors that lacked the DNA spacer between the promoters and the transgene. This is also dependent on the transgene. The DNA spacer comprised the sequence set forth in SEQ ID NO: 120.

Additional Methods

Vector Construction and Preparation of Dual Packaged Lentivirus.

An inducible lentiviral vector encoding constitutively expressed drug inducible transcription factors was constructed. The constructs encoded the HEA4 (p65/S536E/K310Q) double mutant RelA variant (SEQ ID NO: 7) and an eGFP:ffluc reporter. In some cases, constructs encoded the HEA4(p65/S536E/K310Q) double mutant RelA variant and Survivin or CCR(CD122).

The conditional lentiviral vectors (7×HBD/mE1B_eGFP: ffluc_epHIV7.2, 7×HBD/mE1B_Survivin-T2A-Her2tG_epHIV7.2, and 7×HBD/mE1B_CCR(CD122)-T2A-Her2tG_epHIV7.2) were constructed. The synthetic promoter 7×HBD/mE1B was constructed by combining seven minimal Hepatocyte Nuclear Factor1-alpha (HNF-1α) binding sites cloned from the human albumin promoter and the E1B TATA box. In this way, only in the presence of tamoxifen does binding of HEA3 or HEA4 to 7×HBD/mE1B promoter induce the "ON" state of transgene expression The transcriptional regulator, HEA4(p65/S536E/K310Q), is a chimeric transcription factor composed of human subunits including the N-terminal DNA binding domain of Hepatocyte Nuclear Factor 1-alpha (HNF-1α) fused in frame to the mutant tamoxifen-specific ligand binding domain of the estrogen receptor ligand binding domain (ER-LBD) containing 3 amino acid substitutions that abolish sensitivity to estradiol, that is in turn fused to the p65 activation domain of NF-κβ (p65). Two mutations (S536E/K310Q) were introduced into the p65 activation domain to enhance transcriptional activity. In the absence of tamoxifen, HEA4(p65/S536E/K310Q) is excluded from the nucleus by binding of cytosolic heat-shock protein 90 (HSP90) to the tamoxifen binding active site and transgene expression is in the "OFF" state. Nanomolar concentrations of cytosolic tamoxifen actively outcompete HSP90 for ER-LBD binding, resulting in HEA4(p65/S536E/K310Q) translocation to the nucleus. Upon nuclear translocation, HEA4(p65/S536E/K310Q) is readily available to bind its restricted synthetic promoter. Transcriptional responsiveness to HEA4(p65/S536E/K310Q) in the presence of tamoxifen is achieved when transgenes are placed behind an HEA4(p65/S536E/K310Q) responsive synthetic promoter (7×HBD/mE1B). The synthetic promoter 7×HBD/mE1B consists of seven minimal Hepatocyte Nuclear Factor 1-alpha (HNF-1α) binding sites cloned from the human albumin promoter and the E1B promoter TATA box. In this way, only in the presence of tamoxifen does binding of HEA4(p65/S536E/K310Q) to 7×HBD/mE1B promoter induce the "ON" state of transgene expression.

The nucleic acid sequences encoding the chimeric transcription factors were constructed under the control of an EF1a constitutive promoter. The nucleic acid sequences encoding chimeric transcription factors were linked with sequences encoding the self-cleaving T2A sequence and a marker sequence EGFRt and cloned into an epHIV7.2 lentiviral backbone.

The nucleic acid sequences encoding Survivin or CCR (CD122) were linked with sequences encoding the self-cleaving T2A sequence and a marker sequence Her2tG and cloned into an epHIV7.2 lentiviral backbone.

Figure 3A:
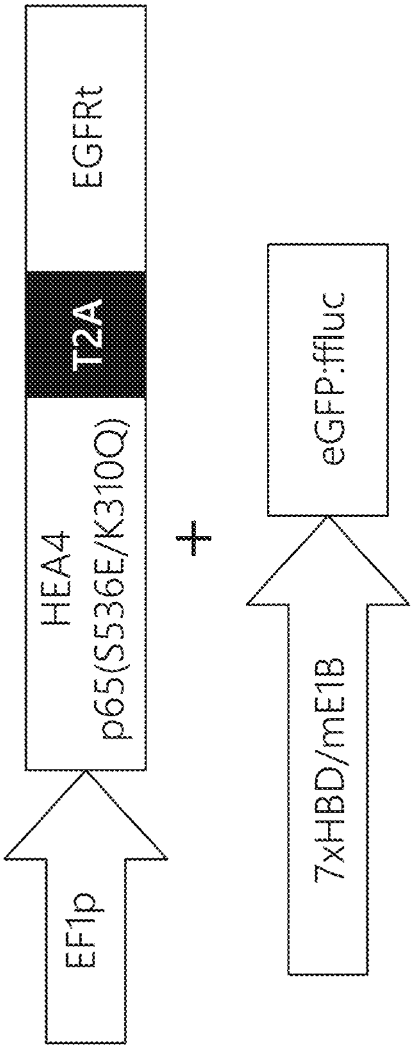
FIGS. 3A to 3C shows the results of dual-packaged lentiviral constructs encoding drug-regulated transcription factor (HEA4 (p65/S536E/K310Q)) and inducible fluorescent reporter eGFP:ffluc, when they are transduced into cells. Shown in the FIG. 3A, CD4 and CD8 T cells were transduced with dual-packaged lentiviral constructs encoding drug-regulated transcription factor (HEA4(p65/S536E/K310Q)) and inducible fluorescent reporter eGFP:ffluc. Following purification and expansion of transduced CD4 and CD8 T cells, (FIG. 3B) Western blot was performed using anti-p65 antibody to confirm expression of chimeric transcription factor.
Figure 4A:
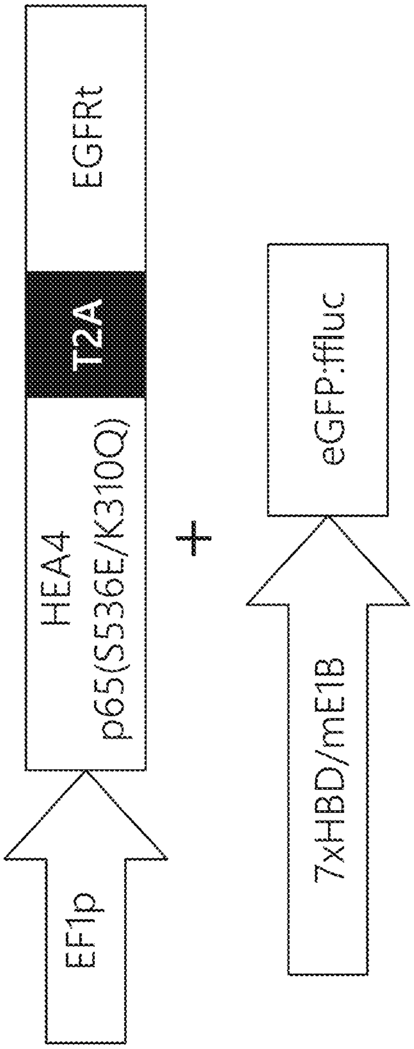
FIGS. 4A to 4B shows the dual-packaged lentiviral constructs encoding drug-regulated transcription factor (HEA4 (p65/S536E/K310Q)) and inducible fluorescent reporter eGFP:ffluc and the results when the lentiviral constructs are transduced into cells.
Figure 5A:
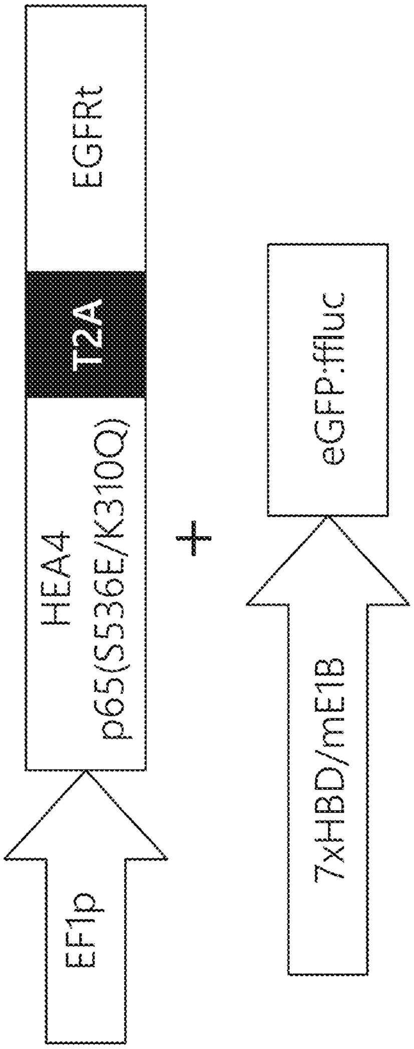
FIGS. 5A to 5E shows dual-packaged lentiviral constructs encoding drug-regulated transcription factor (HEA4(p65/S536E/K310Q)) and inducible fluorescent reporter eGFP:ffluc and the results when the lentiviral constructs are transduced into cells.
Figure 6A:
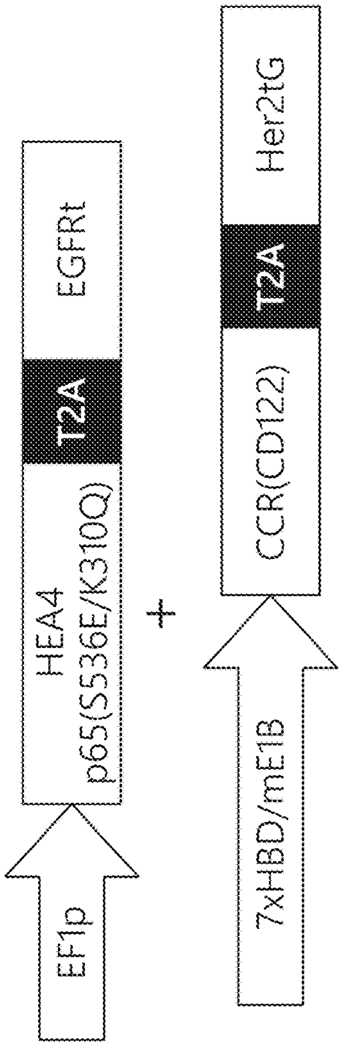
Figure 6B:
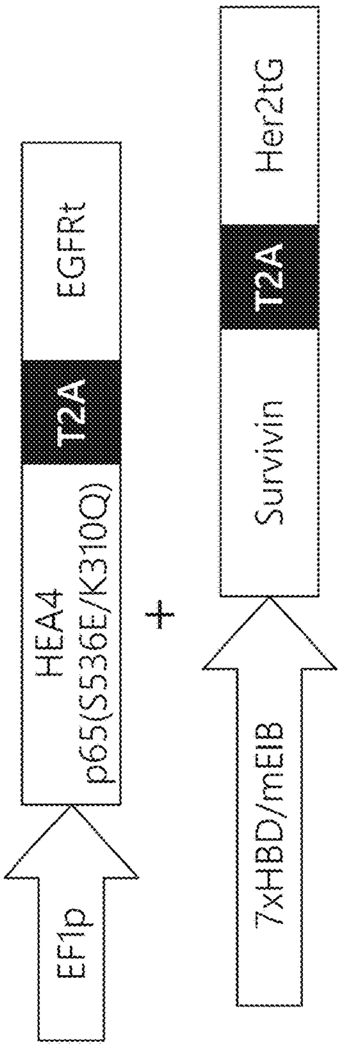

Lentivirus housing the constitutive chimeric transcription factor and the inducible (FIG. 3A, 4A, 5A) 7×HBD/mE1B_eGFP:ffluc, (FIG. 6A) 7×HBD/mE1B_Survivin-T2A-Her2tG, or (FIG. 6B) 7×HBD/mE1B_CCR(CD122)-T2A-Her2tG were produced in 293T cells co-transfected at a 1:2 (HEA4(p65/S536E/K310Q):7×HBD/mE1B) molar ratio with packaging vectors pCHGP-2, pCMV-Rev2 and pCMV-G using Lipofectamine 2000 (Life Technologies). Medium was changed 16 hours after transfection and virus was collected after 72 hours. Virus was concentrated at 24,500 rpm for 1 hour and 34 minutes at 4 C.

Generation of CD4+ and CD8+ T Cells Expressing eGFP: Ffluc when Induced with Tamoxifen.

Human CD4+ and CD8+ T cells were isolated from PBMCs using CD4 and CD8 Microbeads (Miltenyi). CD4+ and CD8+ T cells were cultured separately for the entirety of the experiments. Immediately following isolation, CD4+ and CD8+ T cells were stimulated with Dynabeads Human T-Activator CD3/CD28 for T Cell Expansion (Life Technologies) at a 1:1 bead:cell ratio. CD4+ T cells were cultured with RPMI, 10% FBS, 2 mM L-glutamine, IL-7 (5 ng/mL), and IL-15 (0.5 ng/mL). CD8+ T cells were cultured with RPMI, 10% FBS and 2 mM L-glutamine, IL-2 (50 U/mL), and IL-15 (0.5 ng/mL). Two days following isolation, CD4+ and CD8+ T cells were transduced with lentiviral supernatant (MOI 1.0) supplemented with 1 μg/mL protamine sulfate (Seattle Children's Hospital Pharmacy). 10-15 days following transduction, EGFRt+ cells were enriched using biotinylated cetuximab and anti-biotin magnetic microbeads (Miltenyi). 21 days following start of culture, T cells were expanded for 14 days via the Rapid Expansion Protocol using irradiated TM-LCLs, PBMCs, and anti-CD3 (OKT3) antibody (30 ng/mL). In some cases, T cells underwent a second expansion using the Rapid Expansion Protocol for an additional 14 days.

Schematic of Dual-Packaged Lentiviral Constructs Housing the Constitutively Expressed Drug-Inducible Transcription Factors.

CD4+ and CD8+ T cells expressing (FIGS. 3A, 4A, and 5A) HEA4(p65/S536E/K310) and an eGFP:ffluc reporter were constructed.

Expression of Drug-Inducible Transcription Factor Confirmed by Western Blot.

Figure 3B:
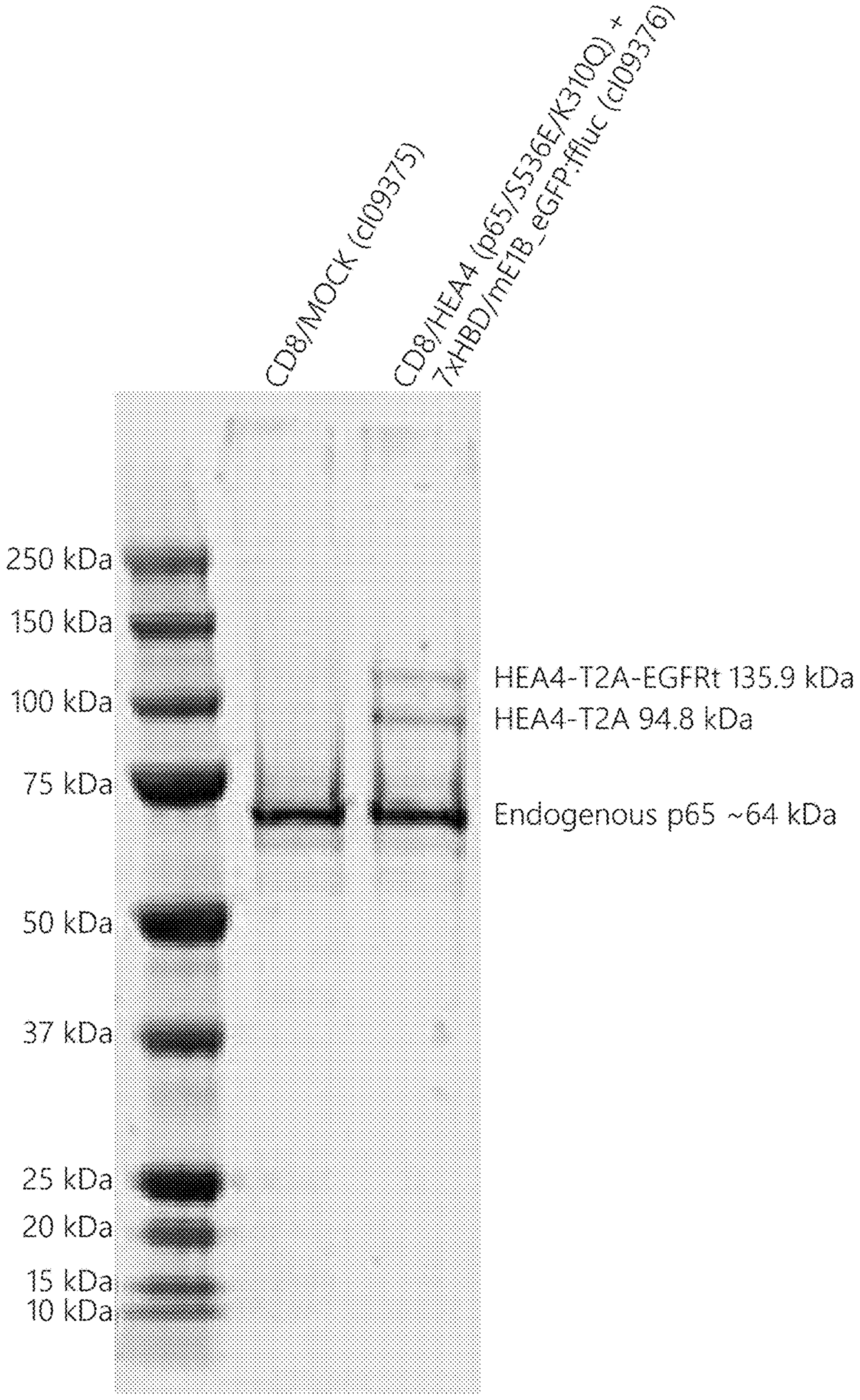

5.0e6 transduced and mock-transduced CD8+ T cells were collected. Cells were lysed with RIPA Buffer supplemented with protease inhibitors. 10 μg of protein was run on NuPAGE 4-12% Bis-Tris gel and transferred to nitrocellulose membrane. Membrane was blocked for 1 hour at room temperature and then probed with rabbit anti-p65 antibody (Cell Signaling) overnight at 4 C. Membrane was washed and probed with goat anti-rabbit IR Dye 800 CW (LiCor). (FIG. 3B) Membrane was washed and imaged using Li-Cor Odyssey CLX Scanner to confirm expression of HEA4(p65/S536E/K310Q).

Expression of Drug-Inducible Transcription Factor and Background Level of eGFP Confirmed by Flow Cytometry.

Figure 3C:
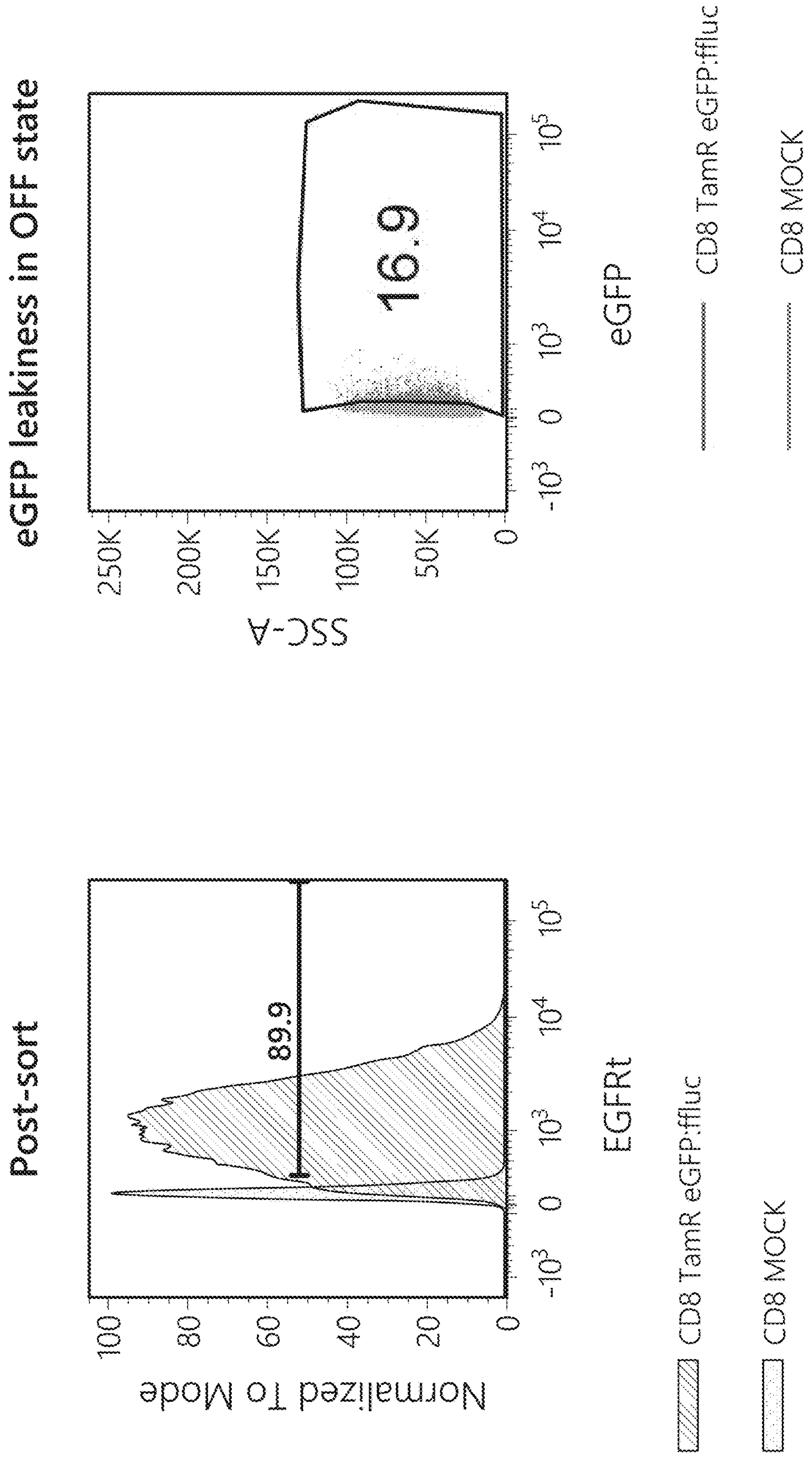

1.0e6 transduced and mock-transduced CD8+ T cells were collected and stained with biotinylated cetuximab and Streptavidin-APC in HBSS containing 2% FBS and 0.1% $NaN_3$ and fixed in PBS with paraformaldehyde. (FIG. 3C) EGFRt and eGFP reporter expression was obtained on a MACSQuant (Miltenyi).

Characterization of "ON" and "OFF" States of HEA4(p65/S536E/K3100) Double Mutant RelA Variant in CD4+ and CD8+ T Cells.

Figure 4B:
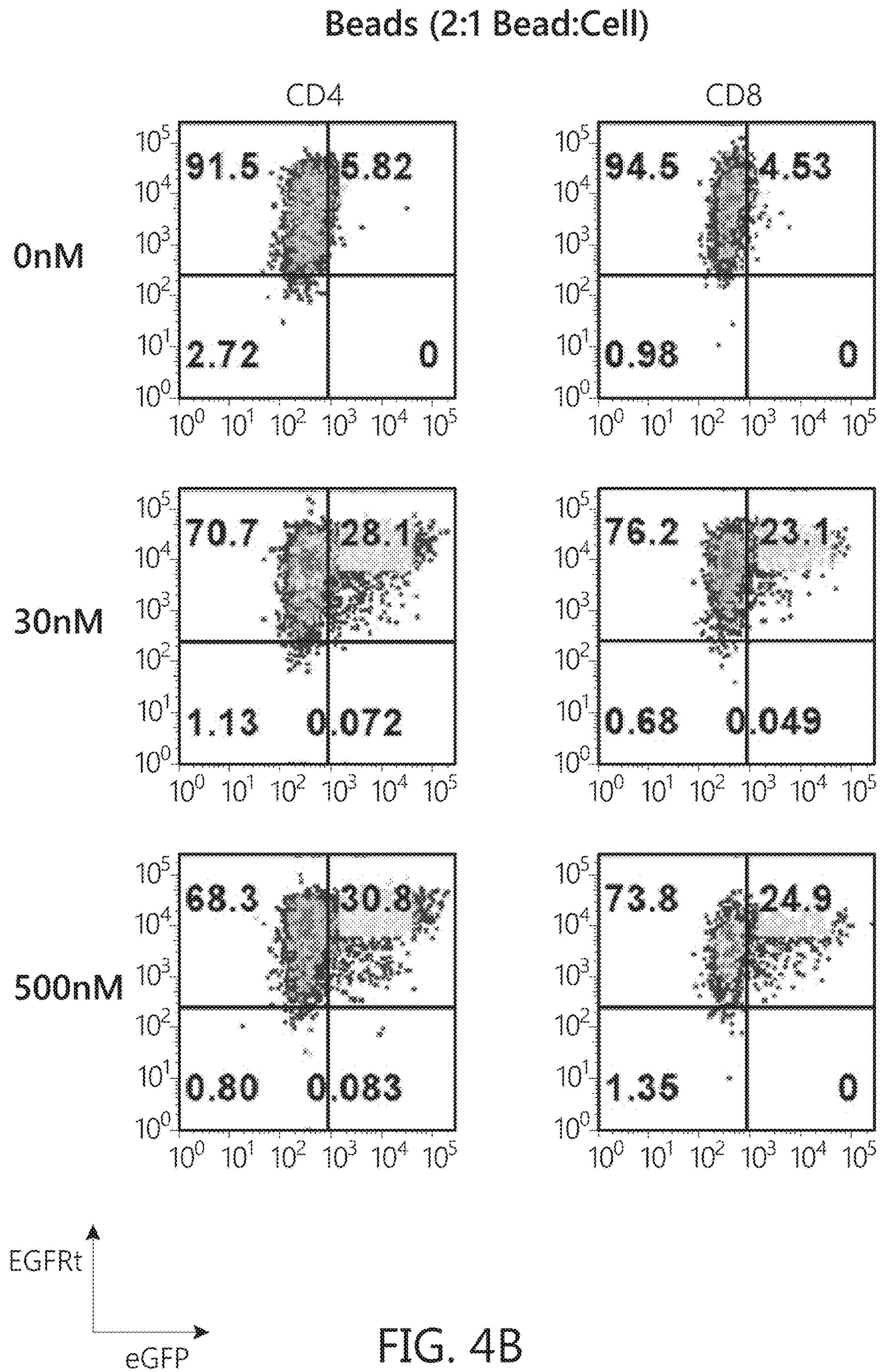
Figure 4B:
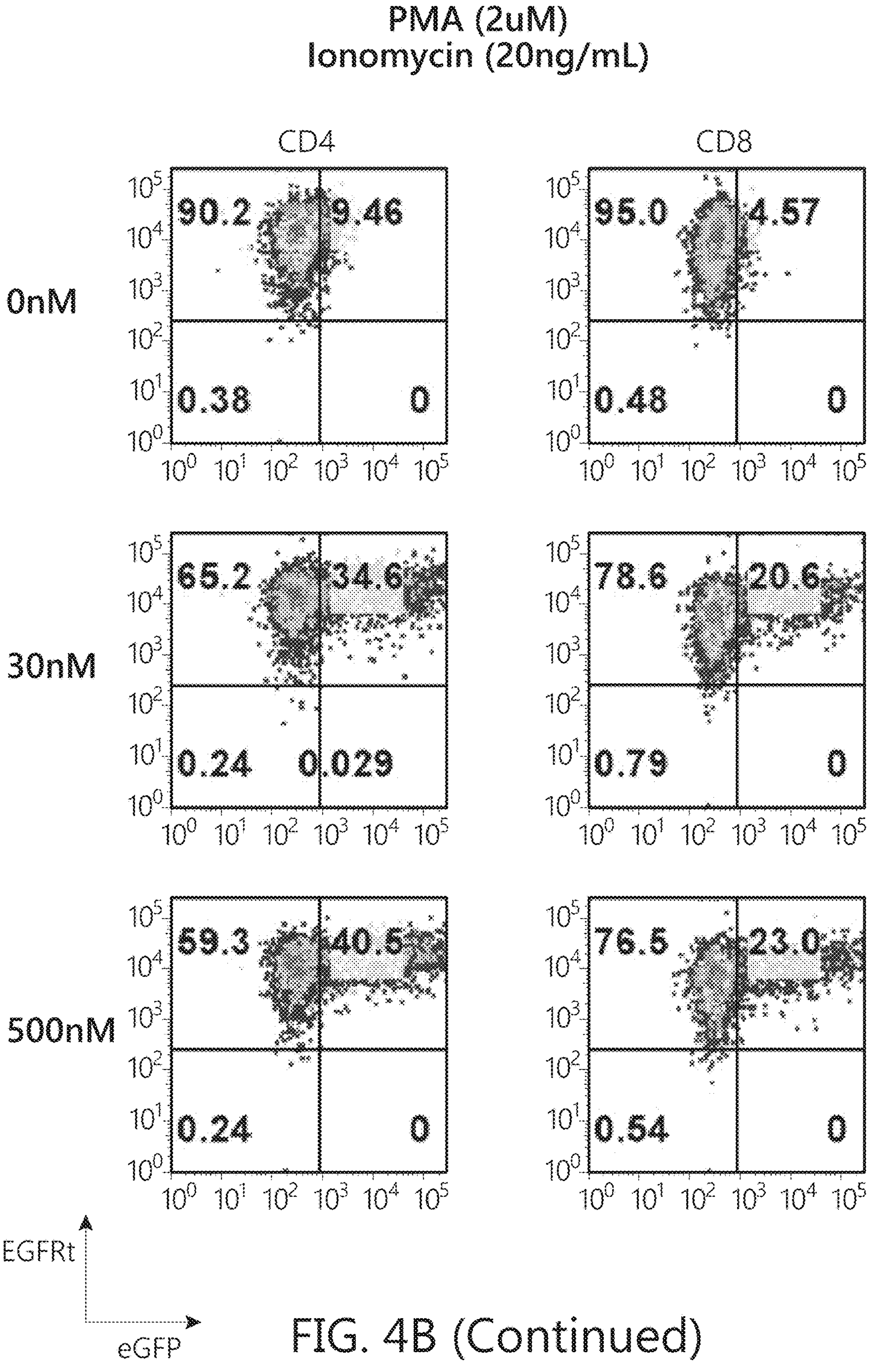
Figure 4B:
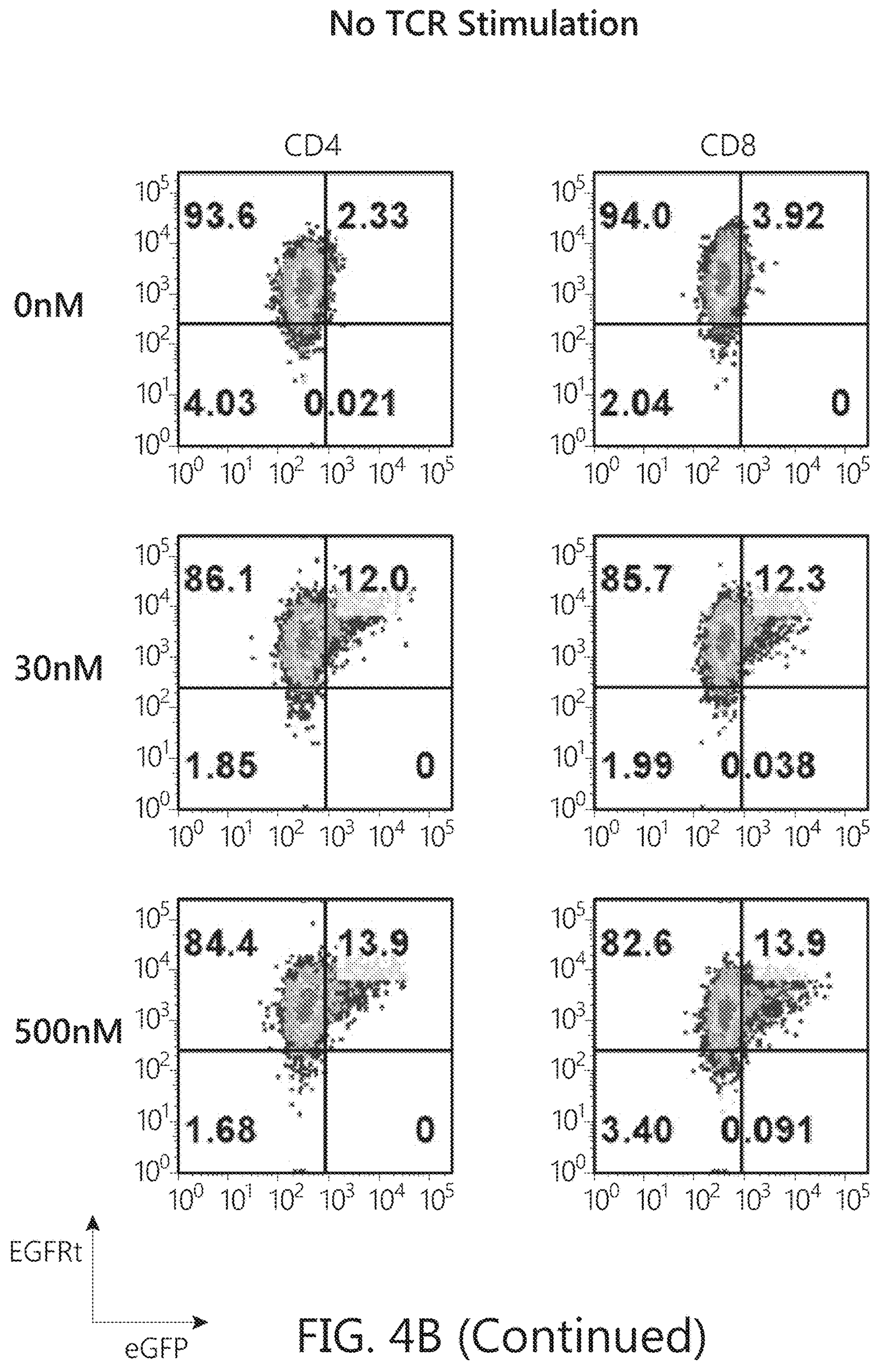

1.0e5 transduced and mock-transduced CD4+ and CD8+ T cells were seeded in the presence or absence of 0-500 nM 4-OHT with or without Dynabeads (2:1 bead:cell ratio) or PMA (2 μM)/Ionomycin (20 ng/mL) for 24 hours. Cells were harvested and stained with biotinylated cetuximab and Streptavidin-APC in HBSS containing 2% FBS and 0.1% $NaN_3$. Cells were fixed in PBS with paraformaldehyde. EGFRt and eGFP reporter expression was obtained on a MACSQuant (Miltenyi). Data was analyzed using FlowJo Version 10. eGFP reporter expression in CD4+ and CD8+ T cells expressing (FIG. 4B) HEA4(S536E/K310Q) variants following 24 hours of culture with 0, 30, or 500 nM 4-OHT are shown.

4-OHT Dose Response of HEA4(S536E/K3100) Double Mutant RelA Variant in CD4+ and CD8+ T Cells.

Figure 5B:
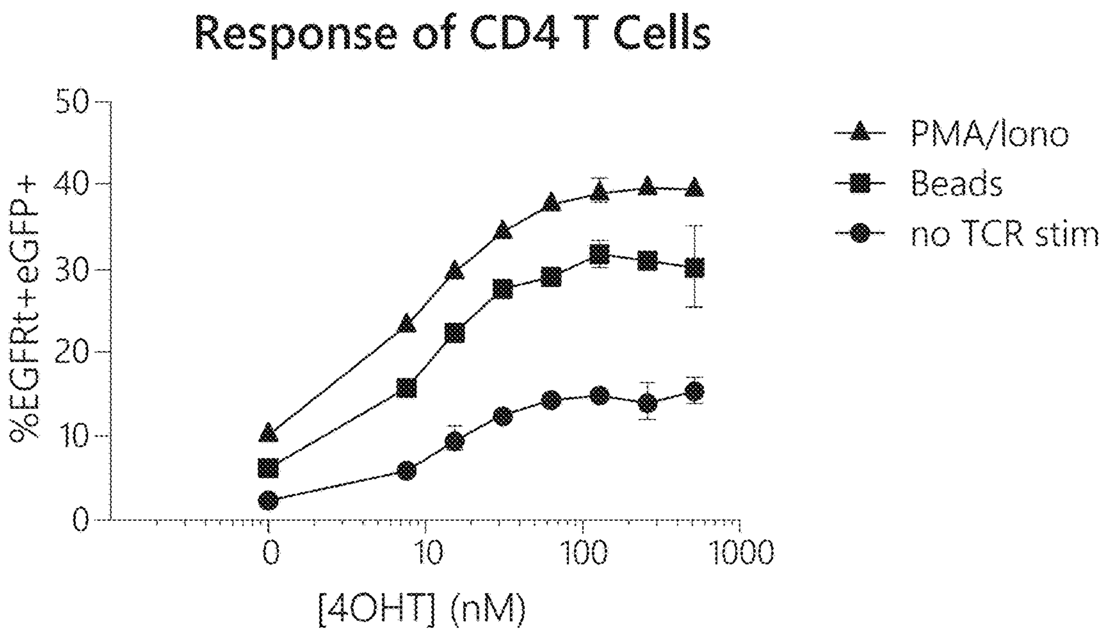
Figure 5C:
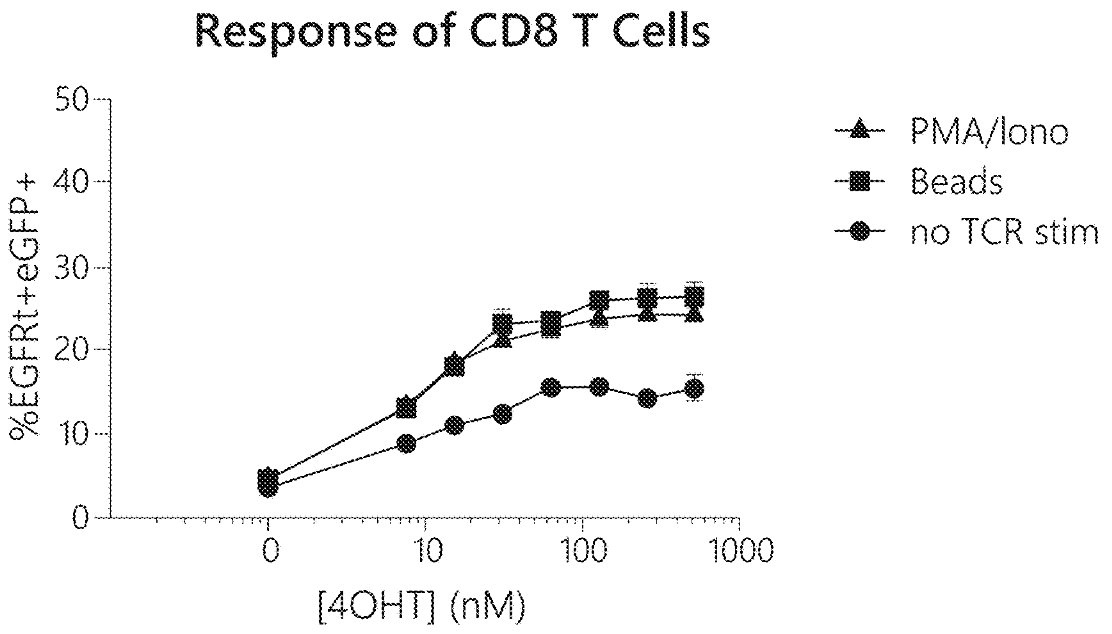
Figure 5D:
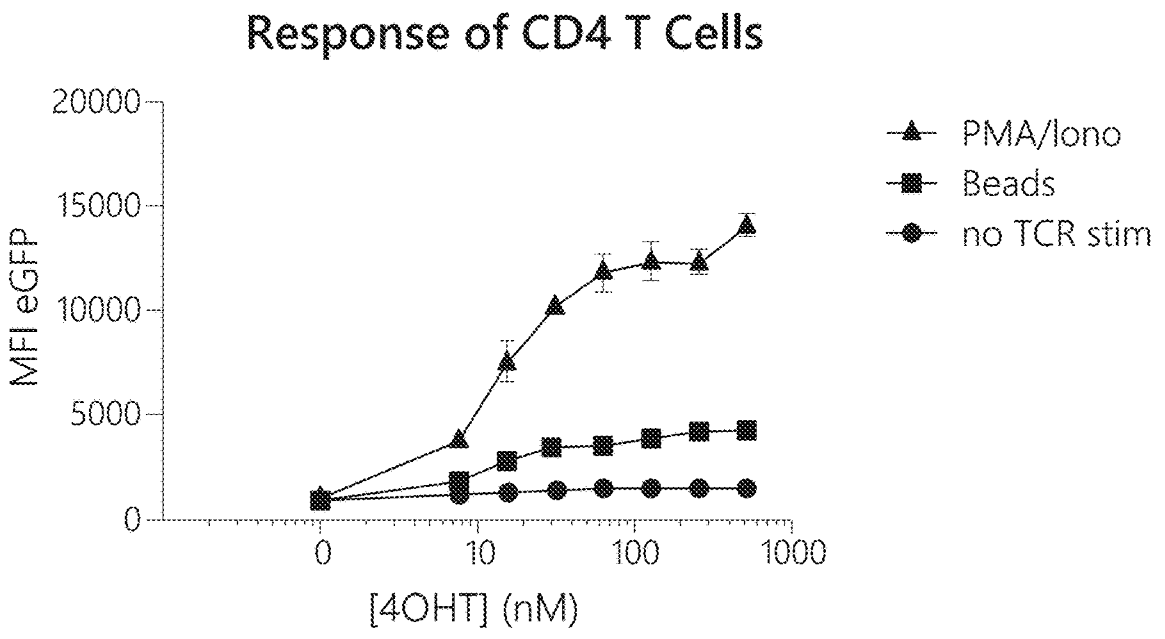
Figure 5E:
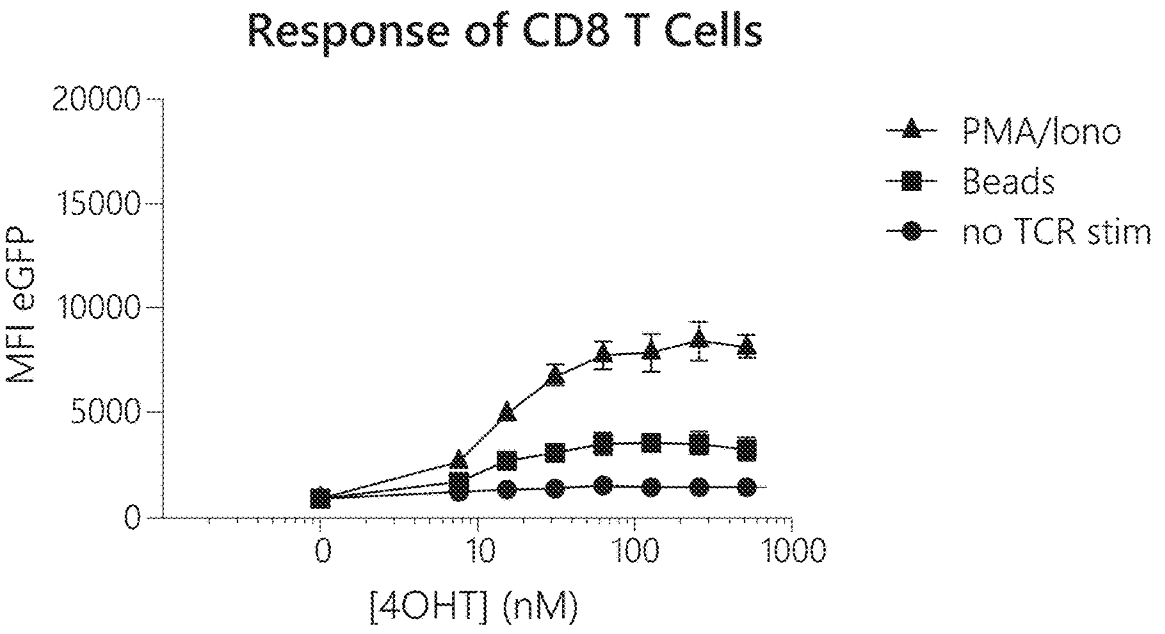

1.0e5 CD4+ and CD8+ transduced or mock control T cells were seeded in the presence or absence of 0-500 nM 4-OHT with or without Dynabeads (2:1 bead:cell ratio) or PMA (2 μM)/Ionomycin (20 ng/mL) for 24 hours. Cells were harvested and stained with biotinylated cetuximab and Streptavidin-APC in HBSS containing 2% FBS and 0.1% $NaN_3$. Cells were fixed in PBS with paraformaldehyde. EGFRt and eGFP reporter expression was obtained on a MACSQuant (Miltenyi). Data was analyzed using FlowJo Version 10. % EGFRt+eGFP+(FIG. 5B) CD4+ and (FIG. 5C) CD8+ T cells and (FIG. 5D-5E) eGFP median fluorescence intensity following 24 hours of culture with 0-500 nM 4-OHT are shown.

Schematic of Dual-Packaged Lentiviral Constructs Housing the Constitutively Expressed Drug-Inducible Transcription Factors.

Jurkat cells expressing HEA4(p65/S536E/K310) and (FIG. 6A) inducible 7×HBD/mE1B_Survivin-T2A-Her2tG or (FIG. 6B) inducible 7×HBD/mE1B_CCR(CD122)-T2A-Her2tG were constructed.

Generation of Jurkat Cell Lines Expressing Survivin or CCR(CD122) when Induced with Tamoxifen.

Jurkat cells were transduced with lentiviral supernatant (MOI≥3.0) supplemented with 1.0 μg/mL protamine sulfate (Seattle Children's Hospital Pharmacy). Jurkat cells were cultured with RPMI, 10% FBS and 2 mM L-glutamine.

Figure 6C:
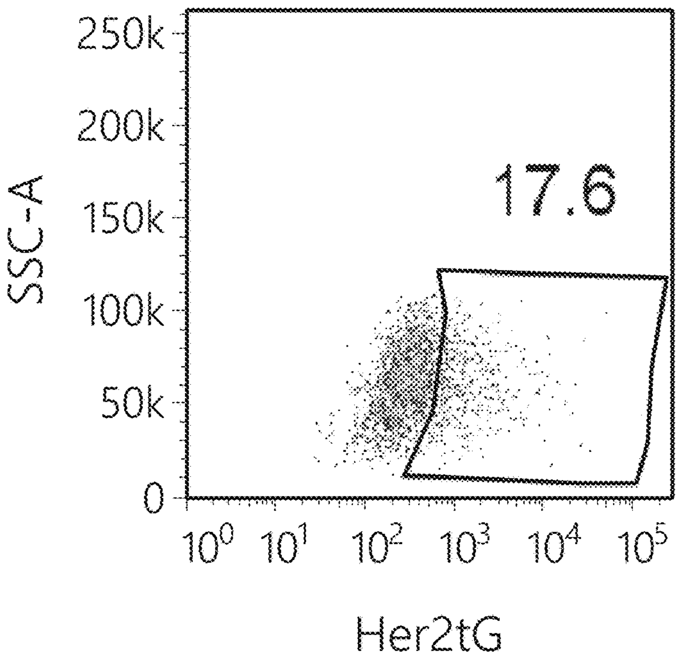
Figure 6C:
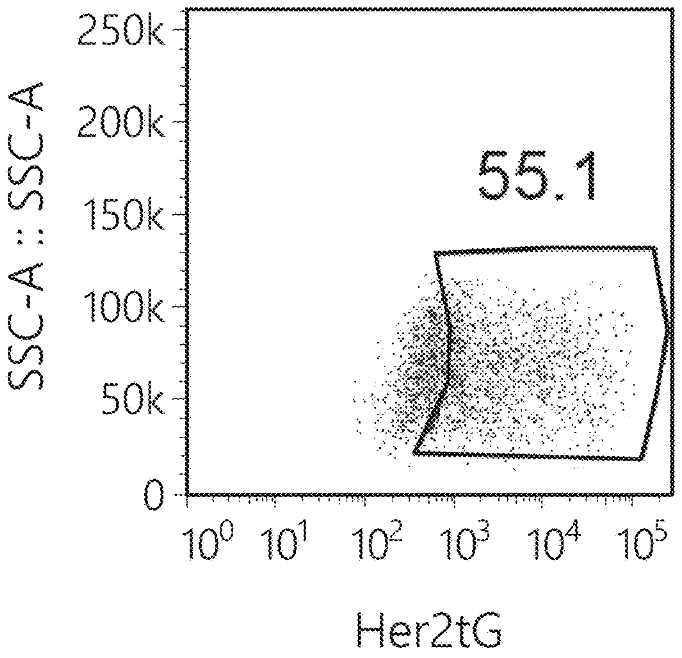

"ON" State Switching of HEA4(p65/S536E/K310Q) Double Mutant RelA Variant and Inducible Survivin or CCR(CD122) in Jurkat Cells Jurkat cells were seeded at 5.0e5 cells/mL in the presence or absence of 500 nM 4-OHT for 24 hours. Cells were harvested and stained with cetuximab-APC, biotinylated Herceptin, and Streptavidin-PE in HBSS containing 2% FBS and 0.1% $NaN_3$. Cells were fixed in PBS with paraformaldehyde. EGFRt and Her2tG expression was obtained on a MACSQuant (Miltenyi). Data was analyzed using FlowJo Version 10. Her2tG expression in Jurkat cells expressing HEA4(S536E/K310Q) double mutant RelA variant and (FIG. 6C) inducible Survivin or (FIG. 6D) inducible CCR(CD122) following 24 hours of culture with 500 nM 4-OHT are shown.

The present invention has been described above with reference to specific alternatives. However, other alternatives than the above described are equally possible within the scope of the invention. Different method steps than those described above, may be provided within the scope of the invention. The different features and steps of the invention may be combined in other combinations than those described. The scope of the invention is only limited by the appended patent claims.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those of skill within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

In addition, where features or aspects of the disclosure are described in terms of Markush groups, those skilled in the art will recognize that the disclosure is also thereby described in terms of any individual member or subgroup of members of the Markush group.

Any of the features of an alternative of the first through eleventh aspects is applicable to all aspects and alternatives identified herein. Moreover, any of the features of an alternative of the first through eleventh aspects is independently combinable, partly or wholly with other alternatives described herein in any way, e.g., one, two, or three or more alternatives may be combinable in whole or in part. Further, any of the features of an alternative of the first through eleventh aspects may be made optional to other aspects or alternatives. Although described above in terms of various example alternatives and implementations, it should be understood that the various features, aspects and functionality described in one or more of the individual alternatives are not limited in their applicability to the particular alternative with which they are described, but instead may be applied, alone or in various combinations, to one or more of the other alternatives of the present application, whether or not such alternatives are described and whether or not such features are presented as being a part of a described alternative. Thus, the breadth and scope of the present application should not be limited by any of the above-described example alternatives.

All references cited herein are incorporated herein by reference in their entirety. To the extent publications and patents or patent applications incorporated by reference contradict the disclosure contained in the specification, the specification is intended to supersede and/or take precedence over any such contradictory material. To the extent publications and patents or patent applications incorporated by reference herein contradict the disclosure contained in the specification, the specification is intended to supersede and/or take precedence over any such contradictory material.

What is claimed is:

1. A system for inducible expression of a first polynucleotide in a cell, the system comprising:

a) a first nucleic acid comprising a first promoter inducible by a drug, wherein the first nucleic acid is operably linked to the first polynucleotide;

b) a second nucleic acid comprising a second promoter operably linked to a second polynucleotide encoding a transcriptional activator for the first promoter, wherein the transcriptional activator comprises an amino acid sequence set forth in any one of SEQ ID NOs: 1-11 or 121; and c) a stimulator selected from phorbol 12-myristate 13-acetate (PMA), ionomycin, or a combination thereof.

2. The system of claim 1, wherein the system is inducible by an amount of the drug less than an amount of the drug in a system in which the transcriptional activator is HEA3, or the system has an enhanced level of transcriptional expression of the first polynucleotide at a given concentration of the drug compared to a system in which the transcriptional activator is HEA3.

3. The system of claim 1, wherein the drug is selected from tamoxifen, a metabolite of tamoxifen, an analog of tamoxifen, a salt of tamoxifen, a hydrate of tamoxifen, 4-hydroxytamoxifen, fulvestrant, an estrogen analog, and CMP8.

4. The system of claim 1, wherein the drug induces expression of the first polynucleotide at a concentration of less than 10 nM.

5. The system of claim 1, wherein the transcriptional activator comprises the amino acid sequence set forth in any one of SEQ ID NOs: 1-3, 8-11 or 121.

6. The system of claim 5, wherein the transcriptional activator comprises the amino acid sequence set forth in any one of SEQ ID NOs: 2, 3, 8-11 or 121.

7. The system of claim 6, wherein the transcriptional activator comprises the amino acid sequence set forth in SEQ ID NO: 121.

8. The system of claim 1, wherein the transcriptional activator comprises the amino acid sequence set forth in any one of SEQ ID NOs: 4-7.

9. The system of claim 1, wherein the first promoter comprises the nucleic acid sequence set forth in SEQ ID NO: 23.

10. The system of claim 1, wherein the second promoter is a constitutive promoter.

11. The system of claim 1, wherein a first vector comprises the first nucleic acid and a second vector comprises the second nucleic acid.

12. The system of claim 1, wherein the first polynucleotide encodes a chimeric antigen receptor, a cytokine, a chemokine receptor, a chimeric cytokine receptor, or a microRNA.

13. The system of claim 1, further comprising an activating stimulator comprising an anti-CD3 antibody or an anti-CD28 antibody; and the drug.

14. The system of claim 1, wherein a host cell comprises the first nucleic acid and the second nucleic acid.

15. A host cell comprising the system of claim 1.

16. The host cell of claim 15, wherein the host cell is selected from a precursor T cell; a hematopoietic stem cell; a CD8+T cytotoxic lymphocyte cell selected from the group consisting of a naïve CD8+ T cell, a central memory CD8+ T cell, an effector memory CD8+ T cell, and a bulk CD8+ T cell; and a CD4+T helper lymphocyte cell selected from the group consisting of a naïve CD4+ T cell, a central memory CD4+ T cell, an effector memory CD4+ T cell, and a bulk CD4+ T cell.

17. A composition comprising the host cell of claim 15, and a pharmaceutically acceptable excipient.

18. An in vitro method for preparing a host cell comprising:

a) providing a system of claim 1;

b) introducing the first nucleic acid and the second nucleic acid into an isolated T lymphocyte population; and c) expanding the isolated T lymphocyte population in vitro.

19. The method of claim 18, further comprising:

d) culturing the isolated T lymphocyte population in the presence of an anti-CD3 antibody, an anti-CD28 antibody, and at least one homeostatic cytokine.

20. A method of treating, inhibiting, or ameliorating a disorder in a subject, comprising:

administering the host cell of claim 15 to the subject in combination with a drug that induces expression of the first polynucleotide in the host cell for the treatment of the disorder.

* * * * *

SEQUENCE LISTING

```
<160> NUMBER OF SEQ ID NOS: 124

<210> SEQ ID NO 1
<211> LENGTH: 862
<212> TYPE: PRT
<213> ORGANISM: Artificial Sequence
<220> FEATURE:
<223> OTHER INFORMATION: chimeric transcription factor composed of human
      subunits

<400> SEQUENCE: 1

Met Val Ser Lys Leu Ser Gln Leu Gln Thr Glu Leu Leu Ala Ala Leu
1               5                   10                  15
```

-continued

```
Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
```

-continued

```
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Arg Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Lys Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Ser Ser Ile
        835                 840                 845

Ala Asp Met Asp Phe Ser Ala Leu Leu Ser Gln Ile Ser Ser
    850                 855                 860
```

<210> SEQ ID NO 2
<211> LENGTH: 862
<212> TYPE: PRT
<213> ORGANISM: Artificial Sequence
<220> FEATURE:
<223> OTHER INFORMATION: HEA3 transcription factor with one point
      mutation in the p65 domain

<400> SEQUENCE: 2

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
```

```
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Arg Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Lys Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780
```

Phe Gln Gln Leu Leu Asn Gln Gly Ile Pro Val Ala Pro His Thr Thr
785 790 795 800

Glu Pro Met Leu Met Glu Tyr Pro Glu Ala Ile Thr Arg Leu Val Thr
805 810 815

Gly Ala Gln Arg Pro Pro Asp Pro Ala Pro Ala Pro Leu Gly Ala Pro
820 825 830

Gly Leu Pro Asn Gly Leu Leu Ser Gly Asp Glu Asp Phe Glu Ser Ile
835 840 845

Ala Asp Met Asp Phe Ser Ala Leu Leu Ser Gln Ile Ser Ser
850 855 860

<210> SEQ ID NO 3
<211> LENGTH: 862
<212> TYPE: PRT
<213> ORGANISM: Artificial Sequence
<220> FEATURE:
<223> OTHER INFORMATION: HEA3 containing one point mutation in the p65 domain

<400> SEQUENCE: 3

Met Val Ser Lys Leu Ser Gln Leu Gln Thr Glu Leu Leu Ala Ala Leu
1 5 10 15

Leu Glu Ser Gly Leu Ser Lys Glu Ala Leu Ile Gln Ala Leu Gly Glu
20 25 30

Pro Gly Pro Tyr Leu Leu Ala Gly Glu Gly Pro Leu Asp Lys Gly Glu
35 40 45

Ser Cys Gly Gly Gly Arg Gly Glu Leu Ala Glu Leu Pro Asn Gly Leu
50 55 60

Gly Glu Thr Arg Gly Ser Glu Asp Glu Thr Asp Asp Asp Gly Glu Asp
65 70 75 80

Phe Thr Pro Pro Ile Leu Lys Glu Leu Glu Asn Leu Ser Pro Glu Glu
85 90 95

Ala Ala His Gln Lys Ala Val Val Glu Thr Leu Leu Gln Glu Asp Pro
100 105 110

Trp Arg Val Ala Lys Met Val Lys Ser Tyr Leu Gln Gln His Asn Ile
115 120 125

Pro Gln Arg Glu Val Val Asp Thr Thr Gly Leu Asn Gln Ser His Leu
130 135 140

Ser Gln His Leu Asn Lys Gly Thr Pro Met Lys Thr Gln Lys Arg Ala
145 150 155 160

Ala Leu Tyr Thr Trp Tyr Val Arg Lys Gln Arg Glu Val Ala Gln Gln
165 170 175

Phe Thr His Ala Gly Gln Gly Gly Leu Ile Glu Glu Pro Thr Gly Asp
180 185 190

Glu Leu Pro Thr Lys Lys Gly Arg Arg Asn Arg Phe Lys Trp Gly Pro
195 200 205

Ala Ser Gln Gln Ile Leu Phe Gln Ala Tyr Glu Arg Gln Lys Asn Pro
210 215 220

Ser Lys Glu Glu Arg Glu Thr Leu Val Glu Glu Cys Asn Arg Ala Glu
225 230 235 240

Cys Ile Gln Arg Gly Val Ser Pro Ser Gln Ala Gln Gly Leu Gly Ser
245 250 255

Asn Leu Val Thr Glu Val Arg Val Tyr Asn Trp Phe Ala Asn Arg Arg
260 265 270

Lys Glu Glu Ala Phe Arg His Lys Leu Ser Ala Gly Asp Met Arg Ala

-continued

```
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Arg Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Gln Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700
```

Ala Pro Ala Pro Ala Met Val Ser Ala Leu Ala Gln Ala Pro Ala Pro
705 710 715 720

Val Pro Val Leu Ala Pro Gly Pro Pro Gln Ala Val Ala Pro Pro Ala
725 730 735

Pro Lys Pro Thr Gln Ala Gly Glu Gly Thr Leu Ser Glu Ala Leu Leu
740 745 750

Gln Leu Gln Phe Asp Asp Glu Asp Leu Gly Ala Leu Leu Gly Asn Ser
755 760 765

Thr Asp Pro Ala Val Phe Thr Asp Leu Ala Ser Val Asp Asn Ser Glu
770 775 780

Phe Gln Gln Leu Leu Asn Gln Gly Ile Pro Val Ala Pro His Thr Thr
785 790 795 800

Glu Pro Met Leu Met Glu Tyr Pro Glu Ala Ile Thr Arg Leu Val Thr
805 810 815

Gly Ala Gln Arg Pro Pro Asp Pro Ala Pro Ala Pro Leu Gly Ala Pro
820 825 830

Gly Leu Pro Asn Gly Leu Leu Ser Gly Asp Glu Asp Phe Ser Ser Ile
835 840 845

Ala Asp Met Asp Phe Ser Ala Leu Leu Ser Gln Ile Ser Ser
850 855 860

<210> SEQ ID NO 4
<211> LENGTH: 862
<212> TYPE: PRT
<213> ORGANISM: Artificial Sequence
<220> FEATURE:
<223> OTHER INFORMATION: HEA4 comprising at least three mutations

<400> SEQUENCE: 4

Met Val Ser Lys Leu Ser Gln Leu Gln Thr Glu Leu Leu Ala Ala Leu
1 5 10 15

Leu Glu Ser Gly Leu Ser Lys Glu Ala Leu Ile Gln Ala Leu Gly Glu
20 25 30

Pro Gly Pro Tyr Leu Leu Ala Gly Glu Gly Pro Leu Asp Lys Gly Glu
35 40 45

Ser Cys Gly Gly Gly Arg Gly Glu Leu Ala Glu Leu Pro Asn Gly Leu
50 55 60

Gly Glu Thr Arg Gly Ser Glu Asp Glu Thr Asp Asp Asp Gly Glu Asp
65 70 75 80

Phe Thr Pro Pro Ile Leu Lys Glu Leu Glu Asn Leu Ser Pro Glu Glu
85 90 95

Ala Ala His Gln Lys Ala Val Val Glu Thr Leu Leu Gln Glu Asp Pro
100 105 110

Trp Arg Val Ala Lys Met Val Lys Ser Tyr Leu Gln Gln His Asn Ile
115 120 125

Pro Gln Arg Glu Val Val Asp Thr Thr Gly Leu Asn Gln Ser His Leu
130 135 140

Ser Gln His Leu Asn Lys Gly Thr Pro Met Lys Thr Gln Lys Arg Ala
145 150 155 160

Ala Leu Tyr Thr Trp Tyr Val Arg Lys Gln Arg Glu Val Ala Gln Gln
165 170 175

Phe Thr His Ala Gly Gln Gly Gly Leu Ile Glu Glu Pro Thr Gly Asp
180 185 190

Glu Leu Pro Thr Lys Lys Gly Arg Arg Asn Arg Phe Lys Trp Gly Pro
195 200 205

```
Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Ala Ala
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Lys Ser Ile Met
    610                 615                 620
```

```
Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Ser Ser Ile
        835                 840                 845

Ala Asp Met Asp Phe Ser Ala Leu Leu Ser Gln Ile Ser Ser
    850                 855                 860


<210> SEQ ID NO 5
<211> LENGTH: 862
<212> TYPE: PRT
<213> ORGANISM: Artificial Sequence
<220> FEATURE:
<223> OTHER INFORMATION: HEA4 containing one point mutation in the p65
      domain

<400> SEQUENCE: 5

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125
```

```
Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Ala Ala
    530                 535                 540
```

```
Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Lys Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Glu Ser Ile
        835                 840                 845

Ala Asp Met Asp Phe Ser Ala Leu Leu Ser Gln Ile Ser Ser
    850                 855                 860
```

<210> SEQ ID NO 6
<211> LENGTH: 862
<212> TYPE: PRT
<213> ORGANISM: Artificial Sequence
<220> FEATURE:
<223> OTHER INFORMATION: HEA4 containing one point mutation in the p65 domain

<400> SEQUENCE: 6

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45
```

-continued

```
Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460
```

```
Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Ala Ala
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Gln Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Ser Ser Ile
        835                 840                 845

Ala Asp Met Asp Phe Ser Ala Leu Leu Ser Gln Ile Ser Ser
    850                 855                 860
```

<210> SEQ ID NO 7
<211> LENGTH: 862
<212> TYPE: PRT

```
<213> ORGANISM: Artificial Sequence
<220> FEATURE:
<223> OTHER INFORMATION: HEA4 containing two point mutations in the p65
      domain that enhance transcriptional activity

<400> SEQUENCE: 7

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380
```

-continued

```
Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Ala Ala
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Gln Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
```

```
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Glu Ser Ile
        835                 840                 845

Ala Asp Met Asp Phe Ser Ala Leu Leu Ser Gln Ile Ser Ser
    850                 855                 860


<210> SEQ ID NO 8
<211> LENGTH: 862
<212> TYPE: PRT
<213> ORGANISM: Artificial Sequence
<220> FEATURE:
<223> OTHER INFORMATION: HEA3 containing three point mutations in the
      ER-LBD

<400> SEQUENCE: 8

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300
```

```
Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Met
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Gly Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Arg Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Lys Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
```

```
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Ser Ser Ile
        835                 840                 845

Ala Asp Met Asp Phe Ser Ala Leu Leu Ser Gln Ile Ser Ser
    850                 855                 860


<210> SEQ ID NO 9
<211> LENGTH: 862
<212> TYPE: PRT
<213> ORGANISM: Artificial Sequence
<220> FEATURE:
<223> OTHER INFORMATION: CMP8-HEA3 containing one point mutation in the
      p65 domain

<400> SEQUENCE: 9

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220
```

-continued

```
Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Met
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Gly Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Arg Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Lys Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
```

```
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Glu Ser Ile
        835                 840                 845

Ala Asp Met Asp Phe Ser Ala Leu Leu Ser Gln Ile Ser Ser
    850                 855                 860


<210> SEQ ID NO 10
<211> LENGTH: 862
<212> TYPE: PRT
<213> ORGANISM: Artificial Sequence
<220> FEATURE:
<223> OTHER INFORMATION: CMP8-HEA3 containing one point mutation in the
      p65 domain

<400> SEQUENCE: 10

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140
```

```
Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Met
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Gly Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Arg Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
```

-continued

```
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Gln Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Ser Ser Ile
        835                 840                 845

Ala Asp Met Asp Phe Ser Ala Leu Leu Ser Gln Ile Ser Ser
    850                 855                 860


<210> SEQ ID NO 11
<211> LENGTH: 862
<212> TYPE: PRT
<213> ORGANISM: Artificial Sequence
<220> FEATURE:
<223> OTHER INFORMATION: CMP8-HEA3 containing two point mutations in the
      p65 domain

<400> SEQUENCE: 11

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60
```

-continued

```
Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Met
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Gly Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
```

```
                485                 490                 495

Leu Gln Gln Gln His Gln Arg Leu Ala Gln Leu Leu Leu Ile Leu Ser
            500                 505                 510

His Ile Arg His Met Ser Asn Lys Arg Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Gln Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780

Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Glu Ser Ile
        835                 840                 845

Ala Asp Met Asp Phe Ser Ala Leu Leu Ser Gln Ile Ser Ser
    850                 855                 860


<210> SEQ ID NO 12
<211> LENGTH: 2586
<212> TYPE: DNA
<213> ORGANISM: Unknown
<220> FEATURE:
<223> OTHER INFORMATION: variant of the wild type HEA3 transcription
      factor
```

<400> SEQUENCE: 12

```
atggtgtcca agctgtccca gctgcagaca gaactgctgg cagcactgct ggaaagcggc     60
ctgagcaaag aggccctgat tcaggcactc ggcgaacctg gaccttatct gctcgctggc    120
gaaggccctc tggataaggg cgagagctgt ggcggaggaa gaggagagct ggccgagctg    180
cctaacggcc tgggcgagac aagaggcagc gaggacgaga cagacgacga cggcgaggac    240
ttcacccccc ccatcctgaa agagctggaa aacctgagcc ccgaggaagc cgcccaccag    300
aaagccgtgg tggagacact gctgcaggaa gatccctggc gggtcgccaa gatggtcaag    360
agctacctgc agcagcacaa catcccccag cgggaggtgg tggacaccac cggcctgaac    420
cagagccacc tgagccagca cctgaacaag ggcacccca tgaaaaccca gaagagagcc    480
gccctgtaca cttggtacgt gcggaagcag agagaggtgg cccagcagtt tacacacgcc    540
ggccagggcg gcctgatcga ggaacctacc ggcgacgagc tgcccaccaa gaagggcaga    600
cggaaccggt ttaagtgggg ccctgcatct cagcagatcc tgttccaggc ctacgagcgg    660
cagaagaacc ccagcaaaga ggaacgggag acactggtgg aagagtgcaa ccgggccgag    720
tgcatccaga gaggcgtgag cccttctcag gctcagggcc tcggcagcaa tctggtcacc    780
gaagtgcggg tgtacaattg gttcgccaac cggcggaaag aggaagcctt ccggcacaag    840
ctgtctgctg gcgatatgag agccgccaac ctgtggccca gcccccctgat gatcaagcgg    900
agcaagaaga acagcctggc cctgagcctg accgccgatc agatggtgtc cgctctgctg    960
gacgccgagc cccctatcct gtacagcgag tacgacccca ccagaccctt cagcgaggcc   1020
agcatgatgg gcctgctgac caacctggcc gaccgggagc tggtgcacat gatcaactgg   1080
gccaagcggg tgcccggctt cgtggacctg accctgcacg accaggtcca cctgctggaa   1140
tgtgcctggc tggaaatcct gatgatcggc ctcgtgtgga gaagcatgga acaccccggc   1200
aagctgctgt tcgcccccaa cctgctcctg gaccggaacc agggaaagtg cgtggagggc   1260
atggtggaga tcttcgacat gctgctggcc acctccagcc ggttccggat gatgaacctg   1320
cagggcgagg aattcgtgtg cctgaagtcc atcatcctgc tgaacagcgg cgtgtacacc   1380
ttcctgtcat ccaccctgaa gtccctggaa gagaaggacc acatccaccg ggtgctggac   1440
aagatcaccg acaccctgat ccacctgatg gccaaggctg gcctgacact ccagcagcag   1500
caccagagac tggcccagct gctgctgatc ctgagccaca tccggcacat gagcaacaag   1560
cggatggaac acctgtacag catgaagtgc aagaacgtgg tgcccctgta cgacctgctg   1620
ctcgagatgc tggatgccca cagactgcac gcccctacaa gcagaggcgg agccagcgtg   1680
gaggaaaccg accagtctca cctggccacc gccggcagca caagcagcca cagcctgcag   1740
aagtactaca tcaccggcga ggccgaggga ttccctgcca ccgtggagtt ccagtacctg   1800
cccgacaccg acgaccggca ccggatcgag gaaaagcgga agcggaccta cgagacattc   1860
aagagcatca tgaagaagtc cccccttcagc ggccccaccg atcccagacc ccccctaga   1920
agaatcgccg tgcccagcag atctagcgcc agcgtgccca agcctgcccc ccagccctac   1980
cctttcacca gcagcctgag caccatcaac tacgacgagt tccctaccat ggtgttcccc   2040
agcggccaga tctctcaggc ctctgctctg gcacctgctc cacctcaggt gctgcctcag   2100
gcccctgctc cagccccagc ccctgccatg gtgtctgcac tggcccaggc tccagctcct   2160
gtgcctgtgc tggcccctgg acctcctcag gctgtggccc ctcctgcccc taaacctacc   2220
caggccgggg agggaacact gtctgaggcc ctgctgcagc tccagttcga cgacgaggat   2280
```

-continued

```
ctgggagcac tgctgggcaa tagcaccgac cccgccgtgt ttaccgacct ggcctccgtg   2340

gacaacagcg agttccagca gctcctcaac cagggcatcc ctgtcgcccc acacaccacc   2400

gagcccatgc tgatggaata ccccgaggcc atcaccagac tggtcacagg cgcccagagg   2460

cctccagatc cagcaccagc tccactggga gcccctggcc tgcctaatgg gctgctgtct   2520

ggcgacgagg acttctccag cattgccgac atggacttca gcgccctgct gtcccagatc   2580

agcagc                                                              2586
```

```
<210> SEQ ID NO 13
<211> LENGTH: 2586
<212> TYPE: DNA
<213> ORGANISM: Unknown
<220> FEATURE:
<223> OTHER INFORMATION: variant of the wild type HEA3 transcription
      factor

<400> SEQUENCE: 13

atggtgtcca agctgtccca gctgcagaca gaactgctgg cagcactgct ggaaagcggc     60

ctgagcaaag aggccctgat tcaggcactc ggcgaacctg gaccttatct gctcgctggc    120

gaaggccctc tggataaggg cgagagctgt ggcggaggaa gaggagagct ggccgagctg    180

cctaacggcc tgggcgagac aagaggcagc gaggacgaga cagacgacga cggcgaggac    240

ttcacccccc ccatcctgaa agagctggaa aacctgagcc ccgaggaagc cgcccaccag    300

aaagccgtgg tggagacact gctgcaggaa gatccctggc gggtcgccaa gatggtcaag    360

agctacctgc agcagcacaa catcccccag cgggaggtgg tggacaccac cggcctgaac    420

cagagccacc tgagccagca cctgaacaag ggcaccccca tgaaaaccca gaagagagcc    480

gccctgtaca cttggtacgt gcggaagcag agagaggtgg cccagcagtt tacacacgcc    540

ggccagggcg gcctgatcga ggaacctacc ggcgacgagc tgcccaccaa gaagggcaga    600

cggaaccggt ttaagtgggg ccctgcatct cagcagatcc tgttccaggc ctacgagcgg    660

cagaagaacc ccagcaaaga ggaacgggag acactggtgg aagagtgcaa ccgggccgag    720

tgcatccaga gaggcgtgag cccttctcag gctcagggcc tcggcagcaa tctggtcacc    780

gaagtgcggg tgtacaattg gttcgccaac cggcggaaag aggaagcctt ccggcacaag    840

ctgtctgctg gcgatatgag agccgccaac ctgtggccca gcccccctgat gatcaagcgg    900

agcaagaaga acagcctggc cctgagcctg accgccgatc agatggtgtc cgctctgctg    960

gacgccgagc cccctatcct gtacagcgag tacgacccca ccagaccctt cagcgaggcc   1020

agcatgatgg gcctgctgac caacctggcc gaccgggagc tggtgcacat gatcaactgg   1080

gccaagcggg tgcccggctt cgtggacctg accctgcacg accaggtcca cctgctggaa   1140

tgtgcctggc tggaaatcct gatgatcggc ctcgtgtgga gaagcatgga acaccccggc   1200

aagctgctgt tcgcccccaa cctgctcctg gaccggaacc agggaaagtg cgtggagggc   1260

atggtggaga tcttcgacat gctgctggcc acctccagcc ggttccggat gatgaacctg   1320

cagggcgagg aattcgtgtg cctgaagtcc atcatcctgc tgaacagcgg cgtgtacacc   1380

ttcctgtcat ccaccctgaa gtccctggaa gagaaggacc acatccaccg ggtgctggac   1440

aagatcaccg acaccctgat ccacctgatg gccaaggctg gcctgacact ccagcagcag   1500

caccagagac tggcccagct gctgctgatc ctgagccaca tccggcacat gagcaacaag   1560

cggatggaac acctgtacag catgaagtgc aagaacgtgg tgcccctgta cgacctgctg   1620

ctcgagatgc tggatgccca cagactgcac gcccctacaa gcagaggcgg agccagcgtg   1680
```

```
gaggaaaccg accagtctca cctggccacc gccggcagca caagcagcca cagcctgcag   1740

aagtactaca tcaccggcga ggccgaggga ttccctgcca ccgtggagtt ccagtacctg   1800

cccgacaccg acgaccggca ccggatcgag gaaaagcgga agcggaccta cgagacattc   1860

aagagcatca tgaagaagtc cccccttcagc ggccccaccg atcccagacc cccccctaga   1920

agaatcgccg tgcccagcag atctagcgcc agcgtgccca agcctgcccc ccagccctac   1980

cctttcacca gcagcctgag caccatcaac tacgacgagt tccctaccat ggtgttcccc   2040

agcggccaga tctctcaggc ctctgctctg gcacctgctc cacctcaggt gctgcctcag   2100

gcccctgctc cagccccagc ccctgccatg gtgtctgcac tggcccaggc tccagctcct   2160

gtgcctgtgc tggcccctgg acctcctcag gctgtggccc ctcctgcccc taaacctacc   2220

caggccgggg agggaacact gtctgaggcc ctgctgcagc tccagttcga cgacgaggat   2280

ctgggagcac tgctgggcaa tagcaccgac cccgccgtgt ttaccgacct ggcctccgtg   2340

gacaacagcg agttccagca gctcctcaac cagggcatcc ctgtcgcccc acacaccacc   2400

gagcccatgc tgatggaata ccccgaggcc atcaccagac tggtcacagg cgcccagagg   2460

cctccagatc cagcaccagc tccactggga gcccctggcc tgcctaatgg gctgctgtct   2520

ggcgacgagg acttcgagag cattgccgac atggacttca gcgccctgct gtcccagatc   2580

agcagc                                                              2586
```

```
<210> SEQ ID NO 14
<211> LENGTH: 2586
<212> TYPE: DNA
<213> ORGANISM: Unknown
<220> FEATURE:
<223> OTHER INFORMATION: variant of the wild type HEA3 transcription
      factor

<400> SEQUENCE: 14

atggtgtcca agctgtccca gctgcagaca gaactgctgg cagcactgct ggaaagcggc     60

ctgagcaaag aggccctgat tcaggcactc ggcgaacctg gaccttatct gctcgctggc    120

gaaggccctc tggataaggg cgagagctgt ggcggaggaa gaggagagct ggccgagctg    180

cctaacggcc tgggcgagac aagaggcagc gaggacgaga cagacgacga cggcgaggac    240

ttcaccccccc ccatcctgaa agagctggaa aacctgagcc ccgaggaagc cgcccaccag    300

aaagccgtgg tggagacact gctgcaggaa gatccctggc gggtcgccaa gatggtcaag    360

agctacctgc agcagcacaa catcccccag cgggaggtgg tggacaccac cggcctgaac    420

cagagccacc tgagccagca cctgaacaag ggcacccccca tgaaaaccca gaagagagcc    480

gccctgtaca cttggtacgt gcggaagcag agagaggtgg cccagcagtt tacacacgcc    540

ggccagggcg gcctgatcga ggaacctacc ggcgacgagc tgcccaccaa gaagggcaga    600

cggaaccggt ttaagtgggg ccctgcatct cagcagatcc tgttccaggc ctacgagcgg    660

cagaagaacc ccagcaaaga ggaacgggag acactggtgg aagagtgcaa ccgggccgag    720

tgcatccaga gaggcgtgag cccttctcag gctcagggcc tcggcagcaa tctggtcacc    780

gaagtgcggg tgtacaattg gttcgccaac cggcggaaag aggaagcctt ccggcacaag    840

ctgtctgctg gcgatatgag agccgccaac ctgtggccca gccccctgat gatcaagcgg    900

agcaagaaga acagcctggc cctgagcctg accgccgatc agatggtgtc cgctctgctg    960

gacgccgagc cccctatcct gtacagcgag tacgacccca ccagaccctt cagcgaggcc   1020

agcatgatgg gcctgctgac caacctggcc gaccgggagc tggtgcacat gatcaactgg   1080
```

gccaagcggg tgcccggctt cgtggacctg accctgcacg accaggtcca cctgctggaa 1140
tgtgcctggc tggaaatcct gatgatcggc ctcgtgtgga gaagcatgga acaccccggc 1200
aagctgctgt tcgcccccaa cctgctcctg gaccggaacc agggaaagtg cgtggagggc 1260
atggtggaga tcttcgacat gctgctggcc acctccagcc ggttccggat gatgaacctg 1320
cagggcgagg aattcgtgtg cctgaagtcc atcatcctgc tgaacagcgg cgtgtacacc 1380
ttcctgtcat ccaccctgaa gtccctggaa gagaaggacc acatccaccg ggtgctggac 1440
aagatcaccg acaccctgat ccacctgatg gccaaggctg gcctgacact ccagcagcag 1500
caccagagac tggcccagct gctgctgatc ctgagccaca tccggcacat gagcaacaag 1560
cggatggaac acctgtacag catgaagtgc aagaacgtgg tgcccctgta cgacctgctg 1620
ctcgagatgc tggatgccca cagactgcac gcccctacaa gcagaggcgg agccagcgtg 1680
gaggaaaccg accagtctca cctggccacc gccggcagca caagcagcca cagcctgcag 1740
aagtactaca tcaccggcga ggccgaggga ttccctgcca ccgtggagtt ccagtacctg 1800
cccgacaccg acgaccggca ccggatcgag gaaaagcgga agcggaccta cgagacattc 1860
cagagcatca tgaagaagtc cccctcagc ggccccaccg atcccagacc ccccctaga 1920 agaatcgccg tgcccagcag atctagcgcc agcgtgccca agcctgcccc ccagccctac 1980
cctttcacca gcagcctgag caccatcaac tacgacgagt tccctaccat ggtgttcccc 2040
agcggccaga tctctcaggc ctctgctctg gcacctgctc cacctcaggt gctgcctcag 2100
gcccctgctc cagccccagc ccctgccatg gtgtctgcac tggcccaggc tccagctcct 2160
gtgcctgtgc tggcccctgg acctcctcag gctgtggccc ctcctgcccc taaacctacc 2220
caggccgggg agggaacact gtctgaggcc ctgctgcagc tccagttcga cgacgaggat 2280
ctgggagcac tgctgggcaa tagcaccgac cccgccgtgt ttaccgacct ggcctccgtg 2340
gacaacagcg agttccagca gctcctcaac cagggcatcc ctgtcgcccc acacaccacc 2400
gagcccatgc tgatggaata ccccgaggcc atcaccagac tggtcacagg cgcccagagg 2460
cctccagatc cagcaccagc tccactggga gcccctggcc tgcctaatgg gctgctgtct 2520
ggcgacgagg acttctccag cattgccgac atggacttca gcgccctgct gtcccagatc 2580
agcagc 2586

<210> SEQ ID NO 15
<211> LENGTH: 2586
<212> TYPE: DNA
<213> ORGANISM: Unknown
<220> FEATURE:
<223> OTHER INFORMATION: variant of the wild type HEA4 transcription factor

<400> SEQUENCE: 15
atggtgtcca agctgtccca gctgcagaca gaactgctgg cagcactgct ggaaagcggc 60
ctgagcaaag aggccctgat tcaggcactc ggcgaacctg gaccttatct gctcgctggc 120
gaaggccctc tggataaggg cgagagctgt ggcggaggaa gaggagagct ggccgagctg 180
cctaacggcc tgggcgagac aagaggcagc gaggacgaga cagacgacga cggcgaggac 240
ttcacccccc ccatcctgaa agagctggaa aacctgagcc ccgaggaagc cgcccaccag 300
aaagccgtgg tggagacact gctgcaggaa gatccctggc gggtcgccaa gatggtcaag 360
agctacctgc agcagcacaa catcccccag cgggaggtgg tggacaccac cggcctgaac 420
cagagccacc tgagccagca cctgaacaag ggcacccca tgaaaaccca gaagagagcc 480

-continued

```
gccctgtaca cttggtacgt gcggaagcag agagaggtgg cccagcagtt tacacacgcc    540

ggccagggcg gcctgatcga ggaacctacc ggcgacgagc tgcccaccaa gaagggcaga    600

cggaaccggt ttaagtgggg ccctgcatct cagcagatcc tgttccaggc ctacgagcgg    660

cagaagaacc ccagcaaaga ggaacgggag acactggtgg aagagtgcaa ccgggccgag    720

tgcatccaga gaggcgtgag cccttctcag gctcagggcc tcggcagcaa tctggtcacc    780

gaagtgcggg tgtacaattg gttcgccaac cggcggaaag aggaagcctt ccggcacaag    840

ctgtctgctg gcgatatgag agccgccaac ctgtggccca gcccccctgat gatcaagcgg    900

agcaagaaga acagcctggc cctgagcctg accgccgatc agatggtgtc cgctctgctg    960

gacgccgagc cccctatcct gtacagcgag tacgacccca ccagaccctt cagcgaggcc   1020

agcatgatgg gcctgctgac caacctggcc gaccgggagc tggtgcacat gatcaactgg   1080

gccaagcggg tgcccggctt cgtggacctg accctgcacg accaggtcca cctgctggaa   1140

tgtgcctggc tggaaatcct gatgatcggc ctcgtgtgga gaagcatgga acaccccgtg   1200

aagctgctgt tcgcccccaa cctgctcctg gaccggaacc agggaaagtg cgtggagggc   1260

atggtggaga tcttcgacat gctgctggcc acctccagcc ggttccggat gatgaacctg   1320

cagggcgagg aattcgtgtg cctgaagtcc atcatcctgc tgaacagcgg cgtgtacacc   1380

ttcctgtcat ccaccctgaa gtccctggaa gagaaggacc acatccaccg ggtgctggac   1440

aagatcaccg acaccctgat ccacctgatg gccaaggctg gcctgacact ccagcagcag   1500

caccagagac tggcccagct gctgctgatc ctgagccaca tccggcacat gagcaacaag   1560

ggaatggaac acctgtacag catgaagtgc aagaacgtgg tgcccctgta cgacctgctg   1620

ctcgaggctg ccgatgccca cagactgcac gcccctacaa gcagaggcgg agccagcgtg   1680

gaggaaaccg accagtctca cctggccacc gccggcagca caagcagcca cagcctgcag   1740

aagtactaca tcaccggcga ggccgaggga ttccctgcca ccgtggagtt ccagtacctg   1800

cccgacaccg acgaccggca ccggatcgag gaaaagcgga agcggaccta cgagacattc   1860

aagagcatca tgaagaagtc cccccttcagc ggccccaccg atcccagacc cccccctaga   1920

agaatcgccg tgcccagcag atctagcgcc agcgtgccca agcctgcccc ccagccctac   1980

cctttcacca gcagcctgag caccatcaac tacgacgagt tccctaccat ggtgttcccc   2040

agcggccaga tctctcaggc ctctgctctg gcacctgctc cacctcaggt gctgcctcag   2100

gcccctgctc cagccccagc ccctgccatg gtgtctgcac tggcccaggc tccagctcct   2160

gtgcctgtgc tggcccctgg acctcctcag gctgtggccc ctcctgcccc taaacctacc   2220

caggccgggg agggaacact gtctgaggcc ctgctgcagc tccagttcga cgacgaggat   2280

ctgggagcac tgctgggcaa tagcaccgac cccgccgtgt ttaccgacct ggcctccgtg   2340

gacaacagcg agttccagca gctcctcaac cagggcatcc ctgtcgcccc acacaccacc   2400

gagcccatgc tgatggaata ccccgaggcc atcaccagac tggtcacagg cgcccagagg   2460

cctccagatc cagcaccagc tccactggga gcccctggcc tgcctaatgg gctgctgtct   2520

ggcgacgagg acttctccag cattgccgac atggacttca gcgccctgct gtcccagatc   2580

agcagc                                                               2586
```

<210> SEQ ID NO 16
<211> LENGTH: 2586
<212> TYPE: DNA
<213> ORGANISM: Unknown
<220> FEATURE:
<223> OTHER INFORMATION: variant of the wild type HEA4 transcription factor

<400> SEQUENCE: 16
atggtgtcca agctgtccca gctgcagaca gaactgctgg cagcactgct ggaaagcggc 60
ctgagcaaag aggccctgat tcaggcactc ggcgaacctg gaccttatct gctcgctggc 120
gaaggccctc tggataaggg cgagagctgt ggcggaggaa gaggagagct ggccgagctg 180
cctaacggcc tgggcgagac aagaggcagc gaggacgaga cagacgacga cggcgaggac 240
ttcacccccc ccatcctgaa agagctggaa aacctgagcc ccgaggaagc cgcccaccag 300
aaagccgtgg tggagacact gctgcaggaa gatccctggc gggtcgccaa gatggtcaag 360
agctacctgc agcagcacaa catcccccag cgggaggtgg tggacaccac cggcctgaac 420
cagagccacc tgagccagca cctgaacaag ggcaccccca tgaaaaccca gaagagagcc 480
gccctgtaca cttggtacgt gcggaagcag agagaggtgg cccagcagtt tacacacgcc 540
ggccagggcg gcctgatcga ggaacctacc ggcgacgagc tgcccaccaa gaagggcaga 600
cggaaccggt ttaagtgggg ccctgcatct cagcagatcc tgttccaggc ctacgagcgg 660
cagaagaacc ccagcaaaga ggaacgggag acactggtgg aagagtgcaa ccgggccgag 720
tgcatccaga gaggcgtgag cccttctcag gctcagggcc tcggcagcaa tctggtcacc 780
gaagtgcggg tgtacaattg gttcgccaac cggcggaaag aggaagcctt ccggcacaag 840
ctgtctgctg gcgatatgag agccgccaac ctgtggccca gcccccctgat gatcaagcgg 900
agcaagaaga acagcctggc cctgagcctg accgccgatc agatggtgtc cgctctgctg 960
gacgccgagc cccctatcct gtacagcgag tacgacccca ccagaccctt cagcgaggcc 1020
agcatgatgg gcctgctgac caacctggcc gaccgggagc tggtgcacat gatcaactgg 1080
gccaagcggg tgcccggctt cgtggacctg accctgcacg accaggtcca cctgctggaa 1140
tgtgcctggc tggaaatcct gatgatcggc ctcgtgtgga gaagcatgga acaccccgtg 1200
aagctgctgt tcgcccccaa cctgctcctg gaccggaacc agggaaagtg cgtggagggc 1260
atggtggaga tcttcgacat gctgctggcc acctccagcc ggttccggat gatgaacctg 1320
cagggcgagg aattcgtgtg cctgaagtcc atcatcctgc tgaacagcgg cgtgtacacc 1380
ttcctgtcat ccaccctgaa gtccctggaa gagaaggacc acatccaccg ggtgctggac 1440
aagatcaccg acaccctgat ccacctgatg gccaaggctg gcctgacact ccagcagcag 1500
caccagagac tggcccagct gctgctgatc ctgagccaca tccggcacat gagcaacaag 1560
ggaatggaac acctgtacag catgaagtgc aagaacgtgg tgcccctgta cgacctgctg 1620
ctcgaggctg ccgatgccca cagactgcac gcccctacaa gcagaggcgg agccagcgtg 1680
gaggaaaccg accagtctca cctggccacc gccggcagca caagcagcca cagcctgcag 1740
aagtactaca tcaccggcga ggccgaggga ttccctgcca ccgtggagtt ccagtacctg 1800
cccgacaccg acgaccggca ccggatcgag gaaaagcgga agcggaccta cgagacattc 1860
aagagcatca tgaagaagtc cccccttcagc ggccccaccg atcccagacc cccccctaga 1920
agaatcgccg tgcccagcag atctagcgcc agcgtgccca agcctgcccc ccagccctac 1980
cctttcacca gcagcctgag caccatcaac tacgacgagt tccctaccat ggtgttcccc 2040
agcggccaga tctctcaggc ctctgctctg gcacctgctc cacctcaggt gctgcctcag 2100
gcccctgctc cagccccagc ccctgccatg gtgtctgcac tggcccaggc tccagctcct 2160
gtgcctgtgc tggcccctgg acctcctcag gctgtggccc ctcctgcccc taaacctacc 2220
caggccgggg agggaacact gtctgaggcc ctgctgcagc tccagttcga cgacgaggat 2280
ctgggagcac tgctgggcaa tagcaccgac cccgccgtgt ttaccgacct ggcctccgtg 2340
gacaacagcg agttccagca gctcctcaac cagggcatcc ctgtcgcccc acacaccacc 2400
gagcccatgc tgatggaata ccccgaggcc atcaccagac tggtcacagg cgcccagagg 2460
cctccagatc cagcaccagc tccactggga gcccctggcc tgcctaatgg gctgctgtct 2520
ggcgacgagg acttcgagag cattgccgac atggacttca gcgccctgct gtcccagatc 2580
agcagc 2586

<210> SEQ ID NO 17
<211> LENGTH: 2586
<212> TYPE: DNA
<213> ORGANISM: Unknown
<220> FEATURE:
<223> OTHER INFORMATION: variant of the wild type HEA4 transcription
factor

<400> SEQUENCE: 17
atggtgtcca agctgtccca gctgcagaca gaactgctgg cagcactgct ggaaagcggc 60
ctgagcaaag aggccctgat tcaggcactc ggcgaacctg gaccttatct gctcgctggc 120
gaaggccctc tggataaggg cgagagctgt ggcggaggaa gaggagagct ggccgagctg 180
cctaacggcc tgggcgagac aagaggcagc gaggacgaga cagacgacga cggcgaggac 240
ttcacccccc ccatcctgaa agagctggaa aacctgagcc ccgaggaagc cgcccaccag 300
aaagccgtgg tggagacact gctgcaggaa gatccctggc gggtcgccaa gatggtcaag 360
agctacctgc agcagcacaa catcccccag cgggaggtgg tggacaccac cggcctgaac 420
cagagccacc tgagccagca cctgaacaag ggcacccccca tgaaaaccca gaagagagcc 480
gccctgtaca cttggtacgt gcggaagcag agagaggtgg cccagcagtt tacacacgcc 540
ggccagggcg gcctgatcga ggaacctacc ggcgacgagc tgcccaccaa gaagggcaga 600
cggaaccggt ttaagtgggg ccctgcatct cagcagatcc tgttccaggc ctacgagcgg 660
cagaagaacc ccagcaaaga ggaacgggag acactggtgg aagagtgcaa ccgggccgag 720
tgcatccaga gaggcgtgag cccttctcag gctcagggcc tcggcagcaa tctggtcacc 780
gaagtgcggg tgtacaattg gttcgccaac cggcggaaag aggaagcctt ccggcacaag 840
ctgtctgctg gcgatatgag agccgccaac ctgtggccca gccccctgat gatcaagcgg 900
agcaagaaga acagcctggc cctgagcctg accgccgatc agatggtgtc cgctctgctg 960
gacgccgagc cccctatcct gtacagcgag tacgacccca ccagaccctt cagcgaggcc 1020
agcatgatgg gcctgctgac caacctggcc gaccgggagc tggtgcacat gatcaactgg 1080
gccaagcggg tgcccggctt cgtggacctg accctgcacg accaggtcca cctgctggaa 1140
tgtgcctggc tggaaatcct gatgatcggc ctcgtgtgga gaagcatgga acacccccgtg 1200 aagctgctgt tcgcccccaa cctgctcctg gaccggaacc agggaaagtg cgtggagggc 1260
atggtggaga tcttcgacat gctgctggcc acctccagcc ggttccggat gatgaacctg 1320
cagggcgagg aattcgtgtg cctgaagtcc atcatcctgc tgaacagcgg cgtgtacacc 1380
ttcctgtcat ccaccctgaa gtccctggaa gagaaggacc acatccaccg ggtgctggac 1440
aagatcaccg acaccctgat ccacctgatg gccaaggctg gcctgacact ccagcagcag 1500
caccagagac tggcccagct gctgctgatc ctgagccaca tccggcacat gagcaacaag 1560
ggaatggaac acctgtacag catgaagtgc aagaacgtgg tgcccctgta cgacctgctg 1620
ctcgaggctg ccgatgccca cagactgcac gcccctacaa gcagaggcgg agccagcgtg 1680
gaggaaaccg accagtctca cctggccacc gccggcagca caagcagcca cagcctgcag 1740
aagtactaca tcaccggcga ggccgaggga ttccctgcca ccgtggagtt ccagtacctg 1800
cccgacaccg acgaccggca ccggatcgag gaaaagcgga agcggaccta cgagacattc 1860
cagagcatca tgaagaagtc cccccttcagc ggccccaccg atcccagacc ccccccctaga 1920 agaatcgccg tgcccagcag atctagcgcc agcgtgccca agcctgcccc ccagccctac 1980
cctttcacca gcagcctgag caccatcaac tacgacgagt tccctaccat ggtgttcccc 2040
agcggccaga tctctcaggc ctctgctctg gcacctgctc cacctcaggt gctgcctcag 2100
gcccctgctc cagccccagc ccctgccatg gtgtctgcac tggcccaggc tccagctcct 2160
gtgcctgtgc tggcccctgg acctcctcag gctgtggccc ctcctgcccc taaacctacc 2220
caggccgggg agggaacact gtctgaggcc ctgctgcagc tccagttcga cgacgaggat 2280
ctgggagcac tgctgggcaa tagcaccgac cccgccgtgt ttaccgacct ggcctccgtg 2340
gacaacagcg agttccagca gctcctcaac cagggcatcc ctgtcgcccc acacaccacc 2400
gagcccatgc tgatggaata ccccgaggcc atcaccagac tggtcacagg cgcccagagg 2460
cctccagatc cagcaccagc tccactggga gcccctggcc tgcctaatgg gctgctgtct 2520
ggcgacgagg acttctccag cattgccgac atggacttca gcgccctgct gtcccagatc 2580
agcagc 2586

<210> SEQ ID NO 18
<211> LENGTH: 2586
<212> TYPE: DNA
<213> ORGANISM: Unknown
<220> FEATURE:
<223> OTHER INFORMATION: variant of the wild type HEA4 transcription factor

<400> SEQUENCE: 18
atggtgtcca agctgtccca gctgcagaca gaactgctgg cagcactgct ggaaagcggc 60
ctgagcaaag aggccctgat tcaggcactc ggcgaacctg gaccttatct gctcgctggc 120
gaaggccctc tggataaggg cgagagctgt ggcggaggaa gaggagagct ggccgagctg 180
cctaacggcc tgggcgagac aagaggcagc gaggacgaga cagacgacga cggcgaggac 240
ttcacccccc ccatcctgaa agagctggaa aacctgagcc ccgaggaagc cgcccaccag 300
aaagccgtgg tggagacact gctgcaggaa gatccctggc gggtcgccaa gatggtcaag 360
agctacctgc agcagcacaa catcccccag cgggaggtgg tggacaccac cggcctgaac 420
cagagccacc tgagccagca cctgaacaag ggcacccccca tgaaaaccca gaagagagcc 480
gccctgtaca cttggtacgt gcggaagcag agagaggtgg cccagcagtt tacacacgcc 540
ggccagggcg gcctgatcga ggaacctacc ggcgacgagc tgcccaccaa gaagggcaga 600
cggaaccggt ttaagtgggg ccctgcatct cagcagatcc tgttccaggc ctacgagcgg 660
cagaagaacc ccagcaaaga ggaacgggag acactggtgg aagagtgcaa ccgggccgag 720
tgcatccaga gaggcgtgag cccttctcag gctcagggcc tcggcagcaa tctggtcacc 780
gaagtgcggg tgtacaattg gttcgccaac cggcggaaag aggaagcctt ccggcacaag 840
ctgtctgctg gcgatatgag agccgccaac ctgtggccca gcccccctgat gatcaagcgg 900 agcaagaaga acagcctggc cctgagcctg accgccgatc agatggtgtc cgctctgctg 960
gacgccgagc cccctatcct gtacagcgag tacgacccca ccagaccctt cagcgaggcc 1020
agcatgatgg gcctgctgac caacctggcc gaccgggagc tggtgcacat gatcaactgg 1080
gccaagcggg tgcccggctt cgtggacctg accctgcacg accaggtcca cctgctggaa 1140
tgtgcctggc tggaaatcct gatgatcggc ctcgtgtgga gaagcatgga acaccccgtg 1200
aagctgctgt tcgcccccaa cctgctcctg gaccggaacc agggaaagtg cgtggagggc 1260
atggtggaga tcttcgacat gctgctggcc acctccagcc ggttccggat gatgaacctg 1320
cagggcgagg aattcgtgtg cctgaagtcc atcatcctgc tgaacagcgg cgtgtacacc 1380
ttcctgtcat ccaccctgaa gtccctggaa gagaaggacc acatccaccg ggtgctggac 1440
aagatcaccg acaccctgat ccacctgatg gccaaggctg gcctgacact ccagcagcag 1500
caccagagac tggcccagct gctgctgatc ctgagccaca tccggcacat gagcaacaag 1560
ggaatggaac acctgtacag catgaagtgc aagaacgtgg tgcccctgta cgacctgctg 1620
ctcgaggctg ccgatgccca cagactgcac gcccctacaa gcagaggcgg agccagcgtg 1680
gaggaaaccg accagtctca cctggccacc gccggcagca caagcagcca cagcctgcag 1740
aagtactaca tcaccggcga ggccgaggga ttccctgcca ccgtggagtt ccagtacctg 1800
cccgacaccg acgaccggca ccggatcgag gaaaagcgga agcggaccta cgagacattc 1860
cagagcatca tgaagaagtc cccccttcagc ggccccaccg atcccagacc ccccccctaga 1920 agaatcgccg tgcccagcag atctagcgcc agcgtgccca agcctgcccc ccagccctac 1980
cctttcacca gcagcctgag caccatcaac tacgacgagt tccctaccat ggtgttcccc 2040
agcggccaga tctctcaggc ctctgctctg gcacctgctc cacctcaggt gctgcctcag 2100
gcccctgctc cagccccagc ccctgccatg gtgtctgcac tggcccaggc tccagctcct 2160
gtgcctgtgc tggcccctgg acctcctcag gctgtggccc ctcctgcccc taaacctacc 2220
caggccgggg agggaacact gtctgaggcc ctgctgcagc tccagttcga cgacgaggat 2280
ctgggagcac tgctgggcaa tagcaccgac cccgccgtgt ttaccgacct ggcctccgtg 2340
gacaacagcg agttccagca gctcctcaac cagggcatcc ctgtcgcccc acacaccacc 2400
gagcccatgc tgatggaata ccccgaggcc atcaccagac tggtcacagg cgcccagagg 2460
cctccagatc cagcaccagc tccactggga gcccctggcc tgcctaatgg gctgctgtct 2520
ggcgacgagg acttcgagag cattgccgac atggacttca gcgccctgct gtcccagatc 2580
agcagc 2586

<210> SEQ ID NO 19
<211> LENGTH: 2586
<212> TYPE: DNA
<213> ORGANISM: Unknown
<220> FEATURE:
<223> OTHER INFORMATION: variant of the wild type HEA3 transcription factor

<400> SEQUENCE: 19
atggtgtcca agctgtccca gctgcagaca gaactgctgg cagcactgct ggaaagcggc 60
ctgagcaaag aggccctgat tcaggcactc ggcgaacctg gaccttatct gctcgctggc 120
gaaggccctc tggataaggg cgagagctgt ggcggaggaa gaggagagct ggccgagctg 180
cctaacggcc tgggcgagac aagaggcagc gaggacgaga cagacgacga cggcgaggac 240
ttcacccccc ccatcctgaa agagctggaa aacctgagcc ccgaggaagc cgcccaccag 300
aaagccgtgg tggagacact gctgcaggaa gatccctggc gggtcgccaa gatggtcaag 360
agctacctgc agcagcacaa catcccccag cgggaggtgg tggacaccac cggcctgaac 420
cagagccacc tgagccagca cctgaacaag ggcacccccca tgaaaaccca gaagagagcc 480

-continued

```
gccctgtaca cttggtacgt gcggaagcag agagaggtgg cccagcagtt tacacacgcc    540
ggccagggcg gcctgatcga ggaacctacc ggcgacgagc tgcccaccaa gaagggcaga    600
cggaaccggt ttaagtgggg ccctgcatct cagcagatcc tgttccaggc ctacgagcgg    660
cagaagaacc ccagcaaaga ggaacgggag acactggtgg aagagtgcaa ccgggccgag    720
tgcatccaga gaggcgtgag cccttctcag gctcagggcc tcggcagcaa tctggtcacc    780
gaagtgcggg tgtacaattg gttcgccaac cggcggaaag aggaagcctt ccggcacaag    840
ctgtctgctg gcgatatgag agccgccaac ctgtggccca gcccccctgat gatcaagcgg    900
agcaagaaga acagcctggc cctgagcctg accgccgatc agatggtgtc cgctctgctg    960
gacgccgagc cccctatcct gtacagcgag tacgacccca ccagaccctt cagcgaggcc   1020
agcatgatgg gcctgctgac caacctggcc gaccgggagc tggtgcacat gatcaactgg   1080
gccaagcggg tgcccggctt cgtggacctg accctgcacg accaggtcca cctgctggaa   1140
tgtgcctgga tggaaatcct gatgatcggc ctcgtgtgga gaagcatgga acaccccggc   1200
aagctgctgt tcgcccccaa cctgctcctg gaccggaacc agggaaagtg cgtggagggc   1260
ggcgtggaga tcttcgacat gctgctggcc acctccagcc ggttccggat gatgaacctg   1320
cagggcgagg aattcgtgtg cctgaagtcc atcatcctgc tgaacagcgg cgtgtacacc   1380
ttcctgtcat ccaccctgaa gtccctggaa gagaaggacc acatccaccg ggtgctggac   1440
aagatcaccg acaccctgat ccacctgatg gccaaggctg gcctgacact ccagcagcag   1500
caccagagac tggcccagct gctgctgatc ctgagccaca tccggcacat gagcaacaag   1560
cggatggaac acctgtacag catgaagtgc aagaacgtgg tgcccctgta cgacctgctg   1620
ctcgagatgc tggatgccca cagactgcac gcccctacaa gcagaggcgg agccagcgtg   1680
gaggaaaccg accagtctca cctggccacc gccggcagca caagcagcca cagcctgcag   1740
aagtactaca tcaccggcga ggccgaggga ttccctgcca ccgtggagtt ccagtacctg   1800
cccgacaccg acgaccggca ccggatcgag gaaaagcgga agcggaccta cgagacattc   1860
aagagcatca tgaagaagtc cccccttcagc ggcccccaccg atcccagacc cccccctaga   1920
agaatcgccg tgcccagcag atctagcgcc agcgtgccca agcctgcccc ccagccctac   1980
cctttcacca gcagcctgag caccatcaac tacgacgagt tccctaccat ggtgttcccc   2040
agcggccaga tctctcaggc ctctgctctg gcacctgctc cacctcaggt gctgcctcag   2100
gcccctgctc cagccccagc ccctgccatg gtgtctgcac tggcccaggc tccagctcct   2160
gtgcctgtgc tggcccctgg acctcctcag gctgtggccc ctcctgcccc taaacctacc   2220
caggccgggg agggaacact gtctgaggcc ctgctgcagc tccagttcga cgacgaggat   2280
ctgggagcac tgctgggcaa tagcaccgac cccgccgtgt ttaccgacct ggcctccgtg   2340
gacaacagcg agttccagca gctcctcaac cagggcatcc ctgtcgcccc acacaccacc   2400
gagcccatgc tgatggaata ccccgaggcc atcaccagac tggtcacagg cgcccagagg   2460
cctccagatc cagcaccagc tccactggga gcccctggcc tgcctaatgg gctgctgtct   2520
ggcgacgagg acttctccag cattgccgac atggacttca gcgccctgct gtcccagatc   2580
agcagc                                                               2586
```

<210> SEQ ID NO 20
<211> LENGTH: 2586
<212> TYPE: DNA
<213> ORGANISM: Unknown
<220> FEATURE:

<223> OTHER INFORMATION: variant of the wild type HEA3 transcription factor

<400> SEQUENCE: 20
atggtgtcca agctgtccca gctgcagaca gaactgctgg cagcactgct ggaaagcggc 60
ctgagcaaag aggccctgat tcaggcactc ggcgaacctg gaccttatct gctcgctggc 120
gaaggccctc tggataaggg cgagagctgt ggcggaggaa gaggagagct ggccgagctg 180
cctaacggcc tgggcgagac aagaggcagc gaggacgaga cagacgacga cggcgaggac 240
ttcacccccc ccatcctgaa agagctggaa aacctgagcc ccgaggaagc cgcccaccag 300
aaagccgtgg tggagacact gctgcaggaa gatccctggc gggtcgccaa gatggtcaag 360
agctacctgc agcagcacaa catcccccag cgggaggtgg tggacaccac cggcctgaac 420
cagagccacc tgagccagca cctgaacaag ggcacccccca tgaaaaccca gaagagagcc 480
gccctgtaca cttggtacgt gcggaagcag agagaggtgg cccagcagtt tacacacgcc 540
ggccagggcg gcctgatcga ggaacctacc ggcgacgagc tgcccaccaa gaagggcaga 600
cggaaccggt ttaagtgggg ccctgcatct cagcagatcc tgttccaggc ctacgagcgg 660
cagaagaacc ccagcaaaga ggaacgggag acactggtgg aagagtgcaa ccgggccgag 720
tgcatccaga gaggcgtgag cccttctcag gctcagggcc tcggcagcaa tctggtcacc 780
gaagtgcggg tgtacaattg gttcgccaac cggcggaaag aggaagcctt ccggcacaag 840
ctgtctgctg gcgatatgag agccgccaac ctgtggccca gcccccctgat gatcaagcgg 900 agcaagaaga acagcctggc cctgagcctg accgccgatc agatggtgtc cgctctgctg 960
gacgccgagc cccctatcct gtacagcgag tacgacccca ccagaccctt cagcgaggcc 1020
agcatgatgg gcctgctgac caacctggcc gaccgggagc tggtgcacat gatcaactgg 1080
gccaagcggg tgcccggctt cgtggacctg accctgcacg accaggtcca cctgctggaa 1140
tgtgcctgga tggaaatcct gatgatcggc ctcgtgtgga gaagcatgga acaccccggc 1200
aagctgctgt tcgcccccaa cctgctcctg gaccggaacc agggaaagtg cgtggagggc 1260
ggcgtggaga tcttcgacat gctgctggcc acctccagcc ggttccggat gatgaacctg 1320
cagggcgagg aattcgtgtg cctgaagtcc atcatcctgc tgaacagcgg cgtgtacacc 1380
ttcctgtcat ccaccctgaa gtccctggaa gagaaggacc acatccaccg ggtgctggac 1440
aagatcaccg acaccctgat ccacctgatg gccaaggctg gcctgacact ccagcagcag 1500
caccagagac tggcccagct gctgctgatc ctgagccaca tccggcacat gagcaacaag 1560
cggatggaac acctgtacag catgaagtgc aagaacgtgg tgcccctgta cgacctgctg 1620
ctcgagatgc tggatgccca cagactgcac gcccctacaa gcagaggcgg agccagcgtg 1680
gaggaaaccg accagtctca cctggccacc gccggcagca caagcagcca cagcctgcag 1740
aagtactaca tcaccggcga ggccgaggga ttccctgcca ccgtggagtt ccagtacctg 1800
cccgacaccg acgaccggca ccggatcgag gaaaagcgga agcggaccta cgagacattc 1860
aagagcatca tgaagaagtc cccccttcagc ggccccaccg atcccagacc ccccccctaga 1920 agaatcgccg tgcccagcag atctagcgcc agcgtgccca agcctgcccc ccagccctac 1980
cctttcacca gcagcctgag caccatcaac tacgacgagt tccctaccat ggtgttcccc 2040
agcggccaga tctctcaggc ctctgctctg gcacctgctc cacctcaggt gctgcctcag 2100
gcccctgctc cagccccagc ccctgccatg gtgtctgcac tggcccaggc tccagctcct 2160
gtgcctgtgc tggcccctgg acctcctcag gctgtggccc ctcctgcccc taaacctacc 2220
caggccgggg agggaacact gtctgaggcc ctgctgcagc tccagttcga cgacgaggat 2280
ctgggagcac tgctgggcaa tagcaccgac cccgccgtgt ttaccgacct ggcctccgtg 2340
gacaacagcg agttccagca gctcctcaac cagggcatcc ctgtcgcccc acacaccacc 2400
gagcccatgc tgatggaata ccccgaggcc atcaccagac tggtcacagg cgcccagagg 2460
cctccagatc cagcaccagc tccactggga gcccctggcc tgcctaatgg gctgctgtct 2520
ggcgacgagg acttcgagag cattgccgac atggacttca gcgccctgct gtcccagatc 2580
agcagc 2586

<210> SEQ ID NO 21
<211> LENGTH: 2586
<212> TYPE: DNA
<213> ORGANISM: Unknown
<220> FEATURE:
<223> OTHER INFORMATION: variant of the wild type HEA3 transcription factor

<400> SEQUENCE: 21
atggtgtcca agctgtccca gctgcagaca gaactgctgg cagcactgct ggaaagcggc 60
ctgagcaaag aggccctgat tcaggcactc ggcgaacctg gaccttatct gctcgctggc 120
gaaggccctc tggataaggg cgagagctgt ggcggaggaa gaggagagct ggccgagctg 180
cctaacggcc tgggcgagac aagaggcagc gaggacgaga cagacgacga cggcgaggac 240
ttcacccccc ccatcctgaa agagctggaa aacctgagcc ccgaggaagc cgcccaccag 300
aaagccgtgg tggagacact gctgcaggaa gatccctggc gggtcgccaa gatggtcaag 360
agctacctgc agcagcacaa catcccccag cgggaggtgg tggacaccac cggcctgaac 420
cagagccacc tgagccagca cctgaacaag ggcaccccca tgaaaaccca gaagagagcc 480
gccctgtaca cttggtacgt gcggaagcag agagaggtgg cccagcagtt tacacacgcc 540
ggccagggcg gcctgatcga ggaacctacc ggcgacgagc tgcccaccaa gaagggcaga 600
cggaaccggt ttaagtgggg ccctgcatct cagcagatcc tgttccaggc ctacgagcgg 660
cagaagaacc ccagcaaaga ggaacgggag acactggtgg aagagtgcaa ccgggccgag 720
tgcatccaga gaggcgtgag cccttctcag gctcagggcc tcggcagcaa tctggtcacc 780
gaagtgcggg tgtacaattg gttcgccaac cggcggaaag aggaagcctt ccggcacaag 840
ctgtctgctg gcgatatgag agccgccaac ctgtggccca gcccccctgat gatcaagcgg 900 agcaagaaga acagcctggc cctgagcctg accgccgatc agatggtgtc cgctctgctg 960
gacgccgagc cccctatcct gtacagcgag tacgacccca ccagaccctt cagcgaggcc 1020
agcatgatgg gcctgctgac caacctggcc gaccgggagc tggtgcacat gatcaactgg 1080
gccaagcggg tgcccggctt cgtggacctg accctgcacg accaggtcca cctgctggaa 1140
tgtgcctgga tggaaatcct gatgatcggc ctcgtgtgga gaagcatgga acaccccggc 1200
aagctgctgt tcgcccccaa cctgctcctg gaccggaacc agggaaagtg cgtggagggc 1260
ggcgtggaga tcttcgacat gctgctggcc acctccagcc ggttccggat gatgaacctg 1320
cagggcgagg aattcgtgtg cctgaagtcc atcatcctgc tgaacagcgg cgtgtacacc 1380
ttcctgtcat ccaccctgaa gtccctggaa gagaaggacc acatccaccg ggtgctggac 1440
aagatcaccg acaccctgat ccacctgatg gccaaggctg gcctgacact ccagcagcag 1500
caccagagac tggcccagct gctgctgatc ctgagccaca tccggcacat gagcaacaag 1560
cggatggaac acctgtacag catgaagtgc aagaacgtgg tgcccctgta cgacctgctg 1620
ctcgagatgc tggatgccca cagactgcac gcccctacaa gcagaggcgg agccagcgtg 1680
gaggaaaccg accagtctca cctggccacc gccggcagca caagcagcca cagcctgcag 1740
aagtactaca tcaccggcga ggccgaggga ttccctgcca ccgtggagtt ccagtacctg 1800
cccgacaccg acgaccggca ccggatcgag gaaaagcgga agcggaccta cgagacattc 1860
cagagcatca tgaagaagtc cccccttcagc ggcccccaccg atcccagacc cccccctaga 1920
agaatcgccg tgcccagcag atctagcgcc agcgtgccca agcctgcccc ccagccctac 1980
cctttcacca gcagcctgag caccatcaac tacgacgagt tccctaccat ggtgttcccc 2040
agcggccaga tctctcaggc ctctgctctg gcacctgctc cacctcaggt gctgcctcag 2100
gcccctgctc cagccccagc ccctgccatg gtgtctgcac tggcccaggc tccagctcct 2160
gtgcctgtgc tggcccctgg acctcctcag gctgtggccc ctcctgcccc taaacctacc 2220
caggccgggg agggaacact gtctgaggcc ctgctgcagc tccagttcga cgacgaggat 2280
ctgggagcac tgctgggcaa tagcaccgac cccgccgtgt ttaccgacct ggcctccgtg 2340
gacaacagcg agttccagca gctcctcaac cagggcatcc ctgtcgcccc acacaccacc 2400
gagcccatgc tgatggaata ccccgaggcc atcaccagac tggtcacagg cgcccagagg 2460
cctccagatc cagcaccagc tccactggga gccccctggcc tgcctaatgg gctgctgtct 2520
ggcgacgagg acttctccag cattgccgac atggacttca gcgccctgct gtcccagatc 2580
agcagc 2586

<210> SEQ ID NO 22
<211> LENGTH: 2586
<212> TYPE: DNA
<213> ORGANISM: Unknown
<220> FEATURE:
<223> OTHER INFORMATION: variant of the wild type HEA3 transcription factor

<400> SEQUENCE: 22
atggtgtcca agctgtccca gctgcagaca gaactgctgg cagcactgct ggaaagcggc 60
ctgagcaaag aggccctgat tcaggcactc ggcgaacctg gaccttatct gctcgctggc 120
gaaggccctc tggataaggg cgagagctgt ggcggaggaa gaggagagct ggccgagctg 180
cctaacggcc tgggcgagac aagaggcagc gaggacgaga cagacgacga cggcgaggac 240
ttcacccccc ccatcctgaa agagctggaa aacctgagcc ccgaggaagc cgcccaccag 300
aaagccgtgg tggagacact gctgcaggaa gatccctggc gggtcgccaa gatggtcaag 360
agctacctgc agcagcacaa catcccccag cgggaggtgg tggacaccac cggcctgaac 420
cagagccacc tgagccagca cctgaacaag ggcaccccca tgaaaaccca gaagagagcc 480
gccctgtaca cttggtacgt gcggaagcag agagaggtgg cccagcagtt tacacacgcc 540
ggccagggcg gcctgatcga ggaacctacc ggcgacgagc tgcccaccaa gaagggcaga 600
cggaaccggt ttaagtgggg ccctgcatct cagcagatcc tgttccaggc ctacgagcgg 660
cagaagaacc ccagcaaaga ggaacgggag acactggtgg aagagtgcaa ccgggccgag 720
tgcatccaga gaggcgtgag cccttctcag gctcagggcc tcggcagcaa tctggtcacc 780
gaagtgcggg tgtacaattg gttcgccaac cggcggaaag aggaagcctt ccggcacaag 840
ctgtctgctg gcgatatgag agccgccaac ctgtggccca gccccctgat gatcaagcgg 900
agcaagaaga acagcctggc cctgagcctg accgccgatc agatggtgtc cgctctgctg 960
gacgccgagc cccctatcct gtacagcgag tacgacccca ccagaccctt cagcgaggcc 1020
agcatgatgg gcctgctgac caacctggcc gaccgggagc tggtgcacat gatcaactgg 1080
gccaagcggg tgcccggctt cgtggacctg accctgcacg accaggtcca cctgctggaa 1140
tgtgcctgga tggaaatcct gatgatcggc ctcgtgtgga gaagcatgga acaccccggc 1200
aagctgctgt tcgcccccaa cctgctcctg gaccggaacc agggaaagtg cgtggagggc 1260
ggcgtggaga tcttcgacat gctgctggcc acctccagcc ggttccggat gatgaacctg 1320
cagggcgagg aattcgtgtg cctgaagtcc atcatcctgc tgaacagcgg cgtgtacacc 1380
ttcctgtcat ccaccctgaa gtccctggaa gagaaggacc acatccaccg ggtgctggac 1440
aagatcaccg acaccctgat ccacctgatg gccaaggctg gcctgacact ccagcagcag 1500
caccagagac tggcccagct gctgctgatc ctgagccaca tccggcacat gagcaacaag 1560
cggatggaac acctgtacag catgaagtgc aagaacgtgg tgcccctgta cgacctgctg 1620
ctcgagatgc tggatgccca cagactgcac gcccctacaa gcagaggcgg agccagcgtg 1680
gaggaaaccg accagtctca cctggccacc gccggcagca caagcagcca cagcctgcag 1740
aagtactaca tcaccggcga ggccgaggga ttccctgcca ccgtggagtt ccagtacctg 1800
cccgacaccg acgaccggca ccggatcgag gaaaagcgga agcggaccta cgagacattc 1860
cagagcatca tgaagaagtc cccctcagc ggccccaccg atcccagacc cccccctaga 1920
agaatcgccg tgcccagcag atctagcgcc agcgtgccca agcctgcccc ccagccctac 1980
cctttcacca gcagcctgag caccatcaac tacgacgagt tccctaccat ggtgttcccc 2040
agcggccaga tctctcaggc ctctgctctg gcacctgctc cacctcaggt gctgcctcag 2100
gcccctgctc cagccccagc ccctgccatg gtgtctgcac tggcccaggc tccagctcct 2160
gtgcctgtgc tggcccctgg acctcctcag gctgtggccc ctcctgcccc taaacctacc 2220
caggccgggg agggaacact gtctgaggcc ctgctgcagc tccagttcga cgacgaggat 2280
ctgggagcac tgctgggcaa tagcaccgac cccgccgtgt ttaccgacct ggcctccgtg 2340
gacaacagcg agttccagca gctcctcaac cagggcatcc ctgtcgcccc acacaccacc 2400
gagcccatgc tgatggaata ccccgaggcc atcaccagac tggtcacagg cgcccagagg 2460
cctccagatc cagcaccagc tccactggga gcccctggcc tgcctaatgg gctgctgtct 2520
ggcgacgagg acttcgagag cattgccgac atggacttca gcgccctgct gtcccagatc 2580
agcagc 2586

<210> SEQ ID NO 23
<211> LENGTH: 138
<212> TYPE: DNA
<213> ORGANISM: Unknown
<220> FEATURE:
<223> OTHER INFORMATION: 7xHBD/mE1B promoter

<400> SEQUENCE: 23
tagttaataa tctacaatag ttaataatct acaatagtta ataatctaca atagttaata 60
atctacaata gttaataatc tacaatagtt aataatctac aatagttaat aatctacaag 120
agctcagggt atataatg 138

<210> SEQ ID NO 24
<211> LENGTH: 1941
<212> TYPE: DNA
<213> ORGANISM: Unknown
<220> FEATURE:
<223> OTHER INFORMATION: HEA4(VP64) chimeric transcription factor

<400> SEQUENCE: 24

```
atggtgtcca agctgtccca gctgcagaca gaactgctgg cagcactgct ggaaagcggc      60
ctgagcaaag aggccctgat tcaggcactc ggcgaacctg gaccttatct gctcgctggc     120
gaaggccctc tggataaggg cgagagctgt ggcggaggaa gaggagagct ggccgagctg     180
cctaacggcc tgggcgagac aagaggcagc gaggacgaga cagacgacga cggcgaggac     240
ttcacccccc ccatcctgaa agagctggaa aacctgagcc ccgaggaagc cgcccaccag     300
aaagccgtgg tggagacact gctgcaggaa gatccctggc gggtcgccaa gatggtcaag     360
agctacctgc agcagcacaa catcccccag cgggaggtgg tggacaccac cggcctgaac     420
cagagccacc tgagccagca cctgaacaag ggcaccccca tgaaaaccca gaagagagcc     480
gccctgtaca cttggtacgt gcggaagcag agagaggtgg cccagcagtt tacacacgcc     540
ggccagggcg gcctgatcga ggaacctacc ggcgacgagc tgcccaccaa gaagggcaga     600
cggaaccggt ttaagtgggg ccctgcatct cagcagatcc tgttccaggc ctacgagcgg     660
cagaagaacc ccagcaaaga ggaacgggag acactggtgg aagagtgcaa ccgggccgag     720
tgcatccaga gaggcgtgag ccccttctcag gctcagggcc tcggcagcaa tctggtcacc     780
gaagtgcggg tgtacaattg gttcgccaac cggcggaaag aggaagcctt ccggcacaag     840
ctgtctgctg gcgatatgag agccgccaac ctgtggccca gcccccctgat gatcaagcgg     900
agcaagaaga acagcctggc cctgagcctg accgccgatc agatggtgtc cgctctgctg     960
gacgccgagc cccctatcct gtacagcgag tacgacccca ccagaccctt cagcgaggcc    1020
agcatgatgg gcctgctgac caacctggcc gaccgggagc tggtgcacat gatcaactgg    1080
gccaagcggg tgcccggctt cgtggacctg accctgcacg accaggtcca cctgctggaa    1140
tgtgcctggc tggaaatcct gatgatcggc ctcgtgtgga gaagcatgga acaccccgtg    1200
aagctgctgt tcgcccccaa cctgctcctg gaccggaacc agggaaagtg cgtggagggc    1260
atggtggaga tcttcgacat gctgctggcc acctccagcc ggttccggat gatgaacctg    1320
cagggcgagg aattcgtgtg cctgaagtcc atcatcctgc tgaacagcgg cgtgtacacc    1380
ttcctgtcat ccaccctgaa gtccctggaa gagaaggacc acatccaccg ggtgctggac    1440
aagatcaccg acaccctgat ccacctgatg gccaaggctg gcctgacact ccagcagcag    1500
caccagagac tggcccagct gctgctgatc ctgagccaca tccggcacat gagcaacaag    1560
ggaatggaac acctgtacag catgaagtgc aagaacgtgg tgcccctgta cgacctgctg    1620
ctcgaggctg ccgatgccca cagactgcac gcccctacaa gcagaggcgg agccagcgtg    1680
gaggaaaccg accagtctca cctggccacc gccggcagca caagcagcca cagcctgcag    1740
aagtactaca tcaccggcga ggccgaggga ttccctgcca ccgtggacgc tctggacgac    1800
ttcgaccttg acatgttggg ttccgacgcg ctggatgatt ttgatttgga catgctggga    1860
agcgacgcac tggatgactt tgatctcgat atgctcggct ctgacgcatt ggacgacttc    1920
gacttggata tgctgggttc t                                             1941
```

<210> SEQ ID NO 25
<211> LENGTH: 647
<212> TYPE: PRT
<213> ORGANISM: Artificial Sequence
<220> FEATURE:
<223> OTHER INFORMATION: HEA4(VP64) chimeric transcription factor

<400> SEQUENCE: 25

```
Met Val Ser Lys Leu Ser Gln Leu Gln Thr Glu Leu Leu Ala Ala Leu
1               5                   10                  15
```

```
Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430
```

```
Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Ala Ala
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Asp Ala Leu Asp Asp Phe Asp Leu Asp Met Leu Gly Ser
        595                 600                 605

Asp Ala Leu Asp Asp Phe Asp Leu Asp Met Leu Gly Ser Asp Ala Leu
    610                 615                 620

Asp Asp Phe Asp Leu Asp Met Leu Gly Ser Asp Ala Leu Asp Asp Phe
625                 630                 635                 640

Asp Leu Asp Met Leu Gly Ser
                645


<210> SEQ ID NO 26
<211> LENGTH: 2262
<212> TYPE: DNA
<213> ORGANISM: Unknown
<220> FEATURE:
<223> OTHER INFORMATION: HEA4(HSF-1) chimeric transcription factor

<400> SEQUENCE: 26

atggtgtcca agctgtccca gctgcagaca gaactgctgg cagcactgct ggaaagcggc     60

ctgagcaaag aggccctgat tcaggcactc ggcgaacctg gaccttatct gctcgctggc    120

gaaggccctc tggataaggg cgagagctgt ggcggaggaa gaggagagct ggccgagctg    180

cctaacggcc tgggcgagac aagaggcagc gaggacgaga cagacgacga cggcgaggac    240

ttcacccccc ccatcctgaa agagctggaa aacctgagcc ccgaggaagc cgcccaccag    300

aaagccgtgg tggagacact gctgcaggaa gatccctggc gggtcgccaa gatggtcaag    360

agctacctgc agcagcacaa catcccccag cgggaggtgg tggacaccac cggcctgaac    420

cagagccacc tgagccagca cctgaacaag ggcaccccca tgaaaaccca gaagagagcc    480

gccctgtaca cttggtacgt gcggaagcag agagaggtgg cccagcagtt tacacacgcc    540

ggccagggcg gcctgatcga ggaacctacc ggcgacgagc tgcccaccaa gaagggcaga    600

cggaaccggt ttaagtgggg ccctgcatct cagcagatcc tgttccaggc ctacgagcgg    660

cagaagaacc ccagcaaaga ggaacgggag acactggtgg aagagtgcaa ccgggccgag    720

tgcatccaga gaggcgtgag cccttctcag gctcagggcc tcggcagcaa tctggtcacc    780

gaagtgcggg tgtacaattg gttcgccaac cggcggaaag aggaagcctt ccggcacaag    840
```

```
ctgtctgctg gcgatatgag agccgccaac ctgtggccca gccccctgat gatcaagcgg    900

agcaagaaga acagcctggc cctgagcctg accgccgatc agatggtgtc cgctctgctg    960

gacgccgagc cccctatcct gtacagcgag tacgacccca ccagaccctt cagcgaggcc   1020

agcatgatgg gcctgctgac caacctggcc gaccgggagc tggtgcacat gatcaactgg   1080

gccaagcggg tgcccggctt cgtggacctg accctgcacg accaggtcca cctgctggaa   1140

tgtgcctggc tggaaatcct gatgatcggc ctcgtgtgga gaagcatgga acaccccgtg   1200

aagctgctgt tcgcccccaa cctgctcctg gaccggaacc agggaaagtg cgtggagggc   1260

atggtggaga tcttcgacat gctgctggcc acctccagcc ggttccggat gatgaacctg   1320

cagggcgagg aattcgtgtg cctgaagtcc atcatcctgc tgaacagcgg cgtgtacacc   1380

ttcctgtcat ccaccctgaa gtccctggaa gagaaggacc acatccaccg ggtgctggac   1440

aagatcaccg acaccctgat ccacctgatg gccaaggctg gcctgacact ccagcagcag   1500

caccagagac tggcccagct gctgctgatc ctgagccaca tccggcacat gagcaacaag   1560

ggaatggaac acctgtacag catgaagtgc aagaacgtgg tgcccctgta cgacctgctg   1620

ctcgaggctg ccgatgccca cagactgcac gcccctacaa gcagaggcgg agccagcgtg   1680

gaggaaaccg accagtctca cctggccacc gccggcagca caagcagcca cagcctgcag   1740

aagtactaca tcaccggcga ggccgaggga ttccctgcca ccgtggaaaa gtgcctcagc   1800

gtagcctgcc tggacaagaa tgagctcagt gaccacttgg atgctatgga ctccaacctg   1860

gataacctgc agaccatgct gagcagccac ggcttcagcg tggacaccag tgccctgctg   1920

gacctgttca gcccctcggt gaccgtgccc gacatgagcc tgcctgacct tgacagcagc   1980

ctggccagta tccaagagct cctgtctccc caggagcccc ccaggcctcc cgaggcagag   2040

aacagcagcc cggattcagg gaagcagctg gtgcactaca cagcgcagcc gctgttcctg   2100

ctggaccccg gctccgtgga caccgggagc aacgacctgc cggtgctgtt tgagctggga   2160

gagggctcct acttctccga aggggacggc ttcgccgagg accccaccat ctccctgctg   2220

acaggctcgg agcctcccaa agccaaggac cccactgtct cc                      2262
```

<210> SEQ ID NO 27
<211> LENGTH: 754
<212> TYPE: PRT
<213> ORGANISM: Artificial Sequence
<220> FEATURE:
<223> OTHER INFORMATION: HEA4(HSF-1) chimeric transcription factor

<400> SEQUENCE: 27

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110
```

```
Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525
```

```
Lys Cys Lys Asn Val Val Pro Leu Tyr Asp Leu Leu Leu Glu Ala Ala
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Lys Cys Leu Ser Val Ala Cys Leu Asp Lys Asn Glu
        595                 600                 605

Leu Ser Asp His Leu Asp Ala Met Asp Ser Asn Leu Asp Asn Leu Gln
    610                 615                 620

Thr Met Leu Ser Ser His Gly Phe Ser Val Asp Thr Ser Ala Leu Leu
625                 630                 635                 640

Asp Leu Phe Ser Pro Ser Val Thr Val Pro Asp Met Ser Leu Pro Asp
                645                 650                 655

Leu Asp Ser Ser Leu Ala Ser Ile Gln Glu Leu Leu Ser Pro Gln Glu
            660                 665                 670

Pro Pro Arg Pro Pro Glu Ala Glu Asn Ser Ser Pro Asp Ser Gly Lys
        675                 680                 685

Gln Leu Val His Tyr Thr Ala Gln Pro Leu Phe Leu Leu Asp Pro Gly
    690                 695                 700

Ser Val Asp Thr Gly Ser Asn Asp Leu Pro Val Leu Phe Glu Leu Gly
705                 710                 715                 720

Glu Gly Ser Tyr Phe Ser Glu Gly Asp Gly Phe Ala Glu Asp Pro Thr
                725                 730                 735

Ile Ser Leu Leu Thr Gly Ser Glu Pro Pro Lys Ala Lys Asp Pro Thr
            740                 745                 750

Val Ser
```

<210> SEQ ID NO 28
<211> LENGTH: 1887
<212> TYPE: DNA
<213> ORGANISM: Unknown
<220> FEATURE:
<223> OTHER INFORMATION: HEA4(Arnt) chimeric transcription factor

<400> SEQUENCE: 28

```
atggtgtcca agctgtccca gctgcagaca gaactgctgg cagcactgct ggaaagcggc     60

ctgagcaaag aggccctgat tcaggcactc ggcgaacctg gaccttatct gctcgctggc    120

gaaggccctc tggataaggg cgagagctgt ggcggaggaa gaggagagct ggccgagctg    180

cctaacggcc tgggcgagac aagaggcagc gaggacgaga cagacgacga cggcgaggac    240

ttcacccccc ccatcctgaa agagctggaa aacctgagcc ccgaggaagc cgcccaccag    300

aaagccgtgg tggagacact gctgcaggaa gatccctggc gggtcgccaa gatggtcaag    360

agctacctgc agcagcacaa catcccccag cgggaggtgg tggacaccac cggcctgaac    420

cagagccacc tgagccagca cctgaacaag ggcaccccca tgaaaaccca gaagagagcc    480

gccctgtaca cttggtacgt gcggaagcag agagaggtgg cccagcagtt tacacacgcc    540

ggccagggcg gcctgatcga ggaacctacc ggcgacgagc tgcccaccaa gaagggcaga    600

cggaaccggt ttaagtgggg ccctgcatct cagcagatcc tgttccaggc ctacgagcgg    660

cagaagaacc ccagcaaaga ggaacgggag acactggtgg aagagtgcaa ccgggccgag    720

tgcatccaga gaggcgtgag cccttctcag gctcagggcc tcggcagcaa tctggtcacc    780
```

```
gaagtgcggg tgtacaattg gttcgccaac cggcggaaag aggaagcctt ccggcacaag    840

ctgtctgctg gcgatatgag agccgccaac ctgtggccca gcccccctgat gatcaagcgg    900

agcaagaaga acagcctggc cctgagcctg accgccgatc agatggtgtc cgctctgctg    960

gacgccgagc cccctatcct gtacagcgag tacgacccca ccagaccctt cagcgaggcc   1020

agcatgatgg gcctgctgac caacctggcc gaccgggagc tggtgcacat gatcaactgg   1080

gccaagcggg tgcccggctt cgtggacctg accctgcacg accaggtcca cctgctggaa   1140

tgtgcctggc tggaaatcct gatgatcggc ctcgtgtgga gaagcatgga acaccccgtg   1200

aagctgctgt tcgcccccaa cctgctcctg gaccggaacc agggaaagtg cgtggagggc   1260

atggtggaga tcttcgacat gctgctggcc acctccagcc ggttccggat gatgaacctg   1320

cagggcgagg aattcgtgtg cctgaagtcc atcatcctgc tgaacagcgg cgtgtacacc   1380

ttcctgtcat ccaccctgaa gtccctggaa gagaaggacc acatccaccg ggtgctggac   1440

aagatcaccg acaccctgat ccacctgatg gccaaggctg gcctgacact ccagcagcag   1500

caccagagac tggcccagct gctgctgatc ctgagccaca tccggcacat gagcaacaag   1560

ggaatggaac acctgtacag catgaagtgc aagaacgtgg tgcccctgta cgacctgctg   1620

ctcgaggctg ccgatgccca cagactgcac gcccctacaa gcagaggcgg agccagcgtg   1680

gaggaaaccg accagtctca cctggccacc gccggcagca caagcagcca cagcctgcag   1740

aagtactaca tcaccggcga ggccgaggga ttccctgcca ccgtgcctga ggtcttccag   1800

gagatgctgt ccatgctggg agatcagagc aacagctaca acaatgaaga attccctgat   1860

ctaactatgt ttcccccctt ttcagaa                                       1887
```

<210> SEQ ID NO 29
<211> LENGTH: 629
<212> TYPE: PRT
<213> ORGANISM: Artificial Sequence
<220> FEATURE:
<223> OTHER INFORMATION: HEA4(Arnt) chimeric transcription factor

<400> SEQUENCE: 29

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160
```

-continued

```
Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Ala Ala
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
```

```
            580                 585                 590

Ala Thr Val Pro Glu Val Phe Gln Glu Met Leu Ser Met Leu Gly Asp
        595                 600                 605

Gln Ser Asn Ser Tyr Asn Asn Glu Glu Phe Pro Asp Leu Thr Met Phe
    610                 615                 620

Pro Pro Phe Ser Glu
625


<210> SEQ ID NO 30
<211> LENGTH: 1074
<212> TYPE: DNA
<213> ORGANISM: Unknown
<220> FEATURE:
<223> OTHER INFORMATION: EGFRt nucleotide sequence

<400> SEQUENCE: 30

atgcttctcc tggtgacaag ccttctgctc tgtgagttac cacacccagc attcctcctg     60

atcccacgca aagtgtgtaa cggaataggt attggtgaat ttaaagactc actctccata    120

aatgctacga atattaaaca cttcaaaaac tgcacctcca tcagtggcga tctccacatc    180

ctgccggtgg catttagggg tgactccttc acacatactc ctcctctgga tccacaggaa    240

ctggatattc tgaaaaccgt aaaggaaatc acagggtttt tgctgattca ggcttggcct    300

gaaaacagga cggacctcca tgcctttgag aacctagaaa tcatacgcgg caggaccaag    360

caacatggtc agttttctct tgcagtcgtc agcctgaaca taacatcctt gggattacgc    420

tccctcaagg agataagtga tggagatgtg ataatttcag gaaacaaaaa tttgtgctat    480

gcaaatacaa taaactggaa aaaactgttt gggacctccg gtcagaaaac caaaattata    540

agcaacagag gtgaaaacag ctgcaaggcc acaggccagg tctgccatgc cttgtgctcc    600

cccgagggct gctggggccc ggagcccagg gactgcgtct cttgccggaa tgtcagccga    660

ggcagggaat gcgtggacaa gtgcaacctt ctggagggtg agccaaggga gtttgtggag    720

aactctgagt gcatacagtg ccacccagag tgcctgcctc aggccatgaa catcacctgc    780

acaggacggg gaccagacaa ctgtatccag tgtgcccact acattgacgg cccccactgc    840

gtcaagacct gcccggcagg agtcatggga gaaaacaaca ccctggtctg gaagtacgca    900

gacgccggcc atgtgtgcca cctgtgccat ccaaactgca cctacggatg cactgggcca    960

ggtcttgaag gctgtccaac gaatgggcct aagatcccgt ccatcgccac tgggatggtg   1020

ggggccctcc tcttgctgct ggtggtggcc ctggggatcg gcctcttcat gtga         1074


<210> SEQ ID NO 31
<211> LENGTH: 357
<212> TYPE: PRT
<213> ORGANISM: Artificial Sequence
<220> FEATURE:
<223> OTHER INFORMATION: EGFRt amino acid sequence
<220> FEATURE:
<223> OTHER INFORMATION: EGFRt amino acid sequence

<400> SEQUENCE: 31

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
```

```
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355
```

<210> SEQ ID NO 32
<211> LENGTH: 408
<212> TYPE: DNA
<213> ORGANISM: Unknown
<220> FEATURE:
<223> OTHER INFORMATION: Her2t

<400> SEQUENCE: 32

```
atgcttctcc tggtgacaag ccttctgctc tgtgagttac cacacccagc attcctcctg      60

atcccatgcc accctgagtg tcagccccag aatggctcag tgacctgttt tggaccggag     120

gctgaccagt gtgtggcctg tgcccactat aaggaccctc ccttctgcgt ggcccgctgc     180

cccagcggtg tgaaacctga cctctcctac atgcccatct ggaagtttcc agatgaggag     240

ggcgcatgcc agccttgccc catcaactgc acccactcct gtgtggacct ggatgacaag     300
```

-continued

```
ggctgccccg ccgagcagag agccagccct ctgacgtcca tcatctctgc ggtggttggc    360

attctgctgg tcgtggtctt gggggtggtc tttgggatcc tcatctga                 408
```

<210> SEQ ID NO 33
<211> LENGTH: 135
<212> TYPE: PRT
<213> ORGANISM: Artificial Sequence
<220> FEATURE:
<223> OTHER INFORMATION: Her2t

<400> SEQUENCE: 33

```
Met Leu Leu Leu Val Thr Ser Leu Leu Leu Cys Glu Leu Pro His Pro
1               5                   10                  15

Ala Phe Leu Leu Ile Pro Cys His Pro Glu Cys Gln Pro Gln Asn Gly
            20                  25                  30

Ser Val Thr Cys Phe Gly Pro Glu Ala Asp Gln Cys Val Ala Cys Ala
        35                  40                  45

His Tyr Lys Asp Pro Pro Phe Cys Val Ala Arg Cys Pro Ser Gly Val
    50                  55                  60

Lys Pro Asp Leu Ser Tyr Met Pro Ile Trp Lys Phe Pro Asp Glu Glu
65                  70                  75                  80

Gly Ala Cys Gln Pro Cys Pro Ile Asn Cys Thr His Ser Cys Val Asp
                85                  90                  95

Leu Asp Asp Lys Gly Cys Pro Ala Glu Gln Arg Ala Ser Pro Leu Thr
            100                 105                 110

Ser Ile Ile Ser Ala Val Val Gly Ile Leu Leu Val Val Val Leu Gly
        115                 120                 125

Val Val Phe Gly Ile Leu Ile
    130                 135
```

<210> SEQ ID NO 34
<211> LENGTH: 429
<212> TYPE: DNA
<213> ORGANISM: Unknown
<220> FEATURE:
<223> OTHER INFORMATION: Her2tG

<400> SEQUENCE: 34

```
atgcttctcc tggtgacaag ccttctgctc tgtgagttac cacacccagc attcctcctg     60

atcccatgcc accctgagtg tcagccccag aatggctcag tgacctgttt tggaccggag    120

gctgaccagt gtgtggcctg tgcccactat aaggaccctc ccttctgcgt ggcccgctgc    180

cccagcggtg tgaaacctga cctctcctac atgcccatct ggaagtttcc agatgaggag    240

ggcgcatgcc agccttgccc catcaactgc acccactcct gtgtggacct ggatgacaag    300

ggctgccccg ccgagcagag agccagcccg ttaacgggtg gaggcagcgg aggtggctcc    360

atcatctctg cggtggttgg cattctgctg gtcgtggtct tgggggtggt ctttgggatc    420

ctcatctga                                                            429
```

<210> SEQ ID NO 35
<211> LENGTH: 142
<212> TYPE: PRT
<213> ORGANISM: Artificial Sequence
<220> FEATURE:
<223> OTHER INFORMATION: Her2tG

<400> SEQUENCE: 35

```
Met Leu Leu Leu Val Thr Ser Leu Leu Leu Cys Glu Leu Pro His Pro
1               5                   10                  15
```

```
Ala Phe Leu Leu Ile Pro Cys His Pro Glu Cys Gln Pro Gln Asn Gly
            20                  25                  30

Ser Val Thr Cys Phe Gly Pro Glu Ala Asp Gln Cys Val Ala Cys Ala
        35                  40                  45

His Tyr Lys Asp Pro Pro Phe Cys Val Ala Arg Cys Pro Ser Gly Val
    50                  55                  60

Lys Pro Asp Leu Ser Tyr Met Pro Ile Trp Lys Phe Pro Asp Glu Glu
65                  70                  75                  80

Gly Ala Cys Gln Pro Cys Pro Ile Asn Cys Thr His Ser Cys Val Asp
                85                  90                  95

Leu Asp Asp Lys Gly Cys Pro Ala Glu Gln Arg Ala Ser Pro Leu Thr
            100                 105                 110

Gly Gly Gly Ser Gly Gly Gly Ser Ile Ile Ser Ala Val Val Gly Ile
        115                 120                 125

Leu Leu Val Val Val Leu Gly Val Val Phe Gly Ile Leu Ile
    130                 135                 140
```

<210> SEQ ID NO 36
<211> LENGTH: 972
<212> TYPE: DNA
<213> ORGANISM: Unknown
<220> FEATURE:
<223> OTHER INFORMATION: CD19t

<400> SEQUENCE: 36

```
atgccacctc ctcgcctcct cttcttcctc ctcttcctca cccccatgga agtcaggccc     60

gaggaacctc tagtggtgaa ggtggaagag ggagataacg ctgtgctgca gtgcctcaag    120

gggacctcag atggccccac tcagcagctg acctggtctc gggagtcccc gcttaaaccc    180

ttcttaaaac tcagcctggg gctgccaggc ctgggaatcc acatgaggcc cctggccatc    240

tggcttttca tcttcaacgt ctctcaacag atgggggggct tctacctgtg ccagccgggg    300

ccccctctg agaaggcctg gcagcctggc tggacagtca atgtggaggg cagcggggag    360

ctgttccggt ggaatgtttc ggacctaggt ggcctgggct gtggcctgaa gaacaggtcc    420

tcagagggcc ccagctcccc ttccgggaag ctcatgagcc ccaagctgta tgtgtgggcc    480

aaagaccgcc ctgagatctg ggagggagag cctccgtgtg tcccaccgag ggacagcctg    540

aaccagagcc tcagccagga cctcaccatg gcccctggct ccacactctg gctgtcctgt    600

ggggtacccc ctgactctgt gtccaggggc cccctctcct ggacccatgt gcaccccaag    660

ggcctaagt cattgctgag cctagagctg aaggacgatc gcccggccag agatatgtgg    720

gtaatggaga cgggtctgtt gttgccccgg gccacagctc aagacgctgg aaagtattat    780

tgtcaccgtg gcaacctgac catgtcattc cacctggaga tcactgctcg gccagtacta    840

tggcactggc tgctgaggac tggtggctgg aaggtctcag ctgtgacttt ggcttatctg    900

atcttctgcc tgtgttccct tgtgggcatt cttcatcttc aaagagccct ggtcctgagg    960

aggaaaagat aa                                                       972
```

<210> SEQ ID NO 37
<211> LENGTH: 323
<212> TYPE: PRT
<213> ORGANISM: Artificial Sequence
<220> FEATURE:
<223> OTHER INFORMATION: CD19t

<400> SEQUENCE: 37

-continued

```
Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg
```

<210> SEQ ID NO 38
<211> LENGTH: 561
<212> TYPE: DNA
<213> ORGANISM: Unknown
<220> FEATURE:
<223> OTHER INFORMATION: DHFRdm

<400> SEQUENCE: 38

```
atggttggtt cgctaaactg catcgtcgct gtgtcccaga acatgggcat cggcaagaac      60

ggggacttcc cctggccacc gctcaggaat gaatccagat atttccagag aatgaccaca     120

acctcttcag tagaaggtaa acagaatctg gtgattatgg gtaagaagac ctggttctcc     180

attcctgaga agaatcgacc tttaaagggt agaattaatt tagttctcag cagagaactc     240
```

```
aaggaacctc cacaaggagc tcattttctt tccagaagtc tagatgatgc cttaaaactt    300

actgaacaac cagaattagc aaataaagta gacatggtct ggatagttgg tggcagttct    360

gtttataagg aagccatgaa tcacccaggc catcttaaac tatttgtgac aaggatcatg    420

caagactttg aaagtgacac gtttttttcca gaaattgatt tggagaaata taaacttctg   480

ccagaatacc caggtgttct ctctgatgtc caggaggaga aaggcattaa gtacaaattt    540

gaagtatatg agaagaatga t                                              561
```

<210> SEQ ID NO 39
<211> LENGTH: 186
<212> TYPE: PRT
<213> ORGANISM: Artificial Sequence
<220> FEATURE:
<223> OTHER INFORMATION: DHFRdm

<400> SEQUENCE: 39

```
Val Gly Ser Leu Asn Cys Ile Val Ala Val Ser Gln Asn Met Gly Ile
1               5                   10                  15

Gly Lys Asn Gly Asp Phe Pro Trp Pro Pro Leu Arg Asn Glu Ser Arg
            20                  25                  30

Tyr Phe Gln Arg Met Thr Thr Thr Ser Ser Val Glu Gly Lys Gln Asn
        35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Tyr Lys Glu Ala Met Asn His Pro
        115                 120                 125

Gly His Leu Lys Leu Phe Val Thr Arg Ile Met Gln Asp Phe Glu Ser
    130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
            180                 185
```

<210> SEQ ID NO 40
<211> LENGTH: 804
<212> TYPE: DNA
<213> ORGANISM: Unknown
<220> FEATURE:
<223> OTHER INFORMATION: huCD19 scFv (G01S)

<400> SEQUENCE: 40

```
atgcttctcc tggtgacaag ccttctgctc tgtgagttac cacacccagc attcctcctg     60

atcccagagg tgcagctggt cgaatccgga ggaggactgg tccagcccgg ccggagcctg    120

agactgagct gtgccgcttc cggattcact tttgacgatt acgcaatgca ttgggtgagg    180

caggcccctg gcaaggggct ggaatgggtc tccggaatct cttggaacag tgggcgcatt    240

ggatatgccg attctgtgaa gggccgattc actatctctc gggacaacgc taaaaatagt    300
```

```
ctgtttctgc agatgaattc cctgcgcgcc gaggataccg ccgtgtacta ttgcgcccga    360

gaccagggct accactacta tgatagcgcc gaacatgcat tcgacatttg gggacaggga    420

actgtggtca ccgtgagctc cggaggagga ggaagcggag gaggagggtc cggaggcggg    480

ggatcacaga gcgcactgac ccagccacgg agcgtgagcg gatttcctgg gcagtctgtc    540

accattagtt gcacaggcac cacatcagac gatgtgagct ggtaccagca gcacccaggg    600

aaggctcccc agctgatgct gtatgacgtg tccaaaagac cttctggcgt cccacatagg    660

tttagtggaa gccggagcgg ccgggcagcc agtctgatca tttcagggct gcagacagag    720

gacgaagctg attatttctg ttctagttac gcaggcagat ataactctgt gctgtttggc    780

gggggaacaa agctgactgt cctg                                           804
```

<210> SEQ ID NO 41
<211> LENGTH: 268
<212> TYPE: PRT
<213> ORGANISM: Artificial Sequence
<220> FEATURE:
<223> OTHER INFORMATION: huCD19 scFv (G01S)

<400> SEQUENCE: 41

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Arg Ser Leu Arg Leu Ser Cys Ala Ala Ser Gly
        35                  40                  45

Phe Thr Phe Asp Asp Tyr Ala Met His Trp Val Arg Gln Ala Pro Gly
    50                  55                  60

Lys Gly Leu Glu Trp Val Ser Gly Ile Ser Trp Asn Ser Gly Arg Ile
65                  70                  75                  80

Gly Tyr Ala Asp Ser Val Lys Gly Arg Phe Thr Ile Ser Arg Asp Asn
                85                  90                  95

Ala Lys Asn Ser Leu Phe Leu Gln Met Asn Ser Leu Arg Ala Glu Asp
            100                 105                 110

Thr Ala Val Tyr Tyr Cys Ala Arg Asp Gln Gly Tyr His Tyr Tyr Asp
        115                 120                 125

Ser Ala Glu His Ala Phe Asp Ile Trp Gly Gln Gly Thr Val Val Thr
    130                 135                 140

Val Ser Ser Gly Gly Gly Gly Ser Gly Gly Gly Gly Ser Gly Gly Gly
145                 150                 155                 160

Gly Ser Gln Ser Ala Leu Thr Gln Pro Arg Ser Val Ser Gly Phe Pro
                165                 170                 175

Gly Gln Ser Val Thr Ile Ser Cys Thr Gly Thr Thr Ser Asp Asp Val
            180                 185                 190

Ser Trp Tyr Gln Gln His Pro Gly Lys Ala Pro Gln Leu Met Leu Tyr
        195                 200                 205

Asp Val Ser Lys Arg Pro Ser Gly Val Pro His Arg Phe Ser Gly Ser
    210                 215                 220

Arg Ser Gly Arg Ala Ala Ser Leu Ile Ile Ser Gly Leu Gln Thr Glu
225                 230                 235                 240

Asp Glu Ala Asp Tyr Phe Cys Ser Ser Tyr Ala Gly Arg Tyr Asn Ser
                245                 250                 255

Val Leu Phe Gly Gly Gly Thr Lys Leu Thr Val Leu
            260                 265
```

<210> SEQ ID NO 42
<211> LENGTH: 801
<212> TYPE: DNA
<213> ORGANISM: Unknown
<220> FEATURE:
<223> OTHER INFORMATION: muCD19 (FMC63) scFv

<400> SEQUENCE: 42
atgctgctgc tggtgaccag cctgctgctg tgcgagctgc cccaccccgc ctttctgctg 60
atccccgaca tccagatgac ccagaccacc tccagcctga gcgccagcct gggcgaccgg 120
gtgaccatca gctgccgggc cagccaggac atcagcaagt acctgaactg gtatcagcag 180
aagcccgacg gcaccgtcaa gctgctgatc taccacacca gccggctgca cagcggcgtg 240
cccagccggt ttagcggcag cggctccggc accgactaca gcctgaccat ctccaacctg 300
gaacaggaag atatcgccac ctacttttgc cagcagggca acacactgcc ctacaccttt 360
ggcggcggaa caaagctgga aatcaccggc agcacctccg gcagcggcaa gcctggcagc 420
ggcgagggca gcaccaaggg cgaggtgaag ctgcaggaaa gcggccctgg cctggtggcc 480
cccagccaga gcctgagcgt gacctgcacc gtgagcggcg tgagcctgcc cgactacggc 540
gtgagctgga tccggcagcc ccccaggaag ggcctggaat ggctgggcgt gatctggggc 600
agcgagacca cctactacaa cagcgccctg aagagccggc tgaccatcat caaggacaac 660
agcaagagcc aggtgttcct gaagatgaac agcctgcaga ccgacgacac cgccatctac 720
tactgcgcca agcactacta ctacggcggc agctacgcca tggactactg gggccagggc 780
accagcgtga ccgtgagcag c 801

<210> SEQ ID NO 43
<211> LENGTH: 267
<212> TYPE: PRT
<213> ORGANISM: Artificial Sequence
<220> FEATURE:
<223> OTHER INFORMATION: muCD19 (FMC63) scFv

<400> SEQUENCE: 43

Met Leu Leu Leu Val Thr Ser Leu Leu Leu Cys Glu Leu Pro His Pro
1 5 10 15

Ala Phe Leu Leu Ile Pro Asp Ile Gln Met Thr Gln Thr Thr Ser Ser
20 25 30

Leu Ser Ala Ser Leu Gly Asp Arg Val Thr Ile Ser Cys Arg Ala Ser
35 40 45

Gln Asp Ile Ser Lys Tyr Leu Asn Trp Tyr Gln Gln Lys Pro Asp Gly
50 55 60

Thr Val Lys Leu Leu Ile Tyr His Thr Ser Arg Leu His Ser Gly Val
65 70 75 80

Pro Ser Arg Phe Ser Gly Ser Gly Ser Gly Thr Asp Tyr Ser Leu Thr
85 90 95

Ile Ser Asn Leu Glu Gln Glu Asp Ile Ala Thr Tyr Phe Cys Gln Gln
100 105 110

Gly Asn Thr Leu Pro Tyr Thr Phe Gly Gly Gly Thr Lys Leu Glu Ile
115 120 125

Thr Gly Ser Thr Ser Gly Ser Gly Lys Pro Gly Ser Gly Glu Gly Ser
130 135 140

Thr Lys Gly Glu Val Lys Leu Gln Glu Ser Gly Pro Gly Leu Val Ala
145 150 155 160

Pro Ser Gln Ser Leu Ser Val Thr Cys Thr Val Ser Gly Val Ser Leu

-continued

```
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser
            260                 265
```

<210> SEQ ID NO 44
<211> LENGTH: 798
<212> TYPE: DNA
<213> ORGANISM: Unknown
<220> FEATURE:
<223> OTHER INFORMATION: CD20 (Leu16) scFv

<400> SEQUENCE: 44

```
atggagacag acacactcct gctatgggtg ctgctgctct gggttccagg ttccacaggt     60

gacattgtgc tgacccaatc tccagctatc ctgtctgcat ctccagggga gaaggtcaca    120

atgacttgca gggccagctc aagtgtaaat tacatggact ggtaccagaa gaagccagga    180

tcctccccca aaccctggat ttatgccaca tccaacctgg cttctggagt ccctgctcgc    240

ttcagtggca gtgggtctgg gacctcttac tctctcacaa tcagcagagt ggaggctgaa    300

gatgctgcca cttattactg ccagcagtgg agttttaatc cacccacgtt cggaggggggg    360

accaagctgg aaataaaagg cagtactagc ggtggtggct ccgggggcgg ttccggtggg    420

ggcggcagca gcgaggtgca gctgcagcag tctggggctg agctggtgaa gcctggggcc    480

tcagtgaaga tgtcctgcaa ggcttctggc tacacattta ccagttacaa tatgcactgg    540

gtaaagcaga cacctggaca gggcctggaa tggattggag ctatttatcc aggaaatggt    600

gatacttcct acaatcagaa gttcaaaggc aaggccacat tgactgcaga caaatcctcc    660

agcacagcct acatgcagct cagcagcctg acatctgagg actctgcgga ctattactgt    720

gcaagatcta attattacgg tagtagctac tggttcttcg atgtctgggg cgcagggacc    780

acggtcaccg tctcctca                                                  798
```

<210> SEQ ID NO 45
<211> LENGTH: 266
<212> TYPE: PRT
<213> ORGANISM: Artificial Sequence
<220> FEATURE:
<223> OTHER INFORMATION: CD20 (Leu16) scFv

<400> SEQUENCE: 45

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ile Leu Ser
            20                  25                  30

Ala Ser Pro Gly Glu Lys Val Thr Met Thr Cys Arg Ala Ser Ser Ser
        35                  40                  45

Val Asn Tyr Met Asp Trp Tyr Gln Lys Lys Pro Gly Ser Ser Pro Lys
    50                  55                  60
```

```
Pro Trp Ile Tyr Ala Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Ser Phe
            100                 105                 110

Asn Pro Pro Thr Phe Gly Gly Gly Thr Lys Leu Glu Ile Lys Gly Ser
        115                 120                 125

Thr Ser Gly Gly Gly Ser Gly Gly Gly Ser Gly Gly Gly Gly Ser Ser
    130                 135                 140

Glu Val Gln Leu Gln Gln Ser Gly Ala Glu Leu Val Lys Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Gly Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Ala Asp Lys Ser Ser Ser Thr Ala Tyr
    210                 215                 220

Met Gln Leu Ser Ser Leu Thr Ser Glu Asp Ser Ala Asp Tyr Tyr Cys
225                 230                 235                 240

Ala Arg Ser Asn Tyr Tyr Gly Ser Ser Tyr Trp Phe Phe Asp Val Trp
                245                 250                 255

Gly Ala Gly Thr Thr Val Thr Val Ser Ser
            260                 265
```

<210> SEQ ID NO 46
<211> LENGTH: 810
<212> TYPE: DNA
<213> ORGANISM: Unknown
<220> FEATURE:
<223> OTHER INFORMATION: CD22 (m971) scFv

<400> SEQUENCE: 46

```
atgcttctcc tggtgacaag ccttctgctc tgtgagttac cacacccagc attcctcctg      60

atcccacagg tacagctgca gcagtcaggt ccaggactgg tgaagccctc gcagaccctc     120

tcactcacct gtgccatctc cggggacagt gtctctagca acagtgctgc ttggaactgg     180

atcaggcagt ccccatcgag aggccttgag tggctgggaa ggacatacta caggtccaag     240

tggtataatg attatgcagt atctgtgaaa agtcgaataa ccatcaaccc agacacatcc     300

aagaaccagt tctccctgca gctgaactct gtgactcccg aggacacggc tgtgtattac     360

tgtgcaagag aagtgactgg ggatctcgag gatgcttttg atatctgggg ccaagggaca     420

atggtcaccg tctcctcagg cggagggggc tctggcggcg gaggatctgg gggagggggc     480

agcgacatcc agatgaccca gtctccatcg tccctgtctg catctgtagg agacagagtc     540

accatcactt gccgggcaag ccagaccatt tggagctact taaattggta tcagcagaga     600

ccagggaaag cccctaacct cctgatctat gctgcatcca gtttgcaaag tggggtccca     660

tcaaggttca gtggcagggg atctgggaca gatttcactc tcaccatcag cagtctgcaa     720

gctgaagatt ttgcaactta ctactgtcaa cagagttaca gtatccctca gacttttggc     780

caggggacca agctggagat caaacgaact                                      810
```

```
<210> SEQ ID NO 47
<211> LENGTH: 270
<212> TYPE: PRT
<213> ORGANISM: Artificial Sequence
<220> FEATURE:
<223> OTHER INFORMATION: CD22 (m971) scFv

<400> SEQUENCE: 47

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
    130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Thr Ile Trp Ser
            180                 185                 190

Tyr Leu Asn Trp Tyr Gln Gln Arg Pro Gly Lys Ala Pro Asn Leu Leu
        195                 200                 205

Ile Tyr Ala Ala Ser Ser Leu Gln Ser Gly Val Pro Ser Arg Phe Ser
    210                 215                 220

Gly Arg Gly Ser Gly Thr Asp Phe Thr Leu Thr Ile Ser Ser Leu Gln
225                 230                 235                 240

Ala Glu Asp Phe Ala Thr Tyr Tyr Cys Gln Gln Ser Tyr Ser Ile Pro
                245                 250                 255

Gln Thr Phe Gly Gln Gly Thr Lys Leu Glu Ile Lys Arg Thr
            260                 265                 270


<210> SEQ ID NO 48
<211> LENGTH: 948
<212> TYPE: DNA
<213> ORGANISM: Unknown
<220> FEATURE:
<223> OTHER INFORMATION: B7H3 (hBRCA84D) scFv

<400> SEQUENCE: 48

atgctgcgtc ggcggggcag ccctggcatg ggtgtgcatg tgggtgcagc cctgggagca      60

ctgtggttct gcctcacagg agccctggag gtccaggtcc ctgaagaccc agtggtggca     120

ctggtgggca ccgatgccac cctgtgctgc tccttctccc ctgagcctgg cttcagcctg     180

gcacagctca acctcatctg gcagctgaca gataccaaac agctggtgca cagctttgct     240

gagggccagg accagggcag cgcctatgcc aaccgcacgg ccctcttccc ggacctgctg     300
```

```
gcacagggca acgcatccct gaggctgcag cgcgtgcgtg tggcggacga gggcagcttc    360

acctgcttcg tgagcatccg ggatttcggc agcgctgccg tcagcctgca ggtggccgct    420

ccctactcga agcccagcat gaccctggag cccaacaagg acctgcggcc aggggacacg    480

gtgaccatca cgtgctccag ctaccagggc taccctgagg ctgaggtgtt ctggcaggat    540

gggcagggtg tgcccctgac tggcaacgtg accacgtcgc agatggccaa cgagcagggc    600

ttgtttgatg tgcacagcat cctgcgggtg gtgctgggtg caaatggcac ctacagctgc    660

ctggtgcgca accccgtgct gcagcaggat gcgcacagct ctgtcaccat cacagggcag    720

cctatgacat tcccccccaga ggccctgtgg gtgaccgtgg ggctgtctgt ctgtctcatt    780

gcactgctgg tggccctggc tttcgtgtgc tggagaaaga tcaaacagag ctgtgaggag    840

gagaatgcag gagctgagga ccaggatggg gagggagaag gctccaagac agccctgcag    900

cctctgaaac actctgacag caaagaagat gatggacaag aaatagcc                948
```

<210> SEQ ID NO 49
<211> LENGTH: 316
<212> TYPE: PRT
<213> ORGANISM: Artificial Sequence
<220> FEATURE:
<223> OTHER INFORMATION: B7H3 (hBRCA84D) scFv

<400> SEQUENCE: 49

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Gly Gln
225                 230                 235                 240

Pro Met Thr Phe Pro Pro Glu Ala Leu Trp Val Thr Val Gly Leu Ser
```

-continued

```
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315
```

<210> SEQ ID NO 50
<211> LENGTH: 792
<212> TYPE: DNA
<213> ORGANISM: Unknown
<220> FEATURE:
<223> OTHER INFORMATION: L1CAM (CE7) scFv

<400> SEQUENCE: 50

```
atgctgctgc tggtgaccag cctgctgctg tgcgagctgc cccaccccgc ctttctgctg      60

atcccccagg tgcagctgca gcagcctggc gccgagctgg tgaagccagg cgccagcgtg     120

aagctgtcct gcaaggccag cggctacacc ttcaccggct actggatgca ctgggtgaag     180

cagagacccg gccacggcct ggaatggatc ggcgagatca accccagcaa cggccggacc     240

aactacaacg agcggttcaa gagcaaggcc accctgaccg tggacaagag cagcaccacc     300

gccttcatgc agctgtccgg cctgaccagc gaggacagcg ccgtgtactt ctgcgccagg     360

gactactacg gcaccagcta caacttcgac tactggggcc agggcaccac actgaccgtg     420

agcagcggcg gagggggctc tggcggcgga ggatctgggg gagggggcag cgacatccag     480

atgacccaga gcagcagcag cttcagcgtg agcctgggcg accgggtgac catcacctgt     540

aaggccaacg aggacatcaa caaccggctg gcctggtatc agcagacccc cggcaacagc     600

cccaggctgc tgatcagcgg cgccaccaac ctggtgaccg gcgtgcccag ccggtttagc     660

ggcagcggct ccggcaagga ctacaccctg accatcacaa gcctgcaggc cgaggacttc     720

gccacctact actgccagca gtactggtcc accccccttca ccttcggcag cggcaccgag     780

ctggaaatca aa                                                         792
```

<210> SEQ ID NO 51
<211> LENGTH: 264
<212> TYPE: PRT
<213> ORGANISM: Artificial Sequence
<220> FEATURE:
<223> OTHER INFORMATION: L1CAM (CE7) scFv

<400> SEQUENCE: 51

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Pro Gly Ala Glu
            20                  25                  30

Leu Val Lys Pro Gly Ala Ser Val Lys Leu Ser Cys Lys Ala Ser Gly
        35                  40                  45

Tyr Thr Phe Thr Gly Tyr Trp Met His Trp Val Lys Gln Arg Pro Gly
    50                  55                  60

His Gly Leu Glu Trp Ile Gly Glu Ile Asn Pro Ser Asn Gly Arg Thr
65                  70                  75                  80

Asn Tyr Asn Glu Arg Phe Lys Ser Lys Ala Thr Leu Thr Val Asp Lys
                85                  90                  95
```

```
Ser Ser Thr Thr Ala Phe Met Gln Leu Ser Gly Leu Thr Ser Glu Asp
            100                 105                 110

Ser Ala Val Tyr Phe Cys Ala Arg Asp Tyr Tyr Gly Thr Ser Tyr Asn
        115                 120                 125

Phe Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asp Ile Gln
145                 150                 155                 160

Met Thr Gln Ser Ser Ser Ser Phe Ser Val Ser Leu Gly Asp Arg Val
                165                 170                 175

Thr Ile Thr Cys Lys Ala Asn Glu Asp Ile Asn Asn Arg Leu Ala Trp
            180                 185                 190

Tyr Gln Gln Thr Pro Gly Asn Ser Pro Arg Leu Leu Ile Ser Gly Ala
        195                 200                 205

Thr Asn Leu Val Thr Gly Val Pro Ser Arg Phe Ser Gly Ser Gly Ser
    210                 215                 220

Gly Lys Asp Tyr Thr Leu Thr Ile Thr Ser Leu Gln Ala Glu Asp Phe
225                 230                 235                 240

Ala Thr Tyr Tyr Cys Gln Gln Tyr Trp Ser Thr Pro Phe Thr Phe Gly
                245                 250                 255

Ser Gly Thr Glu Leu Glu Ile Lys
            260
```

<210> SEQ ID NO 52
<211> LENGTH: 795
<212> TYPE: DNA
<213> ORGANISM: Unknown
<220> FEATURE:
<223> OTHER INFORMATION: EGFR (cetuximab) scFv

<400> SEQUENCE: 52

```
atgcttctcc tggtgacaag ccttctgctc tgtgagttac cacacccagc attcctcctg     60

atcccacagg tgcagctgaa acagagcggc ccgggcctgg tgcagccgag ccagagcctg    120

agcattacct gcaccgtgag cggctttagc ctgaccaact atggcgtgca ttgggtgcgc    180

cagagcccgg gcaaaggcct ggaatggctg ggcgtgattt ggagcggcgg caacaccgat    240

tataacaccc cgtttaccag ccgcctgagc attaacaaag ataacagcaa aagccaggtg    300

ttttttaaaa tgaacagcct gcagagcaac gataccgcga tttattattg cgcgcgcgcg    360

ctgacctatt atgattatga atttgcgtat tggggccagg gcaccctggt gaccgtgagc    420

gcgggcggcg gcggcagcgg cggcggcggc agcggcggcg gcggcagcga tattctgctg    480

acccagagcc cggtgattct gagcgtgagc ccgggcgaac gcgtgagctt tagctgccgc    540

gcgagccaga gcattggcac caacattcat tggtatcagc agcgcaccaa cggcagcccg    600

cgcctgctga ttaaatatgc gagcgaaagc attagcggca ttccgagccg ctttagcggc    660

agcggcagcg gcaccgattt taccctgagc attaacagcg tggaaagcga agatattgcg    720

gattattatt gccagcagaa caacaactgg ccgaccacct ttggcgcggg caccaaactg    780

gaactgaaac gcacc                                                     795
```

<210> SEQ ID NO 53
<211> LENGTH: 265
<212> TYPE: PRT
<213> ORGANISM: Artificial Sequence
<220> FEATURE:
<223> OTHER INFORMATION: EGFR scFv

<400> SEQUENCE: 53

```
Met Leu Leu Leu Val Thr Ser Leu Leu Leu Cys Glu Leu Pro His Pro
1               5                   10                  15

Ala Phe Leu Leu Ile Pro Gln Val Gln Leu Lys Gln Ser Gly Pro Gly
            20                  25                  30

Leu Val Gln Pro Ser Gln Ser Leu Ser Ile Thr Cys Thr Val Ser Gly
        35                  40                  45

Phe Ser Leu Thr Asn Tyr Gly Val His Trp Val Arg Gln Ser Pro Gly
    50                  55                  60

Lys Gly Leu Glu Trp Leu Gly Val Ile Trp Ser Gly Gly Asn Thr Asp
65                  70                  75                  80

Tyr Asn Thr Pro Phe Thr Ser Arg Leu Ser Ile Asn Lys Asp Asn Ser
                85                  90                  95

Lys Ser Gln Val Phe Phe Lys Met Asn Ser Leu Gln Ser Asn Asp Thr
            100                 105                 110

Ala Ile Tyr Tyr Cys Ala Arg Ala Leu Thr Tyr Tyr Asp Tyr Glu Phe
        115                 120                 125

Ala Tyr Trp Gly Gln Gly Thr Leu Val Thr Val Ser Ala Gly Gly Gly
    130                 135                 140

Gly Ser Gly Gly Gly Gly Ser Gly Gly Gly Gly Ser Asp Ile Leu Leu
145                 150                 155                 160

Thr Gln Ser Pro Val Ile Leu Ser Val Ser Pro Gly Glu Arg Val Ser
                165                 170                 175

Phe Ser Cys Arg Ala Ser Gln Ser Ile Gly Thr Asn Ile His Trp Tyr
            180                 185                 190

Gln Gln Arg Thr Asn Gly Ser Pro Arg Leu Leu Ile Lys Tyr Ala Ser
        195                 200                 205

Glu Ser Ile Ser Gly Ile Pro Ser Arg Phe Ser Gly Ser Gly Ser Gly
    210                 215                 220

Thr Asp Phe Thr Leu Ser Ile Asn Ser Val Glu Ser Glu Asp Ile Ala
225                 230                 235                 240

Asp Tyr Tyr Cys Gln Gln Asn Asn Asn Trp Pro Thr Thr Phe Gly Ala
                245                 250                 255

Gly Thr Lys Leu Glu Leu Lys Arg Thr
            260                 265
```

<210> SEQ ID NO 54
<211> LENGTH: 792
<212> TYPE: DNA
<213> ORGANISM: Unknown
<220> FEATURE:
<223> OTHER INFORMATION: EGFRVIII (806) scFv

<400> SEQUENCE: 54

```
atgctgctgc tggtgacaag cctgctgctg tgcgagctgc cacaccctgc tttcctgctg      60

atccctgatg tgcagctgca ggaatcaggc ccaagcctgg tcaaaccctc ccagtctctg     120

agtctgacct gtacagtgac tgggtactcc atcacatctg atttcgcatg gaactggatt     180

aggcagtttc caggcaataa gctggagtgg atgggctaca tctcatatag cgggaacact     240

cgctataatc ccagtctgaa atcacggatc agcattacta gagacaccag caagaaccag     300

ttctttctgc agctgaattc cgtgaccatt gaggataccg ccacatacta ttgcgtcaca     360

gctggcagag gctttccata ctggggacag ggcacactgg tgactgtcag cgccggctcc     420

acctctggga gtggaaaacc tggctccggg gaaggatcta caaagggaga catcctgatg     480
```

actcagtccc caagctccat gtcagtgagc ctgggcgaca ccgtctctat tacatgtcac 540
tctagtcagg atatcaacag taatattggc tggctgcagc agcgacccgg caagtctttc 600
aaagggctga tctatcatgg aactaacctg gacgatgaag tgcctagcag attttccggc 660
tctgggagtg gagctgatta cagtctgacc atttcaagcc tggagtcaga agacttcgca 720
gattactatt gcgtccagta tgcccagttc ccctggactt ttggcggggg aaccaagctg 780
gagatcaaac gg 792

<210> SEQ ID NO 55
<211> LENGTH: 264
<212> TYPE: PRT
<213> ORGANISM: Artificial Sequence
<220> FEATURE:
<223> OTHER INFORMATION: EGFRVIII (806) scFv

<400> SEQUENCE: 55

Met Leu Leu Leu Val Thr Ser Leu Leu Leu Cys Glu Leu Pro His Pro
1 5 10 15

Ala Phe Leu Leu Ile Pro Asp Val Gln Leu Gln Glu Ser Gly Pro Ser
20 25 30

Leu Val Lys Pro Ser Gln Ser Leu Ser Leu Thr Cys Thr Val Thr Gly
35 40 45

Tyr Ser Ile Thr Ser Asp Phe Ala Trp Asn Trp Ile Arg Gln Phe Pro
50 55 60

Gly Asn Lys Leu Glu Trp Met Gly Tyr Ile Ser Tyr Ser Gly Asn Thr
65 70 75 80

Arg Tyr Asn Pro Ser Leu Lys Ser Arg Ile Ser Ile Thr Arg Asp Thr
85 90 95

Ser Lys Asn Gln Phe Phe Leu Gln Leu Asn Ser Val Thr Ile Glu Asp
100 105 110

Thr Ala Thr Tyr Tyr Cys Val Thr Ala Gly Arg Gly Phe Pro Tyr Trp
115 120 125

Gly Gln Gly Thr Leu Val Thr Val Ser Ala Gly Ser Thr Ser Gly Ser
130 135 140

Gly Lys Pro Gly Ser Gly Glu Gly Ser Thr Lys Gly Asp Ile Leu Met
145 150 155 160

Thr Gln Ser Pro Ser Ser Met Ser Val Ser Leu Gly Asp Thr Val Ser
165 170 175

Ile Thr Cys His Ser Ser Gln Asp Ile Asn Ser Asn Ile Gly Trp Leu
180 185 190

Gln Gln Arg Pro Gly Lys Ser Phe Lys Gly Leu Ile Tyr His Gly Thr
195 200 205

Asn Leu Asp Asp Glu Val Pro Ser Arg Phe Ser Gly Ser Gly Ser Gly
210 215 220

Ala Asp Tyr Ser Leu Thr Ile Ser Ser Leu Glu Ser Glu Asp Phe Ala
225 230 235 240

Asp Tyr Tyr Cys Val Gln Tyr Ala Gln Phe Pro Trp Thr Phe Gly Gly
245 250 255

Gly Thr Lys Leu Glu Ile Lys Arg
260

<210> SEQ ID NO 56
<211> LENGTH: 777
<212> TYPE: DNA
<213> ORGANISM: Unknown

<220> FEATURE:
<223> OTHER INFORMATION: EphA2 (2A4) scFv

<400> SEQUENCE: 56
atgcttctcc tggtgacaag ccttctgctc tgtgagttac cacacccagc attcctcctg 60
atcccacagg tgcagctgtt ggagtctggg ggaggcttgg tacagcctgg ggggtccctg 120
agactctcct gtgcagcctc tggattcacc tttagcagct ataccatgtc ttgggtgcga 180
caggcccctg gacaagcgct tgagtggatg ggaaccatta gtagtcgtgg tacttacacc 240
tactatccag acagtgtgaa gggccgattc accatctcca gagacaacgc caagaactca 300
ctgtatctgc aaatgaacag cctgagagcc gaggacacgg ctgtgtatta ctgtgcgaga 360
gaagctatct ttactcactg gggccgtggc accctggtca ccgtctcctc aggtggtggt 420
ggttctggcg gcggcggctc cggtggtggt ggttctgaca tccagttgac ccagtctcca 480
tcctccctgt ctgcatctgt aggagacaga gtcaccatca cttgcaaggc gagtcaggac 540
attaataact atcacagctg gtaccagcag aaacctggcc aggctcccag gctcctcatc 600
tatcgtgcaa acagattggt cgatggggtc ccagacaggt tcagtggcag cgggtatgga 660
acagatttta ccctcacaat taataacata gaatctgagg atgctgcata ttacttctgt 720
ctgaaatata atgtgtttcc gtacacgttc ggccaaggga ccaaggtgga gatcaaa 777

<210> SEQ ID NO 57
<211> LENGTH: 259
<212> TYPE: PRT
<213> ORGANISM: Artificial Sequence
<220> FEATURE:
<223> OTHER INFORMATION: EphA2 (2A4) scFv

<400> SEQUENCE: 57

Met Leu Leu Leu Val Thr Ser Leu Leu Leu Cys Glu Leu Pro His Pro
1 5 10 15

Ala Phe Leu Leu Ile Pro Gln Val Gln Leu Leu Glu Ser Gly Gly Gly
20 25 30

Leu Val Gln Pro Gly Gly Ser Leu Arg Leu Ser Cys Ala Ala Ser Gly
35 40 45

Phe Thr Phe Ser Ser Tyr Thr Met Ser Trp Val Arg Gln Ala Pro Gly
50 55 60

Gln Ala Leu Glu Trp Met Gly Thr Ile Ser Ser Arg Gly Thr Tyr Thr
65 70 75 80

Tyr Tyr Pro Asp Ser Val Lys Gly Arg Phe Thr Ile Ser Arg Asp Asn
85 90 95

Ala Lys Asn Ser Leu Tyr Leu Gln Met Asn Ser Leu Arg Ala Glu Asp
100 105 110

Thr Ala Val Tyr Tyr Cys Ala Arg Glu Ala Ile Phe Thr His Trp Gly
115 120 125

Arg Gly Thr Leu Val Thr Val Ser Ser Gly Gly Gly Gly Ser Gly Gly
130 135 140

Gly Gly Ser Gly Gly Gly Gly Ser Asp Ile Gln Leu Thr Gln Ser Pro
145 150 155 160

Ser Ser Leu Ser Ala Ser Val Gly Asp Arg Val Thr Ile Thr Cys Lys
165 170 175

Ala Ser Gln Asp Ile Asn Asn Tyr His Ser Trp Tyr Gln Gln Lys Pro
180 185 190

Gly Gln Ala Pro Arg Leu Leu Ile Tyr Arg Ala Asn Arg Leu Val Asp
195 200 205

```
Gly Val Pro Asp Arg Phe Ser Gly Ser Gly Tyr Gly Thr Asp Phe Thr
    210                 215                 220

Leu Thr Ile Asn Asn Ile Glu Ser Glu Asp Ala Ala Tyr Tyr Phe Cys
225                 230                 235                 240

Leu Lys Tyr Asn Val Phe Pro Tyr Thr Phe Gly Gln Gly Thr Lys Val
                245                 250                 255

Glu Ile Lys
```

```
<210> SEQ ID NO 58
<211> LENGTH: 777
<212> TYPE: DNA
<213> ORGANISM: Unknown
<220> FEATURE:
<223> OTHER INFORMATION: EpHA2 (4H5) scFv

<400> SEQUENCE: 58

atgcttctcc tggtgacaag ccttctgctc tgtgagttac cacacccagc attcctcctg      60

atcccacagg tgcagctgtt ggagtctggg ggaggcttgg tacagcctgg ggggtccctg     120

agactctcct gtgcagcctc tggattcacc tttagcagct ataccatgtc ttgggtgcga     180

caggcccctg gacaagcgct tgagtggatg ggaaccatta gtagtggtgg tacttacacc     240

tactatccag acagtgtgaa gggccgattc accatctcca gagacaacgc caagaactca     300

ctgtatctgc aaatgaacag cctgagagcc gaggacacgg ctgtgtatta ctgtgcgaga     360

gaagctatct ttacttactg gggccgtggc accctggtca ccgtctcctc aggtggtggt     420

ggttctggcg gcggcggctc cggtggtggt ggttctgaca tccagttgac ccagtctcca     480

tcctccctgt ctgcatctgt aggagacaga gtcaccatca cttgcaaggc gagtcaggac     540

attaataact atttaagctg gtaccagcag aaacctggcc aggctcccag gctcctcatc     600

tatcgtgcaa acagattggt agatggggtc ccagacaggt tcagtggcag cgggtatgga     660

acagatttta ccctcacaat taataacata gaatctgagg atgctgcata ttacttctgt     720

ctgaaatatg atgtgtttcc gtacacgttc ggccaaggga ccaaggtgga gatcaaa        777
```

```
<210> SEQ ID NO 59
<211> LENGTH: 259
<212> TYPE: PRT
<213> ORGANISM: Artificial Sequence
<220> FEATURE:
<223> OTHER INFORMATION: EpHA2 (4H5) scFv

<400> SEQUENCE: 59

Met Leu Leu Leu Val Thr Ser Leu Leu Leu Cys Glu Leu Pro His Pro
1               5                   10                  15

Ala Phe Leu Leu Ile Pro Gln Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Thr Met Ser Trp Val Arg Gln Ala Pro Gly
    50                  55                  60

Gln Ala Leu Glu Trp Met Gly Thr Ile Ser Ser Gly Gly Thr Tyr Thr
65                  70                  75                  80

Tyr Tyr Pro Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110
```

-continued

```
Thr Ala Val Tyr Tyr Cys Ala Arg Glu Ala Ile Phe Thr Tyr Trp Gly
        115                 120                 125

Arg Gly Thr Leu Val Thr Val Ser Ser Gly Gly Gly Gly Ser Gly Gly
    130                 135                 140

Gly Gly Ser Gly Gly Gly Gly Ser Asp Ile Gln Leu Thr Gln Ser Pro
145                 150                 155                 160

Ser Ser Leu Ser Ala Ser Val Gly Asp Arg Val Thr Ile Thr Cys Lys
                165                 170                 175

Ala Ser Gln Asp Ile Asn Asn Tyr Leu Ser Trp Tyr Gln Gln Lys Pro
            180                 185                 190

Gly Gln Ala Pro Arg Leu Leu Ile Tyr Arg Ala Asn Arg Leu Val Asp
        195                 200                 205

Gly Val Pro Asp Arg Phe Ser Gly Ser Gly Tyr Gly Thr Asp Phe Thr
    210                 215                 220

Leu Thr Ile Asn Asn Ile Glu Ser Glu Asp Ala Ala Tyr Tyr Phe Cys
225                 230                 235                 240

Leu Lys Tyr Asp Val Phe Pro Tyr Thr Phe Gly Gln Gly Thr Lys Val
                245                 250                 255

Glu Ile Lys


<210> SEQ ID NO 60
<211> LENGTH: 819
<212> TYPE: DNA
<213> ORGANISM: Unknown
<220> FEATURE:
<223> OTHER INFORMATION: FITC (E2) scFv

<400> SEQUENCE: 60

atgcttctcc tggtgacaag ccttctgctc tgtgagttac cacacccagc attcctcctg      60

atcccaagcg tgctgacaca gcctagctcc gtgtctgccg cccctggcca gaaagtgacc     120

atcagctgta gcggcagcac cagcaacatc ggcaacaact acgtgtcctg gtatcagcag     180

cacccccggca aggcccccaa gctgatgatc tacgacgtgt ccaagcggcc cagcggcgtg    240

cccgatagat tttccggcag caagagcggc aacagcgcca gcctggatat cagcggcctg     300

cagtctgagg acgaggccga ctactattgc gccgcctggg acgatagcct gagcgagttc     360

ctgtttggca ccggcaccaa gctgacagtg ctgggcggag gcggaggatc tggcggcgga     420

ggaagtggcg gagggggatc tcaggtgcag ctggtggaaa gcggcggcaa cctggtgcag     480

cctggcggat ctctgagact gagctgtgcc gccagcggct tcaccttcgg cagcttcagc     540

atgagctggg tgcgccaggc tcctggggga ggactggaat gggtggcagg actgagcgcc     600

agaagcagcc tgacccacta cgccgatagc gtgaagggcc ggttcaccat cagccgggac     660

aacgccaaga acagcgtgta cctgcagatg aacagcctgc gggtggaaga taccgccgtg     720

tactactgcg ccagacggtc ctacgacagc agcggctact ggggccactt ctacagctac     780

atggacgtgt ggggccaggg caccctcgtg acagtgtct                            819


<210> SEQ ID NO 61
<211> LENGTH: 273
<212> TYPE: PRT
<213> ORGANISM: Artificial Sequence
<220> FEATURE:
<223> OTHER INFORMATION: FITC (E2) scFv

<400> SEQUENCE: 61

Met Leu Leu Leu Val Thr Ser Leu Leu Leu Cys Glu Leu Pro His Pro
1               5                   10                  15
```

```
Ala Phe Leu Leu Ile Pro Ser Val Leu Thr Gln Pro Ser Ser Val Ser
            20                  25                  30

Ala Ala Pro Gly Gln Lys Val Thr Ile Ser Cys Ser Gly Ser Thr Ser
        35                  40                  45

Asn Ile Gly Asn Asn Tyr Val Ser Trp Tyr Gln Gln His Pro Gly Lys
    50                  55                  60

Ala Pro Lys Leu Met Ile Tyr Asp Val Ser Lys Arg Pro Ser Gly Val
65                  70                  75                  80

Pro Asp Arg Phe Ser Gly Ser Lys Ser Gly Asn Ser Ala Ser Leu Asp
                85                  90                  95

Ile Ser Gly Leu Gln Ser Glu Asp Glu Ala Asp Tyr Tyr Cys Ala Ala
            100                 105                 110

Trp Asp Asp Ser Leu Ser Glu Phe Leu Phe Gly Thr Gly Thr Lys Leu
        115                 120                 125

Thr Val Leu Gly Gly Gly Gly Gly Ser Gly Gly Gly Gly Ser Gly Gly
    130                 135                 140

Gly Gly Ser Gln Val Gln Leu Val Glu Ser Gly Gly Asn Leu Val Gln
145                 150                 155                 160

Pro Gly Gly Ser Leu Arg Leu Ser Cys Ala Ala Ser Gly Phe Thr Phe
                165                 170                 175

Gly Ser Phe Ser Met Ser Trp Val Arg Gln Ala Pro Gly Gly Gly Leu
            180                 185                 190

Glu Trp Val Ala Gly Leu Ser Ala Arg Ser Ser Leu Thr His Tyr Ala
        195                 200                 205

Asp Ser Val Lys Gly Arg Phe Thr Ile Ser Arg Asp Asn Ala Lys Asn
    210                 215                 220

Ser Val Tyr Leu Gln Met Asn Ser Leu Arg Val Glu Asp Thr Ala Val
225                 230                 235                 240

Tyr Tyr Cys Ala Arg Arg Ser Tyr Asp Ser Ser Gly Tyr Trp Gly His
                245                 250                 255

Phe Tyr Ser Tyr Met Asp Val Trp Gly Gln Gly Thr Leu Val Thr Val
            260                 265                 270

Ser
```

<210> SEQ ID NO 62
<211> LENGTH: 381
<212> TYPE: DNA
<213> ORGANISM: Unknown
<220> FEATURE:
<223> OTHER INFORMATION: GD2 (hu3F8) scFv

<400> SEQUENCE: 62

```
atgcttctcc tggtgacaag ccttctgctc tgtgagttac cacacccagc attcctcctg      60

atcccaagca tcgtgatgac ccagaccccc aagttcctgc tggtgagcgc cggcgacagg     120

gtgaccatca cctgcaaggc cagccagagc gtgagcaacg acgtgacctg gtaccagcag     180

aaggccggcc agagccccaa gctgctgatc tacagcgcca gcaacaggta cagcggcgtg     240

cccgacaggt tcaccggcag cggctacggc accgccttca ccttcaccat cagcaccgtg     300

caggccgagg acctggccgt gtacttctgc cagcaggact acagcagctt cggcggcggc     360

accaagctgg agatcaagag g                                               381
```

<210> SEQ ID NO 63
<211> LENGTH: 127
<212> TYPE: PRT

<213> ORGANISM: Artificial Sequence
<220> FEATURE:
<223> OTHER INFORMATION: GD2 (hu3F8) scFv

<400> SEQUENCE: 63

Met Leu Leu Leu Val Thr Ser Leu Leu Leu Cys Glu Leu Pro His Pro
1 5 10 15

Ala Phe Leu Leu Ile Pro Ser Ile Val Met Thr Gln Thr Pro Lys Phe
20 25 30

Leu Leu Val Ser Ala Gly Asp Arg Val Thr Ile Thr Cys Lys Ala Ser
35 40 45

Gln Ser Val Ser Asn Asp Val Thr Trp Tyr Gln Gln Lys Ala Gly Gln
50 55 60

Ser Pro Lys Leu Leu Ile Tyr Ser Ala Ser Asn Arg Tyr Ser Gly Val
65 70 75 80

Pro Asp Arg Phe Thr Gly Ser Gly Tyr Gly Thr Ala Phe Thr Phe Thr
85 90 95

Ile Ser Thr Val Gln Ala Glu Asp Leu Ala Val Tyr Phe Cys Gln Gln
100 105 110

Asp Tyr Ser Ser Phe Gly Gly Gly Thr Lys Leu Glu Ile Lys Arg
115 120 125

<210> SEQ ID NO 64
<211> LENGTH: 801
<212> TYPE: DNA
<213> ORGANISM: Unknown
<220> FEATURE:
<223> OTHER INFORMATION: Her2 (Herceptin) scFv

<400> SEQUENCE: 64
atgcttctcc tggtgacaag ccttctgctc tgtgagttac cacacccagc attcctcctg 60
atcccagata tccagatgac ccagtccccg agctccctgt ccgcctctgt gggcgatagg 120
gtcaccatca cctgccgtgc cagtcaggat gtgaatactg ctgtagcctg gtatcaacag 180
aaaccaggaa aagctccgaa actactgatt tactcggcat ccttcctcta ctctggagtc 240
ccttctcgct tctctggttc cagatctggg acggatttca ctctgaccat cagcagtctg 300
cagccggaag acttcgcaac ttattactgt cagcaacatt atactactcc tcccacgttc 360
ggacagggta ccaaggtgga gatcaaaggc agtactagcg gcggtggctc cgggggcgga 420
tccggtgggg gcggcagcag cgaggttcag ctggtggagt ctggcggtgg cctggtgcag 480
ccagggggct cactccgttt gtcctgtgca gcttctggct tcaacattaa agacacctat 540
atacactggg tgcgtcaggc cccgggtaag ggcctggaat gggttgcaag gatttatcct 600
acgaatggtt atactagata tgccgatagc gtcaagggcc gtttcactat aagcgcagac 660
acatccaaaa acacagccta cctgcagatg aacagcctgc gtgctgagga cactgccgtc 720
tattattgtt ctagatgggg aggggacggc ttctatgcta tggactactg gggtcaagga 780
accctggtca ccgtctcgag t 801

<210> SEQ ID NO 65
<211> LENGTH: 267
<212> TYPE: PRT
<213> ORGANISM: Artificial Sequence
<220> FEATURE:
<223> OTHER INFORMATION: Her2 (Herceptin) scFv

<400> SEQUENCE: 65

Met Leu Leu Leu Val Thr Ser Leu Leu Leu Cys Glu Leu Pro His Pro

-continued

```
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Val Asn Thr Ala Val Ala Trp Tyr Gln Gln Lys Pro Gly Lys
    50                  55                  60

Ala Pro Lys Leu Leu Ile Tyr Ser Ala Ser Phe Leu Tyr Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

His Tyr Thr Thr Pro Pro Thr Phe Gly Gln Gly Thr Lys Val Glu Ile
        115                 120                 125

Lys Gly Ser Thr Ser Gly Gly Gly Ser Gly Gly Gly Ser Gly Gly Gly
    130                 135                 140

Gly Ser Ser Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Asn Ile
                165                 170                 175

Lys Asp Thr Tyr Ile His Trp Val Arg Gln Ala Pro Gly Lys Gly Leu
            180                 185                 190

Glu Trp Val Ala Arg Ile Tyr Pro Thr Asn Gly Tyr Thr Arg Tyr Ala
        195                 200                 205

Asp Ser Val Lys Gly Arg Phe Thr Ile Ser Ala Asp Thr Ser Lys Asn
    210                 215                 220

Thr Ala Tyr Leu Gln Met Asn Ser Leu Arg Ala Glu Asp Thr Ala Val
225                 230                 235                 240

Tyr Tyr Cys Ser Arg Trp Gly Gly Asp Gly Phe Tyr Ala Met Asp Tyr
                245                 250                 255

Trp Gly Gln Gly Thr Leu Val Thr Val Ser Ser
            260                 265
```

<210> SEQ ID NO 66
<211> LENGTH: 722
<212> TYPE: DNA
<213> ORGANISM: Unknown
<220> FEATURE:
<223> OTHER INFORMATION: IL13R2a (hu08) VlVh scFv

<400> SEQUENCE: 66

```
atgcttctcc tggtgacaag ccttctgctc tgtgagttac cacacccagc attcctcctg      60

atcccagaca tccagatgac ccagtccccc tcttctctgt ctgcctctgt gggcgacaga     120

gtgaccatca cctgtaaggc cagtcaggat gtaggtactg ctgtagcctg gtatcagcag     180

aagcctggca aggctcccaa gctgctgatc tactcggcat cctaccggtc cactggcgtg     240

ccttccagat tctccggctc tggctctggc accgatttca ccctgaccat ctcctccctc     300

cagcctgagg atttcgccac ctactactgc cagcaccatt atagtgctcc gtggacgttt     360

ggcggcggaa caaaggtgga gatcaagggt ggtggtggtt ctggcggcgg cggctccggt     420

ggtggtggtt ctgaggtgca gctggtggag tctggcggcg gactggtgca gcctggcggc     480

tctctgagac tgtcttgtgc cgcctccggc ttcaccttca gtaggaatgg catgtcttgg     540

gtgaggcagg cccctggcaa gggcctggag tgggtggcca ccgttagtag tggtggtagt     600
```

```
tacatctact atgcagacag tgtgaagggg cggttcacca tctccaggga caacgccaag    660

aactccctgt acctccagat gaactccctg agggccgagg ataccgccgt gtactactgt    720

gc                                                                   722
```

<210> SEQ ID NO 67
<211> LENGTH: 240
<212> TYPE: PRT
<213> ORGANISM: Artificial Sequence
<220> FEATURE:
<223> OTHER INFORMATION: IL13RA2 (HU08) VlVh scFv

<400> SEQUENCE: 67

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Val Gly Thr Ala Val Ala Trp Tyr Gln Gln Lys Pro Gly Lys
    50                  55                  60

Ala Pro Lys Leu Leu Ile Tyr Ser Ala Ser Tyr Arg Ser Thr Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln His
            100                 105                 110

His Tyr Ser Ala Pro Trp Thr Phe Gly Gly Gly Thr Lys Val Glu Ile
        115                 120                 125

Lys Gly Gly Gly Gly Ser Gly Gly Gly Gly Ser Gly Gly Gly Gly Ser
    130                 135                 140

Glu Val Gln Leu Val Glu Ser Gly Gly Gly Leu Val Gln Pro Gly Gly
145                 150                 155                 160

Ser Leu Arg Leu Ser Cys Ala Ala Ser Gly Phe Thr Phe Ser Arg Asn
                165                 170                 175

Gly Met Ser Trp Val Arg Gln Ala Pro Gly Lys Gly Leu Glu Trp Val
            180                 185                 190

Ala Thr Val Ser Ser Gly Gly Ser Tyr Ile Tyr Tyr Ala Asp Ser Val
        195                 200                 205

Lys Gly Arg Phe Thr Ile Ser Arg Asp Asn Ala Lys Asn Ser Leu Tyr
    210                 215                 220

Leu Gln Met Asn Ser Leu Arg Ala Glu Asp Thr Ala Val Tyr Tyr Cys
225                 230                 235                 240
```

<210> SEQ ID NO 68
<211> LENGTH: 809
<212> TYPE: DNA
<213> ORGANISM: Unknown
<220> FEATURE:
<223> OTHER INFORMATION: IL13RA2 (HU08) VlVh scFv

<400> SEQUENCE: 68

```
atgcttctcc tggtgacaag ccttctgctc tgtgagttac cacacccagc attcctcctg     60

atcccagagg tgcagctggt ggagtctggc ggcggactgg tgcagcctgg cggctctctg    120

agactgtctt gtgccgcctc cggcttcacc ttcagtagga atggcatgtc ttgggtgagg    180

caggcccctg gcaagggcct ggagtgggtg gccaccgtta gtagtggtgg tagttacatc    240
```

```
tactatgcag acagtgtgaa ggggcggttc accatctcca gggacaacgc caagaactcc    300

ctgtacctcc agatgaactc cctgagggcc gaggataccg ccgtgtacta ctgtgccaga    360

caagggacta cggcactagc tacgaggttc ttcgatgtct ggggccaggg caccctggtg    420

accgtgtcct ctggtggtgg tggttctggc ggcggcggct ccggtggtgg tggttctgac    480

atccagatga cccagtcccc ctcttctctg tctgcctctg tgggcgacag agtgaccatc    540

acctgtaagg ccagtcagga tgtaggtact gctgtagcct ggtatcagca gaagcctggc    600

aaggctccca agctgctgat ctactcggca tcctaccggt ccactggcgt gccttccaga    660

ttctccggct ctggctctgg caccgatttc accctgacca tctcctccct ccagcctgag    720

gatttcgcca cctactactg ccagcaccat tatagtgctc cgtggacgtt tggcggcgga    780

acaaaggtgg agatcaagga atctaagta                                      809
```

<210> SEQ ID NO 69
<211> LENGTH: 269
<212> TYPE: PRT
<213> ORGANISM: Artificial Sequence
<220> FEATURE:
<223> OTHER INFORMATION: IL13RA2 (HU08) VlVh scFv

<400> SEQUENCE: 69

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Arg Asn Gly Met Ser Trp Val Arg Gln Ala Pro Gly
    50                  55                  60

Lys Gly Leu Glu Trp Val Ala Thr Val Ser Ser Gly Gly Ser Tyr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Gln Gly Thr Thr Ala Leu Ala Thr
        115                 120                 125

Arg Phe Phe Asp Val Trp Gly Gln Gly Thr Leu Val Thr Val Ser Ser
    130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Lys Ala Ser Gln Asp Val Gly Thr Ala Val
            180                 185                 190

Ala Trp Tyr Gln Gln Lys Pro Gly Lys Ala Pro Lys Leu Leu Ile Tyr
        195                 200                 205

Ser Ala Ser Tyr Arg Ser Thr Gly Val Pro Ser Arg Phe Ser Gly Ser
    210                 215                 220

Gly Ser Gly Thr Asp Phe Thr Leu Thr Ile Ser Ser Leu Gln Pro Glu
225                 230                 235                 240

Asp Phe Ala Thr Tyr Tyr Cys Gln His His Tyr Ser Ala Pro Trp Thr
                245                 250                 255
```

-continued

```
Phe Gly Gly Gly Thr Lys Val Glu Ile Lys Glu Ser Lys
            260                 265


<210> SEQ ID NO 70
<211> LENGTH: 794
<212> TYPE: DNA
<213> ORGANISM: Unknown
<220> FEATURE:
<223> OTHER INFORMATION: IL13RA2 (HU07) VlVh scFv

<400> SEQUENCE: 70

atgcttctcc tggtgacaag ccttctgctc tgtgagttac cacacccagc attcctcctg      60

atcccagata ttcagatgac ccagagcccg agcagcctga gcgcgagcgt gggcgatcgc     120

gtgaccatta cctgcaccgc gagcctgagc gtgagcagca cctatctgca ttggtatcag     180

cagaaaccgg gcaaagcgcc gaaactgctg atttatagca ccagcaacct ggcgagcggc     240

gtgccgagcc gctttagcgg cagcggcagc ggcaccgatt ttaccctgac cattagcagc     300

ctgcagccgg aagattttgc gacctattat tgccatcagt atcatcgcag cccgctgacc     360

tttggcggcg gcaccaaagt ggaaattaaa ggtggtggtg gttctggcgg cggcggctcc     420

ggtggtggtg gttctgaagt gcagctggtg gaaagcggcg gcggcctggt gcagccgggc     480

ggcagcctgc gcctgagctg cgcggcgagc ggctttacct ttaccaaata tggcgtgcat     540

tgggtgcgcc aggcgccggg caaaggcctg gaatgggtgg cggtgaaatg ggcgggcggc     600

agcaccgatt ataacagcgc gctgatgagc cgctttacca ttagccgcga taacgcgaaa     660

aacagcctgt atctgcagat gaacagcctg cgcgcggaag ataccgcggt gtattattgc     720

gcgcgcgatc atcgcgatgc gatggattat tggggccagg gcaccctggt gaccgtgagc     780

agcgaatcta agta                                                       794


<210> SEQ ID NO 71
<211> LENGTH: 264
<212> TYPE: PRT
<213> ORGANISM: Artificial Sequence
<220> FEATURE:
<223> OTHER INFORMATION: IL13RA2 (HU07) VlVh scFv

<400> SEQUENCE: 71

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Thr Ala Ser
        35                  40                  45

Leu Ser Val Ser Ser Thr Tyr Leu His Trp Tyr Gln Gln Lys Pro Gly
    50                  55                  60

Lys Ala Pro Lys Leu Leu Ile Tyr Ser Thr Ser Asn Leu Ala Ser Gly
65                  70                  75                  80

Val Pro Ser Arg Phe Ser Gly Ser Gly Ser Gly Thr Asp Phe Thr Leu
                85                  90                  95

Thr Ile Ser Ser Leu Gln Pro Glu Asp Phe Ala Thr Tyr Tyr Cys His
            100                 105                 110

Gln Tyr His Arg Ser Pro Leu Thr Phe Gly Gly Gly Thr Lys Val Glu
        115                 120                 125

Ile Lys Gly Gly Gly Gly Ser Gly Gly Gly Gly Ser Gly Gly Gly Gly
    130                 135                 140

Ser Glu Val Gln Leu Val Glu Ser Gly Gly Gly Leu Val Gln Pro Gly
```

```
145                 150                 155                 160

Gly Ser Leu Arg Leu Ser Cys Ala Ala Ser Gly Phe Thr Phe Thr Lys
                165                 170                 175

Tyr Gly Val His Trp Val Arg Gln Ala Pro Gly Lys Gly Leu Glu Trp
            180                 185                 190

Val Ala Val Lys Trp Ala Gly Gly Ser Thr Asp Tyr Asn Ser Ala Leu
        195                 200                 205

Met Ser Arg Phe Thr Ile Ser Arg Asp Asn Ala Lys Asn Ser Leu Tyr
    210                 215                 220

Leu Gln Met Asn Ser Leu Arg Ala Glu Asp Thr Ala Val Tyr Tyr Cys
225                 230                 235                 240

Ala Arg Asp His Arg Asp Ala Met Asp Tyr Trp Gly Gln Gly Thr Leu
                245                 250                 255

Val Thr Val Ser Ser Glu Ser Lys
            260
```

<210> SEQ ID NO 72
<211> LENGTH: 794
<212> TYPE: DNA
<213> ORGANISM: Unknown
<220> FEATURE:
<223> OTHER INFORMATION: IL13RA2 (HU07) VlVh scFv

<400> SEQUENCE: 72

```
atgcttctcc tggtgacaag ccttctgctc tgtgagttac cacacccagc attcctcctg      60

atcccagaag tgcagctggt ggaaagcggc ggcggcctgg tgcagccggg cggcagcctg     120

cgcctgagct gcgcggcgag cggctttacc tttaccaaat atggcgtgca ttgggtgcgc     180

caggcgccgg gcaaaggcct ggaatgggtg gcggtgaaat gggcgggcgg cagcaccgat     240

tataacagcg cgctgatgag ccgctttacc attagccgcg ataacgcgaa aaacagcctg     300

tatctgcaga tgaacagcct gcgcgcggaa gataccgcgg tgtattattg cgcgcgcgat     360

catcgcgatg cgatggatta ttggggccag ggcaccctgg tgaccgtgag cagcggtggt     420

ggtggttctg gcggcggcgg ctccggtggt ggtggttctg atattcagat gacccagagc     480

ccgagcagcc tgagcgcgag cgtgggcgat cgcgtgacca ttacctgcac cgcgagcctg     540

agcgtgagca gcacctatct gcattggtat cagcagaaac cgggcaaagc gccgaaactg     600

ctgatttata gcaccagcaa cctggcgagc ggcgtgccga gccgctttag cggcagcggc     660

agcggcaccg attttaccct gaccattagc agcctgcagc cggaagattt tgcgacctat     720

tattgccatc agtatcatcg cagcccgctg acctttggcg gcggcaccaa agtggaaatt     780

aaagaatcta agta                                                       794
```

<210> SEQ ID NO 73
<211> LENGTH: 264
<212> TYPE: PRT
<213> ORGANISM: Artificial Sequence
<220> FEATURE:
<223> OTHER INFORMATION: IL13RA2 (HU07) VlVh

<400> SEQUENCE: 73

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45
```

```
Phe Thr Phe Thr Lys Tyr Gly Val His Trp Val Arg Gln Ala Pro Gly
    50                  55                  60

Lys Gly Leu Glu Trp Val Ala Val Lys Trp Ala Gly Gly Ser Thr Asp
65                  70                  75                  80

Tyr Asn Ser Ala Leu Met Ser Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Asp His Arg Asp Ala Met Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Thr Ala Ser Leu Ser Val Ser Ser Thr Tyr Leu His Trp Tyr Gln Gln
            180                 185                 190

Lys Pro Gly Lys Ala Pro Lys Leu Leu Ile Tyr Ser Thr Ser Asn Leu
        195                 200                 205

Ala Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys His Gln Tyr His Arg Ser Pro Leu Thr Phe Gly Gly Gly Thr
                245                 250                 255

Lys Val Glu Ile Lys Glu Ser Lys
            260
```

<210> SEQ ID NO 74
<211> LENGTH: 401
<212> TYPE: DNA
<213> ORGANISM: Unknown
<220> FEATURE:
<223> OTHER INFORMATION: Anti-IL13RA2 (IL13 ZETAKINE)

<400> SEQUENCE: 74

```
atgcttctcc tggtgacaag ccttctgctc tgtgagttac cacacccagc attcctcctg      60

atcccaggcc ctgtgcctcc ctctacagcc ctcaggtacc tcattgagga gctggtcaac     120

atcacccaga accagaaggc tccgctctgc aatggcagca tggtatggag catcaacctg     180

acagctggca tgtactgtgc agccctggaa tccctgatca acgtgtcagg ctgcagtgcc     240

atcgagaaga cccagaggat gctgagcgga ttctgcccgc acaaggtctc agctgggcag     300

ttttccagct tgcatgtccg agacaccaaa atcgaggtgg cccagtttgt aaaggacctg     360

ctcttacatt taaagaaact tttcgcgag ggacggttca a                          401
```

<210> SEQ ID NO 75
<211> LENGTH: 133
<212> TYPE: PRT
<213> ORGANISM: Artificial Sequence
<220> FEATURE:
<223> OTHER INFORMATION: Anti-IL13RA2 (IL13 ZETAKINE) A

<400> SEQUENCE: 75

```
Met Leu Leu Leu Val Thr Ser Leu Leu Leu Cys Glu Leu Pro His Pro
1               5                   10                  15
```

```
Ala Phe Leu Leu Ile Pro Gly Pro Val Pro Pro Ser Thr Ala Leu Arg
            20                  25                  30

Tyr Leu Ile Glu Glu Leu Val Asn Ile Thr Gln Asn Gln Lys Ala Pro
        35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
        115                 120                 125

Arg Glu Gly Arg Phe
    130
```

<210> SEQ ID NO 76
<211> LENGTH: 807
<212> TYPE: DNA
<213> ORGANISM: Unknown
<220> FEATURE:
<223> OTHER INFORMATION: OAGD2 (8B6) VLVH SCFV NUCLEOTIDE SEQUENCE

<400> SEQUENCE: 76

```
atgcttctcc tggtgacaag ccttctgctc tgtgagttac cacacccagc attcctcctg     60

atcccagatg ttgtgatgac ccaaactcca ctctccctgc ctgtcagtct tggagatcaa    120

gcctcaatct cttgcagatc tagtcagagc cttctaaaaa ataatggaaa caccttttta    180

cattggtacc tgcagaagtc aggccagtct ccaaagctcc ttatctacaa agtttccaac    240

cgactttctg gggtcccaga caggttcagt ggcagtggat cagggacata tttcacactc    300

aagatcagca gagtggaggc tgaggatctg ggagtttatt tctgctctca aagtacacat    360

attccgtaca cattcggagg ggggaccaag ctcgagctga aacgaggcgg agggggctct    420

ggcggcggag gatctggggg agggggcagc gaggtgaaac tggtggagtc tggaggaggc    480

ttggtgctgc ctggggattc tctgagactc tcctgtgcaa cttctgagtt caccttcact    540

gattactaca tgacttgggt ccgccagcct ccaagaaagg cacttgagtg gttgggtttt    600

attagaaaca gagctaatgg ttacacaaca gagtacaatc catctgtgaa gggtcggttc    660

accatttcca gagataattc ccaaagcatc ctctatcttc aaatgaacac cctgagaact    720

gaggacagtg ccacttatta ctgtgcaaga gtctctaact gggcctttga ctactggggc    780

caaggcacca ctctcacagt ctcctca                                        807
```

<210> SEQ ID NO 77
<211> LENGTH: 269
<212> TYPE: PRT
<213> ORGANISM: Artificial Sequence
<220> FEATURE:
<223> OTHER INFORMATION: OAGD2 (8B6) VlVh scFv

<400> SEQUENCE: 77

```
Met Leu Leu Leu Val Thr Ser Leu Leu Leu Cys Glu Leu Pro His Pro
1               5                   10                  15

Ala Phe Leu Leu Ile Pro Asp Val Val Met Thr Gln Thr Pro Leu Ser
            20                  25                  30
```

-continued

```
Leu Pro Val Ser Leu Gly Asp Gln Ala Ser Ile Ser Cys Arg Ser Ser
        35                  40                  45

Gln Ser Leu Leu Lys Asn Asn Gly Asn Thr Phe Leu His Trp Tyr Leu
    50                  55                  60

Gln Lys Ser Gly Gln Ser Pro Lys Leu Leu Ile Tyr Lys Val Ser Asn
65                  70                  75                  80

Arg Leu Ser Gly Val Pro Asp Arg Phe Ser Gly Ser Gly Ser Gly Thr
                85                  90                  95

Tyr Phe Thr Leu Lys Ile Ser Arg Val Glu Ala Glu Asp Leu Gly Val
            100                 105                 110

Tyr Phe Cys Ser Gln Ser Thr His Ile Pro Tyr Thr Phe Gly Gly Gly
        115                 120                 125

Thr Lys Leu Glu Leu Lys Arg Gly Gly Gly Gly Ser Gly Gly Gly Gly
    130                 135                 140

Ser Gly Gly Gly Gly Ser Glu Val Lys Leu Val Glu Ser Gly Gly Gly
145                 150                 155                 160

Leu Val Leu Pro Gly Asp Ser Leu Arg Leu Ser Cys Ala Thr Ser Glu
                165                 170                 175

Phe Thr Phe Thr Asp Tyr Tyr Met Thr Trp Val Arg Gln Pro Pro Arg
            180                 185                 190

Lys Ala Leu Glu Trp Leu Gly Phe Ile Arg Asn Arg Ala Asn Gly Tyr
        195                 200                 205

Thr Thr Glu Tyr Asn Pro Ser Val Lys Gly Arg Phe Thr Ile Ser Arg
    210                 215                 220

Asp Asn Ser Gln Ser Ile Leu Tyr Leu Gln Met Asn Thr Leu Arg Thr
225                 230                 235                 240

Glu Asp Ser Ala Thr Tyr Tyr Cys Ala Arg Val Ser Asn Trp Ala Phe
                245                 250                 255

Asp Tyr Trp Gly Gln Gly Thr Thr Leu Thr Val Ser Ser
            260                 265
```

<210> SEQ ID NO 78
<211> LENGTH: 810
<212> TYPE: DNA
<213> ORGANISM: Unknown
<220> FEATURE:
<223> OTHER INFORMATION: ROR1 (R12) scFv

<400> SEQUENCE: 78

```
atgctgctgc tggtgacaag cctgctgctg tgcgagctgc cccaccccgc ctttctgctg     60

atcccccagg aacagctcgt cgaaagcggc ggcagactgg tgacacctgg cggcagcctg    120

accctgagct gcaaggccag cggcttcgac ttcagcgcct actacatgag ctgggtccgc    180

caggcccctg gcaagggact ggaatggatc gccaccatct accccagcag cggcaagacc    240

tactacgcca cctgggtgaa cggacggttc accatctcca gcgacaacgc ccagaacacc    300

gtggacctgc agatgaacag cctgacagcc gccgaccggg ccacctactt ttgcgccaga    360

gacagctacg ccgacgacgg cgccctgttc aacatctggg gccctggcac cctggtgaca    420

atctctagcg gcggaggcgg atctggtggc ggaggaagtg gcggcggagg atctgagctg    480

gtgctgaccc agagcccctc tgtgtctgct gccctgggaa gccctgccaa gatcacctgt    540

accctgagca gcgcccacaa gaccgacacc atcgactggt atcagcagct gcagggcgag    600

gcccccagat acctgatgca ggtgcagagc gacggcagct acaccaagag gccaggcgtg    660

cccgaccggt tcagcggatc tagctctggc gccgaccgct acctgatcat ccccagcgtg    720
```

```
caggccgatg acgaggccga ttactactgt ggcgccgact acatcggcgg ctacgtgttc     780

ggcggaggca cccagctgac cgtgaccggc                                      810


<210> SEQ ID NO 79
<211> LENGTH: 270
<212> TYPE: PRT
<213> ORGANISM: Artificial Sequence
<220> FEATURE:
<223> OTHER INFORMATION: ROR1 (R12) scFv

<400> SEQUENCE: 79

Met Leu Leu Leu Val Thr Ser Leu Leu Leu Cys Glu Leu Pro His Pro
1               5                   10                  15

Ala Phe Leu Leu Ile Pro Gln Glu Gln Leu Val Glu Ser Gly Gly Arg
            20                  25                  30

Leu Val Thr Pro Gly Gly Ser Leu Thr Leu Ser Cys Lys Ala Ser Gly
        35                  40                  45

Phe Asp Phe Ser Ala Tyr Tyr Met Ser Trp Val Arg Gln Ala Pro Gly
    50                  55                  60

Lys Gly Leu Glu Trp Ile Ala Thr Ile Tyr Pro Ser Ser Gly Lys Thr
65                  70                  75                  80

Tyr Tyr Ala Thr Trp Val Asn Gly Arg Phe Thr Ile Ser Ser Asp Asn
                85                  90                  95

Ala Gln Asn Thr Val Asp Leu Gln Met Asn Ser Leu Thr Ala Ala Asp
            100                 105                 110

Arg Ala Thr Tyr Phe Cys Ala Arg Asp Ser Tyr Ala Asp Asp Gly Ala
        115                 120                 125

Leu Phe Asn Ile Trp Gly Pro Gly Thr Leu Val Thr Ile Ser Ser Gly
    130                 135                 140

Gly Gly Gly Ser Gly Gly Gly Gly Ser Gly Gly Gly Gly Ser Glu Leu
145                 150                 155                 160

Val Leu Thr Gln Ser Pro Ser Val Ser Ala Ala Leu Gly Ser Pro Ala
                165                 170                 175

Lys Ile Thr Cys Thr Leu Ser Ser Ala His Lys Thr Asp Thr Ile Asp
            180                 185                 190

Trp Tyr Gln Gln Leu Gln Gly Glu Ala Pro Arg Tyr Leu Met Gln Val
        195                 200                 205

Gln Ser Asp Gly Ser Tyr Thr Lys Arg Pro Gly Val Pro Asp Arg Phe
    210                 215                 220

Ser Gly Ser Ser Ser Gly Ala Asp Arg Tyr Leu Ile Ile Pro Ser Val
225                 230                 235                 240

Gln Ala Asp Asp Glu Ala Asp Tyr Tyr Cys Gly Ala Asp Tyr Ile Gly
                245                 250                 255

Gly Tyr Val Phe Gly Gly Gly Thr Gln Leu Thr Val Thr Gly
            260                 265                 270


<210> SEQ ID NO 80
<211> LENGTH: 417
<212> TYPE: DNA
<213> ORGANISM: Unknown
<220> FEATURE:
<223> OTHER INFORMATION: CD33 (H2H12) VlVh scFv

<400> SEQUENCE: 80

atgcttctcc tggtgacaag ccttctgctc tgtgagttac cacacccagc attcctcctg      60

atcccacagg ttcagctggt gcagtctgga gctgaggtga agaagcctgg ggcctcagtg     120
```

-continued

```
aaggtctcct gcaaggcttc tggttacacc tttaccaatt atgatataaa ttgggtgaga    180

caggcccctg gacaagggct tgagtggatt ggatggattt atcctggaga tggtagtacc    240

aaatataatg agaaattcaa ggccaaggct accctgacag ctgacacatc caccagcaca    300

gcctacatgg agctgaggag cctgagatct gatgacacag ctgtgtatta ctgtgcttct    360

ggatatgaag atgctatgga ctactggggg caagggacca cagtcacagt ctcctca       417
```

<210> SEQ ID NO 81
<211> LENGTH: 139
<212> TYPE: PRT
<213> ORGANISM: Artificial Sequence
<220> FEATURE:
<223> OTHER INFORMATION: CD33 (H2H12) VlVh scFv

<400> SEQUENCE: 81

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Asn Tyr Asp Ile Asn Trp Val Arg Gln Ala Pro Gly
    50                  55                  60

Gln Gly Leu Glu Trp Ile Gly Trp Ile Tyr Pro Gly Asp Gly Ser Thr
65                  70                  75                  80

Lys Tyr Asn Glu Lys Phe Lys Ala Lys Ala Thr Leu Thr Ala Asp Thr
                85                  90                  95

Ser Thr Ser Thr Ala Tyr Met Glu Leu Arg Ser Leu Arg Ser Asp Asp
            100                 105                 110

Thr Ala Val Tyr Tyr Cys Ala Ser Gly Tyr Glu Asp Ala Met Asp Tyr
        115                 120                 125

Trp Gly Gln Gly Thr Thr Val Thr Val Ser Ser
    130                 135
```

<210> SEQ ID NO 82
<211> LENGTH: 387
<212> TYPE: DNA
<213> ORGANISM: Unknown
<220> FEATURE:
<223> OTHER INFORMATION: CD33 (H2H12) VlVh scFv

<400> SEQUENCE: 82

```
atgcttctcc tggtgacaag ccttctgctc tgtgagttac cacacccagc attcctcctg     60

atcccagaca tccagatgac ccagtctcca tcctcactgt ctgcatctgt aggagacaga    120

gtcaccatca attgtaaggc tagtcaggac attaatagct atttgagctg gtttcagcag    180

aaaccaggga aagcccctaa gaccctgatc tatagagcaa atagattggt agatggggtc    240

ccatcaaggt tctctggcag tggatctggg caagattata ctctcaccat cagcagcctg    300

cagcctgaag attttgcaac ttattactgc ttgcagtatg atgagtttcc tctcacattt    360

ggaggaggga ccaaggtgga gatcaaa                                        387
```

<210> SEQ ID NO 83
<211> LENGTH: 129
<212> TYPE: PRT
<213> ORGANISM: Artificial Sequence
<220> FEATURE:
<223> OTHER INFORMATION: CD33 (H2H12) VlVh scFv

<400> SEQUENCE: 83

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Asn Cys Lys Ala Ser
        35                  40                  45

Gln Asp Ile Asn Ser Tyr Leu Ser Trp Phe Gln Gln Lys Pro Gly Lys
    50                  55                  60

Ala Pro Lys Thr Leu Ile Tyr Arg Ala Asn Arg Leu Val Asp Gly Val
65                  70                  75                  80

Pro Ser Arg Phe Ser Gly Ser Gly Ser Gly Gln Asp Tyr Thr Leu Thr
                85                  90                  95

Ile Ser Ser Leu Gln Pro Glu Asp Phe Ala Thr Tyr Tyr Cys Leu Gln
            100                 105                 110

Tyr Asp Glu Phe Pro Leu Thr Phe Gly Gly Gly Thr Lys Val Glu Ile
        115                 120                 125

Lys

<210> SEQ ID NO 84
<211> LENGTH: 450
<212> TYPE: DNA
<213> ORGANISM: Unknown
<220> FEATURE:
<223> OTHER INFORMATION: MESOTHELIN (P4) scFv

<400> SEQUENCE: 84
atgcttctcc tggtgacaag ccttctgctc tgtgagttac cacacccagc attcctcctg 60
atcccacagg tacagctgca gcagtcaggt ccaggactcg tgacgccctc gcagaccctc 120
tcactcacct gtgccatctc cggggacagt gtctctagca acagtgctac ttggaactgg 180
atcaggcagt ccccatcgag aggccttgag tggctgggaa ggacatacta caggtccaag 240
tggtataacg actatgcagt atctgtgaaa agtcgaatga gcatcaaccc agacacatcc 300
aagaaccagt tctccctgca gctgaactct gtgactcccg aggacacggc tgtgtattac 360
tgtgcaagag gaatgatgac ttactattac ggtatggacg tctggggcca agggaccacg 420
gtcaccgtct cctcaggaat tctaggatcc 450

<210> SEQ ID NO 85
<211> LENGTH: 150
<212> TYPE: PRT
<213> ORGANISM: Artificial Sequence
<220> FEATURE:
<223> OTHER INFORMATION: MESOTHELIN (P4) scFv

<400> SEQUENCE: 85

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Thr Pro Ser Gln Thr Leu Ser Leu Thr Cys Ala Ile Ser Gly
        35                  40                  45

Asp Ser Val Ser Ser Asn Ser Ala Thr Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

```
Trp Tyr Asn Asp Tyr Ala Val Ser Val Lys Ser Arg Met Ser Ile Asn
            85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Gly Met Met Thr Tyr
        115                 120                 125

Tyr Tyr Gly Met Asp Val Trp Gly Gln Gly Thr Thr Val Thr Val Ser
    130                 135                 140

Ser Gly Ile Leu Gly Ser
145                 150


<210> SEQ ID NO 86
<211> LENGTH: 1344
<212> TYPE: DNA
<213> ORGANISM: Unknown
<220> FEATURE:
<223> OTHER INFORMATION: VAR2CSA (ID1-DBL2XB) scFv

<400> SEQUENCE: 86

atgcttctcc tggtgacaag ccttctgctc tgtgagttac cacacccagc attcctcctg      60

atcccaagtc tcacgaatgg gtataagtgc gacaaatgca aatcaggcac atcccggtcc     120

aaaaaaaaat ggatctggaa aaagagcagc gggaatgagg agggcctgca ggaagaatac     180

gctaacacaa tcggactgcc ccctcgaact caatctctgt accttgggaa cttgcctaaa     240

ctggaaaacg tctgtgaaga cgtcaaggac ataaacttcg atacgaaaga gaagttcctg     300

gctggatgcc ttatcgtgag ctttcacgag ggaaagaatc tgaagaaaag gtacccacag     360

aataaaaact ctggcaataa agagaatttg tgcaaggccc tggagtactc ttttgcggac     420

tatggcgatc tcataaaggg cacaagcatc tgggataatg agtataccaa ggatctggag     480

ctgaatctgc agaataactt tgggaaattg tttgggaagt atattaaaaa aaataatacc     540

gccgagcagg acacatccta ctcttccctc gacgagctgc gggagtcatg gtggaacacc     600

aacaaaaagt atatctggac ggcaatgaaa catggcgcgg aaatgaatat caccacttgt     660

aatgcagacg gctctgtcac cgggtccggt tcttcttgcg atgatatacc aaccatcgat     720

ttgattccgc agtatctgag atttctccaa gagtgggtgg aaaatttttg cgagcagagg     780

caagctaagg tcaaggacgt gatcaccaat tgtaaaagtt gcaaagaatc agggaacaag     840

tgcaaaaccg agtgtaagac gaagtgcaag gacgaatgcg agaaatataa aaaattcatc     900

gaggcttgtg gaacagccgg gggtgggatt gggaccgcag gcagcccatg gagcaagcgg     960

tgggaccaaa tctataaacg atacagcaag cacatcgaag atgccaagcg gaaccgcaaa    1020

gctggcacaa aaaactgtgg gactagcagc acgactaatg ccgcggcaag cactgatgaa    1080

aataaatgcg tgcaaagtga catcgactct ttcttcaaac acctgatcga tatcggtctt    1140

actacgccaa gcagctacct cagtaatgtt ctggatgata atatttgtgg ggcggacaaa    1200

gcaccttgga ctacctacac cacctatacc acaacagaga agtgtaataa agagagagac    1260

aaatcaaagt ctcagagctc tgatacactg gtcgttgtga atgtgccaag ccctttgggg    1320

aatacgccct acagatataa atac                                           1344


<210> SEQ ID NO 87
<211> LENGTH: 448
<212> TYPE: PRT
<213> ORGANISM: Artificial Sequence
<220> FEATURE:
<223> OTHER INFORMATION: VAR2CSA (ID1-DBL2XB) scFv
```

<400> SEQUENCE: 87

```
Met Leu Leu Leu Val Thr Ser Leu Leu Leu Cys Glu Leu Pro His Pro
1               5                   10                  15

Ala Phe Leu Leu Ile Pro Ser Leu Thr Asn Gly Tyr Lys Cys Asp Lys
            20                  25                  30

Cys Lys Ser Gly Thr Ser Arg Ser Lys Lys Lys Trp Ile Trp Lys Lys
        35                  40                  45

Ser Ser Gly Asn Glu Glu Gly Leu Gln Glu Glu Tyr Ala Asn Thr Ile
    50                  55                  60

Gly Leu Pro Pro Arg Thr Gln Ser Leu Tyr Leu Gly Asn Leu Pro Lys
65                  70                  75                  80

Leu Glu Asn Val Cys Glu Asp Val Lys Asp Ile Asn Phe Asp Thr Lys
                85                  90                  95

Glu Lys Phe Leu Ala Gly Cys Leu Ile Val Ser Phe His Glu Gly Lys
            100                 105                 110

Asn Leu Lys Lys Arg Tyr Pro Gln Asn Lys Asn Ser Gly Asn Lys Glu
        115                 120                 125

Asn Leu Cys Lys Ala Leu Glu Tyr Ser Phe Ala Asp Tyr Gly Asp Leu
    130                 135                 140

Ile Lys Gly Thr Ser Ile Trp Asp Asn Glu Tyr Thr Lys Asp Leu Glu
145                 150                 155                 160

Leu Asn Leu Gln Asn Asn Phe Gly Lys Leu Phe Gly Lys Tyr Ile Lys
                165                 170                 175

Lys Asn Asn Thr Ala Glu Gln Asp Thr Ser Tyr Ser Ser Leu Asp Glu
            180                 185                 190

Leu Arg Glu Ser Trp Trp Asn Thr Asn Lys Lys Tyr Ile Trp Thr Ala
        195                 200                 205

Met Lys His Gly Ala Glu Met Asn Ile Thr Thr Cys Asn Ala Asp Gly
    210                 215                 220

Ser Val Thr Gly Ser Gly Ser Ser Cys Asp Asp Ile Pro Thr Ile Asp
225                 230                 235                 240

Leu Ile Pro Gln Tyr Leu Arg Phe Leu Gln Glu Trp Val Glu Asn Phe
                245                 250                 255

Cys Glu Gln Arg Gln Ala Lys Val Lys Asp Val Ile Thr Asn Cys Lys
            260                 265                 270

Ser Cys Lys Glu Ser Gly Asn Lys Cys Lys Thr Glu Cys Lys Thr Lys
        275                 280                 285

Cys Lys Asp Glu Cys Glu Lys Tyr Lys Lys Phe Ile Glu Ala Cys Gly
    290                 295                 300

Thr Ala Gly Gly Gly Ile Gly Thr Ala Gly Ser Pro Trp Ser Lys Arg
305                 310                 315                 320

Trp Asp Gln Ile Tyr Lys Arg Tyr Ser Lys His Ile Glu Asp Ala Lys
                325                 330                 335

Arg Asn Arg Lys Ala Gly Thr Lys Asn Cys Gly Thr Ser Ser Thr Thr
            340                 345                 350

Asn Ala Ala Ala Ser Thr Asp Glu Asn Lys Cys Val Gln Ser Asp Ile
        355                 360                 365

Asp Ser Phe Phe Lys His Leu Ile Asp Ile Gly Leu Thr Thr Pro Ser
    370                 375                 380

Ser Tyr Leu Ser Asn Val Leu Asp Asp Asn Ile Cys Gly Ala Asp Lys
385                 390                 395                 400

Ala Pro Trp Thr Thr Tyr Thr Thr Tyr Thr Thr Thr Glu Lys Cys Asn
                405                 410                 415
```

```
Lys Glu Arg Asp Lys Ser Lys Ser Gln Ser Ser Asp Thr Leu Val Val
            420                 425                 430

Val Asn Val Pro Ser Pro Leu Gly Asn Thr Pro Tyr Arg Tyr Lys Tyr
        435                 440                 445


<210> SEQ ID NO 88
<211> LENGTH: 2202
<212> TYPE: DNA
<213> ORGANISM: Unknown
<220> FEATURE:
<223> OTHER INFORMATION: CCR(CD122)

<400> SEQUENCE: 88

atgcttctcc tggtgacaag ccttctgctc tgtgagttac cacacccagc attcctcctg     60

atcccagatt gtgatattga aggtaaagat ggcaaacaat atgagagtgt tctaatggtc    120

agcatcgatc aattattgga cagcatgaaa gaaattggta gcaattgcct gaataatgaa    180

tttaactttt ttaaaagaca tatctgtgat gctaataagg aaggtatgtt tttattccgt    240

gctgctcgca agttgaggca atttcttaaa atgaatagca ctggtgattt tgatctccac    300

ttattaaaag tttcagaagg cacaacaata ctgttgaact gcactggcca ggttaaagga    360

agaaaaccag ctgccctggg tgaagcccaa ccaacaaaga gtttggaaga aaataaatct    420

ttaaaggaac agaaaaaact gaatgacttg tgtttcctaa agagactatt acaagagata    480

aaaacttgtt ggaataaaat tttgatgggc actaaagaac acggaggcgg tgggagcgga    540

ggcggtggga gcatgacaat tctaggtaca acttttggca tggttttttc tttacttcaa    600

gtcgtttctg gagaaagtgg ctatgctcaa aatggagact tggaagatgc agaactggat    660

gactactcat tctcatgcta tagccagttg gaagtgaatg gatcgcagca ctcactgacc    720

tgtgcttttg aggacccaga tgtcaacatc accaatctgg aatttgaaat atgtggggcc    780

ctcgtggagg taaagtgcct gaatttcagg aaactacaag agatatattt catcgagaca    840

aagaaattct tactgattgg aaagagcaat atatgtgtga aggttggaga aaagagtcta    900

acctgcaaaa aaatagacct aaccactata gttaaacctg aggctccttt tgacctgagt    960

gtcatctatc gggaaggagc caatgacttt gtggtgacat ttaatacatc acacttgcaa   1020

aagaagtatg taaaagtttt aatgcacgat gtagcttacc gccaggaaaa ggatgaaaac   1080

aaatggacgc atgtgaattt atccagcaca aaactgacac tcctgcagag aaagctccaa   1140

ccggcagcaa tgtatgagat taaagttcga tccatccctg atcactattt taaaggcttc   1200

tggagtgaat ggagtccaag ttattacttc agaactccag agatcaataa tagctcaggg   1260

gagatggatc ctatcttact aaccatcagc attttgagtt ttttctctgt cgctctgttg   1320

gtcatcttgg cctgtgtgtt atggaactgc aggaacaccg ggccatggct gaagaaggtc   1380

ctgaagtgta acaccccaga cccctcgaag ttcttttccc agctgagctc agagcatgga   1440

ggagacgtcc agaagtggct ctcttcgccc ttcccctcat cgtccttcag ccctggcggc   1500

ctggcacctg agatctcgcc actagaagtg ctggagaggg acaaggtgac gcagctgctc   1560

ctgcagcagg acaaggtgcc tgagcccgca tccttaagca gcaaccactc gctgaccagc   1620

tgcttcacca accagggtta cttcttcttc cacctcccgg atgccttgga gatagaggcc   1680

tgccaggtgt actttactta cgacccctac tcagaggaag accctgatga gggtgtggcc   1740

ggggcaccca cagggtcttc cccccaaccc ctgcagcctc tgtcagggga ggacgacgcc   1800

tactgcacct tcccctccag ggatgacctg ctgctcttct cccccagtct cctcggtggc   1860
```

-continued

```
cccagccccc caagcactgc ccctgggggc agtggggccg gtgaagagag gatgcccccct   1920

tctttgcaag aaagagtccc cagagactgg gacccccagc cccctggggcc tcccacccca   1980

ggagtcccag acctggtgga ttttcagcca ccccctgagc tggtgctgcg agaggctggg   2040

gaggaggtcc ctgacgctgg ccccagggag ggagtcagtt tcccctggtc caggcctcct   2100

gggcaggggg agttcagggc ccttaatgct cgcctgcccc tgaacactga tgcctacttg   2160

tccctccaag aactccaggg tcaggaccca actcacttgg tg                       2202
```

<210> SEQ ID NO 89
<211> LENGTH: 734
<212> TYPE: PRT
<213> ORGANISM: Artificial Sequence
<220> FEATURE:
<223> OTHER INFORMATION: CCR(CD122)

<400> SEQUENCE: 89

```
Met Leu Leu Leu Val Thr Ser Leu Leu Leu Cys Glu Leu Pro His Pro
1               5                   10                  15

Ala Phe Leu Leu Ile Pro Asp Cys Asp Ile Glu Gly Lys Asp Gly Lys
            20                  25                  30

Gln Tyr Glu Ser Val Leu Met Val Ser Ile Asp Gln Leu Leu Asp Ser
        35                  40                  45

Met Lys Glu Ile Gly Ser Asn Cys Leu Asn Asn Glu Phe Asn Phe Phe
    50                  55                  60

Lys Arg His Ile Cys Asp Ala Asn Lys Glu Gly Met Phe Leu Phe Arg
65                  70                  75                  80

Ala Ala Arg Lys Leu Arg Gln Phe Leu Lys Met Asn Ser Thr Gly Asp
                85                  90                  95

Phe Asp Leu His Leu Leu Lys Val Ser Glu Gly Thr Thr Ile Leu Leu
            100                 105                 110

Asn Cys Thr Gly Gln Val Lys Gly Arg Lys Pro Ala Ala Leu Gly Glu
        115                 120                 125

Ala Gln Pro Thr Lys Ser Leu Glu Glu Asn Lys Ser Leu Lys Glu Gln
    130                 135                 140

Lys Lys Leu Asn Asp Leu Cys Phe Leu Lys Arg Leu Leu Gln Glu Ile
145                 150                 155                 160

Lys Thr Cys Trp Asn Lys Ile Leu Met Gly Thr Lys Glu His Gly Gly
                165                 170                 175

Gly Gly Ser Gly Gly Gly Gly Ser Met Thr Ile Leu Gly Thr Thr Phe
            180                 185                 190

Gly Met Val Phe Ser Leu Leu Gln Val Val Ser Gly Glu Ser Gly Tyr
        195                 200                 205

Ala Gln Asn Gly Asp Leu Glu Asp Ala Glu Leu Asp Asp Tyr Ser Phe
    210                 215                 220

Ser Cys Tyr Ser Gln Leu Glu Val Asn Gly Ser Gln His Ser Leu Thr
225                 230                 235                 240

Cys Ala Phe Glu Asp Pro Asp Val Asn Ile Thr Asn Leu Glu Phe Glu
                245                 250                 255

Ile Cys Gly Ala Leu Val Glu Val Lys Cys Leu Asn Phe Arg Lys Leu
            260                 265                 270

Gln Glu Ile Tyr Phe Ile Glu Thr Lys Lys Phe Leu Leu Ile Gly Lys
        275                 280                 285

Ser Asn Ile Cys Val Lys Val Gly Glu Lys Ser Leu Thr Cys Lys Lys
    290                 295                 300
```

```
Ile Asp Leu Thr Thr Ile Val Lys Pro Glu Ala Pro Phe Asp Leu Ser
305                 310                 315                 320

Val Ile Tyr Arg Glu Gly Ala Asn Asp Phe Val Val Thr Phe Asn Thr
                325                 330                 335

Ser His Leu Gln Lys Lys Tyr Val Lys Val Leu Met His Asp Val Ala
            340                 345                 350

Tyr Arg Gln Glu Lys Asp Glu Asn Lys Trp Thr His Val Asn Leu Ser
        355                 360                 365

Ser Thr Lys Leu Thr Leu Leu Gln Arg Lys Leu Gln Pro Ala Ala Met
    370                 375                 380

Tyr Glu Ile Lys Val Arg Ser Ile Pro Asp His Tyr Phe Lys Gly Phe
385                 390                 395                 400

Trp Ser Glu Trp Ser Pro Ser Tyr Tyr Phe Arg Thr Pro Glu Ile Asn
                405                 410                 415

Asn Ser Ser Gly Glu Met Asp Pro Ile Leu Leu Thr Ile Ser Ile Leu
            420                 425                 430

Ser Phe Phe Ser Val Ala Leu Leu Val Ile Leu Ala Cys Val Leu Trp
        435                 440                 445

Asn Cys Arg Asn Thr Gly Pro Trp Leu Lys Lys Val Leu Lys Cys Asn
    450                 455                 460

Thr Pro Asp Pro Ser Lys Phe Phe Ser Gln Leu Ser Ser Glu His Gly
465                 470                 475                 480

Gly Asp Val Gln Lys Trp Leu Ser Ser Pro Phe Pro Ser Ser Ser Phe
                485                 490                 495

Ser Pro Gly Gly Leu Ala Pro Glu Ile Ser Pro Leu Glu Val Leu Glu
            500                 505                 510

Arg Asp Lys Val Thr Gln Leu Leu Leu Gln Gln Asp Lys Val Pro Glu
        515                 520                 525

Pro Ala Ser Leu Ser Ser Asn His Ser Leu Thr Ser Cys Phe Thr Asn
    530                 535                 540

Gln Gly Tyr Phe Phe Phe His Leu Pro Asp Ala Leu Glu Ile Glu Ala
545                 550                 555                 560

Cys Gln Val Tyr Phe Thr Tyr Asp Pro Tyr Ser Glu Glu Asp Pro Asp
                565                 570                 575

Glu Gly Val Ala Gly Ala Pro Thr Gly Ser Ser Pro Gln Pro Leu Gln
            580                 585                 590

Pro Leu Ser Gly Glu Asp Asp Ala Tyr Cys Thr Phe Pro Ser Arg Asp
        595                 600                 605

Asp Leu Leu Leu Phe Ser Pro Ser Leu Leu Gly Gly Pro Ser Pro Pro
    610                 615                 620

Ser Thr Ala Pro Gly Gly Ser Gly Ala Gly Glu Glu Arg Met Pro Pro
625                 630                 635                 640

Ser Leu Gln Glu Arg Val Pro Arg Asp Trp Asp Pro Gln Pro Leu Gly
                645                 650                 655

Pro Pro Thr Pro Gly Val Pro Asp Leu Val Asp Phe Gln Pro Pro Pro
            660                 665                 670

Glu Leu Val Leu Arg Glu Ala Gly Glu Glu Val Pro Asp Ala Gly Pro
        675                 680                 685

Arg Glu Gly Val Ser Phe Pro Trp Ser Arg Pro Pro Gly Gln Gly Glu
    690                 695                 700

Phe Arg Ala Leu Asn Ala Arg Leu Pro Leu Asn Thr Asp Ala Tyr Leu
705                 710                 715                 720

Ser Leu Gln Glu Leu Gln Gly Gln Asp Pro Thr His Leu Val
```

725 730

<210> SEQ ID NO 90
<211> LENGTH: 1014
<212> TYPE: DNA
<213> ORGANISM: Unknown
<220> FEATURE:
<223> OTHER INFORMATION: PD1ECD-IFNALPHA

<400> SEQUENCE: 90
atgcagatcc ctcaggcccc ttggcctgtc gtgtgggctg tgctgcagct gggatggcgg 60
cctggctggt ttctggacag ccccgacaga ccctggaacc cccctacatt ttcccctgcc 120
ctgctggtcg tgaccgaggg cgacaatgcc accttcacct gtagcttcag caacaccagc 180
gagagcttcg tgctgaactg gtacagaatg agccccagca accagaccga caagctggcc 240
gccttccccg aggatagatc tcagcccggc caggactgcc ggttcagagt gacccagctg 300
cccaacggcc gggacttcca catgtctgtc gtgcgggcca gacggaacga cagcggcaca 360
tatctgtgcg gcgccatcag cctggccccc aaggcccaga tcaaagagag cctgagagcc 420
gagctgagag tgaccgagag aagggccgaa gtgcctaccg cccaccctag cccatctcca 480
agacctgccg gccagttcca gacactcgtg ggcggaggat gcgacctgcc tcagacacac 540
agcctgggca gcagacggac cctgatgctg ctggcccaga tgcggaagat cagcctgttc 600
agctgcctga aggaccggca cgacttcggc ttccctcagg aagagttcgg caaccagttt 660
cagaaggccg agacaatccc cgtgctgcac gagatgatcc agcagatctt caacctgttc 720
tccaccaagg acagcagcgc cgcctgggac gagacactgc tggacaagtt ctacaccgag 780
ctgtaccagc agctgaatga cctggaagcc tgcgtgatcc agggcgtggg cgtgacagag 840
acacccctga tgaaggaaga tagcatcctg gccgtgcgca agtacttcca gcggatcacc 900
ctgtacctga aagagaagaa gtacagcccc tgcgcctggg aggtcgtgcg cgccgagatc 960
atgagaagct tcagcctgag caccaacctg caggaaagcc tgcggagcaa agaa 1014

<210> SEQ ID NO 91
<211> LENGTH: 338
<212> TYPE: PRT
<213> ORGANISM: Artificial Sequence
<220> FEATURE:
<223> OTHER INFORMATION: PD1ECD-IFNALPHA

<400> SEQUENCE: 91

Met Gln Ile Pro Gln Ala Pro Trp Pro Val Val Trp Ala Val Leu Gln
1 5 10 15

Leu Gly Trp Arg Pro Gly Trp Phe Leu Asp Ser Pro Asp Arg Pro Trp
20 25 30

Asn Pro Pro Thr Phe Ser Pro Ala Leu Leu Val Val Thr Glu Gly Asp
35 40 45

Asn Ala Thr Phe Thr Cys Ser Phe Ser Asn Thr Ser Glu Ser Phe Val
50 55 60

Leu Asn Trp Tyr Arg Met Ser Pro Ser Asn Gln Thr Asp Lys Leu Ala
65 70 75 80

Ala Phe Pro Glu Asp Arg Ser Gln Pro Gly Gln Asp Cys Arg Phe Arg
85 90 95

Val Thr Gln Leu Pro Asn Gly Arg Asp Phe His Met Ser Val Val Arg
100 105 110

Ala Arg Arg Asn Asp Ser Gly Thr Tyr Leu Cys Gly Ala Ile Ser Leu
115 120 125

```
Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Gly Gly Gly Cys Asp Leu
                165                 170                 175

Pro Gln Thr His Ser Leu Gly Ser Arg Arg Thr Leu Met Leu Leu Ala
            180                 185                 190

Gln Met Arg Lys Ile Ser Leu Phe Ser Cys Leu Lys Asp Arg His Asp
        195                 200                 205

Phe Gly Phe Pro Gln Glu Glu Phe Gly Asn Gln Phe Gln Lys Ala Glu
    210                 215                 220

Thr Ile Pro Val Leu His Glu Met Ile Gln Gln Ile Phe Asn Leu Phe
225                 230                 235                 240

Ser Thr Lys Asp Ser Ser Ala Ala Trp Asp Glu Thr Leu Leu Asp Lys
                245                 250                 255

Phe Tyr Thr Glu Leu Tyr Gln Gln Leu Asn Asp Leu Glu Ala Cys Val
            260                 265                 270

Ile Gln Gly Val Gly Val Thr Glu Thr Pro Leu Met Lys Glu Asp Ser
        275                 280                 285

Ile Leu Ala Val Arg Lys Tyr Phe Gln Arg Ile Thr Leu Tyr Leu Lys
    290                 295                 300

Glu Lys Lys Tyr Ser Pro Cys Ala Trp Glu Val Val Arg Ala Glu Ile
305                 310                 315                 320

Met Arg Ser Phe Ser Leu Ser Thr Asn Leu Gln Glu Ser Leu Arg Ser
                325                 330                 335

Lys Glu
```

<210> SEQ ID NO 92
<211> LENGTH: 2382
<212> TYPE: DNA
<213> ORGANISM: Unknown
<220> FEATURE:
<223> OTHER INFORMATION: STAT5A

<400> SEQUENCE: 92

```
atggcgggct ggatccaggc ccagcagctg cagggagacg cgctgcgcca gatgcaggtg     60

ctgtacggcc agcacttccc catcgaggtc cggcactact tggcccagtg gattgagagc    120

cagccatggg atgccattga cttggacaat ccccaggaca gagcccaagc cacccagctc    180

ctggagggcc tggtgcagga gctgcagaag aaggcggagc accaggtggg ggaagatggg    240

tttttactga agatcaagct ggggcactac gccacgcagc tccagaaaac atatgaccgc    300

tgcccccctgg agctggtccg ctgcatccgg cacattctgt acaatgaaca gaggctggtc    360

cgagaagcca acaattgcag ctctccggct gggatcctgg ttgacgccat gtcccagaag    420

caccttcaga tcaaccagac atttgaggag ctgcgactgg tcacgcagga cacagagaat    480

gagctgaaga aactgcagca gactcaggag tacttcatca tccagtacca ggagagcctg    540

aggatccaag ctcagtttgc ccagctggcc cagctgagcc cccaggagcg tctgagccgg    600

gagacggccc tccagcagaa gcaggtgtct ctggaggcct ggttgcagcg tgaggcacag    660

acactgcagc agtaccgcgt ggagctggcc gagaagcacc agaagaccct gcagctgctg    720

cggaagcagc agaccatcat cctggatgac gagctgatcc agtggaagcg gcggcagcag    780

ctggccggga acggcgggcc ccccgagggc agcctggacg tgctacagtc ctggtgtgag    840
```

```
aagttggccg agatcatctg gcagaaccgg cagcagatcc gcagggctga gcacctctgc    900

cagcagctgc ccatccccgg cccagtggag gagatgctgg ccgaggtcaa cgccaccatc    960

acggacatta tctcagccct ggtgaccagc acattcatca ttgagaagca gcctcctcag   1020

gtcctgaaga cccagaccaa gtttgcagcc accgtacgcc tgctggtggg cgggaagctg   1080

aacgtgcaca tgaatccccc ccaggtgaag gccaccatca tcagtgagca gcaggccaag   1140

tctctgctta aaaatgagaa cacccgcaac gagtgcagtg gtgagatcct gaacaactgc   1200

tgcgtgatgg agtaccacca agccacgggc accctcagtg cccacttcag gaacatgtca   1260

ctgaagagga tcaagcgtgc tgaccggcgg ggtgcagagt ccgtgacaga ggagaagttc   1320

acagtcctgt ttgagtctca gttcagtgtt ggcagcaatg agcttgtgtt ccaggtgaag   1380

actctgtccc tacctgtggt tgtcatcgtc cacggcagcc aggaccacaa tgccacggct   1440

actgtgctgt gggacaatgc ctttgctgag ccgggcaggg tgccatttgc cgtgcctgac   1500

aaagtgctgt ggccgcagct gtgtgaggcg ctcaacatga aattcaaggc cgaagtgcag   1560

agcaaccggg gcctgaccaa ggagaacctc gtgttcctgg cgcagaaact gttcaacaac   1620

agcagcagcc acctggagga ctacagtggc ctgtccgtgt cctggtccca gttcaacagg   1680

gagaacttgc cgggctggaa ctacaccttc tggcagtggt ttgacggggt gatggaggtg   1740

ttgaagaagc accacaagcc ccactggaat gatggggcca tcctaggttt tgtgaataag   1800

caacaggccc acgacctgct catcaacaag cccgacggga ccttcttgtt gcgctttagt   1860

gactcagaaa tcgggggcat caccatcgcc tggaagtttg attccccgga acgcaacctg   1920

tggaacctga aaccattcac cacgcgggat ttctccatca ggtccctggc tgaccggctg   1980

ggggacctga gctatctcat ctatgtgttt cctgaccgcc ccaaggatga ggtcttctcc   2040

aagtactaca ctcctgtgct ggctaaagct gttgatggat atgtgaaacc acagatcaag   2100

caagtggtcc ctgagtttgt gaatgcatct gcagatgctg gggcagcag cgccacgtac   2160

atggaccagg ccccctcccc agctgtgtgc cccaggctc cctataacat gtacccacag   2220

aaccctgacc atgtactcga tcaggatgga gaattcgacc tggatgagac catggatgtg   2280

gccaggcacg tggaggaact cttacgccga ccaatggaca gtcttgactc ccgcctctcg   2340

ccccctgccg gtcttttcac ctctgccaga ggctccctct ca                       2382


<210> SEQ ID NO 93
<211> LENGTH: 794
<212> TYPE: PRT
<213> ORGANISM: Artificial Sequence
<220> FEATURE:
<223> OTHER INFORMATION: STAT5A

<400> SEQUENCE: 93

Met Ala Gly Trp Ile Gln Ala Gln Gln Leu Gln Gly Asp Ala Leu Arg
1               5                   10                  15

Gln Met Gln Val Leu Tyr Gly Gln His Phe Pro Ile Glu Val Arg His
            20                  25                  30

Tyr Leu Ala Gln Trp Ile Glu Ser Gln Pro Trp Asp Ala Ile Asp Leu
        35                  40                  45

Asp Asn Pro Gln Asp Arg Ala Gln Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Lys
```

```
                85                  90                  95

Thr Tyr Asp Arg Cys Pro Leu Glu Leu Val Arg Cys Ile Arg His Ile
            100                 105                 110

Leu Tyr Asn Glu Gln Arg Leu Val Arg Glu Ala Asn Asn Cys Ser Ser
        115                 120                 125

Pro Ala Gly Ile Leu Val Asp Ala Met Ser Gln Lys His Leu Gln Ile
    130                 135                 140

Asn Gln Thr Phe Glu Glu Leu Arg Leu Val Thr Gln Asp Thr Glu Asn
145                 150                 155                 160

Glu Leu Lys Lys Leu Gln Gln Thr Gln Glu Tyr Phe Ile Ile Gln Tyr
                165                 170                 175

Gln Glu Ser Leu Arg Ile Gln Ala Gln Phe Ala Gln Leu Ala Gln Leu
            180                 185                 190

Ser Pro Gln Glu Arg Leu Ser Arg Glu Thr Ala Leu Gln Gln Lys Gln
        195                 200                 205

Val Ser Leu Glu Ala Trp Leu Gln Arg Glu Ala Gln Thr Leu Gln Gln
    210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
                245                 250                 255

Arg Arg Gln Gln Leu Ala Gly Asn Gly Gly Pro Pro Glu Gly Ser Leu
            260                 265                 270

Asp Val Leu Gln Ser Trp Cys Glu Lys Leu Ala Glu Ile Ile Trp Gln
        275                 280                 285

Asn Arg Gln Gln Ile Arg Arg Ala Glu His Leu Cys Gln Gln Leu Pro
    290                 295                 300

Ile Pro Gly Pro Val Glu Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
        355                 360                 365

Val Lys Ala Thr Ile Ile Ser Glu Gln Gln Ala Lys Ser Leu Leu Lys
    370                 375                 380

Asn Glu Asn Thr Arg Asn Glu Cys Ser Gly Glu Ile Leu Asn Asn Cys
385                 390                 395                 400

Cys Val Met Glu Tyr His Gln Ala Thr Gly Thr Leu Ser Ala His Phe
                405                 410                 415

Arg Asn Met Ser Leu Lys Arg Ile Lys Arg Ala Asp Arg Arg Gly Ala
            420                 425                 430

Glu Ser Val Thr Glu Glu Lys Phe Thr Val Leu Phe Glu Ser Gln Phe
        435                 440                 445

Ser Val Gly Ser Asn Glu Leu Val Phe Gln Val Lys Thr Leu Ser Leu
    450                 455                 460

Pro Val Val Val Ile Val His Gly Ser Gln Asp His Asn Ala Thr Ala
465                 470                 475                 480

Thr Val Leu Trp Asp Asn Ala Phe Ala Glu Pro Gly Arg Val Pro Phe
                485                 490                 495

Ala Val Pro Asp Lys Val Leu Trp Pro Gln Leu Cys Glu Ala Leu Asn
            500                 505                 510
```

```
Met Lys Phe Lys Ala Glu Val Gln Ser Asn Arg Gly Leu Thr Lys Glu
        515                 520                 525

Asn Leu Val Phe Leu Ala Gln Lys Leu Phe Asn Asn Ser Ser Ser His
    530                 535                 540

Leu Glu Asp Tyr Ser Gly Leu Ser Val Ser Trp Ser Gln Phe Asn Arg
545                 550                 555                 560

Glu Asn Leu Pro Gly Trp Asn Tyr Thr Phe Trp Gln Trp Phe Asp Gly
                565                 570                 575

Val Met Glu Val Leu Lys Lys His His Lys Pro His Trp Asn Asp Gly
            580                 585                 590

Ala Ile Leu Gly Phe Val Asn Lys Gln Gln Ala His Asp Leu Leu Ile
        595                 600                 605

Asn Lys Pro Asp Gly Thr Phe Leu Leu Arg Phe Ser Asp Ser Glu Ile
    610                 615                 620

Gly Gly Ile Thr Ile Ala Trp Lys Phe Asp Ser Pro Glu Arg Asn Leu
625                 630                 635                 640

Trp Asn Leu Lys Pro Phe Thr Thr Arg Asp Phe Ser Ile Arg Ser Leu
                645                 650                 655

Ala Asp Arg Leu Gly Asp Leu Ser Tyr Leu Ile Tyr Val Phe Pro Asp
            660                 665                 670

Arg Pro Lys Asp Glu Val Phe Ser Lys Tyr Tyr Thr Pro Val Leu Ala
        675                 680                 685

Lys Ala Val Asp Gly Tyr Val Lys Pro Gln Ile Lys Gln Val Val Pro
    690                 695                 700

Glu Phe Val Asn Ala Ser Ala Asp Ala Gly Gly Ser Ser Ala Thr Tyr
705                 710                 715                 720

Met Asp Gln Ala Pro Ser Pro Ala Val Cys Pro Gln Ala Pro Tyr Asn
                725                 730                 735

Met Tyr Pro Gln Asn Pro Asp His Val Leu Asp Gln Asp Gly Glu Phe
            740                 745                 750

Asp Leu Asp Glu Thr Met Asp Val Ala Arg His Val Glu Glu Leu Leu
        755                 760                 765

Arg Arg Pro Met Asp Ser Leu Asp Ser Arg Leu Ser Pro Pro Ala Gly
    770                 775                 780

Leu Phe Thr Ser Ala Arg Gly Ser Leu Ser
785                 790
```

<210> SEQ ID NO 94
<211> LENGTH: 2382
<212> TYPE: DNA
<213> ORGANISM: Unknown
<220> FEATURE:
<223> OTHER INFORMATION: constitutively active-STAT5A

<400> SEQUENCE: 94

```
atggcgggct ggatccaggc ccagcagctg cagggagacg cgctgcgcca gatgcaggtg     60

ctgtacggcc agcacttccc catcgaggtc cggcactact tggcccagtg gattgagagc    120

cagccatggg atgccattga cttggacaat ccccaggaca gagcccaagc cacccagctc    180

ctggagggcc tggtgcagga gctgcagaag aaggcggagc accaggtggg ggaagatggg    240

tttttactga agatcaagct ggggcactac gccacgcagc tccagaaaac atatgaccgc    300

tgccccctgg agctggtccg ctgcatccgg cacattctgt acaatgaaca gaggctggtc    360

cgagaagcca acaattgcag ctctccggct gggatcctgg ttgacgccat gtcccagaag    420
```

-continued

```
caccttcaga tcaaccagac atttgaggag ctgcgactgg tcacgcagga cacagagaat    480

gagctgaaga aactgcagca gactcaggag tacttcatca tccagtacca ggagagcctg    540

aggatccaag ctcagtttgc ccagctggcc cagctgagcc cccaggagcg tctgagccgg    600

gagacggccc tccagcagaa gcaggtgtct ctggaggcct ggttgcagcg tgaggcacag    660

acactgcagc agtaccgcgt ggagctggcc gagaagcacc agaagaccct gcagctgctg    720

cggaagcagc agaccatcat cctggatgac gagctgatcc agtggaagcg gcggcagcag    780

ctggccggga acggcgggcc ccccgagggc agcctggacg tgctacagtc ctggtgtgag    840

aagttggccg agatcatctg gcagaaccgg cagcagatcc gcagggctga gcgcctctgc    900

cagcagctgc ccatccccgg cccagtggag gagatgctgg ccgaggtcaa cgccaccatc    960

acggacatta tctcagccct ggtgaccagc acattcatca ttgagaagca gcctcctcag   1020

gtcctgaaga cccagaccaa gtttgcagcc accgtacgcc tgctggtggg cgggaagctg   1080

aacgtgcaca tgaatccccc ccaggtgaag gccaccatca tcagtgagca gcaggccaag   1140

tctctgctta aaaatgagaa cacccgcaac gagtgcagtg gtgagatcct gaacaactgc   1200

tgcgtgatgg agtaccacca agccacgggc accctcagtg cccacttcag gaacatgtca   1260

ctgaagagga tcaagcgtgc tgaccggcgg ggtgcagagt ccgtgacaga ggagaagttc   1320

acagtcctgt ttgagtctca gttcagtgtt ggcagcaatg agcttgtgtt ccaggtgaag   1380

actctgtccc tacctgtggt tgtcatcgtc cacggcagcc aggaccacaa tgccacggct   1440

actgtgctgt gggacaatgc ctttgctgag ccgggcaggg tgccatttgc cgtgcctgac   1500

aaagtgctgt ggccgcagct gtgtgaggcg ctcaacatga aattcaaggc cgaagtgcag   1560

agcaaccggg gcctgaccaa ggagaacctc gtgttcctgg cgcagaaact gttcaacaac   1620

agcagcagcc acctggagga ctacagtggc ctgtccgtgt cctggtccca gttcaacagg   1680

gagaacttgc cgggctggaa ctacaccttc tggcagtggt ttgacggggt gatggaggtg   1740

ttgaagaagc accacaagcc ccactggaat gatggggcca tcctaggttt tgtgaataag   1800

caacaggccc acgacctgct catcaacaag cccgacggga ccttcttgtt gcgctttagt   1860

gactcagaaa tcgggggcat caccatcgcc tggaagtttg attccccgga acgcaacctg   1920

tggaacctga aaccattcac cacgcgggat ttctccatca ggtccctggc tgaccggctg   1980

ggggacctga gctatctcat ctatgtgttt cctgaccgcc ccaaggatga ggtcttctcc   2040

aagtactaca ctcctgtgct ggctaaagct gttgatggat atgtgaaacc acagatcaag   2100

caagtggtcc ctgagtttgt gaatgcattt gcagatgctg ggggcagcag cgccacgtac   2160

atggaccagg ccccctcccc agctgtgtgc ccccaggctc cctataacat gtacccacag   2220

aaccctgacc atgtactcga tcaggatgga gaattcgacc tggatgagac catggatgtg   2280

gccaggcacg tggaggaact cttacgccga ccaatggaca gtcttgactc ccgcctctcg   2340

ccccctgccg gtcttttcac ctctgccaga ggctccctct ca                      2382
```

<210> SEQ ID NO 95
<211> LENGTH: 794
<212> TYPE: PRT
<213> ORGANISM: Artificial Sequence
<220> FEATURE:
<223> OTHER INFORMATION: constitutively active-STAT5A
<220> FEATURE:
<223> OTHER INFORMATION: constitutively active-STAT5A

<400> SEQUENCE: 95

Met Ala Gly Trp Ile Gln Ala Gln Gln Leu Gln Gly Asp Ala Leu Arg

-continued

```
1               5                   10                  15

Gln Met Gln Val Leu Tyr Gly Gln His Phe Pro Ile Glu Val Arg His
            20                  25                  30

Tyr Leu Ala Gln Trp Ile Glu Ser Gln Pro Trp Asp Ala Ile Asp Leu
        35                  40                  45

Asp Asn Pro Gln Asp Arg Ala Gln Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Lys
                85                  90                  95

Thr Tyr Asp Arg Cys Pro Leu Glu Leu Val Arg Cys Ile Arg His Ile
            100                 105                 110

Leu Tyr Asn Glu Gln Arg Leu Val Arg Glu Ala Asn Asn Cys Ser Ser
        115                 120                 125

Pro Ala Gly Ile Leu Val Asp Ala Met Ser Gln Lys His Leu Gln Ile
    130                 135                 140

Asn Gln Thr Phe Glu Glu Leu Arg Leu Val Thr Gln Asp Thr Glu Asn
145                 150                 155                 160

Glu Leu Lys Lys Leu Gln Gln Thr Gln Glu Tyr Phe Ile Ile Gln Tyr
                165                 170                 175

Gln Glu Ser Leu Arg Ile Gln Ala Gln Phe Ala Gln Leu Ala Gln Leu
            180                 185                 190

Ser Pro Gln Glu Arg Leu Ser Arg Glu Thr Ala Leu Gln Gln Lys Gln
        195                 200                 205

Val Ser Leu Glu Ala Trp Leu Gln Arg Glu Ala Gln Thr Leu Gln Gln
    210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
                245                 250                 255

Arg Arg Gln Gln Leu Ala Gly Asn Gly Gly Pro Pro Glu Gly Ser Leu
            260                 265                 270

Asp Val Leu Gln Ser Trp Cys Glu Lys Leu Ala Glu Ile Ile Trp Gln
        275                 280                 285

Asn Arg Gln Gln Ile Arg Arg Ala Glu Arg Leu Cys Gln Gln Leu Pro
    290                 295                 300

Ile Pro Gly Pro Val Glu Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
        355                 360                 365

Val Lys Ala Thr Ile Ile Ser Glu Gln Gln Ala Lys Ser Leu Leu Lys
    370                 375                 380

Asn Glu Asn Thr Arg Asn Glu Cys Ser Gly Glu Ile Leu Asn Asn Cys
385                 390                 395                 400

Cys Val Met Glu Tyr His Gln Ala Thr Gly Thr Leu Ser Ala His Phe
                405                 410                 415

Arg Asn Met Ser Leu Lys Arg Ile Lys Arg Ala Asp Arg Arg Gly Ala
            420                 425                 430
```

```
Glu Ser Val Thr Glu Glu Lys Phe Thr Val Leu Phe Glu Ser Gln Phe
        435                 440                 445

Ser Val Gly Ser Asn Glu Leu Val Phe Gln Val Lys Thr Leu Ser Leu
    450                 455                 460

Pro Val Val Val Ile Val His Gly Ser Gln Asp His Asn Ala Thr Ala
465                 470                 475                 480

Thr Val Leu Trp Asp Asn Ala Phe Ala Glu Pro Gly Arg Val Pro Phe
                485                 490                 495

Ala Val Pro Asp Lys Val Leu Trp Pro Gln Leu Cys Glu Ala Leu Asn
            500                 505                 510

Met Lys Phe Lys Ala Glu Val Gln Ser Asn Arg Gly Leu Thr Lys Glu
        515                 520                 525

Asn Leu Val Phe Leu Ala Gln Lys Leu Phe Asn Asn Ser Ser Ser His
    530                 535                 540

Leu Glu Asp Tyr Ser Gly Leu Ser Val Ser Trp Ser Gln Phe Asn Arg
545                 550                 555                 560

Glu Asn Leu Pro Gly Trp Asn Tyr Thr Phe Trp Gln Trp Phe Asp Gly
                565                 570                 575

Val Met Glu Val Leu Lys Lys His His Lys Pro His Trp Asn Asp Gly
            580                 585                 590

Ala Ile Leu Gly Phe Val Asn Lys Gln Gln Ala His Asp Leu Leu Ile
        595                 600                 605

Asn Lys Pro Asp Gly Thr Phe Leu Leu Arg Phe Ser Asp Ser Glu Ile
    610                 615                 620

Gly Gly Ile Thr Ile Ala Trp Lys Phe Asp Ser Pro Glu Arg Asn Leu
625                 630                 635                 640

Trp Asn Leu Lys Pro Phe Thr Thr Arg Asp Phe Ser Ile Arg Ser Leu
                645                 650                 655

Ala Asp Arg Leu Gly Asp Leu Ser Tyr Leu Ile Tyr Val Phe Pro Asp
            660                 665                 670

Arg Pro Lys Asp Glu Val Phe Ser Lys Tyr Tyr Thr Pro Val Leu Ala
        675                 680                 685

Lys Ala Val Asp Gly Tyr Val Lys Pro Gln Ile Lys Gln Val Val Pro
    690                 695                 700

Glu Phe Val Asn Ala Phe Ala Asp Ala Gly Gly Ser Ser Ala Thr Tyr
705                 710                 715                 720

Met Asp Gln Ala Pro Ser Pro Ala Val Cys Pro Gln Ala Pro Tyr Asn
                725                 730                 735

Met Tyr Pro Gln Asn Pro Asp His Val Leu Asp Gln Asp Gly Glu Phe
            740                 745                 750

Asp Leu Asp Glu Thr Met Asp Val Ala Arg His Val Glu Glu Leu Leu
        755                 760                 765

Arg Arg Pro Met Asp Ser Leu Asp Ser Arg Leu Ser Pro Pro Ala Gly
    770                 775                 780

Leu Phe Thr Ser Ala Arg Gly Ser Leu Ser
785                 790
```

<210> SEQ ID NO 96
<211> LENGTH: 837
<212> TYPE: DNA
<213> ORGANISM: Unknown
<220> FEATURE:
<223> OTHER INFORMATION: dominant negative TGFB-RII

<400> SEQUENCE: 96
atgggtcggg ggctgctcag ggcctgtgg ccgctgcaca tcgtcctgtg gacgcgtatc 60
gccagcacga tcccaccgca cgttcagaag tcggttaata acgacatgat agtcactgac 120
aacaacggtg cagtcaagtt tccacaactg tgtaaatttt gtgatgtgag attttccacc 180
tgtgacaacc agaaatcctg catgagcaac tgcagcatca cctccatctg tgagaagcca 240
caggaagtct gtgtggctgt atggagaaag aatgacgaga acataacact agagacagtt 300
tgccatgacc ccaagctccc ctaccatgac tttattctgg aagatgctgc ttctccaaag 360
tgcattatga aggaaaaaaa aaagcctggt gagactttct tcatgtgttc ctgtagctct 420
gatgagtgca atgacaacat catcttctca gaagaatata acaccagcaa tcctgacttg 480
ttgctagtca tatttcaagt gacaggcatc agcctcctgc caccactggg agttgccata 540
tctgtcatca tcatcttcta ctgctaccgc gttaaccggc agcagaagct gagttcaacc 600
tgggaaaccg gcaagacgcg gaagctcatg gagttcagcg agcactgtgc catcatcctg 660
gaagatgacc gctctgacat cagctccacg tgtgccaaca acatcaacca caacacagag 720
ctgctgccca ttgagctgga caccctggtg gggaaaggtc gctttgctga ggtctataag 780
gccaagctga agcagaacac ttcagagcag tttgagacag tggcagtcaa gatcttt 837

<210> SEQ ID NO 97
<211> LENGTH: 279
<212> TYPE: PRT
<213> ORGANISM: Artificial Sequence
<220> FEATURE:
<223> OTHER INFORMATION: dominant negative TGFBRII

<400> SEQUENCE: 97

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg

```
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe
        275


<210> SEQ ID NO 98
<211> LENGTH: 1788
<212> TYPE: DNA
<213> ORGANISM: Unknown
<220> FEATURE:
<223> OTHER INFORMATION: dominant negative SHP1

<400> SEQUENCE: 98

atggtgaggt ggtttcaccg agacctcagt gggctggatg cagagaccct gctcaagggc     60

cgaggtgtcc acggtagctt cctggctcgg cccagtcgca agaaccaggg tgacttctcg    120

ctctccgtca gggtggggga tcaggtgacc catattcgga tccagaactc aggggatttc    180

tatgacctgt atggagggga gaagtttgcg actctgacag agctggtgga gtactacact    240

cagcagcagg gtgtcctgca ggaccgcgac ggcaccatca tccacctcaa gtacccgctg    300

aactgctccg atcccactag tgagaggtgg taccatggcc acatgtctgg cgggcaggca    360

gagacgctgc tgcaggccaa gggcgagccc tggacgtttc ttgtgcgtga gagcctcagc    420

cagcctggag acttcgtgct ttctgtgctc agtgaccagc ccaaggctgg cccaggctcc    480

ccgctcaggg tcacccacat caaggtcatg tgcgagggtg gacgctacac agtgggtggt    540

ttggagacct tcgacagcct cacggacctg gtggagcatt tcaagaagac ggggattgag    600

gaggcctcag gcgcctttgt ctacctgcgg cagccgtact atgccacgag ggtgaatgcg    660

gctgacattg agaaccgagt gttggaactg aacaagaagc aggagtccga ggatacagcc    720

aaggctggct tctgggagga gtttgagagt ttgcagaagc aggaggtgaa gaacttgcac    780

cagcgtctgg aagggcagcg gccagagaac aagggcaaga accgctacaa gaacattctc    840

ccctttgacc acagccgagt gatcctgcag ggacgggaca gtaacatccc cgggtccgac    900

tacatcaatg ccaactacat caagaaccag ctgctaggcc ctgatgagaa cgctaagacc    960

tacatcgcca gccagggctg tctggaggcc acggtcaatg acttctggca gatggcgtgg   1020

caggagaaca gccgtgtcat cgtcatgacc acccgagagg tggagaaagg ccggaacaaa   1080

tgcgtcccat actggcccga ggtgggcatg cagcgtgctt atgggcccta ctctgtgacc   1140

aactgcgggg agcatgacac aaccgaatac aaactccgta ccttacaggt ctccccgctg   1200

gacaatggag acctgattcg ggagatctgg cattaccagt acctgagctg gcccgaccat   1260

ggggtcccca gtgagcctgg gggtgtcctc agcttcctgg accagatcaa ccagcggcag   1320

gaaagtctgc ctcacgcagg gcccatcatc gtgcactcca gcgccggcat cggccgcaca   1380

ggcaccatca ttgtcatcga catgctcatg gagaacatct ccaccaaggg cctggactgt   1440

gacattgaca tccagaagac catccagatg gtgcgggcgc agcgctcggg catggtgcag   1500

acggaggcgc agtacaagtt catctacgtg gccatcgccc agttcattga aaccactaag   1560

aagaagctgg aggtcctgca gtcgcagaag ggccaggagt cggagtacgg gaacatcacc   1620

tatcccccag ccatgaagaa tgcccatgcc aaggcctccc gcacctcgtc caaacacaag   1680
```

```
gaggatgtgt atgagaacct gcacactaag aacaagaggg aggagaaagt gaagaagcag   1740

cggtcagcag acaaggagaa gagcaagggt tccctcaaga ggaagtga                1788


<210> SEQ ID NO 99
<211> LENGTH: 595
<212> TYPE: PRT
<213> ORGANISM: Artificial Sequence
<220> FEATURE:
<223> OTHER INFORMATION: dominant negative SHP1

<400> SEQUENCE: 99

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                325                 330                 335

Gln Met Ala Trp Gln Glu Asn Ser Arg Val Ile Val Met Thr Thr Arg
```

```
            340                 345                 350

Glu Val Glu Lys Gly Arg Asn Lys Cys Val Pro Tyr Trp Pro Glu Val
        355                 360                 365

Gly Met Gln Arg Ala Tyr Gly Pro Tyr Ser Val Thr Asn Cys Gly Glu
    370                 375                 380

His Asp Thr Thr Glu Tyr Lys Leu Arg Thr Leu Gln Val Ser Pro Leu
385                 390                 395                 400

Asp Asn Gly Asp Leu Ile Arg Glu Ile Trp His Tyr Gln Tyr Leu Ser
                405                 410                 415

Trp Pro Asp His Gly Val Pro Ser Glu Pro Gly Gly Val Leu Ser Phe
            420                 425                 430

Leu Asp Gln Ile Asn Gln Arg Gln Glu Ser Leu Pro His Ala Gly Pro
        435                 440                 445

Ile Ile Val His Ser Ser Ala Gly Ile Gly Arg Thr Gly Thr Ile Ile
    450                 455                 460

Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
                485                 490                 495

Gly Met Val Gln Thr Glu Ala Gln Tyr Lys Phe Ile Tyr Val Ala Ile
            500                 505                 510

Ala Gln Phe Ile Glu Thr Thr Lys Lys Lys Leu Glu Val Leu Gln Ser
        515                 520                 525

Gln Lys Gly Gln Glu Ser Glu Tyr Gly Asn Ile Thr Tyr Pro Pro Ala
    530                 535                 540

Met Lys Asn Ala His Ala Lys Ala Ser Arg Thr Ser Ser Lys His Lys
545                 550                 555                 560

Glu Asp Val Tyr Glu Asn Leu His Thr Lys Asn Lys Arg Glu Glu Lys
                565                 570                 575

Val Lys Lys Gln Arg Ser Ala Asp Lys Glu Lys Ser Lys Gly Ser Leu
            580                 585                 590

Lys Arg Lys
        595
```

<210> SEQ ID NO 100
<211> LENGTH: 1035
<212> TYPE: DNA
<213> ORGANISM: Unknown
<220> FEATURE:
<223> OTHER INFORMATION: PD1TM-MYD88

<400> SEQUENCE: 100

```
atgcttctcc tggtgacaag ccttctgctc tgtgagttac cacacccagc attcctcctg      60

atcccaggcg gaggagtggg agtcgtgggc ggactgctgg gatctctggt gctgctcgtg     120

tgggtgctgg ccgtgattgg cggaggaatg gctgctggcg gacctggcgc tggatctgct     180

gctcctgtgt ctagcaccag cagcctgcct ctggccgccc tgaatatgag agtgcggcgg     240

agactgagcc tgttcctgaa cgtgcggaca caggtggccg ccgattggac agctctggcc     300

gaggaaatgg acttcgagta cctggaaatc cggcagctgg aaacccaggc cgaccctaca     360

ggacgcctgc tggatgcttg gcagggcaga ccaggcgctt ctgtggggag actgctggaa     420

ctgctgacca agctgggccg ggacgacgtg ctgctggaac tgggccctag catcgaagag     480

gactgccaga agtacatcct gaagcagcag caggaagagg ccgagaagcc tctgcaggtg     540

gcagccgtgg atagcagcgt gccaagaaca gctgagctgg ccggaatcac caccctggac     600
```

```
gatcctctgg gccacatgcc cgagagattc gacgccttca tctgctactg ccccagcgac    660

atccagttcg tgcaggaaat gatcagacag ctggaacaga ccaactaccg gctgaagctg    720

tgcgtgtccg accgggatgt gctgcctggc acctgtgtgt ggtctatcgc cagcgagctg    780

atcgagaagc ggtgcagacg gatggtcgtg gtggtgtccg acgactacct gcagtccaaa    840

gagtgcgact tccagaccaa gttcgccctg agcctgagcc ctggcgccca ccagaagaga    900

ctgatcccca tcaagtacaa ggccatgaag aaagagttcc ccagcatcct gcggttcatc    960

accgtgtgcg actacaccaa cccctgcacc aagtcctggt tctggaccag actggccaag   1020

gccctgtctc tgcct                                                    1035
```

```
<210> SEQ ID NO 101
<211> LENGTH: 345
<212> TYPE: PRT
<213> ORGANISM: Artificial Sequence
<220> FEATURE:
<223> OTHER INFORMATION: PD1TM-MYD88

<400> SEQUENCE: 101

Met Leu Leu Leu Val Thr Ser Leu Leu Leu Cys Glu Leu Pro His Pro
1               5                   10                  15

Ala Phe Leu Leu Ile Pro Gly Gly Gly Val Gly Val Val Gly Gly Leu
            20                  25                  30

Leu Gly Ser Leu Val Leu Leu Val Trp Val Leu Ala Val Ile Gly Gly
        35                  40                  45

Gly Met Ala Ala Gly Gly Pro Gly Ala Gly Ser Ala Ala Pro Val Ser
    50                  55                  60

Ser Thr Ser Ser Leu Pro Leu Ala Ala Leu Asn Met Arg Val Arg Arg
65                  70                  75                  80

Arg Leu Ser Leu Phe Leu Asn Val Arg Thr Gln Val Ala Ala Asp Trp
                85                  90                  95

Thr Ala Leu Ala Glu Glu Met Asp Phe Glu Tyr Leu Glu Ile Arg Gln
            100                 105                 110

Leu Glu Thr Gln Ala Asp Pro Thr Gly Arg Leu Leu Asp Ala Trp Gln
        115                 120                 125

Gly Arg Pro Gly Ala Ser Val Gly Arg Leu Leu Glu Leu Leu Thr Lys
    130                 135                 140

Leu Gly Arg Asp Asp Val Leu Leu Glu Leu Gly Pro Ser Ile Glu Glu
145                 150                 155                 160

Asp Cys Gln Lys Tyr Ile Leu Lys Gln Gln Gln Glu Glu Ala Glu Lys
                165                 170                 175

Pro Leu Gln Val Ala Ala Val Asp Ser Ser Val Pro Arg Thr Ala Glu
            180                 185                 190

Leu Ala Gly Ile Thr Thr Leu Asp Asp Pro Leu Gly His Met Pro Glu
        195                 200                 205

Arg Phe Asp Ala Phe Ile Cys Tyr Cys Pro Ser Asp Ile Gln Phe Val
    210                 215                 220

Gln Glu Met Ile Arg Gln Leu Glu Gln Thr Asn Tyr Arg Leu Lys Leu
225                 230                 235                 240

Cys Val Ser Asp Arg Asp Val Leu Pro Gly Thr Cys Val Trp Ser Ile
                245                 250                 255

Ala Ser Glu Leu Ile Glu Lys Arg Cys Arg Arg Met Val Val Val Val
            260                 265                 270

Ser Asp Asp Tyr Leu Gln Ser Lys Glu Cys Asp Phe Gln Thr Lys Phe
```

-continued

```
        275                 280                 285

Ala Leu Ser Leu Ser Pro Gly Ala His Gln Lys Arg Leu Ile Pro Ile
    290                 295                 300

Lys Tyr Lys Ala Met Lys Lys Glu Phe Pro Ser Ile Leu Arg Phe Ile
305                 310                 315                 320

Thr Val Cys Asp Tyr Thr Asn Pro Cys Thr Lys Ser Trp Phe Trp Thr
                325                 330                 335

Arg Leu Ala Lys Ala Leu Ser Leu Pro
            340                 345


<210> SEQ ID NO 102
<211> LENGTH: 36
<212> TYPE: DNA
<213> ORGANISM: Unknown
<220> FEATURE:
<223> OTHER INFORMATION: IGG4 HINGE

<400> SEQUENCE: 102

gagagcaagt acggaccgcc ctgccccct tgccct                               36


<210> SEQ ID NO 103
<211> LENGTH: 12
<212> TYPE: PRT
<213> ORGANISM: Artificial Sequence
<220> FEATURE:
<223> OTHER INFORMATION: IGG4 HINGE

<400> SEQUENCE: 103

Glu Ser Lys Tyr Gly Pro Pro Cys Pro Pro Cys Pro
1               5                   10


<210> SEQ ID NO 104
<211> LENGTH: 330
<212> TYPE: DNA
<213> ORGANISM: Unknown
<220> FEATURE:
<223> OTHER INFORMATION: IGG4-CH2(L235D, N297Q)

<400> SEQUENCE: 104

gcccccgagt tcgacggcgg acccagcgtg ttcctgttcc cccccaagcc caaggacacc     60

ctgatgatca gccggacccc cgaggtgacc tgcgtggtgg tggacgtgag ccaggaagat    120

cccgaggtcc agttcaattg gtacgtggac ggcgtggaag tgcacaacgc caagaccaag    180

cccagagagg aacagttcca gagcacctac cgggtggtgt ctgtgctgac cgtgctgcac    240

caggactggc tgaacggcaa agaatacaag tgcaaggtgt ccaacaaggg cctgcccagc    300

agcatcgaaa agaccatcag caaggccaag                                     330


<210> SEQ ID NO 105
<211> LENGTH: 110
<212> TYPE: PRT
<213> ORGANISM: Artificial Sequence
<220> FEATURE:
<223> OTHER INFORMATION: IGG4-CH2(L235D, N297Q)

<400> SEQUENCE: 105

Ala Pro Glu Phe Asp Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45
```

Val Asp Gly Val Glu Val His Asn Ala Lys Thr Lys Pro Arg Glu Glu
    50                  55                  60

Gln Phe Gln Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 106
<211> LENGTH: 321
<212> TYPE: DNA
<213> ORGANISM: Unknown
<220> FEATURE:
<223> OTHER INFORMATION: IGG4-CH3

<400> SEQUENCE: 106
ggccagcctc gcgagcccca ggtgtacacc ctgcctccct cccaggaaga gatgaccaag 60
aaccaggtgt ccctgacctg cctggtgaag ggcttctacc ccagcgacat cgccgtggag 120
tgggagagca acggccagcc tgagaacaac tacaagacca cccctcccgt gctggacagc 180
gacggcagct tcttcctgta cagccggctg accgtggaca agagccggtg gcaggaaggc 240
aacgtcttta gctgcagcgt gatgcacgag gccctgcaca accactacac ccagaagagc 300
ctgagcctgt ccctgggcaa g 321

<210> SEQ ID NO 107
<211> LENGTH: 107
<212> TYPE: PRT
<213> ORGANISM: Artificial Sequence
<220> FEATURE:
<223> OTHER INFORMATION: IGG4-CH3

<400> SEQUENCE: 107

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 108
<211> LENGTH: 225
<212> TYPE: DNA
<213> ORGANISM: Unknown
<220> FEATURE:
<223> OTHER INFORMATION: CD8 hinge/transmembrane domain

<400> SEQUENCE: 108
gaatctaagt acggaccggc caagcctacc accacccctg cccctagacc tccaacaccc 60
gccccaacaa tcgccagcca gcctctgtct ctgaggcccg aggcttgtag accagctgct 120
ggcggagccg tgcacaccag aggactggat ttcgcctgcg acatctacat ctgggcccct 180
ctggccggca catgtggcgt gctgctgctg agcctcgtga tcacc 225

<210> SEQ ID NO 109
<211> LENGTH: 75
<212> TYPE: PRT
<213> ORGANISM: Artificial Sequence
<220> FEATURE:
<223> OTHER INFORMATION: CD8 hinge/transmembrane domain

<400> SEQUENCE: 109

Glu Ser Lys Tyr Gly Pro Ala Lys Pro Thr Thr Thr Pro Ala Pro Arg
1 5 10 15

Pro Pro Thr Pro Ala Pro Thr Ile Ala Ser Gln Pro Leu Ser Leu Arg
20 25 30

Pro Glu Ala Cys Arg Pro Ala Ala Gly Gly Ala Val His Thr Arg Gly
35 40 45

Leu Asp Phe Ala Cys Asp Ile Tyr Ile Trp Ala Pro Leu Ala Gly Thr
50 55 60

Cys Gly Val Leu Leu Leu Ser Leu Val Ile Thr
65 70 75

<210> SEQ ID NO 110
<211> LENGTH: 84
<212> TYPE: DNA
<213> ORGANISM: Unknown
<220> FEATURE:
<223> OTHER INFORMATION: CD28 transmembrane domain

<400> SEQUENCE: 110
atgttctggg tgctggtggt ggtcggaggc gtgctggcct gctacagcct gctggtcacc 60
gtggccttca tcatcttttg ggtg 84

<210> SEQ ID NO 111
<211> LENGTH: 28
<212> TYPE: PRT
<213> ORGANISM: Artificial Sequence
<220> FEATURE:
<223> OTHER INFORMATION: CD28 transmembrane domain

<400> SEQUENCE: 111

Met Phe Trp Val Leu Val Val Val Gly Gly Val Leu Ala Cys Tyr Ser
1 5 10 15

Leu Leu Val Thr Val Ala Phe Ile Ile Phe Trp Val
20 25

<210> SEQ ID NO 112
<211> LENGTH: 225
<212> TYPE: DNA
<213> ORGANISM: Unknown
<220> FEATURE:
<223> OTHER INFORMATION: CD8 hinge/ transmembrane domain

<400> SEQUENCE: 112
gaatctaagt acggaccggc caagcctacc accacccctg cccctagacc tccaacaccc 60
gccccaacaa tcgccagcca gcctctgtct ctgaggcccg aggcttgtag accagctgct 120
ggcggagccg tgcacaccag aggactggat ttcgcctgcg acatctacat ctgggcccct 180
ctggccggca catgtggcgt gctgctgctg agcctcgtga tcacc 225

<210> SEQ ID NO 113
<211> LENGTH: 75
<212> TYPE: PRT
<213> ORGANISM: Artificial Sequence
<220> FEATURE:
<223> OTHER INFORMATION: CD8 hinge/ transmembrane domain

<400> SEQUENCE: 113

```
Glu Ser Lys Tyr Gly Pro Ala Lys Pro Thr Thr Thr Pro Ala Pro Arg
1               5                   10                  15

Pro Pro Thr Pro Ala Pro Thr Ile Ala Ser Gln Pro Leu Ser Leu Arg
            20                  25                  30

Pro Glu Ala Cys Arg Pro Ala Ala Gly Gly Ala Val His Thr Arg Gly
        35                  40                  45

Leu Asp Phe Ala Cys Asp Ile Tyr Ile Trp Ala Pro Leu Ala Gly Thr
    50                  55                  60

Cys Gly Val Leu Leu Leu Ser Leu Val Ile Thr
65                  70                  75
```

<210> SEQ ID NO 114
<211> LENGTH: 336
<212> TYPE: DNA
<213> ORGANISM: Unknown
<220> FEATURE:
<223> OTHER INFORMATION: CD3 Zeta

<400> SEQUENCE: 114

```
cgggtgaagt tcagcagaag cgccgacgcc cctgcctacc agcagggcca gaatcagctg     60

tacaacgagc tgaacctggg cagaagggaa gagtacgacg tcctggataa gcggagaggc    120

cgggaccctg agatgggcgg caagcctcgg cggaagaacc cccaggaagg cctgtataac    180

gaactgcaga aagacaagat ggccgaggcc tacagcgaga tcggcatgaa gggcgagcgg    240

aggcggggca agggccacga cggcctgtat cagggcctgt ccaccgccac caaggatacc    300

tacgacgccc tgcacatgca ggccctgccc ccaagg                              336
```

<210> SEQ ID NO 115
<211> LENGTH: 112
<212> TYPE: PRT
<213> ORGANISM: Artificial Sequence
<220> FEATURE:
<223> OTHER INFORMATION: CD3 Zeta

<400> SEQUENCE: 115

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 116

<211> LENGTH: 126
<212> TYPE: DNA
<213> ORGANISM: Unknown
<220> FEATURE:
<223> OTHER INFORMATION: 4-1BB

<400> SEQUENCE: 116
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 117
<211> LENGTH: 42
<212> TYPE: PRT
<213> ORGANISM: Artificial Sequence
<220> FEATURE:
<223> OTHER INFORMATION: 4-1BB

<400> SEQUENCE: 117

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 118
<211> LENGTH: 123
<212> TYPE: DNA
<213> ORGANISM: Unknown
<220> FEATURE:
<223> OTHER INFORMATION: CD28 cytoplasmic domain

<400> SEQUENCE: 118
cgcagcaagc ggagcagagg cggccacagc gactacatga acatgacccc tagacggcct 60
ggccccacca gaaagcacta ccagccctac gcccctcccc gggactttgc cgcctacaga 120
agc 123

<210> SEQ ID NO 119
<211> LENGTH: 41
<212> TYPE: PRT
<213> ORGANISM: Artificial Sequence
<220> FEATURE:
<223> OTHER INFORMATION: CD28 cytoplasmic domain

<400> SEQUENCE: 119

Arg Ser Lys Arg Ser Arg Gly Gly His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 120
<211> LENGTH: 46
<212> TYPE: DNA
<213> ORGANISM: Artificial Sequence
<220> FEATURE:
<223> OTHER INFORMATION: DNA spacer

<400> SEQUENCE: 120
gctagcgttt aaacttaagc ttggtaccga gctcggatcc gccacc 46

<210> SEQ ID NO 121
<211> LENGTH: 862
<212> TYPE: PRT
<213> ORGANISM: Artificial Sequence
<220> FEATURE:
<223> OTHER INFORMATION: HEA3(p65/S536E/K310Q) amino acid sequence variant

<400> SEQUENCE: 121

```
Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

Ser Cys Gly Gly Gly Arg Gly Glu Leu Ala Glu Leu Pro Asn Gly Leu
    50                  55                  60

Gly Glu Thr Arg Gly Ser Glu Asp Glu Thr Asp Asp Asp Gly Glu Asp
65                  70                  75                  80

Phe Thr Pro Pro Ile Leu Lys Glu Leu Glu Asn Leu Ser Pro Glu Glu
                85                  90                  95

Ala Ala His Gln Lys Ala Val Val Glu Thr Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240

Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
```

```
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Gly
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495

Leu Gln Gln Gln His Gln Arg Leu Ala Gln Leu Leu Leu Ile Leu Ser
            500                 505                 510

His Ile Arg His Met Ser Asn Lys Arg Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val Glu Phe Gln Tyr Leu Pro Asp Thr Asp Asp Arg His Arg
        595                 600                 605

Ile Glu Glu Lys Arg Lys Arg Thr Tyr Glu Thr Phe Gln Ser Ile Met
    610                 615                 620

Lys Lys Ser Pro Phe Ser Gly Pro Thr Asp Pro Arg Pro Pro Pro Arg
625                 630                 635                 640

Arg Ile Ala Val Pro Ser Arg Ser Ser Ala Ser Val Pro Lys Pro Ala
                645                 650                 655

Pro Gln Pro Tyr Pro Phe Thr Ser Ser Leu Ser Thr Ile Asn Tyr Asp
            660                 665                 670

Glu Phe Pro Thr Met Val Phe Pro Ser Gly Gln Ile Ser Gln Ala Ser
        675                 680                 685

Ala Leu Ala Pro Ala Pro Pro Gln Val Leu Pro Gln Ala Pro Ala Pro
    690                 695                 700

Ala Pro Ala Pro Ala Met Val Ser Ala Leu Ala Gln Ala Pro Ala Pro
705                 710                 715                 720

Val Pro Val Leu Ala Pro Gly Pro Pro Gln Ala Val Ala Pro Pro Ala
                725                 730                 735

Pro Lys Pro Thr Gln Ala Gly Glu Gly Thr Leu Ser Glu Ala Leu Leu
            740                 745                 750

Gln Leu Gln Phe Asp Asp Glu Asp Leu Gly Ala Leu Leu Gly Asn Ser
        755                 760                 765

Thr Asp Pro Ala Val Phe Thr Asp Leu Ala Ser Val Asp Asn Ser Glu
    770                 775                 780
```

```
Phe Gln Gln Leu Leu Asn Gln Gly Ile Pro Val Ala Pro His Thr Thr
785                 790                 795                 800

Glu Pro Met Leu Met Glu Tyr Pro Glu Ala Ile Thr Arg Leu Val Thr
                805                 810                 815

Gly Ala Gln Arg Pro Pro Asp Pro Ala Pro Ala Pro Leu Gly Ala Pro
            820                 825                 830

Gly Leu Pro Asn Gly Leu Leu Ser Gly Asp Glu Asp Phe Glu Ser Ile
        835                 840                 845

Ala Asp Met Asp Phe Ser Ala Leu Leu Ser Gln Ile Ser Ser
    850                 855                 860


<210> SEQ ID NO 122
<211> LENGTH: 2586
<212> TYPE: DNA
<213> ORGANISM: Artificial Sequence
<220> FEATURE:
<223> OTHER INFORMATION: HEA3(p65/S536E/K310Q) variant nucleotide
      sequence

<400> SEQUENCE: 122

atggtgtcca agctgtccca gctgcagaca gaactgctgg cagcactgct ggaaagcggc     60

ctgagcaaag aggccctgat tcaggcactc ggcgaacctg gaccttatct gctcgctggc    120

gaaggccctc tggataaggg cgagagctgt ggcggaggaa gaggagagct ggccgagctg    180

cctaacggcc tgggcgagac aagaggcagc gaggacgaga cagacgacga cggcgaggac    240

ttcacccccc ccatcctgaa agagctggaa aacctgagcc ccgaggaagc cgcccaccag    300

aaagccgtgg tggagacact gctgcaggaa gatccctggc gggtcgccaa gatggtcaag    360

agctacctgc agcagcacaa catcccccag cgggaggtgg tggacaccac cggcctgaac    420

cagagccacc tgagccagca cctgaacaag ggcacccccca tgaaaaccca gaagagagcc    480

gccctgtaca cttggtacgt gcggaagcag agagaggtgg cccagcagtt tacacacgcc    540

ggccagggcg gcctgatcga ggaacctacc ggcgacgagc tgcccaccaa gaagggcaga    600

cggaaccggt ttaagtgggg ccctgcatct cagcagatcc tgttccaggc ctacgagcgg    660

cagaagaacc ccagcaaaga ggaacgggag acactggtgg aagagtgcaa ccgggccgag    720

tgcatccaga gaggcgtgag cccttctcag gctcagggcc tcggcagcaa tctggtcacc    780

gaagtgcggg tgtacaattg gttcgccaac cggcggaaag aggaagcctt ccggcacaag    840

ctgtctgctg gcgatatgag agccgccaac ctgtggccca gccccctgat gatcaagcgg    900

agcaagaaga acagcctggc cctgagcctg accgccgatc agatggtgtc cgctctgctg    960

gacgccgagc cccctatcct gtacagcgag tacgacccca ccagaccctt cagcgaggcc   1020

agcatgatgg gcctgctgac caacctggcc gaccgggagc tggtgcacat gatcaactgg   1080

gccaagcggg tgcccggctt cgtggacctg accctgcacg accaggtcca cctgctggaa   1140

tgtgcctggc tggaaatcct gatgatcggc ctcgtgtgga gaagcatgga acaccccggc   1200

aagctgctgt tcgcccccaa cctgctcctg gaccggaacc agggaaagtg cgtggagggc   1260

atggtggaga tcttcgacat gctgctggcc acctccagcc ggttccggat gatgaacctg   1320

cagggcgagg aattcgtgtg cctgaagtcc atcatcctgc tgaacagcgg cgtgtacacc   1380

ttcctgtcat ccaccctgaa gtccctggaa gagaaggacc acatccaccg ggtgctggac   1440

aagatcaccg acaccctgat ccacctgatg gccaaggctg gcctgacact ccagcagcag   1500

caccagagac tggcccagct gctgctgatc ctgagccaca tccggcacat gagcaacaag   1560
```

```
cggatggaac acctgtacag catgaagtgc aagaacgtgg tgcccctgta cgacctgctg   1620

ctcgagatgc tggatgccca cagactgcac gcccctacaa gcagaggcgg agccagcgtg   1680

gaggaaaccg accagtctca cctggccacc gccggcagca caagcagcca cagcctgcag   1740

aagtactaca tcaccggcga ggccgaggga ttccctgcca ccgtggagtt ccagtacctg   1800

cccgacaccg acgaccggca ccggatcgag gaaaagcgga agcggaccta cgagacattc   1860

cagagcatca tgaagaagtc cccttcagc ggccccaccg atcccagacc ccccctaga   1920

agaatcgccg tgcccagcag atctagcgcc agcgtgccca agcctgcccc ccagccctac   1980

cctttcacca gcagcctgag caccatcaac tacgacgagt tccctaccat ggtgttcccc   2040

agcggccaga tctctcaggc ctctgctctg gcacctgctc cacctcaggt gctgcctcag   2100

gcccctgctc cagccccagc cctgccatg gtgtctgcac tggcccaggc tccagctcct   2160

gtgcctgtgc tggcccctgg acctcctcag gctgtggccc ctcctgcccc taaacctacc   2220

caggccgggg agggaacact gtctgaggcc ctgctgcagc tccagttcga cgacgaggat   2280

ctgggagcac tgctgggcaa tagcaccgac cccgccgtgt ttaccgacct ggcctccgtg   2340

gacaacagcg agttccagca gctcctcaac cagggcatcc ctgtcgcccc acacaccacc   2400

gagcccatgc tgatggaata ccccgaggcc atcaccagac tggtcacagg cgcccagagg   2460

cctccagatc cagcaccagc tccactggga gcccctggcc tgcctaatgg gctgctgtct   2520

ggcgacgagg acttcgagag cattgccgac atggacttca gcgccctgct gtcccagatc   2580

agcagc                                                              2586
```

<210> SEQ ID NO 123
<211> LENGTH: 142
<212> TYPE: PRT
<213> ORGANISM: Artificial Sequence
<220> FEATURE:
<223> OTHER INFORMATION: Survivin amino acid sequence

<400> SEQUENCE: 123

```
Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Val
        115                 120                 125

Lys Lys Val Arg Arg Ala Ile Glu Gln Leu Ala Ala Met Asp
    130                 135                 140
```

<210> SEQ ID NO 124
<211> LENGTH: 426
<212> TYPE: DNA
<213> ORGANISM: Artificial Sequence
<220> FEATURE:

-continued

```
<223> OTHER INFORMATION: Survivin nucleotide sequence

<400> SEQUENCE: 124

atgggtgccc cgacgttgcc ccctgcctgg cagccctttc tcaaggacca ccgcatctct      60

acattcaaga actggccctt cttggagggc tgcgcctgca ccccggagcg gatggccgag     120

gctggcttca tccactgccc cactgagaac gagccagact tggcccagtg tttcttctgc     180

ttcaaggagc tggaaggctg ggagccagat gacgacccca tagaggaaca taaaaagcat     240

tcgtccggtt gcgctttcct ttctgtcaag aagcagtttg aagaattaac ccttggtgaa     300

tttttgaaac tggacagaga aagagccaag aacaaaattg caaaggaaac caacaataag     360

aagaaagaat ttgaggaaac tgtgaagaaa gtgcgccgtg ccatcgagca gctggctgca     420

atggat                                                                426
```